US011759515B2

(12) United States Patent
Sullivan et al.

(10) Patent No.: US 11,759,515 B2
(45) Date of Patent: Sep. 19, 2023

(54) COMPOSITIONS AND METHODS FOR INDUCING IMMUNE RESPONSES

(71) Applicant: Arcturus Therapeutics, Inc., San Diego, CA (US)

(72) Inventors: Sean Michael Sullivan, Escondido, CA (US); Daiki Matsuda, San Diego, CA (US); Kiyoshi Tachikawa, San Diego, CA (US); Padmanabh Chivukula, San Diego, CA (US); Priya Prakash Karmali, San Diego, CA (US); Jared Henry Davis, Poway, CA (US); Yanjie Bao, San Diego, CA (US)

(73) Assignee: ARCTURUS THERAPEUTICS, INC., San Diego, CA (US)

( * ) Notice: Subject to any disclaimer, the term of this patent is extended or adjusted under 35 U.S.C. 154(b) by 295 days.

(21) Appl. No.: 17/196,890

(22) Filed: Mar. 9, 2021

(65) Prior Publication Data

US 2021/0290752 A1 Sep. 23, 2021

Related U.S. Application Data

(60) Provisional application No. 63/073,900, filed on Sep. 2, 2020, provisional application No. 62/987,191, filed on Mar. 9, 2020.

(51) Int. Cl.

| | |
|---|---|
| ***A61K 39/215*** | (2006.01) |
| ***C07K 14/005*** | (2006.01) |
| ***C12N 15/86*** | (2006.01) |
| ***A61K 47/20*** | (2006.01) |
| ***A61K 47/26*** | (2006.01) |
| ***A61K 47/10*** | (2017.01) |
| ***A61K 9/51*** | (2006.01) |
| ***A61K 39/12*** | (2006.01) |
| ***C07K 14/18*** | (2006.01) |
| ***C12N 7/00*** | (2006.01) |
| ***A61K 39/00*** | (2006.01) |
| ***A61K 38/00*** | (2006.01) |

(52) U.S. Cl.

CPC .......... *A61K 39/215* (2013.01); *A61K 9/5123* (2013.01); *A61K 39/12* (2013.01); *A61K 47/10* (2013.01); *A61K 47/20* (2013.01); *A61K 47/26* (2013.01); *C07K 14/005* (2013.01); *C07K 14/1808* (2013.01); *C12N 7/00* (2013.01); *C12N 15/86* (2013.01); *A61K 38/00* (2013.01); *A61K 2039/53* (2013.01); *C12N 2770/20022* (2013.01); *C12N 2770/20034* (2013.01); *C12N 2770/36122* (2013.01); *C12N 2770/36134* (2013.01); *C12N 2830/42* (2013.01); *C12N 2830/50* (2013.01)

(58) Field of Classification Search

CPC .... A61K 39/215; A61K 9/5123; A61K 39/12; A61K 47/10; A61K 47/20; A61K 47/26; A61K 38/00; A61K 2039/53; A61K 39/395; A61K 2039/507; A61K 2039/884; A61K 2039/55555; A61K 2039/572; A61K 2039/575; C07K 14/005; C07K 14/1808; C07K 2317/76; C07K 16/2818; C07K 16/2827; C12N 7/00; C12N 15/86; C12N 2770/20022; C12N 2770/20034; C12N 2770/36122; C12N 2770/36134; C12N 2830/42; C12N 2830/50; C12N 2740/13071; C12N 2760/16134; C12N 2760/16171; C12N 2740/13034; A61P 35/00; A61P 31/14; A61P 31/16; Y02A 50/30

See application file for complete search history.

(56) References Cited

U.S. PATENT DOCUMENTS

| | | | |
|---|---|---|---|
| 7,332,322 | B2 | 2/2008 | Frolov et al. |
| 7,425,337 | B2 | 9/2008 | Smith et al. |
| 7,442,381 | B2 | 10/2008 | Smith et al. |
| 8,093,367 | B2 | 1/2012 | Kore et al. |
| 8,158,601 | B2 | 4/2012 | Chen et al. |
| 8,304,529 | B2 | 11/2012 | Kore et al. |
| 8,961,995 | B2 | 2/2015 | Frolov et al. |
| 9,254,265 | B2 | 2/2016 | Geall et al. |
| 9,295,646 | B2 | 3/2016 | Brito et al. |
| 9,730,997 | B2 | 8/2017 | Perri et al. |
| 9,770,463 | B2 | 9/2017 | Geall et al. |
| 10,238,733 | B2 | 3/2019 | Brito et al. |
| 10,487,105 | B2 | 11/2019 | Chivukula et al. |
| 2011/0171255 | A1 | 7/2011 | Kiiver et al. |

(Continued)

FOREIGN PATENT DOCUMENTS

| | | |
|---|---|---|
| EP | 2 591 114 B1 | 6/2016 |
| EP | 3 471 778 A2 | 4/2019 |

(Continued)

OTHER PUBLICATIONS

Boles KS, et al. Synthetic construct H7N9 HA gene, complete cds. GenBank: KY199425.1, Dep. Jul. 18, 2017. (Year: 2017).*

(Continued)

*Primary Examiner* — Rachel B Gill

(74) *Attorney, Agent, or Firm* — Mintz, Levin, Cohn, Ferris, Glovsky and Popeo, P.C.

(57) ABSTRACT

Provided herein are nucleic acid molecules encoding viral replication proteins and antigenic proteins or fragments thereof. Also provided herein are compositions that include nucleic acid molecules encoding viral replication and antigenic proteins, and lipids. Nucleic acid molecules provided herein are useful for inducing immune responses.

27 Claims, 11 Drawing Sheets

Specification includes a Sequence Listing.

(56) References Cited

U.S. PATENT DOCUMENTS

| | | | | |
|---|---|---|---|---|
| 2011/0207223 | A1 | 8/2011 | Tang et al. | |
| 2011/0256175 | A1 | 10/2011 | Hope et al. | |
| 2012/0027803 | A1 | 2/2012 | Manoharan et al. | |
| 2012/0128760 | A1 | 5/2012 | Manoharan et al. | |
| 2012/0156251 | A1* | 6/2012 | Brito | A61P 31/12 424/193.1 |
| 2013/0171241 | A1 | 7/2013 | Geall | |
| 2013/0195968 | A1 | 8/2013 | Geall et al. | |
| 2014/0227346 | A1 | 8/2014 | Geall et al. | |
| 2014/0242152 | A1 | 8/2014 | Geall et al. | |
| 2015/0024002 | A1 | 1/2015 | Perri et al. | |
| 2016/0074500 | A1 | 3/2016 | Pushko et al. | |
| 2016/0348132 | A1 | 12/2016 | Rayner et al. | |
| 2018/0036398 | A1 | 2/2018 | Hagen et al. | |
| 2018/0104359 | A1 | 4/2018 | Kamrud | |
| 2018/0171340 | A1 | 6/2018 | Kamrud et al. | |
| 2018/0273576 | A1 | 9/2018 | Hogrefe et al. | |
| 2018/0327471 | A1 | 11/2018 | Limphong et al. | |
| 2019/0091329 | A1 | 3/2019 | Brito et al. | |
| 2019/0224299 | A1 | 7/2019 | Kamrud et al. | |
| 2019/0321458 | A1 | 10/2019 | Sahin et al. | |
| 2019/0374650 | A1 | 12/2019 | Moon et al. | |
| 2020/0010849 | A1 | 1/2020 | Blair et al. | |
| 2020/0113830 | A1 | 4/2020 | Geall et al. | |
| 2020/0113831 | A1 | 4/2020 | Geall et al. | |
| 2020/0222332 | A1 | 7/2020 | Irvine et al. | |
| 2020/0230058 | A1 | 7/2020 | Geall et al. | |
| 2020/0297634 | A1 | 9/2020 | Karmali et al. | |
| 2020/0330585 | A1 | 10/2020 | Mogler et al. | |
| 2021/0030859 | A1 | 2/2021 | Bucala et al. | |
| 2021/0290756 | A1 | 9/2021 | Sullivan et al. | |
| 2022/0347298 | A1* | 11/2022 | Sullivan | A61K 39/3955 |

FOREIGN PATENT DOCUMENTS

| | | | | |
|---|---|---|---|---|
| EP | 3433369 | B1 | 3/2020 | |
| EP | 2 729 126 | B1 | 12/2020 | |
| WO | WO-2009/086558 | A1 | 7/2009 | |
| WO | WO-2009/127060 | A1 | 10/2009 | |
| WO | WO-2010/048536 | A2 | 4/2010 | |
| WO | WO-2010/054406 | A1 | 5/2010 | |
| WO | WO-2010/088537 | A2 | 8/2010 | |
| WO | WO-2010/129709 | A1 | 11/2010 | |
| WO | WO-2011/153493 | A2 | 12/2011 | |
| WO | 2014170493 | A2 | 10/2014 | |
| WO | WO-2015/051169 | A2 | 4/2015 | |
| WO | WO-2015/061491 | A1 | 4/2015 | |
| WO | WO-2017/223085 | A2 | 12/2017 | |
| WO | WO-2018/078053 | A1 | 5/2018 | |
| WO | WO-2018/208856 | A1 | 11/2018 | |
| WO | WO-2018/222890 | A1 | 12/2018 | |
| WO | WO-2018222926 | A1* | 12/2018 | A61K 31/7115 |
| WO | 2019023566 | A1 | 1/2019 | |
| WO | 2020014654 | A1 | 1/2020 | |
| WO | WO-2020/035609 | A2 | 2/2020 | |
| WO | 2020254804 | A1 | 12/2020 | |
| WO | WO-2020/255055 | A1 | 12/2020 | |
| WO | WO-2021/067181 | A1 | 4/2021 | |

OTHER PUBLICATIONS (Apr. 27, 2019) Cloning Vector pCMV-VEE-GFP, Complete Sequence, GenBank ID: MH891622.1, 7 pages.

(Jul. 18, 2020) Surface Glycoprotein [Severe Acute Respiratory Syndrome Coronavirus 2], GenBank ID: YP_009724390, 3 pages.

Wu et al. (Mar. 12, 2020) "A New Coronavirus Associated with Human Respiratory Disease in China", Nature, 579(7798):265-269(20 pages).

Altschul et al. (1990) "Basic Local Alignment Search Tool", Journal of Molecular Biology, 215(3):403-410.

Altschul et al. (1997) "Gapped BLAST and PSI-BLAST: A New Generation of Protein Database Search Programs", Nucleic Acids Research, 25(17):3389-3402.

Bochicchio et al. (2014) "Liposomes as siRNA Delivery Vectors", Current Drug Metabolism,15(9):882-892.

Both et al. (Mar. 1975) "Methylation-Dependent Translation Of Viral Messenger RNAs In Vitro", Proceedings of the National Academy of Sciences, 72(3):1189-1193.

Bouloy et al. (Jul. 1980) "Both the 7-Methyl And the 2'-O-Methyl Groups in the Cap of mRNA Strongly Influence its Ability to Act as Primer for Influenza Virus RNA Transcription", Proceedings of the National Academy of Sciences, 77(7):3952-3956.

Chan, C.Y. et al. (2017) "Early molecular correlates of adverse events following yellow fever vaccination", JCI Insight, 2(19):96031. 12 pages.

Chan, K.R. et al. (2016) "Cross-reactive antibodies enhance live attenuated virus infection for increased immunogenicity", Nat Microbiol, 1: Article No. 16164, 10 pages.

Chan, K.R. et al. (2019) "Metabolic perturbations and cellular stress underpin susceptibility to symptomatic live-attenuated yellow fever infection", Nat Med, 25(8):1218-1224.

Chu et al. (1978) "Paradoxical Observations on the 5' Terminus of Ovalbumin Messenger Ribonucleic Acid", Journal of Biological Chemistry, 253(15):5228-5231.

Cirelli et al. (2019) "Slow Delivery Immunization Enhances HIV Neutralizing Antibody and Germinal Center Responses via Modulation of Immunodominance", Cell, 177(5):1153-1171. e28.

Conticello et al. (2008) "Interaction between Antibody-Diversification Enzyme AID and Spliceosome-Associated Factor CTNNBL1", Mol Cell, 31(4):474-484.

Dabkowska et al. (Mar. 7, 2012) "The Effect of Neutral Helper Lipids on The Structure of Cationic Lipid Monolayer", Journal of the Royal Society Interface, 9(68):548-561.

Dua et al. (Apr.-Jun. 2012) "Liposome: Methods of Preparation and Applications", International Journal of Pharmaceutical Studies and Research, 3:14-20.

Dupuis et al. (Sep. 1, 2000) "Distribution of DNA Vaccines Determines Their Immunogenicity After Intramuscular Injection in Mice", J Immunol, 165 (5) 2850-2858.

Ehrchen et al. (2009) "The endogenous Toll-like receptor 4 agonist S100A8/S100A9 (calprotectin) as innate amplifier of infection, autoimmunity, and cancer", J Leukoc Biol, 86(3): 557-566.

Geall et al. (Sep. 4, 2012) "Nonviral delivery of self-amplifying RNA vaccines", PNAS Sep. 4, 2012 109 (36):14604-14609.

Groom et al. (2011) "CXCR3 in T cell function", Exp Cell Res, 317(5): 620-631.

Gustafsson et al. (Jul. 2004) "Codon Bias and Heterologous Protein Expression", Trends in Biotechnology, 22(7):346-353.

Hashem et al. (2019) "A Highly Immunogenic, Protective, and Safe Adenovirus-Based Vaccine Expressing Middle East Respiratory Syndrome Coronavirus S1-CD40L Fusion Protein in a Transgenic Human Dipeptidyl Peptidase 4 Mouse Model", J Infect Dis, 220(10): 1558-1567.

Hassett et al. (2019) "Optimization of Lipid Nanoparticles for Intramuscular Administration of mRNA Vaccines", Mol Ther Nucleic Acids, 15: 1-11.

Higgins et al. (2019) "Programming Isotype-Specific Plasma Cell Function", Trends Immunol, 40(4): 345-357.

Honda-Okubo et al. (2015, e-published Dec. 17, 2014) "Severe acute respiratory syndrome-associated coronavirus vaccines formulated with delta inulin adjuvants provide enhanced protection while ameliorating lung eosinophilic immunopathology", J Virol, 89(6): p. 2995-3007.

Huang et al. (Aug. 2011) "In Vivo Delivery of RNAi with Lipid-Based Nanoparticles", Annual Review of Biomedical Engineering, 13:507-530.

Hyde et al. (2015, e-published Jan. 25, 2015) "The 5' and 3' ends of alphavirus RNAs—Non-coding is not non-functional", Virus Res. 206:99-107.

Ishikawa et al. (Sep. 27, 2009) "Preparation of Eukaryotic mRNA having Differently Methylated Adenosine at the 5' Terminus and the Effect of the Methyl Group in Translation", Nucleic Acids Symposium, 53(1):129-130.

Jackson et al. (2020) "The promise of mRNA vaccines: a biotech and industrial perspective", NPJ Vaccines, 5:11: 6 pages.

(56) References Cited

OTHER PUBLICATIONS

Jin et al. (2010) "Immunomodulatory Effects of dsRNA and Its Potential as Vaccine Adjuvant", J Biomed Biotechnol, Article ID 690438, 17 pages.
Jokerst et al. (Jun. 2011) "Nanoparticle PEGylation for Imaging and Therapy", Nanomedicine (Lond), 6(4):715-728(27 pages).
Karlin et al. (Mar. 1990) "Methods for Assessing the Statistical Significance of Molecular Sequence Features by Using General Scoring Schemes", Proceedings of the National Academy of Sciences, 87(6):2264-2268.
Karlin et al. (Jun. 1993) "Applications and Statistics for Multiple High-Scoring Segments in Molecular Sequences", Proceedings of the National Academy of Sciences, 90(12):5873-5877.
Kasturi et al. (2011) "Programming the magnitude and persistence of antibody responses with innate immunity", Nature, 470(7335):543-547.
Kawabata et al. (1995) "The Fate of Plasmid DNA After Intravenous Injection in Mice: Involvement of Scavenger Receptors in Its Hepatic Uptake", Pharmaceutical Research, 12:825-830.
Kirchdoerfer et al. (2018, e-published Oct. 24, 2018) "Stabilized coronavirus spikes are resistant to conformational changes induced by receptor recognition or proteolysis", Sci Rep 8, Article No. 15701. 11 pages.
Kowalski et al. (2019, e-published Feb. 19, 2019) "Delivering the Messenger: Advances in Technologies for Therapeutic mRNA Delivery", Mol Ther.; 27(4):710-728.
Kozak, Marilyn (Feb. 1989) "The Scanning Model For Translation: An Update", Journal of Cell Biology, 108(2):229-241.
Kozak, Marilyn (1988) "Leader Length And Secondary Structure Modulate mRNA Function Under Conditions Of Stress", Molecular and Cellular Biology, 8:2737-2744.
Kozak, Marilyn (Nov. 1990) "Downstream Secondary Structure Facilitates Recognition of Initiator Codons by Eukaryotic Ribosomes", Proceedings of the National Academy of Sciences, 87(21):8301-8305.
Kozak, Marilyn (Oct. 25, 1991) "Structural Features In Eukaryotic mRNAs That Modulate the Initiation of Translation", Journal of Biological Chemistry, 266(30):19867-19870.
Kreiter et al. (Jan. 1, 2008) "Increased Antigen Presentation Efficiency by Coupling Antigens to MHC Class I Trafficking Signals", Journal of Immunology, 180(1):309-318.
Kulasegaran-Shylini et al. (2009, e-published Mar. 17, 2009) "The 5'UTR-specific mutation in VEEV TC-83 genome has a strong effect on RNA replication and subgenomic RNA synthesis, but not on translation of the encoded proteins", Virology, 387(1):211-221.
Kulkarni et al. (2018) "Lipid Nanoparticles Enabling Gene Therapies: From Concepts to Clinical Utility", Nucleic Acid Therapeutics, 28(3): 146-157.
Lasic, Dan D. (Jul. 1, 1998) "Novel Applications of Liposomes", Trends in Biotechnology, 16(7):307-321.
Li, S-D et al. (Aug. 3, 2010) "Stealth Nanoparticles: High Density but Sheddable PEG is a Key for Tumor Targeting", Journal of Controlled Release, 145(3):178-181(8 pages).
Li, X. et al. (2011) "Biosynthesis of Nanoparticles by Microorganisms and Their Applications", J. Nanomaterial, Article ID 270974, 16 pages.
Lin et al. (2014) "Lipid-based Nanoparticles in the Systemic Delivery of siRNA", Nanomedicine, 9(1):105-120.
Love et al. (2010) "Lipid-like Materials for Low-dose, In Vivo Gene Silencing", Proceedings of the National Academy of Sciences, 107(5):1864-1869.
Magini et al. (2016) "Self-Amplifying mRNA Vaccines Expressing Multiple Conserved Influenza Antigens Confer Protection against Homologous and Heterosubtypic Viral Challenge", PloS one, 11(8), e0161193. 25 pages.
Maruggi et al. (2019) "mRNA as a Transformative Technology for Vaccine Development to Control Infectious Diseases", Molecular Therapy, vol. 27, No. 427, 757-772.
Maruggi et al. (2013, e-published Oct. 5, 2013) "Engineered alphavirus replicon vaccines based on known attenuated viral mutants show limited effects on immunogenicity", Virology, 447, 254-264.
Muthukrishnan et al. (1975) "5'-Terminal 7-Methylguanosine in Eukaryotic mRNA is Required for Translation", Nature, 255:33-37.
Patil et al. (Jan. 2014, e-published, Nov. 9, 2013) "Novel Methods for Liposome Preparation", Chemistry and Physics of Lipids, 177:8-18.
Pearson et al. (Apr. 1988) "Improved Tools For Biological Sequence Comparison", Proceedings of the National Academy of Sciences, 85:2444-2448.
Pepini et al. (2017, e-published Apr. 17, 2017) "Induction of an IFN-Mediated Antiviral Response by a Self-Amplifying RNA Vaccine: Implications for Vaccine Design", J Immunol, 198(10): p. 4012-4024.
Petkov et al. (2018) "DNA immunization site determines the level of gene expression and the magnitude, but not the type of the induced immune response", PLoS One 13(6): e0197902. 22 pages.
Querec, et al. (2009, e-published Nov. 23, 2008) "Systems biology approach predicts immunogenicity of the yellow fever vaccine in humans", Nat Immunol, 10(1):116-125.
Querec, T.D. and Pulendran, B. (2007) "Understanding the Role of Innate Immunity in the Mechanism of Action of the Live Attenuated Yellow Fever Vaccine 17D", In: Katsikis P.D., Schoenberger S.P., Pulendran B. (eds) Crossroads between Innate and Adaptive Immunity. Advances in Experimental Medicine and Biology, vol. 590. pp. 45-53. Springer, Boston, MA.
Ramanathan, A. et al. (2016, e-published Jun. 17, 2016). "mRNA capping: biological functions and applications", Nucleic Acids Research, vol. 44, No. 16, 7511-7526.
Rodriguez-Gascon et al. (2014) "Development of Nucleic Acid Vaccines: Use of Self-Amplifying RNA in Lipid Nanoparticles", International Journal of Nanomedicine, 9:1833-1843.
Salti et al. (2011, e-published Nov. 14, 2011) "Granzyme B Regulates Antiviral $CD8^+T$ Cell Responses", J Immunol, 187(12):6301-6309.
Sercombe et al. (Dec. 1, 2015) "Advances and Challenges of Liposome Assisted Drug Delivery", Frontiers in Pharmacology, 6(286):13 Pages.
Slansky et al. (Oct. 2000) "Enhanced Antigen-Specific Antitumor Immunity with Altered Peptide Ligands that Stabilize the MHC-Peptide-TCR Complex", Immunity, 13(4):529-538.
Tam et al. (2016, e-published Oct. 4, 2016) "Sustained antigen availability during germinal center initiation enhances antibody responses to vaccination", Proc Natl Acad Sci, USA, 113(43):E6639-E6648.
Taverniti et al. (Jan. 9, 2015, e-published Nov. 28, 2014) "Elimination of Cap Structures Generated by mRNA Decay Involves the New Scavenger mRNA Decapping Enzyme Aph1/FHIT Together with DcpS", Nucleic Acids Research, 43(1):482-492.
Thompson et al. (2006) "Mucosal and systemic adjuvant activity of alphavirus replicon particles", Proc Natl Acad Sci, USA, 103(10): p. 3722-3727.
Villalobos et al. (2006) "Gene Designer: A Synthetic Biology Tool for Constructing Artificial DNA Segments", BMC Bioinformatics, 7:285. 8 pages.
Von Herrath et al. (2003) "Immune responsiveness, tolerance and dsRNA: implications for traditional paradigms", Trends Immunol. 24(6):289-293.
Wootton et al. (Jun. 1993) "Statistics of Local Complexity in Amino Acid Sequences and Sequence Databases", Computers & Chemistry, 17(2):149-163.
Yu et al. (2000) "APRIL and TALL-I and receptors BCMA and TACI: system for regulating humoral immunity", Nature Immunology, 1(3):252-256.

* cited by examiner

COMPOSITIONS AND METHODS FOR INDUCING IMMUNE RESPONSES

CROSS-REFERENCES TO RELATED APPLICATIONS

This application claims the benefit of U.S. Provisional Application No. 62/987,191, filed Mar. 9, 2020 and U.S. Provisional Application No. 63/073,900, filed Sep. 2, 2020.

REFERENCE TO A SEQUENCE LISTING

The instant application contains a Sequence Listing which has been submitted electronically in ASCII format and is hereby incorporated by reference in its entirety. Said ASCII copy, created on Mar. 8, 2021 is named 049386-530001US_SequenceListing_ST25.txt and is 390,698 bytes in size.

TECHNICAL FIELD

The present disclosure relates generally to inducing immune responses against infectious agents and tumor antigens and more specifically to self-transcribing and replicating RNA for antigen expression.

BACKGROUND

Infectious diseases and cancer represent significant burdens on health worldwide. According to the World Health Organization (WHO), lower respiratory tract infection was the deadliest infectious disease worldwide in 2016, causing approximately 3 million deaths. Current control measures to curb the rapid worldwide spread of infection diseases, such as national lockdowns, closure of work places and schools, and reduction of international travel are threatening to result in a global economic recession to an extent not seen since the Great Depression.

Cancer is the second leading cause of death globally, accounting for approximately 9.6 million deaths worldwide in 2018. Cancer is a large group of diseases that can affect almost any organ or tissue in the body. Cancer burden continues to grow globally, exerting physical, emotional, and financial strains on patients and health care providers. Self-replicating ribonucleic acids (RNAs), e.g., derived from viral replicons, are useful for expression of proteins, such as heterologous proteins, for a variety of purposes, such as expression of therapeutic proteins and expression of antigens for vaccines. A desirable property of such replicons is the ability for sustained expression of the protein.

Few treatments for infections caused by viruses and eukaryotic organisms are available, and resistance to antibiotics for the treatment of bacterial infections is increasing. In addition, rapid responses, including rapid vaccine development, are required to effectively control emerging infectious diseases and pandemics. Moreover, many cancer treatments include costly and painful surgeries and chemotherapies that are often unsuccessful or only modestly prolong life despite serious side effects. Thus, there exists a need for the prevention and/or treatment of infectious diseases and cancer.

SUMMARY

In one aspect, the present disclosure provides a nucleic acid molecule comprising a first polynucleotide encoding one or more viral replication proteins, wherein the first polynucleotide is codon-optimized as compared to a wild-type polynucleotide encoding the one or more viral replication proteins; and a second polynucleotide comprising a first transgene encoding a first antigenic protein or a fragment thereof.

In some embodiments, the one or more viral replication proteins may be alphavirus proteins or rubivirus proteins.

In some embodiments, the alphavirus proteins are from Venezuelan Equine Encephalitis Virus (VEEV), Eastern Equine Encephalitis Virus (EEEV), Everglades Virus (EVEV), Mucambo Virus (MUCV), Semliki Forest Virus (SFV), Pixuna Virus (PIXV), Middleburg Virus (MIDV), Chikungunya Virus (CHIKV), O'Nyong-Nyong Virus (ONNV), Ross River Virus (RRV), Barmah Forest Virus (BFV), Getah Virus (GETV), Sagiyama Virus (SAGV), Bebaru Virus (BEBV), Mayaro Virus (MAYV), Una Virus (UNAV), Sindbis Virus (SINV), Aura Virus (AURAV), Whataroa Virus (WHAV), Babanki Virus (BABV), Kyzylagach Virus (KYZV), Western Equine Encephalitis Virus (WEEV), Highland J Virus (HJV), Fort Morgan Virus (FMV), Ndumu Virus (NDUV), Salmonid Alphavirus (SAV), Buggy Creek Virus (BCRV), or any combination thereof.

In some embodiments, the first polynucleotide encodes a polyprotein comprising an alphavirus nsP1 protein, an alphavirus nsP2 protein, an alphavirus nsP3 protein, an alphavirus nsP4 protein, or any combination thereof.

In some embodiments, the first polynucleotide encodes a polyprotein comprising an alphavirus nsP1 protein, an alphavirus nsP2 protein, an alphavirus nsP3 protein, or any combination thereof, and an alphavirus nsP4 protein.

In some embodiments, the nucleic acid molecule further comprises a first intergenic region between a sequence encoding the polyprotein comprising an alphavirus nsP1 protein, an alphavirus nsP2 protein, an alphavirus nsP3 protein, or any combination thereof, and a sequence encoding an alphavirus nsP4 protein.

In some embodiments, the first intergenic region comprises an alphavirus sequence.

In some embodiments, the first polynucleotide comprises a sequence having at least 80% identity to a sequence of SEQ ID NO:72.

In some embodiments, the nucleic acid molecule further comprises a 5' untranslated region (UTR), such as a viral 5' UTR, a non-viral 5' UTR, or a combination of viral and non-viral 5' UTR sequences. In some embodiments, the 5' UTR comprises an alphavirus 5' UTR.

In some embodiments, the alphavirus 5' UTR comprises a Venezuelan Equine Encephalitis Virus (VEEV), Eastern Equine Encephalitis Virus (EEEV), Everglades Virus (EVEV), Mucambo Virus (MUCV), Semliki Forest Virus (SFV), Pixuna Virus (PIXV), Middleburg Virus (MIDV), Chikungunya Virus (CHIKV), O'Nyong-Nyong Virus (ONNV), Ross River Virus (RRV), Barmah Forest Virus (BFV), Getah Virus (GETV), Sagiyama Virus (SAGV), Bebaru Virus (BEBV), Mayaro Virus (MAYV), Una Virus (UNAV), Sindbis Virus (SINV), Aura Virus (AURAV), Whataroa Virus (WHAV), Babanki Virus (BABV), Kyzylagach Virus (KYZV), Western Equine Encephalitis Virus (WEEV), Highland J Virus (HJV), Fort Morgan Virus (FMV), Ndumu Virus (NDUV), Salmonid Alphavirus (SAV), or Buggy Creek Virus (BCRV) 5' UTR sequence.

In some embodiments, the 5' UTR comprises a sequence of SEQ ID NO:73, SEQ ID NO:74, or SEQ ID NO:75.

In some embodiments, the nucleic acid molecule further comprises a 3' untranslated region (UTR). In some embodiments, the 3' UTR comprises a viral 3' UTR, a non-viral 3'

UTR, or a combination of viral and non-viral 3' UTR sequences. In some embodiments, the 3' UTR comprises an alphavirus 3' UTR.

In some embodiments, the alphavirus 3' UTR comprises a Venezuelan Equine Encephalitis Virus (VEEV), Eastern Equine Encephalitis Virus (EEEV), Everglades Virus (EVEV), Mucambo Virus (MUCV), Semliki Forest Virus (SFV), Pixuna Virus (PIXV), Middleburg Virus (MIDV), Chikungunya Virus (CHIKV), O'Nyong-Nyong Virus (ONNV), Ross River Virus (RRV), Barmah Forest Virus (BFV), Getah Virus (GETV), Sagiyama Virus (SAGV), Bebaru Virus (BEBV), Mayaro Virus (MAYV), Una Virus (UNAV), Sindbis Virus (SINV), Aura Virus (AURAV), Whataroa Virus (WHAV), Babanki Virus (BABV), Kyzylagach Virus (KYZV), Western Equine Encephalitis Virus (WEEV), Highland J Virus (HJV), Fort Morgan Virus (FMV), Ndumu Virus (NDUV), Salmonid Alphavirus (SAV), or Buggy Creek Virus (BCRV) 3' UTR sequence.

In some embodiments, the 3' UTR comprises a poly-A sequence. In some embodiments, the 3' UTR comprises a sequence of SEQ ID NO:76.

In some embodiments, the antigenic protein is a viral protein, a bacterial protein, a fungal protein, a protozoan protein, a parasite protein, or a tumor protein.

In some embodiments, the viral protein is an orthomyxovirus protein, a paramyxovirus protein, a picornavirus protein, a flavivirus protein, a filovirus protein, a rhabdovirus protein, a togavirus protein, an arterivirus protein, a bunyavirus protein, an arenavirus protein, a reovirus protein, a bornavirus protein, a retrovirus protein, an adenovirus protein, a herpesvirus protein, a polyomavirus protein, a papillomavirus protein, a poxvirus protein, or a hepadnavirus protein.

In some embodiments, the antigenic protein is an influenza virus protein, a respiratory syncytial virus (RSV) protein, a human immunodeficiency virus (HJV) protein, a hepatitis C virus (HCV) protein, a cytomegalovirus (CMV) protein, a Lassa Fever Virus (LFV) protein, an Ebola Virus (EBOV) protein, a *Mycobacterium* protein, a *Bacillus* protein, a *Yersinia* protein, a *Streptococcus* protein, a *Pseudomonas* protein, a *Shigella* protein, a *Campylobacter* protein, a *Salmonella* protein, a *Plasmodium* protein, or a *Toxoplasma* protein.

In some embodiments, the tumor protein is a kidney cancer, renal cancer, urinary bladder cancer, prostate cancer, uterine cancer, breast cancer, cervical cancer, ovarian cancer, lung cancer, liver cancer, stomach cancer, colon cancer, rectal cancer, oral cavity cancer, pharynx cancer, pancreatic cancer, thyroid cancer, melanoma, skin cancer, head and neck cancer, brain cancer, hematopoietic cancer, leukemia, lymphoma, bone cancer, or sarcoma protein.

In some embodiments, the second polynucleotide comprises at least two transgenes.

In some embodiments, a second transgene encodes a second antigenic protein or a fragment thereof or an immunomodulatory protein.

In some embodiments, the second polynucleotide further comprises a sequence encoding a 2A peptide, an internal ribosomal entry site (IRES), or a combination thereof, located between transgenes.

In some embodiments, the immunomodulatory protein is a cytokine, a chemokine, or an interleukin.

In some embodiments, the first and second transgenes encode viral proteins, bacterial proteins, fungal proteins, protozoan proteins, parasite proteins, tumor proteins, immunomodulatory proteins, or any combination thereof.

In some embodiments, the first polynucleotide is located 5' of the second polynucleotide.

In some embodiments, the nucleic acid molecule further comprises a second intergenic region located between the first polynucleotide and the second polynucleotide.

In some embodiments, the second intergenic region comprises a sequence having at least 85% identity to a sequence of SEQ ID NO:77.

In some embodiments, the nucleic acid molecule is a DNA molecule; or an RNA molecule, wherein T is substituted with U.

In some embodiments, the DNA molecule further comprises a promoter. In some embodiments, the promoter is located 5' of the 5'UTR.

In some embodiments, the promoter is a T7 promoter, a T3 promoter, or an SP6 promoter.

In some embodiments, the RNA molecule is a self-replicating RNA molecule.

In some embodiments, the RNA molecule further comprises a 5' cap. In some embodiments, the 5' cap has a Cap 1 structure, a Cap 1 (m6A) structure, a Cap 2 structure, a Cap 0 structure, or any combination thereof.

In another aspect, provided herein is a nucleic acid molecule comprising a sequence of SEQ ID NO:78; or a sequence of SEQ ID NO:72, SEQ ID NO:73, SEQ ID NO:76, and SEQ ID NO:77, wherein T is substituted with U.

In some embodiments, the nucleic acid molecule is an RNA molecule.

In some embodiments, the nucleic acid molecule further comprises a 5' cap having a Cap 1 structure.

In yet another aspect, provided herein is a nucleic acid molecule comprising a first polynucleotide comprising a sequence having at least 80% identity to a sequence of SEQ ID NO:72; and a second polynucleotide comprising a first transgene encoding a first antigenic protein or a fragment thereof.

In some embodiments, the nucleic acid molecule further comprises a 5' untranslated region (UTR).

In some embodiments, the 5' UTR comprises a viral 5' UTR, a non-viral 5' UTR, or a combination of viral and non-viral 5' UTR sequences. In some embodiments, the 5' UTR comprises an alphavirus 5' UTR.

In some embodiments, the alphavirus 5' UTR comprises a Venezuelan Equine Encephalitis Virus (VEEV), Eastern Equine Encephalitis Virus (EEEV), Everglades Virus (EVEV), Mucambo Virus (MUCV), Semliki Forest Virus (SFV), Pixuna Virus (PIXV), Middleburg Virus (MIDV), Chikungunya Virus (CHIKV), O'Nyong-Nyong Virus (ONNV), Ross River Virus (RRV), Barmah Forest Virus (BFV), Getah Virus (GETV), Sagiyama Virus (SAGV), Bebaru Virus (BEBV), Mayaro Virus (MAYV), Una Virus (UNAV), Sindbis Virus (SINV), Aura Virus (AURAV), Whataroa Virus (WHAV), Babanki Virus (BABV), Kyzylagach Virus (KYZV), Western Equine Encephalitis Virus (WEEV), Highland J Virus (HJV), Fort Morgan Virus (FMV), Ndumu Virus (NDUV), Salmonid Alphavirus (SAV), or Buggy Creek Virus (BCRV) 5' UTR sequence.

In some embodiments, the 5' UTR comprises a sequence of SEQ ID NO:73, SEQ ID NO:74, or SEQ ID NO:75.

In some embodiments, the nucleic acid molecule further comprises a 3' untranslated region (UTR).

In some embodiments, the 3' UTR comprises a viral 3' UTR, a non-viral 3' UTR, or a combination of viral and non-viral 3' UTR sequences. In some embodiments, the 3' UTR comprises an alphavirus 3' UTR.

In some embodiments, the alphavirus 3' UTR comprises a Venezuelan Equine Encephalitis Virus (VEEV), Eastern Equine Encephalitis Virus (EEEV), Everglades Virus (EVEV), Mucambo Virus (MUCV), Semliki Forest Virus (SFV), Pixuna Virus (PIXV), Middleburg Virus (MIDV), Chikungunya Virus (CHIKV), O'Nyong-Nyong Virus (ONNV), Ross River Virus (RRV), Barmah Forest Virus (BFV), Getah Virus (GETV), Sagiyama Virus (SAGV), Bebaru Virus (BEBV), Mayaro Virus (MAYV), Una Virus (UNAV), Sindbis Virus (SINV), Aura Virus (AURAV), Whataroa Virus (WHAV), Babanki Virus (BABV), Kyzylagach Virus (KYZV), Western Equine Encephalitis Virus (WEEV), Highland J Virus (HJV), Fort Morgan Virus (FMV), Ndumu Virus (NDUV), Salmonid Alphavirus (SAV), or Buggy Creek Virus (BCRV) 3' UTR sequence.

In some embodiments, the 3' UTR comprises a poly-A sequence.

In some embodiments, the 3' UTR comprises a sequence of SEQ ID NO:76.

In some embodiments, the antigenic protein is a viral protein, a bacterial protein, a fungal protein, a protozoan protein, a parasite protein, or a tumor protein.

In some embodiments, the viral protein is an orthomyxovirus protein, a paramyxovirus protein, a picornavirus protein, a flavivirus protein, a filovirus protein, a rhabdovirus protein, a togavirus protein, an arterivirus protein, a bunyavirus protein, an arenavirus protein, a reovirus protein, a bornavirus protein, a retrovirus protein, an adenovirus protein, a herpesvirus protein, a polyomavirus protein, a papillomavirus protein, a poxvirus protein, or a hepadnavirus protein.

In some embodiments, the antigenic protein is an influenza virus protein, a respiratory syncytial virus (RSV) protein, a human immunodeficiency virus (HJV) protein, a hepatitis C virus (HCV) protein, a cytomegalovirus (CMV) protein, a Lassa Fever Virus (LFV) protein, an Ebola Virus (EBOV) protein, a *Mycobacterium* protein, a *Bacillus* protein, a *Yersinia* protein, a *Streptococcus* protein, a *Pseudomonas* protein, a *Shigella* protein, a *Campylobacter* protein, a *Salmonella* protein, a *Plasmodium* protein, or a *Toxoplasma* protein.

In some embodiments, the tumor protein is a kidney cancer, renal cancer, urinary bladder cancer, prostate cancer, uterine cancer, breast cancer, cervical cancer, ovarian cancer, lung cancer, liver cancer, stomach cancer, colon cancer, rectal cancer, oral cavity cancer, pharynx cancer, pancreatic cancer, thyroid cancer, melanoma, skin cancer, head and neck cancer, brain cancer, hematopoietic cancer, leukemia, lymphoma, bone cancer, or sarcoma protein.

In some embodiments, the second polynucleotide comprises at least two transgenes. In some embodiments, a second transgene encodes a second antigenic protein or a fragment thereof or an immunomodulatory protein.

In some embodiments, the second polynucleotide further comprises a sequence encoding a 2A peptide, an internal ribosomal entry site (IRES), or a combination thereof, located between transgenes.

In some embodiments, the immunomodulatory protein is a cytokine, a chemokine, or an interleukin.

In some embodiments, the first and second transgenes encode viral proteins, bacterial proteins, fungal proteins, protozoan proteins, parasite proteins, tumor proteins, immunomodulatory proteins, or any combination thereof.

In some embodiments, the first polynucleotide is located 5' of the second polynucleotide.

In some embodiments, the nucleic acid molecule further comprises a second intergenic region located between the first polynucleotide and the second polynucleotide. In some embodiments, the second intergenic region comprises a sequence having at least 85% identity to a sequence of SEQ ID NO:77.

In some embodiments, the nucleic acid molecule is a DNA molecule; or an RNA molecule, wherein T is substituted with U.

In some embodiments, the DNA molecule further comprises a promoter. In some embodiments, the promoter is located 5' of the 5'UTR.

In some embodiments, the promoter is a T7 promoter, a T3 promoter, or an SP6 promoter.

In some embodiments, the RNA molecule is a self-replicating RNA molecule.

In some embodiments, the RNA molecule further comprises a 5' cap. In some embodiments, the 5' cap has a Cap 1 structure, a Cap 1 (m6A) structure, a Cap 2 structure, a Cap 0 structure, or any combination thereof.

In yet another aspect, provided herein is a composition comprising any one of the nucleic acid molecules described herein.

In some embodiments, the lipid comprises an ionizable cationic lipid. In some embodiments, the ionizable cationic lipid has a structure of

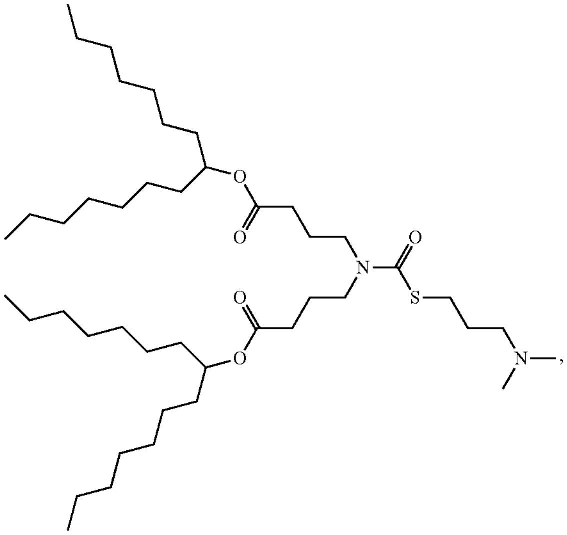 [SMILES: CCCCCCCC(CCCCCCC)OC(=O)CCCN(CCCC(=O)OC(CCCCCCC)CCCCCCC)C(=O)SCCCN(C)C]
,

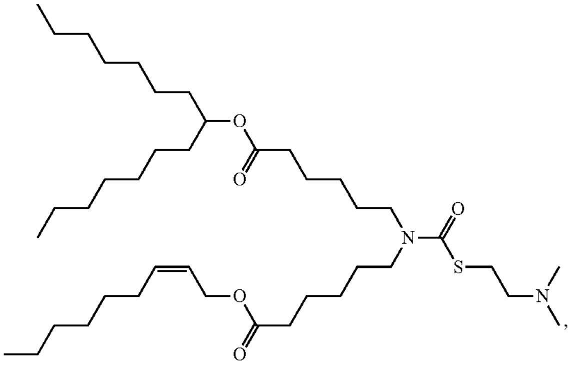
,

-continued

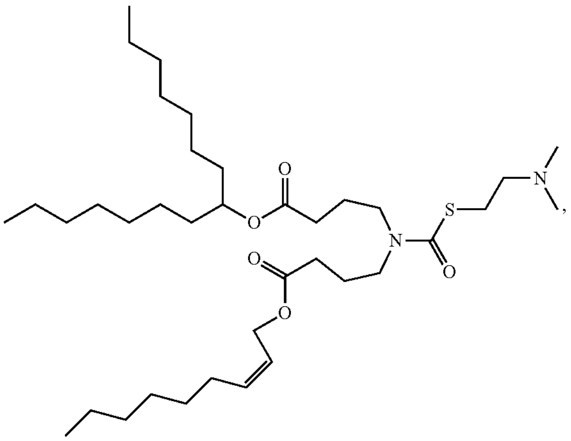

or a pharmaceutically acceptable salt thereof.

In yet another aspect, provided herein is a pharmaceutical composition comprising any one of the nucleic acid molecules described herein, and a lipid formulation.

In some embodiments, the lipid formulation comprises an ionizable cationic lipid. In some embodiments, the ionizable cationic lipid has a structure of

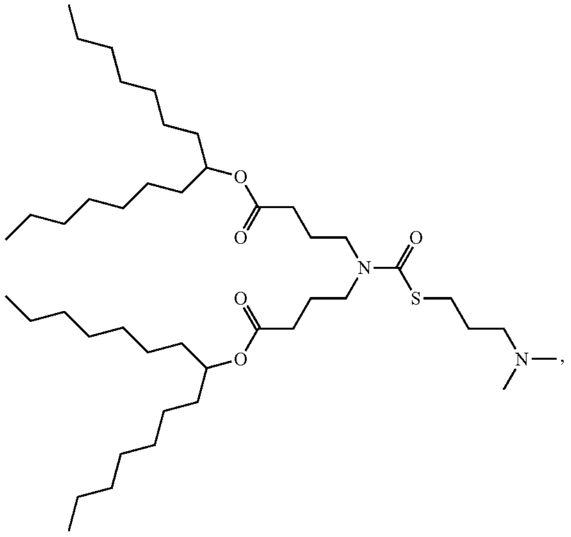 [SMILES: CCCCCCCC(CCCCCCC)OC(=O)CCCN(CCCC(=O)OC(CCCCCCC)CCCCCCC)C(=O)SCCCN(C)C]

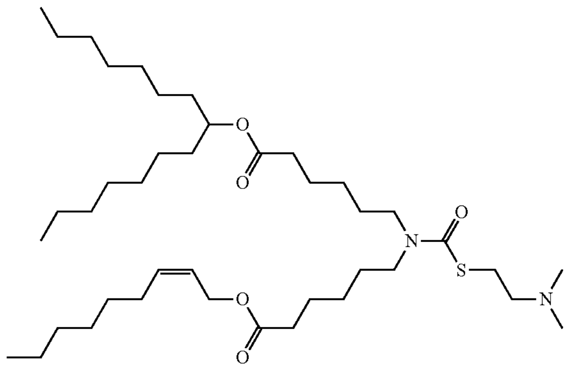

-continued

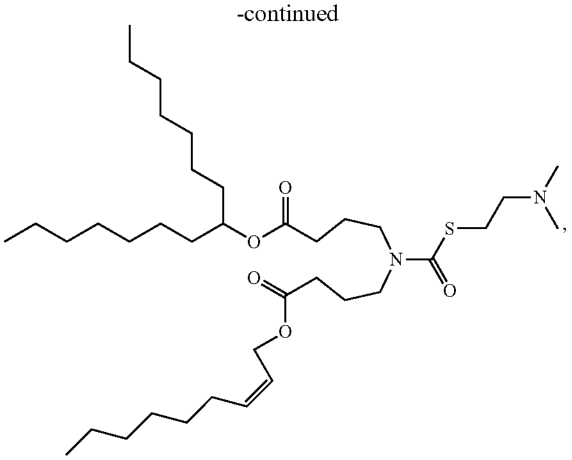

or a pharmaceutically acceptable salt thereof.

In yet another aspect, provided herein is a method of inducing an immune response in a subject comprising administering to the subject an effective amount of any one of the nucleic acid molecules described herein.

In some embodiments, the method comprises administering the nucleic acid molecule intramuscularly, subcutaneously, intradermally, transdermally, intranasally, orally, sublingually, intravenously, intraperitoneally, topically, by aerosol, or by a pulmonary route.

In yet another aspect, provided herein is a method of inducing an immune response in a subject comprising administering to the subject an effective amount of any one of the compositions described herein.

In some embodiments, the method comprises administering the composition intramuscularly, subcutaneously, intradermally, transdermally, intranasally, orally, sublingually, intravenously, intraperitoneally, topically, by aerosol, or by a pulmonary route.

In yet another aspect, provided herein is a method of inducing an immune response in a subject comprising administering to the subject an effective amount of any one of the pharmaceutical compositions described herein.

In some embodiments, the method may comprise administering the pharmaceutical composition intramuscularly, subcutaneously, intradermally, transdermally, intranasally, orally, sublingually, intravenously, intraperitoneally, topically, by aerosol, or by a pulmonary route.

In yet another aspect, the present disclosure provides any of the nucleic acid molecules described herein for use in inducing an immune response to the first antigenic protein or fragment thereof.

In yet another aspect, the present disclosure provides use of any one of the nucleic acid molecules described herein in the manufacture of a medicament for inducing an immune response to the first antigenic protein or fragment thereof.

IVIS picture of three mice (6 injection sites) per group on day 14 is shown for each group that was administered with the test article labeled below the picture. (2C) Luciferase expression from mice that were intramuscularly injected with STARR™ FLuc was monitored by IVIS up to 63 days post administration. (2D) Effect of prior administration of replicon backbone was examined for STARR™ (upper panel) and SINV (lower panel). Replicon encoding FLuc was IM injected at 7 days post dose of replicon with homologous backbone with an irrelevant gene/sequence (labeled STARR™ in or SINV irr) at day 0. As a reference, a mouse group with PBS administration at day 0 was included in each of STARR™ and SINV group.

Figure 3:
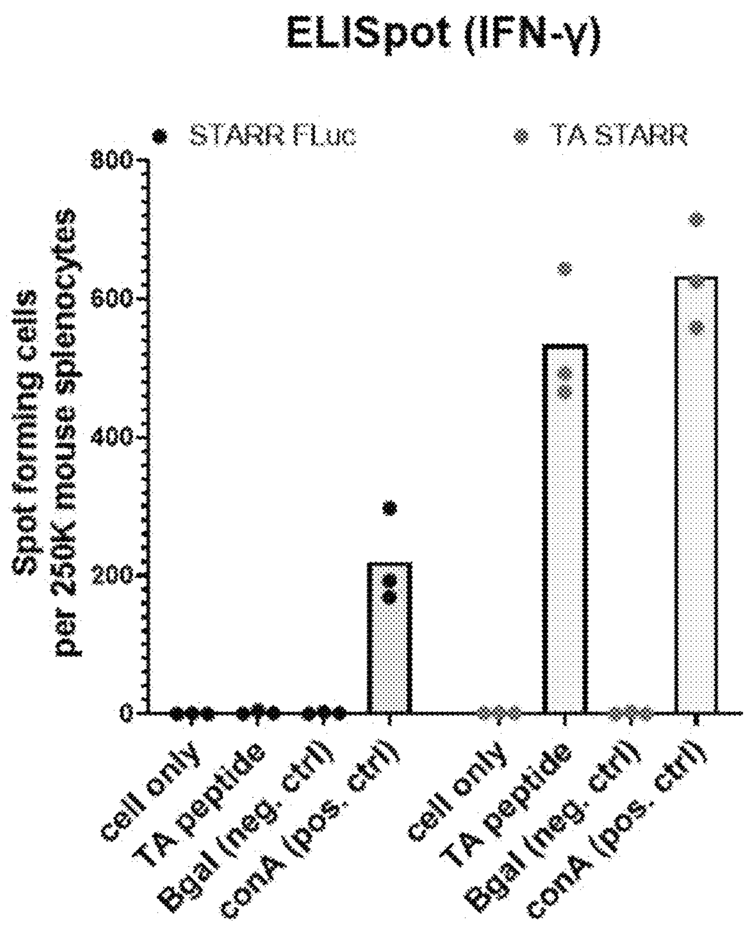
Figure 4A:
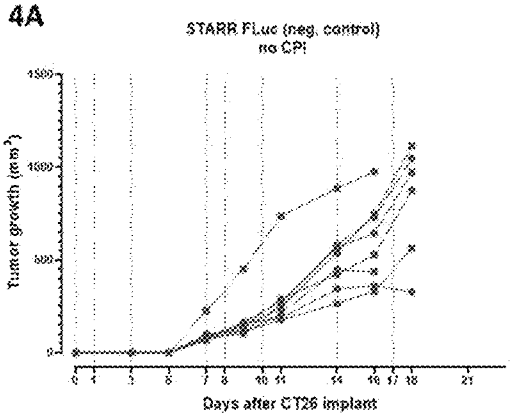
Figure 4B:
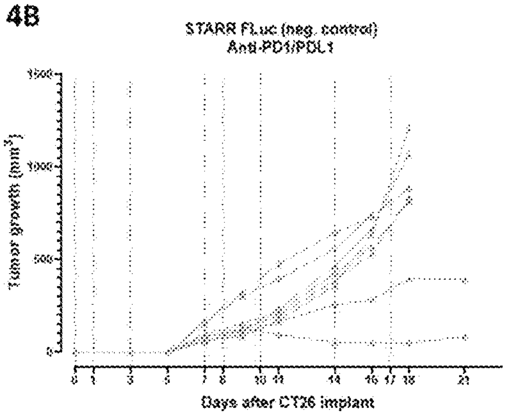
Figure 4C:
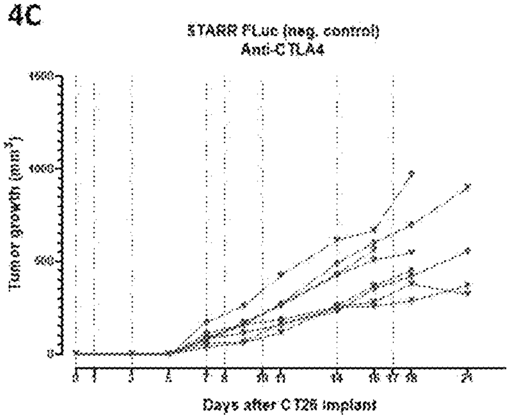
Figure 4D:
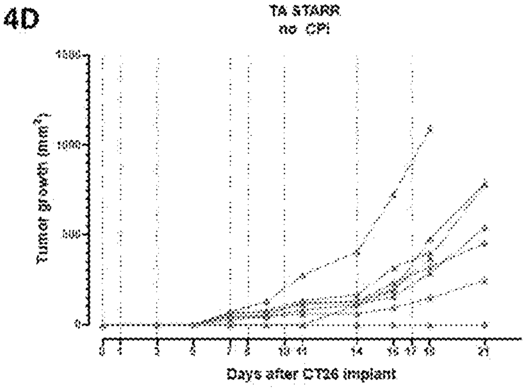
Figure 4E:
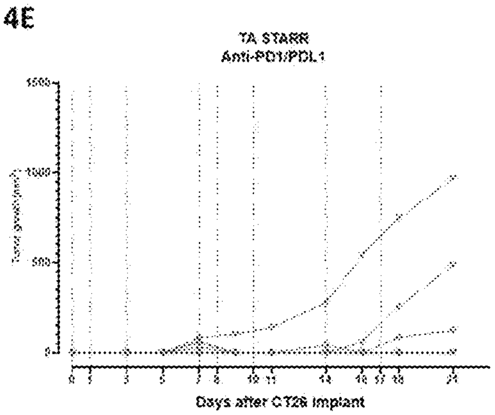
Figure 4F:
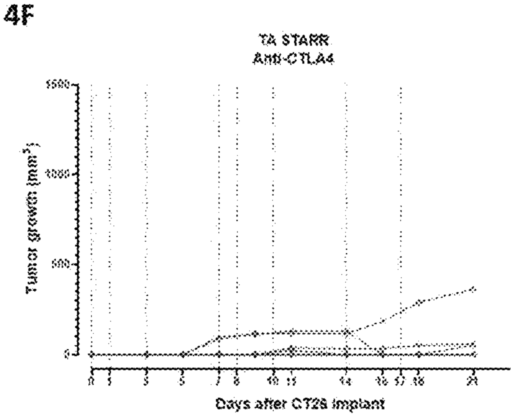

FIG. 3 shows that STARR™ elicits antigen-specific IFN-gamma response. Enzyme-linked immune absorbent spot ELISpot was used to count the number of splenocytes that were specifically stimulated by an antigen peptide of the same amino acid sequence encoded in TA STARR™. Neither no peptide (cell only) nor irrelevant peptide (Bgal) elicited significant IFN-gamma from splenocytes from mice vaccinated with STARR™ FLuc or TA STARR™. Stimulation with AH1-A5 peptide resulted in the detection of IFN-gamma-producing cells specifically from the mice that were vaccinated with TA STARR™. Concanavalin A (ConA) was used as a positive control of IFN-gamma production.

FIGS. 4A-4F illustrate reduced tumor growth rate by TA STARR™ vaccination in a CT26 syngeneic mouse model. CT26 murine colorectal carcinoma cells ($5\times10^5$) were subcutaneously implanted in 10-week old female BALB/c mice (n=8 per group). On days 1 and 8, the mice were vaccinated with STARR™ FLuc, a negative control, or TA STARR™, which encodes AH1A5 epitope. Tumor growth was monitored in mice vaccinated with (4A) STARR™ FLuc without checkpoint inhibitor treatment; (4B) STARR™ FLuc with a combination anti-PD1/PDL1 treatment; (4C) STARR™ FLuc with a combination anti-CTLA4 treatment; (4D) STARR™ vaccine without checkpoint inhibitor treatment; (4E) STARR™ vaccine with a combination treatment of anti-PD1 and anti-PDL1; and (4F) STARR™ vaccine with a combination treatment of anti-CTLA4. The individual tumor growth curves from a mouse group that were administered with STARR™ FLuc and TA STARR™ are shown in upper and lower panels, respectively.

Figure 5:
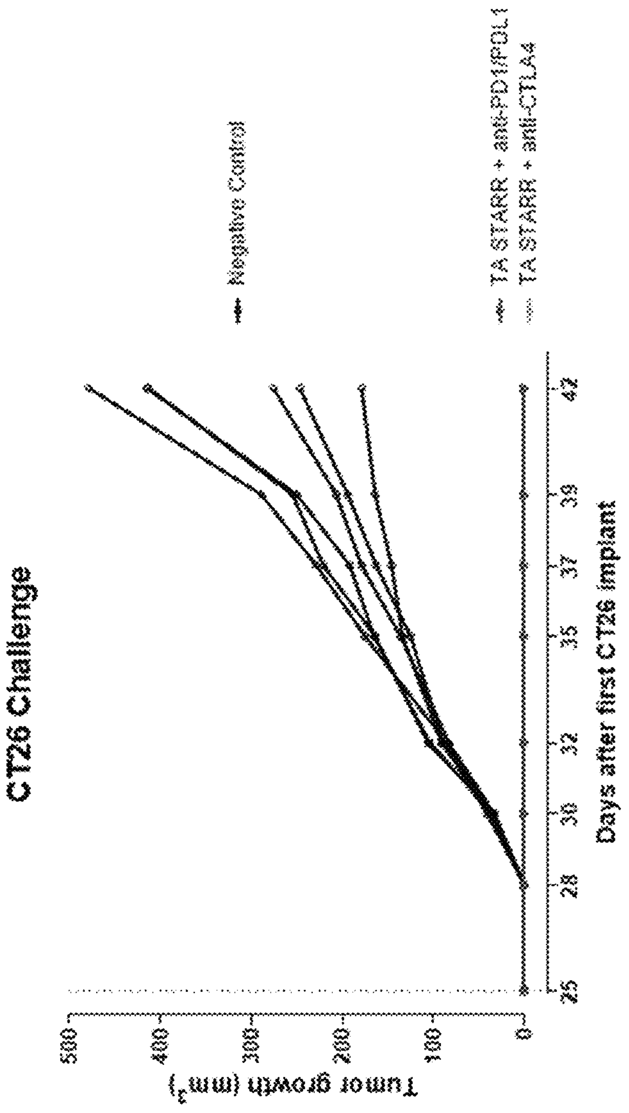

FIG. 5 illustrates prolonged protection by combination treatment of TA STARR™ Vaccine with checkpoint inhibitors. Mice that were treated with TA STARR™ combined with anti-PD1/PDL1 or anti-CTLA4 were found to be resistant to tumor development following the CT26 challenge at day 25 to 42. Naïve mice were used as a control for the CT26 tumor growth.

Figure 6A:
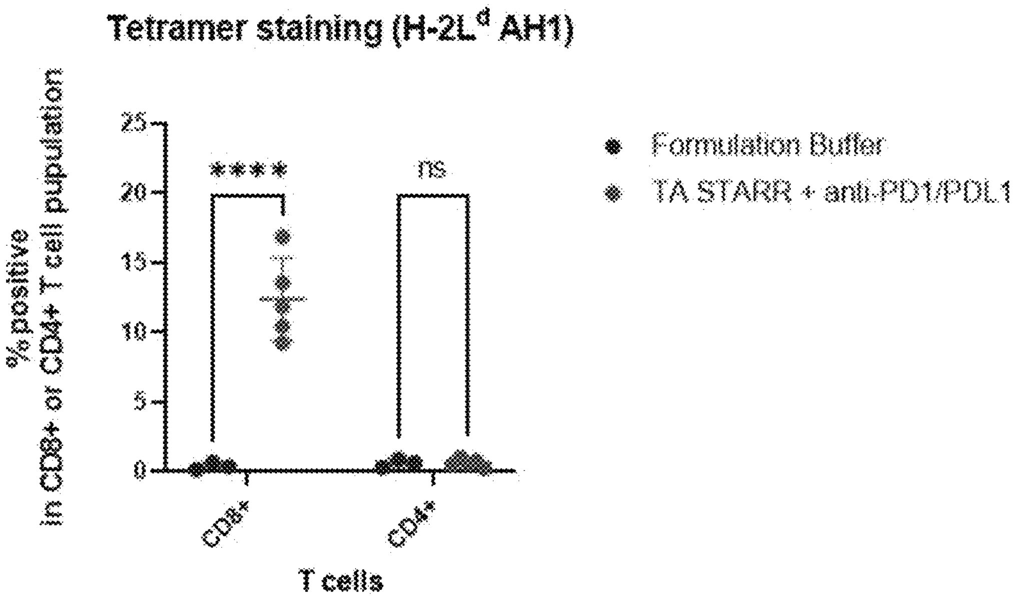
Figure 6B:
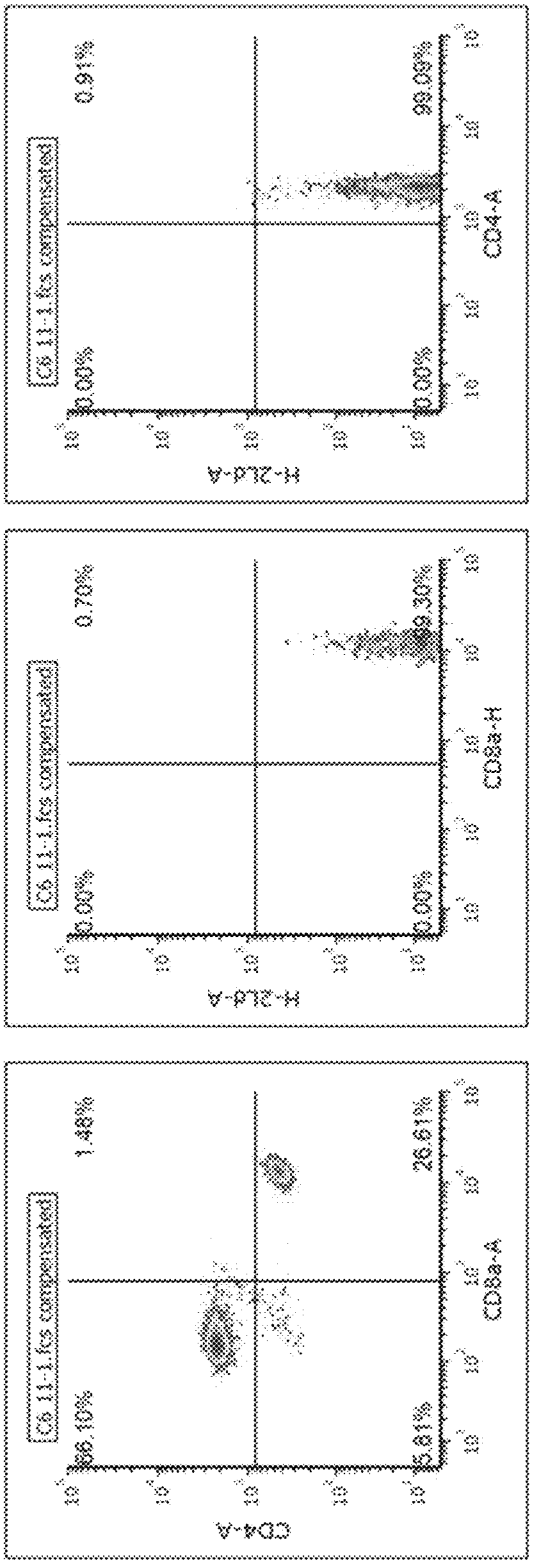
Figure 6C:
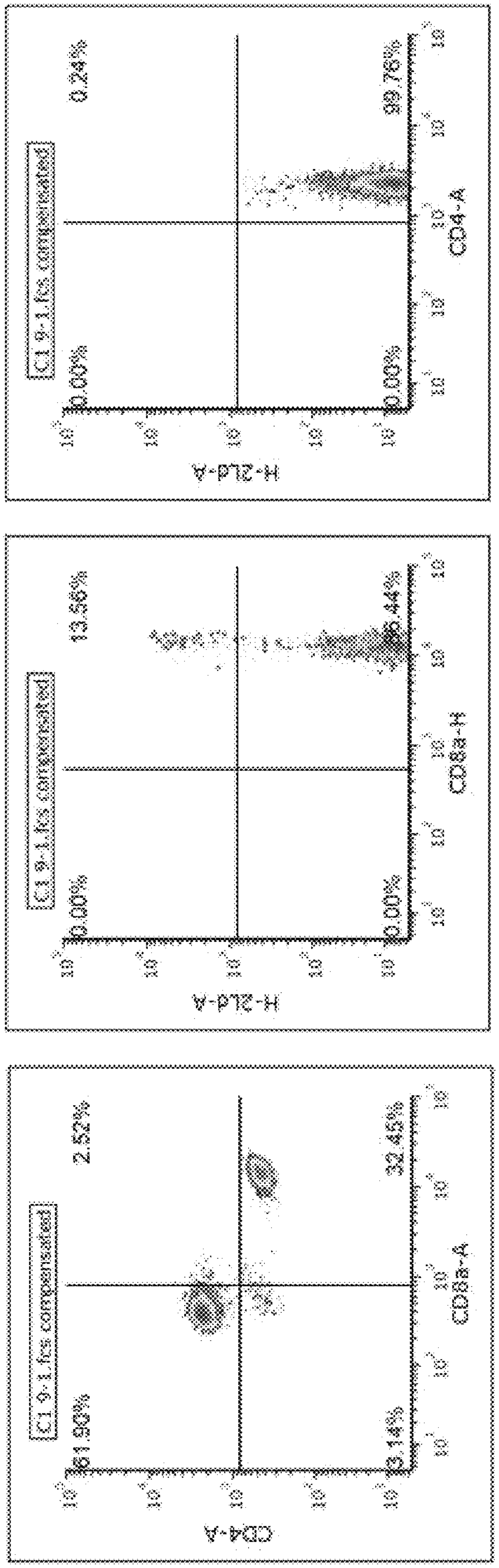

FIGS. 6A-6C show results from AH1-tetramer staining of CD8+ T-cells in the form of (6A) a graph and (6B and 6C) plots. Splenocytes from the mice group with combination treatment of TA STARR™ and anti-PD1/PDL1 at day 42 were stained with AH1 (H-2Ld)-tetramer. The staining was specific to CD8+ T cells from the mouse group with TA STARR™ treatment, and the population represented 9-17% of total CD8+ T cells from the splenocytes.

Figure 7:
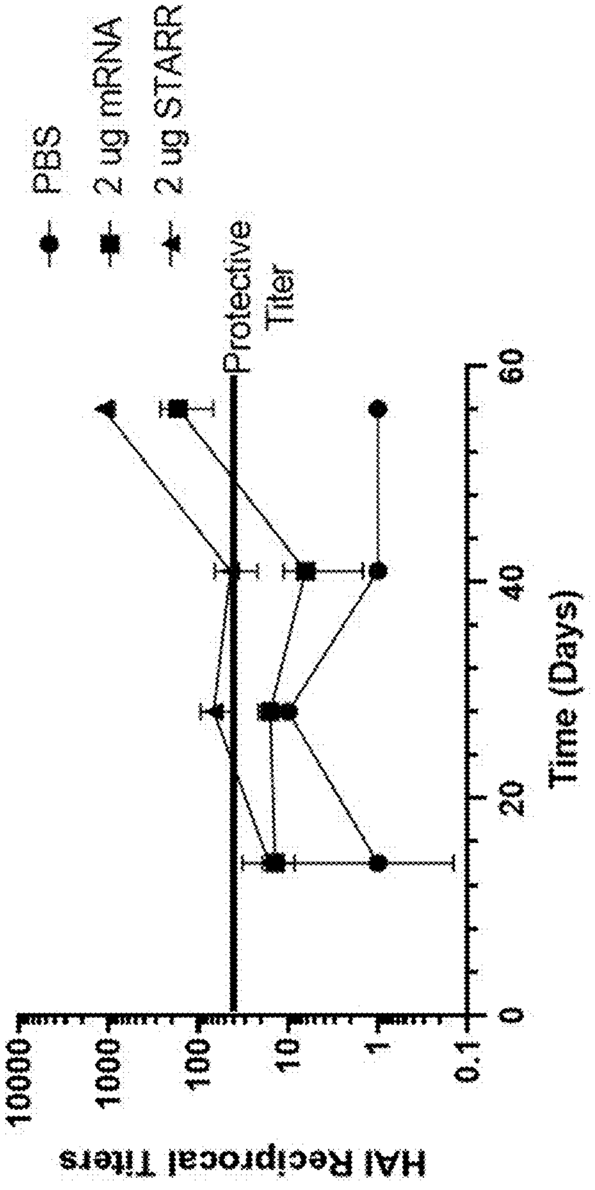

FIG. 7 shows HAI titers obtained for self-replicating RNA (STARR™) and mRNA constructs encoding the hemagglutinin of influenza virus A/California/07/2009 (H1N1).

Figure 8A:
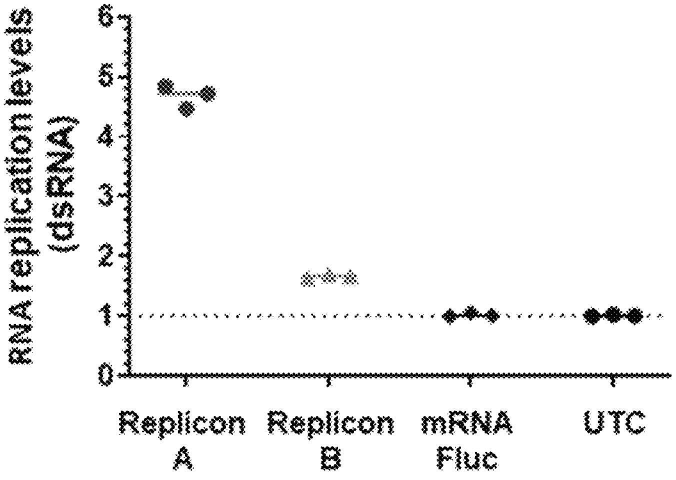
Figure 8B:
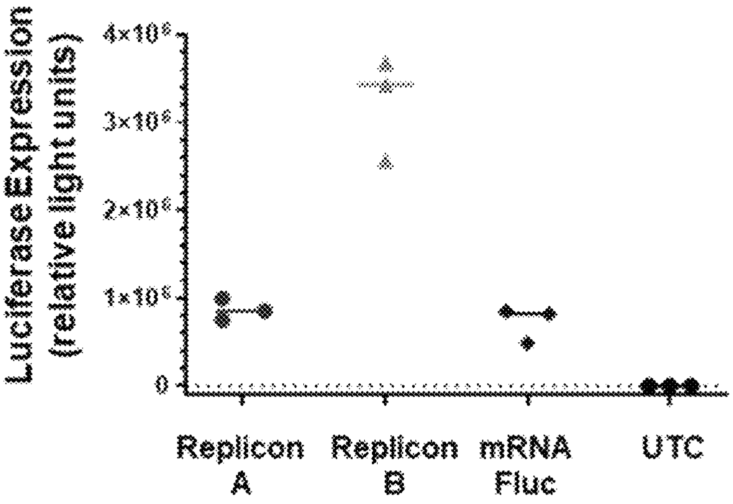

FIGS. 8A-8B show (8A) RNA replication levels and (8B) luciferase reporter gene expression levels for the indicated self-replicating (replicon) RNAs as compared to mRNA.

Figure 9A:
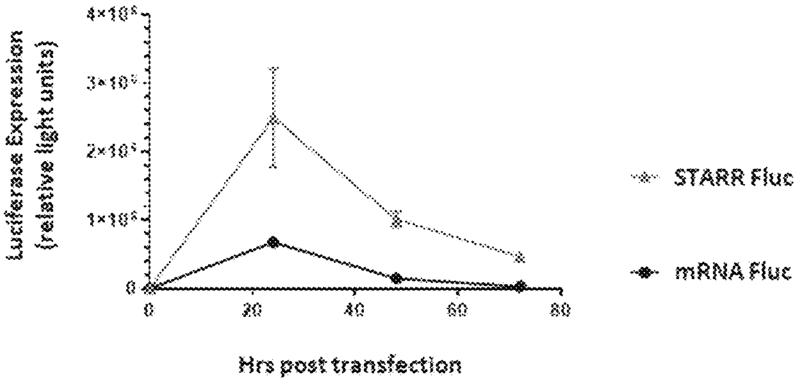
Figure 9B:
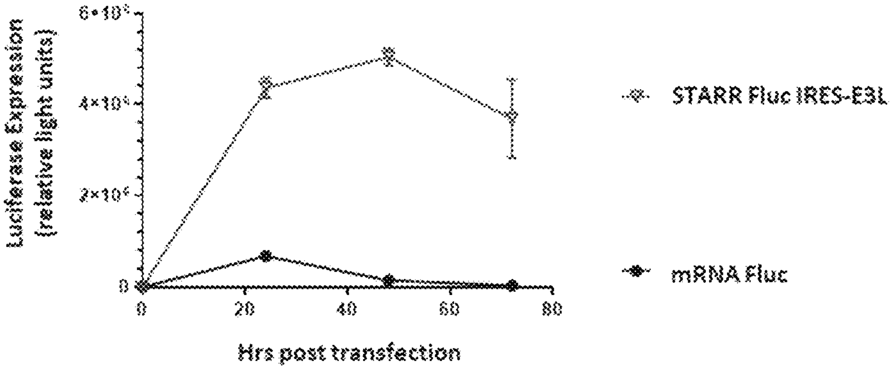
Figure 9C:
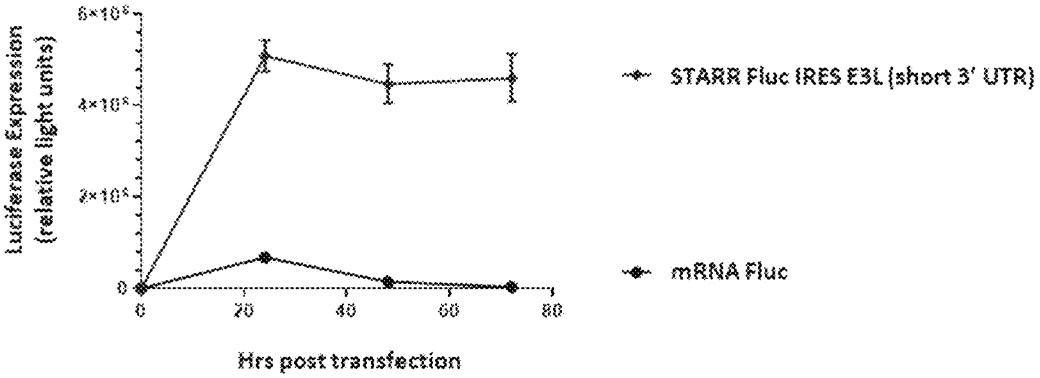

FIGS. 9A-9C shows duration of luciferase reporter gene expression for self-replicating (replicon) RNA (STARR™), such as (9A) STARR™ FLuc, (9B) STARR™ FLuc IRES-E3L, and (9C) STARR™ FLuc IRES E3L (short 3' UTR) as compared to mRNA.

DETAILED DESCRIPTION

The present disclosure relates to self-replicating RNAs and nucleic acids encoding the same for expression of transgenes such as antigenic proteins and tumor antigens, for example. Also provided herein are methods of administration (e.g., to a host, such as a mammalian subject) of self-replicating RNAs, whereby the self-replicating RNA is translated in vivo and the heterologous protein-coding sequence is expressed and, e.g., can elicit an immune response to the heterologous protein-coding sequence in the recipient or provide a therapeutic effect, where the heterologous protein-coding sequence is a therapeutic protein. Self-replicating RNAs provided herein are useful as vaccines that can be rapidly generated and that can be effective at low and/or single doses. The present disclosure further relates to methods of inducing an immune response using self-replicating RNAs provided herein.

Definitions

As used herein, the singular forms "a," "an," and "the" include plural references unless the context clearly dictates otherwise. Thus, for example, references to "the method" includes one or more methods, and/or steps of the type described herein which will become apparent to those persons skilled in the art upon reading this disclosure and so forth.

"About" as used herein when referring to a measurable value such as an amount, a temporal duration, and the like, is meant to encompass variations of +20%, or ±10%, or ±5%, or even ±1% from the specified value, as such variations are appropriate for the disclosed methods or to perform the disclosed methods.

As used herein, the term "fragment," when referring to a protein or nucleic acid, for example, means any shorter sequence than the full-length protein or nucleic acid. Accordingly, any sequence of a nucleic acid or protein other than the full-length nucleic acid or protein sequence can be a fragment. In some aspects, a protein fragment includes an epitope. In other aspects, a protein fragment is an epitope.

As used herein, the term "nucleic acid" refers to any deoxyribonucleic acid (DNA) molecule, ribonucleic acid (RNA) molecule, or nucleic acid analogues. A DNA or RNA molecule can be double-stranded or single-stranded and can be of any size. Exemplary nucleic acids include, but are not limited to, chromosomal DNA, plasmid DNA, cDNA, cell-free DNA (cfDNA), mitochondrial DNA, chloroplast DNA, viral DNA, mRNA, tRNA, rRNA, long non-coding RNA, siRNA, micro RNA (miRNA or miR), hnRNA, and viral RNA. Exemplary nucleic analogues include peptide nucleic acid, morpholino- and locked nucleic acid, glycol nucleic acid, and threose nucleic acid. As used herein, the term "nucleic acid molecule" is meant to include fragments of nucleic acid molecules as well as any full-length or non-fragmented nucleic acid molecule, for example. As used herein, the terms "nucleic acid" and "nucleic acid molecule" can be used interchangeably, unless context clearly indicates otherwise.

As used herein, the term "protein" refers to any polymeric chain of amino acids. The terms "peptide" and "polypeptide" can be used interchangeably with the term protein, unless context clearly indicates otherwise, and can also refer to a polymeric chain of amino acids. The term "protein" encompasses native or artificial proteins, protein fragments and polypeptide analogs of a protein sequence. A protein may be monomeric or polymeric. The term "protein" encompasses fragments and variants (including fragments of variants) thereof, unless otherwise contradicted by context.

In general, "sequence identity" or "sequence homology," which can be used interchangeably, refer to an exact nucleotide-to-nucleotide or amino acid-to-amino acid correspondence of two polynucleotides or polypeptide sequences, respectively. Typically, techniques for determining sequence identity include determining the nucleotide sequence of a polynucleotide and/or determining the amino acid sequence encoded thereby or the amino acid sequence of a polypeptide, and comparing these sequences to a second nucleotide or amino acid sequence.

As used herein, the term "percent (%) sequence identity" or "percent (%) identity," also including "homology," refers to the percentage of amino acid residues or nucleotides in a sequence that are identical with the amino acid residues or nucleotides in a reference sequence after aligning the sequences and introducing gaps, if necessary, to achieve the maximum percent sequence identity, and not considering any conservative substitutions as part of the sequence identity. Thus, two or more sequences (polynucleotide or amino acid) can be compared by determining their "percent identity," also referred to as "percent homology." The percent identity to a reference sequence (e.g., nucleic acid or amino acid sequences), which may be a sequence within a longer molecule (e.g., polynucleotide or polypeptide), may be calculated as the number of exact matches between two optimally aligned sequences divided by the length of the reference sequence and multiplied by 100. Percent identity may also be determined, for example, by comparing sequence information using the advanced BLAST computer program, including version 2.2.9, available from the National Institutes of Health. The BLAST program is based on the alignment method of Karlin and Altschul, Proc. Natl. Acad. Sci. USA 87:2264-2268 (1990) and as discussed in Altschul et al., J. Mol. Biol. 215:403-410 (1990); Karlin and Altschul, Proc. Natl. Acad. sci. USA 90:5873-5877 (1993); and Altschul et al., Nucleic Acids Res. 25:3389-3402 (1997). Briefly, the BLAST program defines identity as the number of identical aligned symbols (i.e., nucleotides or amino acids), divided by the total number of symbols in the shorter of the two sequences. The program may be used to determine percent identity over the entire length of the sequences being compared. Default parameters are provided to optimize searches with short query sequences, for example, with the blastp program. The program also allows use of an SEG filter to mask-off segments of the query sequences as determined by the SEG program of Wootton and Federhen, Computers and Chemistry 17: 149-163 (1993). Ranges of desired degrees of sequence identity are approximately 80% to 100% and integer values in between. Percent identities between a reference sequence and a claimed sequence can be at least 80%, at least 85%, at least 90%, at least 95%, at least 98%, at least 99%, at least 99.5%, or at least 99.9%. In general, an exact match indicates 100% identity over the length of the reference sequence. Additional programs and methods for comparing sequences and/or assessing sequence identity include the Needleman-Wunsch algorithm (see, e.g., the EMBOSS Needle aligner available at ebi.ac.uk/Tools/psa/emboss needle/, optionally with default settings), the Smith-Waterman algorithm (see, e.g., the EMBOSS Water aligner available at ebi.ac.uk/Tools/psa/emboss water/, optionally with default settings), the similarity search method of Pearson and Lipman, 1988, Proc. Natl. Acad. Sci. USA 85, 2444, or computer programs which use these algorithms (GAP, BESTFIT, FASTA, BLAST P, BLAST N and TFASTA in Wisconsin Genetics Software Package, Genetics Computer Group. 575 Science Drive, Madison, Wis.). In some aspects, reference to percent sequence identity refers to sequence identity as measured using BLAST (Basic Local Alignment Search Tool). In other aspects, ClustalW is used for multiple sequence alignment. Optimal alignment may be assessed using any suitable parameters of a chosen algorithm, including default parameters.

The term "expression" refers to the process by which a nucleic acid sequence or a polynucleotide is transcribed from a DNA template (such as into mRNA or other RNA transcript) and/or the process by which a transcribed mRNA or other RNA is subsequently translated into peptides, polypeptides, or proteins. Transcripts and encoded polypeptides may be collectively referred to as "gene product."

As used herein, "operably linked," "operable linkage," "operatively linked," or grammatical equivalents thereof refer to juxtaposition of genetic elements, e.g., a promoter, an enhancer, a polyadenylation sequence, etc., wherein the elements are in a relationship permitting them to operate in the expected manner. For instance, a regulatory element, which can comprise promoter and/or enhancer sequences, is operatively linked to a coding region if the regulatory element helps initiate transcription of the coding sequence. There may be intervening residues between the regulatory element and coding region so long as this functional relationship is maintained.

As used herein, the term "drug" or "medicament," means a pharmaceutical formulation or composition as described herein.

The phrases "administered in combination" or "combined administration" means that two or more agents are administered to a subject at the same time or within an interval such that there may be an overlap of an effect of each agent on the patient. In some embodiments, they are administered within about 60, 30, 15, 10, 5, or 1 minute of one another. In some embodiments, the administrations of the agents are spaced sufficiently closely together such that a ombinatorial (e.g., a synergistic) effect is achieved.

As used herein, the terms "self-replicating RNA," "self-transcribing and self-replicating RNA," "self-amplifying RNA (saRNA)," and "replicon" may be used interchangeably, unless context clearly indicates otherwise. Generally, the term "replicon" or "viral replicon" refers to a self-replicating subgenomic RNA derived from a viral genome that includes viral genes encoding non-structural proteins important for viral replication and that lacks viral genes encoding structural proteins. A self-replicating RNA can encode further subgenomic RNAs that are not able to self-replicate.

Nucleic Acid Molecules

In some embodiments, provided herein are nucleic acid molecules comprising: (i) a first polynucleotide encoding one or more viral replication proteins, wherein the first polynucleotide is codon-optimized as compared to a wild-type polynucleotide encoding the one or more viral replication proteins; and (ii) a second polynucleotide comprising a first transgene encoding a first antigenic protein or a fragment thereof.

An RNA molecule can encode a single polypeptide immunogen or multiple polypeptides. Multiple immunogens can be presented as a single polypeptide immunogen (fusion polypeptide) or as separate polypeptides. If immunogens are expressed as separate polypeptides from a replicon then one or more of these may be provided with an upstream IRES or an additional viral promoter element. Alternatively, multiple immunogens may be expressed from a polyprotein that encodes individual immunogens fused to a short autocatalytic protease (e.g. foot-and-mouth disease virus 2A protein), or as inteins.

Also provided herein, in some embodiments, are nucleic acid molecules comprising: (i) a first polynucleotide comprising a sequence having at least 80% identity to a sequence of SEQ ID NO:72; and (ii) a second polynucleotide comprising a first transgene encoding a first antigenic protein or a fragment thereof.

Codon Optimization

In some embodiments, first polynucleotides of nucleic acid molecules provided herein encoding one or more viral replication proteins include codon-optimized sequences. As used herein, the term "codon-optimized" means a polynucleotide, nucleic acid sequence, or coding sequence has been redesigned as compared to a wild-type or reference polynucleotide, nucleic acid sequence, or coding sequence by choosing different codons without altering the amino acid sequence of the encoded protein. Accordingly, codon-optimization generally refers to replacement of codons with synonymous codons to optimize expression of a protein while keeping the amino acid sequence of the translated protein the same. Codon optimization of a sequence can increase protein expression levels (Gustafsson et al., Codon bias and heterologous protein expression. 2004, Trends Biotechnol 22: 346-53) of the encoded proteins, for example, and provide other advantages. Variables such as codon usage preference as measured by codon adaptation index (CAI), for example, the presence or frequency of U and other nucleotides, mRNA secondary structures, cis-regulatory sequences, GC content, and other variables may correlate with protein expression levels (Villalobos et al., Gene Designer: a synthetic biology tool for constructing artificial DNA segments. 2006, BMC Bioinformatics 7:285).

Any method of codon optimization can be used to codon optimize polynucleotides and nucleic acid molecules provided herein, and any variable can be altered by codon optimization. Accordingly, any combination of codon optimization methods can be used. Exemplary methods include the high codon adaptation index (CAI) method, the Low U method, and others. The CAI method chooses a most frequently used synonymous codon for an entire protein coding sequence. As an example, the most frequently used codon for each amino acid can be deduced from 74,218 protein-coding genes from a human genome. The Low U method targets U-containing codons that can be replaced with a synonymous codon with fewer U moieties, generally without changing other codons. If there is more than one choice for replacement, the more frequently used codon can be selected. Any polynucleotide, nucleic acid sequence, or codon sequence provided herein can be codon-optimized. This method may be used in conjunction with the disclosed RNAs to design coding sequences that are to be synthesized with, for example, 5-methoxyuridine or N1-methyl pseudouridine. Methods of codon optimization in combination with the use of a modified nucleotide monomer are described in U.S. 2018/0327471, the contents of which are herein incorporated by reference.

In some embodiments, the nucleotide sequence of any region of the RNA or DNA templates described herein may be codon optimized. Preferably, the primary cDNA template may include reducing the occurrence or frequency of appearance of certain nucleotides in the template strand. For example, the occurrence of a nucleotide in a template may be reduced to a level below 25% of said nucleotides in the template. In further examples, the occurrence of a nucleotide in a template may be reduced to a level below 20% of said nucleotides in the template. In some examples, the occurrence of a nucleotide in a template may be reduced to a level below 16% of said nucleotides in the template. Preferably, the occurrence of a nucleotide in a template may be reduced to a level below 15%, and preferably may be reduced to a level below 12% of said nucleotides in the template.

In some embodiments, the nucleotide reduced is uridine. For example, the present disclosure provides nucleic acids with altered uracil content wherein at least one codon in the wild-type sequence has been replaced with an alternative codon to generate a uracil-altered sequence. Altered uracil sequences can have at least one of the following properties:

(i) an increase or decrease in global uracil content (i.e., the percentage of uracil of the total nucleotide content in the nucleic acid of a section of the nucleic acid, e.g., the open reading frame);

(ii) an increase or decrease in local uracil content (i.e., changes in uracil content are limited to specific subsequences);

(iii) a change in uracil distribution without a change in the global uracil content;

(iv) a change in uracil clustering (e.g., number of clusters, location of clusters, or distance between clusters); or (v) combinations thereof.

In some embodiments, the percentage of uracil nucleobases in the nucleic acid sequence is reduced with respect to the percentage of uracil nucleobases in the wild-type nucleic acid sequence. For example, 30% of nucleobases may be uracil in the wild-type sequence but the nucleobases that are uracil are preferably lower than 15%, preferably lower than 12% and preferably lower than 10% of the nucleobases in the nucleic acid sequences of the disclosure. The percentage uracil content can be determined by dividing the number of uracil in a sequence by the total number of nucleotides and multiplying by 100.

In some embodiments, the percentage of uracil nucleobases in a subsequence of the nucleic acid sequence is reduced with respect to the percentage of uracil nucleobases in the corresponding subsequence of the wild-type sequence. For example, the wild-type sequence may have a 5'-end region (e.g., 30 codons) with a local uracil content of 30%, and the uracil content in that same region could be reduced to preferably 15% or lower, preferably 12% or lower and preferably 10% or lower in the nucleic acid sequences of the disclosure. These subsequences can also be part of the wild-type sequences of the heterologous 5' and 3' UTR sequences of the present disclosure.

In some embodiments, codons in the nucleic acid sequence of the disclosure reduce or modify, for example, the number, size, location, or distribution of uracil clusters that could have deleterious effects on protein translation. Although lower uracil content is desirable in certain aspects, the uracil content, and in particular the local uracil content, of some subsequences of the wild-type sequence can be greater than the wild-type sequence and still maintain beneficial features (e.g., increased expression).

In some embodiments, the uracil-modified sequence induces a lower Toll-Like Receptor (TLR) response when compared to the wild-type sequence. Several TLRs recognize and respond to nucleic acids. Double-stranded (ds) RNA, a frequent viral constituent, has been shown to activate TLR3. Single-stranded (ss)RNA activates TLR7. RNA oligonucleotides, for example RNA with phosphorothioate internucleotide linkages, are ligands of human TLR8. DNA containing unmethylated CpG motifs, characteristic of bacterial and viral DNA, activate TLR9.

As used herein, the term "TLR response" is defined as the recognition of single-stranded RNA by a TLR7 receptor, and preferably encompasses the degradation of the RNA and/or physiological responses caused by the recognition of the single-stranded RNA by the receptor. Methods to determine and quantify the binding of an RNA to a TLR7 are known in the art. Similarly, methods to determine whether an RNA has triggered a TLR7-mediated physiological response (e.g., cytokine secretion) are well known in the art. In some embodiments, a TLR response can be mediated by TLR3, TLR8, or TLR9 instead of TLR7. Suppression of TLR7-mediated response can be accomplished via nucleoside modification. RNA undergoes over a hundred different nucleoside modifications in nature. Human rRNA, for example, has ten times more pseudouracil ('P) and 25 times more 2'-O-methylated nucleosides than bacterial rRNA. Bacterial RNA contains no nucleoside modifications, whereas mammalian RNAs have modified nucleosides such as 5-methylcytidine (m5C), N6-methyladenosine (m6A), inosine and many 2'-O-methylated nucleosides in addition to N7-methylguanosine (m7G).

In some embodiments, the uracil content of polynucleotides disclosed herein is less than about 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2% or 1% of the total nucleobases in the sequence in the reference sequence. In some embodiments, the uracil content of polynucleotides disclosed herein is between about 5% and about 25%. In some embodiments, the uracil content of polynucleotides disclosed herein is between about 15% and about 25%.

In some embodiments, first polynucleotides of nucleic acid molecules provided herein comprise a sequence having at least 80%, at least 85%, at least 90%, at least 91%, at least 92%, at least 93%, at least 94%, at least 95%, at least 96%, at least 97%, at least 97.5%, at least 98%, at least 98.5%, at least 99%, at least 99.5%, at least 99.6%, at least 99.7%, at least 99.8%, at least 99.9%, and any number or range in between, identity to a sequence of SEQ ID NO:72. In some embodiments, first polynucleotides of nucleic acid molecules provided herein comprise a sequence of SEQ ID NO:72.

In some aspects, first polynucleotides and second polynucleotides of nucleic acid molecules provided herein are included in the same (i.e., a single) or in separate nucleic acid molecules. Generally, first polynucleotides and second polynucleotides of nucleic acid molecules provided herein are included in a single nucleic acid molecule. In one aspect, the first polynucleotide is located 5' of the second polynucleotide. In one aspect, first polynucleotides and second polynucleotides of nucleic acid molecules provided herein are included in separate nucleic acid molecules. In yet another aspect, first polynucleotides and second polynucleotides are included in two separate nucleic acid molecules.

In some aspects, first polynucleotides and second polynucleotides are included in the same (i.e., a single) nucleic acid molecule. First polynucleotides and second polynucleotides of nucleic acid molecules provided herein can be contiguous, i.e., adjacent to each other without nucleotides in between. In one aspect, an intergenic region is located between the first polynucleotide and the second polynucleotide. In another aspect, the intergenic region located between the first polynucleotide and the second polynucleotide is a second intergenic region, with a first intergenic region included in the first polynucleotide as described below. As used herein, the terms "intergenic region" and intergenic sequence" can be used interchangeably, unless context clearly indicates otherwise.

An intergenic region located between the first polynucleotide and the second polynucleotide can be of any length and can have any nucleotide sequence. As an example, the intergenic region between the first polynucleotide and the second polynucleotide can include about one nucleotide, about two nucleotides, about three nucleotides, about four nucleotides, about five nucleotides, about six nucleotides, about seven nucleotides, about eight nucleotides, about nine nucleotides, about ten nucleotides, about 11 nucleotides, about 12 nucleotides, about 13 nucleotides, about 14 nucleotides, about 15 nucleotides, about 16 nucleotides, about 17 nucleotides, about 18 nucleotides, about 19 nucleotides, about 20 nucleotides, about 21 nucleotides, about 22 nucleotides, about 23 nucleotides, about 24 nucleotides, about 25 nucleotides, about 26 nucleotides, about 27 nucleotides, about 28 nucleotides, about 29 nucleotides, about 30 nucleotides, about 31 nucleotides, about 32 nucleotides, about 33 nucleotides, about 34 nucleotides, about 35 nucleotides, about 36 nucleotides, about 37 nucleotides, about 38 nucleotides, about 39 nucleotides, about 40 nucleotides, about 41 nucleotides, about 42 nucleotides, about 43 nucleotides, about 44 nucleotides, about 45 nucleotides, about 46 nucleotides, about 47 nucleotides, about 48 nucleotides, about 49 nucleotides, about 50 nucleotides, about 60 nucleotides, about 70 nucleotides, about 80 nucleotides, about 90 nucleotides, about 100 nucleotides, about 125 nucleotides, about 150 nucleotides, about 175 nucleotides, about 200 nucleotides, about 250 nucleotides, about 300 nucleotides, about 350 nucleotides, about 400 nucleotides, about 450 nucleotides, about 500 nucleotides, about 600 nucleotides, about 700 nucleotides, about 800 nucleotides, about 1,000 nucleotides, about 1,500 nucleotides, about 2,000 nucleotides, about 2,500 nucleotides, about 3,000 nucleotides, about 3,500 nucleotides, about 4,000 nucleotides, about 4,500 nucleotides, about 5,000 nucleotides, about 6,000 nucleotides, about 7,000 nucleotides, about 8,000 nucleotides, about 9,000 nucleotides, about 10,000 nucleotides, and any number or range in between. In one aspect, the intergenic region between first and second polynucleotides includes about 10-100 nucleotides, about 10-200 nucleotides, about 10-300 nucleotides, about 10-400 nucleotides, or about 10-500 nucleotides. In another aspect, the intergenic region between first and second polynucleotides includes about 1-10 nucleotides, about 1-20 nucleotides, about 1-30 nucleotides, about 1-40 nucleotides, or about 1-50 nucleotides. In yet another aspect, the region includes about 44 nucleotides. In one aspect, the intergenic region between first and second polynucleotides of nucleic acid molecules provided herein is a second intergenic region.

In one aspect, the intergenic region between first and second polynucleotides includes a viral sequence. The intergenic region between first and second polynucleotides can include a sequence from any virus, such as alphaviruses and rubiviruses, for example. In one aspect, the intergenic region between the first polynucleotide and the second polynucleotide comprises an alphavirus sequence, such as a sequence from Venezuelan Equine Encephalitis Virus (VEEV), Eastern Equine Encephalitis Virus (EEEV), Everglades Virus (EVEV), Mucambo Virus (MUCV), Semliki Forest Virus (SFV), Pixuna Virus (PIXV), Middleburg Virus (MIDV), Chikungunya Virus (CHIKV), O'Nyong-Nyong Virus (ONNV), Ross River Virus (RRV), Barmah Forest Virus (BFV), Getah Virus (GETV), Sagiyama Virus (SAGV), Bebaru Virus (BEBV), Mayaro Virus (MAYV), Una Virus (UNAV), Sindbis Virus (SINV), Aura Virus (AURAV), Whataroa Virus (WHAV), Babanki Virus (BABV), Kyzylagach Virus (KYZV), Western Equine Encephalitis Virus (WEEV), Highland J Virus (HJV), Fort Morgan Virus (FMV), Ndumu Virus (NDUV), Salmonid Alphavirus (SAV), Buggy Creek Virus (BCRV), or any combination thereof. In another aspect, the intergenic region between first and second polynucleotides comprises a sequence from Venezuelan Equine Encephalitis Virus (VEEV). In yet another aspect, the intergenic region between first and second polynucleotides comprises a sequence having at least 85%, at least 90%, at least 91%, at least 92%, at least 93%, at least 94%, at least 95%, at least 96%, at least 97%, at least 97.5%, at least 98%, at least 98.5%, at least 99%, at least 99.5%, at least 99.6%, at least 99.7%, at least 99.8%, at least 99.9%, and any number or range in between, identity to SEQ ID NO:77. In a further aspect, the intergenic region between first and second polynucleotides comprises a sequence of SEQ ID NO:77. In yet a further aspect, the intergenic region between first and second polynucleotides is a second intergenic region comprising a sequence having at least 85% identity to SEQ ID NO:77.

Natural and Modified Nucleotides

A self-replicating RNA of the disclosure can comprise one or more chemically modified nucleotides. Examples of nucleic acid monomers include non-natural, modified, and chemically-modified nucleotides, including any such nucleotides known in the art. Nucleotides can be artificially modified at either the base portion or the sugar portion. In nature, most polynucleotides comprise nucleotides that are "unmodified" or "natural" nucleotides, which include the purine bases adenine (A) and guanine (G), and the pyrimidine bases thymine (T), cytosine (C) and uracil (U). These bases are typically fixed to a ribose or deoxy ribose at the 1' position. The use of RNA polynucleotides comprising chemically modified nucleotides have been shown to improve RNA expression, expression rates, half-life and/or expressed protein concentrations. RNA polynucleotides comprising chemically modified nucleotides have also been useful in optimizing protein localization thereby avoiding deleterious bio-responses such as immune responses and/or degradation pathways.

Examples of modified or chemically-modified nucleotides include 5-hydroxycytidines, 5-alkylcytidines, 5-hydroxyalkylcytidines, 5-carboxycytidines, 5-formylcytidines, 5-alkoxycytidines, 5-alkynylcytidines, 5-halocytidines, 2-thiocytidines, N4-alkylcytidines, N4-aminocytidines, N4-acetylcytidines, and N4,N4-dialkylcytidines.

Examples of modified or chemically-modified nucleotides include 5-hydroxycytidine, 5-methylcytidine, 5-hydroxymethylcytidine, 5-carboxycytidine, 5-formylcytidine, 5-methoxycytidine, 5-propynylcytidine, 5-bromocytidine, 5-iodocytidine, 2-thiocytidine; N4-methylcytidine, N4-aminocytidine, N4-acetylcytidine, and N4,N4-dimethylcytidine.

Examples of modified or chemically-modified nucleotides include 5-hydroxyuridines, 5-alkyluridines, 5-hydroxyalkyluridines, 5-carboxyuridines, 5-carboxyalkylesteruridines, 5-formyluridines, 5-alkoxyuridines, 5-alkynyluridines, 5-halouridines, 2-thiouridines, and 6-alkyluridines.

Examples of modified or chemically-modified nucleotides include 5-hydroxyuridine, 5-methyluridine, 5-hydroxymethyluridine, 5-carboxyuridine, 5-carboxymethylesteruridine, 5-formyluridine, 5-methoxyuridine (also referred to herein as "5MeOU"), 5-propynyluridine, 5-bromouridine, 5-fluorouridine, 5-iodouridine, 2-thiouridine, and 6-methyluridine.

Examples of modified or chemically-modified nucleotides include 5-methoxycarbonylmethyl-2-thiouridine, 5-methylaminomethyl-2-thiouridine, 5-carbamoylmethyluridine, 5-carbamoylmethyl-2'-O-methyluridine, 1-methyl-3-(3-amino-3-carboxypropy)pseudouridine, 5-methylaminomethyl-2-selenouridine, 5-carboxymethyluridine, 5-methyldihydrouridine, 5-taurinomethyluridine, 5-taurinomethyl-2-thiouridine, 5-(isopentenylaminomethyl)uridine, 2'-O-methylpseudouridine, 2-thio-2'O-methyluridine, and 3,2'-O-dimethyluridine.

Examples of modified or chemically-modified nucleotides include N6-methyladenosine, 2-aminoadenosine, 3-methyladenosine, 8-azaadenosine, 7-deazaadenosine, 8-oxoadenosine, 8-bromoadenosine, 2-methylthio-N6-methyladenosine, N6-isopentenyladenosine, 2-methylthio-N6-isopentenyladenosine, N6-(cis-hydroxyisopentenyl) adenosine, 2-methylthio-N6-(cis-hydroxyisopentenyl) adenosine, N6-glycinylcarbamoyladenosine, N6-threonylcarbamoyl-adenosine, N6-methyl-N6-threonylcarbamoyl-adenosine, 2-methylthio-N6-threonylcarbamoyladenosine, N6,N6-dimethyladenosine, N6-hydroxynorvalylcarbamoyladenosine, 2-methylthio-N6-hydroxynorvalylcarbamoyl-adenosine, N6-acetyladenosine, 7-methyl-adenine, 2-methylthio-adenine, 2-methoxy-adenine, alpha-thio-adenosine, 2'-O-methyl-adenosine, N6,2'-O-dimethyl-adenosine, N6,N6,2'-O-trimethyl-adenosine, 1,2'-O-dimethyl-adenosine, 2'-O-ribosyladenosine, 2-amino-N6-methyl-purine, 1-thio-adenosine, 2'-F-ara-adenosine, 2'-F-adenosine, 2'-OH-ara-adenosine, and N6-(19-amino-pentaoxanonadecyl)-adenosine.

Examples of modified or chemically-modified nucleotides include N1-alkylguanosines, N2-alkylguanosines, thienoguanosines, 7-deazaguanosines, 8-oxoguanosines, 8-bromoguanosines, O6-alkylguanosines, xanthosines, inosines, and N1-alkylinosines.

Examples of modified or chemically-modified nucleotides include N1-methylguanosine, N2-methylguanosine, thienoguanosine, 7-deazaguanosine, 8-oxoguanosine, 8-bromoguanosine, O6-methylguanosine, xanthosine, inosine, and N1-methylinosine.

Examples of modified or chemically-modified nucleotides include pseudouridines. Examples of pseudouridines include N1-alkylpseudouridines, N1-cycloalkylpseudouridines, N1-hydroxypseudouridines, N1-hydroxyalkylpseudouridines, N1-phenylpseudouridines, N1-phenylalkylpseudouridines, N1-aminoalkylpseudouridines, N3-alkylpseudouridines, N6-alkylpseudouridines, N6-alkoxypseudouridines, N6-hydroxypseudouridines, N6-hydroxyalkylpseudouridines, N6-morpholinopseudouridines, N6-phenylpseudouridines, and N6-halopseudouridines. Examples of pseudouridines include N1-alkyl-N6-alkylpseudouridines, N1-alkyl-N6-alkoxypseudouridines, N1-alkyl-N6-hydroxypseudouridines, N1-alkyl-N6-hydroxyalkylpseudouridines, N1-alkyl-N6-morpholinopseudouridines, N1-alkyl-N6-phenylpseudouridines, and N1-alkyl-N6-halopseudouridines. In these examples, the alkyl, cycloalkyl, and phenyl substituents may be unsubstituted, or further substituted with alkyl, halo, haloalkyl, amino, or nitro substituents.

Examples of pseudouridines include N1-methylpseudouridine (also referred to herein as "N1MPU"), N1-ethylpseudouridine, N1-propylpseudouridine, N1-cyclopropylpseudouridine, N1-phenylpseudouridine, N1-aminomethylpseudouridine, N3-methylpseudouridine, N1-hydroxypseudouridine, and N1-hydroxymethylpseudouridine.

Examples of nucleic acid monomers include modified and chemically-modified nucleotides, including any such nucleotides known in the art.

Examples of modified and chemically-modified nucleotide monomers include any such nucleotides known in the art, for example, 2'-O-methyl ribonucleotides, 2'-O-methyl purine nucleotides, 2'-deoxy-2'-fluoro ribonucleotides, 2'-deoxy-2'-fluoro pyrimidine nucleotides, 2'-deoxy ribonucleotides, 2'-deoxy purine nucleotides, universal base nucleotides, 5-C-methyl-nucleotides, and inverted deoxyabasic monomer residues.

Examples of modified and chemically-modified nucleotide monomers include 3'-end stabilized nucleotides, 3'-glyceryl nucleotides, 3'-inverted abasic nucleotides, and 3'-inverted thymidine.

Examples of modified and chemically-modified nucleotide monomers include locked nucleic acid nucleotides (LNA), 2'-O,4'-C-methylene-(D-ribofuranosyl) nucleotides, 2'-methoxyethoxy (MOE) nucleotides, 2'-methyl-thio-ethyl, 2'-deoxy-2'-fluoro nucleotides, and 2'-O-methyl nucleotides. In an exemplary embodiment, the modified monomer is a locked nucleic acid nucleotide (LNA).

Examples of modified and chemically-modified nucleotide monomers include 2',4'-constrained 2'-O-methoxyethyl (cMOE) and 2'-O-Ethyl (cEt) modified DNAs.

Examples of modified and chemically-modified nucleotide monomers include 2'-amino nucleotides, 2'-O-amino nucleotides, 2'-C-allyl nucleotides, and 2'-O-allyl nucleotides.

Examples of modified and chemically-modified nucleotide monomers include N6-methyladenosine nucleotides.

Examples of modified and chemically-modified nucleotide monomers include nucleotide monomers with modified bases 5-(3-amino)propyluridine, 5-(2-mercapto)ethyluridine, 5-bromouridine; 8-bromoguanosine, or 7-deazaadenosine.

Examples of modified and chemically-modified nucleotide monomers include 2'-O-aminopropyl substituted nucleotides.

Examples of modified and chemically-modified nucleotide monomers include replacing the 2'—OH group of a nucleotide with a 2'-R, a 2'-OR, a 2'-halogen, a 2'-SR, or a 2'-amino, where R can be H, alkyl, alkenyl, or alkynyl.

Example of base modifications described above can be combined with additional modifications of nucleoside or nucleotide structure, including sugar modifications and linkage modifications. Certain modified or chemically-modified nucleotide monomers may be found in nature.

Preferred nucleotide modifications include N1-methylpseudouridine and 5-methoxyuridine.

Viral Replication Proteins and Polynucleotides Encoding them

Provided herein, in some embodiments, are nucleic acid molecules comprising a first polynucleotide encoding one or more viral replication proteins. As used herein, the term "replication protein" or "viral replication protein" refers to any protein or any protein subunit of a protein complex that functions in replication of a viral genome. Generally, viral replication proteins are non-structural proteins. Viral replication proteins encoded by nucleic acid molecules provided herein can function in the replication of any viral genome. The viral genome can be a single-stranded positive-sense RNA genome, a single-stranded negative-sense RNA genome, a double-stranded RNA genome, a single-stranded positive-sense DNA genome, a single-stranded negative-sense DNA genome, or a double-stranded DNA genome. Viral genomes can include a single nucleic acid molecule or more than one nucleic acid molecule. Nucleic acid molecules provided herein can encode one or more viral replication proteins from any virus or virus family, including animal viruses and plant viruses, for example. Viral replication proteins encoded by first polynucleotides included in nucleic acid molecules provided herein can be expressed from self-replicating RNA.

First polynucleotide sequences of nucleic acid molecules provided herein can encode one or more togavirus replication proteins. In some aspects, the one or more viral replication proteins encoded by first polynucleotides of nucleic acid molecules provided herein are alphavirus proteins. In some embodiments, the one or more viral replication proteins encoded by first polynucleotides of nucleic acid molecules provided herein are rubivirus proteins. First polynucleotide sequences of nucleic acid molecules provided herein can encode any alphavirus replication protein and any rubivirus replication protein. Exemplary replication proteins from alphaviruses include proteins from Venezuelan Equine Encephalitis Virus (VEEV), Eastern Equine Encephalitis Virus (EEEV), Everglades Virus (EVEV), Mucambo Virus (MUCV), Semliki Forest Virus (SFV), Pixuna Virus (PIXV), Middleburg Virus (MIDV), Chikungunya Virus (CHIKV), O'Nyong-Nyong Virus (ONNV), Ross River Virus (RRV), Barmah Forest Virus (BFV), Getah Virus (GETV), Sagiyama Virus (SAGV), Bebaru Virus (BEBV), Mayaro Virus (MAYV), Una Virus (UNAV), Sindbis Virus (SINV), Aura Virus (AURAV), Whataroa Virus (WHAV), Babanki Virus (BABV), Kyzylagach Virus (KYZV), Western Equine Encephalitis Virus (WEEV), Highland J Virus (HJV), Fort Morgan Virus (FMV), Ndumu Virus (NDUV), Salmonid Alphavirus (SAV), Buggy Creek Virus (BCRV), and any combination thereof. Exemplary rubivirus replication proteins include proteins from rubella virus.

Viral replication proteins encoded by first polynucleotides of nucleic acid molecules provided herein can be expressed as one or more polyproteins or as separate or single proteins. Generally, polyproteins are precursor proteins that are cleaved to generate individual or separate proteins. Accordingly, proteins derived from a precursor polyprotein can be expressed from a single open reading frame (ORF). As used herein, the term "ORF" refers to a nucleotide sequence that begins with a start codon, generally ATG, and that ends with a stop codon, such as TAA, TAG, or TGA, for example. It will be appreciated that T is present in DNA, while U is present in RNA. Accordingly, a start codon of ATG in DNA corresponds to AUG in RNA, and the stop codons TAA, TAG, and TGA in DNA correspond to UAA, UAG, and UGA in RNA. It will further be appreciated that for any sequence provided in the present disclosure, T is present in DNA, while U is present in RNA. Accordingly, for any sequence provided herein, T present in DNA is substituted with U for an RNA molecule, and U present in RNA is substituted with T for a DNA molecule.

The protease cleaving a polyprotein can be a viral protease or a cellular protease. In some aspects, the first polynucleotide of nucleic acid molecules provided herein encodes a polyprotein comprising an alphavirus nsP1 protein, an alphavirus nsP2 protein, an alphavirus nsP3 protein, an alphavirus nsP4 protein, or any combination thereof. In other aspects, the first polynucleotide of nucleic acid molecules provided herein encodes a polyprotein comprising an alphavirus nsP1 protein, an alphavirus nsP2 protein, an alphavirus nsP3 protein, or any combination thereof, and an alphavirus nsP4 protein. In some aspects, the polyprotein is a VEEV polyprotein. In other aspects, the alphavirus nsP1, nsP2, nsP3, and nsP4 proteins are VEEV proteins.

In one aspect, first polynucleotides of nucleic acid molecules provided herein lack a stop codon between sequences encoding an nsP3 protein and an nsP4 protein. Accordingly, in some aspects, first polynucleotides of nucleic acid molecules provided herein encode a P1234 polyprotein comprising nsP1, nsP2, nsP3, and nsP4. First polynucleotides of nucleic acid molecules provided herein can also include a stop codon between sequences encoding an nsP3 and an nsP4 protein. Accordingly, in some aspects, first polynucleotides of nucleic acid molecules provided herein encode a P123 polyprotein comprising nsP1, nsP2, and nsP3 and a P1234 polyprotein comprising nsP1, nsP2, nsP3, and nsP4 as a result of stop codon readthrough, for example. In other aspects, first polynucleotides of nucleic acid molecules provided herein encode a polyprotein having at least 80%, at least 85%, at least 90%, at least 91%, at least 92%, at least 93%, at least 94%, at least 95%, at least 96%, at least 97%, at least 97.5%, at least 98%, at least 98.5%, at least 99%, at least 99.5%, at least 99.6%, at least 99.7%, at least 99.8%, at least 99.9%, and any number or range in between, identity to a sequence of SEQ ID NO:79. In some embodiments, first polynucleotides of nucleic acid molecules provided herein encode a polyprotein having a sequence of SEQ ID NO:79. Further exemplary polyproteins comprise a sequence of SEQ ID NO:80 or SEQ ID NO:81. In one aspect, nsP2 and nsP3 proteins include mutations. Exemplary mutations include G1309R and S1583G mutations of VEEV proteins. In another aspect, the nsP1, nsP2, and nsP4 proteins are VEEV proteins, and the nsP3 protein is a chikungunya virus (CHIKV) nsP3 protein.

In some aspects, first polynucleotides of nucleic acid molecules provided herein can include a first intergenic region. In some aspects, the first intergenic region is located between a sequence encoding a polyprotein comprising an alphavirus nsP1 protein, an alphavirus nsP2 protein, an alphavirus nsP3 protein, or any combination thereof, and a sequence encoding an alphavirus nsP4 protein. A first intergenic region can comprise any sequence, such as any viral or non-viral sequence. In one aspect, the first intergenic region comprises a viral sequence. In another aspect, the first intergenic region comprises an alphavirus sequence. In yet another aspect, the alphavirus is VEEV. In one aspect, nsP2 and nsP3 proteins include mutations. Exemplary mutations include G1309R and S1583G mutations of VEEV proteins. In another aspect, the nsP1, nsP2, and nsP4 proteins are VEEV proteins, and the nsP3 protein is a chikungunya virus (CHIKV) nsP3 protein.

5' Untranslated Region (5' UTR)

Nucleic acid molecules provided herein can further comprise untranslated regions (UTRs). Untranslated regions, including 5' UTRs and 3' UTRs, for example, can affect RNA stability and/or efficiency of RNA translation, such as translation of cellular and viral mRNAs, for example. 5' UTRs and 3' UTRs can also affect stability and translation of viral genomic RNAs and self-replicating RNAs, including virally derived self-replicating RNAs or replicons. Exemplary viral genomic RNAs whose stability and/or efficiency of translation can be affected by 5' UTRs and 3' UTRs include the genome nucleic acid of positive-sense RNA viruses. Both genome nucleic acid of positive-sense RNA viruses and self-replicating RNAs, including virally derived self-replicating RNAs or replicons, can be translated upon infection or introduction into a cell.

In some aspects, nucleic acid molecules provided herein further include a 5' untranslated region (5' UTR). Any 5' UTR sequence can be included in nucleic acid molecules provided herein. In some embodiments, nucleic acid molecules provided herein include a viral 5' UTR. In one aspect, nucleic acid molecules provided herein include a non-viral 5' UTR. Any non-viral 5' UTR can be included in nucleic acid molecules provided herein, such as 5' UTRs of transcripts expressed in any cell or organ, including muscle, skin, subcutaneous tissue, liver, spleen, lymph nodes, antigen-presenting cells, and others. In another aspect, nucleic acid molecules provided herein include a 5' UTR comprising viral and non-viral sequences. Accordingly, a 5' UTR included in nucleic acid molecules provided herein can comprise a combination of viral and non-viral 5' UTR sequences. In some aspects, the 5' UTR included in nucleic acid molecules provided herein is located upstream of or 5' of the first polynucleotide that encodes one or more viral replication proteins. In other aspects, the 5' UTR is located 5' of or upstream of the first polynucleotide of nucleic acid molecules provided herein that encodes one or more viral replication proteins, and the first polynucleotide is located 5' of or upstream of the second polynucleotide of nucleic acid molecules provided herein.

In one aspect, the 5' UTR of nucleic acid molecules provided herein comprises an alphavirus 5' UTR. A 5' UTR from any alphavirus can be included in nucleic acid molecules provided herein, including 5' UTR sequences from Venezuelan Equine Encephalitis Virus (VEEV), Eastern Equine Encephalitis Virus (EEEV), Everglades Virus (EVEV), Mucambo Virus (MUCV), Semliki Forest Virus (SFV), Pixuna Virus (PIXV), Middleburg Virus (MIDV), Chikungunya Virus (CHIKV), O'Nyong-Nyong Virus (ONNV), Ross River Virus (RRV), Barmah Forest Virus (BFV), Getah Virus (GETV), Sagiyama Virus (SAGV), Bebaru Virus (BEBV), Mayaro Virus (MAYV), Una Virus (UNAV), Sindbis Virus (SINV), Aura Virus (AURAV), Whataroa Virus (WHAV), Babanki Virus (BABV), Kyzylagach Virus (KYZV), Western Equine Encephalitis Virus (WEEV), Highland J Virus (HJV), Fort Morgan Virus (FMV), Ndumu Virus (NDUV), Salmonid Alphavirus (SAV), or Buggy Creek Virus (BCRV). In another aspect, the 5' UTR comprises a sequence having at least 80%, at least 85%, at least 90%, at least 91%, at least 92%, at least 93%, at least 94%, at least 95%, at least 96%, at least 97%, at least 97.5%, at least 98%, at least 98.5%, at least 99%, at least 99.5%, at least 99.6%, at least 99.7%, at least 99.8%, at least 99.9%, and any number or range in between, identity to a sequence of SEQ ID NO:73, SEQ ID NO:74, or SEQ ID NO:75. In yet another aspect, the 5' UTR comprises a sequence of SEQ ID NO:73, SEQ ID NO:74, or SEQ ID NO:75.

In some embodiments, the 5' UTR comprises a sequence selected from the 5' UTRs of human IL-6, alanine aminotransferase 1, human apolipoprotein E, human fibrinogen alpha chain, human transthyretin, human haptoglobin, human alpha-1-antichymotrypsin, human antithrombin, human alpha-1-antitrypsin, human albumin, human beta globin, human complement C3, human complement C5, SynK (thylakoid potassium channel protein derived from the cyanobacteria, *Synechocystis* sp.), mouse beta globin, mouse albumin, and a tobacco etch virus, or fragments of any of the foregoing. Preferably, the 5' UTR is derived from a tobacco etch virus (TEV). Preferably, an mRNA described herein comprises a 5' UTR sequence that is derived from a gene expressed by *Arabidopsis thaliana*. Preferably, the 5' UTR sequence of a gene expressed by *Arabidopsis thaliana* is AT1G58420. Examples of 5 UTRs and 3' UTRs are described in PCT/US2018/035419, the contents of which are herein incorporated by reference. Preferred 5' UTR sequences comprise SEQ ID NOs: 5, 25-27 and 28-45: as shown in Table 1.

TABLE 1

5' UTR Sequences

| Name | Sequence | Seq ID No.: |
|---|---|---|
| EV | UCAACACAACAUAUACAAAACAAACGAAUCUCAAGCAAUC AAGCAUUCUACUUCUAUUGCAGCAAUUUAAAUCAUUUCU UUUAAAGCAAAAGCAAUUUUCUGAAAAUUUUCACCAUUU ACGAACGAUAG | SEQ ID NO: 5 |
| AT1G58420 | AUUAUUACAUCAAAACAAAAAGCCGCCA | SEQ ID NO: 6 |
| ARC5-2 | CUUAAGGGGGCGCUGCCUACGGAGGUGGCAGCCAUCUCCU UCUCGGCAUCAAGCUUACCAUGGUGCCCCAGGCCCUGCUC UUGGUCCCGCUGCUGGUGUUCCCCCUCUGCUUCGGCAAGU UCCCCAUCUACACCAUCCCCGACAAGCUGGGGCCGUGGAG CCCCAUCGACAUCCACCACCUGUCCUGCCCCAACAACCUCG UGGUCGAGGACGAGGGCUGCACCAACCUGAGCGGGUUCUC CUAC | SEQ ID NO: 7 |
| HCV | UGAGUGUCGU ACAGCCUCCA GGCCCCCCCC UCCCGGGAGA GCCAUAGUGG UCUGCGGAACCGGUGAGUAC ACCGGAAUUG CCGGGAAGAC UGGGUCCUUU CUUGGAUAAA CCCACUCUAUGCCCGGCCAU UUGGGCGUGC CCCCGCAAGA CUGCUAGCCG AGUAGUGUUG GGUUGCG | SEQ ID NO: 8 |
| HUMAN ALBUMIN | AAUUAUUGGUUAAAGAAGUAUAUUAGUGCUAAUUUCCCU CCGUUUGUCCUAGCUUUUCUCUUCUGUCAACCCCACACGC CUUUGGCACA | SEQ ID NO: 9 |
| EMCV | CUCCCUCCCC CCCCCCUAAC GUUACUGGCC GAAGCCGCUU GGAAUAAGGC CGGUGUGCGU UUGUCUAUAU GUUAUUUUCC ACCAUAUUGC CGUCUUUUGG CAAUGUGAGG GCCCGGAAAC CUGGCCCUGU CUUCUUGACG AGCAUUCCUA GGGGUCUUUC CCCUCUCGCC AAAGGAAUGC AAGGUCUGUU GAAUGUCGUG AAGGAAGCAG UUCCUCUGGA AGCUUCUUGA AGACAAACAA CGUCUGUAGC GACCCUUUGC AGGCAGCGGA ACCCCCCACC UGGCGACAGG UGCCUCUGCG GCCAAAAGCC ACGUGUAUAA GAUACACCUG CAAAGGCGGC ACAACCCCAG UGCCACGUUG UGAGUUGGAU AGUUGUGGAA AGAGUCAAAU GGCUCUCCUC AAGCGUAUUC AACAAGGGGC UGAAGGAUGC CCAGAAGGUA CCCCAUUGUA UGGGAUCUGA UCUGGGGCCU CGGUGCACAU GCUUUACGUG UGUUUAGUCG AGGUUAAAAA ACGUCUAGGC CCCCCGAACC ACGGGGACGU GGUUUUCCUU UGAAAAACAC GAUGAUAAU | SEQ ID NO: 10 |
| AT1G67090 | CACAAAGAGUAAAGAAGAACA | SEQ ID NO: 25 |
| AT1G35720 | AACACUAAAAGUAGAAGAAAA | SEQ ID NO: 26 |
| AT5G45900 | CUCAGAAAGAUAAGAUCAGCC | SEQ ID NO: 27 |
| AT5G61250 | AACCAAUCGAAAGAAACCAAA | SEQ ID NO: 28 |
| AT5G46430 | CUCUAAUCACCAGGAGUAAAA | SEQ ID NO: 29 |
| AT5G47110 | GAGAGAGAUCUUAACAAAAAA | SEQ ID NO: 30 |
| AT1G03110 | UGUGUAACAACAACAACAACA | SEQ ID NO: 31 |
| AT3G12380 | CCGCAGUAGGAAGAGAAAGCC | SEQ ID NO: 32 |
| AT5G45910 | AAAAAAAAAGAAAUCAUAAA | SEQ ID NO: 33 |
| AT1G07260 | GAGAGAAGAAAGAAGAAGACG | SEQ ID NO: 34 |
| AT3G55500 | CAAUUAAAAAUACUUACCAAA | SEQ ID NO: 35 |
| AT3G46230 | GCAAACAGAGUAAGCGAAACG | SEQ ID NO: 36 |
| AT2G36170 | GCGAAGAAGACGAACGCAAAG | SEQ ID NO: 37 |

TABLE 1-continued

| 5' UTR Sequences | | |
|---|---|---|
| Name | Sequence | Seq ID No.: |
| AT1G10660 | UUAGGACUGUAUUGACUGGCC | SEQ ID NO: 38 |
| AT4G14340 | AUCAUCGGAAUUCGGAAAAAG | SEQ ID NO: 39 |
| AT1G49310 | AAAACAAAAGUUAAAGCAGAC | SEQ ID NO: 40 |
| AT4G14360 | UUUAUCUCAAAUAAGAAGGCA | SEQ ID NO: 41 |
| AT1G28520 | GGUGGGGAGGUGAGAUUUCUU | SEQ ID NO: 42 |
| AT1G20160 | UGAUUAGGAAACUACAAAGCC | SEQ ID NO: 43 |
| AT5G37370 | CAUUUUUCAAUUUCAUAAAAC | SEQ ID NO: 44 |
| AT4G11320 | UUACUUUUAAGCCCAACAAAA | SEQ ID NO: 45 |
| AT5G40850 | GGCGUGUGUGUGUGUUGUUGA | SEQ ID NO: 46 |
| AT1G06150 | GUGGUGAAGGGGAAGGUUUAG | SEQ ID NO: 47 |
| AT2G26080 | UUGUUUUUUUUUGGUUUGGUU | SEQ ID NO: 48 |

3' Untranslated Region (3' UTR)

In some aspects, nucleic acid molecules provided herein further include a 3' untranslated region (3' UTR). Any 3' UTR sequence can be included in nucleic acid molecules provided herein. In one aspect, nucleic acid molecules provided herein include a viral 3' UTR. In another aspect, nucleic acid molecules provided herein include a non-viral 3' UTR. Any non-viral 3' UTR can be included in nucleic acid molecules provided herein, such as 3' UTRs of transcripts expressed in any cell or organ, including muscle, skin, subcutaneous tissue, liver, spleen, lymph nodes, antigen-presenting cells, and others. In some aspects, nucleic acid molecules provided herein include a 3' UTR comprising viral and non-viral sequences. Accordingly, a 3' UTR included in nucleic acid molecules provided herein can comprise a combination of viral and non-viral 3' UTR sequences. In one aspect, the 3' UTR is located 3' of or downstream of the second polynucleotide of nucleic acid molecules provided herein that comprises a first transgene encoding a first antigenic protein or a fragment thereof. In another aspect, the 3' UTR is located 3' of or downstream of the second polynucleotide of nucleic acid molecules provided herein that comprises a first transgene encoding a first antigenic protein or a fragment thereof, and the second polynucleotide is located 3' of or downstream of the first polynucleotide of nucleic acid molecules provided herein.

In one aspect, the 3' UTR of nucleic acid molecules provided herein comprises an alphavirus 3' UTR. A 3' UTR from any alphavirus can be included in nucleic acid molecules provided herein, including 3' UTR sequences from Venezuelan Equine Encephalitis Virus (VEEV), Eastern Equine Encephalitis Virus (EEEV), Everglades Virus (EVEV), Mucambo Virus (MUCV), Semliki Forest Virus (SFV), Pixuna Virus (PIXV), Middleburg Virus (MIDV), Chikungunya Virus (CHIKV), O'Nyong-Nyong Virus (ONNV), Ross River Virus (RRV), Barmah Forest Virus (BFV), Getah Virus (GETV), Sagiyama Virus (SAGV), Bebaru Virus (BEBV), Mayaro Virus (MAYV), Una Virus (UNAV), Sindbis Virus (SINV), Aura Virus (AURAV), Whataroa Virus (WHAV), Babanki Virus (BABV), Kyzylagach Virus (KYZV), Western Equine Encephalitis Virus (WEEV), Highland J Virus (HJV), Fort Morgan Virus (FMV), Ndumu Virus (NDUV), Salmonid Alphavirus (SAV), or Buggy Creek Virus (BCRV). In another aspect, the 3' UTR comprises a sequence having at least 80%, at least 85%, at least 90%, at least 91%, at least 92%, at least 93%, at least 94%, at least 95%, at least 96%, at least 97%, at least 97.5%, at least 98%, at least 98.5%, at least 99%, at least 99.5%, at least 99.6%, at least 99.7%, at least 99.8%, at least 99.9%, and any number or range in between, identity to a sequence of SEQ ID NO:5. In yet another aspect, the 3' UTR comprises a poly-A sequence. In a further aspect, the 3' UTR comprises a sequence of SEQ ID NO:5.

In some embodiments, the 3' UTR comprises a sequence selected from the 3' UTRs of alanine aminotransferase 1, human apolipoprotein E, human fibrinogen alpha chain, human haptoglobin, human antithrombin, human alpha globin, human beta globin, human complement C3, human growth factor, human hepcidin, MALAT-1, mouse beta globin, mouse albumin, and *Xenopus* beta globin, or fragments of any of the foregoing. In some embodiments, the 3' UTR is derived from *Xenopus* beta globin. Exemplary 3' UTR sequences include SEQ ID NOs: 16-22 as shown in Table 2.

TABLE 2

| 3' UTR sequences. | | |
|---|---|---|
| Name | Sequence | Seq ID No.: |
| XBG | CUAGUGACUGACUAGGAUCUGGUUACCACUAAACCAG CCUCAAGAACACCCGAAUGGAGUCUCUAAGCUACAUA AUACCAACUUACACUUACAAAAUGUUGUCCCCCAAAA UGUAGCCAUUCGUAUCUGCUCCUAAUAAAAAGAAAGU UUCUUCACAU | SEQ ID NO: 16 |

TABLE 2-continued

| 3' UTR sequences. | | |
|---|---|---|
| Name | Sequence | Seq ID No.: |
| HUMAN HAPTOGLOBIN | UGCAAGGCUGGCCGGAAGCCCUUGCCUGAAAGCAAGA UUUCAGCCUGGAAGAGGGCAAAGUGGACGGGAGUGG ACAGGAGUGGAUGCGAUAAGAUGUGGUUUGAAGCUG AUGGGUGCCAGCCCUGCAUUGCUGAGUCAAUCAAUAA AGAGCUUUCUUUUGACCCAU | SEQ ID NO: 17 |
| HUMAN APOLIPOPROTEIN E | ACGCCGAAGCCUGCAGCCAUGCGACCCCACGCCACCCC GUGCCUCCUGCCUCCGCGCAGCCUGCAGCGGGAGACC CUGUCCCCGCCCCAGCCGUCCUCCUGGGGUGGACCCU AGUUUAAUAAAGAUUCACCAAGUUUCACGCA | SEQ ID NO: 18 |
| HCV | UAGAGCGGCAAACCCUAGCUACACUCCAUAGCUAGUU UCUUUUUUUUUUGUUUUUUUUUUUUUUUUUUUUUUU UUUUUUUUUUUUUUUUUCCUUUCUUUUCCUUCUUUUU UUCCUCUUUUCUUGGUGGCUCCAUCUUAGCCCUAGUC ACGGCUAGCUGUGAAAGGUCCGUGAGCCGCAUGACUG CAGAGAGUGCCGUAACUGGUCUCUCUGCAGAUCAUGU | SEQ ID NO: 19 |
| MOUSE ALBUMIN | ACACAUCACAACCACAACCUUCUCAGGCUACCCUGAG AAAAAAAGACAUGAAGACUCAGGACUCAUCUUUUCUG UUGGUGUAAAAUCAACACCCUAAGGAACACAAAUUUC UUUAAACAUUUGACUUCUUGUCUCUGUGCUGCAAUUA AUAAAAAAUGGAAAGAAUCUAC | SEQ ID NO: 20 |
| HUMAN ALPHA GLOBIN | GCUGGAGCCUCGGUAGCCGUUCCUCCUGCCCGCUGGG CCUCCCAACGGGCCCUCCUCCCCUCCUUGCACCGGCCC UUCCUGGUCUUUGAAUAAAGUCUGAGUGGGCAGCA | SEQ ID NO: 21 |
| EMCV | UAGUGCAGUCAC UGGCACAACG CGUUGCCCGG UAAGCCAAUC GGGUAUACAC GGUCGUCAUACUGCAGACAG GGUUCUUCUA CUUUGCAAGA UAGUCUAGAG UAGUAAAAUA AAUAGUAUAAG | SEQ ID NO: 22 |

Triple Stop Codon

In some embodiments, the self-replicating RNA may comprise a sequence immediately downstream of a coding region (i.e., ORF) that creates a triple stop codon. A triple stop codon is a sequence of three consecutive stop codons. The triple stop codon can ensure total insulation of an expression cassette and may be incorporated to enhance the efficiency of translation. In some embodiments, a self-replicating RNA of the disclosure may comprise a triple combination of any of the sequences UAG, UGA, or UAA immediately downstream of a ORF described herein. The triple combination can be three of the same codons, three different codons, or any other permutation of the three stop codons.

Translation Enhancers and Kozak Sequences

For translation initiation, proper interactions between ribosomes and mRNAs must be established to determine the exact position of the translation initiation region. However, ribosomes also must dissociate from the translation initiation region to slide toward the downstream sequence during mRNA translation. Translation enhancers upstream from initiation sequences of mRNAs enhance the yields of protein biosynthesis. Several studies have investigated the effects of translation enhancers. In some embodiments, an mRNA described herein comprises a translation enhancer sequence. These translation enhancer sequences enhance the translation efficiency of a self-replicating RNA of the disclosure and thereby provide increased production of the protein encoded by the mRNA. The translation enhancer region may be located in the 5' or 3' UTR of an mRNA sequence. Examples of translation enhancer regions include naturally-occurring enhancer regions from the TEV 5' UTR and the *Xenopus* beta-globin 3' UTR. Exemplary 5' UTR enhancer sequences include but are not limited to those derived from mRNAs encoding human heat shock proteins (HSP) including HSP70-P2, HSP70-M1 HSP72-M2, HSP17.9 and HSP70-P1. Preferred translation enhancer sequences used in accordance with the embodiments of the present disclosure are represented by SEQ ID Nos: 11-15 as shown in Table 3.

TABLE 3

| 5' UTR Enhancers | | |
|---|---|---|
| Name | Sequence | Seq ID No.: |
| HSP70-P2 | GUCAGCUUUCAAACUCUUUGUUUCUUGUUUGUUGAUUGAGAA UA | SEQ ID NO: 11 |
| HSP70-M1 | CUCUCGCCUGAGAAAAAAAAUCCACGAACCAAUUUCUCAGCA ACCAGCAGCACG | SEQ ID NO: 12 |

TABLE 3-continued

| 5' UTR Enhancers | | |
|---|---|---|
| Name | Sequence | Seq ID No.: |
| HSP72-M2 | ACCUGUGAGGGUUCGAAGGAAGUAGCAGUGUUUUUUGUUCCUAGAGGAAGAG | SEQ ID NO: 13 |
| HSP17.9 | ACACAGAAACAUUCGCAAAAACAAAAUCCCAGUAUCAAAAUUCUUCUCUUUUUUUCAUAUUUCGCAAAGAC | SEQ ID NO: 14 |
| HSP70-P1 | CAGAAAAAUUUGCUACAUUGUUUCACAAACUUCAAAUAUUAUUCAUUUAUUU | SEQ ID NO: 15 |

In some embodiments, a self-replicating RNA of the disclosure comprises a Kozak sequence. As is understood in the art, a Kozak sequence is a short consensus sequence centered around the translational initiation site of eukaryotic mRNAs that allows for efficient initiation of translation of the mRNA. See, for example, Kozak, Marilyn (1988) Mol. and Cell Biol, 8:2737-2744; Kozak, Marilyn (1991) J. Biol. Chem, 266: 19867-19870; Kozak, Marilyn (1990) Proc Natl. Acad. Sci. USA, 87:8301-8305; and Kozak, Marilyn (1989) J. Cell Biol, 108:229-241. It ensures that a protein is correctly translated from the genetic message, mediating ribosome assembly and translation initiation. The ribosomal translation machinery recognizes the AUG initiation codon in the context of the Kozak sequence. A Kozak sequence may be inserted upstream of the coding sequence for the protein of interest, downstream of a 5' UTR or inserted upstream of the coding sequence for the protein of interest and downstream of a 5' UTR. In some embodiments, a self-replicating RNA described herein comprises a Kozak sequence having the amino acid sequence GCCACC (SEQ ID NO: 23). Preferably a self-replicating RNA described herein comprises a partial Kozak sequence "p" having the amino acid sequence GCCA (SEQ ID NO: 24).

Transgenes

Transgenes included in nucleic acid molecules provided herein can encode an antigenic protein or a fragment thereof. In some embodiments, second polynucleotides of nucleic acid molecules provided herein comprise a first transgene. A first transgene included in second polynucleotides of nucleic acid molecules provided herein can encode a first antigenic protein or a fragment thereof. A transgene included in second polynucleotides of nucleic acid molecules provided herein can comprise a sequence encoding the full amino acid sequence of an antigenic protein or a sequence encoding any suitable portion or fragment of the full amino acid sequence of an antigenic protein. Any antigenic protein can be encoded by transgenes included in nucleic acid molecules provided herein. In one aspect, the antigenic protein is a viral protein, a bacterial protein, a fungal protein, a protozoan protein, a parasite protein, or a tumor protein or tumor antigen. Transgenes included in nucleic acid molecules provided herein can be expressed from a subgenomic RNA.

In another embodiment, the antigenic protein, when administered to a mammalian subject, raises an immune response to a pathogen, optionally wherein the pathogen is bacterial, viral, fungal, protozoan, or cancerous. In some more particular embodiments, the antigenic protein is expressed on the outer surface of the pathogen; while in other more particular embodiments, the antigen may be a non-surface antigen, e.g., useful as a T-cell epitope. The immunogen may elicit an immune response against a pathogen (e.g. a bacterium, a virus, a fungus or a parasite) but, in some other embodiments, it elicits an immune response against an allergen or a tumor antigen. The immune response may comprise an antibody response (usually including IgG) and/or a cell mediated immune response. The polypeptide immunogen will typically elicit an immune response that recognizes the corresponding pathogen (or allergen or tumor) polypeptide, but in some embodiments, the polypeptide may act as a mimotope to elicit an immune response that recognizes a saccharide. The immunogen will typically be a surface polypeptide e.g. an adhesin, a hemagglutinin, an envelope glycoprotein, a spike glycoprotein, etc.

Any viral, bacterial, fungal, protozoan, parasite, or tumor protein can be encoded by transgenes included in nucleic acid molecules provided herein. A protein from any infectious agent can be encoded by transgenes included in nucleic acid molecules provided herein. As used herein, the term "infectious agent" refers to any agent capable of infecting an organism, including humans and animals, and causing disease or deterioration in health. The terms "infectious agent" and "infectious pathogen" may be used interchangeably, unless context clearly indicates otherwise.

In some aspects, the viral protein encoded by transgenes included in nucleic acid molecules provided herein is an orthomyxovirus protein, a paramyxovirus protein, a picornavirus protein, a flavivirus protein, a filovirus protein, a rhabdovirus protein, a togavirus protein, an arterivirus protein, a bunyavirus protein, an arenavirus protein, a reovirus protein, a bornavirus protein, a retrovirus protein, an adenovirus protein, a herpesvirus protein, a polyomavirus protein, a papillomavirus protein, a poxvirus protein, or a hepadnavirus protein. In other aspects, the antigenic protein is an influenza virus protein, a respiratory syncytial virus (RSV) protein, a human immunodeficiency virus (HJV) protein, a hepatitis C virus (HCV) protein, a cytomegalovirus (CMV) protein, a Lassa Fever Virus (LFV) protein, an Ebola Virus (EBOV) protein, a *Mycobacterium* protein, a *Bacillus* protein, a *Yersinia* protein, a *Streptococcus* protein, a *Pseudomonas* protein, a *Shigella* protein, a *Campylobacter* protein, a *Salmonella* protein, a *Plasmodium* protein, or a *Toxoplasma* protein.

In one aspect, the antigenic protein is from a prokaryotic organism, including gram positive bacteria, gram negative bacteria, or other bacteria, such as *Bacillus* (e.g., *Bacillus anthracis*), *Mycobacterium* (e.g., *Mycobacterium tuberculosis, Mycobacterium Leprae*), *Shigella* (e.g., *Shigella sonnei, Shigella dysenteriae, Shigella flexneri*), *Helicobacter* (e.g., *Helicobacter pylori*), *Salmonella* (e.g., *Salmonella enterica, Salmonella typhi, Salmonella typhimurium*), *Neisseria* (e.g., *Neisseria gonorrhoeae, Neisseria meningitidis*), *Moraxella* (e.g., *Moraxella catarrhalis*), *Haemophilus* (e.g., *Haemophilus influenzae*), *Klebsiella* (e.g., *Klebsiella pneumoniae*), *Legionella* (e.g., *Legionella pneumophila*), *Pseudomonas* (e.g., *Pseudomonas aeruginosa*), *Acinetobacter* (e.g., *Acinetobacter baumannii*), *Listeria* (e.g., *List-*

*eria monocytogenes*), *Staphylococcus* (e.g., *Staphylococcus aureus*), *Streptococcus* (e.g., *Streptococcus pneumoniae, Streptococcus pyogenes, Streptococcus agalactiae*), *Corynebacterium* (e.g., *Corynebacterium diphtheria*), *Clostridium* (e.g., *Clostridium botulinum, Clostridium tetani, Clostridium difficile*), *Chlamydia* (e.g., *Chlamydia pneumonia, Chlamydia trachomatis*), *Caphylobacter* (e.g., *Caphylobacter jejuni*), *Bordetella* (e.g., *Bordetella pertussis*), *Enterococcus* (e.g., *Enterococcus faecalis, Enterococcus faecum*), *Vibrio* (e.g., *Vibrio cholerae*), *Yersinia* (e.g., *Yersinia pestis*), *Burkholderia* (e.g., *Burkholderia cepacia* complex), *Coxiella* (e.g., *Coxiella burnetti*), *Francisella* (e.g., *Francisella tularensis*), and *Escherichia* (e.g., enterotoxigenic, enterohemorrhagic or Shiga toxin producing *E. coli*, such as ETEC, EHEC, EPEC, EIEC, and EAEC)). In another aspect, the antigenic protein is from a eukaryotic organism, including protists and fungi, such as *Plasmodium* (e.g., *Plasmodium falciparum, Plasmodium vivax, Plasmodium ovale, Plasmodium malariae, Plasmodium diarrhea*), *Candida* (e.g., *Candida albicans*), *Aspergillus* (e.g., *Aspergillus fumigatus*), *Cryptococcus* (e.g., *Cryptococcus neoformans*), *Histoplasma* (e.g., *Histoplasma capsulatum*), *Pneumocystis* (e.g., *Pneumocystis jirovecii*), and *Coccidiodes* (e.g., *Coccidiodes immitis*).

In one aspect, the antigenic protein encoded by first transgenes of second polynucleotides included in nucleic acid molecules provided herein is an influenza virus protein or a fragment thereof. In another aspect, the second polynucleotide includes one or more transgenes encoding one or more influenza virus proteins or fragments thereof. Exemplary influenza virus proteins that can be encoded by transgenes of second polynucleotides included in nucleic acid molecules provided herein include proteins from any human or animal virus, including influenza A virus, influenza B virus, influenza C virus, influenza D virus, or any combination thereof. Exemplary influenza proteins include hemagglutinin (HA), neuraminidase (NA), M2, M1, NP, NS1, NS2, PA, PB1, PB2, and PB1-F2. Hemagglutinin proteins from any influenza virus subtype, such as H1-H18 and any emerging hemagglutinin, and neuraminidase proteins from any influenza virus subtype, such as N1-N11 and any emerging neuraminidase, can be antigenic proteins encoded by transgenes included in second polynucleotides of nucleic acid molecules provided herein. Any suitable fragment of influenza virus proteins can be encoded by transgenes included in second polynucleotides of nucleic acid molecules provided herein, including, for example, one or more helper T lymphocyte (HTL) epitope, one or more cytotoxic T lymphocyte (CTL) epitope, or any combination thereof.

Transgenes included in second polynucleotides of nucleic acid molecules provided herein can express tumor proteins or tumor antigens. Tumor proteins or tumor antigens can be from any tumor, including solid and liquid tumors, for example. As used herein, the terms "tumor protein" or "tumor antigen," which may be used interchangeably unless context clearly indicates otherwise, refer to any protein antigen that is present on the surface of a tumor cell or expressed in a tumor cell. Tumor proteins or tumor antigens include tumor-specific antigens that are present on tumor cells but generally not on other cells and tumor-associated antigens that are generally present on tumor cells and on normal cells. Tumor proteins or tumor antigens also include neoantigens. As used herein, the term "neoantigen" refers to tumor-specific mutations that can be unique to a patient's cancer or tumor.

As used herein, the term "tumor" refers to a mass or lump of tissue that is formed by an accumulation of abnormal cells. A tumor can be benign (i.e., not cancer), malignant (i.e., cancer), or premalignant (i.e., precancerous). The terms "tumor" and "neoplasm" can be used interchangeably. Generally, a cancerous tumor is malignant. As used herein, the term "solid tumor" refers to an abnormal mass of tissue that usually does not contain cysts or liquid areas. Exemplary solid tumors include sarcomas and carcinomas. As used herein, the term "liquid tumors" refers to tumors or cancers present in body fluids such as blood and bone marrow. Exemplary liquid tumors include hematopoietic tumors, such as leukemias and lymphomas, notwithstanding the ability of lymphomas to grow as solid tumors by growing in a lymph node, for example. The term "liquid tumor" can be used interchangeably with the term "blood cancer," unless context clearly indicates otherwise.

Exemplary tumor proteins or tumor antigens include products of mutated oncogenes, products of mutated tumor suppressor genes, products of mutated genes other than oncogenes or tumor suppressors, tumor antigens produced by oncogenic viruses, altered cell surface glycoproteins, oncofetal antigens, and others. Tumor proteins or tumor antigens also include immune regulatory molecules, such as immune checkpoint inhibitors and immune stimulatory molecules. Tumor antigens further include altered cell surface glycolipids. In some aspects, the tumor protein or tumor antigen encoded by transgenes included in second polynucleotides of nucleic acid molecules provided herein is a kidney cancer, renal cancer, urinary bladder cancer, prostate cancer, uterine cancer, breast cancer, cervical cancer, ovarian cancer, lung cancer, liver cancer, stomach cancer, colon cancer, rectal cancer, oral cavity cancer, pharynx cancer, pancreatic cancer, thyroid cancer, melanoma, skin cancer, head and neck cancer, brain cancer, hematopoietic cancer, leukemia, lymphoma, bone cancer, or sarcoma protein. Exemplary tumor proteins or tumor antigens include KRAS, NRAS, HRAS, HER2, BRCA1, BRCA2, carcinoembryonic antigen (CEA), MUC1, guanylyl-cyclase C, NY-ESO-1, melanoma-associated antigen (e.g., MAGE-1, MAGE-3), p53, survivin, alphafetoprotein (AFP), CA-125, epithelial tumor antigen (ETA), tyrosinase, prostate-specific antigen (PSA), prostate-specific membrane antigen (PSMA), prostate stem cell antigen (PSCA), human aspartyl (asparaginyl) β-hydroxylase (HAAH), EphA2, and others.

In some aspects, the tumor protein or tumor antigen encoded by transgenes included in nucleic acid molecules provided herein is a wild-type protein or a fragment or epitope thereof. In other aspects, the tumor protein or tumor antigen encoded by transgenes included in second polynucleotides of nucleic acid molecules provided herein is a mutant protein or a fragment or epitope thereof. In one aspect, the tumor protein or tumor antigen is KRAS, NRAS, HRAS, HER2, BRCA1, BRCA2, carcinoembryonic antigen (CEA), MUC1, guanylyl-cyclase C, NY-ESO-1, melanoma-associated antigen (e.g., MAGE-1, MAGE-3), p53, survivin, alphafetoprotein (AFP), CA-125, epithelial tumor antigen (ETA), tyrosinase, prostate-specific antigen (PSA), prostate-specific membrane antigen (PSMA), prostate stem cell antigen (PSCA), human aspartyl (asparaginyl) β-hydroxylase (HAAH), EphA2, or any mutant thereof. In another aspect, the tumor protein or tumor antigen is KRAS or a fragment or epitope thereof. In another aspect, the tumor protein or tumor antigen is KRASG12D, KRASG12C, KRASG12V, or KRASG13D. Any KRAS that includes any mutation can be encoded by transgenes included in second polynucleotides of nucleic acid molecules provided herein.

In some aspects, transgenes included in second polynucleotides of nucleic acid molecules provided herein encode a reporter or a marker, including selectable markers. Reporters and markers can include fluorescent proteins, such as green fluorescent protein (GFP), red fluorescent protein (RFP), yellow fluorescent protein (YFP), luciferase enzymes, such as firefly and *Renilla* luciferases, and antibiotic selection markers, for example.

In some aspects, the second polynucleotide of nucleic acid molecules provided herein comprises at least two transgenes. Any number of transgenes can be included in second polynucleotides of nucleic acid molecules provided herein, such as one, two, three, four, five, six, seven, eight, nine, ten, or more transgenes. In one aspect, the second polynucleotide of nucleic acid molecules provided herein includes a second transgene encoding a second antigenic protein or a fragment thereof or an immunomodulatory protein. In one aspect, the second polynucleotide further comprises an internal ribosomal entry site (IRES), a sequence encoding a 2A peptide, or a combination thereof, located between transgenes. As used herein, the term "2A peptide" refers to a small (generally 18-22 amino acids) sequence that allows for efficient, stoichiometric production of discrete protein products within a single reading frame through a ribosomal skipping event within the 2A peptide sequence. As used herein, the term "internal ribosomal entry site" or "IRES" refers to a nucleotide sequence that allows for the initiation of protein translation of a messenger RNA (mRNA) sequence in the absence of an AUG start codon or without using an AUG start codon. An IRES can be found anywhere in an mRNA sequence, such as at or near the beginning, at or near the middle, or at or near the end of the mRNA sequence, for example.

Any number of transgenes included in second polynucleotides of nucleic acid molecules provided herein can be expressed via any combination of 2A peptide and IRES sequences. For example, a second transgene located 3' of a first transgene can be expressed via a 2A peptide sequence or via an IRES sequence. As another example, a second transgene located 3' of a first transgene and a third transgene located 3' of the second transgene can be expressed via 2A peptide sequences located between the first and second transgenes and the second and third transgenes, via an IRES sequence located between the first and second transgenes and the second and third transgenes, via a 2A peptide sequence located between the first and second transgenes and an IRES located between the second and third transgenes, or via an IRES sequence located between the first and second transgenes and a 2A peptide sequence located between the second and third transgenes. Similar configurations and combinations of 2A peptide and IRES sequences located between transgenes are contemplated for any number of transgenes included in second polynucleotides of nucleic acid molecules provided herein. In addition to expression via 2A peptide and IRES sequences, two or more transgenes included in nucleic acid molecules provided herein can also be expressed from separate subgenomic RNAs.

A second, third, fourth, fifth, sixth, seventh, eighth, ninth, tenth, etc., transgene included in second polynucleotides of nucleic acid molecules provided herein can encode an immunomodulatory protein or a functional fragment or functional variant thereof. Any immunomodulatory protein or a functional fragment or functional variant thereof can be encoded by a transgene included in second polynucleotides.

As used herein, the terms "functional variant" or "functional fragment" refer to a molecule, including a nucleic acid or protein, for example, that comprises a nucleotide and/or amino acid sequence that is altered by one or more nucleotides and/or amino acids compared to the nucleotide and/or amino acid sequences of the parent or reference molecule. For a protein, a functional variant is still able to function in a manner that is similar to the parent molecule. In other words, the modifications in the amino acid and/or nucleotide sequence of the parent molecule do not significantly affect or alter the functional characteristics of the molecule encoded by the nucleotide sequence or containing the amino acid sequence. The functional variant may have conservative sequence modifications including nucleotide and amino acid substitutions, additions and deletions. These modifications can be introduced by standard techniques known in the art, such as site-directed mutagenesis and random PCR-mediated mutagenesis. Functional variants can also include, but are not limited to, derivatives that are substantially similar in primary structural sequence, but which contain, e.g., in vitro or in vivo modifications, chemical and/or biochemical, that are not found in the parent molecule. Such modifications include, inter alia, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI-anchor formation, hydroxylation, iodination, methylation, myristoylation, oxidation, pegylation, proteolytic processing, phosphorylation, prenylation, racemization, selenoylation, sulfation, transfer-RNA-mediated addition of amino acids to proteins such as arginylation, ubiquitination, and the like.

In one aspect, a second transgene included in second polynucleotides of nucleic acid molecules provided herein encodes a cytokine, a chemokine, or an interleukin. Exemplary cytokines include interferons, TNF-α, TGF-β, G-CSF, and GM-CSF. Exemplary chemokines include CCL3, CCL26, and CXCL7. Exemplary interleukins include IL-I, IL-2, IL-3, IL-4, IL-5, IL-6, IL-7, IL-8, IL-10, IL-12, IL-15, IL-18, IL-21, and IL-23. Any transgene or combination of transgenes encoding any cytokine, chemokine, interleukin, or combinations thereof, can be included in second polynucleotides of nucleic acid molecules provided herein.

In one aspect, first and second transgenes included in second polynucleotides of nucleic acid molecules provided herein encode viral proteins, bacterial proteins, fungal proteins, protozoan proteins, parasite proteins, tumor proteins, immunomodulatory proteins, or any combination thereof. In yet another aspect, first, second, third, fourth, fifth, sixth, seventh, eighth, ninth, tenth, or more transgenes included in second polynucleotides of nucleic acid molecules provided herein encode viral proteins, bacterial proteins, fungal proteins, protozoan proteins, parasite proteins, tumor proteins, immunomodulatory proteins, or any combination thereof.

DNA and RNA Molecules

Nucleic acid molecules provided herein can be DNA molecules or RNA molecules. It will be appreciated that T present in DNA is substituted with U in RNA, and vice versa. In one aspect, nucleic acid molecules provided herein are DNA molecules. In another aspect, DNA molecules provided herein further comprise a promoter. As used herein, the term "promoter" refers to a regulatory sequence that initiates transcription. A promoter can be operably linked to first and second polynucleotides of nucleic acid molecules provided herein. Generally, promoters included in DNA molecules provided herein include promoters for in vitro transcription (IVT). Any suitable promoter for in vitro transcription can be included in DNA molecules provided herein, such as a T7 promoter, a T3 promoter, an SP6 promoter, and others. In one aspect, DNA molecules provided herein comprise a T7 promoter. In another aspect, the promoter is located 5' of the 5' UTR included in DNA molecules provided herein. In yet another aspect, the promoter is a T7 promoter located 5' of the 5' UTR included in DNA molecules provided herein. In yet another aspect, the promoter overlaps with the 5' UTR. A promoter and a 5' UTR can overlap by about one nucleotide, about two nucleotides, about three nucleotides, about four nucleotides, about five nucleotides, about six nucleotides, about seven nucleotides, about eight nucleotides, about nine nucleotides, about ten nucleotides, about 11 nucleotides, about 12 nucleotides, about 13 nucleotides, about 14 nucleotides, about 15 nucleotides, about 16 nucleotides, about 17 nucleotides, about 18 nucleotides, about 19 nucleotides, about 20 nucleotides, about 21 nucleotides, about 22 nucleotides, about 23 nucleotides, about 24 nucleotides, about 25 nucleotides, about 26 nucleotides, about 27 nucleotides, about 28 nucleotides, about 29 nucleotides, about 30 nucleotides, about 31 nucleotides, about 32 nucleotides, about 33 nucleotides, about 34 nucleotides, about 35 nucleotides, about 36 nucleotides, about 37 nucleotides, about 38 nucleotides, about 39 nucleotides, about 40 nucleotides, about 41 nucleotides, about 42 nucleotides, about 43 nucleotides, about 44 nucleotides, about 45 nucleotides, about 46 nucleotides, about 47 nucleotides, about 48 nucleotides, about 49 nucleotides, about 50 nucleotides, or more nucleotides.

In some aspects, DNA molecules provided herein include a promoter for in vivo transcription. Generally, the promoter for in vivo transcription is an RNA polymerase II (RNA pol II) promoter. Any RNA pol II promoter can be included in DNA molecules provided herein, including constitutive promoters, inducible promoters, and tissue-specific promoters. Exemplary constitutive promoters include a cytomegalovirus (CMV) promoter, an EF1α promoter, an SV40 promoter, a PGK1 promoter, a Ubc promoter, a human beta actin promoter, a CAG promoter, and others. Any tissue-specific promoter can be included in DNA molecules provided herein. In one aspect, the RNA pol II promoter is a muscle-specific promoter, skin-specific promoter, subcutaneous tissue-specific promoter, liver-specific promoter, spleen-specific promoter, lymph node-specific promoter, or a promoter with any other tissue specificity. DNA molecules provided herein can also include an enhancer. Any enhancer that increases transcription can be included in DNA molecules provided herein.

In some aspects, nucleic acid molecules provided herein are RNA molecules. An RNA molecule provided herein can be generated by in vitro transcription (IVT) of DNA molecules provided herein. In one aspect, RNA molecules provided herein are self-replicating RNA molecules. In another aspect, RNA molecules provided herein further comprise a 5' cap. Any 5' cap can be included in RNA molecules provided herein, including 5' caps having a Cap 1 structure, a Cap 1 (m6A) structure, a Cap 2 structure, a Cap 0 structure, or any combination thereof. In one aspect, RNA molecules provided herein include a 5' cap having Cap 1 structure. In yet another aspect, RNA molecules provided herein are self-replicating RNA molecules comprising a 5' cap having a Cap 1 structure. In a further aspect, RNA molecules provided herein comprise a cap having a Cap 1 structure, wherein a m7G is linked via a 5'-5' triphosphate to the 5' end of the 5' UTR. In yet a further aspect, RNA molecules provided herein comprise a cap having a Cap 1 structure, wherein a m7G is linked via a 5'-5' triphosphate to the 5' end of the 5' UTR comprising a sequence of SEQ ID NO:73. Any method of capping can be used, including, but not limited to using a Vaccinia Capping enzyme (New England Biolabs, Ipswich, Mass.) and co-transcriptional capping or capping at or shortly after initiation of in vitro transcription (IVT), by for example, including a capping agent as part of an in vitro transcription (IVT) reaction. (Nuc. Acids Symp. (2009) 53:129).

Provided herein, in some embodiments, are nucleic acid molecules comprising (a) a sequence of SEQ ID NO:78; or (b) a sequence of SEQ ID NO:72, SEQ ID NO:73, SEQ ID NO:76, and SEQ ID NO:77, wherein T is substituted with U. In one aspect, nucleic acid molecules provided herein are RNA molecules. In another aspect, RNA molecules provided herein further comprise a 5' cap having a Cap 1 structure. Any RNA molecules provided herein can be self-replicating RNA molecules.

Only those mRNAs that carry the Cap structure are active in Cap dependent translation; "decapitation" of mRNA results in an almost complete loss of their template activity for protein synthesis (Nature, 255:33-37, (1975); J. Biol. Chem., vol. 253:5228-5231, (1978); and Proc. Natl. Acad. Sci. USA, 72:1189-1193, (1975)).

Another element of eukaryotic mRNA is the presence of 2'-O-methyl nucleoside residues at transcript position 1 (Cap 1), and in some cases, at transcript positions 1 and 2 (Cap 2). The 2'-O-methylation of mRNA provides higher efficacy of mRNA translation in vivo (Proc. Natl. Acad. Sci. USA, 77:3952-3956 (1980)) and further improves nuclease stability of the 5'-capped mRNA. The mRNA with Cap 1 (and Cap 2) is a distinctive mark that allows cells to recognize the bona fide mRNA 5' end, and in some instances, to discriminate against transcripts emanating from infectious genetic elements (Nucleic Acid Research 43: 482-492 (2015)).

Some examples of 5' cap structures and methods for preparing mRNAs comprising the same are given in WO2015/051169A2, WO/2015/061491, US 2018/0273576, and U.S. Pat. Nos. 8,093,367, 8,304,529, and 10,487,105. In some embodiments, the 5' cap is m7GpppAmpG, which is known in the art. In some embodiments, the 5' cap is m7GpppG or m7GpppGm, which are known in the art. Structural formulas for embodiments of 5' cap structures are provided below.

In some embodiments, a self-replicating RNA of the disclosure comprises a 5' cap having the structure of Formula (Cap I).

(Cap I)

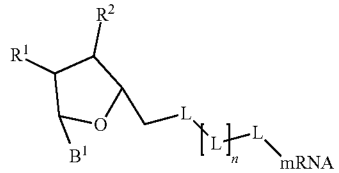

wherein $B^1$ is a natural or modified nucleobase; $R^1$ and $R^2$ are each independently selected from a halogen, OH, and $OCH_3$; each L is independently selected from the group consisting of phosphate, phophorothioate, and boranophosphate wherein each L is linked by diester bonds; n is 0 or 1. and mRNA represents an mRNA of the present disclosure linked at its 5' end. In some embodiments $B^1$ is G, $m^7G$, or A. In some embodiments, n is 0. In some embodiments n is 1. In some embodiments, $B^1$ is A or $m^6A$ and $R^1$ is $OCH_3$;

wherein G is guanine, $m^7G$ is 7-methylguanine, A is adenine, and $m^6A$ is $N^6$-methyladenine.

In some embodiments, a self-replicating RNA of the disclosure comprises a 5' cap having the structure of Formula (Cap II).

(Cap II)

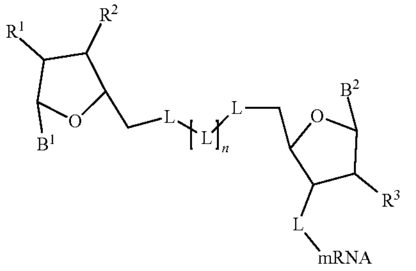

wherein $B^1$ and $B^2$ are each independently a natural or modified nucleobase; $R^1$, $R^2$, and $R^3$ are each independently selected from a halogen, OH, and $OCH_3$, each L is independently selected from the group consisting of phosphate, phophorothioate, and boranophosphate wherein each L is linked by diester bonds; mRNA represents an mRNA of the present disclosure linked at its 5' end; and n is 0 or 1. In some embodiments $B^1$ is G, $m^7G$, or A. In some embodiments, n is 0. In some embodiments, n is 1. In some embodiments, $B^1$ is A or $m^6A$ and $R^1$ is $OCH_3$; wherein G is guanine, $m^7G$ is 7-methylguanine, A is adenine, and $m^6A$ is $N^6$-methyladenine.

In some embodiments, a self-replicating RNA of the disclosure comprises a 5' cap having the structure of Formula (Cap III).

(Cap III)

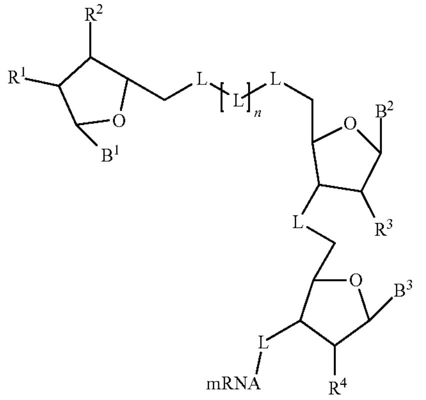

wherein $B^1$, $B^2$, and $B^3$ are each independently a natural or modified nucleobase; $R^1$, $R^2$, $R^3$, and $R^4$ are each independently selected from a halogen, OH, and $OCH_3$; each L is independently selected from the group consisting of phosphate, phosphorothioate, and boranophosphate wherein each L is linked by diester bonds; mRNA represents an mRNA of the present disclosure linked at its 5' end; and n is 0 or 1. In some embodiments, at least one of $R^1$, $R^2$, $R^3$, and $R^4$ is OH. In some embodiments $B^1$ is G, $m^7G$, or A. In some embodiments, $B^1$ is A or $m^6A$ and $R^1$ is $OCH_3$; wherein G is guanine, $m^7G$ is 7-methylguanine, A is adenine, and $m^6A$ is $N^6$-methyladenine. In some embodiments, n is 1.

In some embodiments, a self-replicating RNA of the disclosure comprises a m7GpppG 5' cap analog having the structure of Formula (Cap IV).

(Cap IV)

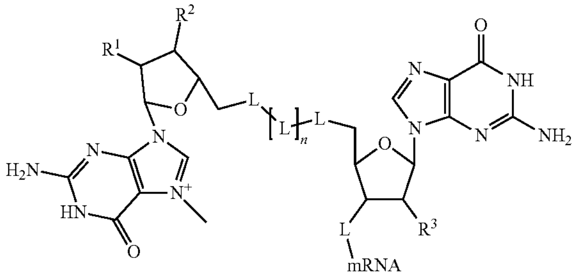

wherein, $R^1$, $R^2$, and $R^3$ are each independently selected from a halogen, OH, and $OCH_3$, each L is independently selected from the group consisting of phosphate, phosphorothioate, and boranophosphate wherein each L is linked by diester bonds; mRNA represents an mRNA of the present disclosure linked at its 5' end; n is 0 or 1. In some embodiments, at least one of $R^1$, $R^2$, and $R^3$ is OH. In some embodiments, the 5' cap is $m^7GpppG$ wherein $R^1$, $R^2$, and $R^3$ are each OH, n is 1, and each L is a phosphate. In some embodiments, n is 1. In some embodiments, the 5' cap is m7GpppGm, wherein $R^1$ and $R^2$ are each OH, $R^3$ is $OCH_3$, each L is a phosphate, mRNA is the mRNA encoding an enzyme having OTC activity linked at its 5' end, and n is 1.

In some embodiments, a self-replicating RNA of the disclosure comprises a m7Gpppm7G 5' cap analog having the structure of Formula (Cap V).

(Cap V)

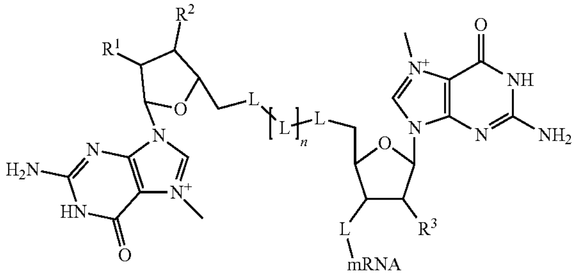

wherein, $R^1$, $R^2$, and $R^3$ are each independently selected from a halogen, OH, and $OCH_3$, each L is independently selected from the group consisting of phosphate, phosphorothioate, and boranophosphate wherein each L is linked by diester bonds; mRNA represents an mRNA of the present disclosure linked at its 5' end; and n is 0 or 1. In some embodiments, at least one of $R^1$, $R^2$, and $R^3$ is OH. In some embodiments, n is 1.

In some embodiments, a self-replicating RNA of the disclosure comprises a m7Gpppm7GpN, 5' cap analog, wherein N is a natural or modified nucleotide, the 5' cap analog having the structure of Formula (Cap VI).

(Cap VI)

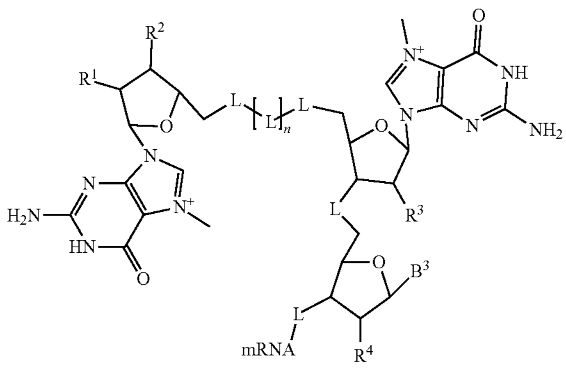

wherein $B^3$ is a natural or modified nucleobase; $R^1$, $R^2$, $R^3$, and $R^4$ are each independently selected from a halogen, OH, and $OCH_3$, each L is independently selected from the group consisting of phosphate, phosphorothioate, and boranophosphate wherein each L is linked by diester bonds; mRNA represents an mRNA of the present disclosure linked at its 5' end; and n is 0 or 3. In some embodiments, at least one of $R^1$, $R^2$, $R^3$, and $R^4$ is OH. In some embodiments $B^1$ is G, $m^7G$, or A. In some embodiments, $B^1$ is A or $m^6A$ and $R^1$ is $OCH_3$; wherein G is guanine, $m^7G$ is 7-methylguanine, A is adenine, and $m^6A$ is $N^6$-methyladenine. In some embodiments, n is 1.

In some embodiments, a self-replicating RNA of the disclosure comprises a m7Gpppm7GpG 5' cap analog having the structure of Formula (Cap VII).

(Cap VII)

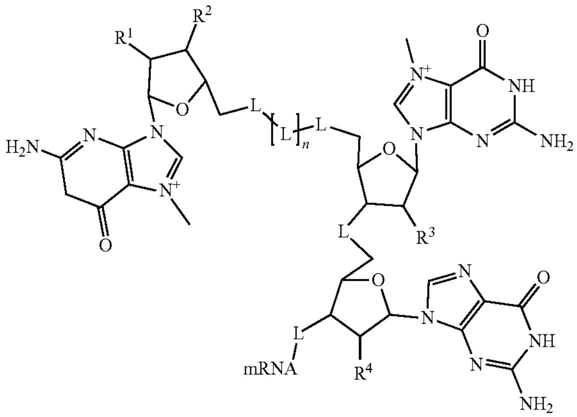

wherein, $R^1$, $R^2$, $R^3$, and $R^4$ are each independently selected from a halogen, OH, and $OCH_3$, each L is independently selected from the group consisting of phosphate, phosphorothioate, and boranophosphate wherein each L is linked by diester bonds; mRNA represents an mRNA of the present disclosure linked at its 5' end; and n is 0 or 1. In some embodiments, at least one of $R^1$, $R^2$, $R^3$, and $R^4$ is OH. In some embodiments, n is 1.

In some embodiments, a self-replicating RNA of the disclosure comprises a m7Gpppm7Gpm7G 5' cap analog having the structure of Formula (Cap VIII).

(Cap VIII)

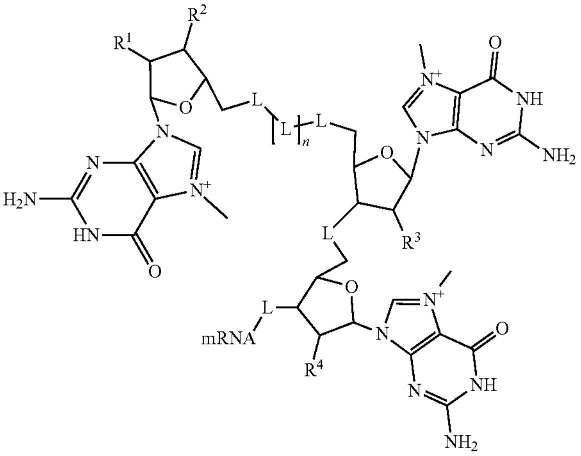

wherein, $R^1$, $R^2$, $R^3$, and $R^4$ are each independently selected from a halogen, OH, and $OCH_3$, each L is independently selected from the group consisting of phosphate, phosphorothioate, and boranophosphate wherein each L is linked by diester bonds; mRNA represents an mRNA of the present disclosure linked at its 5' end; n is 0 or 1. In some embodiments, at least one of $R^1$, $R^2$, $R^3$, and $R^4$ is OH. In some embodiments, n is 1.

In some embodiments, a self-replicating RNA of the disclosure comprises a m7GpppA 5' cap analog having the structure of Formula (Cap IX).

(Cap IX)

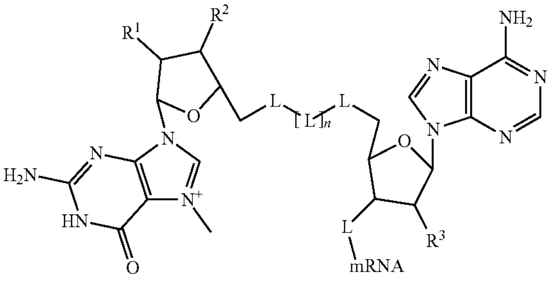

wherein, $R^1$, $R^2$, and $R^3$ are each independently selected from a halogen, OH, and $OCH_3$, each L is independently selected from the group consisting of phosphate, phosphorothioate, and boranophosphate wherein each L is linked by diester bonds; mRNA represents an mRNA of the present disclosure linked at its 5' end; and n is 0 or 1. In some embodiments, at least one of $R^1$, $R^2$, and $R^3$ is OH. In some embodiments, n is 1.

In some embodiments, a self-replicating RNA of the disclosure comprises a m7GpppApN 5' cap analog, wherein N is a natural or modified nucleotide, and the 5' cap has the structure of Formula (Cap X).

(Cap X)

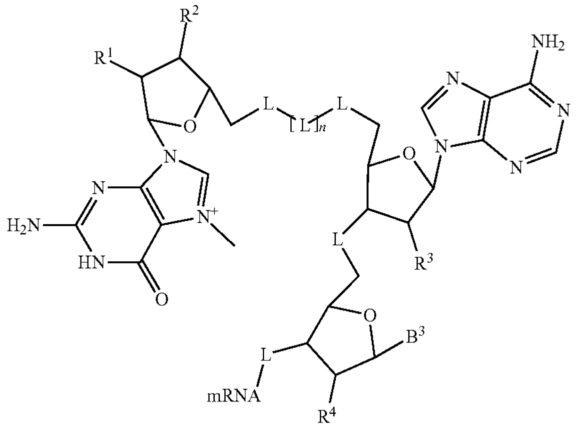

wherein $B^3$ is a natural or modified nucleobase; $R^1$, $R^2$, $R^3$, and $R^4$ are each independently selected from a halogen, OH, and $OCH_3$, each L is independently selected from the group consisting of phosphate, phosphorothioate, and boranophosphate wherein each L is linked by diester bonds; mRNA represents an mRNA of the present disclosure linked at its 5' end; and n is 0 or 1. In some embodiments, at least one of $R^1$, $R^2$, $R^3$, and $R^4$ is OH. In some embodiments $B^3$ is G, $m^7G$, A or $m^6A$; wherein G is guanine, $m^7G$ is 7-methylguanine, A is adenine, and $m^6A$ is $N^6$-methyladenine. In some embodiments, n is 1.

In some embodiments, a self-replicating RNA of the disclosure comprises a m7GpppAmpG 5' cap analog having the structure of Formula (Cap XI).

(Cap XI)

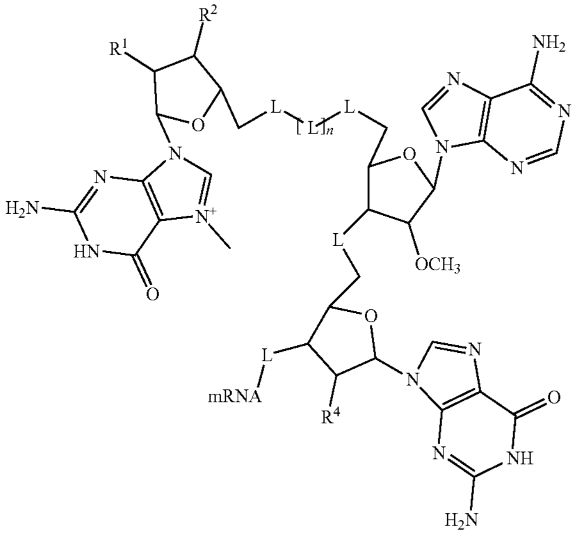

wherein, $R^1$, $R^2$, and $R^4$ are each independently selected from a halogen, OH, and $OCH_3$, each L is independently selected from the group consisting of phosphate, phosphorothioate, and boranophosphate wherein each L is linked by diester bonds; mRNA represents an mRNA of the present disclosure linked at its 5' end; and n is 0 or 1. In some embodiments, at least one of $R^1$, $R^2$, and $R^4$ is OH. In some embodiments, the compound of Formula Cap XI is $m^7GpppAmpG$, wherein $R^1$, $R^2$, and $R^4$ are each OH, n is 1, and each L is a phosphate linkage. In some embodiments, n is 1.

In some embodiments, a self-replicating RNA of the disclosure comprises a m7GpppApm7G 5' cap analog having the structure of Formula (Cap XII).

(Cap XII)

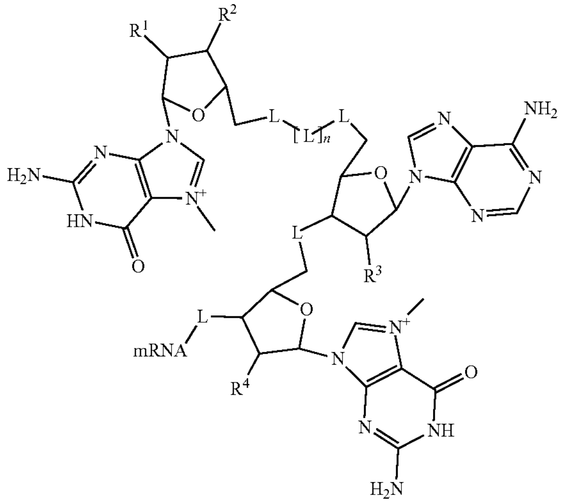

wherein, $R^1$, $R^2$, $R^3$, and $R^4$ are each independently selected from a halogen, OH, and $OCH_3$, each L is independently selected from the group consisting of phosphate, phosphorothioate, and boranophosphate wherein each L is linked by diester bonds; mRNA represents an mRNA of the present disclosure linked at its 5' end; and n is 0 or 1. In some embodiments, at least one of $R^1$, $R^2$, $R^3$, and $R^4$ is OH. In some embodiments, n is 1.

In some embodiments, a self-replicating RNA of the disclosure comprises a m7GpppAmpm7G 5' cap analog having the structure of Formula (Cap XIII).

(Cap XIII)

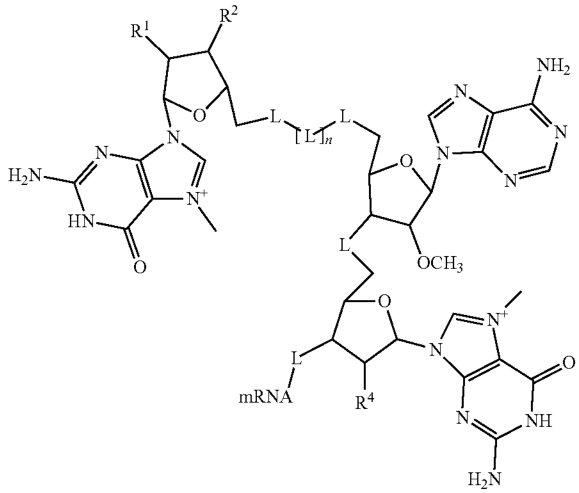

wherein, $R^1$, $R^2$, and $R^4$ are each independently selected from a halogen, OH, and $OCH_3$, each L is independently selected from the group consisting of phosphate, phosphorothioate, and boranophosphate wherein each L is linked by diester bonds; mRNA represents an mRNA of the present disclosure linked at its 5' end; and n is 0 or 1. In some embodiments, at least one of $R^1$, $R^2$, and $R^4$ is OH. In some embodiments, n is 1.

Poly-Adenine (Poly-A) Tail

Polyadenylation is the addition of a poly(A) tail, a chain of adenine nucleotides usually about 100-120 monomers in length, to a mRNA. In eukaryotes, polyadenylation is part of the process that produces mature mRNA for translation and begins as the transcription of a gene terminates. The 3'-most segment of a newly made pre-mRNA is first cleaved off by a set of proteins; these proteins then synthesize the poly(A) tail at the 3' end. The poly(A) tail is important for the nuclear export, translation, and stability of mRNA. The tail is shortened over time, and, when it is short enough, the mRNA is enzymatically degraded. However, in a few cell types, mRNAs with short poly(A) tails are stored for later activation by re-polyadenylation in the cytosol.

Preferably, a self-replicating RNA of the disclosure comprises a 3' tail region, which can serve to protect the RNA from exonuclease degradation. The tail region may be a 3'poly(A) and/or 3'poly(C) region. Preferably, the tail region is a 3' poly(A) tail. As used herein a "3' poly(A) tail" is a polymer of sequential adenine nucleotides that can range in size from, for example: 10 to 250 sequential adenine nucleotides; 60-125 sequential adenine nucleotides, 90-125 sequential adenine nucleotides, 95-125 sequential adenine nucleotides, 95-121 sequential adenine nucleotides, 100 to 121 sequential adenine nucleotides, 110-121 sequential adenine nucleotides; 112-121 sequential adenine nucleotides; 114-121 adenine sequential nucleotides; or 115 to 121 sequential adenine nucleotides. Preferably, a 3' poly(A) tail as described herein comprise 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, or 125 sequential adenine nucleotides. 3' Poly(A) tails can be added using a variety of methods known in the art, e.g., using poly(A) polymerase to add tails to synthetic or in vitro transcribed RNA. Other methods include the use of a transcription vector to encode poly(A) tails or the use of a ligase (e.g., via splint ligation using a T4 RNA ligase and/or T4 DNA ligase), wherein poly(A) may be ligated to the 3' end of a sense RNA. In some embodiments, a combination of any of the above methods is utilized.

Design and Synthesis of Self-Replicating RNA

The constructs for exemplary self-replicating RNA sequences of the present disclosure are provided in Table 4.

TABLE 4

Comparison of STARR™ self-replicating RNA of the disclosure with comparative self-replicating RNA as described

| Construct | Position | Sequence Type | Sequence |
|---|---|---|---|
| STARR™ (SEQ ID NO: 49) | 5′ UTR | nucleotide | ATGGGCGGCGCATGAGAGAAGCCCAGACCAATTACCT ACCCAAA |
| STARR™ (SEQ ID NO: 50) | non-structural gene ORF | nucleotide | ATGGAGAAAGTTCACGTTGACATCGAGGAAGACAGCC CATTCCTCAGAGCTTTGCAGCGGAGCTTCCCGCAGTTT GAGGTAGAAGCCAAGCAGGTCACTGATAATGACCATG CTAATGCCAGAGCGTTTTCGCATCTGGCTTCAAAACTG ATCGAAACGGAGGTGGACCCATCCGACACGATCCTTG ACATTGGAAGTGCGCCCGCCCGCAGAATGTATTCTAA GCACAAGTATCATTGTATCTGTCCGATGAGATGTGCGG AAGATCCGGACAGATTGTATAAGTATGCAACTAAGCT GAAGAAAAACTGTAAGGAAATAACTGATAAGGAATTG GACAAGAAAATGAAGGAGCTGGCCGCCGTCATGAGCG ACCCTGACCTGGAAACTGAGACTATGTGCCTCCACGA CGACGAGTCGTGTCGCTACGAAGGGCAAGTCGCTGTT TACCAGGATGTATACGCCGTCGACGGCCCCACCAGCC TGTACCACCAGGCCAACAAGGGCGTGAGGGTGGCCTA CTGGATCGGCTTCGACACCACACCCTTCATGTTCAAGA ACCTGGCCGGCGCCTACCCCAGCTACAGCACCAACTG GGCCGACGAGACCGTGCTGACCGCCAGGAACATCGGC CTGTGCAGCAGCGACGTGATGGAGAGGAGCCGGAGAG GCATGAGCATCCTGAGGAAGAAATACCTGAAGCCCAG CAACAACGTGCTGTTCAGCGTGGGCAGCACCATCTAC CACGAGAAGAGGGACCTGCTCAGGAGCTGGCACCTGC CCAGCGTGTTCCACCTGAGGGGCAAGCAGAACTACAC CTGCAGGTGCGAGACCATCGTGAGCTGCGACGGCTAC GTGGTGAAGAGGATCGCCATCAGCCCCGGCCTGTACG GCAAGCCCAGCGGCTACGCCGCTACAATGCACAGGGA GGGCTTCCTGTGCTGCAAGGTGACCGACACCCTGAAC GGCGAGAGGGTGAGCTTCCCCGTGTGCACCTACGTGC CCGCCACCCTGTGCGACCAGATGACCGGCATCCTGGC CACCGACGTGAGCGCCGACGACGCCCAGAAGCTGCTC GTGGGCCTGAACCAGAGGATCGTGGTCAACGGCAGGA CCCAGAGGAACACCAACACAATGAAGAACTACCTGCT GCCCGTGGTGGCCCAGGCTTTCGCCAGGTGGGCCAAG GAGTACAAGGAGGACCAGGAAGACGAGAGGCCCCTG GGCCTGAGGGACAGGCAGCTGGTGATGGGCTGCTGCT GGGCCTTCAGGCGGCACAAGATCACCAGCATCTACAA GAGGCCCGACACCCAGACCATCATCAAGGTGAACAGC GACTTCCACAGCTTCGTGCTGCCCAGGATCGGCAGCA ACACCCTGGAGATCGGCCTGAGGACCCGGATCAGGAA |

TABLE 4-continued

Comparison of STARR$^{TM}$ self-replicating RNA of the disclosure with comparative self-replicating RNA as described

| Construct | Position | Sequence Type | Sequence |
|---|---|---|---|
| | | | GATGCTGGAGGAACACAAGGAGCCCAGCCCACTGATC<br>ACCGCCGAGGACGTGCAGGAGGCCAAGTGCGCTGCCG<br>ACGAGGCCAAGGAGGTGAGGGAGGCCGAGGAACTGA<br>GGGCCGCCCTGCCACCCCTGGCTGCCGACGTGGAGGA<br>ACCCACCCTGGAAGCCGACGTGGACCTGATGCTGCAG<br>GAGGCCGGCGCCGGAAGCGTGGAGACACCCAGGGGC<br>CTGATCAAGGTGACCAGCTACGACGGCGAGGACAAGA<br>TCGGCAGCTACGCCGTGCTGAGCCCACAGGCCGTGCT<br>GAAGTCCGAGAAGCTGAGCTGCATCCACCCACTGGCC<br>GAGCAGGTGATCGTGATCACCCACAGCGGCAGGAAGG<br>GCAGGTACGCCGTGGAGCCCTACCACGGCAAGGTGGT<br>CGTGCCCGAGGGCCACGCCATCCCCGTGCAGGACTTC<br>CAGGCCCTGAGCGAGAGCGCCACCATCGTGTACAACG<br>AGAGGGAGTTCGTGAACAGGTACCTGCACCATATCGC<br>CACCCACGGCGGAGCCCTGAACACCGACGAGGAATAC<br>TACAAGACCGTGAAGCCCAGCGAGCACGACGGCGAGT<br>ACCTGTACGACATCGACAGGAAGCAGTGCGTGAAGAA<br>AGAGCTGGTGACCGGCCTGGGACTGACCGGCGAGCTG<br>GTGGACCCACCCTTCCACGAGTTCGCCTACGAGAGCCT<br>GAGGACCAGACCCGCCGCTCCCTACCAGGTGCCCACC<br>ATCGGCGTGTACGGCGTGCCCGGCAGCGGAAAGAGCG<br>GCATCATCAAGAGCGCCGTGACCAAGAAAGACCTGGT<br>GGTCAGCGCCAAGAAAGAGAACTGCGCCGAGATCATC<br>AGGGACGTGAAGAAGATGAAAGGCCTGGACGTGAAC<br>GCGCGCACCGTGGACAGCGTGCTGCTGAACGGCTGCA<br>AGCACCCCGTGGAGACCCTGTACATCGACGAGGCCTT<br>CGCTTGCCACGCCGGCACCCTGAGGGCCCTGATCGCC<br>ATCATCAGGCCCAAGAAAGCCGTGCTGTGCGGCGACC<br>CCAAGCAGTGCGGCTTCTTCAACATGATGTGCCTGAAG<br>GTGCACTTCAACCACGAGATCTGCACCCAGGTGTTCCA<br>CAAGAGCATCAGCAGGCGGTGCACCAAGAGCGTGACC<br>AGCGTCGTGAGCACCCTGTTCTACGACAAGAAAATGA<br>GGACCACCAACCCCAAGGAGACCAAAATCGTGATCGA<br>CACCACAGGCAGCACCAAGCCCAAGCAGGACGACCTG<br>ATCCTGACCTGCTTCAGGGGCTGGGTGAAGCAGCTGC<br>AGATCGACTACAAGGGCAACGAGATCATGACCGCCGC<br>TGCCAGCCAGGGCCTGACCAGGAAGGGCGTGTACGCC<br>GTGAGGTACAAGGTGAACGAGAACCCACTGTACGCTC<br>CCACCAGCGAGCACGTGAACGTGCTGCTGACCAGGAC<br>CGAGGACAGGATCGTGTGGAAGACCCTGGCCGGCGAC<br>CCCTGGATCAAGACCCTGACCGCCAAGTACCCCGGCA<br>ACTTCACCGCCACCATCGAAGAGTGGCAGGCCGAGCA<br>CGACGCCATCATGAGGCACATCCTGGAGAGGCCCGAC<br>CCCACCGACGTGTTCCAGAACAAGGCCAACGTGTGCT<br>GGGCCAAGGCCCTGGTGCCCGTGCTGAAGACCGCCGG<br>CATCGACATGACCACAGAGCAGTGGAACACCGTGGAC<br>TACTTCGAGACCGACAAGGCCCACAGCGCCGAGATCG<br>TGCTGAACCAGCTGTGCGTGAGGTTCTTCGGCCTGGAC<br>CTGGACAGCGGCCTGTTCAGCGCCCCCACCGTGCCACT<br>GAGCATCAGGAACAACCACTGGGACAACAGCCCCAGC<br>CCAAACATGTACGGCCTGAACAAGGAGGTGGTCAGGC<br>AGCTGAGCAGGCGGTACCCACAGCTGCCCAGGGCCGT<br>GGCCACCGGCAGGGTGTACGACATGAACACCGGCACC<br>CTGAGGAACTACGACCCCAGGATCAACCTGGTGCCCG<br>TGAACAGGCGGCTGCCCCACGCCCTGGTGCTGCACCA<br>CAACGAGCACCCACAGAGCGACTTCAGCTCCTTCGTG<br>AGCAAGCTGAAAGGCAGGACCGTGCTGGTCGTGGGCG<br>AGAAGCTGAGCGTGCCCGGCAAGATGGTGGACTGGCT<br>GAGCGACAGGCCCGAGGCCACCTTCCGGGCCAGGCTG<br>GACCTCGGCATCCCCGGCGACGTGCCCAAGTACGACA<br>TCATCTTCGTGAACGTCAGGACCCCATACAAGTACCAC<br>CATTACCAGCAGTGCGAGGACCACGCCATCAAGCTGA<br>GCATGCTGACCAAGAAGGCCTGCCTGCACCTGAACCC<br>CGGAGGCACCTGCGTGAGCATCGGCTACGGCTACGCC<br>GACAGGGCCAGCGAGAGCATCATTGGCGCCATCGCCA<br>GGCTGTTCAAGTTCAGCAGGGTGTGCAAACCCAAGAG<br>CAGCCTGGAGGAAACCGAGGTGCTGTTCGTGTTCATC<br>GGCTACGACCGGAAGGCCAGGACCCACAACCCCTACA<br>AGCTGAGCAGCACCCTGACAAACATCTACACCGGCAG<br>CAGGCTGCACGAGGCCGGCTGCGCCCCCAGCTACCAC<br>GTGGTCAGGGGCGATATCGCCACCGCCACCGAGGGCG<br>TGATCATCAACGCTGCCAACAGCAAGGGCCAGCCCGG<br>AGGCGGAGTGTGCGGCGCCCTGTACAAGAAGTTCCCC<br>GAGAGCTTCGACCTGCAGCCCATCGAGGTGGGCAAGG |

TABLE 4-continued

Comparison of STARR™ self-replicating RNA of the disclosure with comparative self-replicating RNA as described

| Construct | Position | Sequence Type | Sequence |
|---|---|---|---|
| | | | CCAGGCTGGTGAAGGGCGCCGCTAAGCACATCATCCA |
| | | | CGCCGTGGGCCCCAACTTCAACAAGGTGAGCGAGGTG |
| | | | GAAGGCGACAAGCAGCTGGCCGAAGCCTACGAGAGC |
| | | | ATCGCCAAGATCGTGAACGACAATAACTACAAGAGCG |
| | | | TGGCCATCCCACTGCTCAGCACCGGCATCTTCAGCGGC |
| | | | AACAAGGACAGGCTGACCCAGAGCCTGAACCACCTGC |
| | | | TCACCGCCCTGGACACCACCGATGCCGACGTGGCCAT |
| | | | CTACTGCAGGGACAAGAAGTGGGAGATGACCCTGAAG |
| | | | GAGGCCGTGGCCAGGCGGGAGGCCGTGGAAGAGATCT |
| | | | GCATCAGCGACGACTCCAGCGTGACCGAGCCCGACGC |
| | | | CGAGCTGGTGAGGGTGCACCCCAAGAGCTCCCTGGCC |
| | | | GGCAGGAAGGGCTACAGCACCAGCGACGGCAAGACCT |
| | | | TCAGCTACCTGGAGGGCACCAAGTTCCACCAGGCCGC |
| | | | TAAGGACATCGCCGAGATCAACGCTATGTGGCCCGTG |
| | | | GCCACCGAGGCCAACGAGCAGGTGTGCATGTACATCC |
| | | | TGGGCGAGAGCATGTCCAGCATCAGGAGCAAGTGCCC |
| | | | CGTGGAGGAAAGCGAGGCCAGCACACCACCCAGCACC |
| | | | CTGCCCTGCCTGTGCATCCACGCTATGACACCCGAGAG |
| | | | GGTGCAGCGGCTGAAGGCCAGCAGGCCCGAGCAGATC |
| | | | ACCGTGTGCAGCTCCTTCCCACTGCCCAAGTACAGGAT |
| | | | CACCGGCGTGCAGAAGATCCAGTGCAGCCAGCCCATC |
| | | | CTGTTCAGCCCAAAGGTGCCCGCCTACATCCACCCCAG |
| | | | GAAGTACCTGGTGGAGACCCCACCCGTGGACGAGACA |
| | | | CCCGAGCCAAGCGCCGAGAACCAGAGCACCGAGGGC |
| | | | ACACCCGAGCAGCCACCCCTGATCACCGAGGACGAGA |
| | | | CAAGGACCCGGACCCCAGAGCCCATCATTATCGAGGA |
| | | | AGAGGAAGAGGACAGCATCAGCCTGCTGAGCGACGGC |
| | | | CCCACCCACCAGGTGCTGCAGGTGGAGGCCGACATCC |
| | | | ACGGCCCACCCAGCGTGTCCAGCTCCAGCTGGAGCAT |
| | | | CCCACACGCCAGCGACTTCGACGTGGACAGCCTGAGC |
| | | | ATCCTGGACACCCTGGAGGGCGCCAGCGTGACCTCCG |
| | | | GCGCCACCAGCGCCGAGACCAACAGCTACTTCGCCAA |
| | | | GAGCATGGAGTTCCTGGCCAGGCCCGTGCCAGCTCCC |
| | | | AGGACCGTGTTCAGGAACCCACCCCACCCAGCTCCCA |
| | | | GGACCAGGACCCCAAGCCTGGCTCCCAGCAGGGCCTG |
| | | | CAGCAGGACCAGCCTGGTGAGCACCCCACCCGGCGTG |
| | | | AACAGGGTGATCACCAGGGAGGAACTGGAGGCCCTGA |
| | | | CACCCAGCAGGACCCCCAGCAGGTCCGTGAGCAGGAC |
| | | | TAGTCTGGTGTCCAACCCACCCGGCGTGAACAGGGTG |
| | | | ATCACCAGGGAGGAATTCGAGGCCTTCGTGGCCCAGC |
| | | | AACAGAGACGGTTCGACGCCGGCGCCTACATCTTCAG |
| | | | CAGCGACACCGGCCAGGGACACCTGCAGCAAAAGAGC |
| | | | GTGAGGCAGACCGTGCTGAGCGAGGTGGTGCTGGAGA |
| | | | GGACCGAGCTGGAAATCAGCTACGCCCCCAGGCTGGA |
| | | | CCAGGAGAAGGAGGAACTGCTCAGGAAGAAACTGCA |
| | | | GCTGAACCCCACCCCAGCCAACAGGAGCAGGTACCAG |
| | | | AGCAGGAAGGTGGAGAACATGAAGGCCATCACCGCCA |
| | | | GGCGGATCCTGCAGGGCCTGGGACACTACCTGAAGGC |
| | | | CGAGGGCAAGGTGGAGTGCTACAGGACCCTGCACCCC |
| | | | GTGCCACTGTACAGCTCCAGCGTGAACAGGGCCTTCTC |
| | | | CAGCCCCAAGGTGGCCGTGGAGGCCTGCAACGCTATG |
| | | | CTGAAGGAGAACTTCCCCACCGTGGCCAGCTACTGCA |
| | | | TCATCCCCGAGTACGACGCCTACCTGGACATGGTGGA |
| | | | CGGCGCCAGCTGCTGCCTGGACACCGCCAGCTTCTGCC |
| | | | CCGCCAAGCTGAGGAGCTTCCCCAAGAAACACAGCTA |
| | | | CCTGGAGCCCACCATCAGGAGCGCCGTGCCCAGCGCC |
| | | | ATCCAGAACACCCTGCAGAACGTGCTGGCCGCTGCCA |
| | | | CCAAGAGGAACTGCAACGTGACCCAGATGAGGGAGCT |
| | | | GCCCGTGCTGGACAGCGCTGCCTTCAACGTGGAGTGCT |
| | | | TCAAGAAATACGCCTGCAACAACGAGTACTGGGAGAC |
| | | | CTTCAAGGAGAACCCCATCAGGCTGACCGAAGAGAAC |
| | | | GTGGTGAACTACATCACCAAGCTGAAGGGCCCCAAGG |
| | | | CCGCTGCCCTGTTCGCTAAGACCCACAACCTGAACATG |
| | | | CTGCAGGACATCCCAATGGACAGGTTCGTGATGGACC |
| | | | TGAAGAGGGACGTGAAGGTGACACCCGGCACCAAGCA |
| | | | CACCGAGGAGAGGCCCAAGGTGCAGGTGATCCAGGCC |
| | | | GCTGACCCACTGGCCACCGCCTACCTGTGCGGCATCCA |
| | | | CAGGGAGCTGGTGAGGCGGCTGAACGCCGTGCTGCTG |
| | | | CCCAACATCCACACCCTGTTCGACATGAGCGCCGAGG |
| | | | ACTTCGACGCCATCATCGCCGAGCACTTCCAGCCCGGC |
| | | | GACTGCGTGCTGGAGACCGACATCGCCAGCTTCGACA |
| | | | AGAGCGAGGATGACGCTATGGCCCTGACCGCTCTGAT |
| | | | GATCCTGGAGGACCTGGGCGTGGACGCCGAGCTGCTC |
| | | | ACCCTGATCGAGGCTGCCTTCGGCGAGATCAGCTCCAT |

TABLE 4-continued

Comparison of STARR™ self-replicating RNA of the disclosure with comparative self-replicating RNA as described

| Construct | Position | Sequence Type | Sequence |
|---|---|---|---|
| | | | CCACCTGCCCACCAAGACCAAGTTCAAGTTCGGCGCT<br>ATGATGAAAAGCGGAATGTTCCTGACCCTGTTCGTGA<br>ACACCGTGATCAACATTGTGATCGCCAGCAGGGTGCT<br>GCGGGAGAGGCTGACCGGCAGCCCCTGCGCTGCCTTC<br>ATCGGCGACGACAACATCGTGAAGGGCGTGAAAAGCG<br>ACAAGCTGATGGCCGACAGGTGCGCCACCTGGCTGAA<br>CATGGAGGTGAAGATCATCGACGCCGTGGTGGGCGAG<br>AAGGCCCCCTACTTCTGCGGCGGATTCATCCTGTGCGA<br>CAGCGTGACCGGCACCGCCTGCAGGGTGGCCGACCCC<br>CTGAAGAGGCTGTTCAAGCTGGGCAAGCCACTGGCCG<br>CTGACGATGAGCACGACGATGACAGGCGGAGGGCCCT<br>GCACGAGGAAAGCACCAGGTGGAACAGGGTGGGCAT<br>CCTGAGCGAGCTGTGCAAGGCCGTGGAGAGCAGGTAC<br>GAGACCGTGGGCACCAGCATCATCGTGATGGCTATGA<br>CCACACTGGCCAGCTCCGTCAAGAGCTTCTCCTACCTG<br>AGGGGGGCCCCTATAACTCTCTACGGCTAA |
| STARR™ (SEQ ID NO: 51) | non-structural gene ORF | amino acid | MEKVHVDIEEDSPFLRALQRSFPQFEVEAKQVTDNDHAN<br>ARAFSHLASKLIETEVDPSDTILDIGSAPARRMYSKHKYH<br>CICPMRCAEDPDRLYKYATKLKKNCKEITDKELDKKMK<br>ELAAVMSDPDLETETMCLHDDESCRYEGQVAVYQDVY<br>AVDGPTSLYHQANKGVRVAYWIGFDTTPFMFKNLAGAY<br>PSYSTNWADETVLTARNIGLCSSDVMERSRRGMSILRKK<br>YLKPSNNVLFSVGSTIYHEKRDLLRSWHLPSVFHLRGKQ<br>NYTCRCETIVSCDGYVVKRIAISPGLYGKPSGYAATMHR<br>EGFLCCKVTDTLNGERVSFPVCTYVPATLCDQMTGILAT<br>DVSADDAQKLLVGLNQRIVVNGRTQRNTNTMKNYLLPV<br>VAQAFARWAKEYKEDQEDERPLGLRDRQLVMGCCWAF<br>RRHKITSIYKRPDTQTIIKVNSDFHSFVLPRIGSNTLEIGLR<br>TRIRKMLEEHKEPSPLITAEDVQEAKCAADEAKEVREAE<br>ELRAALPPLAADVEEPTLEADVDLMLQEAGAGSVETPRG<br>LIKVTSYDGEDKIGSYAVLSPQAVLKSEKLSCIHPLAEQVI<br>VITHSGRKGRYAVEPYHGKVVVPEGHAIPVQDFQALSES<br>ATIVYNEREFVNRYLHHIATHGGALNTDEEYYKTVKPSE<br>HDGEYLYDIDRKQCVKKELVTGLGLTGELVDPPFHEFAY<br>ESLRTRPAAPYQVPTIGVYGVPGSGKSGIIKSAVTKKDLV<br>VSAKKENCAEIIRDVKKMKGLDVNARTVDSVLLNGCKH<br>PVETLYIDEAFACHAGTLRALIAIIRPKKAVLCGDPKQCG<br>FFNMMCLKVHFNHEICTQVFHKSISRRCTKSVTSVVSTLF<br>YDKKMRTTNPKETKIVIDTTGSTKPKQDDLILTCFRGWV<br>KQLQIDYKGNEIMTAAASQGLTRKGVYAVRYKVNENPL<br>YAPTSEHVNVLLTRTEDRIVWKTLAGDPWIKTLTAKYPG<br>NFTATIEEWQAEHDAIMRHILERPDPTDVFQNKANVCWA<br>KALVPVLKTAGIDMTTEQWNTVDYFETDKAHSAEIVLN<br>QLCVRFFGLDLDSGLFSAPTVPLSIRNNHWDNSPSPNMY<br>GLNKEVVRQLSRRYPQLPRAVATGRVYDMNTGTLRNYD<br>PRINLVPVNRRLPHALVLHHNEHPQSDFSSFVSKLKGRTV<br>LVVGEKLSVPGKMVDWLSDRPEATFRARLDLGIPGDVP<br>KYDIIFVNVRTPYKYHHYQQCEDHAIKLSMLTKKACLHL<br>NPGGTCVSIGYGYADRASESIIGAIARLFKFSRVCKPKSSL<br>EETEVLFVFIGYDRKARTHNPYKLSSTLTNIYTGSRLHEA<br>GCAPSYHVVRGDIATATEGVIINAANSKGQPGGGVCGAL<br>YKKFPESFDLQPIEVGKARLVKGAAKHIIHAVGPNFNKVS<br>EVEGDKQLAEAYESIAKIVNDNNYKSVAIPLLSTGIFSGN<br>KDRLTQSLNHLLTALDTTDADVAIYCRDKKWEMTLKEA<br>VARREAVEEICISDDSSVTEPDAELVRVHPKSSLAGRKGY<br>STSDGKTFSYLEGTKFHQAAKDIAEINAMWPVATEANEQ<br>VCMYILGESMSSIRSKCPVEESEASTPPSTLPCLCIHAMTP<br>ERVQRLKASRPEQITVCSSFPLPKYRITGVQKIQCSQPILFS<br>PKVPAYIHPRKYLVETPPVDETPEPSAENQSTEGTPEQPPL<br>ITEDETRTRTPEPIIIEEEEEDSISLLSDGPTHQVLQVEADIH<br>GPPSVSSSSWSIPHASDFDVDSLSILDTLEGASVTSGATSA<br>ETNSYFAKSMEFLARPVPAPRTVFRNPPHPAPRTRTPSLA<br>PSRACSRTSLVSTPPGVNRVITREELEALTPSRTPSRSVSR<br>TSLVSNPPGVNRVITREEFEAFVAQQQRRFDAGAYIFSSD<br>TGQGHLQQKSVRQTVLSEVVLERTELEISYAPRLDQEKE<br>ELLRKKLQLNPTPANRSRYQSRKVENMKAITARRILQGL<br>GHYLKAEGKVECYRTLHPVPLYSSSVNRAFSSPKVAVEA<br>CNAMLKENFPTVASYCIIPEYDAYLDMVDGASCCLDTAS<br>FCPAKLRSFPKKHSYLEPTIRSAVPSAIQNTLQNVLAAAT<br>KRNCNVTQMRELPVLDSAAFNVECFKKYACNNEYWETF<br>KENPIRLTEENVVNYITKLKGPKAAALFAKTHNLNMLQD<br>IPMDRFVMDLKRDVKVTPGTKHTEERPKVQVIQAADPL<br>ATAYLCGIHRELVRRLNAVLLPNIHTLFDMSAEDFDAIIA |

TABLE 4-continued

Comparison of STARR™ self-replicating RNA of the disclosure with comparative self-replicating RNA as described

| Construct | Position | Sequence Type | Sequence |
|---|---|---|---|
| | | | EHFQPGDCVLETDIASFDKSEDDAMALTALMILEDLGVD AELLTLIEAAFGEISSIHLPTKTKFKFGAMMKSGMFLTLF VNTVINIVIASRVLRERLTGSPCAAFIGDDNIVKGVKSDK LMADRCATWLNMEVKIIDAVVGEKAPYFCGGFILCDSVT GTACRVADPLKRLFKLGKPLAADDEHDDDRRRALHEES TRWNRVGILSELCKAVESRYETVGTSIIVMAMTTLASSV KSFSYLRGAPITLYG* |
| STARR™ (SEQ ID NO: 52) | intergenic region | nucleotide | CCTGAATGGACTACGACATAGTCTAGTCCGCCAAGGC CGCCACC |
| STARR™ | transgene ORF | nucleotide | n/a (depends on gene of our interest) |
| STARR™ (SEQ ID NO: 53) | 3' UTR | nucleotide | ACTCGAGTATGTTACGTGCAAAGGTGATTGTCACCCCC CGAAAGACCATATTGTGACACACCCTCAGTATCACGC CCAAACATTTACAGCCGCGGTGTCAAAAACCGCGTGG ACGTGGTTAACATCCCTGCTGGGAGGATCAGCCGTAA TTATTATAATTGGCTTGGTGCTGGCTACTATTGTGGCC ATGTACGTGCTGACCAACCAGAAACATAATTGAATAC AGCAGCAATTGGCAAGCTGCTTACATAGAACTCGCGG CGATTGGCATGCCGCCTTAAAATTTTTATTTTATTTTTT CTTTTCTTTTCCGAATCGGATTTTGTTTTTAATATTTCA AAAAAAAAAAAAAAAAAAAAAAAATCTAGAAAAAAA AAAAAAAAAAAAAAAAAAAAAAAAAAAAAAAAAAA AAAAAAAAAAAAAAAAAAAAAAAAAAAAAAAAAAA AAAAAAAAAAAAAAAAAAAAAA |
| Comparitive | 5' UTR | nucleotide | unknown |
| Original (SEQ ID NO: 54) | non-structural gene ORF | nucleotide | ATGCCCGAGAAGGTGCACGTGGACATCGAGGAGGACA GCCCCTTCCTGAGGGCCCTGCAGAGGAGCTTCCCACA GTTCGAAGTGGAGGCCAAGCAGGTGACCGACAACGAC CACGCCAACGCCAGGGCCTTCAGCCACCTGGCCAGCA AGCTGATCGAGACCGAGGTGGACCCCAGCGACACCAT CCTGGACATCGGCAGCGCCCCAGCCAGGAGAATGTAC AGCAAGCACAAGTACCACTGCATCTGCCCCATGAGGT GCGCCGAGGACCCCGACAGGCTGTACAAGTACGCCAC CAAACTGAAGAAGAACTGCAAGGAGATCACCGACAA GGAGCTGGACAAGAAAATGAAGGAGCTGGCCGCCGTG ATGAGCGACCCCGACCTGGAGACCGAGACAATGTGCC TGCACGACGACGAGAGCTGCAGGTACGAGGGCCAGGT GGCCGTCTACCAGGACGTGTACGCCGTCGACGGCCCC ACCAGCCTGTACCACCAGGCCAACAAGGGCGTGAGGG TGGCCTACTGGATCGGCTTCGACACCACACCCTTCATG TTCAAGAACCTGGCCGGCGCCTACCCCAGCTACAGCA CCAACTGGGCCGACGAGACCGTGCTGACCGCCAGGAA CATCGGCCTGTGCAGCAGCGACGTGATGGAGAGGAGC CGGAGAGGCATGAGCATCCTGAGGAAGAAATACCTGA AGCCCAGCAACAACGTGCTGTTCAGCGTGGGCAGCAC CATCTACCACGAGAAGAGGGACCTGCTCAGGAGCTGG CACCTGCCCAGCGTGTTCCACCTGAGGGGCAAGCAGA ACTACACCTGCAGGTGCGAGACCATCGTGAGCTGCGA CGGCTACGTGGTGAAGAGGATCGCCATCAGCCCCGGC CTGTACGGCAAGCCCAGCGGCTACGCCGCTACAATGC ACAGGGAGGGCTTCCTGTGCTGCAAGGTGACCGACAC CCTGAACGGCGAGAGGGTGAGCTTCCCCGTGTGCACC TACGTGCCCGCCACCCTGTGCGACCAGATGACCGGCA TCCTGGCCACCGACGTGAGCGCCGACGACGCCCAGAA GCTGCTCGTGGGCCTGAACCAGAGGATCGTGGTCAAC GGCAGGACCCAGAGGAACACCAACACAATGAAGAAC TACCTGCTGCCCGTGGTGGCCCAGGCTTTCGCCAGGTG GGCCAAGGAGTACAAGGAGGACCAGGAAGACGAGAG GCCCCTGGGCCTGAGGGACAGGCAGCTGGTGATGGGC TGCTGCTGGGCCTTCAGGCGGCACAAGATCACCAGCA TCTACAAGAGGCCCGACACCCAGACCATCATCAAGGT GAACAGCGACTTCCACAGCTTCGTGCTGCCCAGGATC GGCAGCAACACCCTGGAGATCGGCCTGAGGACCCGGA TCAGGAAGATGCTGGAGGAACACAAGGAGCCCAGCCC ACTGATCACCGCCGAGGACGTGCAGGAGGCCAAGTGC GCTGCCGACGAGGCCAAGGAGGTGAGGGAGGCCGAG GAACTGAGGGCCGCCCTGCCACCCCTGGCTGCCGACG TGGAGGAACCCACCCTGGAAGCCGACGTGGACCTGAT |

TABLE 4-continued

Comparison of STARR™ self-replicating RNA of the disclosure with comparative self-replicating RNA as described

| Construct | Position | Sequence Type | Sequence |
|---|---|---|---|
| | | | GCTGCAGGAGGCCGGCGCCGGAAGCGTGGAGACACCC<br>AGGGGCCTGATCAAGGTGACCAGCTACGACGGCGAGG<br>ACAAGATCGGCAGCTACGCCGTGCTGAGCCCACAGGC<br>CGTGCTGAAGTCCGAGAAGCTGAGCTGCATCCACCCA<br>CTGGCCGAGCAGGTGATCGTGATCACCCACAGCGGCA<br>GGAAGGGCAGGTACGCCGTGGAGCCCTACCACGGCAA<br>GGTGGTCGTGCCCGAGGGCCACGCCATCCCCGTGCAG<br>GACTTCCAGGCCCTGAGCGAGAGCGCCACCATCGTGT<br>ACAACGAGAGGGAGTTCGTGAACAGGTACCTGCACCA<br>TATCGCCACCCACGGCGGAGCCCTGAACACCGACGAG<br>GAATACTACAAGACCGTGAAGCCCAGCGAGCACGACG<br>GCGAGTACCTGTACGACATCGACAGGAAGCAGTGCGT<br>GAAGAAAGAGCTGGTGACCGGCCTGGGACTGACCGGC<br>GAGCTGGTGGACCCACCCTTCCACGAGTTCGCCTACGA<br>GAGCCTGAGGACCAGACCCGCCGCTCCCTACCAGGTG<br>CCCACCATCGGCGTGTACGGCGTGCCCGGCAGCGGAA<br>AGAGCGGCATCATCAAGAGCGCCGTGACCAAGAAAGA<br>CCTGGTGGTCAGCGCCAAGAAAGAGAACTGCGCCGAG<br>ATCATCAGGGACGTGAAGAAGATGAAAGGCCTGGACG<br>TGAACGCGCGCACCGTGGACAGCGTGCTGCTGAACGG<br>CTGCAAGCACCCCGTGGAGACCCTGTACATCGACGAG<br>GCCTTCGCTTGCCACGCCGGCACCCTGAGGGCCCTGAT<br>CGCCATCATCAGGCCCAAGAAAGCCGTGCTGTGCGGC<br>GACCCCAAGCAGTGCGGCTTCTTCAACATGATGTGCCT<br>GAAGGTGCACTTCAACCACGAGATCTGCACCCAGGTG<br>TTCCACAAGAGCATCAGCAGGCGGTGCACCAAGAGCG<br>TGACCAGCGTCGTGAGCACCCTGTTCTACGACAAGAA<br>AATGAGGACCACCAACCCCAAGGAGACCAAAATCGTG<br>ATCGACACCACAGGCAGCACCAAGCCCAAGCAGGACG<br>ACCTGATCCTGACCTGCTTCAGGGGCTGGGTGAAGCA<br>GCTGCAGATCGACTACAAGGGCAACGAGATCATGACC<br>GCCGCTGCCAGCCAGGGCCTGACCAGGAAGGGCGTGT<br>ACGCCGTGAGGTACAAGGTGAACGAGAACCCACTGTA<br>CGCTCCCACCAGCGAGCACGTGAACGTGCTGCTGACC<br>AGGACCGAGGACAGGATCGTGTGGAAGACCCTGGCCG<br>GCGACCCCTGGATCAAGACCCTGACCGCCAAGTACCC<br>CGGCAACTTCACCGCCACCATCGAAGAGTGGCAGGCC<br>GAGCACGACGCCATCATGAGGCACATCCTGGAGAGGC<br>CCGACCCCACCGACGTGTTCCAGAACAAGGCCAACGT<br>GTGCTGGGCCAAGGCCCTGGTGCCCGTGCTGAAGACC<br>GCCGGCATCGACATGACCACAGAGCAGTGGAACACCG<br>TGGACTACTTCGAGACCGACAAGGCCCACAGCGCCGA<br>GATCGTGCTGAACCAGCTGTGCGTGAGGTTCTTCGGCC<br>TGGACCTGGACAGCGGCCTGTTCAGCGCCCCCACCGT<br>GCCACTGAGCATCAGGAACAACCACTGGGACAACAGC<br>CCCAGCCCAAACATGTACGGCCTGAACAAGGAGGTGG<br>TCAGGCAGCTGAGCAGGCGGTACCCACAGCTGCCCAG<br>GGCCGTGGCCACCGGCAGGGTGTACGACATGAACACC<br>GGCACCCTGAGGAACTACGACCCCAGGATCAACCTGG<br>TGCCCGTGAACAGGCGGCTGCCCCACGCCCTGGTGCT<br>GCACCACAACGAGCACCCACAGAGCGACTTCAGCTCC<br>TTCGTGAGCAAGCTGAAAGGCAGGACCGTGCTGGTCG<br>TGGGCGAGAAGCTGAGCGTGCCCGGCAAGATGGTGGA<br>CTGGCTGAGCGACAGGCCCGAGGCCACCTTCCGGGCC<br>AGGCTGGACCTCGGCATCCCCGGCGACGTGCCCAAGT<br>ACGACATCATCTTCGTGAACGTCAGGACCCCATACAA<br>GTACCACCATTACCAGCAGTGCGAGGACCACGCCATC<br>AAGCTGAGCATGCTGACCAAGAAGGCCTGCCTGCACC<br>TGAACCCCGGAGGCACCTGCGTGAGCATCGGCTACGG<br>CTACGCCGACAGGGCCAGCGAGAGCATCATTGGCGCC<br>ATCGCCAGGCTGTTCAAGTTCAGCAGGGTGTGCAAAC<br>CCAAGAGCAGCCTGGAGGAAACCGAGGTGCTGTTCGT<br>GTTCATCGGCTACGACCGGAAGGCCAGGACCCACAAC<br>CCCTACAAGCTGAGCAGCACCCTGACAAACATCTACA<br>CCGGCAGCAGGCTGCACGAGGCCGGCTGCGCCCCCAG<br>CTACCACGTGGTCAGGGGCGATATCGCCACCGCCACC<br>GAGGGCGTGATCATCAACGCTGCCAACAGCAAGGGCC<br>AGCCCGGAGGCGGAGTGTGCGGCGCCCTGTACAAGAA<br>GTTCCCCGAGAGCTTCGACCTGCAGCCCATCGAGGTG<br>GGCAAGGCCAGGCTGGTGAAGGGCGCCGCTAAGCACA<br>TCATCCACGCCGTGGGCCCCAACTTCAACAAGGTGAG<br>CGAGGTGGAAGGCGACAAGCAGCTGGCCGAAGCCTAC<br>GAGAGCATCGCCAAGATCGTGAACGACAATAACTACA<br>AGAGCGTGGCCATCCCACTGCTCAGCACCGGCATCTTC |

TABLE 4-continued

Comparison of STARR™ self-replicating RNA of the disclosure with comparative self-replicating RNA as described

| Construct | Position | Sequence Type | Sequence |
|---|---|---|---|
| | | | AGCGGCAACAAGGACAGGCTGACCCAGAGCCTGAACC |
| | | | ACCTGCTCACCGCCCTGGACACCACCGATGCCGACGT |
| | | | GGCCATCTACTGCAGGGACAAGAAGTGGGAGATGACC |
| | | | CTGAAGGAGGCCGTGGCCAGGCGGGAGGCCGTGGAA |
| | | | GAGATCTGCATCAGCGACGACTCCAGCGTGACCGAGC |
| | | | CCGACGCCGAGCTGGTGAGGGTGCACCCCAAGAGCTC |
| | | | CCTGGCCGGCAGGAAGGGCTACAGCACCAGCGACGGC |
| | | | AAGACCTTCAGCTACCTGGAGGGCACCAAGTTCCACC |
| | | | AGGCCGCTAAGGACATCGCCGAGATCAACGCTATGTG |
| | | | GCCCGTGGCCACCGAGGCCAACGAGCAGGTGTGCATG |
| | | | TACATCCTGGGCGAGAGCATGTCCAGCATCAGGAGCA |
| | | | AGTGCCCCGTGGAGGAAAGCGAGGCCAGCACACCACC |
| | | | CAGCACCCTGCCCTGCCTGTGCATCCACGCTATGACAC |
| | | | CCGAGAGGGTGCAGCGGCTGAAGGCCAGCAGGCCCGA |
| | | | GCAGATCACCGTGTGCAGCTCCTTCCCACTGCCCAAGT |
| | | | ACAGGATCACCGGCGTGCAGAAGATCCAGTGCAGCCA |
| | | | GCCCATCCTGTTCAGCCCAAAGGTGCCCGCCTACATCC |
| | | | ACCCCAGGAAGTACCTGGTGGAGACCCCACCCGTGGA |
| | | | CGAGACACCCGAGCCAAGCGCCGAGAACCAGAGCACC |
| | | | GAGGGCACACCCGAGCAGCCACCCCTGATCACCGAGG |
| | | | ACGAGACAAGGACCCGGACCCCAGAGCCCATCATTAT |
| | | | CGAGGAAGAGGAAGAGGACAGCATCAGCCTGCTGAG |
| | | | CGACGGCCCCACCCACCAGGTGCTGCAGGTGGAGGCC |
| | | | GACATCCACGGCCCACCCAGCGTGTCCAGCTCCAGCT |
| | | | GGAGCATCCCACACGCCAGCGACTTCGACGTGGACAG |
| | | | CCTGAGCATCCTGGACACCCTGGAGGGCGCCAGCGTG |
| | | | ACCTCCGGCGCCACCAGCGCCGAGACCAACAGCTACT |
| | | | TCGCCAAGAGCATGGAGTTCCTGGCCAGGCCCGTGCC |
| | | | AGCTCCCAGGACCGTGTTCAGGAACCCACCCCACCCA |
| | | | GCTCCCAGGACCAGGACCCCAAGCCTGGCTCCCAGCA |
| | | | GGGCCTGCAGCAGGACCAGCCTGGTGAGCACCCCACC |
| | | | CGGCGTGAACAGGGTGATCACCAGGGAGGAACTGGAG |
| | | | GCCCTGACACCCAGCAGGACCCCCAGCAGGTCCGTGA |
| | | | GCAGGACTAGTCTGGTGTCCAACCCACCCGGCGTGAA |
| | | | CAGGGTGATCACCAGGGAGGAATTCGAGGCCTTCGTG |
| | | | GCCCAGCAACAGAGACGGTTCGACGCCGGCGCCTACA |
| | | | TCTTCAGCAGCGACACCGGCCAGGGACACCTGCAGCA |
| | | | AAAGAGCGTGAGGCAGACCGTGCTGAGCGAGGTGGTG |
| | | | CTGGAGAGGACCGAGCTGGAAATCAGCTACGCCCCCA |
| | | | GGCTGGACCAGGAGAAGGAGGAACTGCTCAGGAAGA |
| | | | AACTGCAGCTGAACCCCACCCCAGCCAACAGGAGCAG |
| | | | GTACCAGAGCAGGAAGGTGGAGAACATGAAGGCCATC |
| | | | ACCGCCAGGCGGATCCTGCAGGGCCTGGGACACTACC |
| | | | TGAAGGCCGAGGGCAAGGTGGAGTGCTACAGGACCCT |
| | | | GCACCCCGTGCCACTGTACAGCTCCAGCGTGAACAGG |
| | | | GCCTTCTCCAGCCCCAAGGTGGCCGTGGAGGCCTGCA |
| | | | ACGCTATGCTGAAGGAGAACTTCCCCACCGTGGCCAG |
| | | | CTACTGCATCATCCCCGAGTACGACGCCTACCTGGACA |
| | | | TGGTGGACGGCGCCAGCTGCTGCCTGGACACCGCCAG |
| | | | CTTCTGCCCCGCCAAGCTGAGGAGCTTCCCCAAGAAA |
| | | | CACAGCTACCTGGAGCCCACCATCAGGAGCGCCGTGC |
| | | | CCAGCGCCATCCAGAACACCCTGCAGAACGTGCTGGC |
| | | | CGCTGCCACCAAGAGGAACTGCAACGTGACCCAGATG |
| | | | AGGGAGCTGCCCGTGCTGGACAGCGCTGCCTTCAACG |
| | | | TGGAGTGCTTCAAGAAATACGCCTGCAACAACGAGTA |
| | | | CTGGGAGACCTTCAAGGAGAACCCCATCAGGCTGACC |
| | | | GAAGAGAACGTGGTGAACTACATCACCAAGCTGAAGG |
| | | | GCCCCAAGGCCGCTGCCCTGTTCGCTAAGACCCACAA |
| | | | CCTGAACATGCTGCAGGACATCCCAATGGACAGGTTC |
| | | | GTGATGGACCTGAAGAGGGACGTGAAGGTGACACCCG |
| | | | GCACCAAGCACACCGAGGAGAGGCCCAAGGTGCAGGT |
| | | | GATCCAGGCCGCTGACCCACTGGCCACCGCCTACCTGT |
| | | | GCGGCATCCACAGGGAGCTGGTGAGGCGGCTGAACGC |
| | | | CGTGCTGCTGCCCAACATCCACACCCTGTTCGACATGA |
| | | | GCGCCGAGGACTTCGACGCCATCATCGCCGAGCACTT |
| | | | CCAGCCCGGCGACTGCGTGCTGGAGACCGACATCGCC |
| | | | AGCTTCGACAAGAGCGAGGATGACGCTATGGCCCTGA |
| | | | CCGCTCTGATGATCCTGGAGGACCTGGGCGTGGACGC |
| | | | CGAGCTGCTCACCCTGATCGAGGCTGCCTTCGGCGAG |
| | | | ATCAGCTCCATCCACCTGCCCACCAAGACCAAGTTCAA |
| | | | GTTCGGCGCTATGATGAAAAGCGGAATGTTCCTGACC |
| | | | CTGTTCGTGAACACCGTGATCAACATTGTGATCGCCAG |
| | | | CAGGGTGCTGCGGGAGAGGCTGACCGGCAGCCCCTGC |
| | | | GCTGCCTTCATCGGCGACGACAACATCGTGAAGGGCG |

TABLE 4-continued

Comparison of STARR™ self-replicating RNA of the disclosure with comparative self-replicating RNA as described

| Construct | Position | Sequence Type | Sequence |
|---|---|---|---|
| | | | TGAAAAGCGACAAGCTGATGGCCGACAGGTGCGCCAC<br>CTGGCTGAACATGGAGGTGAAGATCATCGACGCCGTG<br>GTGGGCGAGAAGGCCCCCTACTTCTGCGGCGGATTCA<br>TCCTGTGCGACAGCGTGACCGGCACCGCCTGCAGGGT<br>GGCCGACCCCCTGAAGAGGCTGTTCAAGCTGGGCAAG<br>CCACTGGCCGCTGACGATGAGCACGACGATGACAGGO<br>GGAGGGCCCTGCACGAGGAAAGCACCAGGTGGAACA<br>GGGTGGGCATCCTGAGCGAGCTGTGCAAGGCCGTGGA<br>GAGCAGGTACGAGACCGTGGGCACCAGCATCATCGTG<br>ATGGCTATGACCACACTGGCCAGCTCCGTCAAGAGCTT<br>CTCCTACCTGAGGGGGGCCCCTATAACTCTCTACGGCT<br>AA |
| Comparitive (SEQ ID NO: 55) | non-structural gene ORF | amino acid | MPEKVHVDIEEDSPFLRALQRSFPQFEVEAKQVTDNDHA<br>NARAFSHLASKLIETEVDPSDTILDIGSAPARRMYSKHKY<br>HCICPMRCAEDPDRLYKYATKLKKNCKEITDKELDKKM<br>KELAAVMSDPDLETETMCLHDDESCRYEGQVAVYQDV<br>YAVDGPTSLYHQANKGVRVAYWIGFDTTPFMFKNLAGA<br>YPSYSTNWADETVLTARNIGLCSSDVMERSRRGMSILRK<br>KYLKPSNNVLFSVGSTIYHEKRDLLRSWHLPSVFHLRGK<br>QNYTCRCETIVSCDGYVVKRIAISPGLYGKPSGYAATMH<br>REGFLCCKVTDTLNGERVSFPVCTYVPATLCDQMTGILA<br>TDVSADDAQKLLVGLNQRIVVNGRTQRNTNTMKNYLLP<br>VVAQAFARWAKEYKEDQEDERPLGLRDRQLVMGCCWA<br>FRRHKITSIYKRPDTQTIIKVNSDFHSFVLPRIGSNTLEIGL<br>RTRIRKMLEEHKEPSPLITAEDVQEAKCAADEAKEVREA<br>EELRAALPPLAADVEEPTLEADVDLMLQEAGAGSVETPR<br>GLIKVTSYDGEDKIGSYAVLSPQAVLKSEKLSCIHPLAEQ<br>VIVITHSGRKGRYAVEPYHGKVVVPEGHAIPVQDFQALS<br>ESATIVYNEREFVNRYLHHIATHGGALNTDEEYYKTVKP<br>SEHDGEYLYDIDRKQCVKKELVTGLGLTGELVDPPFHEF<br>AYESLRTRPAAPYQVPTIGVYGVPGSGKSGIIKSAVTKKD<br>LVVSAKKENCAEIIRDVKKMKGLDVNARTVDSVLLNGC<br>KHPVETLYIDEAFACHAGTLRALIAIIRPKKAVLCGDPKQ<br>CGFFNMMCLKVHFNHEICTQVFHKSISRRCTKSVTSVVS<br>TLFYDKKMRTTNPKETKIVIDTTGSTKPKQDDLILTCFRG<br>WVKQLQIDYKGNEIMTAAASQGLTRKGVYAVRYKVNE<br>NPLYAPTSEHVNVLLTRTEDRIVWKTLAGDPWIKTLTAK<br>YPGNFTATIEEWQAEHDAIMRHILERPDPTDVFQNKANV<br>CWAKALVPVLKTAGIDMTTEQWNTVDYFETDKAHSAEI<br>VLNQLCVRFFGLDLDSGLFSAPTVPLSIRNNHWDNSPSPN<br>MYGLNKEVVRQLSRRYPQLPRAVATGRVYDMNTGTLR<br>NYDPRINLVPVNRRLPHALVLHHNEHPQSDFSSFVSKLK<br>GRTVLVVGEKLSVPGKMVDWLSDRPEATFRARLDLGIP<br>GDVPKYDIIFVNVRTPYKYHHYQQCEDHAIKLSMLTKKA<br>CLHLNPGGTCVSIGYGYADRASESIIGAIARLFKFSRVCKP<br>KSSLEETEVLFVFIGYDRKARTHNPYKLSSTLTNIYTGSRL<br>HEAGCAPSYHVVRGDIATATEGVIINAANSKGQPGGGVC<br>GALYKKFPESFDLQPIEVGKARLVKGAAKHIIHAVGPNF<br>NKVSEVEGDKQLAEAYESIAKIVNDNNYKSVAIPLLSTGI<br>FSGNKDRLTQSLNHLLTALDTTDADVAIYCRDKKWEMT<br>LKEAVARREAVEEICISDDSSVTEPDAELVRVHPKSSLAG<br>RKGYSTSDGKTFSYLEGTKFHQAAKDIAEINAMWPVATE<br>ANEQVCMYILGESMSSIRSKCPVEESEASTPPSTLPCLCIH<br>AMTPERVQRLKASRPEQITVCSSFPLPKYRITGVQKIQCS<br>QPILFSPKVPAYIHPRKYLVETPPVDETPEPSAENQSTEGT<br>PEQPPLITEDETRTRTPEPIIIEEEEEDSISLLSDGPTHQVLQ<br>VEADIHGPPSVSSSSWSIPHASDFDVDSLSILDTLEGASVT<br>SGATSAETNSYFAKSMEFLARPVPAPRTVFRNPPHPAPRT<br>RTPSLAPSRACSRTSLVSTPPGVNRVITREELEALTPSRTP<br>SRSVSRTSLVSNPPGVNRVITREEFEAFVAQQQRRFDAGA<br>YIFSSDTGQGHLQQKSVRQTVLSEVVLERTELEISYAPRL<br>DQEKEELLRKKLQLNPTPANRSRYQSRKVENMKAITARR<br>ILQGLGHYLKAEGKVECYRTLHPVPLYSSSVNRAFSSPK<br>VAVEACNAMLKENFPTVASYCIIPEYDAYLDMVDGASC<br>CLDTASFCPAKLRSFPKKHSYLEPTIRSAVPSAIQNTLQNV<br>LAAATKRNCNVTQMRELPVLDSAAFNVECFKKYACNNE<br>YWETFKENPIRLTEENVVNYITKLKGPKAAALFAKTHNL<br>NMLQDIPMDRFVMDLKRDVKVTPGTKHTEERPKVQVIQ<br>AADPLATAYLCGIHRELVRRLNAVLLPNIHTLFDMSAED<br>FDAIIAEHFQPGDCVLETDIASFDKSEDDAMALTALMILE<br>DLGVDAELLTLIEAAFGEISSIHLPTKTKFKFGAMMKSGM<br>FLTLFVNTVINIVIASRVLRERLTGSPCAAFIGDDNIVKGV<br>KSDKLMADRCATWLNMEVKIIDAVVGEKAPYFCGGFIL |

TABLE 4-continued

Comparison of STARR$^{TM}$ self-replicating RNA of the disclosure with comparative self-replicating RNA as described

| Construct | Position | Sequence Type | Sequence |
|---|---|---|---|
| | | | CDSVTGTACRVADPLKRLFKLGKPLAADDEHDDDRRRA LHEESTRWNRVGILSELCKAVESRYETVGTSIIVMAMTTL ASSVKSFSYLRGAPITLYG* |
| Comparitive | intergenic region | nucleotide | unknown |
| Comparitive | 3' UTR | nucleotide | unknown |

RNA sequences can include any combination of the RNA sequences listed in Table 4. In some embodiments, RNA sequences of the present disclosure include any combination of the RNA sequences listed in Table 4 in which 0% to 100%, 1% to 100%, 25% to 100%, 50% to 100% and 75% to 100% of the uracil nucleotides of the mRNA sequences are modified. In some embodiments, 1% to 100% of the uracil nucleotides are N1-methylpseudouridine or 5-methoxyuridine. In some embodiments, 100% of the uracil nucleotides are N1-methylpseudouridine. In some embodiments, 100% of the uracil nucleotides are 5-methoxyuridine.

A self-replicating RNA of the disclosure may be obtained by any suitable means. Methods for the manufacture of self-replicating RNA are known in the art and would be readily apparent to a person of ordinary skill. A self-replicating RNA of the disclosure may be prepared according to any available technique including, but not limited to chemical synthesis, in vitro transcription (IVT) or enzymatic or chemical cleavage of a longer precursor, etc.

In some embodiments, a self-replicating RNA of the disclosure is produced from a primary complementary DNA (cDNA) construct. The cDNA constructs can be produced on an RNA template by the action of a reverse transcriptase (e.g., RNA-dependent DNA-polymerase). The process of design and synthesis of the primary cDNA constructs described herein generally includes the steps of gene construction, RNA production (either with or without modifications) and purification. In the IVT method, a target polynucleotide sequence encoding a self-replicating RNA of the disclosure is first selected for incorporation into a vector which will be amplified to produce a cDNA template. Optionally, the target polynucleotide sequence and/or any flanking sequences may be codon optimized. The cDNA template is then used to produce a self-replicating RNA of the disclosure through in vitro transcription (IVT). After production, the self-replicating RNA of the disclosure may undergo purification and clean-up processes. The steps of which are provided in more detail below.

The step of gene construction may include, but is not limited to gene synthesis, vector amplification, plasmid purification, plasmid linearization and clean-up, and cDNA template synthesis and clean-up. Once a protein of interest is selected for production, a primary construct is designed. Within the primary construct, a first region of linked nucleosides encoding the polypeptide of interest may be constructed using an open reading frame (ORF) of a selected nucleic acid (DNA or RNA) transcript. The ORF may comprise the wild type ORF, an isoform, variant or a fragment thereof. As used herein, an "open reading frame" or "ORF" is meant to refer to a nucleic acid sequence (DNA or RNA) which is capable of encoding a polypeptide of interest. ORFs often begin with the start codon, ATG and end with a nonsense or termination codon or signal.

The cDNA templates may be transcribed to produce a self-replicating RNA of the disclosure using an in vitro transcription (IVT) system. The system typically comprises a transcription buffer, nucleotide triphosphates (NTPs), an RNase inhibitor and a polymerase. The NTPs may be selected from, but are not limited to, those described herein including natural and unnatural (modified) NTPs. The polymerase may be selected from, but is not limited to, T7 RNA polymerase, T3 RNA polymerase and mutant polymerases such as, but not limited to, polymerases able to incorporate modified nucleic acids.

The primary cDNA template or transcribed RNA sequence may also undergo capping and/or tailing reactions. A capping reaction may be performed by methods known in the art to add a 5' cap to the 5' end of the primary construct. Methods for capping include, but are not limited to, using a Vaccinia Capping enzyme (New England Biolabs, Ipswich, Mass.) or capping at initiation of in vitro transcription, by for example, including a capping agent as part of the IVT reaction. (Nuc. Acids Symp. (2009) 53:129). A poly(A) tailing reaction may be performed by methods known in the art, such as, but not limited to, 2' O-methyltransferase and by methods as described herein. If the primary construct generated from cDNA does not include a poly-T, it may be beneficial to perform the poly(A)-tailing reaction before the primary construct is cleaned.

The present disclosure also provides expression vectors comprising a nucleotide sequence encoding a self-replicating RNA that is preferably operably linked to at least one regulatory sequence. Regulatory sequences are art-recognized and are selected to direct expression of the encoded polypeptide.

Accordingly, the term regulatory sequence includes promoters, enhancers, and other expression control elements. The design of the expression vector may depend on such factors as the choice of the host cell to be transformed and/or the type of protein desired to be expressed.

The present disclosure also provides polynucleotides (e.g. DNA, RNA, cDNA, mRNA, etc.) directed to a self-replicating RNA of the disclosure that may be operably linked to one or more regulatory nucleotide sequences in an expression construct, such as a vector or plasmid. In certain embodiments, such constructs are DNA constructs. Regulatory nucleotide sequences will generally be appropriate for a host cell used for expression. Numerous types of appropriate expression vectors and suitable regulatory sequences are known in the art for a variety of host cells.

Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the embodiments of the present disclosure. The promoters may be either naturally occurring promoters, or hybrid promoters that combine elements of more than one promoter.

An expression construct may be present in a cell on an episome, such as a plasmid, or the expression construct may be inserted in a chromosome. In some embodiments, the expression vector contains a selectable marker gene to allow the selection of transformed host cells. Selectable marker genes are well known in the art and will vary with the host cell used.

The present disclosure also provides a host cell transfected with a self-replicating RNA or DNA described herein. The host cell may be any prokaryotic or eukaryotic cell. For example, a polypeptide encoded by a self-replicating RNA may be expressed in bacterial cells such as *E. coli*, insect cells (e.g., using a baculovirus expression system), yeast, or mammalian cells. Other suitable host cells are known to those skilled in the art.

The present disclosure also provides a host cell comprising a vector comprising a polynucleotide which encodes a self-replicating RNA sequence provided herein.

A host cell transfected with an expression vector comprising a self-replicating RNA of the disclosure can be cultured under appropriate conditions to allow expression of the amplification of the self-replicating RNA and translation of the polypeptide to occur. The polypeptide may be secreted and isolated from a mixture of cells and medium containing the polypeptides. Alternatively, the polypeptides may be retained in the cytoplasm or in a membrane fraction and the cells harvested, lysed and the protein isolated. A cell culture includes host cells, media and other byproducts. Suitable media for cell culture are well known in the art.

The expressed proteins described herein can be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of the polypeptide.

Compositions and Pharmaceutical Compositions

Provided herein, in some embodiments, are compositions comprising any of the nucleic acid molecules provided herein. Compositions provided herein can include a lipid. Any lipid can be included in compositions provided herein. In one aspect, the lipid is an ionizable cationic lipid. Any ionizable cationic lipid can be included in compositions comprising nucleic acid molecules provided herein.

Also provided herein, in some embodiments, are pharmaceutical compositions comprising any of the nucleic acid molecules provided herein and a lipid formulation. Any lipid can be included in lipid formulations of pharmaceutical compositions provided herein. In one aspect, lipid formulations of pharmaceutical compositions provided herein include an ionizable cationic lipid. Exemplary ionizable cationic lipids of compositions and pharmaceutical compositions provided herein include the following:

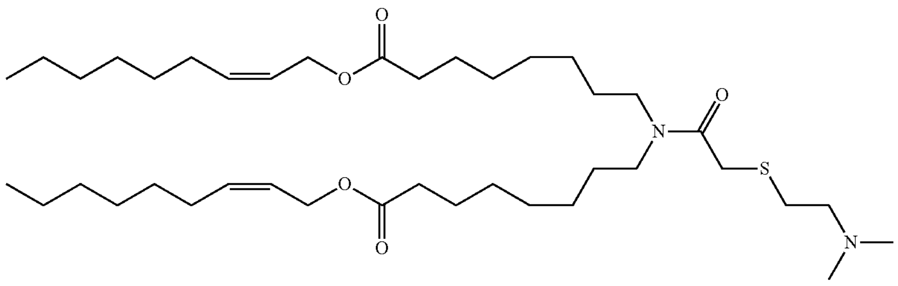

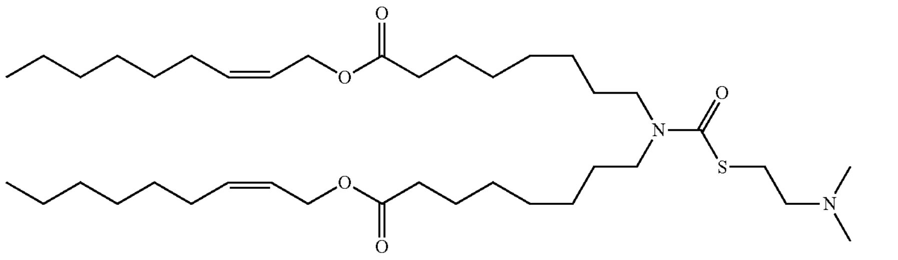 [SMILES: CCCCCC/C=C\COC(=O)CCCCCCCN(CCCCCCCC(=O)OC/C=C\CCCCCC)C(=O)SCCN(C)C]

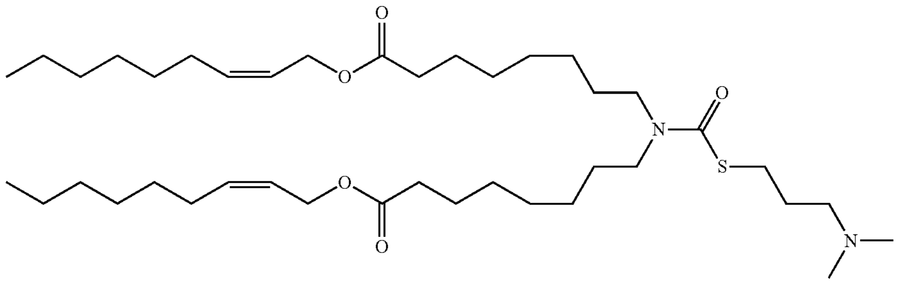

-continued
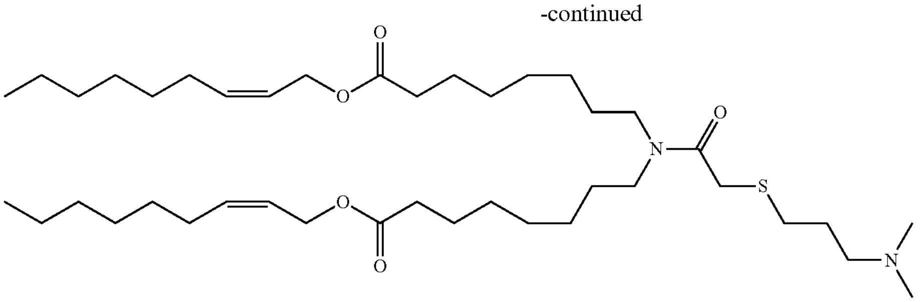
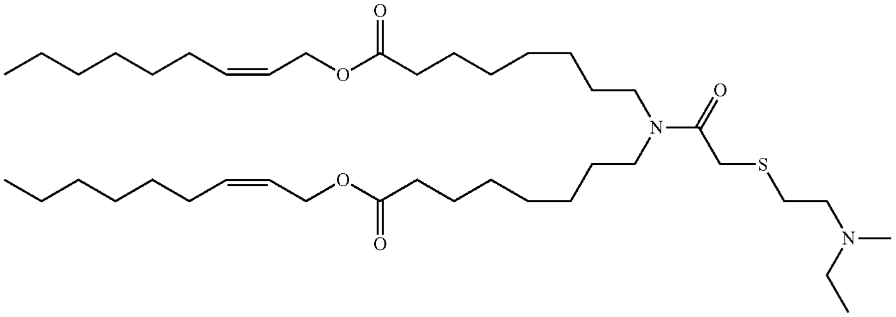
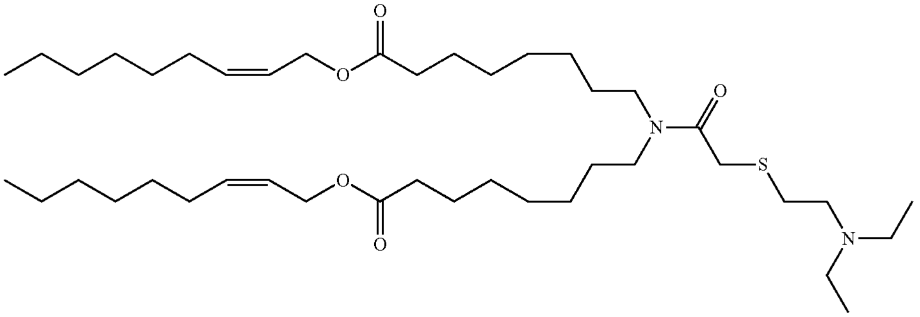
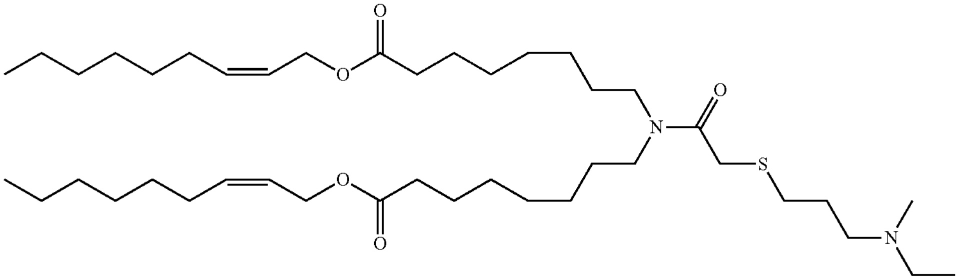
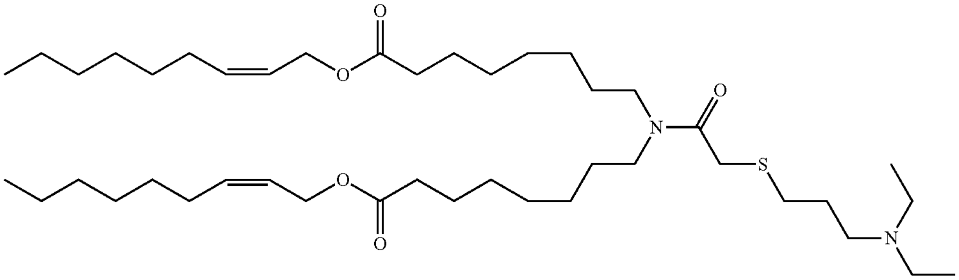
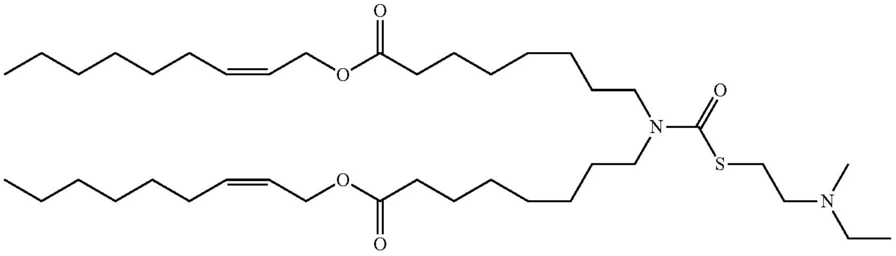

-continued
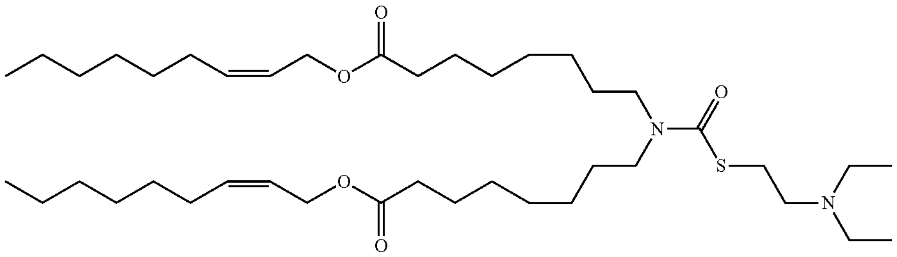
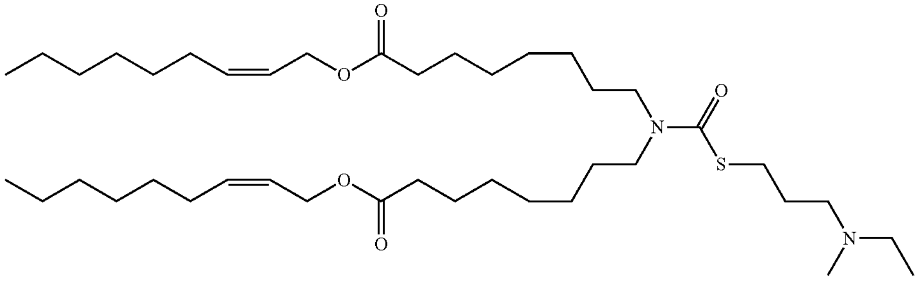
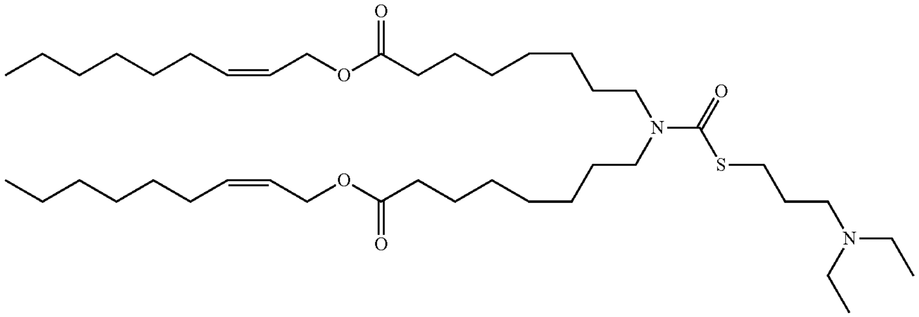
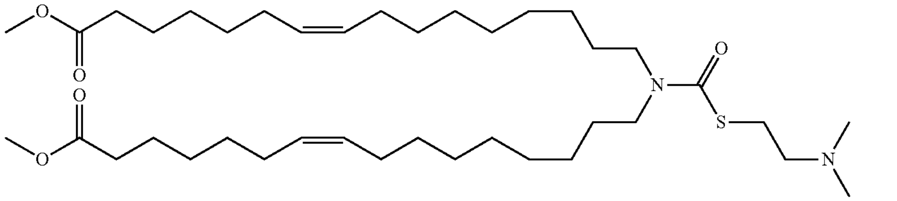
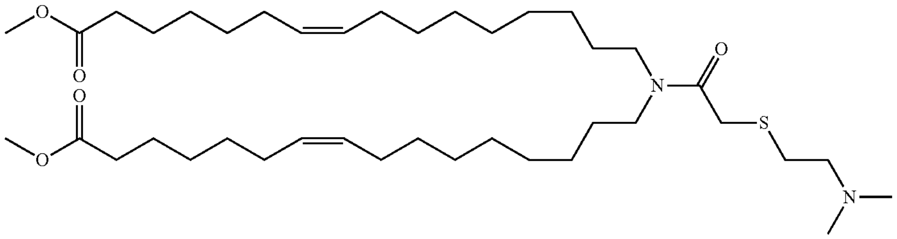
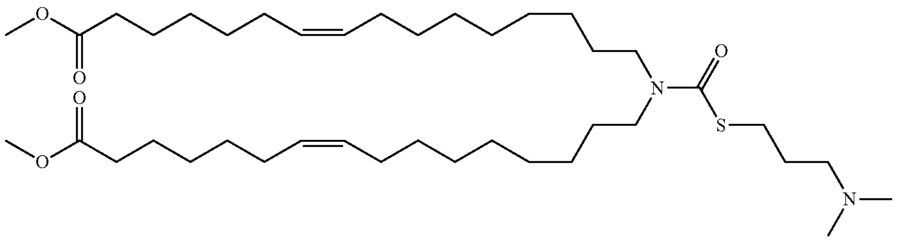

-continued
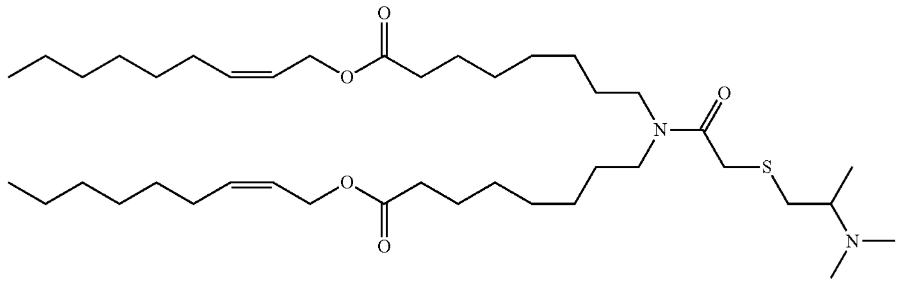
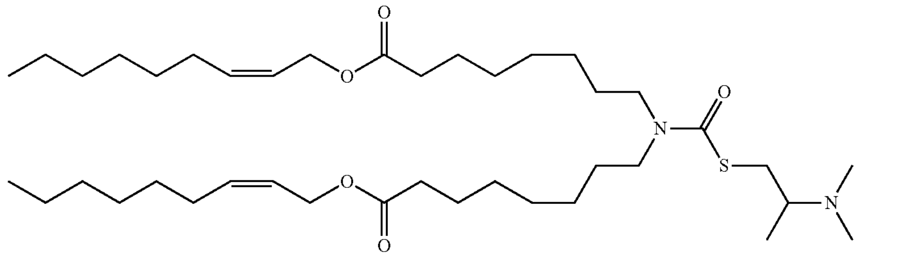
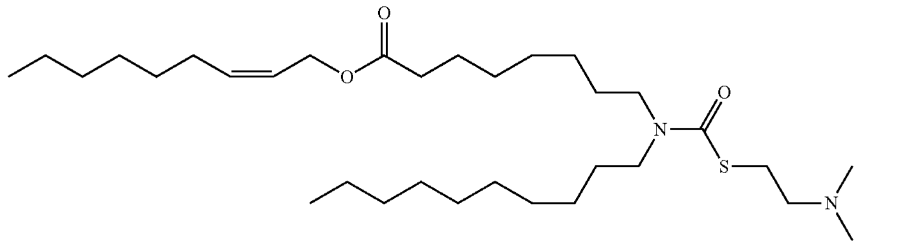
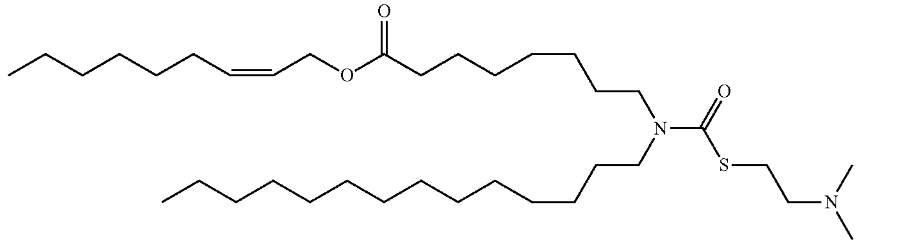
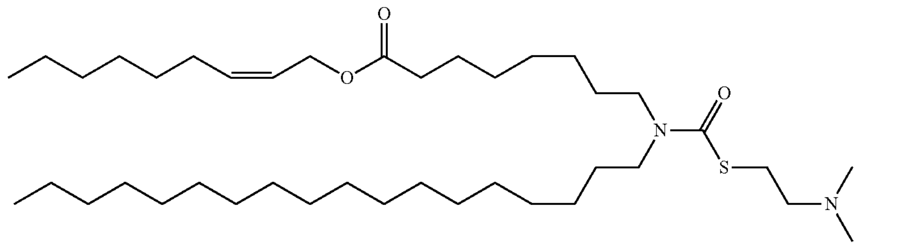
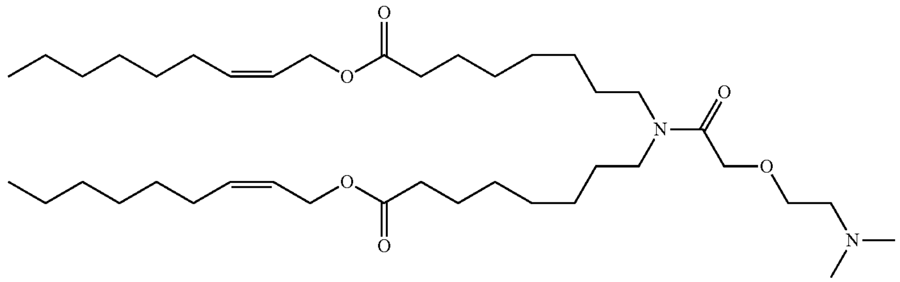

-continued
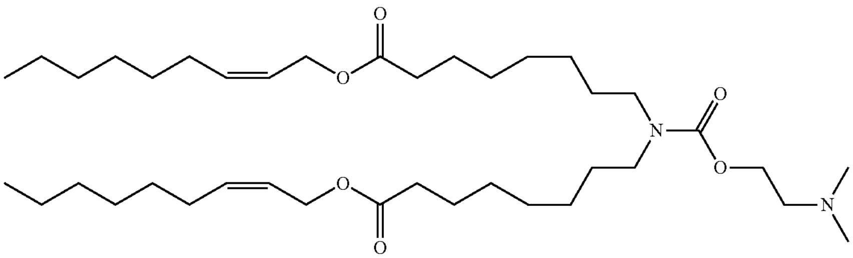
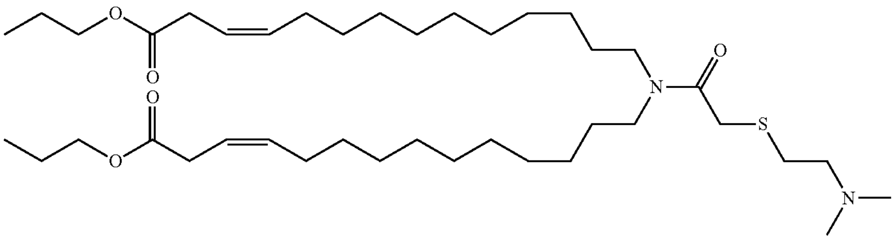
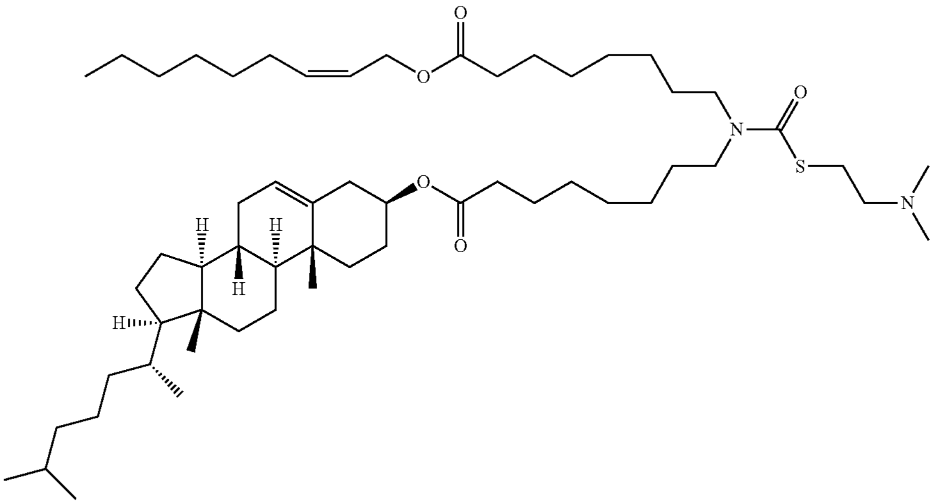
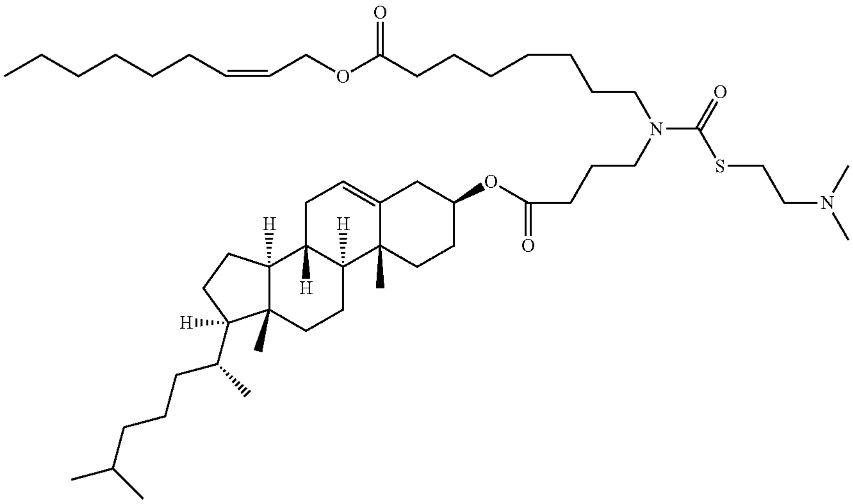

-continued
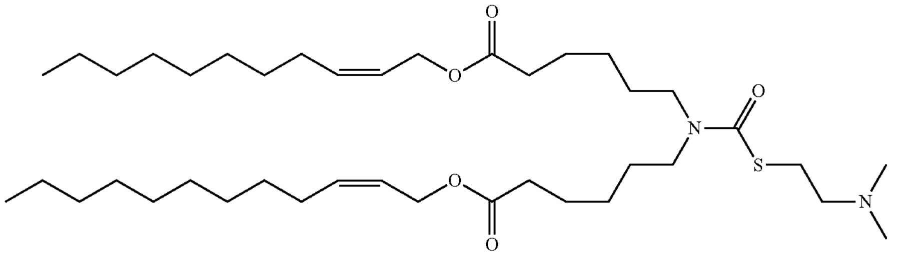
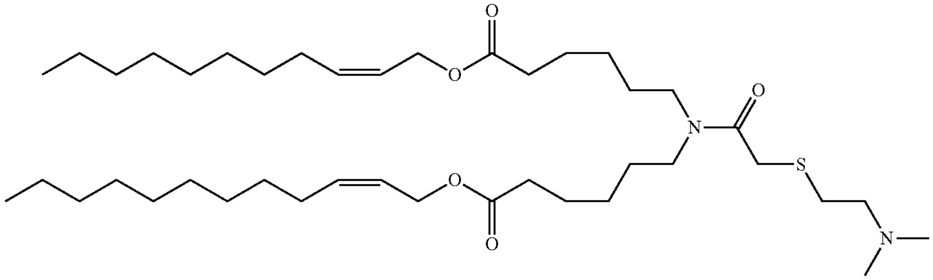
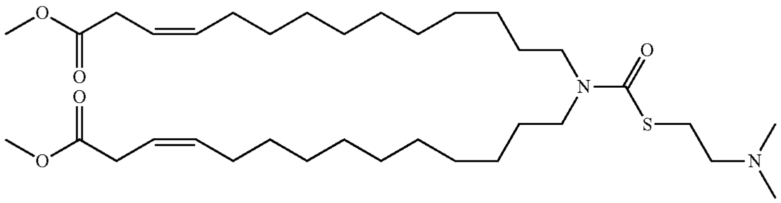
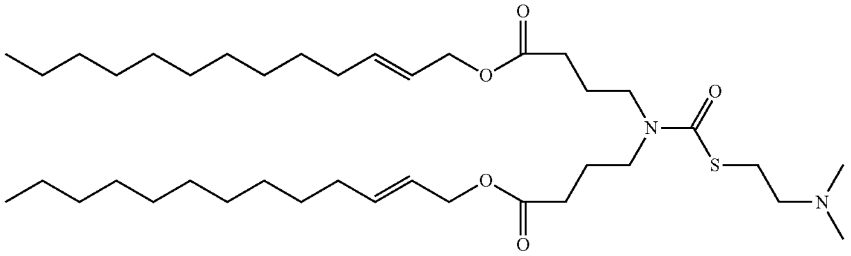
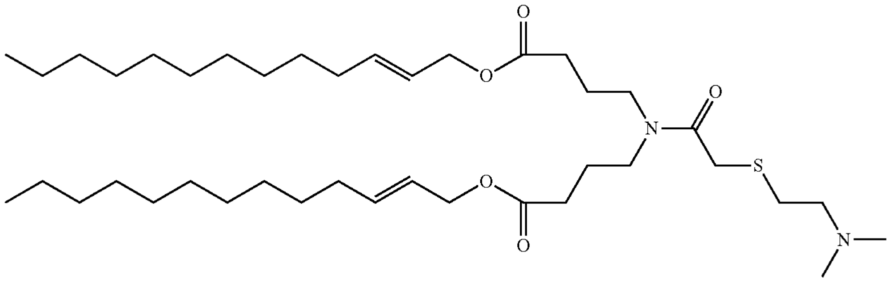
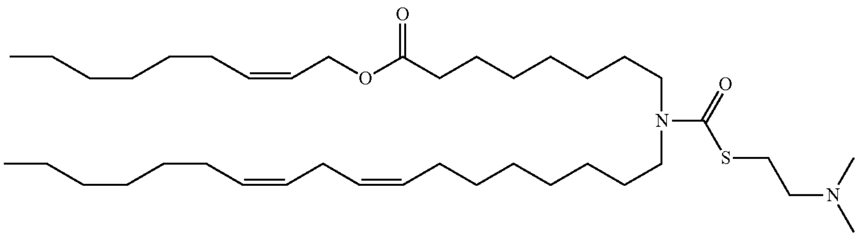
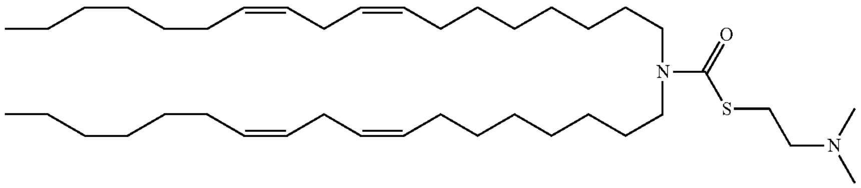

-continued
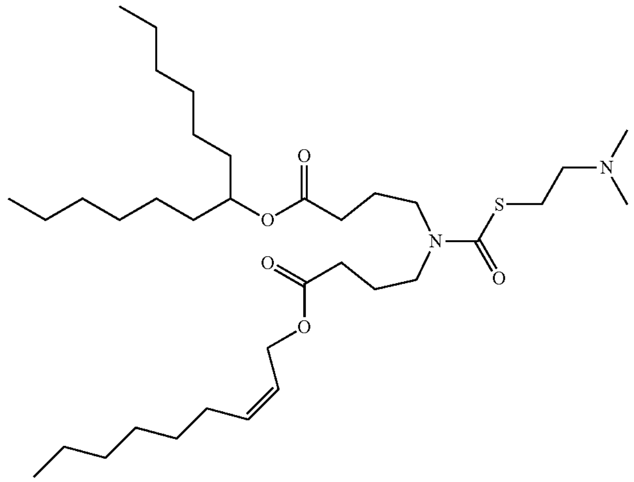
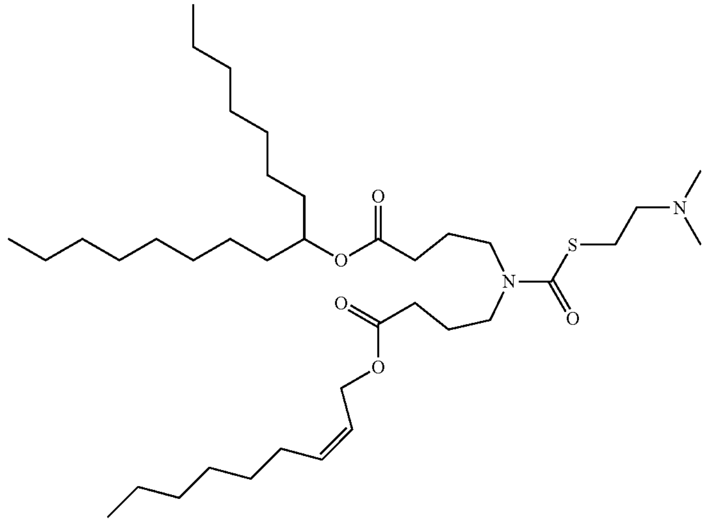
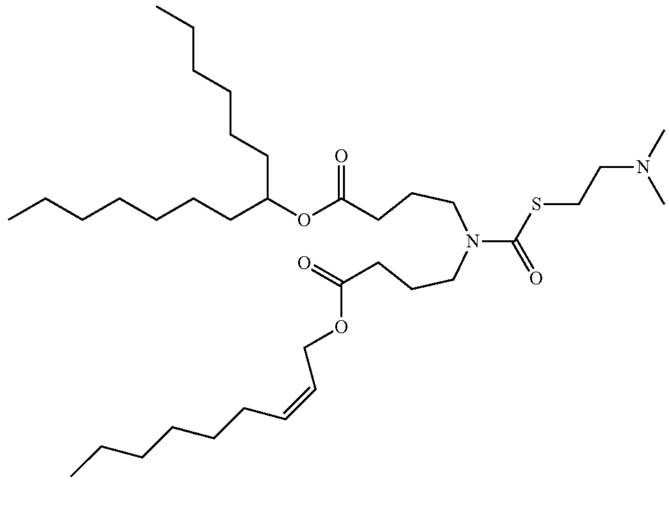

-continued
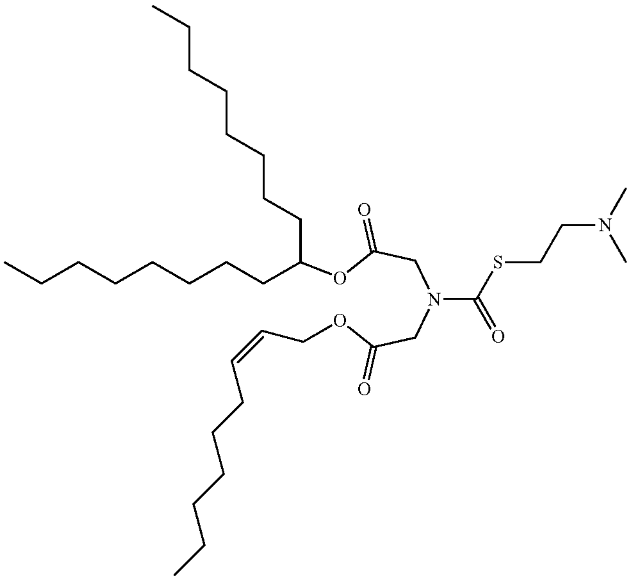
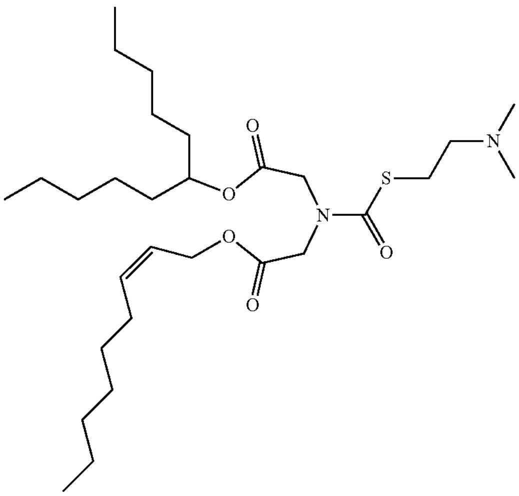
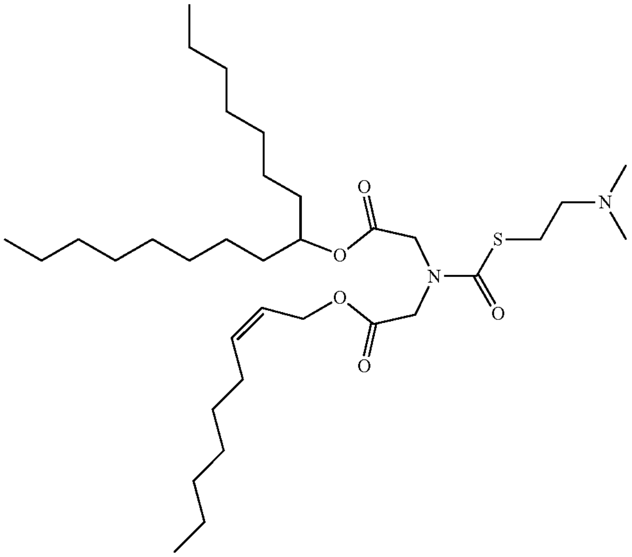
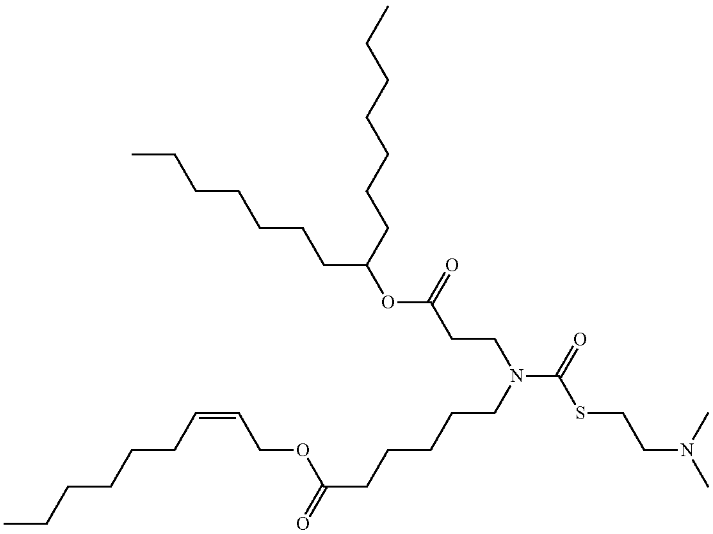

-continued
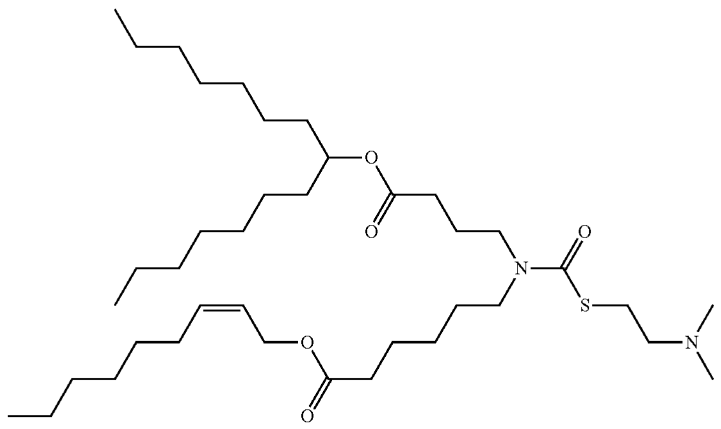
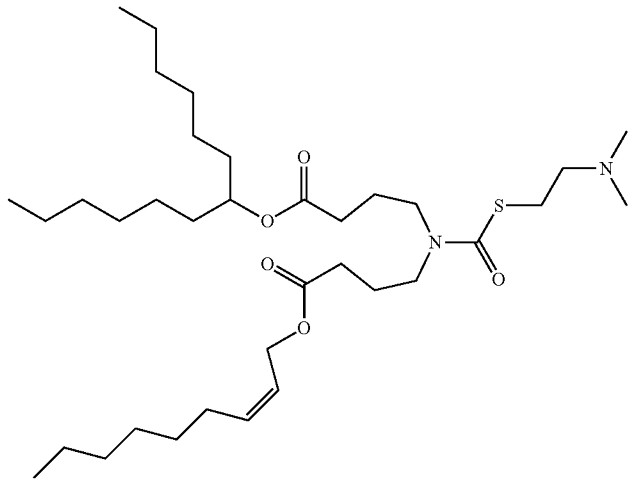
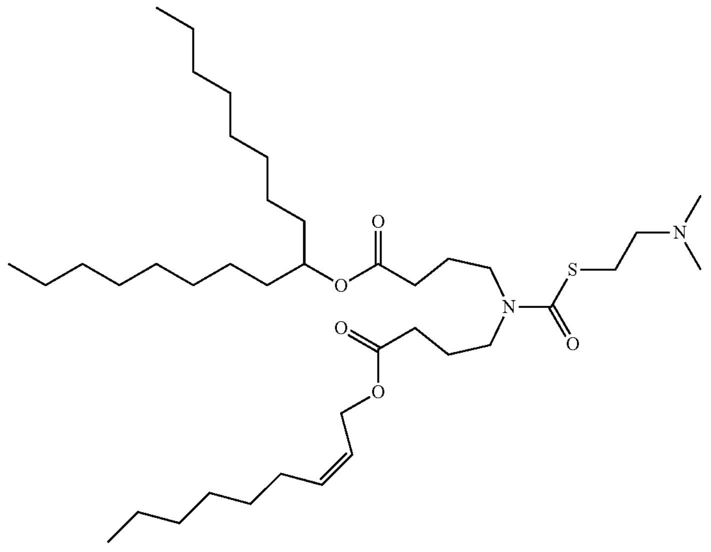

-continued
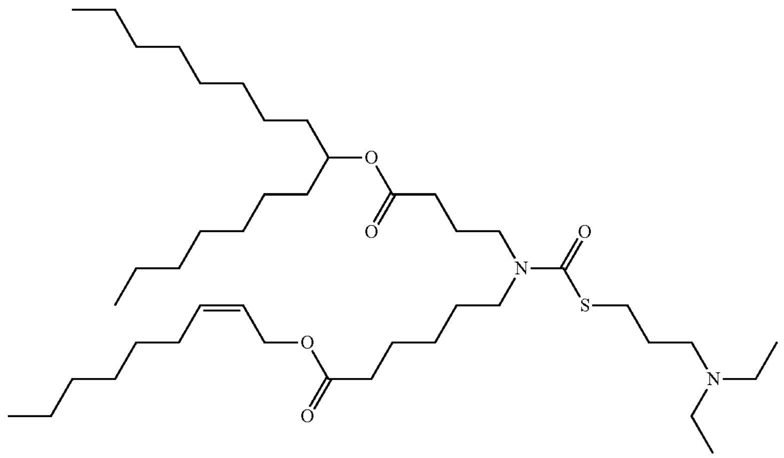
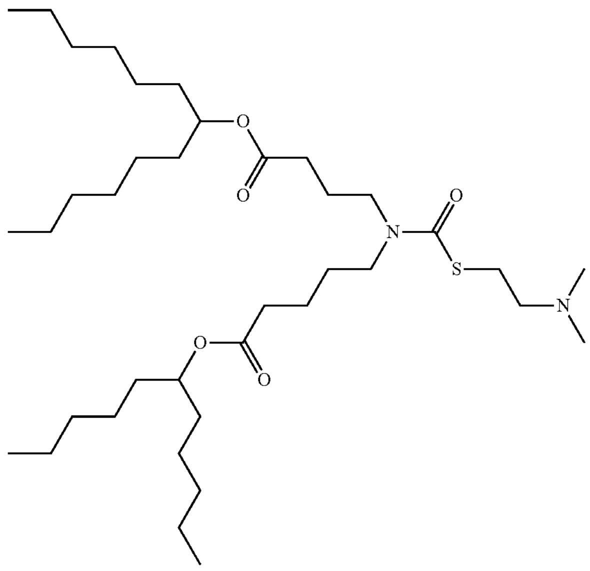
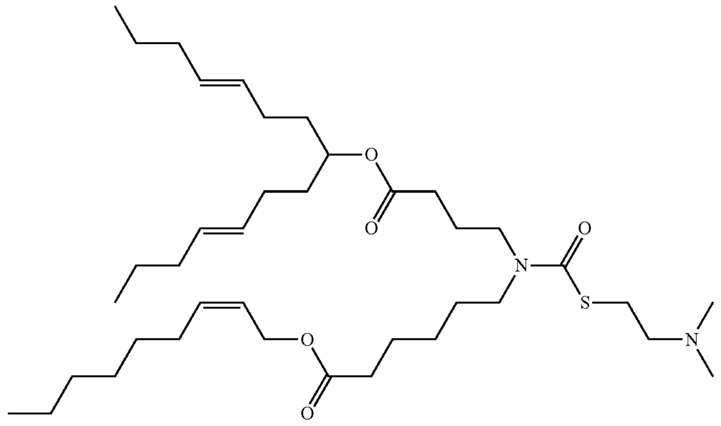

-continued
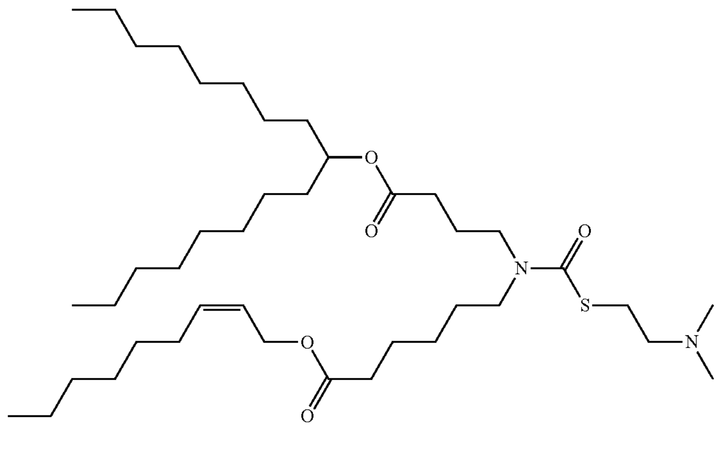
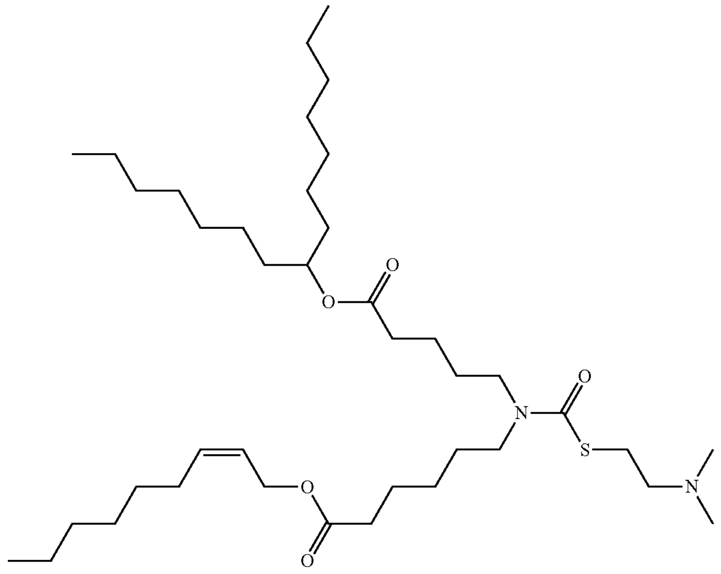
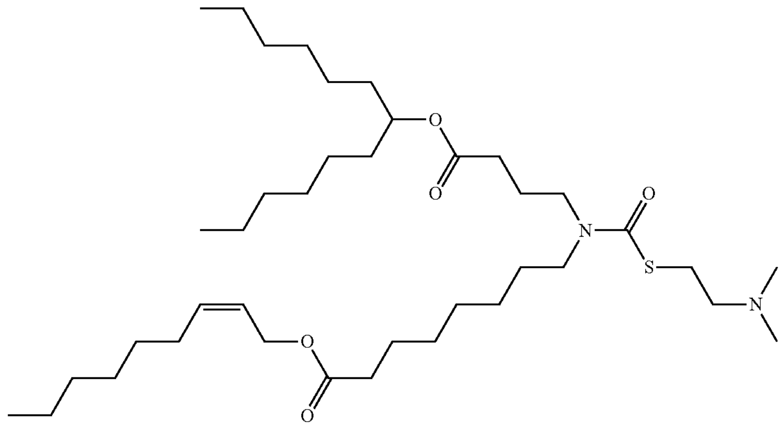

-continued
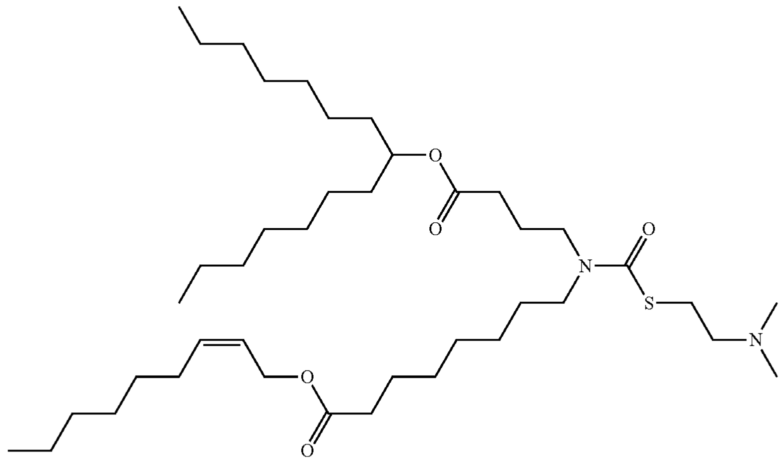
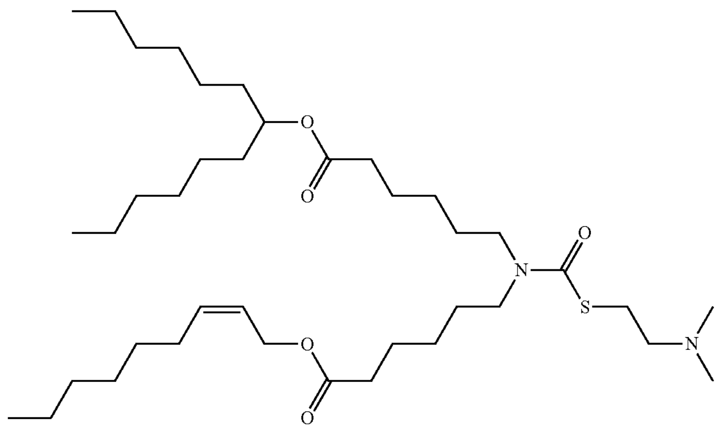
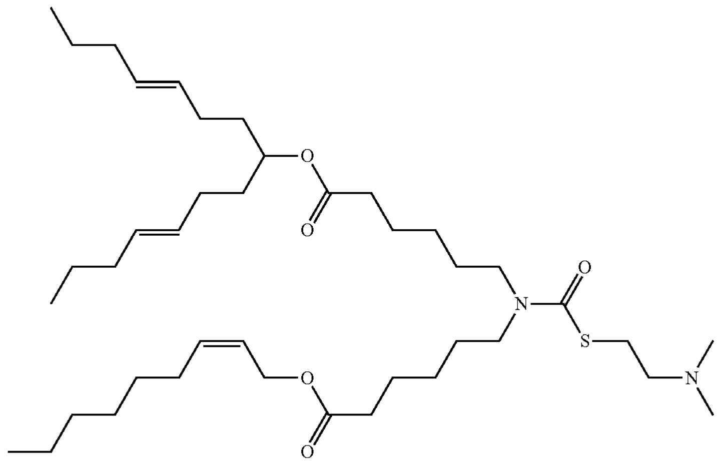

-continued
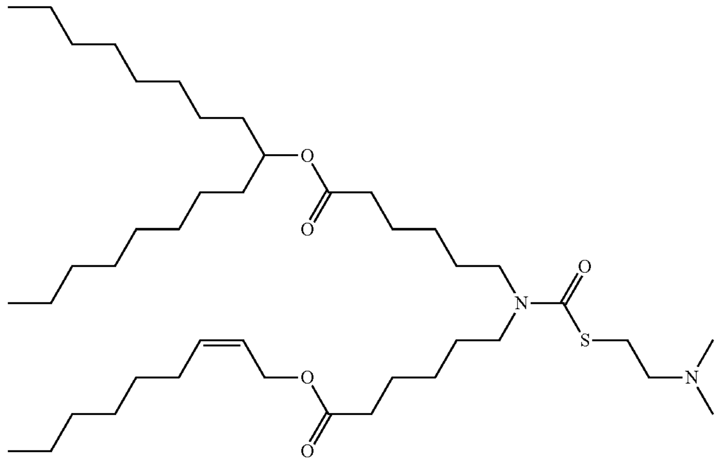
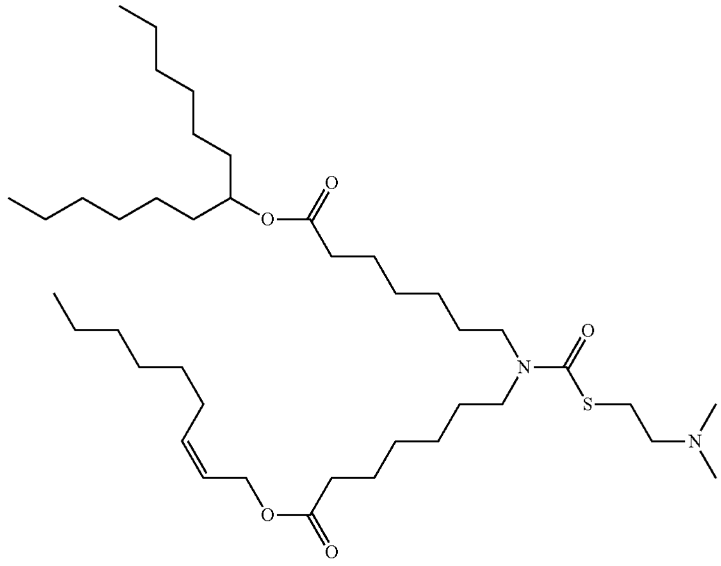
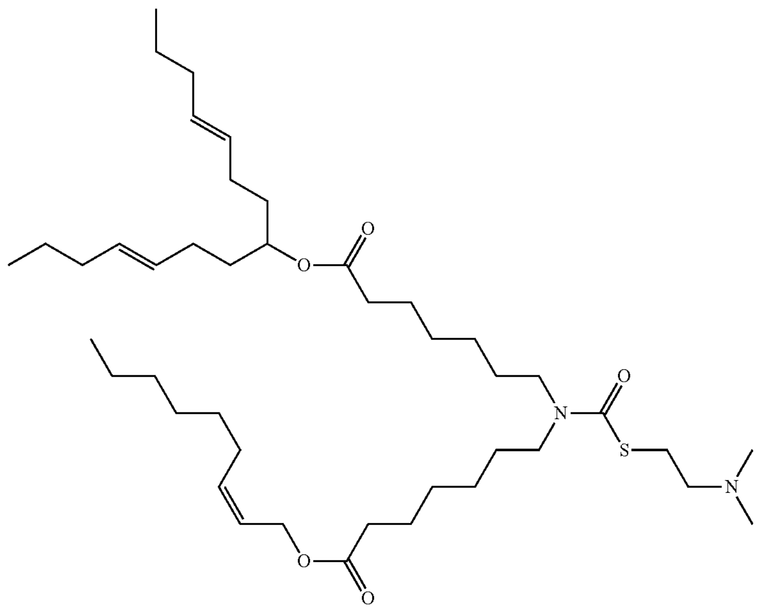

-continued
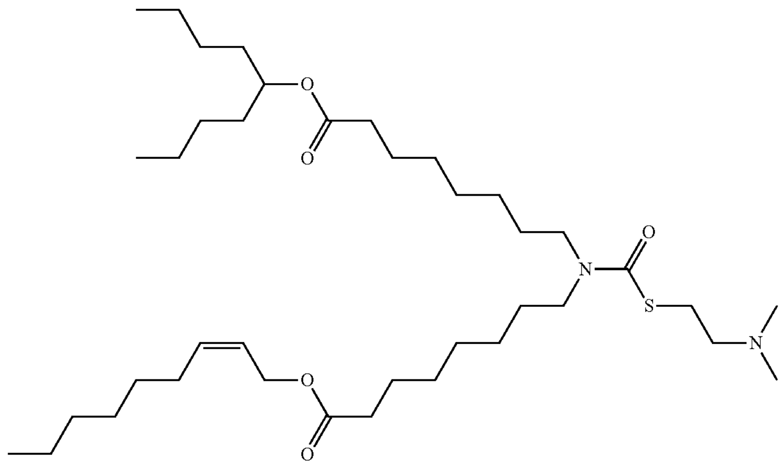
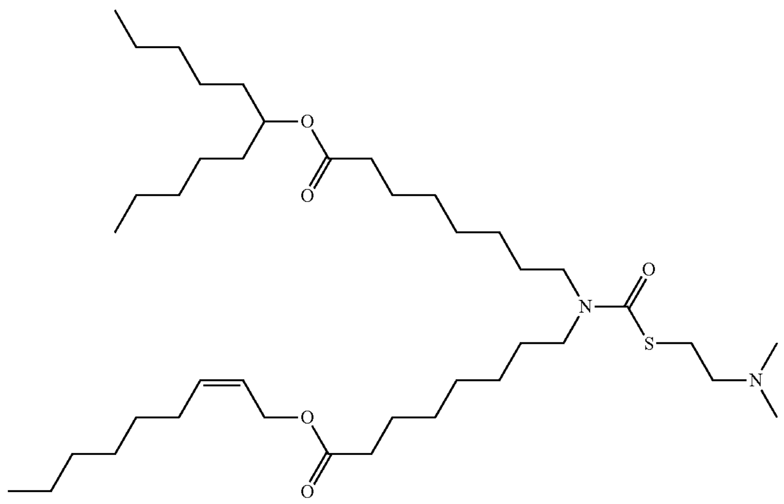
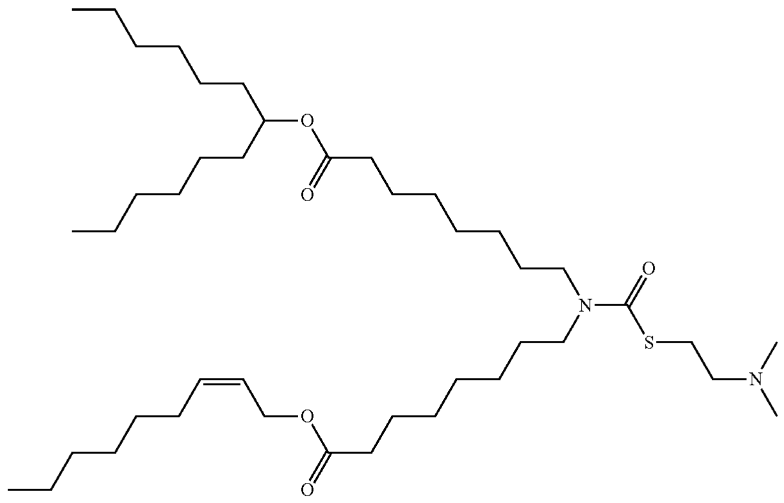

-continued
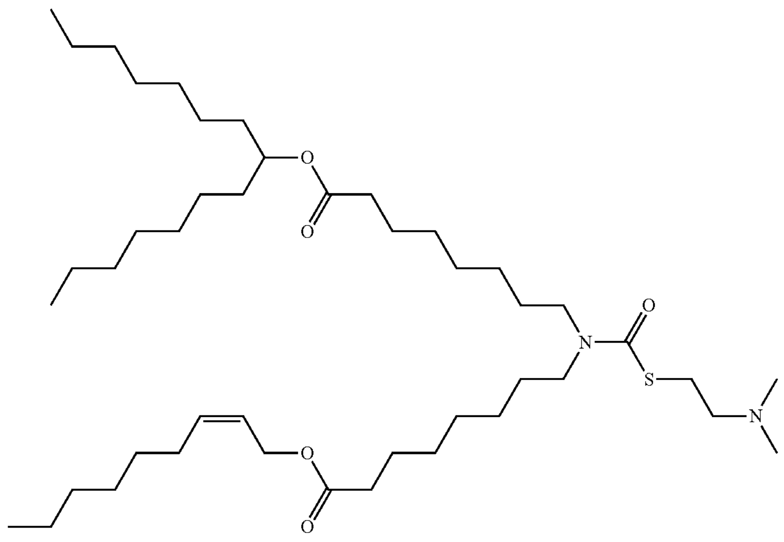
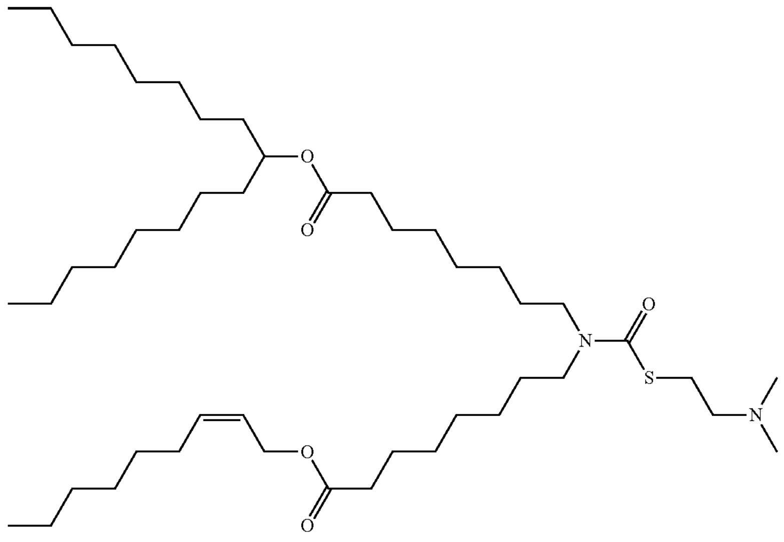
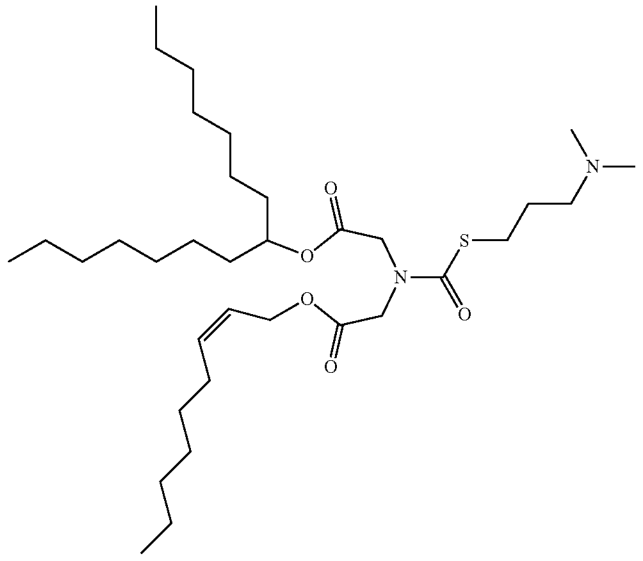

-continued
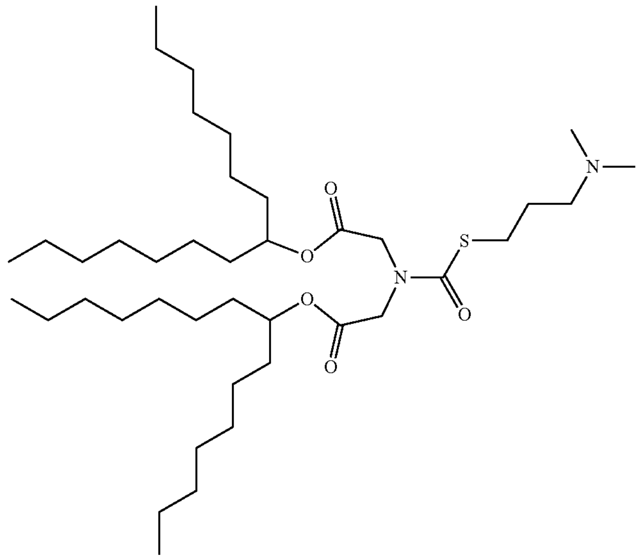
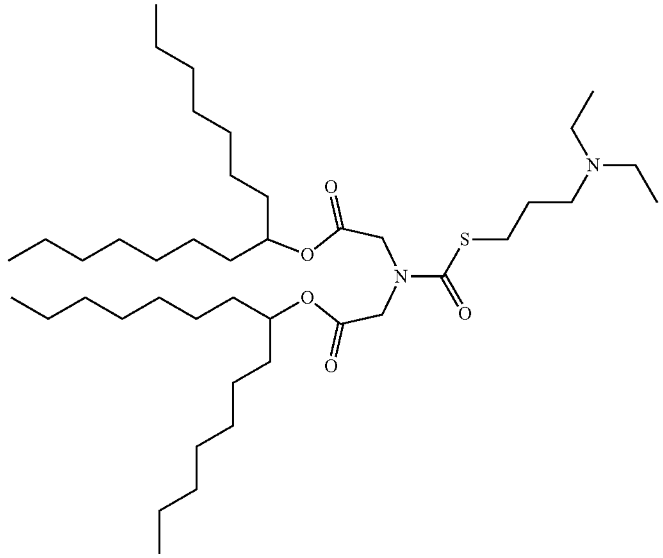
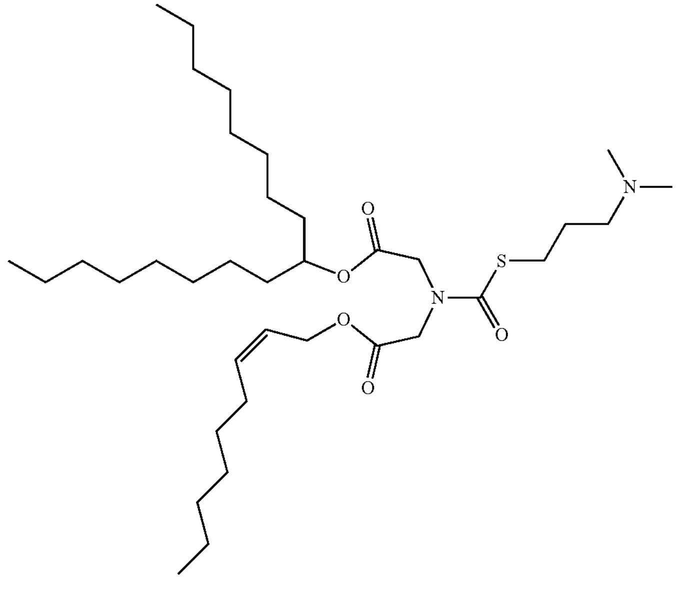

-continued
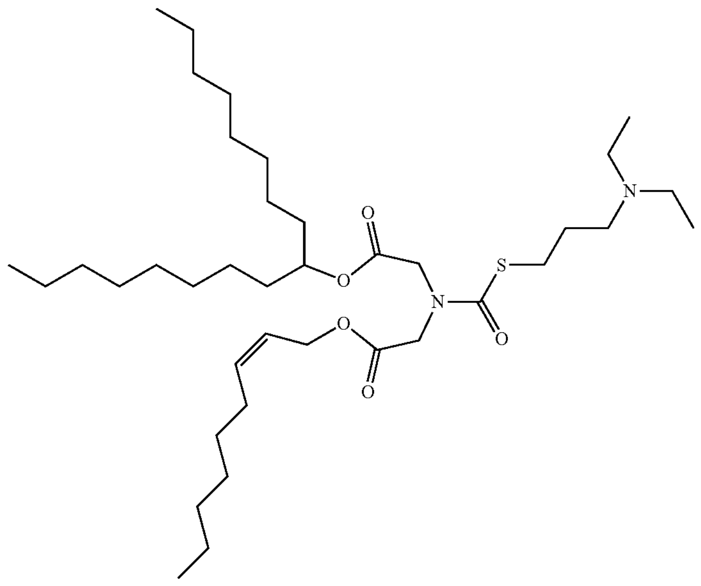
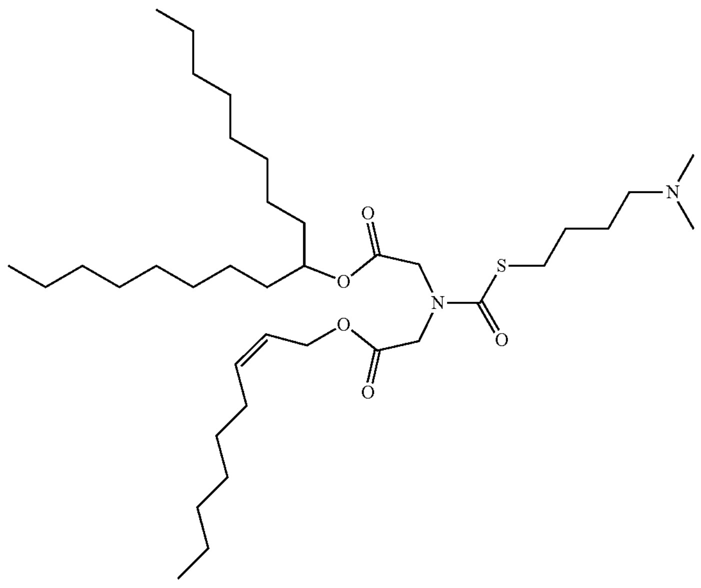

-continued
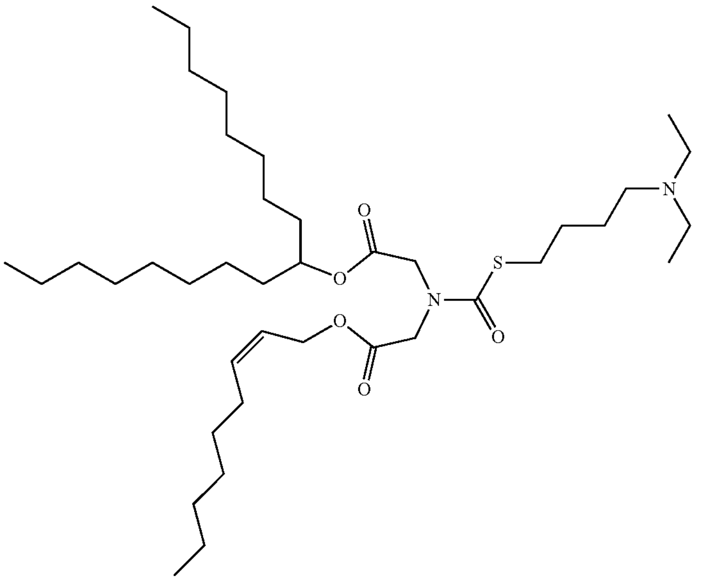
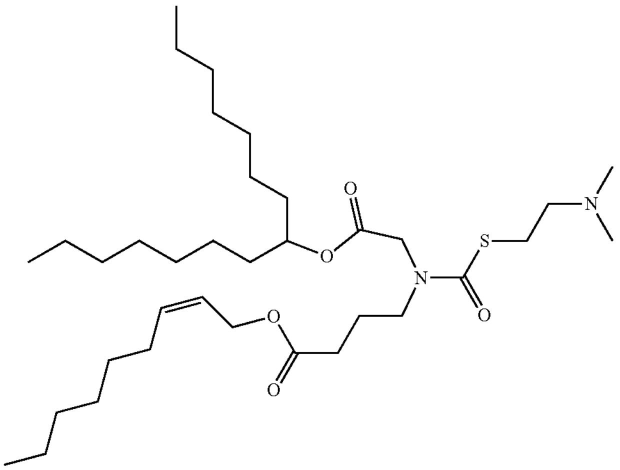
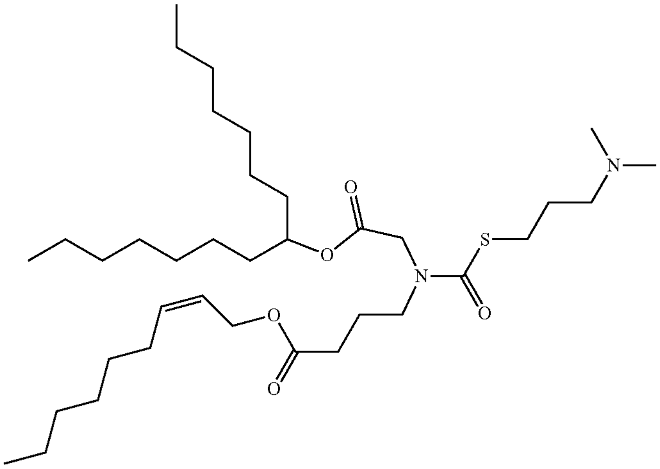

-continued
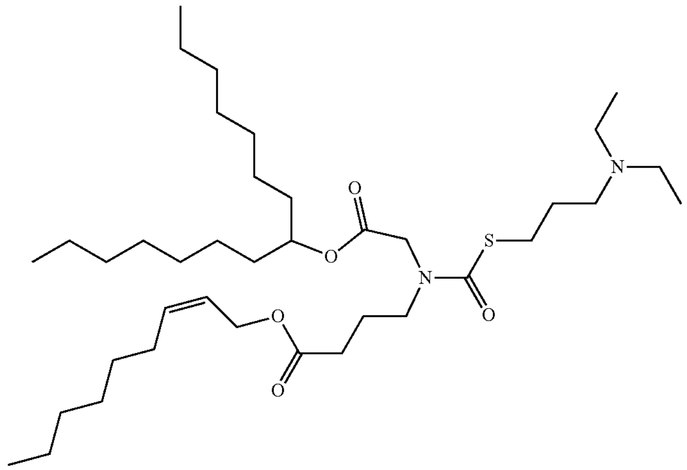
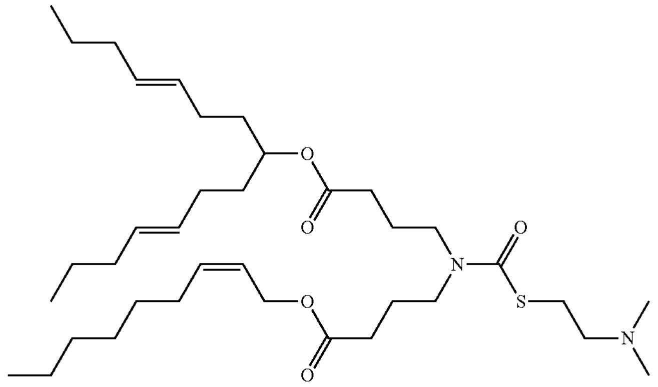
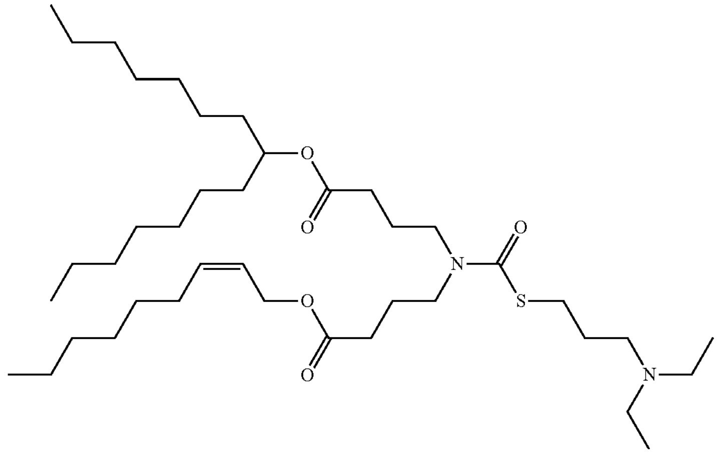

-continued
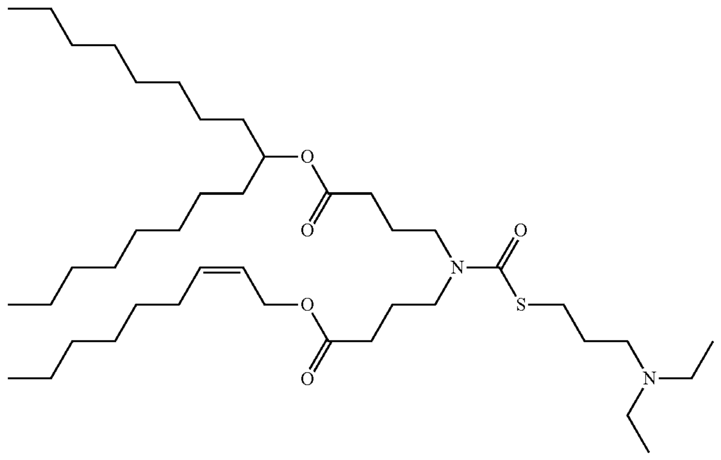
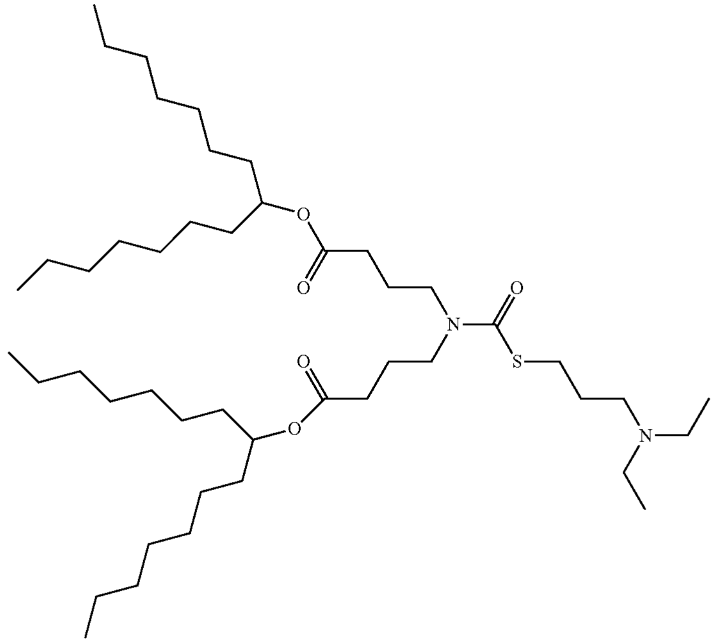
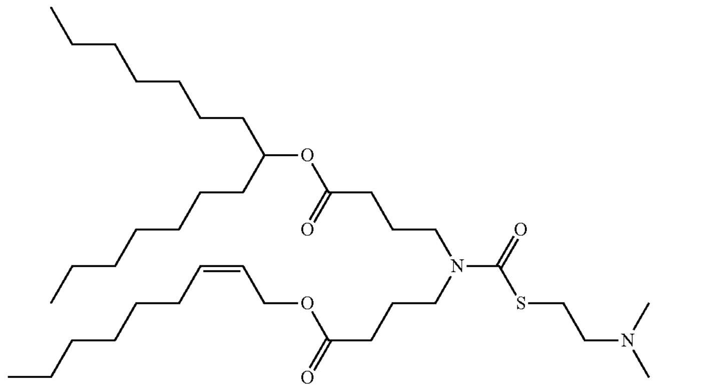

-continued
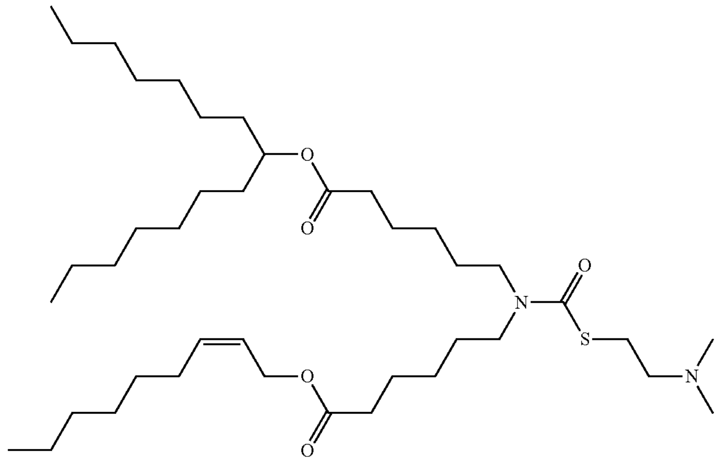
and
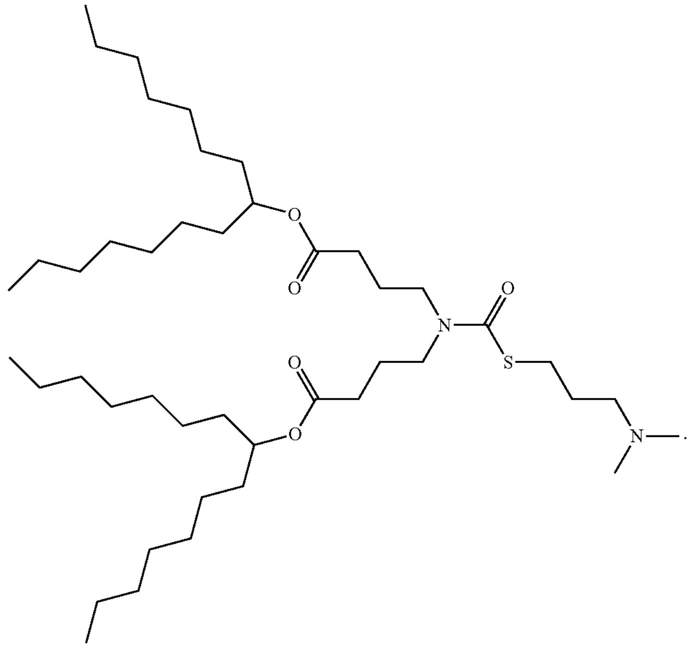
.

In one aspect, the ionizable cationic lipid of compositions provided herein has a structure of

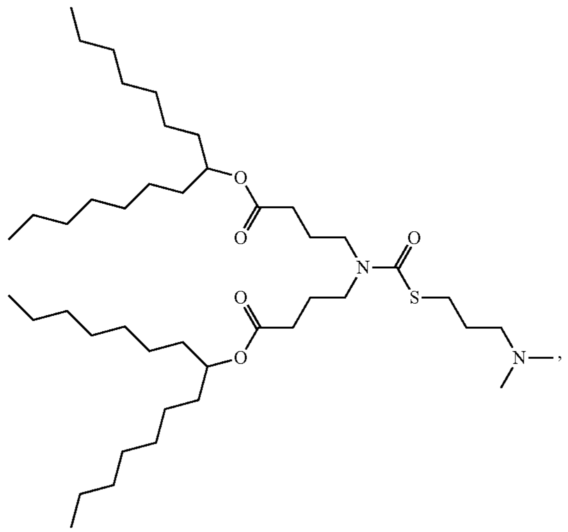

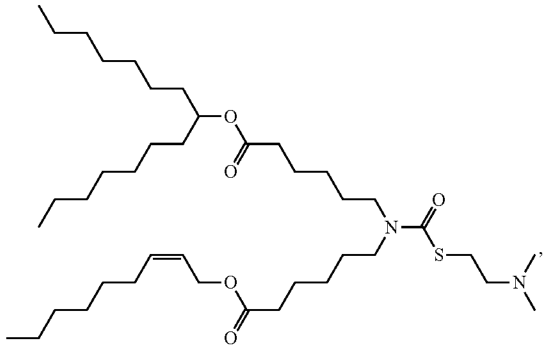

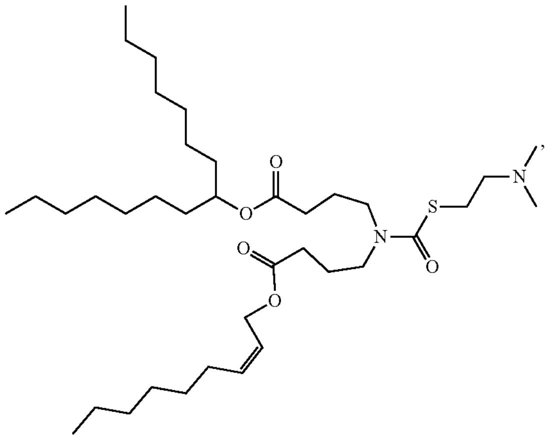

or a pharmaceutically acceptable salt thereof.

In another aspect, the ionizable cationic lipid of compositions provided herein has a structure of

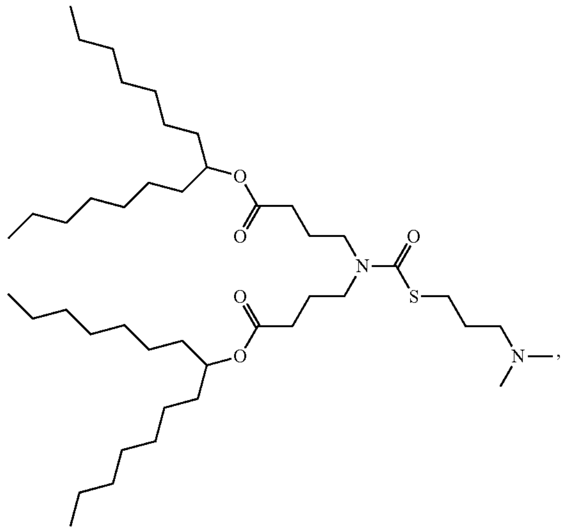

or a pharmaceutically acceptable salt thereof.

In one aspect, the ionizable cationic lipid included in lipid formulations of pharmaceutical compositions provided herein has a structure of

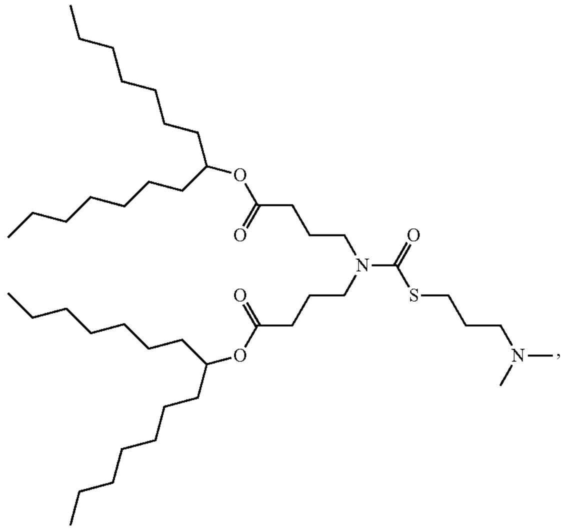

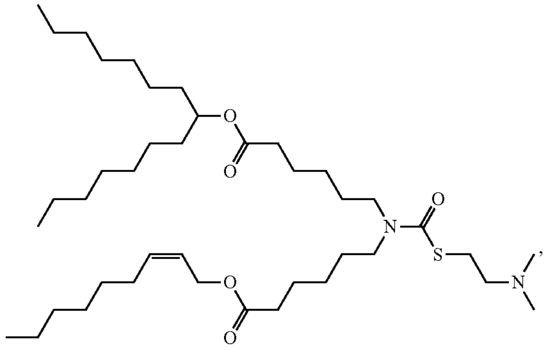

-continued

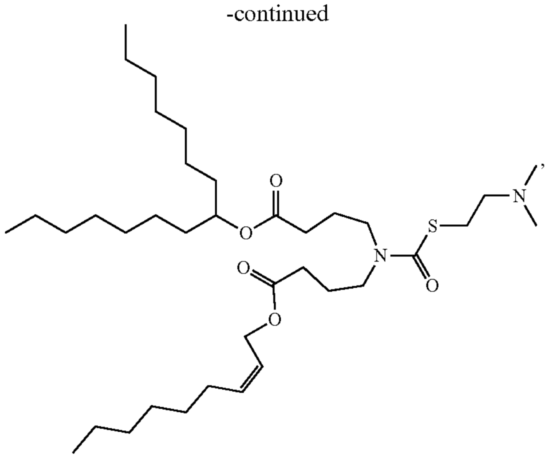

or a pharmaceutically acceptable salt thereof.

In another aspect, the ionizable cationic lipid included in lipid formulations of pharmaceutical compositions provided herein has a structure of

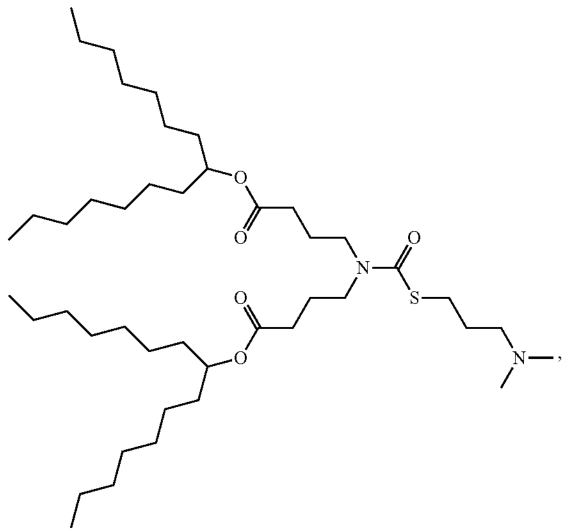

or a pharmaceutically acceptable salt thereof.

Lipid Formulations/LNPs

Therapies based on the intracellular delivery of nucleic acids to target cells face both extracellular and intracellular barriers. Indeed, naked nucleic acid materials cannot be easily systemically administered due to their toxicity, low stability in serum, rapid renal clearance, reduced uptake by target cells, phagocyte uptake and their ability in activating the immune response, all features that preclude their clinical development. When exogenous nucleic acid material (e.g., mRNA) enters the human biological system, it is recognized by the reticuloendothelial system (RES) as foreign pathogens and cleared from blood circulation before having the chance to encounter target cells within or outside the vascular system. It has been reported that the half-life of naked nucleic acid in the blood stream is around several minutes (Kawabata K, Takakura Y, Hashida MPharm Res. 1995 June; 12(6):825-30). Chemical modification and a proper delivery method can reduce uptake by the RES and protect nucleic acids from degradation by ubiquitous nucleases, which increase stability and efficacy of nucleic acid-based therapies. In addition, RNAs or DNAs are anionic hydrophilic polymers that are not favorable for uptake by cells, which are also anionic at the surface. The success of nucleic acid-based therapies thus depends largely on the development of vehicles or vectors that can efficiently and effectively deliver genetic material to target cells and obtain sufficient levels of expression in vivo with minimal toxicity.

Moreover, upon internalization into a target cell, nucleic acid delivery vectors are challenged by intracellular barriers, including endosome entrapment, lysosomal degradation, nucleic acid unpacking from vectors, translocation across the nuclear membrane (for DNA), release at the cytoplasm (for RNA), and so on. Successful nucleic acid-based therapy thus depends upon the ability of the vector to deliver the nucleic acids to the target sites inside of the cells in order to obtain sufficient levels of a desired activity such as expression of a gene.

While several gene therapies have been able to successfully utilize a viral delivery vector (e.g., AAV), lipid-based formulations have been increasingly recognized as one of the most promising delivery systems for RNA and other nucleic acid compounds due to their biocompatibility and their ease of large-scale production. One of the most significant advances in lipid-based nucleic acid therapies happened in August 2018 when Patisiran (ALN-TTR02) was the first siRNA therapeutic approved by the Food and Drug Administration (FDA) and by the European Commission (EC). ALN-TTR02 is an siRNA formulation based upon the so-called Stable Nucleic Acid Lipid Particle (SNALP) transfecting technology. Despite the success of Patisiran, the delivery of nucleic acid therapeutics, including mRNA, via lipid formulations is still under ongoing development.

Some art-recognized lipid-formulated delivery vehicles for nucleic acid therapeutics include, according to various embodiments, polymer based carriers, such as polyethyleneimine (PEI), lipid nanoparticles and liposomes, nanoliposomes, ceramide-containing nanoliposomes, multivesicular liposomes, proteoliposomes, both natural and synthetically-derived exosomes, natural, synthetic and semi-synthetic lamellar bodies, nanoparticulates, micelles, and emulsions. These lipid formulations can vary in their structure and composition, and as can be expected in a rapidly evolving field, several different terms have been used in the art to describe a single type of delivery vehicle. At the same time, the terms for lipid formulations have varied as to their intended meaning throughout the scientific literature, and this inconsistent use has caused confusion as to the exact meaning of several terms for lipid formulations. Among the several potential lipid formulations, liposomes, cationic liposomes, and lipid nanoparticles are specifically described in detail and defined herein for the purposes of the present disclosure.

Liposomes

Conventional liposomes are vesicles that consist of at least one bilayer and an internal aqueous compartment. Bilayer membranes of liposomes are typically formed by amphiphilic molecules, such as lipids of synthetic or natural origin that comprise spatially separated hydrophilic and hydrophobic domains (Lasic, Trends Biotechnol., 16: 307-321, 1998). Bilayer membranes of the liposomes can also be formed by amphiphilic polymers and surfactants (e.g., polymerosomes, niosomes, etc.). They generally present as spherical vesicles and can range in size from 20 nm to a few microns. Liposomal formulations can be prepared as a colloidal dispersion or they can be lyophilized to reduce stability risks and to improve the shelf-life for liposome-based drugs. Methods of preparing liposomal compositions are known in the art and would be within the skill of an ordinary artisan.

Liposomes that have only one bilayer are referred to as being unilamellar, and those having more than one bilayer are referred to as multilamellar. The most common types of liposomes are small unilamellar vesicles (SUV), large unilamellar vesicle (LUV), and multilamellar vesicles (MLV). In contrast to liposomes, lysosomes, micelles, and reversed micelles are composed of monolayers of lipids. Generally, a liposome is thought of as having a single interior compartment, however some formulations can be multivesicular liposomes (MVL), which consist of numerous discontinuous internal aqueous compartments separated by several nonconcentric lipid bilayers.

Liposomes have long been perceived as drug delivery vehicles because of their superior biocompatibility, given that liposomes are basically analogs of biological membranes, and can be prepared from both natural and synthetic phospholipids (Int J Nanomedicine. 2014; 9:1833-1843). In their use as drug delivery vehicles, because a liposome has an aqueous solution core surrounded by a hydrophobic membrane, hydrophilic solutes dissolved in the core cannot readily pass through the bilayer, and hydrophobic compounds will associate with the bilayer. Thus, a liposome can be loaded with hydrophobic and/or hydrophilic molecules. When a liposome is used to carry a nucleic acid such as RNA, the nucleic acid will be contained within the liposomal compartment in an aqueous phase.

Cationic Liposomes

Liposomes can be composed of cationic, anionic, and/or neutral lipids. As an important subclass of liposomes, cationic liposomes are liposomes that are made in whole or part from positively charged lipids, or more specifically a lipid that comprises both a cationic group and a lipophilic portion. In addition to the general characteristics profiled above for liposomes, the positively charged moieties of cationic lipids used in cationic liposomes provide several advantages and some unique structural features. For example, the lipophilic portion of the cationic lipid is hydrophobic and thus will direct itself away from the aqueous interior of the liposome and associate with other nonpolar and hydrophobic species. Conversely, the cationic moiety will associate with aqueous media and more importantly with polar molecules and species with which it can complex in the aqueous interior of the cationic liposome. For these reasons, cationic liposomes are increasingly being researched for use in gene therapy due to their favorability towards negatively charged nucleic acids via electrostatic interactions, resulting in complexes that offer biocompatibility, low toxicity, and the possibility of the large-scale production required for in vivo clinical applications. Cationic lipids suitable for use in cationic liposomes are listed herein below.

Lipid Nanoparticles

In contrast to liposomes and cationic liposomes, lipid nanoparticles (LNP) have a structure that includes a single monolayer or bilayer of lipids that encapsulates a compound in a solid phase. Thus, unlike liposomes, lipid nanoparticles do not have an aqueous phase or other liquid phase in its interior, but rather the lipids from the bilayer or monolayer shell are directly complexed to the internal compound thereby encapsulating it in a solid core. Lipid nanoparticles are typically spherical vesicles having a relatively uniform dispersion of shape and size. While sources vary on what size qualifies a lipid particle as being a nanoparticle, there is some overlap in agreement that a lipid nanoparticle can have a diameter in the range of from 10 nm to 1000 nm. However, more commonly they are considered to be smaller than 120 nm or even 100 nm.

For lipid nanoparticle nucleic acid delivery systems, the lipid shell is formulated to include an ionizable cationic lipid which can complex to and associate with the negatively charged backbone of the nucleic acid core. Ionizable cationic lipids with apparent pKa values below about 7 have the benefit of providing a cationic lipid for complexing with the nucleic acid's negatively charged backbone and loading into the lipid nanoparticle at pH values below the pKa of the ionizable lipid where it is positively charged. Then, at physiological pH values, the lipid nanoparticle can adopt a relatively neutral exterior allowing for a significant increase in the circulation half-lives of the particles following i.v. administration. In the context of nucleic acid delivery, lipid nanoparticles offer many advantages over other lipid-based nucleic acid delivery systems including high nucleic acid encapsulation efficiency, potent transfection, improved penetration into tissues to deliver therapeutics, and low levels of cytotoxicity and immunogenicity.

Prior to the development of lipid nanoparticle delivery systems for nucleic acids, cationic lipids were widely studied as synthetic materials for delivery of nucleic acid medicines. In these early efforts, after mixing together at physiological pH, nucleic acids were condensed by cationic lipids to form lipid-nucleic acid complexes known as lipoplexes. However, lipoplexes proved to be unstable and characterized by broad size distributions ranging from the submicron scale to a few microns. Lipoplexes, such as the Lipofectamine® reagent, have found considerable utility for in vitro transfection. However, these first-generation lipoplexes have not proven useful in vivo. The large particle size and positive charge (imparted by the cationic lipid) result in rapid plasma clearance, hemolytic and other toxicities, as well as immune system activation.

In some aspects, nucleic acid molecules provided herein and lipids or lipid formulations provided herein form a lipid nanoparticle (LNP).

In other aspects, nucleic acid molecules provided herein are incorporated into a lipid formulation (i.e., a lipid-based delivery vehicle).

In the context of the present disclosure, a lipid-based delivery vehicle typically serves to transport a desired RNA to a target cell or tissue. The lipid-based delivery vehicle can be any suitable lipid-based delivery vehicle known in the art. In some aspects, the lipid-based delivery vehicle is a liposome, a cationic liposome, or a lipid nanoparticle containing a self-replicating RNA of the disclosure. In some aspects, the lipid-based delivery vehicle comprises a nanoparticle or a bilayer of lipid molecules and a self-replicating RNA of the disclosure. In some aspects, the lipid bilayer further comprises a neutral lipid or a polymer. In some aspects, the lipid formulation comprises a liquid medium. In some aspects, the formulation further encapsulates a nucleic acid. In some aspects, the lipid formulation further comprises a nucleic acid and a neutral lipid or a polymer. In some aspects, the lipid formulation encapsulates the nucleic acid.

The description provides lipid formulations comprising one or more self-replicating RNA molecules encapsulated within the lipid formulation. In some aspects, the lipid formulation comprises liposomes. In some aspects, the lipid formulation comprises cationic liposomes. In some aspects, the lipid formulation comprises lipid nanoparticles.

In some aspects, the self-replicating RNA is fully encapsulated within the lipid portion of the lipid formulation such that the RNA in the lipid formulation is resistant in aqueous solution to nuclease degradation. In other aspects, the lipid formulations described herein are substantially non-toxic to animals such as humans and other mammals.

The lipid formulations of the disclosure also typically have a total lipid:RNA ratio (mass/mass ratio) of from about 1:1 to about 100:1, from about 1:1 to about 50:1, from about 2:1 to about 45:1, from about 3:1 to about 40:1, from about 5:1 to about 45:1, or from about 10:1 to about 40:1, or from about 15:1 to about 40:1, or from about 20:1 to about 40:1; or from about 25:1 to about 45:1; or from about 30:1 to about 45:1; or from about 32:1 to about 42:1; or from about 34:1 to about 42:1. In some aspects, the total lipid:RNA ratio (mass/mass ratio) is from about 30:1 to about 45:1. The ratio may be any value or subvalue within the recited ranges, including endpoints.

The lipid formulations of the present disclosure typically have a mean diameter of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, or about 30 nm, about 35 nm, about 40 nm, about 45 nm, about 50 nm, about 55 nm, about 60 nm, about 65 nm, about 70 nm, about 75 nm, about 80 nm, about 85 nm, about 90 nm, about 95 nm, about 100 nm, about 105 nm, about 110 nm, about 115 nm, about 120 nm, about 125 nm, about 130 nm, about 135 nm, about 140 nm, about 145 nm, or about 150 nm, and are substantially non-toxic. The diameter may be any value or subvalue within the recited ranges, including endpoints. In addition, nucleic acids, when present in the lipid nanoparticles of the present disclosure, generally are resistant in aqueous solution to degradation with a nuclease.

In some aspects, the lipid formulations comprise a self-replicating RNA, a cationic lipid (e.g., one or more cationic lipids or salts thereof described herein), a phospholipid, and a conjugated lipid that inhibits aggregation of the particles (e.g., one or more PEG-lipid conjugates). The lipid formulations can also include cholesterol. In one aspect, the cationic lipid is an ionizable cationic lipid.

In the nucleic acid-lipid formulations, the RNA may be fully encapsulated within the lipid portion of the formulation, thereby protecting the nucleic acid from nuclease degradation. In some aspects, a lipid formulation comprising an RNA is fully encapsulated within the lipid portion of the lipid formulation, thereby protecting the nucleic acid from nuclease degradation. In certain aspects, the RNA in the lipid formulation is not substantially degraded after exposure of the particle to a nuclease at 37° C. for at least 20, 30, 45, or 60 minutes. In certain other aspects, the RNA in the lipid formulation is not substantially degraded after incubation of the formulation in serum at 37° C. for at least 30, 45, or 60 minutes or at least 2, 3, 4, 5, 6, 7, 8, 9, 10, 12, 14, 16, 18, 20, 22, 24, 26, 28, 30, 32, 34, or 36 hours. In some aspects, the RNA is complexed with the lipid portion of the formulation. One of the benefits of the formulations of the present disclosure is that the nucleic acid-lipid compositions are substantially non-toxic to animals such as humans and other mammals.

In the context of nucleic acids, full encapsulation may be determined by performing a membrane-impermeable fluorescent dye exclusion assay, which uses a dye that has enhanced fluorescence when associated with nucleic acid. Encapsulation is determined by adding the dye to a lipid formulation, measuring the resulting fluorescence, and comparing it to the fluorescence observed upon addition of a small amount of nonionic detergent. Detergent-mediated disruption of the lipid layer releases the encapsulated nucleic acid, allowing it to interact with the membrane-impermeable dye. Nucleic acid encapsulation may be calculated as $E=(I0-I)/I0$, where/and I0 refers to the fluorescence intensities before and after the addition of detergent.

In some aspects, the present disclosure provides a nucleic acid-lipid composition comprising a plurality of nucleic acid-liposomes, nucleic acid-cationic liposomes, or nucleic acid-lipid nanoparticles. In some aspects, the nucleic acid-lipid composition comprises a plurality of RNA-liposomes. In some aspects, the nucleic acid-lipid composition comprises a plurality of RNA-cationic liposomes. In some aspects, the nucleic acid-lipid composition comprises a plurality of RNA-lipid nanoparticles.

In some aspects, the lipid formulations comprise RNA that is fully encapsulated within the lipid portion of the formulation, such that from about 30% to about 100%, from about 40% to about 100%, from about 50% to about 100%, from about 60% to about 100%, from about 70% to about 100%, from about 80% to about 100%, from about 90% to about 100%, from about 30% to about 95%, from about 40% to about 95%, from about 50% to about 95%, from about 60% to about 95%, from about 70% to about 95%, from about 80% to about 95%, from about 85% to about 95%, from about 90% to about 95%, from about 30% to about 90%, from about 40% to about 90%, from about 50% to about 90%, from about 60% to about 90%, from about 70% to about 90%, from about 80% to about 90%, or at least about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, or about 99% (or any fraction thereof or range therein) of the particles have the RNA encapsulated therein. The amount may be any value or subvalue within the recited ranges, including endpoints. The RNA included in any RNA-lipid composition or RNA-lipid formulation provided herein can be a self-replicating RNA.

Depending on the intended use of the lipid formulation, the proportions of the components can be varied, and the delivery efficiency of a particular formulation can be measured using assays known in the art.

In some aspects, nucleic acid molecules provided herein are lipid formulated. The lipid formulation is preferably selected from, but not limited to, liposomes, cationic liposomes, and lipid nanoparticles. In one aspect, a lipid formulation is a cationic liposome or a lipid nanoparticle (LNP) comprising:

(a) an RNA of the present disclosure,
(b) a cationic lipid,
(c) an aggregation reducing agent (such as polyethylene glycol (PEG) lipid or PEG-modified lipid),
(d) optionally a non-cationic lipid (such as a neutral lipid), and
(e) optionally, a sterol.

In another aspect, the cationic lipid is an ionizable cationic lipid. Any ionizable cationic lipid can be included in lipid formulations, including exemplary cationic lipids provided herein.

Cationic Lipids

In one aspect, the lipid nanoparticle formulation comprises (i) at least one cationic lipid; (ii) a helper lipid; (iii) a sterol (e.g., cholesterol); and (iv) a PEG-lipid. In another aspect, the cationic lipid is an ionizable cationic lipid. In yet another aspect, the lipid nanoparticle formulation comprises (i) at least one cationic lipid; (ii) a helper lipid; (iii) a sterol (e.g., cholesterol); and (iv) a PEG-lipid, in a molar ratio of about 40-70% ionizable cationic lipid: about 2-15% helper lipid: about 20-45% sterol; about 0.5-5% PEG-lipid. In a further aspect, the cationic lipid is an ionizable cationic lipid.

In one aspect, the lipid nanoparticle formulation consists of (i) at least one cationic lipid; (ii) a helper lipid; (iii) a sterol (e.g., cholesterol); and (iv) a PEG-lipid. In another aspect, the cationic lipid is an ionizable cationic lipid. In yet another aspect, the lipid nanoparticle formulation consists of (i) at least one cationic lipid; (ii) a helper lipid; (iii) a sterol (e.g., cholesterol); and (iv) a PEG-lipid, in a molar ratio of about 40-70% ionizable cationic lipid: about 2-15% helper lipid: about 20-45% sterol; about 0.5-5% PEG-lipid. In a further aspect, the cationic lipid is an ionizable cationic lipid.

In the presently disclosed lipid formulations, the cationic lipid may be, for example, N,N-dioleyl-N,N-dimethylammonium chloride (DODAC), N,N-distearyl-N,N-dimethylammonium bromide (DDAB), 1,2-dioleoyltrimethylammoniumpropane chloride (DOTAP) (also known as N-(2,3-dioleoyloxy)propyl)-N,N,N-trimethylammonium chloride and 1,2-Dioleyloxy-3-trimethylaminopropane chloride salt), N-(1-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-di-y-linolenyloxy-N,N-dimethylaminopropane (γ-DLenDMA), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleyoxy-3-morpholinopropane (DLin-MA),1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP),1,2-Dilinoleyloxy-3-trimethylaminopropane chloride salt (DLin-TMA·Cl),1,2-Dilinoleoyl-3-trimethylaminopropane chloride salt (DLin-TAP·Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanediol (DOAP), 1,2-Dilinoleyloxo-3-(2-N,N-dimethylamino)ethoxypropane (DLin-EG-DMA), 2,2-Dilinoleyl-4-dimethylaminomethyl)-[1,3]-dioxolane (DLin-K-DMA) or analogs thereof, (3aR,5s,6aS)-N,N-dimethyl-2,2-di((9Z,12Z)-octadeca-9,12-dienyl)tetrahydro-3aH-cyclopenta[d][1,3]dioxol-5-amine, (6Z,9Z,28Z,31Z)-heptatriaconta-6,9,28,31-tetraen-19-yl4-(dimethylamino)butanoate (MC3), 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (C12-200), 2,2-dilinoleyl-4-(2-dimethylaminoethyl)-[1,3]-dioxolane (DLin-K-C2-DMA), 2,2-dilinoleyl-4-dimethylaminomethyl-[1,3]-dioxolane (DLin-K-DMA), (6Z,9Z,28Z,31Z)-heptatriaconta-6,9,28,31-tetraen-19-yl 4-(dimethylamino) butanoate (DLin-M-C3-DMA), 3-((6Z,9Z,28Z,31Z)-heptatriaconta-6,9,28,31-tetraen-19-yloxy)-N,N-dimethylpropan-1-amine (MC3 Ether), 4-((6Z,9Z,28Z,31 Z)-heptatriaconta-6,9,28,31-tetraen-19-yloxy)-N,N-dimethylbutan-1-amine (MC4 Ether), or any combination thereof. Other cationic lipids include, but are not limited to, N,N-distearyl-N,N-dimethylammonium bromide (DDAB), 3P—(N—(N',N'-dimethylaminoethane)-carbamoyl)cholesterol (DC-Choi), N-(1-(2,3-dioleyloxy)propyl)-N-2-(sperminecarboxamido)ethyl)-N,N-dimethylammonium trifluoracetate (DOSPA), dioctadecylamidoglycyl carboxyspermine (DOGS), 1,2-dileoyl-sn-3-phosphoethanolamine (DOPE), 1,2-dioleoyl-3-dimethylammonium propane (DODAP), N-(1,2-dimyristyloxyprop-3-yl)-N,N-dimethyl-N-hydroxyethyl ammonium bromide (DMRIE), and 2,2-Dilinoleyl-4-dimethylaminoethyl[1,3]-dioxolane (XTC). Additionally, commercial preparations of cationic lipids can be used, such as, e.g., LIPOFECTIN (including DOTMA and DOPE, available from GIBCO/BRL), and Lipofectamine (comprising DOSPA and DOPE, available from GIBCO/BRL).

Other suitable cationic lipids are disclosed in International Publication Nos. WO 09/086558, WO 09/127060, WO 10/048536, WO 10/054406, WO 10/088537, WO 10/129709, and WO 2011/153493; U.S. Patent Publication Nos. 2011/0256175, 2012/0128760, and 2012/0027803; U.S. Pat. No. 8,158,601; and Love et al., PNAS, 107(5), 1864-69, 2010, the contents of which are herein incorporated by reference.

The RNA-lipid formulations of the present disclosure can comprise a helper lipid, which can be referred to as a neutral helper lipid, non-cationic lipid, non-cationic helper lipid, anionic lipid, anionic helper lipid, or a neutral lipid. It has been found that lipid formulations, particularly cationic liposomes and lipid nanoparticles have increased cellular uptake if helper lipids are present in the formulation. (Curr. Drug Metab. 2014; 15(9):882-92). For example, some studies have indicated that neutral and zwitterionic lipids such as 1,2-dioleoylsn-glycero-3-phosphatidylcholine (DOPC), Di-Oleoyl-Phosphatidyl-Ethanoalamine (DOPE) and 1,2-DiStearoyl-sn-glycero-3-PhosphoCholine (DSPC), being more fusogenic (i.e., facilitating fusion) than cationic lipids, can affect the polymorphic features of lipid-nucleic acid complexes, promoting the transition from a lamellar to a hexagonal phase, and thus inducing fusion and a disruption of the cellular membrane. (Nanomedicine (Lond). 2014 January; 9(1):105-20). In addition, the use of helper lipids can help to reduce any potential detrimental effects from using many prevalent cationic lipids such as toxicity and immunogenicity.

Non-limiting examples of non-cationic lipids suitable for lipid formulations of the present disclosure include phospholipids such as lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), palmitoyloleyol-phosphatidylglycerol (POPG), dioleoylphosphatidylethanolamine 4-(N-maleimidomethyl)-cyclohexane-1-carboxylate (DOPE-mal), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), lysophosphatidylcholine, dilinoleoylphosphatidylcholine, and mixtures thereof. Other diacylphosphatidylcholine and diacylphosphatidylethanolamine phospholipids can also be used. The acyl groups in these lipids are preferably acyl groups derived from fatty acids having C10-C24 carbon chains, e.g., lauroyl, myristoyl, palmitoyl, stearoyl, or oleoyl.

Additional examples of non-cationic lipids include sterols such as cholesterol and derivatives thereof. As a helper lipid, cholesterol increases the spacing of the charges of the lipid layer interfacing with the nucleic acid making the charge distribution match that of the nucleic acid more closely. (J. R. Soc. Interface. 2012 Mar. 7; 9(68): 548-561). Non-limiting examples of cholesterol derivatives include polar analogues such as 5α-cholestanol, 5α-coprostanol, cholesteryl-(2'-hydroxy)-ethyl ether, cholesteryl-(4'-hydroxy)-butyl ether, and 6-ketocholestanol; non-polar analogues such as 5α-cholestane, cholestenone, 5α-cholestanone, 5α-cholestanone, and cholesteryl decanoate; and mixtures thereof. In some aspects, the cholesterol derivative is a polar analogue such as cholesteryl-(4'-hydroxy)-butyl ether.

In some aspects, the helper lipid present in the lipid formulation comprises or consists of a mixture of one or more phospholipids and cholesterol or a derivative thereof. In other aspects, the neutral lipid present in the lipid formulation comprises or consists of one or more phospholipids, e.g., a cholesterol-free lipid formulation. In yet other aspects, the neutral lipid present in the lipid formulation comprises or consists of cholesterol or a derivative thereof, e.g., a phospholipid-free lipid formulation.

Other examples of helper lipids include nonphosphorous containing lipids such as, e.g., stearylamine, dodecylamine, hexadecylamine, acetyl palmitate, glycerol ricinoleate, hexadecyl stearate, isopropyl myristate, amphoteric acrylic polymers, triethanolamine-lauryl sulfate, alkyl-aryl sulfate polyethyloxylated fatty acid amides, dioctadecyldimethyl ammonium bromide, ceramide, and sphingomyelin.

Other suitable cationic lipids include those having alternative fatty acid groups and other dialkylamino groups, including those, in which the alkyl substituents are different (e.g., N-ethyl-N-methylamino-, and N-propyl-N-ethylamino-). These lipids are part of a subcategory of cationic lipids referred to as amino lipids. In some embodiments of the lipid formulations described herein, the cationic lipid is an amino lipid. In general, amino lipids having less saturated acyl chains are more easily sized, particularly when the complexes must be sized below about 0.3 microns, for purposes of filter sterilization. Amino lipids containing unsaturated fatty acids with carbon chain lengths in the range of C14 to C22 may be used. Other scaffolds can also be used to separate the amino group and the fatty acid or fatty alkyl portion of the amino lipid.

In some embodiments, the lipid formulation comprises the cationic lipid with Formula I according to the patent application PCT/EP2017/064066. In this context, the disclosure of PCT/EP2017/064066 is also incorporated herein by reference.

In some embodiments, amino or cationic lipids of the present disclosure are ionizable and have at least one protonatable or deprotonatable group, such that the lipid is positively charged at a pH at or below physiological pH (e.g., pH 7.4), and neutral at a second pH, preferably at or above physiological pH. Of course, it will be understood that the addition or removal of protons as a function of pH is an equilibrium process, and that the reference to a charged or a neutral lipid refers to the nature of the predominant species and does not require that all of the lipid be present in the charged or neutral form. Lipids that have more than one protonatable or deprotonatable group, or which are zwitterionic, are not excluded from use in the disclosure. In certain embodiments, the protonatable lipids have a pKa of the protonatable group in the range of about 4 to about 11. In some embodiments, the ionizable cationic lipid has a pKa of about 5 to about 7. In some embodiments, the pKa of an ionizable cationic lipid is about 6 to about 7.

In some embodiments, the lipid formulation comprises an ionizable cationic lipid of Formula I:

(I)

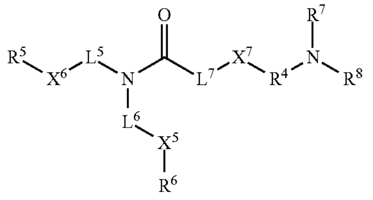

or a pharmaceutically acceptable salt or solvate thereof, wherein R5 and R6 are each independently selected from the group consisting of a linear or branched C1-C31 alkyl, C2-C31 alkenyl or C2-C31 alkynyl and cholesteryl; L5 and L6 are each independently selected from the group consisting of a linear C1-C20 alkyl and C2-C20 alkenyl; X5 is —C(O)O—, whereby —C(O)O—R6 is formed or —OC(O)— whereby —OC(O)—R6 is formed; X6 is —C(O)O— whereby —C(O)O—R5 is formed or —OC(O)— whereby —OC(O)—R5 is formed; X7 is S or O; L7 is absent or lower alkyl; R4 is a linear or branched C1-C6 alkyl; and R7 and R8 are each independently selected from the group consisting of a hydrogen and a linear or branched C1-C6 alkyl.

In some embodiments, X7 is S.

In some embodiments, X5 is —C(O)O—, whereby —C(O)O—R6 is formed and X6 is —C(O)O— whereby —C(O)O—R5 is formed.

In some embodiments, R7 and R8 are each independently selected from the group consisting of methyl, ethyl and isopropyl.

In some embodiments, L5 and L6 are each independently a C1-C10 alkyl. In some embodiments, L5 is C1-C3 alkyl, and L6 is C1-C5 alkyl. In some embodiments, L6 is C1-C2 alkyl. In some embodiments, L5 and L6 are each a linear C7 alkyl. In some embodiments, L5 and L6 are each a linear C9 alkyl.

In some embodiments, R5 and R6 are each independently an alkenyl. In some embodiments, R6 is alkenyl. In some embodiments, R6 is C2-C9 alkenyl. In some embodiments, the alkenyl comprises a single double bond. In some embodiments, R5 and R6 are each alkyl. In some embodiments, R5 is a branched alkyl. In some embodiments, R5 and R6 are each independently selected from the group consisting of a C9 alkyl, C9 alkenyl and C9 alkynyl. In some embodiments, R5 and R6 are each independently selected from the group consisting of a C11 alkyl, C11 alkenyl and C11 alkynyl. In some embodiments, R5 and R6 are each independently selected from the group consisting of a C7 alkyl, C7 alkenyl and C7 alkynyl. In some embodiments, R5 is —CH((CH2)pCH3)2 or —CH((CH2)pCH3)((CH2)p-1CH3), wherein p is 4-8. In some embodiments, p is 5 and L5 is a C1-C3 alkyl. In some embodiments, p is 6 and L5 is a C3 alkyl. In some embodiments, p is 7. In some embodiments, p is 8 and L5 is a C1-C3 alkyl. In some embodiments, R5 consists of —CH((CH2)pCH3)((CH2)p-1CH3), wherein p is 7 or 8.

In some embodiments, R4 is ethylene or propylene. In some embodiments, R4 is n-propylene or isobutylene.

In some embodiments, L7 is absent, R4 is ethylene, X7 is S and R7 and R8 are each methyl. In some embodiments, L7 is absent, R4 is n-propylene, X7 is S and R7 and R8 are each methyl. In some embodiments, L7 is absent, R4 is ethylene, X7 is S and R7 and R8 are each ethyl.

In some embodiments, X7 is S, X5 is —C(O)O—, whereby —C(O)O—R6 is formed, X6 is —C(O)O— whereby —C(O)O—R5 is formed, L5 and L6 are each independently a linear C3-C7 alkyl, L7 is absent, R5 is —CH((CH2)pCH3)$_2$, and R6 is C7-C12 alkenyl. In some further embodiments, p is 6 and R6 is C9 alkenyl.

In some embodiments, the lipid formulation can comprise an ionizable cationic lipid selected from the group consisting of LIPID #1 to LIPID #8:

TABLE 5

| LIPID # | STRUCTURE |
|---|---|
| 1 | 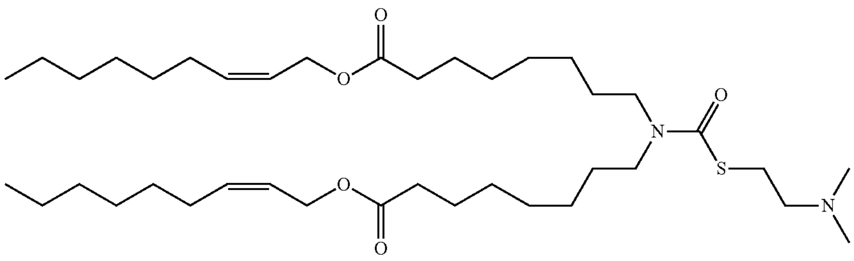 |
| 2 | 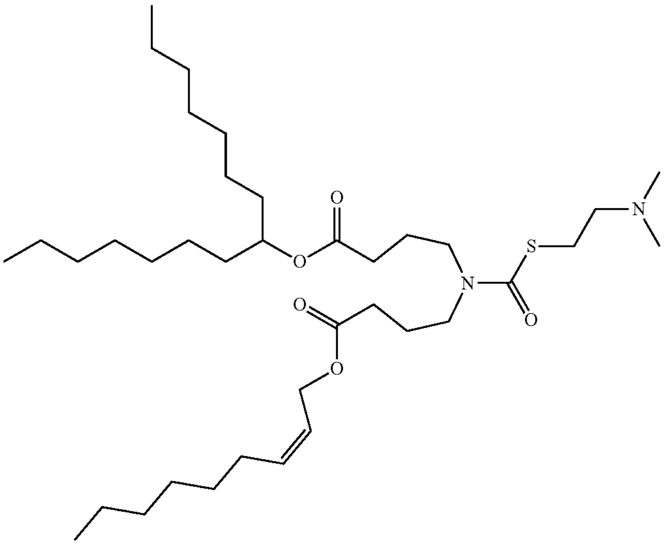 [SMILES: CCCCCC/C=C\COC(=O)CCCN(CCCC(=O)OC(CCCCCCC)CCCCCCC)C(=O)SCCN(C)C] |
| 3 | 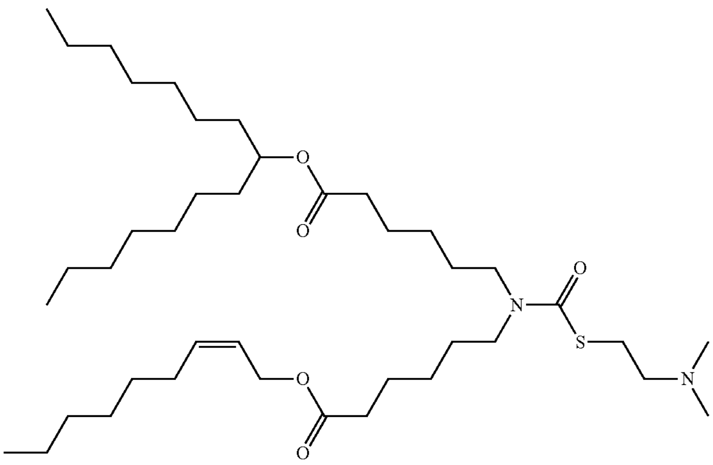 [SMILES: CCCCCC/C=C\COC(=O)CCCCCN(CCCCCC(=O)OC(CCCCCCC)CCCCCCC)C(=O)SCCN(C)C] |

TABLE 5-continued
| LIPID # | STRUCTURE |
| --- | --- |
| 4 | 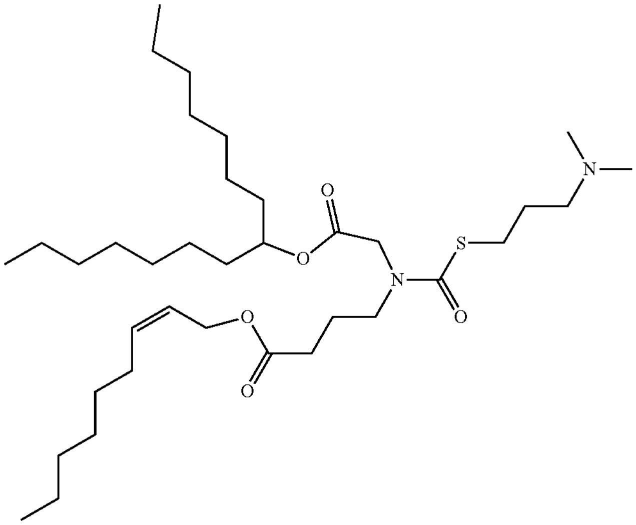 [SMILES: CCCCCC/C=C\COC(=O)CCCN(CC(=O)OC(CCCCCCC)CCCCCCC)C(=O)SCCCN(C)C] |
| 5 | 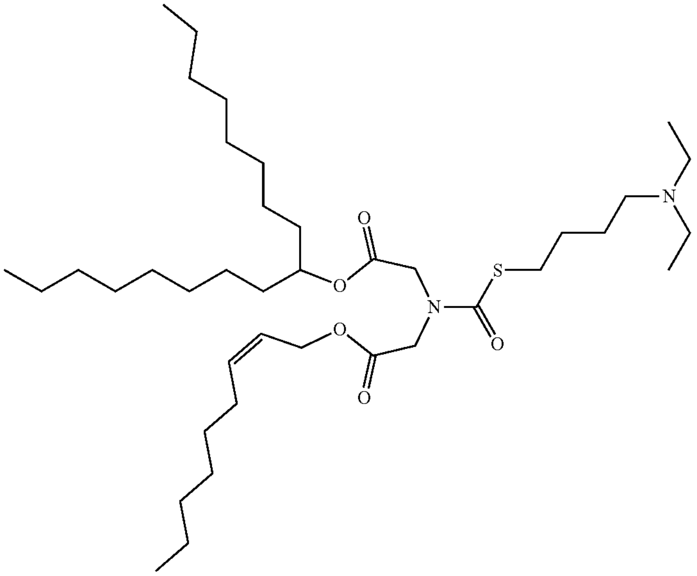 [SMILES: CCCCCC/C=C\COC(=O)CN(CC(=O)OC(CCCCCCCC)CCCCCCCC)C(=O)SCCCCN(CC)CC] |
| 6 | 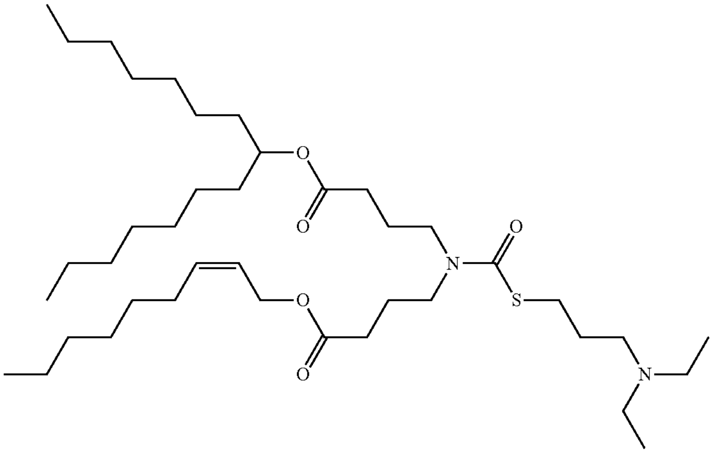 [SMILES: CCCCCC/C=C\COC(=O)CCCN(CCCC(=O)OC(CCCCCCC)CCCCCCC)C(=O)SCCCN(CC)CC] |

TABLE 5-continued
| LIPID # | STRUCTURE |
| --- | --- |
| 7 | 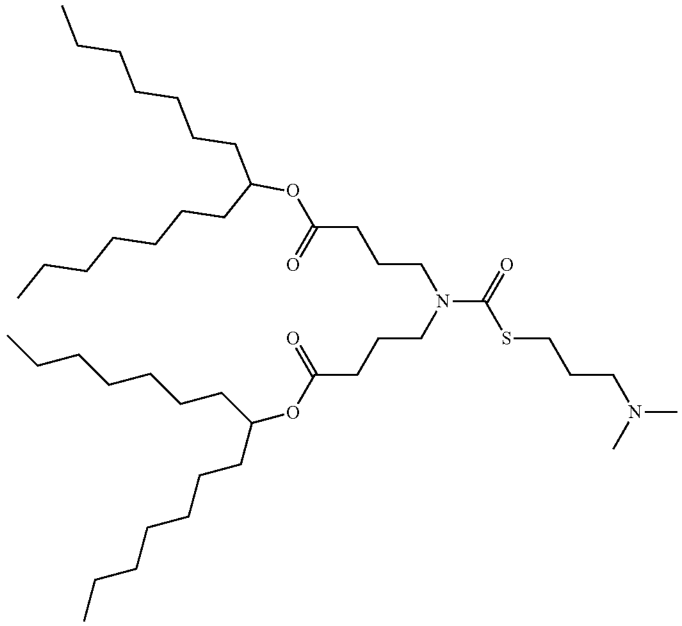 [SMILES: CCCCCCCC(CCCCCCC)OC(=O)CCCN(CCCC(=O)OC(CCCCCCC)CCCCCCC)C(=O)SCCCN(C)C] |
| 8 | 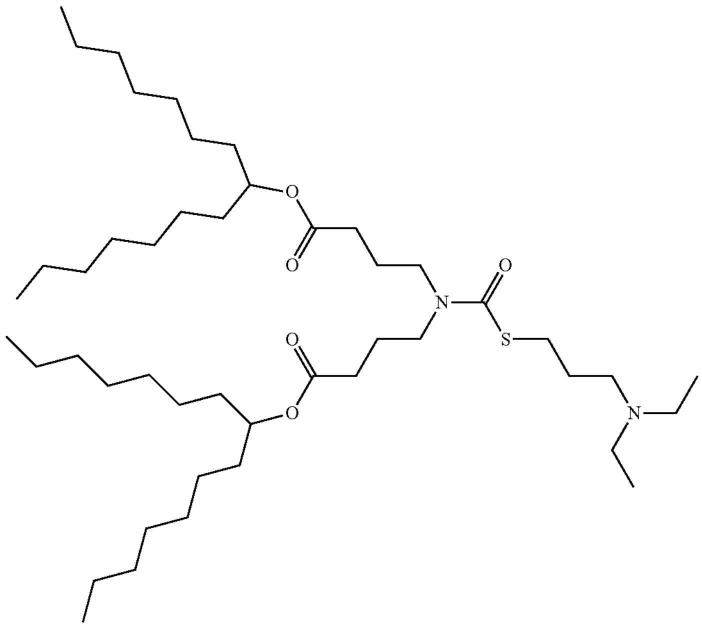 [SMILES: CCCCCCCC(CCCCCCC)OC(=O)CCCN(CCCC(=O)OC(CCCCCCC)CCCCCCC)C(=O)SCCCN(CC)CC] |

In some embodiments, the lipid formulation comprises an ionizable cationic lipid having a structure selected from

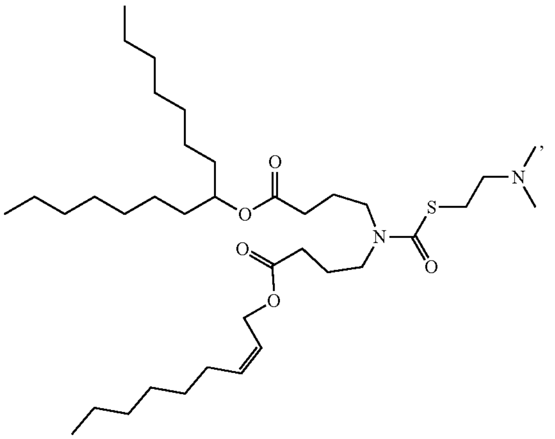 [SMILES: CCCCCC/C=C\COC(=O)CCCN(CCCC(=O)OC(CCCCCCC)CCCCCCC)C(=O)SCCN(C)C]

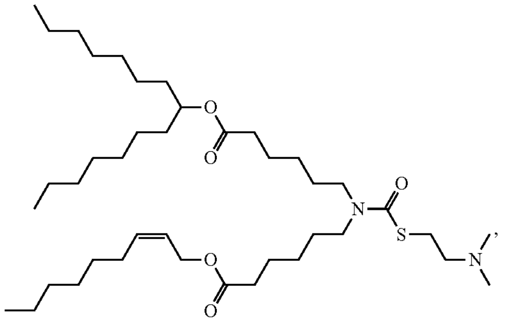

and

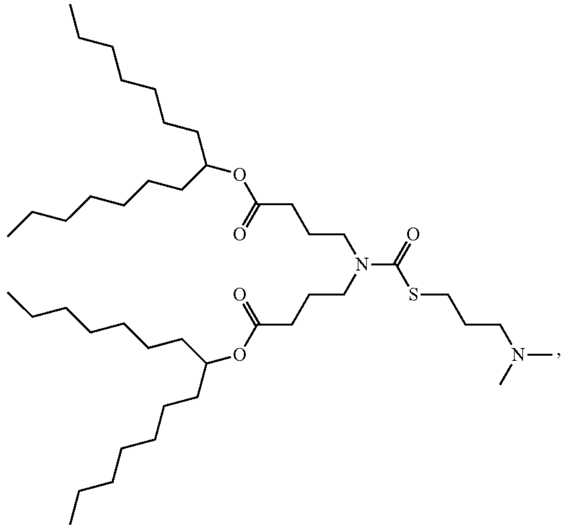

or a pharmaceutically acceptable salt thereof.

In some preferred embodiments, the lipid formulation comprises an ionizable cationic lipid having the structure

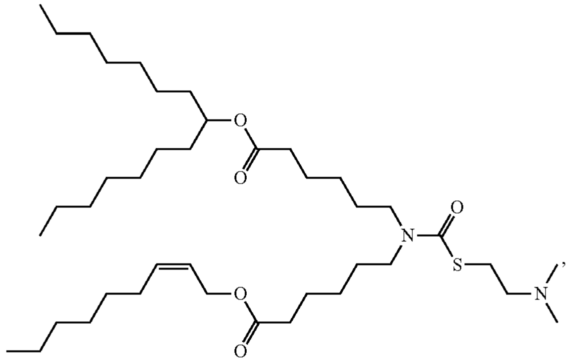 [SMILES: CCCCCC/C=C\COC(=O)CCCCCN(CCCCCC(=O)OC(CCCCCCC)CCCCCCC)C(=O)SCCN(C)C]

or a pharmaceutically acceptable salt thereof.

In embodiments, any one or more lipids recited herein may be expressly excluded.

In some aspects, the helper lipid comprises from about 2 mol % to about 20 mol %, from about 3 mol % to about 18 mol %, from about 4 mol % to about 16 mol %, about 5 mol % to about 14 mol %, from about 6 mol % to about 12 mol %, from about 5 mol % to about 10 mol %, from about 5 mol % to about 9 mol %, or about 2 mol %, about 3 mol %, about 4 mol %, about 5 mol %, about 6 mol %, about 7 mol %, about 8 mol %, about 9 mol %, about 10 mol %, about 11 mol %, or about 12 mol % (or any fraction thereof or the range therein) of the total lipid present in the lipid formulation.

The cholesterol or cholesterol derivative in the lipid formulation may comprise up to about 40 mol %, about 45 mol %, about 50 mol %, about 55 mol %, or about 60 mol % of the total lipid present in the lipid formulation. In some aspects, the cholesterol or cholesterol derivative comprises about 15 mol % to about 45 mol %, about 20 mol % to about 40 mol %, about 25 mol % to about 35 mol %, or about 28 mol % to about 35 mol %; or about 25 mol %, about 26 mol %, about 27 mol %, about 28 mol %, about 29 mol %, about 30 mol %, about 31 mol %, about 32 mol %, about 33 mol %, about 34 mol %, about 35 mol %, about 36 mol %, or about 37 mol % of the total lipid present in the lipid formulation.

In some aspects, the phospholipid component in the mixture may comprise from about 2 mol % to about 20 mol %, from about 3 mol % to about 18 mol %, from about 4 mol % to about 16 mol %, about 5 mol % to about 14 mol %, from about 6 mol % to about 12 mol %, from about 5 mol % to about 10 mol %, from about 5 mol % to about 9 mol %, or about 2 mol %, about 3 mol %, about 4 mol %, about 5 mol %, about 6 mol %, about 7 mol %, about 8 mol %, about 9 mol %, about 10 mol %, about 11 mol %, or about 12 mol % (or any fraction thereof or the range therein) of the total lipid present in the lipid formulation.

The percentage of helper lipid present in the lipid formulation is a target amount, and the actual amount of helper lipid present in the formulation may vary, for example, by ±5 mol %.

A lipid formulation that includes a cationic lipid compound or ionizable cationic lipid compound may be on a molar basis about 30-70% cationic lipid compound, about 25-40% cholesterol, about 2-15% helper lipid, and about 0.5-5% of a polyethylene glycol (PEG) lipid, wherein the percent is of the total lipid present in the formulation. In some aspects, the composition is about 40-65% cationic lipid compound, about 25-35% cholesterol, about 3-9% helper lipid, and about 0.5-3% of a PEG-lipid, wherein the percent is of the total lipid present in the formulation.

The formulation may be a lipid particle formulation, for example containing 8-30% nucleic acid compound, 5-30% helper lipid, and 0-20% cholesterol; 4-25% cationic lipid, 4-25% helper lipid, 2-25% cholesterol, 10-35% cholesterol-PEG, and 5% cholesterol-amine; or 2-30% cationic lipid, 2-30% helper lipid, 1-15% cholesterol, 2-35% cholesterol-PEG, and 1-20% cholesterol-amine; or up to 90% cationic lipid and 2-10% helper lipids, or even 100% cationic lipid.

Lipid Conjugates

The lipid formulations described herein may further comprise a lipid conjugate. The conjugated lipid is useful in that it prevents the aggregation of particles. Suitable conjugated lipids include, but are not limited to, PEG-lipid conjugates, cationic-polymer-lipid conjugates, and mixtures thereof. Furthermore, lipid delivery vehicles can be used for specific targeting by attaching ligands (e.g., antibodies, peptides, and carbohydrates) to its surface or to the terminal end of the attached PEG chains (Front Pharmacol. 2015 Dec. 1; 6:286).

In some aspects, the lipid conjugate is a PEG-lipid. The inclusion of polyethylene glycol (PEG) in a lipid formulation as a coating or surface ligand, a technique referred to as PEGylation, helps to protect nanoparticles from the immune system and their escape from RES uptake (Nanomedicine (Lond). 2011 June; 6(4):715-28). PEGylation has been used to stabilize lipid formulations and their payloads through physical, chemical, and biological mechanisms. Detergent-like PEG lipids (e.g., PEG-DSPE) can enter the lipid formulation to form a hydrated layer and steric barrier on the surface. Based on the degree of PEGylation, the surface layer can be generally divided into two types, brush-like and mushroom-like layers. For PEG-DSPE-stabilized formulations, PEG will take on the mushroom conformation at a low degree of PEGylation (usually less than 5 mol %) and will shift to brush conformation as the content of PEG-DSPE is increased past a certain level (Journal of Nanomaterials. 2011; 2011:12). PEGylation leads to a significant increase in the circulation half-life of lipid formulations (Annu. Rev. Biomed. Eng. 2011 Aug. 15; 130:507-30; J. Control Release. 2010 Aug. 3; 145(3):178-81).

Examples of PEG-lipids include, but are not limited to, PEG coupled to dialkyloxypropyls (PEG-DAA), PEG coupled to diacylglycerol (PEG-DAG), PEG coupled to phospholipids such as phosphatidylethanolamine (PEG-PE), PEG conjugated to ceramides, PEG conjugated to cholesterol or a derivative thereof, and mixtures thereof.

PEG is a linear, water-soluble polymer of ethylene PEG repeating units with two terminal hydroxyl groups. PEGs are classified by their molecular weights and include the following: monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-NH2), monomethoxypolyethylene glycol-tresylate (MePEG-TRES), monomethoxypolyethylene glycol-imidazolyl-carbonyl (MePEG-IM), as well as such compounds containing a terminal hydroxyl group instead of a terminal methoxy group (e.g., HO-PEG-S, HO-PEG-S-NHS, HO-PEG-NH2).

The PEG moiety of the PEG-lipid conjugates described herein may comprise an average molecular weight ranging from about 550 daltons to about 10,000 daltons. In certain aspects, the PEG moiety has an average molecular weight of from about 750 daltons to about 5,000 daltons (e.g., from about 1,000 daltons to about 5,000 daltons, from about 1,500 daltons to about 3,000 daltons, from about 750 daltons to about 3,000 daltons, from about 750 daltons to about 2,000 daltons). In some aspects, the PEG moiety has an average molecular weight of about 2,000 daltons or about 750 daltons. The average molecular weight may be any value or subvalue within the recited ranges, including endpoints.

In certain aspects, the PEG can be optionally substituted by an alkyl, alkoxy, acyl, or aryl group. The PEG can be conjugated directly to the lipid or may be linked to the lipid via a linker moiety. Any linker moiety suitable for coupling the PEG to a lipid can be used including, e.g., non-ester-containing linker moieties and ester-containing linker moieties. In one aspect, the linker moiety is a non-ester-containing linker moiety. Exemplary non-ester-containing linker moieties include, but are not limited to, amido (—C(O)NH—), amino (—NR—), carbonyl (—C(O)—), carbamate (—NHC(O)O—), urea (—NHC(O)NH—), disulfide (—S—S—), ether (—O—), succinyl (—(O)CCH2CH2C(O)—), succinamidyl (—NHC(O)CH2CH2C(O)NH—), ether, as well as combinations thereof (such as a linker containing both a carbamate linker moiety and an amido linker moiety). In one aspect, a carbamate linker is used to couple the PEG to the lipid.

In some aspects, an ester-containing linker moiety is used to couple the PEG to the lipid. Exemplary ester-containing linker moieties include, e.g., carbonate (—OC(O)O—), succinoyl, phosphate esters (—O—(O)POH—O—), sulfonate esters, and combinations thereof.

Phosphatidylethanolamines having a variety of acyl chain groups of varying chain lengths and degrees of saturation can be conjugated to PEG to form the lipid conjugate. Such phosphatidylethanolamines are commercially available or can be isolated or synthesized using conventional techniques known to those of skill in the art. Phosphatidylethanolamines containing saturated or unsaturated fatty acids with carbon chain lengths in the range of C10 to C20 are preferred. Phosphatidylethanolamines with mono- or di-unsaturated fatty acids and mixtures of saturated and unsaturated fatty acids can also be used. Suitable phosphatidylethanolamines include, but are not limited to, dimyristoyl-phosphatidylethanolamine (DMPE), dipalmitoyl-phosphatidylethanolamine (DPPE), dioleoyl-phosphatidylethanolamine (DOPE), and distearoyl-phosphatidylethanolamine (DSPE).

In some aspects, the PEG-DAA conjugate is a PEG-didecyloxypropyl (C10) conjugate, a PEG-dilauryloxypropyl (C12) conjugate, a PEG-dimyristyloxypropyl (C14) conjugate, a PEG-dipalmityloxypropyl (C16) conjugate, or a PEG-distearyloxypropyl (C18) conjugate. In some aspects, the PEG has an average molecular weight of about 750 or about 2,000 daltons. In some aspects, the terminal hydroxyl group of the PEG is substituted with a methyl group.

In addition to the foregoing, other hydrophilic polymers can be used in place of PEG. Examples of suitable polymers that can be used in place of PEG include, but are not limited to, polyvinylpyrrolidone, polymethyloxazoline, polyethyloxazoline, polyhydroxypropyl, methacrylamide, polymethacrylamide, and polydimethylacrylamide, polylactic acid, polyglycolic acid, and derivatized celluloses such as hydroxymethylcellulose or hydroxyethylcellulose.

In some aspects, the lipid conjugate (e.g., PEG-lipid) comprises from about 0.1 mol % to about 2 mol %, from about 0.5 mol % to about 2 mol %, from about 1 mol % to about 2 mol %, from about 0.6 mol % to about 1.9 mol %, from about 0.7 mol % to about 1.8 mol %, from about 0.8 mol % to about 1.7 mol %, from about 0.9 mol % to about 1.6 mol %, from about 0.9 mol % to about 1.8 mol %, from about 1 mol % to about 1.8 mol %, from about 1 mol % to about 1.7 mol %, from about 1.2 mol % to about 1.8 mol %, from about 1.2 mol % to about 1.7 mol %, from about 1.3 mol % to about 1.6 mol %, or from about 1.4 mol % to about 1.6 mol % (or any fraction thereof or range therein) of the total lipid present in the lipid formulation. In other embodiments, the lipid conjugate (e.g., PEG-lipid) comprises about 0.5%, 0.6%, 0.7%, 0.8%, 0.9%, 1.0%, 1.2%, 1.3%, 1.4%, 1.5%, 1.6%, 1.7%, 1.8%, 1.9%, 2.0%, 2.5%, 3.0%, 3.5%, 4.0%, 4.5%, or 5%, (or any fraction thereof or range therein) of the total lipid present in the lipid formulation. The amount may be any value or subvalue within the recited ranges, including endpoints.

The percentage of lipid conjugate (e.g., PEG-lipid) present in the lipid formulations of the disclosure is a target amount, and the actual amount of lipid conjugate present in the formulation may vary, for example, by ±0.5 mol %. One of ordinary skill in the art will appreciate that the concentration of the lipid conjugate can be varied depending on the lipid conjugate employed and the rate at which the lipid formulation is to become fusogenic.

Mechanism of Action for Cellular Uptake of Lipid Formulations

In some aspects, lipid formulations for the intracellular delivery of nucleic acids, particularly liposomes, cationic liposomes, and lipid nanoparticles, are designed for cellular uptake by penetrating target cells through exploitation of the target cells' endocytic mechanisms where the contents of the lipid delivery vehicle are delivered to the cytosol of the target cell. (Nucleic Acid Therapeutics, 28(3):146-157, 2018). Prior to endocytosis, functionalized ligands such as PEG-lipid at the surface of the lipid delivery vehicle are shed from the surface, which triggers internalization into the target cell. During endocytosis, some part of the plasma membrane of the cell surrounds the vector and engulfs it into a vesicle that then pinches off from the cell membrane, enters the cytosol and ultimately enters and moves through the endolysosomal pathway. For ionizable cationic lipid-containing delivery vehicles, the increased acidity as the endosome ages results in a vehicle with a strong positive charge on the surface. Interactions between the delivery vehicle and the endosomal membrane then result in a membrane fusion event that leads to cytosolic delivery of the payload. For RNA payloads, the cell's own internal translation processes will then translate the RNA into the encoded protein. The encoded protein can further undergo postranslational processing, including transportation to a targeted organelle or location within the cell or excretion from the cell.

By controlling the composition and concentration of the lipid conjugate, one can control the rate at which the lipid conjugate exchanges out of the lipid formulation and, in turn, the rate at which the lipid formulation becomes fusogenic. In addition, other variables including, e.g., pH, temperature, or ionic strength, can be used to vary and/or control the rate at which the lipid formulation becomes fusogenic. Other methods which can be used to control the rate at which the lipid formulation becomes fusogenic will become apparent to those of skill in the art upon reading this disclosure. Also, by controlling the composition and concentration of the lipid conjugate, one can control the liposomal or lipid particle size.

Lipid Formulation Manufacture

There are many different methods for the preparation of lipid formulations comprising a nucleic acid. (Curr. Drug Metabol. 2014, 15, 882-892; Chem. Phys. Lipids 2014, 177, 8-18; Int. J. Pharm. Stud. Res. 2012, 3, 14-20). The techniques of thin film hydration, double emulsion, reverse phase evaporation, microfluidic preparation, dual assymetric centrifugation, ethanol injection, detergent dialysis, spontaneous vesicle formation by ethanol dilution, and encapsulation in preformed liposomes are briefly described herein.

Thin Film Hydration

In Thin Film Hydration (TFH) or the Bangham method, the lipids are dissolved in an organic solvent, then evaporated through the use of a rotary evaporator leading to a thin lipid layer formation. After the layer hydration by an aqueous buffer solution containing the compound to be loaded, Multilamellar Vesicles (MLVs) are formed, which can be reduced in size to produce Small or Large Unilamellar vesicles (LUV and SUV) by extrusion through membranes or by the sonication of the starting MLV.

Double Emulsion

Lipid formulations can also be prepared through the Double Emulsion technique, which involves lipids dissolution in a water/organic solvent mixture. The organic solution, containing water droplets, is mixed with an excess of aqueous medium, leading to a water-in-oil-in-water (W/O/W) double emulsion formation. After mechanical vigorous shaking, part of the water droplets collapse, giving Large Unilamellar Vesicles (LUVs).

Reverse Phase Evaporation

The Reverse Phase Evaporation (REV) method also allows one to achieve LUVs loaded with nucleic acid. In this technique a two-phase system is formed by phospholipids dissolution in organic solvents and aqueous buffer. The resulting suspension is then sonicated briefly until the mixture becomes a clear one-phase dispersion. The lipid formulation is achieved after the organic solvent evaporation under reduced pressure. This technique has been used to encapsulate different large and small hydrophilic molecules including nucleic acids.

Microfluidic Preparation

The Microfluidic method, unlike other bulk techniques, gives the possibility of controlling the lipid hydration process. The method can be classified in continuous-flow microfluidic and droplet-based microfluidic, according to the way in which the flow is manipulated. In the microfluidic hydrodynamic focusing (MHF) method, which operates in a continuous flow mode, lipids are dissolved in isopropyl alcohol which is hydrodynamically focused in a microchannel cross junction between two aqueous buffer streams. Vesicles size can be controlled by modulating the flow rates, thus controlling the lipids solution/buffer dilution process. The method can be used for producing oligonucleotide (ON) lipid formulations by using a microfluidic device consisting of three-inlet and one-outlet ports.

Dual Asymmetric Centrifugation

Dual Asymmetric Centrifugation (DAC) differs from more common centrifugation as it uses an additional rotation around its own vertical axis. An efficient homogenization is achieved due to the two overlaying movements generated: the sample is pushed outwards, as in a normal centrifuge, and then it is pushed towards the center of the vial due to the additional rotation. By mixing lipids and an NaCl-solution a viscous vesicular phospholipid gel (VPC) is achieved, which is then diluted to obtain a lipid formulation dispersion. The lipid formulation size can be regulated by optimizing DAC speed, lipid concentration and homogenization time.

Ethanol Injection

The Ethanol Injection (EI) method can be used for nucleic acid encapsulation. This method provides the rapid injection of an ethanolic solution, in which lipids are dissolved, into an aqueous medium containing nucleic acids to be encapsulated, through the use of a needle. Vesicles are spontaneously formed when the phospholipids are dispersed throughout the medium.

Detergent Dialysis

The Detergent dialysis method can be used to encapsulate nucleic acids. Briefly lipid and plasmid are solubilized in a detergent solution of appropriate ionic strength, after removing the detergent by dialysis, a stabilized lipid formulation is formed. Unencapsulated nucleic acid is then removed by ion-exchange chromatography and empty vesicles by sucrose density gradient centrifugation. The technique is highly sensitive to the cationic lipid content and to the salt concentration of the dialysis buffer, and the method is also difficult to scale.

Spontaneous Vesicle Formation by Ethanol Dilution

Stable lipid formulations can also be produced through the Spontaneous Vesicle Formation by Ethanol Dilution method in which a stepwise or dropwise ethanol dilution provides the instantaneous formation of vesicles loaded with nucleic acid by the controlled addition of lipid dissolved in ethanol to a rapidly mixing aqueous buffer containing the nucleic acid.

Encapsulation in Preformed Liposomes

The entrapment of nucleic acids can also be obtained starting with preformed liposomes through two different methods: (1) A simple mixing of cationic liposomes with nucleic acids which gives electrostatic complexes called "lipoplexes", where they can be successfully used to transfect cell cultures, but are characterized by their low encapsulation efficiency and poor performance in vivo; and (2) a liposomal destabilization, slowly adding absolute ethanol to a suspension of cationic vesicles up to a concentration of 40% v/v followed by the dropwise addition of nucleic acids achieving loaded vesicles; however, the two main steps characterizing the encapsulation process are too sensitive, and the particles have to be downsized.

Excipients

The pharmaceutical compositions disclosed herein can be formulated using one or more excipients to: (1) increase stability; (2) increase cell transfection; (3) permit a sustained or delayed release (e.g., from a depot formulation of the polynucleotide, primary construct, or RNA); (4) alter the biodistribution (e.g., target the polynucleotide, primary construct, or RNA to specific tissues or cell types); (5) increase the translation of encoded protein in vivo; and/or (6) alter the release profile of encoded protein in vivo.

The pharmaceutical compositions described herein may be prepared by any method known or hereafter developed in the art of pharmacology. In general, such preparatory methods include the step of associating the active ingredient (i.e., nucleic acid) with an excipient and/or one or more other accessory ingredients. A pharmaceutical composition in accordance with the present disclosure may be prepared, packaged, and/or sold in bulk, as a single unit dose, and/or as a plurality of single unit doses.

Pharmaceutical compositions may additionally comprise a pharmaceutically acceptable excipient, which, as used herein, includes, but is not limited to, any and all solvents, dispersion media, diluents, or other liquid vehicles, dispersion or suspension aids, surface active agents, isotonic agents, thickening or emulsifying agents, preservatives, and the like, as suited to the particular dosage form desired.

In addition to traditional excipients such as any and all solvents, dispersion media, diluents, or other liquid vehicles, dispersion or suspension aids, surface active agents, isotonic agents, thickening or emulsifying agents, preservatives, excipients of the present disclosure can include, without limitation, liposomes, lipid nanoparticles, polymers, lipoplexes, core-shell nanoparticles, peptides, proteins, cells transfected with primary DNA construct, or RNA (e.g., for transplantation into a subject), hyaluronidase, nanoparticle mimics and combinations thereof.

Accordingly, the pharmaceutical compositions described herein can include one or more excipients, each in an amount that together increases the stability of the nucleic acid in the lipid formulation, increases cell transfection by the nucleic acid, increases the expression of the encoded protein, and/or alters the release profile of encoded proteins. Further, the RNA of the present disclosure may be formulated using self-assembled nucleic acid nanoparticles.

Various excipients for formulating pharmaceutical compositions and techniques for preparing the composition are known in the art (see Remington: The Science and Practice of Pharmacy, 21st Edition, A. R. Gennaro, Lippincott, Williams & Wilkins, Baltimore, Md., 2006; incorporated herein by reference in its entirety). The use of a conventional excipient medium may be contemplated within the scope of the embodiments of the present disclosure, except insofar as any conventional excipient medium may be incompatible with a substance or its derivatives, such as by producing any undesirable biological effect or otherwise interacting in a deleterious manner with any other component(s) of the pharmaceutical composition.

The pharmaceutical compositions of this disclosure may further contain as pharmaceutically acceptable carriers substances as required to approximate physiological conditions, such as pH adjusting and buffering agents, tonicity adjusting agents, and wetting agents, for example, sodium acetate, sodium lactate, sodium chloride, potassium chloride, calcium chloride, sorbitan monolaurate, triethanolamine oleate, and mixtures thereof. For solid compositions, conventional nontoxic pharmaceutically acceptable carriers can be used which include, for example, pharmaceutical grades of mannitol, lactose, starch, magnesium stearate, sodium saccharin, talcum, cellulose, glucose, sucrose, magnesium carbonate, and the like.

In certain embodiments of the disclosure, the RNA-lipid formulation may be administered in a time release formulation, for example in a composition which includes a slow release polymer. The active agent can be prepared with carriers that will protect against rapid release, for example a controlled release vehicle such as a polymer, microencapsulated delivery system, or a bioadhesive gel. Prolonged delivery of the RNA, in various compositions of the disclosure can be brought about by including in the composition agents that delay absorption, for example, aluminum monostearate hydrogels and gelatin.

Methods of Inducing Immune Responses

Provided herein, in some embodiments, are methods of inducing an immune response in a subject. Any type of immune response can be induced using the methods provided herein, including adaptive and innate immune responses. In one aspect, immune responses induced using the methods provided herein include an antibody response, a cellular immune response, or both an antibody response and a cellular immune response.

Methods of inducing an immune response provided herein include administering to a subject an effective amount of any nucleic acid molecule provided herein. In one aspect, methods of inducing an immune response include administering to a subject an effective amount of any composition comprising a nucleic acid molecule and a lipid provided herein. In another aspect, methods of inducing an immune response include administering to a subject an effective amount of any pharmaceutical composition comprising a nucleic acid molecule and a lipid formulation provided herein. In some aspects, nucleic acid molecules, compositions, and pharmaceutical composition provided here are vaccines that can elicit a protective or a therapeutic immune response, for example.

As used herein, the term “subject” refers to any individual or patient on which the methods disclosed herein are performed. The term “subject” can be used interchangeably with the term “individual” or “patient.” The subject can be a human, although the subject may be an animal, as will be appreciated by those in the art. Thus, other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject. As used herein, the term “effective amount” or “therapeutically effective amount” refers to that amount of a nucleic acid molecule, composition, or pharmaceutical composition described herein that is sufficient to effect the intended application, including but not limited to inducing an immune response and/or disease treatment, as defined herein. The therapeutically effective amount may vary depending upon the intended application (e.g., inducing an immune response, treatment, application in vivo), or the subject or patient and disease condition being treated, e.g., the weight and age of the subject, the species, the severity of the disease condition, the manner of administration and the like, which can readily be determined by one of ordinary skill in the art. The term also applies to a dose that will induce a particular response in a target cell. The specific dose will vary depending on the particular nucleic acid molecule, composition, or pharmaceutical composition chosen, the dosing regimen to be followed, whether it is administered in combination with other compounds, timing of administration, the tissue to which it is administered, and the physical delivery system in which it is carried.

Exemplary doses of nucleic acid molecules that can be administered include about 0.01 μg, about 0.02 μg, about 0.03 μg, about 0.04 μg, about 0.05 μg, about 0.06 μg, about 0.07 μg, about 0.08 μg, about 0.09 μg, about 0.1 μg, about 0.2 μg, about 0.3 μg, about 0.4 μg, about 0.5 μg, about 0.6 μg, about 0.7 μg, about 0.8 μg, about 0.9 μg, about 1.0 μg, about 1.5 μg, about 2.0 μg, about 2.5 μg, about 3.0 μg, about 3.5 μg, about 4.0 μg, about 4.5 μg, about 5.0 μg, about 5.5 μg, about 6.0 μg, about 6.5 μg, about 7.0 μg, about 7.5 μg, about 8.0 μg, about 8.5 μg, about 9.0 μg, about 9.5 μg, about 10 μg, about 11 μg, about 12 μg, about 13μ, about 14 μg, about 15 μg, about 16 μg, about 17 μg, about 18 μg, about 19 μg, about 20 μg, about 21 μg, about 22 μg, about 23 μg, about 24 μg, about 25 μg, about 26 μg, about 27 μg, about 28 μg, about 29 μg, about 30 μg, about 35 μg, about 40 μg, about 45 μg, about 50 μg, about 55 μg, about 60 μg, about 65 μg, about 70 μg, about 75 μg, about 80 μg, about 85 μg, about 90 μg, about 95 μg, about 100 μg, about 125 μg, about 150 μg, about 175 μg, about 200 μg, about 250 μg, about 300 μg, about 350 μg, about 400 μg, about 450 μg, about 500 μg, about 600 μg, about 700 μg, about 800 μg, about 900 μg, about 1,000 μg, or more, and any number or range in between. In one aspect, the nucleic acid molecules are RNA molecules. In another aspect, the nucleic acid molecules are DNA molecules. Nucleic acid molecules can have a unit dosage comprising about 0.01 μg to about 1,000 μg or more nucleic acid in a single dose.

In some aspects, compositions provided herein that can be administered include about 0.01 μg, about 0.02 μg, about 0.03 μg, about 0.04 μg, about 0.05 μg, about 0.06 μg, about 0.07 μg, about 0.08 μg, about 0.09 μg, about 0.1 μg, about 0.2 μg, about 0.3 μg, about 0.4 μg, about 0.5 μg, about 0.6 μg, about 0.7 μg, about 0.8 μg, about 0.9 μg, about 1.0 μg, about 1.5 μg, about 2.0 μg, about 2.5 μg, about 3.0 μg, about 3.5 μg, about 4.0 μg, about 4.5 μg, about 5.0 μg, about 5.5 μg, about 6.0 μg, about 6.5 μg, about 7.0 μg, about 7.5 μg, about 8.0 μg, about 8.5 μg, about 9.0 μg, about 9.5 μg, about 10 μg, about 11 μg, about 12 μg, about 13 μg, about 14 μg, about 15 μg, about 16 μg, about 17 μg, about 18 μg, about 19 μg, about 20 μg, about 21 μg, about 22 μg, about 23 μg, about 24 μg, about 25 μg, about 26 μg, about 27 μg, about 28 μg, about 29 μg, about 30 μg, about 35 μg, about 40 μg, about 45 μg, about 50 μg, about 55 μg, about 60 μg, about 65 μg, about 70 μg, about 75 μg, about 80 μg, about 85 μg, about 90 μg, about 95 μg, about 100 μg, about 125 μg, about 150 μg, about 175 μg, about 200 μg, about 250 μg, about 300 μg, about 350 μg, about 400 μg, about 450 μg, about 500 μg, about 600 μg, about 700 μg, about 800 μg, about 900 μg, about 1,000 μg, or more, and any number or range in between, nucleic acid and lipid. In other aspects, pharmaceutical compositions provided herein that can be administered include about 0.01 μg, about 0.02 μg, about 0.03 μg, about 0.04 μg, about 0.05 μg, about 0.06 μg, about 0.07 μg, about 0.08 μg, about 0.09 μg, about 0.1 μg, about 0.2 μg, about 0.3 μg, about 0.4 μg, about 0.5 μg, about 0.6 μg, about 0.7 μg, about 0.8 μg, about 0.9 μg, about 1.0 μg, about 1.5 μg, about 2.0 μg, about 2.5 μg, about 3.0 μg, about 3.5 μg, about 4.0 μg, about 4.5 μg, about 5.0 μg, about 5.5 μg, about 6.0 μg, about 6.5 μg, about 7.0 μg, about 7.5 μg, about 8.0 μg, about 8.5 μg, about 9.0 μg, about 9.5 μg, about 10 μg, about 11 μg, about 12 μg, about 13 μg, about 14 μg, about 15 μg, about 16 μg, about 17 μg, about 18 μg, about 19 μg, about 20 μg, about 21 μg, about 22 μg, about 23 μg, about 24 μg, about 25 μg, about 26 μg, about 27 μg, about 28 μg, about 29 μg, about 30 μg, about 35 μg, about 40 μg, about 45 μg, about 50 μg, about 55 μg, about 60 μg, about 65 μg, about 70 μg, about 75 μg, about 80 μg, about 85 μg, about 90 μg, about 95 μg, about 100 μg, about 125 μg, about 150 μg, about 175 μg, about 200 μg, about 250 μg, about 300 μg, about 350 μg, about 400 μg, about 450 μg, about 500 μg, about 600 μg, about 700 μg, about 800 μg, about 900 μg, about 1,000 μg, or more, and any number or range in between, nucleic acid and lipid formulation.

In one aspect, compositions provided herein can have a unit dosage comprising about 0.01 μg to about 1,000 μg or more nucleic acid and lipid in a single dose. In another aspect, pharmaceutical compositions provided herein can have a unit dosage comprising about 0.01 μg to about 1,000 μg or more nucleic acid and lipid formulation in a single dose. A vaccine unit dosage can correspond to the unit dosage of nucleic acid molecules, compositions, or pharmaceutical compositions provided herein and that can be administered to a subject. In one aspect, vaccine compositions of the instant disclosure have a unit dosage comprising about 0.01 μg to about 1,000 μg or more nucleic acid and lipid formulation in a single dose. In another aspect, vaccine compositions of the instant disclosure have a unit dosage comprising about 0.01 μg to about 50 μg nucleic acid and lipid formulation in a single dose. In yet another aspect, vaccine compositions of the instant disclosure have a unit dosage comprising about 0.2 μg to about 20 μg nucleic acid and lipid formulation in a single dose.

A dosage form of the composition of this disclosure can be solid, which can be reconstituted in a liquid prior to administration. The solid can be administered as a powder. The solid can be in the form of a capsule, tablet, or gel. In some embodiments, the pharmaceutical composition comprises a nucleic acid lipid formulation that has been lyophilized.

In a preferred embodiment, the dosage form of the pharmaceutical compositions described herein can be a liquid suspension of self-replicating RNA lipid nanoparticles described herein. In some embodiments, the liquid suspension is in a buffered solution. In some embodiments, the buffered solution comprises a buffer selected from the group consisting of HEPES, MOPS, TES, and TRIS. In some embodiments, the buffer has a pH of about 7.4. In some preferred embodiments, the buffer is HEPES. In some further embodiments, the buffered solution further comprises a cryoprotectant. In some embodiments, the cryoprotectant is selected from a sugar and glycerol or a combination of a sugar and glycerol. In some embodiments, the sugar is a dimeric sugar. In some embodiments, the sugar is sucrose. In some preferred embodiments, the buffer comprises HEPES, sucrose, and glycerol at a pH of 7.4. In some embodiments, the suspension is frozen during storage and thawed prior to administration. In some embodiments, the suspension is frozen at a temperature below about 70° C. In some embodiments, the suspension is diluted with sterile water during intravenous administration. In some embodiments, intravenous administration comprises diluting the suspension with about 2 volumes to about 6 volumes of sterile water. In some embodiments, the suspension comprises about 0.1 mg to about 3.0 mg self-replicating RNA/mL, about 15 mg/mL to about 25 mg/mL of an ionizable cationic lipid, about 0.5 mg/mL to about 2.5 mg/mL of a PEG-lipid, about 1.8 mg/mL to about 3.5 mg/mL of a helper lipid, about 4.5 mg/mL to about 7.5 mg/mL of a cholesterol, about 7 mg/mL to about 15 mg/mL of a buffer, about 2.0 mg/mL to about 4.0 mg/mL of NaCl, about 70 mg/mL to about 110 mg/mL of sucrose, and about 50 mg/mL to about 70 mg/mL of glycerol. In some embodiments, a lyophilized self-replicating RNA-lipid nanoparticle formulation can be resuspended in a buffer as described herein.

In some embodiments, the compositions of the disclosure are administered to a subject such that a self-replicating RNA concentration of at least about 0.05 mg/kg, at least about 0.1 mg/kg, at least about 0.5 mg/kg, at least about 1.0 mg/kg, at least about 2.0 mg/kg, at least about 3.0 mg/kg, at least about 4.0 mg/kg, at least about 5.0 mg/kg of body weight is administered in a single dose or as part of single treatment cycle. In some embodiments, the compositions of the disclosure are administered to a subject such that a total amount of at least about 0.1 mg, at least about 0.5 mg, at least about 1.0 mg, at least about 2.0 mg, at least about 3.0 mg, at least about 4.0 mg, at least about 5.0 mg, at least about 6.0 mg, at least about 7.0 mg, at least about 8.0 mg, at least about 9.0 mg, at least about 10 mg, at least about 15 mg, at least about 20 mg, at least about 25 mg, at least about 30 mg, at least about 35 mg, at least about 40 mg, at least about 45 mg, at least about 50 mg, at least about 55 mg, at least about 60 mg, at least about 65 mg, at least about 70 mg, at least about 75 mg, at least about 80 mg, at least about 85 mg, at least about 90 mg, at least about 95 mg, at least about 100 mg, at least about 105 mg, at least about 110 mg, at least about 115 mg, at least about 120 mg, or at least about 125 mg self-replicating RNA is administered in one or more doses up to a maximum dose of about 300 mg, about 350 mg, about 400 mg, about 450 mg, or about 500 mg self-replicating RNA.

Any route of administration can be included in methods provided herein. In some aspects, nucleic acid molecules, compositions, and pharmaceutical compositions provided herein are administered intramuscularly, subcutaneously, intradermally, transdermally, intranasally, orally, sublingually, intravenously, intraperitoneally, topically, by aerosol, or by a pulmonary route, such as by inhalation or by nebulization, for example. In some embodiments, the pharmaceutical compositions described are administered systemically. Suitable routes of administration include, for example, rectal, vaginal, transmucosal, or intestinal administration; parenteral delivery, including intramedullary injections, as well as intrathecal, direct intraventricular, intravenous, intraperitoneal, or intranasal. In particular embodiments, the intramuscular administration is to a muscle selected from the group consisting of skeletal muscle, smooth muscle and cardiac muscle. In some embodiments, the pharmaceutical composition is administered intravenously.

Pharmaceutical compositions may be administered to any desired tissue. In some embodiments, the self-replicating RNA delivered is expressed in a tissue different from the tissue in which the lipid formulation or pharmaceutical composition was administered. In preferred embodiments, self-replicating RNA is delivered and expressed in the liver.

In other aspects, nucleic acid molecules, compositions, and pharmaceutical compositions provided herein are administered intramuscularly.

In some aspects, the subject in which an immune response is induced is a healthy subject. As used herein, the term "healthy subject" refers to a subject not having a condition or disease, including an infectious disease or cancer, for example, or not having a condition or disease against which an immune response is induced. Accordingly, in some aspects, a nucleic acid molecule, composition, or pharmaceutical composition provided herein is administered prophylactically to prevent an infectious disease or cancer, for example. In other aspects, the subject in which an immune response is induced has cancer. The subject may suffer from any cancer or have any tumor, including solid and liquid tumors. In one aspect, the cancer is kidney cancer, renal cancer, urinary bladder cancer, prostate cancer, uterine cancer, breast cancer, cervical cancer, ovarian cancer, lung cancer, liver cancer, stomach cancer, colon cancer, rectal cancer, oral cavity cancer, pharynx cancer, pancreatic cancer, thyroid cancer, melanoma, skin cancer, head and neck cancer, brain cancer, hematopoietic cancer, leukemia, lymphoma, bone cancer, or sarcoma. Accordingly, a nucleic acid molecule, composition, or pharmaceutical composition provided herein can be administered therapeutically, i.e., to treat a condition or disease, such as cancer, after the onset of the condition or disease.

As used herein, the terms "treat," "treatment," "therapy," "therapeutic," and the like refer to obtaining a desired pharmacologic and/or physiologic effect, including, but not limited to, alleviating, delaying or slowing the progression, reducing the effects or symptoms, preventing onset, inhibiting, ameliorating the onset of a diseases or disorder, obtaining a beneficial or desired result with respect to a disease, disorder, or medical condition, such as a therapeutic benefit and/or a prophylactic benefit. "Treatment," as used herein, includes any treatment of a disease in a mammal, particularly in a human, and includes: (a) preventing the disease from occurring in a subject, including a subject which is predisposed to the disease or at risk of acquiring the disease but has not yet been diagnosed as having it; (b) inhibiting the disease, i.e., arresting its development; and (c)

relieving the disease, i.e., causing regression of the disease. A therapeutic benefit includes eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. In some aspects, for prophylactic benefit, treatment or compositions for treatment, including pharmaceutical compositions, are administered to a subject at risk of developing a particular disease, or to a subject reporting one or more of the physiological symptoms of a disease, even though a diagnosis of this disease may not have been made. The methods of the present disclosure may be used with any mammal or other animal. In some aspects, treatment results in a decrease or cessation of symptoms. A prophylactic effect includes delaying or eliminating the appearance of a disease or condition, delaying or eliminating the onset of symptoms of a disease or condition, slowing, halting, or reversing the progression of a disease or condition, or any combination thereof.

Nucleic acid molecules, compositions, and pharmaceutical compositions provided herein can be administered once or multiple times. Accordingly, nucleic acid molecules, compositions, and pharmaceutical compositions provided herein can be administered one, two, three, four, five, six, seven, eight, nine, ten, or more times. Timing between two or more administrations can be one week, two weeks, three weeks, four weeks, five weeks, six weeks, seven weeks, eight weeks, nine weeks, weeks, ten weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, or more weeks, and any number or range in between. In some aspects, timing between two or more administrations is one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months, 24 months, or more months, and any number or range in between. In other aspects, timing between two or more administrations can be one year, two years, three years, four years, five years, six years, seven years, eight years, nine years, ten years, or more years, and any number or range in between, Timing between the first and any subsequent administration can be the same or different. In one aspect, nucleic acid molecules, compositions, or pharmaceutical compositions provided herein are administered once.

More than one nucleic acid molecule, composition, or pharmaceutical composition can be administered in the methods provided herein. In one aspect, two or more nucleic acid molecules, compositions, or pharmaceutical compositions provided herein are administered simultaneously. In another aspect, two or more nucleic acid molecules, compositions, or pharmaceutical compositions provided herein are administered sequentially. Simultaneous and sequential administrations can include any number and any combination of nucleic acid molecules, compositions, or pharmaceutical compositions provided herein. Multiple nucleic acid molecules, compositions, or pharmaceutical compositions that are administered together or sequentially can include transgenes encoding different antigenic proteins or fragments thereof. In this manner, immune responses against different antigenic targets can be induced. Two, three, four, five, six, seven, eight, nine, ten, or more nucleic acid molecules, compositions, or pharmaceutical compositions including transgenes encoding different antigenic proteins or fragments thereof can be administered simultaneously or sequentially. Any combination of nucleic acid molecules, compositions, and pharmaceutical compositions including any combination of transgenes can be administered simultaneously or sequentially. In some aspects, administration is simultaneous. In other aspects, administration is sequential. Timing between two or more administrations can be one week, two weeks, three weeks, four weeks, five weeks, six weeks, seven weeks, eight weeks, nine weeks, weeks, ten weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, or more weeks, and any number or range in between. In some aspects, timing between two or more administrations is one month, two months, three months, four months, five months, six months, seven months, eight months, nine months, ten months, 11 months, 12 months, 13 months, 14 months, 15 months, months, 16 months, 17 months, 18 months, 19 months, 20 months, 21 months, 22 months, 23 months, 24 months, or more months, and any number or range in between. In other aspects, timing between two or more administrations can be one year, two years, three years, four years, five years, six years, seven years, eight years, nine years, ten years, or more years, and any number or range in between, Timing between the first and any subsequent administration can be the same or different. Nucleic acid molecules, compositions, and pharmaceutical compositions provided herein can be administered with any other vaccine or treatment.

Following administration of the composition to the subject, the protein product encoded by the self-replicating RNA of the disclosure (e.g., an antigen) is detectable in the target tissues for at least about one to seven days or longer. For example, the protein product may be detectable in the target tissues at a concentration (e.g., a therapeutic concentration) of at least about 0.025-1.5 μg/ml (e.g., at least about 0.050 μg/ml, at least about 0.075 μg/ml, at least about 0.1 μg/ml, at least about 0.2 μg/ml, at least about 0.3 μg/ml, at least about 0.4 μg/ml, at least about 0.5 μg/ml, at least about 0.6 μg/ml, at least about 0.7 μg/ml, at least about 0.8 μg/ml, at least about 0.9 μg/ml, at least about 1.0 μg/ml, at least about 1.1 μg/ml, at least about 1.2 μg/ml, at least about 1.3 μg/ml, at least about 1.4 μg/ml, or at least about 1.5 μg/ml), for at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45 days or longer following administration of the composition to the subject.

In some embodiments, a pharmaceutical composition of the present disclosure is administered to a subject once per month. In some embodiments, a pharmaceutical composition of the present disclosure is administered to a subject twice per month. In some embodiments, a pharmaceutical composition of the present disclosure is administered to a subject three times per month. In some embodiments, a pharmaceutical composition of the present disclosure is administered to a subject four times per month.

Alternatively, the compositions of the present disclosure may be administered in a local rather than systemic manner, for example, via injection of the pharmaceutical composition directly into a targeted tissue, preferably in a depot or sustained release formulation. Local delivery can be affected in various ways, depending on the tissue to be targeted. For example, aerosols containing compositions of the present disclosure can be inhaled (for nasal, tracheal, or bronchial delivery); compositions of the present disclosure can be injected into the site of injury, disease manifestation, or pain, for example; compositions can be provided in lozenges for oral, tracheal, or esophageal application; can be supplied in liquid, tablet or capsule form for administration to the stomach or intestines, can be supplied in suppository form for rectal or vaginal application; or can even be delivered to the eye by use of creams, drops, or even injection. Formulations containing compositions of the present disclosure complexed with therapeutic molecules or ligands can even be surgically administered, for example in association with a polymer or other structure or substance that can allow the compositions to diffuse from the site of implantation to surrounding cells. Alternatively, they can be applied surgically without the use of polymers or supports.

The self-replicating RNA, formulations thereof, or encoded proteins described herein may be used in combination with one or more other therapeutic, prophylactic, diagnostic, or imaging agents. By "in combination with," it is not intended to imply that the agents must be administered at the same time and/or formulated for delivery together, although these methods of delivery are within the scope of the present disclosure. Compositions can be administered concurrently with, prior to, or subsequent to, one or more other desired therapeutics or medical procedures. In general, each agent will be administered at a dose and/or on a time schedule determined for that agent. Preferably, the methods of treatment of the present disclosure encompass the delivery of pharmaceutical, prophylactic, diagnostic, or imaging compositions in combination with agents that may improve their bioavailability, reduce and/or modify their metabolism, inhibit their excretion, and/or modify their distribution within the body. As a non-limiting example, a self-replicating RNA of the disclosure may be used in combination with a pharmaceutical agent for immunizing or vaccinating a subject. In general, it is expected that agents utilized in combination with the presently disclosed self-replicating RNA and formulations thereof be utilized at levels that do not exceed the levels at which they are utilized individually. In some embodiments, the levels utilized in combination will be lower than those utilized individually. In one embodiment, the combinations, each or together may be administered according to the split dosing regimens as are known in the art.

Ranges: throughout this disclosure, various aspects can be presented in range format. It should be understood that any description in range format is merely for convenience and brevity and not meant to be limiting. Accordingly, the description of a range should be considered to have specifically disclosed all possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example 1, 2, 2.1, 2.2, 2.5, 3, 4, 4.75, 4.8, 4.85, 4.95, 5, 5.5, 5.75, 5.9, 5.00, and 6. This applies to a range of any breadth.

Example 1

This example describes characterization of self-replicating (STARR™) technology using firefly luciferase transgene expression. In vitro transcripts were formulated with lipid nanoparticles (LNP) at a concentration of 0.1 mg/ml, and injected intramuscularly in both legs of female BALB/C mice (n=3) at a dose of 5 ug per leg. Expression of firefly luciferase (FLuc) was measured by IVIS Lumina LT Series III (PerkinElmer) by administering 100 ul of 1.5 mg Xenolight D-luciferin (PerkinElmer) in PBS via intraperitoneal injection ~10 min prior to the measurement. Six data points per group of mice were obtained at each time point (FIGS. 2A-2D).

Figure 1:
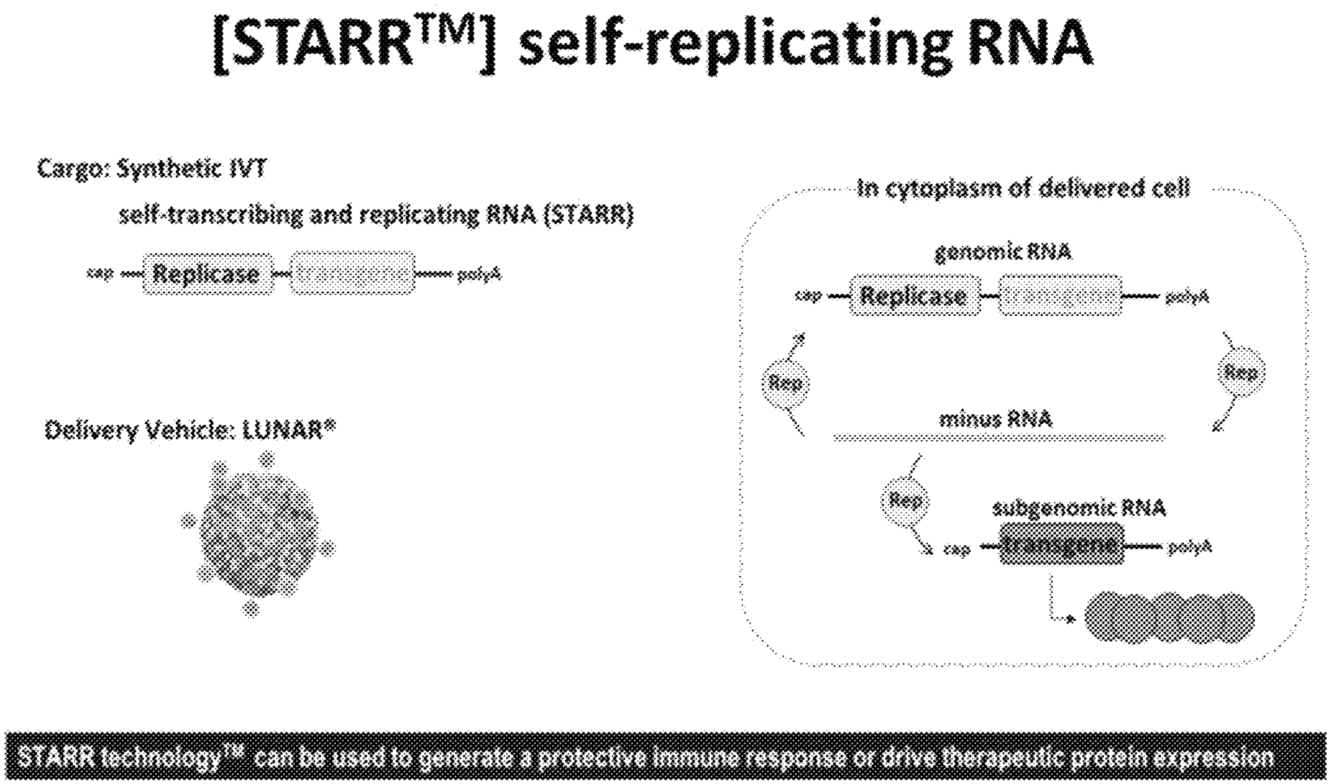
FIG. 1 shows a schematic illustrating one aspect of STARR™ technology.
Figure 2A:
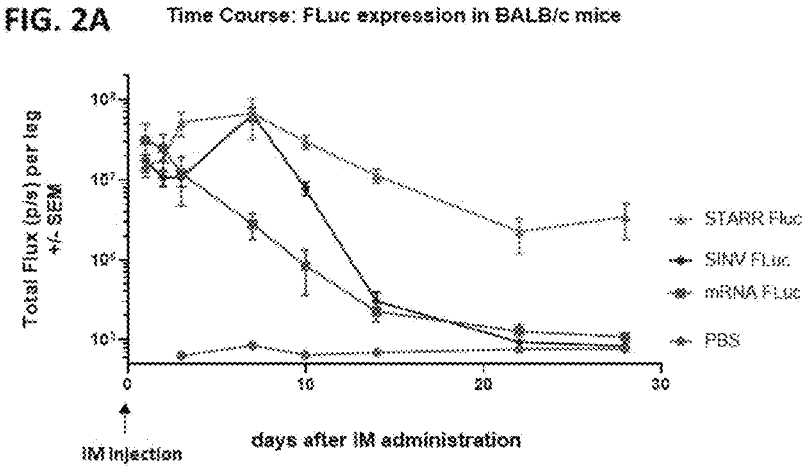
FIGS. 2A-2D show characterization of STARR™ technology with firefly luciferase transgene expression. (2A) Firefly luciferase (FLuc) expression from STARR™ Fluc, SINV FLuc, and mRNA FLuc was monitored up to day 28 by In Vivo Imaging System (IVIS). The average of total flux (p/s) from 6 injection sites in a mouse group was plotted at each time point with a standard error of mean, SEM. (2B)
Figure 2B:
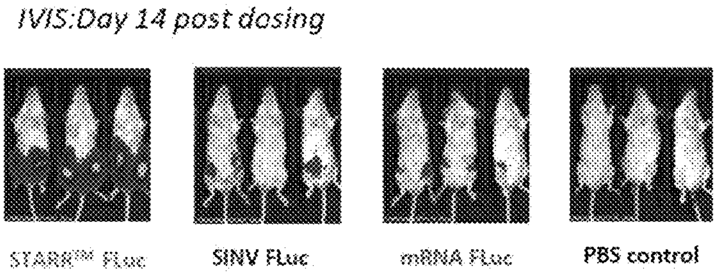
Figure 2C:
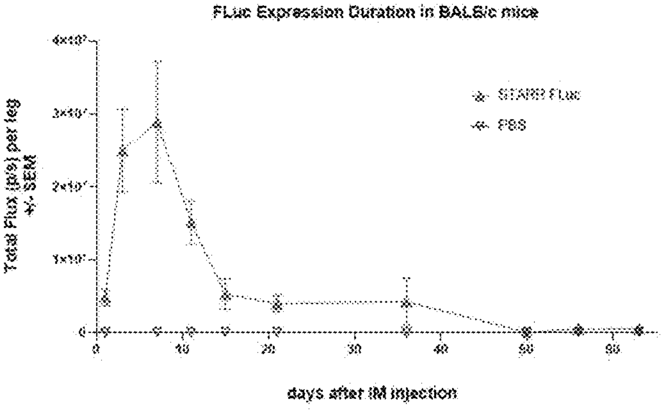
Figure 2D:
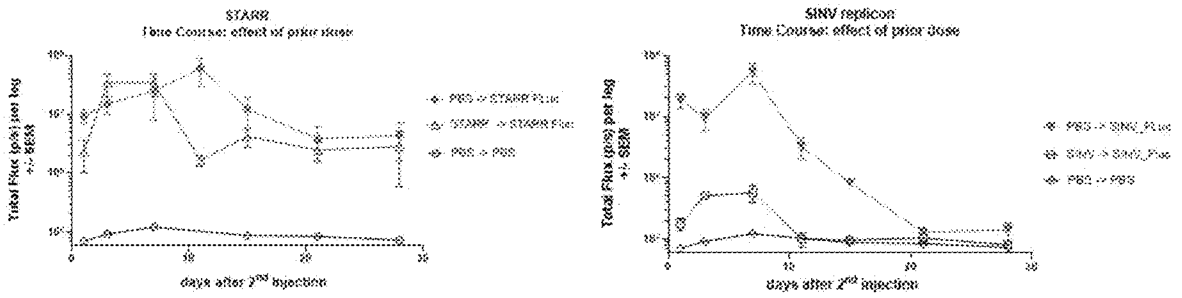

Firefly luciferase (FLuc) expression was monitored from STARR™ Fluc, SINV FLuc, and mRNA FLuc up to day 28 by In Vivo Imaging System (IVIS). Enhanced levels and durations of transgene expression from STARR™ were observed. The expression from STARR™ Fluc peaked around day 3 to 7 and declined until day 22. Fluc expression from SINV FLuc also peaked on day 10, however, the expression was reduced at a significantly faster rate than STARR™ FLuc. Additionally, the expression on day 3 was significantly lower than STARR™ FLuc. FLuc expression from the conventional mRNA backbone was highest at day 1, the earliest time point in this study, and declined at a slightly faster rate than that of STARR™-Fluc (FIG. 2A). FIG. 2B shows that at 14 days post dosing, FLuc expression from STARR™ FLuc was higher than the other groups by about two orders of magnitude. FIG. 2D shows that the effect of the STARR™ backbone remained minimal throughout the experimental period (up to day 28), while prior administration of SINV replicon backbone resulted in a reduction of FLuc transgene expression by orders of magnitude.

A cancer vaccine substrate, TA STARR™, was constructed next with the STARR™ backbone that encodes AH1A5 epitope from gp70, an envelope glycoprotein of endogenous Murine leukemia virus. AH1 (SPSYVYHQF) (SEQ ID NO:110) is an H-2Ld-restricted antigen of gp70423-431, which is expressed in tumor cells such as the CT26 colorectal cancer cell line, but not expressed in most of the normal tissues. AH1-A5 is a mutated sequence with SPSYAYHQF (SEQ ID NO:111) (the mutation underlined) with enhanced affinity to the T cell receptor (Slansky, et al., 2000, Immunity 13: 529-538). The open reading frame of the TA STARR™ subgenomic RNA contains a cassette with a signal peptide from the HLA class I antigen, gp70 sequence containing AH1A5 epitope, ovalbumin epitope (OVA323-339), and MHC class I trafficking signal (Kreiter, et al. 2008, J Immunol 180: 309-318). Three female BALB/c mice were intramuscularly injected with 10 ug of LNP formulated STARR™ transcripts, STARR™ FLuc or TA STARR™, on day 0 and day 7. On day 16, the spleens were harvested and the splenocytes were isolated. Splenocytes ($2.5\times10^5$ cells) were incubated with or without AH1A5 (SPSYAYHQF) (SEQ ID NO:111), beta-gal peptide (TPHPARIGL) (SEQ ID NO:112) at 1 ug/ml, and 1× Concanavalin A (Life Technologies). ELISpot detecting murine IFN-gamma (ImmunoSpot) was performed according to the manufacturer's instructions. As can be seen in FIG. 3, TA STARR™ elicited antigen-specific IFN-gamma responses.

BALB/c mice, 10 week-old female, were subcutaneously implanted in the right flank with $5\times10^5$ cells of CT26 cells in PBS. A day later, LNP formulated STARR™ RNA was injected intramuscularly in the left leg at a dose of 10 ug in 100 ul. The mice were administered another booster shot on day 8 with the same dose. For a group with combination treatment of anti-mouse PD1 (RMP1-14, BioXCell) and anti-mouse PDL1 (10F.9G2, BioXcell), the combined checkpoint inhibitor (100 ug each) was administered via intraperitoneal injection in the right quadrant twice weekly for two weeks starting on day 3. For a group with the treatment of anti-mouse CTLA4 (9H10, BioxCell), 200 ug of the checkpoint inhibitor was administered in the same manner but starting on day 7. Five mice of the group with the combo treatment of TA STARR™ vaccine and the checkpoint inhibitors remained tumor-free on day 25, and were further challenged by subcutaneous implantation of CT26 (5×105 cells) in the right flank where the implantation site was slightly above the first implantation site. Naïve mice were used as a control group. The tumor growth was monitored for another 17 days (i.e. up to day 42 since the first CT26 implantation) before euthanization. FIGS. 4A-4F illustrate reduced tumor growth resulting from TA STARR™ vaccination and FIG. 5 shows prolonged protection resulting from treatment with the TA STARR™ vaccine in combination with checkpoint inhibitors.

Splenocytes from the combination treatment group with TA STARR™ and anti-PD1/PDL1 were harvested for tetramer staining with AH1 peptide. Splenocytes from the control group with the LNP formulation buffer with the same dosing schedule were used as a negative control. The splenocytes ($2\times10^6$ cells) were incubated with AH1 (H-2Ld)-tetramer (MBL) followed by appropriate fluorescent-labeled antibodies (Alexa Fluor 488 anti-CD8a (53-6.7), Pacific Orange anti-CD4 (RM4-5), and Pacific Blue anti-mouse CD3E (145-2C11), (eBioscience) and DRAQ7 (Invitrogen) by following the manufacture's recommendation, and 500K events were analyzed by ZE5 Cell Analyzer (Bio-Rad). Results are shown in FIGS. 6A-6C.

TABLE 9

Transgene ORF nucleotide sequence

| mARM # | RNA back bone | Transgene | Sequence |
|---|---|---|---|
| 2809 (SEQ ID NO:84) | STARR™ | Fluc | AUGGAAGAUGCCAAAAACAUUAAGAAGGGCCCAGCGCCAUUCUACC<br>CACUCGAAGACGGGACCGCCGGCGAGCAGCUGCACAAAGCCAUGAA<br>GCGCUACGCCCUGGUGCCCGGCACCAUCGCCUUUACCGACGCACAU<br>AUCGAGGUGGACAUUACCUACGCCGAGUACUUCGAGAUGAGCGUUC<br>GGCUGGCAGAAGCUAUGAAGCGCUAUGGGCUGAAUACAAACCAUCG<br>GAUCGUGGUGUGCAGCGAGAAUAGCUUGCAGUUCUUCAUGCCCGUG<br>UUGGGUGCCCUGUUCAUCGGUGUGGCUGUGGCCCCAGCUAACGACA<br>UCUACAACGAGCGCGAGCUGCUGAACAGCAUGGGCAUCAGCCAGCC<br>CACCGUCGUAUUCGUGAGCAAGAAAGGGCUGCAAAAGAUCCUCAAC<br>GUGCAAAAGAAGCUACCGAUCAUACAAAAGAUCAUCAUCAUGGAUA<br>GCAAGACCGACUACCAGGGCUUCCAAAGCAUGUACACCUUCGUGAC<br>UUCCCAUUUGCCACCCGGCUUCAACGAGUACGACUUCGUGCCCGAG<br>AGCUUCGACCGGGACAAAACCAUCGCCCUGAUCAUGAACAGUAGUG<br>GCAGUACCGGAUUGCCCAAGGGCGUAGCCCUACCGCACCGCACCGC<br>UUGUGUCCGAUUCAGUCAUGCCCGCGACCCCAUCUUCGGCAACCAG<br>AUCAUCCCCGACACCGCUAUCCUCAGCGUGGUGCCAUUUCACCACG<br>GCUUCGGCAUGUUCACCACGCUGGGCUACUUGAUCUGCGGCUUUCG<br>GGUCGUGCUCAUGUACCGCUUCGAGGAGGAGCUAUUCUUGCGCAGC<br>UUGCAAGACUAUAAGAUUCAAUCUGCCCUGCUGGUGCCCACACUAU<br>UUAGCUUCUUCGCUAAGAGCACUCUCAUCGACAAGUACGACCUAAG<br>CAACUUGCACGAGAUCGCCAGCGGCGGGGCGCCGCUCAGCAAGGAG<br>GUAGGUGAGGCCGUGGCCAAACGCUUCCACCUACCAGGCAUCCGAC<br>AGGGCUACGGCCUGACAGAAACAACCAGCGCCAUUCUGAUCACCCC<br>CGAAGGGGACGACAAGCCUGGCGCAGUAGGCAAGGUGGUGCCCUUC<br>UUCGAGGCUAAGGUGGUGGACUUGGACACCGGUAAGACACUGGGUG<br>UGAACCAGCGCGGCGAGCUGUGCGUCCGUGGCCCCAUGAUCAUGAG<br>CGGCUACGUUAACAACCCCGAGGCUACAAACGCUCUCAUCGACAAG<br>GACGGCUGGCUGCACAGCGGCGACAUCGCCUACUGGGACGAGGACG<br>AGCACUUCUUCAUCGUGGACCGGCUGAAGUCCCUGAUCAAAUACAA<br>GGGCUACCAGGUAGCCCCAGCCGAACUGGAGAGCAUCCUGCUGCAA<br>CACCCCAACAUCUUCGACGCCGGGGUCGCCGGCCUGCCCGACGACG<br>AUGCCGGCGAGCUGCCCGCCGCAGUCGUCGUGCUGGAACACGGUAA<br>AACCAUGACCGAGAAGGAGAUCGUGGACUAUGUGGCCAGCCAGGUU<br>ACAACCGCCAAGAAGCUGCGCGGUGGUGUUGUGUUCGUGGACGAGG<br>UGCCUAAAGGACUGACCGGCAAGUUGGACGCCCGCAAGAUCCGCGA<br>GAUUCUCAUUAAGGCCAAGAAGGGCGGCAAGAUCGCCGUGUAA |
| 2842 (SEQ ID NO:85) | SINV replicon | Fluc | AUGGAAGAUGCCAAAAACAUUAAGAAGGGCCCAGCGCCAUUCUACC<br>CACUCGAAGACGGGACCGCCGGCGAGCAGCUGCACAAAGCCAUGAA<br>GCGCUACGCCCUGGUGCCCGGCACCAUCGCCUUUACCGACGCACAU<br>AUCGAGGUGGACAUUACCUACGCCGAGUACUUCGAGAUGAGCGUUC<br>GGCUGGCAGAAGCUAUGAAGCGCUAUGGGCUGAAUACAAACCAUCG<br>GAUCGUGGUGUGCAGCGAGAAUAGCUUGCAGUUCUUCAUGCCCGUG<br>UUGGGUGCCCUGUUCAUCGGUGUGGCUGUGGCCCCAGCUAACGACA<br>UCUACAACGAGCGCGAGCUGCUGAACAGCAUGGGCAUCAGCCAGCC<br>CACCGUCGUAUUCGUGAGCAAGAAAGGGCUGCAAAAGAUCCUCAAC<br>GUGCAAAAGAAGCUACCGAUCAUACAAAAGAUCAUCAUCAUGGAUA<br>GCAAGACCGACUACCAGGGCUUCCAAAGCAUGUACACCUUCGUGAC<br>UUCCCAUUUGCCACCCGGCUUCAACGAGUACGACUUCGUGCCCGAG<br>AGCUUCGACCGGGACAAAACCAUCGCCCUGAUCAUGAACAGUAGUG<br>GCAGUACCGGAUUGCCCAAGGGCGUAGCCCUACCGCACCGCACCGC<br>UUGUGUCCGAUUCAGUCAUGCCCGCGACCCCAUCUUCGGCAACCAG |

TABLE 9-continued

| | | | |
|---|---|---|---|
| | | | AUCAUCCCCGACACCGCUAUCCUCAGCGUGGUGCCAUUUCACCACG<br>GCUUCGGCAUGUUCACCACGCUGGGCUACUUGAUCUGCGGCUUUCG<br>GGUCGUGCUCAUGUACCGCUUCGAGGAGGAGCUAUUCUUGCGCAGC<br>UUGCAAGACUAUAAGAUUCAAUCUGCCCUGCUGGUGCCCACACUAU<br>UUAGCUUCUUCGCUAAGAGCACUCUCAUCGACAAGUACGACCUAAG<br>CAACUUGCACGAGAUCGCCAGCGGCGGGGCGCCGCUCAGCAAGGAG<br>GUAGGUGAGGCCGUGGCCAAACGCUUCCACCUACCAGGCAUCCGAC<br>AGGGCUACGGCCUGACAGAAACAACCAGCGCCAUUCUGAUCACCCC<br>CGAAGGGGACGACAAGCCUGGCGCAGUAGGCAAGGUGGUGCCCUUC<br>UUCGAGGCUAAGGUGGUGGACUUGGACACCGGUAAGACACUGGGUG<br>UGAACCAGCGCGGCGAGCUGUGCGUCCGUGGCCCCAUGAUCAUGAG<br>CGGCUACGUUAACAACCCCGAGGCUACAAACGCUCUCAUCGACAAG<br>GACGGCUGGCUGCACAGCGGCGACAUCGCCUACUGGGACGAGGACG<br>AGCACUUCUUCAUCGUGGACCGGCUGAAGUCCCUGAUCAAAUACAA<br>GGGCUACCAGGUAGCCCCAGCCGAACUGGAGAGCAUCCUGCUGCAA<br>CACCCCAACAUCUUCGACGCCGGGGUCGCCGGCCUGCCCGACGACG<br>AUGCCGGCGAGCUGCCCGCCGCAGUCGUCGUGCUGGAACACGGUAA<br>AACCAUGACCGAGAAGGAGAUCGUGGACUAUGUGGCCAGCCAGGUU<br>ACAACCGCCAAGAAGCUGCGCGGUGGUGUUGUGUUCGUGGACGAGG<br>UGCCUAAAGGACUGACCGGCAAGUUGGACGCCCGCAAGAUCCGCGA<br>GAUUCUCAUUAAGGCCAAGAAGGGCGGCAAGAUCGCCGUGUAA |
| 1782 (SEQ ID NO:86) | mRNA (TEV-XbG) | Fluc | AUGGAAGAUGCCAAAAACAUUAAGAAGGGCCCAGCGCCAUUCUACC<br>CACUCGAAGACGGGACCGCCGGCGAGCAGCUGCACAAAGCCAUGAA<br>GCGCUACGCCCUGGUGCCCGGCACCAUCGCCUUUACCGACGCACAU<br>AUCGAGGUGGACAUUACCUACGCCGAGUACUUCGAGAUGAGCGUUC<br>GGCUGGCAGAAGCUAUGAAGCGCUAUGGGCUGAAUACAAACCAUCG<br>GAUCGUGGUGUGCAGCGAGAAUAGCUUGCAGUUCUUCAUGCCCGUG<br>UUGGGUGCCCUGUUCAUCGGUGUGGCUGUGGCCCCAGCUAACGACA<br>UCUACAACGAGCGCGAGCUGCUGAACAGCAUGGGCAUCAGCCAGCC<br>CACCGUCGUAUUCGUGAGCAAGAAAGGGCUGCAAAAGAUCCUCAAC<br>GUGCAAAAGAAGCUACCGAUCAUACAAAAGAUCAUCAUCAUGGAUA<br>GCAAGACCGACUACCAGGGCUUCCAAAGCAUGUACACCUUCGUGAC<br>UUCCCAUUUGCCACCCGGCUUCAACGAGUACGACUUCGUGCCCGAG<br>AGCUUCGACCGGGACAAAACCAUCGCCCUGAUCAUGAACAGUAGUG<br>GCAGUACCGGAUUGCCCAAGGGCGUAGCCCUACCGCACCGCACCGC<br>UUGUGUCCGAUUCAGUCAUGCCCGCGACCCCAUCUUCGGCAACCAG<br>AUCAUCCCCGACACCGCUAUCCUCAGCGUGGUGCCAUUUCACCACG<br>GCUUCGGCAUGUUCACCACGCUGGGCUACUUGAUCUGCGGCUUUCG<br>GGUCGUGCUCAUGUACCGCUUCGAGGAGGAGCUAUUCUUGCGCAGC<br>UUGCAAGACUAUAAGAUUCAAUCUGCCCUGCUGGUGCCCACACUAU<br>UUAGCUUCUUCGCUAAGAGCACUCUCAUCGACAAGUACGACCUAAG<br>CAACUUGCACGAGAUCGCCAGCGGCGGGGCGCCGCUCAGCAAGGAG<br>GUAGGUGAGGCCGUGGCCAAACGCUUCCACCUACCAGGCAUCCGAC<br>AGGGCUACGGCCUGACAGAAACAACCAGCGCCAUUCUGAUCACCCC<br>CGAAGGGGACGACAAGCCUGGCGCAGUAGGCAAGGUGGUGCCCUUC<br>UUCGAGGCUAAGGUGGUGGACUUGGACACCGGUAAGACACUGGGUG<br>UGAACCAGCGCGGCGAGCUGUGCGUCCGUGGCCCCAUGAUCAUGAG<br>CGGCUACGUUAACAACCCCGAGGCUACAAACGCUCUCAUCGACAAG<br>GACGGCUGGCUGCACAGCGGCGACAUCGCCUACUGGGACGAGGACG<br>AGCACUUCUUCAUCGUGGACCGGCUGAAGUCCCUGAUCAAAUACAA<br>GGGCUACCAGGUAGCCCCAGCCGAACUGGAGAGCAUCCUGCUGCAA<br>CACCCCAACAUCUUCGACGCCGGGGUCGCCGGCCUGCCCGACGACG<br>AUGCCGGCGAGCUGCCCGCCGCAGUCGUCGUGCUGGAACACGGUAA<br>AACCAUGACCGAGAAGGAGAUCGUGGACUAUGUGGCCAGCCAGGUU<br>ACAACCGCCAAGAAGCUGCGCGGUGGUGUUGUGUUCGUGGACGAGG<br>UGCCUAAAGGACUGACCGGCAAGUUGGACGCCCGCAAGAUCCGCGA<br>GAUUCUCAUUAAGGCCAAGAAGGGCGGCAAGAUCGCCGUGUAA |
| 2847 (SEQ ID NO:87) | STARR™ | KRAS epitope wt | AUGAAGUUGGUGGUUGUGGGGGCCGGGGGUGUUGGCAAAAGCGCCC<br>UUACAAUUUGA |
| 2862 (SEQ ID NO:88) | SINV replicon | Empty | AUGGAUCCUAGACGCUACGCCCCAAUGAUCCGACCAGCAAAACUCG<br>AUGUACUUCCGAGGAACUGA |
| 3060 (SEQ ID NO:89) | STARR™ | Signal peptide-gp70 with AH1A5-MITD | AUGAGAGUGACAGCCCCUAGAACCUUACUGCUUCUGCUUUGGGGAG<br>CUGUUGCUCUGACAGAGACAUGGGCUGGAUCUCUGAGCGAGGUGAC<br>CGGCCAGGGCCUGUGCAUCGGCGCCGUGCCCAAGACCCACCAGGUG<br>CUGUGCAACACCACCCAGAAGACCAGCGACGGCAGCUACUACCUGG<br>CCGCUCCCACCGGCACCACCUGGGCCUGCAGCACCGGCCUGACCCC<br>UUGCAUCAGCACCACCAUCCUGAACCUGACCACCGACUACUGCGUG<br>CUGGUGGAGCUGUGGCCCAGGGUGACCUACCACAGCCCCAGCUACG<br>CCUACCACCAGUUCGAGAGGAGGGCCAAGUACAAGAGGGAGCCCGU<br>GAGCCUGACCCUGGCCCUGCUGCUGGGCGGCCUGACAAUGGGCGGC<br>AUCGCCGCCGGCGUGGGCACCGGCACCACCGCCCUGGUGGCCACCC<br>AGCAGUUCCAGCAGCUGCAGGCCGCCAUGCACGACGACCUGAAGGA |

TABLE 9-continued

| | | | |
|---|---|---|---|
| | | | GGUGGAGAAGUCCAUCACCAACCUGGAGAAGUCCCCUGACCAGCCUG<br>AGCGAGGUGGUGCUGCAGAACAGGAGGGGCCUGGACCUGCUGUUCC<br>UGAAGGAGGGCGGCCUGUGCGCCGCCCUGAAGGAGGAGUGCUGCCU<br>GUACGCCGACCACACCGGCCUGGUGAUCGUGGGCAUUGUCGCUGGC<br>CUGGCCGUCCUCGCCGUGGUGGUGAUUGGAGCUGUGGUCGCAGCUG<br>UUAUGUGCAGAAGAAAGUCAUCCGGCGGAAAGGGAGGCUCCUACUC<br>UCAGGCUGCUUCUGCUACAGUGCCUAGAGCUCUUAUGUGUUUAUCU<br>CAGCUGUAA |
| 3061 (SEQ ID NO:90) | STARR™ | Signal peptide-AH1A5 OVA-MITD | AUGAGAGUGACAGCCCCUAGAACCUUACUGCUUCUGCUUUGGGGAG<br>CUGUUGCUCUGACAGAGACAUGGGCUGGAUCUUACCACAGCCCCAG<br>CUACGCCUACCACCAGUUCGAGAGGGGGGGAGGAGGCUCCGGGGGA<br>GGAGGCUCCCUGAAGAUCAGCCAGGCCGUGCACGCCGCCCACGCCG<br>AGAUCAACGAGGCCGGCCGGGAGGUGAUCGUGGGCAUUGUCGCUGG<br>CCUGGCCGUCCUCGCCGUGGUGGUGAUUGGAGCUGUGGUCGCAGCU<br>GUUAUGUGCAGAAGAAAGUCAUCCGGCGGAAAGGGAGGCUCCUACU<br>CUCAGGCUGCUUCUGCUACAGUGCCUAGAGCUCUUAUGUGUUUAUC<br>UCAGCUGUAA |
| 3076 (SEQ ID NO:91) | STARR™ | Signal peptide-gp70 with AH1A5-MITD-FLAG | AUGAGAGUGACAGCCCCUAGAACCUUACUGCUUCUGCUUUGGGGAG<br>CUGUUGCUCUGACAGAGACAUGGGCUGGAUCUCUGAGCGAGGUGAC<br>CGGCCAGGGCCUGUGCAUCGGCGCCGUGCCCAAGACCCACCAGGUG<br>CUGUGCAACACCACCCAGAAGACCAGCGACGGCAGCUACUACCUGG<br>CCGCUCCCACCGGCACCACCUGGGCCUGCAGCACCGGCCUGACCCC<br>UUGCAUCAGCACCACCAUCCUGAACCUGACCACCGACUACUGCGUG<br>CUGGUGGAGCUGUGGCCCAGGGUGACCUACCACAGCCCCAGCUACG<br>CCUACCACCAGUUCGAGAGGAGGGCCAAGUACAAGAGGGAGCCCGU<br>GAGCCUGACCCUGGCCCUGCUGCUGGGCGGCCUGACAAUGGGCGGC<br>AUCGCCGCCGGCGUGGGCACCGGCACCACCGCCCUGGUGGCCACCC<br>AGCAGUUCCAGCAGCUGCAGGCCGCCAUGCACGACGACCUGAAGGA<br>GGUGGAGAAGUCCAUCACCAACCUGGAGAAGUCCCCUGACCAGCCUG<br>AGCGAGGUGGUGCUGCAGAACAGGAGGGGCCUGGACCUGCUGUUCC<br>UGAAGGAGGGCGGCCUGUGCGCCGCCCUGAAGGAGGAGUGCUGCCU<br>GUACGCCGACCACACCGGCCUGGUGAUCGUGGGCAUUGUCGCUGGC<br>CUGGCCGUCCUCGCCGUGGUGGUGAUUGGAGCUGUGGUCGCAGCUG<br>UUAUGUGCAGAAGAAAGUCAUCCGGCGGAAAGGGAGGCUCCUACUC<br>UCAGGCUGCUUCUGCUACAGUGCCUAGAGCUCUUAUGUGUUUAUCU<br>CAGCUGGGCGGCGGAGGCAGCGACUACAAGGACGACGAUGACAAGU<br>AA |
| 3068 (SEQ ID NO:92) | STARR | Signal peptide-AH1A5 OVA-MITD-FLAG | AUGAGAGUGACAGCCCCUAGAACCUUACUGCUUCUGCUUUGGGGAG<br>CUGUUGCUCUGACAGAGACAUGGGCUGGAUCUUACCACAGCCCCAG<br>CUACGCCUACCACCAGUUCGAGAGGGGGGGAGGAGGCUCCGGGGGA<br>GGAGGCUCCCUGAAGAUCAGCCAGGCCGUGCACGCCGCCCACGCCG<br>AGAUCAACGAGGCCGGCCGGGAGGUGAUCGUGGGCAUUGUCGCUGG<br>CCUGGCCGUCCUCGCCGUGGUGGUGAUUGGAGCUGUGGUCGCAGCU<br>GUUAUGUGCAGAAGAAAGUCAUCCGGCGGAAAGGGAGGCUCCUACU<br>CUCAGGCUGCUUCUGCUACAGUGCCUAGAGCUCUUAUGUGUUUAUC<br>UCAGCUGGGCGGCGGAGGCAGCGACUACAAGGACGACGAUGACAAG<br>UAA |

Transgene ORF amino acid sequence

| mARM # | transgene description | Sequence |
|---|---|---|
| 2809, 2842, 1782 (SEQ ID NO:93) | Fluc | MEDAKNIKKGPAPFYPLEDGTAGEQLHKAMKRYALVPGTIAFTDAH<br>IEVDITYAEYFEMSVRLAEAMKRYGLNTNHRIVVCSENSLQFFMPV<br>LGALFIGVAVAPANDIYNERELLNSMGISQPTVVFVSKKGLQKILN<br>VQKKLPIIQKIIIMDSKTDYQGFQSMYTFVTSHLPPGFNEYDFVPE<br>SFDRDKTIALIMNSSGSTGLPKGVALPHRTACVRFSHARDPIFGNQ<br>IIPDTAILSVVPFHHGFGMFTTLGYLICGFRVVLMYRFEEELFLRS<br>LQDYKIQSALLVPTLFSFFAKSTLIDKYDLSNLHEIASGGAPLSKE<br>VGEAVAKRFHLPGIRQGYGLTETTSAILITPEGDDKPGAVGKVVPF<br>FEAKVVDLDTGKTLGVNQRGELCVRGPMIMSGYVNNPEATNALIDK<br>DGWLHSGDIAYWDEDEHFFIVDRLKSLIKYKGYQVAPAELESILLQ<br>HPNIFDAGVAGLPDDDAGELPAAVVVLEHGKTMTEKEIVDYVASQV<br>TTAKKLRGGVVFVDEVPKGLTGKLDARKIREILIKAKKGGKIAV* |
| 2847 (SEQ ID NO:94) | KRAS epitope wt | MKLVVVGAGGVGKSALTI* |

TABLE 9-continued

| | | |
|---|---|---|
| 2862 (SEQ ID NO:95) | Empty | MDPRRYAPMIRPAKLDVLPRN* |
| 3060 (SEQ ID NO:96) | Signal peptide-gp70 with AH1A5-MITD | MRVTAPRTLLLLLWGAVALTETWAGSLSEVTGQGLCIGAVPKTHQV<br>LCNTTQKTSDGSYYLAAPTGTTWACSTGLTPCISTTILNLTTDYCV<br>LVELWPRVTYHSPSYAYHQFERRAKYKREPVSLTLALLLGGLTMGG<br>IAAGVGTGTTALVATQQFQQLQAAMHDDLKEVEKSITNLEKSLTSL<br>SEVVLQNRRGLDLLFLKEGGLCAALKEECCLYADHTGLVIVGIVAG<br>LAVLAVVVIGAVVAAVMCRRKSSGGKGGSYSQAASATVPRALMCLS<br>QL* |
| 3061 (SEQ ID NO:97) | Signal peptide-AH1A5 OVA-MITD | MRVTAPRTLLLLLWGAVALTETWAGSYHSPSYAYHQFERGGGGSGG<br>GGSLKISQAVHAAHAEINEAGREVIVGIVAGLAVLAVVVIGAVVAA<br>VMCRRKSSGGKGGSYSQAASATVPRALMCLSQL* |
| 3076 (SEQ ID NO:98) | Signal peptide-gp70 with AH1A5-MITD-FLAG | MRVTAPRTLLLLLWGAVALTETWAGSLSEVTGQGLCIGAVPKTHQV<br>LCNTTQKTSDGSYYLAAPTGTTWACSTGLTPCISTTILNLTTDYCV<br>LVELWPRVTYHSPSYAYHQFERRAKYKREPVSLTLALLLGGLTMGG<br>IAAGVGTGTTALVATQQFQQLQAAMHDDLKEVEKSITNLEKSLTSL<br>SEVVLQNRRGLDLLFLKEGGLCAALKEECCLYADHTGLVIVGIVAG<br>LAVLAVVVIGAVVAAVMCRRKSSGGKGGSYSQAASATVPRALMCLS<br>QLGGGGSDYKDDDDK* |
| 3068 (SEQ NO:99) | Signal peptide-AH1A5 OVA-MITD-FLAG | MRVTAPRTLLLLLWGAVALTETWAGSYHSPSYAYHQFERGGGGSGG<br>GGSLKISQAVHAAHAEINEAGREVIVGIVAGLAVLAVVVIGAVVAA<br>VMCRRKSSGGKGGSYSQAASATVPRALMCLSQLGGGGSDYKDDDDK<br>* |

whole RNA sequence

| mARM # | brief name | | Sequence |
|---|---|---|---|
| 2809 (SEQ ID NO:100) | STARR™ Fluc | 2809 | AUGGGCGGCGCAUGAGAGAAGCCCAGACCAAUUACCUACCCAAAAU<br>GGAGAAAGUUCACGUUGACAUCGAGGAAGACAGCCCAUUCCUCAGA<br>GCUUUGCAGCGGAGCUUCCCGCAGUUUGAGGUAGAAGCCAAGCAGG<br>UCACUGAUAAUGACCAUGCUAAUGCCAGAGCGUUUUCGCAUCUGGC<br>UUCAAAACUGAUCGAAACGGAGGUGGACCCAUCCGACACGAUCCUU<br>GACAUUGGAAGUGCGCCCGCCCGCAGAAUGUAUUCUAAGCACAAGU<br>AUCAUUGUAUCUGUCCGAUGAGAUGUGCGGAAGAUCCGGACAGAUU<br>GUAUAAGUAUGCAACUAAGCUGAAGAAAAACUGUAAGGAAAUAACU<br>GAUAAGGAAUUGGACAAGAAAAUGAAGGAGCUGGCCGCCGUCAUGA<br>GCGACCCUGACCUGGAAACUGAGACUAUGUGCCUCCACGACGACGA<br>GUCGUGUCGCUACGAAGGGCAAGUCGCUGUUUACCAGGAUGUAUAC<br>GCCGUCGACGGCCCCACCAGCCUGUACCACCAGGCCAACAAGGGCG<br>UGAGGGUGGCCUACUGGAUCGGCUUCGACACCACACCCUUCAUGUU<br>CAAGAACCUGGCCGGCGCCUACCCCAGCUACAGCACCAACUGGGCC<br>GACGAGACCGUGCUGACCGCCAGGAACAUCGGCCUGUGCAGCAGCG<br>ACGUGAUGGAGAGGAGCCGGAGAGGCAUGAGCAUCCUGAGGAAGAA<br>AUACCUGAAGCCCAGCAACAACGUGCUGUUCAGCGUGGGCAGCACC<br>AUCUACCACGAGAAGAGGGACCUGCUCAGGAGCUGGCACCUGCCCA<br>GCGUGUUCCACCUGAGGGGCAAGCAGAACUACACCUGCAGGUGCGA<br>GACCAUCGUGAGCUGCGACGGCUACGUGGUGAAGAGGAUCGCCAUC<br>AGCCCCGGCCUGUACGGCAAGCCCAGCGGCUACGCCGCUACAAUGC<br>ACAGGGAGGGCUUCCUGUGCUGCAAGGUGACCGACACCCUGAACGG<br>CGAGAGGGUGAGCUUCCCCGUGUGCACCUACGUGCCCGCCACCCUG<br>UGCGACCAGAUGACCGGCAUCCUGGCCACCGACGUGAGCGCCGACG<br>ACGCCCAGAAGCUGCUCGUGGGCCUGAACCAGAGGAUCGUGGUCAA<br>CGGCAGGACCCAGAGGAACACCAACACAAUGAAGAACUACCUGCUG<br>CCCGUGGUGGCCCAGGCUUUCGCCAGGUGGGCCAAGGAGUACAAGG<br>AGGACCAGGAAGACGAGAGGCCCCUGGGCCUGAGGGACAGGCAGCU<br>GGUGAUGGGCUGCUGCUGGGCCUUCAGGCGGCACAAGAUCACCAGC<br>AUCUACAAGAGGCCCGACACCCAGACCAUCAUCAAGGUGAACAGCG<br>ACUUCCACAGCUUCGUGCUGCCCAGGAUCGGCAGCAACACCCUGGA<br>GAUCGGCCUGAGGACCCGGAUCAGGAAGAUGCUGGAGGAACACAAG<br>GAGCCCAGCCCACUGAUCACCGCCGAGGACGUGCAGGAGGCCAAGU<br>GCGCUGCCGACGAGGCCAAGGAGGUGAGGGAGGCCGAGGAACUGAG<br>GGCCGCCCUGCCACCCCUGGCUGCCGACGUGGAGGAACCCACCCUG<br>GAAGCCGACGUGGACCUGAUGCUGCAGGAGGCCGGCGCCGGAAGCG<br>UGGAGACACCCAGGGGCCUGAUCAAGGUGACCAGCUACGACGGCGA<br>GGACAAGAUCGGCAGCUACGCCGUGCUGAGCCCACAGGCCGUGCUG<br>AAGUCCGAGAAGCUGAGCUGCAUCCACCCACUGGCCGAGCAGGUGA<br>UCGUGAUCACCCACAGCGGCAGGAAGGGCAGGUACGCCGUGGAGCC<br>CUACCACGGCAAGGUGGUCGUGCCCGAGGGCCACGCCAUCCCCGUG<br>CAGGACUUCCAGGCCCUGAGCGAGAGCGCCACCAUCGUGUACAACG<br>AGAGGGAGUUCGUGAACAGGUACCUGCACCAUAUCGCCACCCACGG |

TABLE 9-continued

| |
|---|
| CGGAGCCCUGAACACCGACGAGGAAUACUACAAGACCGUGAAGCCC<br>AGCGAGCACGACGGCGAGUACCUGUACGACAUCGACAGGAAGCAGU<br>GCGUGAAGAAAGAGCUGGUGACCGGCCUGGGACUGACCGGCGAGCU<br>GGUGGACCCACCCUUCCACGAGUUCGCCUACGAGAGCCUGAGGACC<br>AGACCCGCCGCUCCCUACCAGGUGCCCACCAUCGGCGUGUACGGCG<br>UGCCCGGCAGCGGAAAGAGCGGCAUCAUCAAGAGCGCCGUGACCAA<br>GAAAGACCUGGUGGUCAGCGCCAAGAAAGAGAACUGCGCCGAGAUC<br>AUCAGGGACGUGAAGAAGAUGAAAGGCCUGGACGUGAACGCGCGCA<br>CCGUGGACAGCGUGCUGCUGAACGGCUGCAAGCACCCCGUGGAGAC<br>CCUGUACAUCGACGAGGCCUUCGCUUGCCACGCCGGCACCCUGAGG<br>GCCCUGAUCGCCAUCAUCAGGCCCAAGAAAGCCGUGCUGUGCGGCG<br>ACCCCAAGCAGUGCGGCUUCUUCAACAUGAUGUGCCUGAAGGUGCA<br>CUUCAACCACGAGAUCUGCACCCAGGUGUUCCACAAGAGCAUCAGC<br>AGGCGGUGCACCAAGAGCGUGACCAGCGUCGUGAGCACCCUGUUCU<br>ACGACAAGAAAAUGAGGACCACCAACCCCAAGGAGACCAAAAUCGU<br>GAUCGACACCACAGGCAGCACCAAGCCCAAGCAGGACGACCUGAUC<br>CUGACCUGCUUCAGGGGCUGGGUGAAGCAGCUGCAGAUCGACUACA<br>AGGGCAACGAGAUCAUGACCGCCGCUGCCAGCCAGGGCCUGACCAG<br>GAAGGGCGUGUACGCCGUGAGGUACAAGGUGAACGAGAACCCACUG<br>UACGCUCCCACCAGCGAGCACGUGAACGUGCUGCUGACCAGGACCG<br>AGGACAGGAUCGUGUGGAAGACCCUGGCCGGCGACCCCUGGAUCAA<br>GACCCUGACCGCCAAGUACCCCGGCAACUUCACCGCCACCAUCGAA<br>GAGUGGCAGGCCGAGCACGACGCCAUCAUGAGGCACAUCCUGGAGA<br>GGCCCGACCCCACCGACGUGUUCCAGAACAAGGCCAACGUGUGCUG<br>GGCCAAGGCCCUGGUGCCCGUGCUGAAGACCGCCGGCAUCGACAUG<br>ACCACAGAGCAGUGGAACACCGUGGACUACUUCGAGACCGACAAGG<br>CCCACAGCGCCGAGAUCGUGCUGAACCAGCUGUGCGUGAGGUUCUU<br>CGGCCUGGACCUGGACAGCGGCCUGUUCAGCGCCCCCACCGUGCCA<br>CUGAGCAUCAGGAACAACCACUGGGACAACAGCCCCAGCCCAAACA<br>UGUACGGCCUGAACAAGGAGGUGGUCAGGCAGCUGAGCAGGCGGUA<br>CCCACAGCUGCCCAGGGCCGUGGCCACCGGCAGGGUGUACGACAUG<br>AACACCGGCACCCUGAGGAACUACGACCCCAGGAUCAACCUGGUGC<br>CCGUGAACAGGCGGCUGCCCCACGCCCUGGUGCUGCACCACAACGA<br>GCACCCACAGAGCGACUUCAGCUCCUUCGUGAGCAAGCUGAAAGGC<br>AGGACCGUGCUGGUCGUGGGCGAGAAGCUGAGCGUGCCCGGCAAGA<br>UGGUGGACUGGCUGAGCGACAGGCCCGAGGCCACCUUCCGGGCCAG<br>GCUGGACCUCGGCAUCCCCGGCGACGUGCCCAAGUACGACAUCAUC<br>UUCGUGAACGUCAGGACCCCAUACAAGUACCACCAUUACCAGCAGU<br>GCGAGGACCACGCCAUCAAGCUGAGCAUGCUGACCAAGAAGGCCUG<br>CCUGCACCUGAACCCCGGAGGCACCUGCGUGAGCAUCGGCUACGGC<br>UACGCCGACAGGGCCAGCGAGAGCAUCAUUGGCGCCAUCGCCAGGC<br>UGUUCAAGUUCAGCAGGGUGUGCAAACCCAAGAGCAGCCUGGAGGA<br>AACCGAGGUGCUGUUCGUGUUCAUCGGCUACGACCGGAAGGCCAGG<br>ACCCACAACCCCUACAAGCUGAGCAGCACCCUGACAAACAUCUACA<br>CCGGCAGCAGGCUGCACGAGGCCGGCUGCGCCCCCAGCUACCACGU<br>GGUCAGGGGCGAUAUCGCCACCGCCACCGAGGGCGUGAUCAUCAAC<br>GCUGCCAACAGCAAGGGCCAGCCCGGAGGCGGAGUGUGCGGCGCCC<br>UGUACAAGAAGUUCCCCGAGAGCUUCGACCUGCAGCCCAUCGAGGU<br>GGGCAAGGCCAGGCUGGUGAAGGGCGCCGCUAAGCACAUCAUCCAC<br>GCCGUGGGCCCCAACUUCAACAAGGUGAGCGAGGUGGAAGGCGACA<br>AGCAGCUGGCCGAAGCCUACGAGAGCAUCGCCAAGAUCGUGAACGA<br>CAAUAACUACAAGAGCGUGGCCAUCCCACUGCUCAGCACCGGCAUC<br>UUCAGCGGCAACAAGGACAGGCUGACCCAGAGCCUGAACCACCUGC<br>UCACCGCCCUGGACACCACCGAUGCCGACGUGGCCAUCUACUGCAG<br>GGACAAGAAGUGGGAGAUGACCCUGAAGGAGGCCGUGGCCAGGCGG<br>GAGGCCGUGGAAGAGAUCUGCAUCAGCGACGACUCCAGCGUGACCG<br>AGCCCGACGCCGAGCUGGUGAGGGUGCACCCCAAGAGCUCCCUGGC<br>CGGCAGGAAGGGCUACAGCACCAGCGACGGCAAGACCUUCAGCUAC<br>CUGGAGGGCACCAAGUUCCACCAGGCCGCUAAGGACAUCGCCGAGA<br>UCAACGCUAUGUGGCCCGUGGCCACCGAGGCCAACGAGCAGGUGUG<br>CAUGUACAUCCUGGGCGAGAGCAUGUCCAGCAUCAGGAGCAAGUGC<br>CCCGUGGAGGAAAGCGAGGCCAGCACACCACCCAGCACCCUGCCCU<br>GCCUGUGCAUCCACGCUAUGACACCCGAGAGGGUGCAGCGGCUGAA<br>GGCCAGCAGGCCCGAGCAGAUCACCGUGUGCAGCUCCUUCCCACUG<br>CCCAAGUACAGGAUCACCGGCGUGCAGAAGAUCCAGUGCAGCCAGC<br>CCAUCCUGUUCAGCCCAAAGGUGCCCGCCUACAUCCACCCCAGGAA<br>GUACCUGGUGGAGACCCCACCCGUGGACGAGACACCCGAGCCAAGC<br>GCCGAGAACCAGAGCACCGAGGGCACACCCGAGCAGCCACCCCUGA<br>UCACCGAGGACGAGACAAGGACCCGGACCCCAGAGCCCAUCAUUAU<br>CGAGGAAGAGGAAGAGGACAGCAUCAGCCUGCUGAGCGACGGCCCC<br>ACCCACCAGGUGCUGCAGGUGGAGGCCGACAUCCACGGCCCACCCA<br>GCGUGUCCAGCUCCAGCUGGAGCAUCCCACACGCCAGCGACUUCGA<br>CGUGGACAGCCUGAGCAUCCUGGACACCCUGGAGGGCGCCAGCGUG<br>ACCUCCGGCGCCACCAGCGCCGAGACCAACAGCUACUUCGCCAAGA<br>GCAUGGAGUUCCUGGCCAGGCCCGUGCCAGCUCCCAGGACCGUGUU<br>CAGGAACCCACCCCACCCAGCUCCCAGGACCAGGACCCCAAGCCUG<br>GCUCCCAGCAGGGCCUGCAGCAGGACCAGCCUGGUGAGCACCCCAC<br>CCGGCGUGAACAGGGUGAUCACCAGGGAGGAACUGGAGGCCCUGAC<br>ACCCAGCAGGACCCCCAGCAGGUCCGUGAGCAGGACUAGUCUGGUG<br>UCCAACCCACCCGGCGUGAACAGGGUGAUCACCAGGGAGGAAUUCG |

TABLE 9-continued

| |
|---|
| AGGCCUUCGUGGCCCAGCAACAGAGACGGUUCGACGCCGGCGCCUA<br>CAUCUUCAGCAGCGACACCGGCCAGGGACACCUGCAGCAAAAGAGC<br>GUGAGGCAGACCGUGCUGAGCGAGGUGGUGCUGGAGAGGACCGAGC<br>UGGAAAUCAGCUACGCCCCCAGGCUGGACCAGGAGAAGGAGGAACU<br>GCUCAGGAAGAAACUGCAGCUGAACCCCACCCCAGCCAACAGGAGC<br>AGGUACCAGAGCAGGAAGGUGGAGAACAUGAAGGCCAUCACCGCCA<br>GGCGGAUCCUGCAGGGCCUGGGACACUACCUGAAGGCCGAGGGCAA<br>GGUGGAGUGCUACAGGACCCUGCACCCCGUGCCACUGUACAGCUCC<br>AGCGUGAACAGGGCCUUCUCCAGCCCCAAGGUGGCCGUGGAGGCCU<br>GCAACGCUAUGCUGAAGGAGAACUUCCCCACCGUGGCCAGCUACUG<br>CAUCAUCCCCGAGUACGACGCCUACCUGGACAUGGUGGACGGCGCC<br>AGCUGCUGCCUGGACACCGCCAGCUUCUGCCCCGCCAAGCUGAGGA<br>GCUUCCCCAAGAAACACAGCUACCUGGAGCCCACCAUCAGGAGCGC<br>CGUGCCCAGCGCCAUCCAGAACACCCUGCAGAACGUGCUGGCCGCU<br>GCCACCAAGAGGAACUGCAACGUGACCCAGAUGAGGGAGCUGCCCG<br>UGCUGGACAGCGCUGCCUUCAACGUGGAGUGCUUCAAGAAAUACGC<br>CUGCAACAACGAGUACUGGGAGACCUUCAAGGAGAACCCCAUCAGG<br>CUGACCGAAGAGAACGUGGUGAACUACAUCACCAAGCUGAAGGGCC<br>CCAAGGCCGCUGCCCUGUUCGCUAAGACCCACAACCUGAACAUGCU<br>GCAGGACAUCCCAAUGGACAGGUUCGUGAUGGACCUGAAGAGGGAC<br>GUGAAGGUGACACCCGGCACCAAGCACACCGAGGAGAGGCCCAAGG<br>UGCAGGUGAUCCAGGCCGCUGACCCACUGGCCACCGCCUACCUGUG<br>CGGCAUCCACAGGGAGCUGGUGAGGCGGCUGAACGCCGUGCUGCUG<br>CCCAACAUCCACACCCUGUUCGACAUGAGCGCCGAGGACUUCGACG<br>CCAUCAUCGCCGAGCACUUCCAGCCCGGCGACUGCGUGCUGGAGAC<br>CGACAUCGCCAGCUUCGACAAGAGCGAGGAUGACGCUAUGGCCCUG<br>ACCGCUCUGAUGAUCCUGGAGGACCUGGGCGUGGACGCCGAGCUGC<br>UCACCCUGAUCGAGGCUGCCUUCGGCGAGAUCAGCUCCAUCCACCU<br>GCCCACCAAGACCAAGUUCAAGUUCGGCGCUAUGAUGAAAAGCGGA<br>AUGUUCCUGACCCUGUUCGUGAACACCGUGAUCAACAUUGUGAUCG<br>CCAGCAGGGUGCUGCGGGAGAGGCUGACCGGCAGCCCCUGCGCUGC<br>CUUCAUCGGCGACGACAACAUCGUGAAGGGCGUGAAAAGCGACAAG<br>CUGAUGGCCGACAGGUGCGCCACCUGGCUGAACAUGGAGGUGAAGA<br>UCAUCGACGCCGUGGUGGGCGAGAAGGCCCCCUACUUCUGCGGCGG<br>AUUCAUCCUGUGCGACAGCGUGACCGGCACCGCCUGCAGGGUGGCC<br>GACCCCCUGAAGAGGCUGUUCAAGCUGGGCAAGCCACUGGCCGCUG<br>ACGAUGAGCACGACGAUGACAGGCGGAGGGCCCUGCACGAGGAAAG<br>CACCAGGUGGAACAGGGUGGGCAUCCUGAGCGAGCUGUGCAAGGCC<br>GUGGAGAGCAGGUACGAGACCGUGGGCACCAGCAUCAUCGUGAUGG<br>CUAUGACCACACUGGCCAGCUCCGUCAAGAGCUUCUCCUACCUGAG<br>GGGGGCCCCUAUAACUCUCUACGGCUAACCUGAAUGGACUACGACA<br>UAGUCUAGUCCGCCAAGGCCGCCACCAUGGAAGAUGCCAAAAACAU<br>UAAGAAGGGCCCAGCGCCAUUCUACCCACUCGAAGACGGGACCGCC<br>GGCGAGCAGCUGCACAAAGCCAUGAAGCGCUACGCCCUGGUGCCCG<br>GCACCAUCGCCUUUACCGACGCACAUAUCGAGGUGGACAUUACCUA<br>CGCCGAGUACUUCGAGAUGAGCGUUCGGCUGGCAGAAGCUAUGAAG<br>CGCUAUGGGCUGAAUACAAACCAUCGGAUCGUGGUGUGCAGCGAGA<br>AUAGCUUGCAGUUCUUCAUGCCCGUGUUGGGUGCCCUGUUCAUCGG<br>UGUGGCUGUGGCCCCAGCUAACGACAUCUACAACGAGCGCGAGCUG<br>CUGAACAGCAUGGGCAUCAGCCAGCCCACCGUCGUAUUCGUGAGCA<br>AGAAAGGGCUGCAAAAGAUCCUCAACGUGCAAAAGAAGCUACCGAU<br>CAUACAAAAGAUCAUCAUCAUGGAUAGCAAGACCGACUACCAGGGC<br>UUCCAAAGCAUGUACACCUUCGUGACUUCCCAUUUGCCACCCGGCU<br>UCAACGAGUACGACUUCGUGCCCGAGAGCUUCGACCGGGACAAAAC<br>CAUCGCCCUGAUCAUGAACAGUAGUGGCAGUACCGGAUUGCCCAAG<br>GGCGUAGCCCUACCGCACCGCACCGCUUGUGUCCGAUUCAGUCAUG<br>CCCGCGACCCCAUCUUCGGCAACCAGAUCAUCCCCGACACCGCUAU<br>CCUCAGCGUGGUGCCAUUUCACCACGGCUUCGGCAUGUUCACCACG<br>CUGGGCUACUUGAUCUGCGGCUUUCGGGUCGUGCUCAUGUACCGCU<br>UCGAGGAGGAGCUAUUCUUGCGCAGCUUGCAAGACUAUAAGAUUCA<br>AUCUGCCCUGCUGGUGCCCACACUAUUUAGCUUCUUCGCUAAGAGC<br>ACUCUCAUCGACAAGUACGACCUAAGCAACUUGCACGAGAUCGCCA<br>GCGGCGGGGCGCCGCUCAGCAAGGAGGUAGGUGAGGCCGUGGCCAA<br>ACGCUUCCACCUACCAGGCAUCCGACAGGGCUACGGCCUGACAGAA<br>ACAACCAGCGCCAUUCUGAUCACCCCCGAAGGGGACGACAAGCCUG<br>GCGCAGUAGGCAAGGUGGUGCCCUUCUUCGAGGCUAAGGUGGUGGA<br>CUUGGACACCGGUAAGACACUGGGUGUGAACCAGCGCGGCGAGCUG<br>UGCGUCCGUGGCCCCAUGAUCAUGAGCGGCUACGUUAACAACCCCG<br>AGGCUACAAACGCUCUCAUCGACAAGGACGGCUGGCUGCACAGCGG<br>CGACAUCGCCUACUGGGACGAGGACGAGCACUUCUUCAUCGUGGAC<br>CGGCUGAAGUCCCUGAUCAAAUACAAGGGCUACCAGGUAGCCCCAG<br>CCGAACUGGAGAGCAUCCUGCUGCAACACCCCAACAUCUUCGACGC<br>CGGGGUCGCCGGCCUGCCCGACGACGAUGCCGGCGAGCUGCCCGCC<br>GCAGUCGUCGUGCUGGAACACGGUAAAACCAUGACCGAGAAGGAGA<br>UCGUGGACUAUGUGGCCAGCCAGGUUACAACCGCCAAGAAGCUGCG<br>CGGUGGUGUUGUGUUCGUGGACGAGGUGCCUAAAGGACUGACCGGC<br>AAGUUGGACGCCCGCAAGAUCCGCGAGAUUCUCAUUAAGGCCAAGA<br>AGGGCGGCAAGAUCGCCGUGUAACUCGAGUAUGUUACGUGCAAAGG<br>UGAUUGUCACCCCCCGAAAGACCAUAUUGUGACACACCCUCAGUAU<br>CACGCCCAAACAUUUACAGCCGCGGUGUCAAAAACCGCGUGGACGU |

TABLE 9-continued

| | | | |
|---|---|---|---|
| | | | GGUUAACAUCCCUGCUGGGAGGAUCAGCCGUAAUUAUUAUAAUUGG<br>CUUGGUGCUGGCUACUAUUGUGGCCAUGUACGUGCUGACCAACCAG<br>AAACAUAAUUGAAUACAGCAGCAAUUGGCAAGCUGCUUACAUAGAA<br>CUCGCGGCGAUUGGCAUGCCGCCUUAAAAUUUUUAUUUUAUUUUUU<br>CUUUUCUUUUCCGAAUCGGAUUUUGUUUUUAAUAUUUCAAAAAAA<br>AAAAAAAAAAAAAAAAAUCUAGAAAAAAAAAAAAAAAAAAAAAAAAAA<br>AAAAAAAAAAAAAAAAAAAAAAAAAAAAAAAAAAAAAAAAAAAAAAAA<br>AAAAAAAAAAAAAAAAAAAAAAAAAAAAAAA |
| 2842 (SEQ ID NO:101) | SINV Fluc | 2842 | AUUGACGGCGUAGUACACACUAUUGAAUCAAACAGCCGACCAAUUG<br>CACUACCAUCACAAUGGAGAAGCCAGUAGUAAACGUAGACGUAGAC<br>CCCCAGAGUCCGUUUGUCGUGCAACUGCAAAAAAGCUUCCCGCAAU<br>UUGAGGUAGUAGCACAGCAGGUCACUCCAAAUGACCAUGCUAAUGC<br>CAGAGCAUUUUCGCAUCUGGCCAGUAAACUAAUCGAGCUGGAGGUU<br>CCUACCACAGCGACGAUCUUGGACAUAGGCAGCGCACCGGCUCGUA<br>GAAUGUUUUCCGAGCACCAGUAUCAUUGUGUCUGCCCCAUGCGUAG<br>UCCAGAAGACCCGGACCGCAUGAUGAAAUAUGCCAGUAAACUGGCG<br>GAAAAAGCGUGCAAGAUUACAAACAAGAACUUGCAUGAGAAGAUUA<br>AGGAUCUCCGGACCGUACUUGAUACGCCGGAUGCUGAAACACCAUC<br>GCUCUGCUUUCACAACGAUGUUACCUGCAACAUGCGUGCCGAAUAU<br>UCCGUCAUGCAGGACGUGUAUAUCAACGCUCCCGGAACUAUCUAUC<br>AUCAGGCUAUGAAAGGCGUGCGGACCCUGUACUGGAUUGGCUUCGA<br>CACCACCCAGUUCAUGUUCUCGGCUAUGGCAGGUUCGUACCCUGCG<br>UACAACACCAACUGGGCCGACGAGAAAGUCCUUGAAGCGCGUAACA<br>UCGGACUUUGCAGCACAAAGCUGAGUGAAGGUAGGACAGGAAAAUU<br>GUCGAUAAUGAGGAAGAAGGAGUUGAAGCCCGGGUCGCGGGUUUAU<br>UUCUCCGUAGGAUCGACACUUUAUCCAGAACACAGAGCCAGCUUGC<br>AGAGCUGGCAUCUUCCAUCGGUGUUCCACUUGAAUGGAAAGCAGUC<br>GUACACUUGCCGCUGUGAUACAGUGGUGAGUUGCGAAGGCUACGUA<br>GUGAAGAAAAUCACCAUCAGUCCCGGGAUCACGGGAGAAACCGUGG<br>GAUACGCGGUUACACACAAUAGCGAGGGCUUCUUGCUAUGCAAAGU<br>UACUGACACAGUAAAAGGAGAACGGGUAUCGUUCCCUGUGUGCACG<br>UACAUCCCGGCCACCAUAUGCGAUCAGAUGACUGGUAUAAUGGCCA<br>CGGAUAUAUCACCUGACGAUGCACAAAAACUUCUGGUUGGGCUCAA<br>CCAGCGAAUUGUCAUUAACGGUAGGACUAACAGGAACACCAACACC<br>AUGCAAAAUUACCUUCUGCCGAUCAUAGCACAAGGGUUCAGCAAAU<br>GGGCUAAGGAGCGCAAGGAUGAUCUUGAUAACGAGAAAAUGCUGGG<br>UACUAGAGAACGCAAGCUUACGUAUGGCUGCUUGUGGGCGUUUCGC<br>ACUAAGAAAGUACAUUCGUUUUAUCGCCCACCUGGAACGCAGACCU<br>GCGUAAAAGUCCCAGCCUCUUUUAGCGCUUUUCCCAUGUCGUCCGU<br>AUGGACGACCUCUUUGCCCAUGUCGCUGAGGCAGAAAUUGAAACUG<br>GCAUUGCAACCAAAGAAGGAGGAAAAACUGCUGCAGGUCUCGGAGG<br>AAUUAGUCAUGGAGGCCAAGGCUGCUUUUGAGGAUGCUCAGGAGGA<br>AGCCAGAGCGGAGAAGCUCCGAGAAGCACUUCCACCAUUAGUGGCA<br>GACAAAGGCAUCGAGGCAGCCGCAGAAGUUGUCUGCGAAGUGGAGG<br>GGCUCCAGGCGGACAUCGGAGCAGCAUUAGUUGAAACCCCGCGCGG<br>UCACGUAAGGAUAAUACCUCAAGCAAAUGACCGUAUGAUCGGACAG<br>UAUAUCGUUGUCUCGCCAAACUCUGUGCUGAAGAAUGCCAAACUCG<br>CACCAGCGCACCCGCUAGCAGAUCAGGUUAAGAUCAUAACACACUC<br>CGGAAGAUCAGGAAGGUACGCGGUCGAACCAUACGACGCUAAAGUA<br>CUGAUGCCAGCAGGAGGUGCCGUACCAUGGCCAGAAUUCCUAGCAC<br>UGAGUGAGAGCGCCACGUUAGUGUACAACGAAAGAGAGUUUGUGAA<br>CCGCAAACUAUACCACAUUGCCAUGCAUGGCCCCGCCAAGAAUACA<br>GAAGAGGAGCAGUACAAGGUUACAAAGGCAGAGCUUGCAGAAACAG<br>AGUACGUGUUUGACGUGGACAAGAAGCGUUGCGUUAAGAAGGAAGA<br>AGCCUCAGGUCUGGUCCUCUCGGGAGAACUGACCAACCCUCCCUAU<br>CAUGAGCUAGCUCUGGAGGGACUGAAGACCCGACCUGCGGUCCCGU<br>ACAAGGUCGAAACAAUAGGAGUGAUAGGCACACCGGGGUCGGGCAA<br>GUCAGCUAUUAUCAAGUCAACUGUCACGGCACGAGAUCUUGUUACC<br>AGCGGAAAGAAAGAAAAUUGUCGCGAAAUUGAGGCCGACGUGCUAA<br>GACUGAGGGGUAUGCAGAUUACGUCGAAGACAGUAGAUUCGGUUAU<br>GCUCAACGGAUGCCACAAAGCCGUAGAAGUGCUGUACGUUGACGAA<br>GCGUUCGCGUGCCACGCAGGAGCACUACUUGCCUUGAUUGCUAUCG<br>UCAGGCCCCGCAAGAAGGUAGUACUAUGCGGAGACCCCAUGCAAUG<br>CGGAUUCUUCAACAUGAUGCAACUAAAGGUACAUUUCAAUCACCCU<br>GAAAAAGACAUAUGCACCAAGACAUUCUACAAGUAUAUCUCCCGGC<br>GUUGCACACAGCCAGUUACAGCUAUUGUAUCGACACUGCAUUACGA<br>UGGAAAGAUGAAAACCACGAACCCGUGCAAGAAGAACAUUGAAAUC<br>GAUAUUACAGGGGCCACAAAGCCGAAGCCAGGGGAUAUCAUCCUGA<br>CAUGUUUCCGCGGGUGGGUUAAGCAAUUGCAAAUCGACUAUCCCGG<br>ACAUGAAGUAAUGACAGCCGCGGCCUCACAAGGGCUAACCAGAAAA<br>GGAGUGUAUGCCGUCCGGCAAAAAGUCAAUGAAAACCCACUGUACG<br>CGAUCACAUCAGAGCAUGUGAACGUGUUGCUCACCCGCACUGAGGA<br>CAGGCUAGUGUGGAAAACCUUGCAGGGCGACCCAUGGAUUAAGCAG<br>CUCACUAACAUACCUAAAGGAAACUUUCAGGCUACUAUAGAGGACU<br>GGGAAGCUGAACACAAGGGAAUAAUUGCUGCAAUAAACAGCCCCAC<br>UCCCCGUGCCAAUCCGUUCAGCUGCAAGACCAACGUUUGCUGGGCG<br>AAAGCAUUGGAACCGAUACUAGCCACGGCCGGUAUCGUACUUACCG<br>GUUGCCAGUGGAGCGAACUGUUCCCACAGUUUGCGGAUGACAAACC<br>ACAUUCGGCCAUUUACGCCUUAGACGUAAUUUGCAUUAAGUUUUUC |

TABLE 9-continued

GGCAUGGACUUGACAAGCGGACUGUUUUCUAAACAGAGCAUCCCAC
UAACGUACCAUCCCGCCGAUUCAGCGAGGCCGGUAGCUCAUUGGGA
CAACAGCCCAGGAACCCGCAAGUAUGGGUACGAUCACGCCAUUGCC
GCCGAACUCUCCCGUAGAUUUCCGGUGUUCCAGCUAGCUGGGAAGG
GCACACAACUUGAUUUGCAGACGGGGAGAACCAGAGUUAUCUCUGC
ACAGCAUAACCUGGUCCCGGUGAACCGCAAUCUUCCUCACGCCUUA
GUCCCCGAGUACAAGGAGAAGCAACCCGGCCCGGUCGAAAAAUUCU
UGAACCAGUUCAAACACCACUCAGUACUUGUGGUAUCAGAGGAAAA
AAUUGAAGCUCCCCGUAAGAGAAUCGAAUGGAUCGCCCCGAUUGGC
AUAGCCGGUGCAGAUAAGAACUACAACCUGGCUUUCGGGUUUCCGC
CGCAGGCACGGUACGACCUGGUGUUCAUCAACAUUGGAACUAAAUA
CAGAAACCACCACUUUCAGCAGUGCGAAGACCAUGCGGCGACCUUA
AAAACCCUUUCGCGUUCGGCCCUGAAUUGCCUUAACCCAGGAGGCA
CCCUCGUGGUGAAGUCCUAUGGCUACGCCGACCGCAACAGUGAGGA
CGUAGUCACCGCUCUUGCCAGAAAGUUUGUCAGGGUGUCUGCAGCG
AGACCAGAUUGUGUCUCAAGCAAUACAGAAAUGUACCUGAUUUUCC
GACAACUAGACAACAGCCGUACACGGCAAUUCACCCCGCACCAUCU
GAAUUGCGUGAUUUCGUCCGUGUAUGAGGGUACAAGAGAUGGAGUU
GGAGCCGCGCCGUCAUACCGCACCAAAAGGGAGAAUAUUGCUGACU
GUCAAGAGGAAGCAGUUGUCAACGCAGCCAAUCCGCUGGGUAGACC
AGGCGAAGGAGUCUGCCGUGCCAUCUAUAAACGUUGGCCGACCAGU
UUUACCGAUUCAGCCACGGAGACAGGCACCGCAAGAAUGACUGUGU
GCCUAGGAAAGAAAGUGAUCCACGCGGUCGGCCCUGAUUUCCGGAA
GCACCCAGAAGCAGAAGCCUUGAAAUUGCUACAAAACGCCUACCAU
GCAGUGGCAGACUUAGUAAAUGAACAUAACAUCAAGUCUGUCGCCA
UUCCACUGCUAUCUACAGGCAUUUACGCAGCCGGAAAAGACCGCCU
UGAAGUAUCACUUAACUGCUUGACAACCGCGCUAGACAGAACUGAC
GCGGACGUAACCAUCUAUUGCCUGGAUAAGAAGUGGAAGGAAAGAA
UCGACGCGGCACUCCAACUUAAGGAGUCUGUAACAGAGCUGAAGGA
UGAAGAUAUGGAGAUCGACGAUGAGUUAGUAUGGAUCCAUCCAGAC
AGUUGCUUGAAGGGAAGAAAGGGAUUCAGUACUACAAAAGGAAAAU
UGUAUUCGUACUUCGAAGGCACCAAAUUCCAUCAAGCAGCAAAAGA
CAUGGCGGAGAUAAAGGUCCUGUUCCCUAAUGACCAGGAAAGUAAU
GAACAACUGUGUGCCUACAUAUUGGGUGAGACCAUGGAAGCAAUCC
GCGAAAAGUGCCCGGUCGACCAUAACCCGUCGUCUAGCCCGCCCAA
AACGUUGCCGUGCCUUUGCAUGUAUGCCAUGACGCCAGAAAGGGUC
CACAGACUUAGAAGCAAUAACGUCAAAGAAGUUACAGUAUGCUCCU
CCACCCCCCUUCCUAAGCACAAAAUUAAGAAUGUUCAGAAGGUUCA
GUGCACGAAAGUAGUCCUGUUUAAUCCGCACACUCCCGCAUUCGUU
CCCGCCCGUAAGUACAUAGAAGUGCCAGAACAGCCUACCGCUCCUC
CUGCACAGGCCGAGGAGGCCCCCGAAGUUGUAGCGACACCGUCACC
AUCUACAGCUGAUAACACCUCGCUUGAUGUCACAGACAUCUCACUG
GAUAUGGAUGACAGUAGCGAAGGCUCACUUUUUUCGAGCUUUAGCG
GAUCGGACAACUCUAUUACUAGUAUGGACAGUUGGUCGUCAGGACC
UAGUUCACUAGAGAUAGUAGACCGAAGGCAGGUGGUGGUGGCUGAC
GUUCAUGCCGUCCAAGAGCCUGCCCCUAUUCCACCGCCAAGGCUAA
AGAAGAUGGCCCGCCUGGCAGCGGCAAGAAAAGAGCCCACUCCACC
GGCAAGCAAUAGCUCUGAGUCCCUCCACCUCUCUUUUGGUGGGGUA
UCCAUGUCCCUCGGAUCAAUUUUCGACGGAGAGACGGCCCGCCAGG
CAGCGGUACAACCCCUGGCAACAGGCCCCACGGAUGUGCCUAUGUC
UUUCGGAUCGUUUUCCGACGGAGAGAUUGAUGAGCUGAGCCGCAGA
GUAACUGAGUCCGAACCCGUCCUGUUUGGAUCAUUUGAACCGGGCG
AAGUGAACUCAAUUAUAUCGUCCCGAUCAGCCGUAUCUUUUCCUCU
ACGCAAGCAGAGACGUAGACGCAGGAGCAGGAGGACUGAAUACUGA
CUAACCGGGGUAGGUGGGUACAUAUUUUCGACGGACACAGGCCCUG
GGCACUUGCAAAAGAAGUCCGUUCUGCAGAACCAGCUUACAGAACC
GACCUUGGAGCGCAAUGUCCUGGAAAGAAUUCAUGCCCCGGUGCUC
GACACGUCGAAAGAGGAACAACUCAAACUCAGGUACCAGAUGAUGC
CCACCGAAGCCAACAAAAGUAGGUACCAGUCUCGUAAAGUAGAAAA
UCAGAAAGCCAUAACCACUGAGCGACUACUGUCAGGACUACGACUG
UAUAACUCUGCCACAGAUCAGCCAGAAUGCUAUAAGAUCACCUAUC
CGAAACCAUUGUACUCCAGUAGCGUACCGGCGAACUACUCCGAUCC
ACAGUUCGCUGUAGCUGUCUGUAACAACUAUCUGCAUGAGAACUAU
CCGACAGUAGCAUCUUAUCAGAUUACUGACGAGUACGAUGCUUACU
UGGAUAUGGUAGACGGGACAGUCGCCUGCCUGGACACUGCAACCUU
CUGCCCCGCUAAGCUUAGAAGUUACCCGAAAAAACAUGAGUAUAGA
GCCCCGAAUAUCCGCAGUGCGGUUCCAUCAGCGAUGCAGAACACGC
UACAAAAUGUGCUCAUUGCCGCAACUAAAAGAAAUUGCAACGUCAC
GCAGAUGCGUGAACUGCCAACACUGGACUCAGCGACAUUCAAUGUC
GAAUGCUUUCGAAAAUAUGCAUGUAAUGACGAGUAUUGGGAGGAGU
UCGCUCGGAAGCCAAUUAGGAUUACCACUGAGUUUGUCACCGCAUA
UGUAGCUAGACUGAAAGGCCCUAAGGCCGCCGCACUAUUUGCAAAG
ACGUAUAAUUUGGUCCCAUUGCAAGAAGUGCCUAUGGAUAGAUUCG
UCAUGGACAUGAAAAGAGACGUGAAAGUUACACCAGGCACGAAACA
CACAGAAGAAAGACCGAAAGUACAAGUGAUACAAGCCGCAGAACCC
CUGGCGACUGCUUACUUAUGCGGGAUUCACCGGGAAUUAGUGCGUA
GGCUUACGGCCGUCUUGCUUCCAAACAUUCACACGCUUUUUGACAU
GUCGGCGGAGGAUUUUGAUGCAAUCAUAGCAGAACACUUCAAGCAA
GGCGACCCGGUACUGGAGACGGAUAUCGCAUCAUUCGACAAAAGCC
AAGACGACGCUAUGGCGUUAACCGGUCUGAUGAUCUUGGAGGACCU

TABLE 9-continued

| | | | |
|---|---|---|---|
| | | | GGGUGUGGAUCAACCACUACUCGACUUGAUCGAGUGCGCCUUUGGA<br>GAAAUAUCAUCCACCCAUCUACCUACGGGUACUCGUUUUAAAUUCG<br>GGGCGAUGAUGAAAUCCGGAAUGUUCCUCACACUUUUUGUCAACAC<br>AGUUUUGAAUGUCGUUAUCGCCAGCAGAGUACUAGAGGAGCGGCUU<br>AAAACGUCCAGAUGUGCAGCGUUCAUUGGCGACGACAACAUCAUAC<br>AUGGAGUAGUAUCUGACAAAGAAAUGGCUGAGAGGUGCGCCACCUG<br>GCUCAACAUGGAGGUUAAGAUCAUCGACGCAGUCAUCGGUGAGAGA<br>CCACCUUACUUCUGCGGCGGAUUUAUCUUGCAAGAUUCGGUUACUU<br>CCACAGCGUGCCGCGUGGCGGAUCCCCUGAAAAGGCUGUUUAAGUU<br>GGGUAAACCGCUCCCAGCCGACGACGAGCAAGACGAAGACAGAAGA<br>CGCGCUCUGCUAGAUGAAACAAAGGCGUGGUUUAGAGUAGGUAUAA<br>CAGGCACUUUAGCAGUGGCCGUGACGACCCGGUAUGAGGUAGACAA<br>UAUUACACCUGUCCUACUGGCAUUGAGAACUUUUGCCCAGAGCAAA<br>AGAGCAUUCCAAGCCAUCAGAGGGGAAAUAAAGCAUCUCUACGGUG<br>GUCCUAAAUAGUCAGCAUAGUACAUUUCAUCUGACUAAUACUACAA<br>CACCACCACCAUGGAAGAUGCCAAAAACAUUAAGAAGGGCCCAGCG<br>CCAUUCUACCCACUCGAAGACGGGACCGCCGGCGAGCAGCUGCACA<br>AAGCCAUGAAGCGCUACGCCCUGGUGCCCGGCACCAUCGCCUUUAC<br>CGACGCACAUAUCGAGGUGGACAUUACCUACGCCGAGUACUUCGAG<br>AUGAGCGUUCGGCUGGCAGAAGCUAUGAAGCGCUAUGGGCUGAAUA<br>CAAACCAUCGGAUCGUGGUGUGCAGCGAGAAUAGCUUGCAGUUCUU<br>CAUGCCCGUGUUGGGUGCCCUGUUCAUCGGUGUGGCUGUGGCCCCA<br>GCUAACGACAUCUACAACGAGCGCGAGCUGCUGAACAGCAUGGGCA<br>UCAGCCAGCCCACCGUCGUAUUCGUGAGCAAGAAAGGGCUGCAAAA<br>GAUCCUCAACGUGCAAAAGAAGCUACCGAUCAUACAAAAGAUCAUC<br>AUCAUGGAUAGCAAGACCGACUACCAGGGCUUCCAAAGCAUGUACA<br>CCUUCGUGACUUCCCAUUUGCCACCCGGCUUCAACGAGUACGACUU<br>CGUGCCCGAGAGCUUCGACCGGGACAAAACCAUCGCCCUGAUCAUG<br>AACAGUAGUGGCAGUACCGGAUUGCCCAAGGGCGUAGCCCUACCGC<br>ACCGCACCGCUUGUGUCCGAUUCAGUCAUGCCCGCGACCCCAUCUU<br>CGGCAACCAGAUCAUCCCCGACACCGCUAUCCUCAGCGUGGUGCCA<br>UUUCACCACGGCUUCGGCAUGUUCACCACGCUGGGCUACUUGAUCU<br>GCGGCUUUCGGGUCGUGCUCAUGUACCGCUUCGAGGAGGAGCUAUU<br>CUUGCGCAGCUUGCAAGACUAUAAGAUUCAAUCUGCCCUGCUGGUG<br>CCCACACUAUUUAGCUUCUUCGCUAAGAGCACUCUCAUCGACAAGU<br>ACGACCUAAGCAACUUGCACGAGAUCGCCAGCGGCGGGGCGCCGCU<br>CAGCAAGGAGGUAGGUGAGGCCGUGGCCAAACGCUUCCACCUACCA<br>GGCAUCCGACAGGGCUACGGCCUGACAGAAACAACCAGCGCCAUUC<br>UGAUCACCCCCGAAGGGGACGACAAGCCUGGCGCAGUAGGCAAGGU<br>GGUGCCCUUCUUCGAGGCUAAGGUGGUGGACUUGGACACCGGUAAG<br>ACACUGGGUGUGAACCAGCGCGGCGAGCUGUGCGUCCGUGGCCCCA<br>UGAUCAUGAGCGGCUACGUUAACAACCCCGAGGCUACAAACGCUCU<br>CAUCGACAAGGACGGCUGGCUGCACAGCGGCGACAUCGCCUACUGG<br>GACGAGGACGAGCACUUCUUCAUCGUGGACCGGCUGAAGUCCCUGA<br>UCAAAUACAAGGGCUACCAGGUAGCCCCAGCCGAACUGGAGAGCAU<br>CCUGCUGCAACACCCCAACAUCUUCGACGCCGGGGUCGCCGGCCUG<br>CCCGACGACGAUGCCGGCGAGCUGCCCGCCGCAGUCGUCGUGCUGG<br>AACACGGUAAAACCAUGACCGAGAAGGAGAUCGUGGACUAUGUGGC<br>CAGCCAGGUUACAACCGCCAAGAAGCUGCGCGGUGGUGUUGUGUUC<br>GUGGACGAGGUGCCUAAAGGACUGACCGGCAAGUUGGACGCCCGCA<br>AGAUCCGCGAGAUUCUCAUUAAGGCCAAGAAGGGCGGCAAGAUCGC<br>CGUGUAAACGCGUGCUAGACCAUGGAUCCUAGACGCUACGCCCCAA<br>UGAUCCGACCAGCAAAACUCGAUGUACUUCCGAGGAACUGAUGUGC<br>AUAAUGCAUCAGGCUGGUACAUUAGAUCCCCGCUUACCGCGGGCAA<br>UAUAGCAACACUAAAAACUCGAUGUACUUCCGAGGAAGCGCAGUGC<br>AUAAUGCUGCGCAGUGUUGCCACAUAACCACUAUAUUAACCAUUUA<br>UCUAGCGGACGCCAAAAACUCAAUGUAUUUCUGAGGAAGCGUGGUG<br>CAUAAUGCCACGCAGCGUCUGCAUAACUUUUAUUAUUUCUUUUAUU<br>AAUCAACAAAAUUUUGUUUUUAACAUUUCAAAAAAAAAAAAAAAAA<br>AAAAAAAAUCUAGAAAAAAAAAAAAAAAAAAAAAAAAAAAAAAAAA<br>AAAAAAAAAAAAAAAAAAAAAAAAAAAAAAAAAAAAAAAAAAAAAA<br>AAAAAAAAAAAAAAAAAAAA |
| 1782 (SEQ ID NO:102) | mRNA Fluc | 1782 | AGGAAACUUAAGUCAACACAACAUAUACAAAACAAACGAAUCUCAA<br>GCAAUCAAGCAUUCUACUUCUAUUGCAGCAAUUUAAAUCAUUUCUU<br>UUAAAGCAAAAGCAAUUUUCUGAAAAUUUUCACCAUUUACGAACGA<br>UAGCCAUGGAAGAUGCCAAAAACAUUAAGAAGGGCCCAGCGCCAUU<br>CUACCCACUCGAAGACGGGACCGCCGGCGAGCAGCUGCACAAAGCC<br>AUGAAGCGCUACGCCCUGGUGCCCGGCACCAUCGCCUUUACCGACG<br>CACAUAUCGAGGUGGACAUUACCUACGCCGAGUACUUCGAGAUGAG<br>CGUUCGGCUGGCAGAAGCUAUGAAGCGCUAUGGGCUGAAUACAAAC<br>CAUCGGAUCGUGGUGUGCAGCGAGAAUAGCUUGCAGUUCUUCAUGC<br>CCGUGUUGGGUGCCCUGUUCAUCGGUGUGGCUGUGGCCCCAGCUAA<br>CGACAUCUACAACGAGCGCGAGCUGCUGAACAGCAUGGGCAUCAGC<br>CAGCCCACCGUCGUAUUCGUGAGCAAGAAAGGGCUGCAAAAGAUCC<br>UCAACGUGCAAAAGAAGCUACCGAUCAUACAAAAGAUCAUCAUCAU<br>GGAUAGCAAGACCGACUACCAGGGCUUCCAAAGCAUGUACACCUUC<br>GUGACUUCCCAUUUGCCACCCGGCUUCAACGAGUACGACUUCGUGC<br>CCGAGAGCUUCGACCGGGACAAAACCAUCGCCCUGAUCAUGAACAG<br>UAGUGGCAGUACCGGAUUGCCCAAGGGCGUAGCCCUACCGCACCGC |

TABLE 9-continued

| | | | |
|---|---|---|---|
| | | | ACCGCUUGUGUCCGAUUCAGUCAUGCCCGCGACCCCAUCUUCGGCA<br>ACCAGAUCAUCCCCGACACCGCUAUCCUCAGCGUGGUGCCAUUUCA<br>CCACGGCUUCGGCAUGUUCACCACGCUGGGCUACUUGAUCUGCGGC<br>UUUCGGGUCGUGCUCAUGUACCGCUUCGAGGAGGAGCUAUUCUUGC<br>GCAGCUUGCAAGACUAUAAGAUUCAAUCUGCCCUGCUGGUGCCCAC<br>ACUAUUUAGCUUCUUCGCUAAGAGCACUCUCAUCGACAAGUACGAC<br>CUAAGCAACUUGCACGAGAUCGCCAGCGGCGGGGCGCCGCUCAGCA<br>AGGAGGUAGGUGAGGCCGUGGCCAAACGCUUCCACCUACCAGGCAU<br>CCGACAGGGCUACGGCCUGACAGAAACAACCAGCGCCAUUCUGAUC<br>ACCCCCGAAGGGGACGACAAGCCUGGCGCAGUAGGCAAGGUGGUGC<br>CCUUCUUCGAGGCUAAGGUGGUGGACUUGGACACCGGUAAGACACU<br>GGGUGUGAACCAGCGCGGCGAGCUGUGCGUCCGUGGCCCCAUGAUC<br>AUGAGCGGCUACGUUAACAACCCCGAGGCUACAAACGCUCUCAUCG<br>ACAAGGACGGCUGGCUGCACAGCGGCGACAUCGCCUACUGGGACGA<br>GGACGAGCACUUCUUCAUCGUGGACCGGCUGAAGUCCCUGAUCAAA<br>UACAAGGGCUACCAGGUAGCCCCAGCCGAACUGGAGAGCAUCCUGC<br>UGCAACACCCCAACAUCUUCGACGCCGGGGUCGCCGGCCUGCCCGA<br>CGACGAUGCCGGCGAGCUGCCCGCCGCAGUCGUCGUGCUGGAACAC<br>GGUAAAACCAUGACCGAGAAGGAGAUCGUGGACUAUGUGGCCAGCC<br>AGGUUACAACCGCCAAGAAGCUGCGCGGUGGUGUUGUGUUCGUGGA<br>CGAGGUGCCUAAAGGACUGACCGGCAAGUUGGACGCCCGCAAGAUC<br>CGCGAGAUUCUCAUUAAGGCCAAGAAGGGCGGCAAGAUCGCCGUGU<br>AACUCGAGCUAGUGACUGACUAGGAUCUGGUUACCACUAAACCAGC<br>CUCAAGAACACCCGAAUGGAGUCUCUAAGCUACAUAAUACCAACUU<br>ACACUUACAAAAUGUUGUCCCCCAAAAUGUAGCCAUUCGUAUCUGC<br>UCCUAAUAAAAAGAAAGUUUCUUCACAUUCUAGAAAAAAAAAAAAAA<br>AAAAAAAAAAAAAAAAAAAAAAAAAAAAAAAAAAAAAAAAAAAAAA<br>AAAAAAAAAAAAAAAAAAAAAAAAAAAAAAAAAAAAAAAAAAAAAA<br>AAAAAAAAAAAAAAAA |
| 2847 (SEQ ID NO:103) | STARR™ KRAS wt | 2847 | AUGGGCGGCGCAUGAGAGAAGCCCAGACCAAUUACCUACCCAAAAU<br>GGAGAAAGUUCACGUUGACAUCGAGGAAGACAGCCCAUUCCUCAGA<br>GCUUUGCAGCGGAGCUUCCCGCAGUUUGAGGUAGAAGCCAAGCAGG<br>UCACUGAUAAUGACCAUGCUAAUGCCAGAGCGUUUUCGCAUCUGGC<br>UUCAAAACUGAUCGAAACGGAGGUGGACCCAUCCGACACGAUCCUU<br>GACAUUGGAAGUGCGCCCGCCCGCAGAAUGUAUUCUAAGCACAAGU<br>AUCAUUGUAUCUGUCCGAUGAGAUGUGCGGAAGAUCCGGACAGAUU<br>GUAUAAGUAUGCAACUAAGCUGAAGAAAAACUGUAAGGAAAUAACU<br>GAUAAGGAAUUGGACAAGAAAAUGAAGGAGCUGGCCGCCGUCAUGA<br>GCGACCCUGACCUGGAAACUGAGACUAUGUGCCUCCACGACGACGA<br>GUCGUGUCGCUACGAAGGGCAAGUCGCUGUUUACCAGGAUGUAUAC<br>GCCGUCGACGGCCCCACCAGCCUGUACCACCAGGCCAACAAGGGCG<br>UGAGGGUGGCCUACUGGAUCGGCUUCGACACCACACCCUUCAUGUU<br>CAAGAACCUGGCCGGCGCCUACCCCAGCUACAGCACCAACUGGGCC<br>GACGAGACCGUGCUGACCGCCAGGAACAUCGGCCUGUGCAGCAGCG<br>ACGUGAUGGAGAGGAGCCGGAGAGGCAUGAGCAUCCUGAGGAAGAA<br>AUACCUGAAGCCCAGCAACAACGUGCUGUUCAGCGUGGGCAGCACC<br>AUCUACCACGAGAAGAGGGACCUGCUCAGGAGCUGGCACCUGCCCA<br>GCGUGUUCCACCUGAGGGGCAAGCAGAACUACACCUGCAGGUGCGA<br>GACCAUCGUGAGCUGCGACGGCUACGUGGUGAAGAGGAUCGCCAUC<br>AGCCCCGGCCUGUACGGCAAGCCCAGCGGCUACGCCGCUACAAUGC<br>ACAGGGAGGGCUUCCUGUGCUGCAAGGUGACCGACACCCUGAACGG<br>CGAGAGGGUGAGCUUCCCCGUGUGCACCUACGUGCCCGCCACCCUG<br>UGCGACCAGAUGACCGGCAUCCUGGCCACCGACGUGAGCGCCGACG<br>ACGCCCAGAAGCUGCUCGUGGGCCUGAACCAGAGGAUCGUGGUCAA<br>CGGCAGGACCCAGAGGAACACCAACACAAUGAAGAACUACCUGCUG<br>CCCGUGGUGGCCCAGGCUUUCGCCAGGUGGGCCAAGGAGUACAAGG<br>AGGACCAGGAAGACGAGAGGCCCCUGGGCCUGAGGGACAGGCAGCU<br>GGUGAUGGGCUGCUGCUGGGCCUUCAGGCGGCACAAGAUCACCAGC<br>AUCUACAAGAGGCCCGACACCCAGACCAUCAUCAAGGUGAACAGCG<br>ACUUCCACAGCUUCGUGCUGCCCAGGAUCGGCAGCAACACCCUGGA<br>GAUCGGCCUGAGGACCCGGAUCAGGAAGAUGCUGGAGGAACACAAG<br>GAGCCCAGCCCACUGAUCACCGCCGAGGACGUGCAGGAGGCCAAGU<br>GCGCUGCCGACGAGGCCAAGGAGGUGAGGGAGGCCGAGGAACUGAG<br>GGCCGCCCUGCCACCCCUGGCUGCCGACGUGGAGGAACCCACCCUG<br>GAAGCCGACGUGGACCUGAUGCUGCAGGAGGCCGGCGCCGGAAGCG<br>UGGAGACACCCAGGGGCCUGAUCAAGGUGACCAGCUACGACGGCGA<br>GGACAAGAUCGGCAGCUACGCCGUGCUGAGCCCACAGGCCGUGCUG<br>AAGUCCGAGAAGCUGAGCUGCAUCCACCCACUGGCCGAGCAGGUGA<br>UCGUGAUCACCCACAGCGGCAGGAAGGGCAGGUACGCCGUGGAGCC<br>CUACCACGGCAAGGUGGUCGUGCCCGAGGGCCACGCCAUCCCCGUG<br>CAGGACUUCCAGGCCCUGAGCGAGAGCGCCACCAUCGUGUACAACG<br>AGAGGGAGUUCGUGAACAGGUACCUGCACCAUAUCGCCACCCACGG<br>CGGAGCCCUGAACACCGACGAGGAAUACUACAAGACCGUGAAGCCC<br>AGCGAGCACGACGGCGAGUACCUGUACGACAUCGACAGGAAGCAGU<br>GCGUGAAGAAAGAGCUGGUGACCGGCCUGGGACUGACCGGCGAGCU<br>GGUGGACCCACCCUUCCACGAGUUCGCCUACGAGAGCCUGAGGACC<br>AGACCCGCCGCUCCCUACCAGGUGCCCACCAUCGGCGUGUACGGCG<br>UGCCCGGCAGCGGAAAGAGCGGCAUCAUCAAGAGCGCCGUGACCAA<br>GAAAGACCUGGUGGUCAGCGCCAAGAAAGAGAACUGCGCCGAGAUC |

TABLE 9-continued

AUCAGGGACGUGAAGAAGAUGAAAGGCCUGGACGUGAACGCGCGCA
CCGUGGACAGCGUGCUGCUGAACGGCUGCAAGCACCCCGUGGAGAC
CCUGUACAUCGACGAGGCCUUCGCUUGCCACGCCGGCACCCUGAGG
GCCCUGAUCGCCAUCAUCAGGCCCAAGAAAGCCGUGCUGUGCGGCG
ACCCCAAGCAGUGCGGCUUCUUCAACAUGAUGUGCCUGAAGGUGCA
CUUCAACCACGAGAUCUGCACCCAGGUGUUCCACAAGAGCAUCAGC
AGGCGGUGCACCAAGAGCGUGACCAGCGUCGUGAGCACCCUGUUCU
ACGACAAGAAAAUGAGGACCACCAACCCCAAGGAGACCAAAAUCGU
GAUCGACACCACAGGCAGCACCAAGCCCAAGCAGGACGACCUGAUC
CUGACCUGCUUCAGGGGCUGGGUGAAGCAGCUGCAGAUCGACUACA
AGGGCAACGAGAUCAUGACCGCCGCUGCCAGCCAGGGCCUGACCAG
GAAGGGCGUGUACGCCGUGAGGUACAAGGUGAACGAGAACCCACUG
UACGCUCCCACCAGCGAGCACGUGAACGUGCUGCUGACCAGGACCG
AGGACAGGAUCGUGUGGAAGACCCUGGCCGGCGACCCCUGGAUCAA
GACCCUGACCGCCAAGUACCCCGGCAACUUCACCGCCACCAUCGAA
GAGUGGCAGGCCGAGCACGACGCCAUCAUGAGGCACAUCCUGGAGA
GGCCCGACCCCACCGACGUGUUCCAGAACAAGGCCAACGUGUGCUG
GGCCAAGGCCCUGGUGCCCGUGCUGAAGACCGCCGGCAUCGACAUG
ACCACAGAGCAGUGGAACACCGUGGACUACUUCGAGACCGACAAGG
CCCACAGCGCCGAGAUCGUGCUGAACCAGCUGUGCGUGAGGUUCUU
CGGCCUGGACCUGGACAGCGGCCUGUUCAGCGCCCCCACCGUGCCA
CUGAGCAUCAGGAACAACCACUGGGACAACAGCCCCAGCCCAAACA
UGUACGGCCUGAACAAGGAGGUGGUCAGGCAGCUGAGCAGGCGGUA
CCCACAGCUGCCCAGGGCCGUGGCCACCGGCAGGGUGUACGACAUG
AACACCGGCACCCUGAGGAACUACGACCCCAGGAUCAACCUGGUGC
CCGUGAACAGGCGGCUGCCCCACGCCCUGGUGCUGCACCACAACGA
GCACCCACAGAGCGACUUCAGCUCCUUCGUGAGCAAGCUGAAAGGC
AGGACCGUGCUGGUCGUGGGCGAGAAGCUGAGCGUGCCCGGCAAGA
UGGUGGACUGGCUGAGCGACAGGCCCGAGGCCACCUUCCGGGCCAG
GCUGGACCUCGGCAUCCCCGGCGACGUGCCCAAGUACGACAUCAUC
UUCGUGAACGUCAGGACCCCAUACAAGUACCACCAUUACCAGCAGU
GCGAGGACCACGCCAUCAAGCUGAGCAUGCUGACCAAGAAGGCCUG
CCUGCACCUGAACCCCGGAGGCACCUGCGUGAGCAUCGGCUACGGC
UACGCCGACAGGGCCAGCGAGAGCAUCAUUGGCGCCAUCGCCAGGC
UGUUCAAGUUCAGCAGGGUGUGCAAACCCAAGAGCAGCCUGGAGGA
AACCGAGGUGCUGUUCGUGUUCAUCGGCUACGACCGGAAGGCCAGG
ACCCACAACCCCUACAAGCUGAGCAGCACCCUGACAAACAUCUACA
CCGGCAGCAGGCUGCACGAGGCCGGCUGCGCCCCCAGCUACCACGU
GGUCAGGGGCGAUAUCGCCACCGCCACCGAGGGCGUGAUCAUCAAC
GCUGCCAACAGCAAGGGCCAGCCCGGAGGCGGAGUGUGCGGCGCCC
UGUACAAGAAGUUCCCCGAGAGCUUCGACCUGCAGCCCAUCGAGGU
GGGCAAGGCCAGGCUGGUGAAGGGCGCCGCUAAGCACAUCAUCCAC
GCCGUGGGCCCCAACUUCAACAAGGUGAGCGAGGUGGAAGGCGACA
AGCAGCUGGCCGAAGCCUACGAGAGCAUCGCCAAGAUCGUGAACGA
CAAUAACUACAAGAGCGUGGCCAUCCCACUGCUCAGCACCGGCAUC
UUCAGCGGCAACAAGGACAGGCUGACCCAGAGCCUGAACCACCUGC
UCACCGCCCUGGACACCACCGAUGCCGACGUGGCCAUCUACUGCAG
GGACAAGAAGUGGGAGAUGACCCUGAAGGAGGCCGUGGCCAGGCGG
GAGGCCGUGGAAGAGAUCUGCAUCAGCGACGACUCCAGCGUGACCG
AGCCCGACGCCGAGCUGGUGAGGGUGCACCCCAAGAGCUCCCUGGC
CGGCAGGAAGGGCUACAGCACCAGCGACGGCAAGACCUUCAGCUAC
CUGGAGGGCACCAAGUUCCACCAGGCCGCUAAGGACAUCGCCGAGA
UCAACGCUAUGUGGCCCGUGGCCACCGAGGCCAACGAGCAGGUGUG
CAUGUACAUCCUGGGCGAGAGCAUGUCCAGCAUCAGGAGCAAGUGC
CCCGUGGAGGAAAGCGAGGCCAGCACACCACCCAGCACCCUGCCCU
GCCUGUGCAUCCACGCUAUGACACCCGAGAGGGUGCAGCGGCUGAA
GGCCAGCAGGCCCGAGCAGAUCACCGUGUGCAGCUCCUUCCCACUG
CCCAAGUACAGGAUCACCGGCGUGCAGAAGAUCCAGUGCAGCCAGC
CCAUCCUGUUCAGCCCAAAGGUGCCCGCCUACAUCCACCCCAGGAA
GUACCUGGUGGAGACCCCACCCGUGGACGAGACACCCGAGCCAAGC
GCCGAGAACCAGAGCACCGAGGGCACACCCGAGCAGCCACCCCUGA
UCACCGAGGACGAGACAAGGACCCGGACCCCAGAGCCCAUCAUUAU
CGAGGAAGAGGAAGAGGACAGCAUCAGCCUGCUGAGCGACGGCCCC
ACCCACCAGGUGCUGCAGGUGGAGGCCGACAUCCACGGCCCACCCA
GCGUGUCCAGCUCCAGCUGGAGCAUCCCACACGCCAGCGACUUCGA
CGUGGACAGCCUGAGCAUCCUGGACACCCUGGAGGGCGCCAGCGUG
ACCUCCGGCGCCACCAGCGCCGAGACCAACAGCUACUUCGCCAAGA
GCAUGGAGUUCCUGGCCAGGCCCGUGCCAGCUCCCAGGACCGUGUU
CAGGAACCCACCCCACCCAGCUCCCAGGACCAGGACCCCAAGCCUG
GCUCCCAGCAGGGCCUGCAGCAGGACCAGCCUGGUGAGCACCCCAC
CCGGCGUGAACAGGGUGAUCACCAGGGAGGAACUGGAGGCCCUGAC
ACCCAGCAGGACCCCCAGCAGGUCCGUGAGCAGGACUAGUCUGGUG
UCCAACCCACCCGGCGUGAACAGGGUGAUCACCAGGGAGGAAUUCG
AGGCCUUCGUGGCCCAGCAACAGAGACGGUUCGACGCCGGCGCCUA
CAUCUUCAGCAGCGACACCGGCCAGGGACACCUGCAGCAAAAGAGC
GUGAGGCAGACCGUGCUGAGCGAGGUGGUGCUGGAGAGGACCGAGC
UGGAAAUCAGCUACGCCCCCAGGCUGGACCAGGAGAAGGAGGAACU
GCUCAGGAAGAAACUGCAGCUGAACCCCACCCCAGCCAACAGGAGC
AGGUACCAGAGCAGGAAGGUGGAGAACAUGAAGGCCAUCACCGCCA
GGCGGAUCCUGCAGGGCCUGGGACACUACCUGAAGGCCGAGGGCAA

TABLE 9-continued

| | | | |
|---|---|---|---|
| | | | GGUGGAGUGCUACAGGACCCUGCACCCCGUGCCACUGUACAGCUCC<br>AGCGUGAACAGGGCCUUCUCCAGCCCCAAGGUGGCCGUGGAGGCCU<br>GCAACGCUAUGCUGAAGGAGAACUUCCCCACCGUGGCCAGCUACUG<br>CAUCAUCCCCGAGUACGACGCCUACCUGGACAUGGUGGACGGCGCC<br>AGCUGCUGCCUGGACACCGCCAGCUUCUGCCCCGCCAAGCUGAGGA<br>GCUUCCCCAAGAAACACAGCUACCUGGAGCCCACCAUCAGGAGCGC<br>CGUGCCCAGCGCCAUCCAGAACACCCUGCAGAACGUGCUGGCCGCU<br>GCCACCAAGAGGAACUGCAACGUGACCCAGAUGAGGGAGCUGCCCG<br>UGCUGGACAGCGCUGCCUUCAACGUGGAGUGCUUCAAGAAAUACGC<br>CUGCAACAACGAGUACUGGGAGACCUUCAAGGAGAACCCCAUCAGG<br>CUGACCGAAGAGAACGUGGUGAACUACAUCACCAAGCUGAAGGGCC<br>CCAAGGCCGCUGCCCUGUUCGCUAAGACCCACAACCUGAACAUGCU<br>GCAGGACAUCCCAAUGGACAGGUUCGUGAUGGACCUGAAGAGGGAC<br>GUGAAGGUGACACCCGGCACCAAGCACACCGAGGAGAGGCCCAAGG<br>UGCAGGUGAUCCAGGCCGCUGACCCACUGGCCACCGCCUACCUGUG<br>CGGCAUCCACAGGGAGCUGGUGAGGCGGCUGAACGCCGUGCUGCUG<br>CCCAACAUCCACACCCUGUUCGACAUGAGCGCCGAGGACUUCGACG<br>CCAUCAUCGCCGAGCACUUCCAGCCCGGCGACUGCGUGCUGGAGAC<br>CGACAUCGCCAGCUUCGACAAGAGCGAGGAUGACGCUAUGGCCCUG<br>ACCGCUCUGAUGAUCCUGGAGGACCUGGGCGUGGACGCCGAGCUGC<br>UCACCCUGAUCGAGGCUGCCUUCGGCGAGAUCAGCUCCAUCCACCU<br>GCCCACCAAGACCAAGUUCAAGUUCGGCGCUAUGAUGAAAAGCGGA<br>AUGUUCCUGACCCUGUUCGUGAACACCGUGAUCAACAUUGUGAUCG<br>CCAGCAGGGUGCUGCGGGAGAGGCUGACCGGCAGCCCCUGCGCUGC<br>CUUCAUCGGCGACGACAACAUCGUGAAGGGCGUGAAAAGCGACAAG<br>CUGAUGGCCGACAGGUGCGCCACCUGGCUGAACAUGGAGGUGAAGA<br>UCAUCGACGCCGUGGUGGGCGAGAAGGCCCCCUACUUCUGCGGCGG<br>AUUCAUCCUGUGCGACAGCGUGACCGGCACCGCCUGCAGGGUGGCC<br>GACCCCCUGAAGAGGCUGUUCAAGCUGGGCAAGCCACUGGCCGCUG<br>ACGAUGAGCACGACGAUGACAGGCGGAGGGCCCUGCACGAGGAAAG<br>CACCAGGUGGAACAGGGUGGGCAUCCUGAGCGAGCUGUGCAAGGCC<br>GUGGAGAGCAGGUACGAGACCGUGGGCACCAGCAUCAUCGUGAUGG<br>CUAUGACCACACUGGCCAGCUCCGUCAAGAGCUUCUCCUACCUGAG<br>GGGGGCCCCUAUAACUCUCUACGGCUAACCUGAAUGGACUACGACA<br>UAGUCUAGUCCGCCAAGGCCGCCACCCAUGAAGUUGGUGGUUGUGG<br>GGGCCGGGGGUGUUGGCAAAAGCGCCCUUACAAUUUGACUCGAGUA<br>UGUUACGUGCAAAGGUGAUUGUCACCCCCCGAAAGACCAUAUUGUG<br>ACACACCCUCAGUAUCACGCCCAAACAUUUACAGCCGCGGUGUCAA<br>AAACCGCGUGGACGUGGUUAACAUCCCUGCUGGGAGGAUCAGCCGU<br>AAUUAUUAUAAUUGGCUUGGUGCUGGCUACUAUUGUGGCCAUGUAC<br>GUGCUGACCAACCAGAAACAUAAUUGAAUACAGCAGCAAUUGGCAA<br>GCUGCUUACAUAGAACUCGCGGCGAUUGGCAUGCCGCCUUAAAAUU<br>UUUAUUUUAUUUUUUCUUUUCUUUUCCGAAUCGGAUUUUGUUUUUA<br>AUAUUUCAAAAAAAAAAAAAAAAAAAAAAAAAUCUAGAAAAAAAAAAA<br>AAAAAAAAAAAAAAAAAAAAAAAAAAAAAAAAAAAAAAAAAAAAAAAA<br>AAAAAAAAAAAAAAAAAAAAAAAAAAAAAAAAAAAAAAAAAAAAAAA |
| 2862 (SEQ ID NO:104) | SINV empty | 2862 | AUUGACGGCGUAGUACACACUAUUGAAUCAAACAGCCGACCAAUUG<br>CACUACCAUCACAAUGGAGAAGCCAGUAGUAAACGUAGACGUAGAC<br>CCCCAGAGUCCGUUUGUCGUGCAACUGCAAAAAAGCUUCCCGCAAU<br>UUGAGGUAGUAGCACAGCAGGUCACUCCAAAUGACCAUGCUAAUGC<br>CAGAGCAUUUUCGCAUCUGGCCAGUAAACUAAUCGAGCUGGAGGUU<br>CCUACCACAGCGACGAUCUUGGACAUAGGCAGCGCACCGGCUCGUA<br>GAAUGUUUUCCGAGCACCAGUAUCAUUGUGUCUGCCCCAUGCGUAG<br>UCCAGAAGACCCGGACCGCAUGAUGAAAUAUGCCAGUAAACUGGCG<br>GAAAAAGCGUGCAAGAUUACAAACAAGAACUUGCAUGAGAAGAUUA<br>AGGAUCUCCGGACCGUACUUGAUACGCCGGAUGCUGAAACACCAUC<br>GCUCUGCUUUCACAACGAUGUUACCUGCAACAUGCGUGCCGAAUAU<br>UCCGUCAUGCAGGACGUGUAUAUCAACGCUCCCGGAACUAUCUAUC<br>AUCAGGCUAUGAAAGGCGUGCGGACCCUGUACUGGAUUGGCUUCGA<br>CACCACCCAGUUCAUGUUCUCGGCUAUGGCAGGUUCGUACCCUGCG<br>UACAACACCAACUGGGCCGACGAGAAAGUCCUUGAAGCGCGUAACA<br>UCGGACUUUGCAGCACAAAGCUGAGUGAAGGUAGGACAGGAAAAUU<br>GUCGAUAAUGAGGAAGAAGGAGUUGAAGCCCGGGUCGCGGGUUUAU<br>UUCUCCGUAGGAUCGACACUUUAUCCAGAACACAGAGCCAGCUUGC<br>AGAGCUGGCAUCUUCCAUCGGUGUUCCACUUGAAUGGAAAGCAGUC<br>GUACACUUGCCGCUGUGAUACAGUGGUGAGUUGCGAAGGCUACGUA<br>GUGAAGAAAAUCACCAUCAGUCCCGGGAUCACGGGAGAAACCGUGG<br>GAUACGCGGUUACACACAAUAGCGAGGGCUUCUUGCUAUGCAAAGU<br>UACUGACACAGUAAAAGGAGAACGGGUAUCGUUCCCUGUGUGCACG<br>UACAUCCCGGCCACCAUAUGCGAUCAGAUGACUGGUAUAAUGGCCA<br>CGGAUAUAUCACCUGACGAUGCACAAAAACUUCUGGUUGGGCUCAA<br>CCAGCGAAUUGUCAUUAACGGUAGGACUAACAGGAACACCAACACC<br>AUGCAAAAUUACCUUCUGCCGAUCAUAGCACAAGGGUUCAGCAAAU<br>GGGCUAAGGAGCGCAAGGAUGAUCUUGAUAACGAGAAAAUGCUGGG<br>UACUAGAGAACGCAAGCUUACGUAUGGCUGCUUGUGGGCGUUUCGC<br>ACUAAGAAAGUACAUUCGUUUUAUCGCCCACCUGGAACGCAGACCU<br>GCGUAAAAGUCCCAGCCUCUUUUAGCGCUUUUCCCAUGUCGUCCGU<br>AUGGACGACCUCUUUGCCCAUGUCGCUGAGGCAGAAAUUGAAACUG<br>GCAUUGCAACCAAAGAAGGAGGAAAAACUGCUGCAGGUCUCGGAGG |

TABLE 9-continued

AAUUAGUCAUGGAGGCCAAGGCUGCUUUUGAGGAUGCUCAGGAGGA
AGCCAGAGCGGAGAAGCUCCGAGAAGCACUUCCACCAUUAGUGGCA
GACAAAGGCAUCGAGGCAGCCGCAGAAGUUGUCUGCGAAGUGGAGG
GGCUCCAGGCGGACAUCGGAGCAGCAUUAGUUGAAACCCCGCGCGG
UCACGUAAGGAUAAUACCUCAAGCAAAUGACCGUAUGAUCGGACAG
UAUAUCGUUGUCUCGCCAAACUCUGUGCUGAAGAAUGCCAAACUCG
CACCAGCGCACCCGCUAGCAGAUCAGGUUAAGAUCAUAACACACUC
CGGAAGAUCAGGAAGGUACGCGGUCGAACCAUACGACGCUAAAGUA
CUGAUGCCAGCAGGAGGUGCCGUACCAUGGCCAGAAUUCCUAGCAC
UGAGUGAGAGCGCCACGUUAGUGUACAACGAAAGAGAGUUUGUGAA
CCGCAAACUAUACCACAUUGCCAUGCAUGGCCCCGCCAAGAAUACA
GAAGAGGAGCAGUACAAGGUUACAAAGGCAGAGCUUGCAGAAACAG
AGUACGUGUUUGACGUGGACAAGAAGCGUUGCGUUAAGAAGGAAGA
AGCCUCAGGUCUGGUCCUCUCGGGAGAACUGACCAACCCUCCCUAU
CAUGAGCUAGCUCUGGAGGGACUGAAGACCCGACCUGCGGUCCCGU
ACAAGGUCGAAACAAUAGGAGUGAUAGGCACACCGGGGUCGGGCAA
GUCAGCUAUUAUCAAGUCAACUGUCACGGCACGAGAUCUUGUUACC
AGCGGAAAGAAAGAAAAUUGUCGCGAAAUUGAGGCCGACGUGCUAA
GACUGAGGGGUAUGCAGAUUACGUCGAAGACAGUAGAUUCGGUUAU
GCUCAACGGAUGCCACAAAGCCGUAGAAGUGCUGUACGUUGACGAA
GCGUUCGCGUGCCACGCAGGAGCACUACUUGCCUUGAUUGCUAUCG
UCAGGCCCCGCAAGAAGGUAGUACUAUGCGGAGACCCCAUGCAAUG
CGGAUUCUUCAACAUGAUGCAACUAAAGGUACAUUUCAAUCACCCU
GAAAAAGACAUAUGCACCAAGACAUUCUACAAGUAUAUCUCCCGGC
GUUGCACACAGCCAGUUACAGCUAUUGUAUCGACACUGCAUUACGA
UGGAAAGAUGAAAACCACGAACCCGUGCAAGAAGAACAUUGAAAUC
GAUAUUACAGGGGCCACAAAGCCGAAGCCAGGGGAUAUCAUCCUGA
CAUGUUUCCGCGGGUGGGUUAAGCAAUUGCAAAUCGACUAUCCCGG
ACAUGAAGUAAUGACAGCCGCGGCCUCACAAGGGCUAACCAGAAAA
GGAGUGUAUGCCGUCCGGCAAAAAGUCAAUGAAAACCCACUGUACG
CGAUCACAUCAGAGCAUGUGAACGUGUUGCUCACCCGCACUGAGGA
CAGGCUAGUGUGGAAAACCUUGCAGGGCGACCCAUGGAUUAAGCAG
CUCACUAACAUACCUAAAGGAAACUUUCAGGCUACUAUAGAGGACU
GGGAAGCUGAACACAAGGGAAUAAUUGCUGCAAUAAACAGCCCCAC
UCCCCGUGCCAAUCCGUUCAGCUGCAAGACCAACGUUUGCUGGGCG
AAAGCAUUGGAACCGAUACUAGCCACGGCCGGUAUCGUACUUACCG
GUUGCCAGUGGAGCGAACUGUUCCCACAGUUUGCGGAUGACAAACC
ACAUUCGGCCAUUUACGCCUUAGACGUAAUUUGCAUUAAGUUUUUC
GGCAUGGACUUGACAAGCGGACUGUUUUCUAAACAGAGCAUCCCAC
UAACGUACCAUCCCGCCGAUUCAGCGAGGCCGGUAGCUCAUUGGGA
CAACAGCCCAGGAACCCGCAAGUAUGGGUACGAUCACGCCAUUGCC
GCCGAACUCUCCCGUAGAUUUCCGGUGUUCCAGCUAGCUGGGAAGG
GCACACAACUUGAUUUGCAGACGGGGAGAACCAGAGUUAUCUCUGC
ACAGCAUAACCUGGUCCCGGUGAACCGCAAUCUUCCUCACGCCUUA
GUCCCCGAGUACAAGGAGAAGCAACCCGGCCCGGUCGAAAAAUUCU
UGAACCAGUUCAAACACCACUCAGUACUUGUGGUAUCAGAGGAAAA
AAUUGAAGCUCCCCGUAAGAGAAUCGAAUGGAUCGCCCCGAUUGGC
AUAGCCGGUGCAGAUAAGAACUACAACCUGGCUUUCGGGUUUCCGC
CGCAGGCACGGUACGACCUGGUGUUCAUCAACAUUGGAACUAAAUA
CAGAAACCACCACUUUCAGCAGUGCGAAGACCAUGCGGCGACCUUA
AAAACCCUUUCGCGUUCGGCCCUGAAUUGCCUUAACCCAGGAGGCA
CCCUCGUGGUGAAGUCCUAUGGCUACGCCGACCGCAACAGUGAGGA
CGUAGUCACCGCUCUUGCCAGAAAGUUUGUCAGGGUGUCUGCAGCG
AGACCAGAUUGUGUCUCAAGCAAUACAGAAAUGUACCUGAUUUUCC
GACAACUAGACAACAGCCGUACACGGCAAUUCACCCCGCACCAUCU
GAAUUGCGUGAUUUCGUCCGUGUAUGAGGGUACAAGAGAUGGAGUU
GGAGCCGCGCCGUCAUACCGCACCAAAAGGGAGAAUAUUGCUGACU
GUCAAGAGGAAGCAGUUGUCAACGCAGCCAAUCCGCUGGGUAGACC
AGGCGAAGGAGUCUGCCGUGCCAUCUAUAAACGUUGGCCGACCAGU
UUUACCGAUUCAGCCACGGAGACAGGCACCGCAAGAAUGACUGUGU
GCCUAGGAAAGAAAGUGAUCCACGCGGUCGGCCCUGAUUUCCGGAA
GCACCCAGAAGCAGAAGCCUUGAAAUUGCUACAAAACGCCUACCAU
GCAGUGGCAGACUUAGUAAAUGAACAUAACAUCAAGUCUGUCGCCA
UUCCACUGCUAUCUACAGGCAUUUACGCAGCCGGAAAAGACCGCCU
UGAAGUAUCACUUAACUGCUUGACAACCGCGCUAGACAGAACUGAC
GCGGACGUAACCAUCUAUUGCCUGGAUAAGAAGUGGAAGGAAAGAA
UCGACGCGGCACUCCAACUUAAGGAGUCUGUAACAGAGCUGAAGGA
UGAAGAUAUGGAGAUCGACGAUGAGUUAGUAUGGAUCCAUCCAGAC
AGUUGCUUGAAGGGAAGAAAGGGAUUCAGUACUACAAAAGGAAAAU
UGUAUUCGUACUUCGAAGGCACCAAAUUCCAUCAAGCAGCAAAAGA
CAUGGCGGAGAUAAAGGUCCUGUUCCCUAAUGACCAGGAAAGUAAU
GAACAACUGUGUGCCUACAUAUUGGGUGAGACCAUGGAAGCAAUCC
GCGAAAAGUGCCCGGUCGACCAUAACCCGUCGUCUAGCCCGCCCAA
AACGUUGCCGUGCCUUUGCAUGUAUGCCAUGACGCCAGAAAGGGUC
CACAGACUUAGAAGCAAUAACGUCAAAGAAGUUACAGUAUGCUCCU
CCACCCCCCUUCCUAAGCACAAAAUUAAGAAUGUUCAGAAGGUUCA
GUGCACGAAAGUAGUCCUGUUUAAUCCGCACACUCCCGCAUUCGUU
CCCGCCCGUAAGUACAUAGAAGUGCCAGAACAGCCUACCGCUCCUC
CUGCACAGGCCGAGGAGGCCCCCGAAGUUGUAGCGACACCGUCACC
AUCUACAGCUGAUAACACCUCGCUUGAUGUCACAGACAUCUCACUG

TABLE 9-continued

| | | | |
|---|---|---|---|
| | | | GAUAUGGAUGACAGUAGCGAAGGCUCACUUUUUUCGAGCUUUAGCG<br>GAUCGGACAACUCUAUUACUAGUAUGGACAGUUGGUCGUCAGGACC<br>UAGUUCACUAGAGAUAGUAGACCGAAGGCAGGUGGUGGUGGCUGAC<br>GUUCAUGCCGUCCAAGAGCCUGCCCCUAUUCCACCGCCAAGGCUAA<br>AGAAGAUGGCCCGCCUGGCAGCGGCAAGAAAAGAGCCCACUCCACC<br>GGCAAGCAAUAGCUCUGAGUCCCUCCACCUCUCUUUUGGUGGGGUA<br>UCCAUGUCCCUCGGAUCAAUUUUCGACGGAGAGACGGCCCGCCAGG<br>CAGCGGUACAACCCCUGGCAACAGGCCCCACGGAUGUGCCUAUGUC<br>UUUCGGAUCGUUUUCCGACGGAGAGAUUGAUGAGCUGAGCCGCAGA<br>GUAACUGAGUCCGAACCCGUCCUGUUUGGAUCAUUUGAACCGGGCG<br>AAGUGAACUCAAUUAUAUCGUCCCGAUCAGCCGUAUCUUUUCCUCU<br>ACGCAAGCAGAGACGUAGACGCAGGAGCAGGAGGACUGAAUACUGA<br>CUAACCGGGGUAGGUGGGUACAUAUUUUCGACGGACACAGGCCCUG<br>GGCACUUGCAAAAGAAGUCCGUUCUGCAGAACCAGCUUACAGAACC<br>GACCUUGGAGCGCAAUGUCCUGGAAAGAAUUCAUGCCCCGGUGCUC<br>GACACGUCGAAAGAGGAACAACUCAAACUCAGGUACCAGAUGAUGC<br>CCACCGAAGCCAACAAAAGUAGGUACCAGUCUCGUAAAGUAGAAAA<br>UCAGAAAGCCAUAACCACUGAGCGACUACUGUCAGGACUACGACUG<br>UAUAACUCUGCCACAGAUCAGCCAGAAUGCUAUAAGAUCACCUAUC<br>CGAAACCAUUGUACUCCAGUAGCGUACCGGCGAACUACUCCGAUCC<br>ACAGUUCGCUGUAGCUGUCUGUAACAACUAUCUGCAUGAGAACUAU<br>CCGACAGUAGCAUCUUAUCAGAUUACUGACGAGUACGAUGCUUACU<br>UGGAUAUGGUAGACGGGACAGUCGCCUGCCUGGACACUGCAACCUU<br>CUGCCCCGCUAAGCUUAGAAGUUACCCGAAAAAACAUGAGUAUAGA<br>GCCCCGAAUAUCCGCAGUGCGGUUCCAUCAGCGAUGCAGAACACGC<br>UACAAAAUGUGCUCAUUGCCGCAACUAAAAGAAAUUGCAACGUCAC<br>GCAGAUGCGUGAACUGCCAACACUGGACUCAGCGACAUUCAAUGUC<br>GAAUGCUUUCGAAAAUAUGCAUGUAAUGACGAGUAUUGGGAGGAGU<br>UCGCUCGGAAGCCAAUUAGGAUUACCACUGAGUUUGUCACCGCAUA<br>UGUAGCUAGACUGAAAGGCCCUAAGGCCGCCGCACUAUUUGCAAAG<br>ACGUAUAAUUUGGUCCCAUUGCAAGAAGUGCCUAUGGAUAGAUUCG<br>UCAUGGACAUGAAAAGAGACGUGAAAGUUACACCAGGCACGAAACA<br>CACAGAAGAAAGACCGAAAGUACAAGUGAUACAAGCCGCAGAACCC<br>CUGGCGACUGCUUACUUAUGCGGGAUUCACCGGGAAUUAGUGCGUA<br>GGCUUACGGCCGUCUUGCUUCCAAACAUUCACACGCUUUUUGACAU<br>GUCGGCGGAGGAUUUUGAUGCAAUCAUAGCAGAACACUUCAAGCAA<br>GGCGACCCGGUACUGGAGACGGAUAUCGCAUCAUUCGACAAAAGCC<br>AAGACGACGCUAUGGCGUUAACCGGUCUGAUGAUCUUGGAGGACCU<br>GGGUGUGGAUCAACCACUACUCGACUUGAUCGAGUGCGCCUUUGGA<br>GAAAUAUCAUCCACCCAUCUACCUACGGGUACUCGUUUUAAAUUCG<br>GGGCGAUGAUGAAAUCCGGAAUGUUCCUCACACUUUUUGUCAACAC<br>AGUUUUGAAUGUCGUUAUCGCCAGCAGAGUACUAGAGGAGCGGCUU<br>AAAACGUCCAGAUGUGCAGCGUUCAUUGGCGACGACAACAUCAUAC<br>AUGGAGUAGUAUCUGACAAAGAAAUGGCUGAGAGGUGCGCCACCUG<br>GCUCAACAUGGAGGUUAAGAUCAUCGACGCAGUCAUCGGUGAGAGA<br>CCACCUUACUUCUGCGGCGGAUUUAUCUUGCAAGAUUCGGUUACUU<br>CCACAGCGUGCCGCGUGGCGGAUCCCCUGAAAAGGCUGUUUAAGUU<br>GGGUAAACCGCUCCCAGCCGACGACGAGCAAGACGAAGACAGAAGA<br>CGCGCUCUGCUAGAUGAAACAAAGGCGUGGUUUAGAGUAGGUAUAA<br>CAGGCACUUUAGCAGUGGCCGUGACGACCCGGUAUGAGGUAGACAA<br>UAUUACACCUGUCCUACUGGCAUUGAGAACUUUUGCCCAGAGCAAA<br>AGAGCAUUCCAAGCCAUCAGAGGGGAAAUAAAGCAUCUCUACGGUG<br>GUCCUAAAUAGUCAGCAUAGUACAUUUCAUCUGACUAAUACUACAA<br>CACCACCACCACGCGUGCUAGACCAUGGAUCCUAGACGCUACGCCC<br>CAAUGAUCCGACCAGCAAAACUCGAUGUACUUCCGAGGAACUGAUG<br>UGCAUAAUGCAUCAGGCUGGUACAUUAGAUCCCCGCUUACCGCGGG<br>CAAUAUAGCAACACUAAAAACUCGAUGUACUUCCGAGGAAGCGCAG<br>UGCAUAAUGCUGCGCAGUGUUGCCACAUAACCACUAUAUUAACCAU<br>UUAUCUAGCGGACGCCAAAAACUCAAUGUAUUUCUGAGGAAGCGUG<br>GUGCAUAAUGCCACGCAGCGUCUGCAUAACUUUUAUUAUUUCUUUU<br>AUUAAUCAACAAAAUUUUGUUUUUAACAUUUCAAAAAAAAAAAAAA<br>AAAAAAAAAAAUCUAGAAAAAAAAAAAAAAAAAAAAAAAAAAAAAA<br>AAAAAAAAAAAAAAAAAAAAAAAAAAAAAAAAAAAAAAAAAAAAAA<br>AAAAAAAAAAAAAAAAAAAAAAAA |
| 3060 (SEQ ID NO:105) | STARR™ gp70 | 3060 | AUGGGCGGCGCAUGAGAGAAGCCCAGACCAAUUACCUACCCAAAAU<br>GGAGAAAGUUCACGUUGACAUCGAGGAAGACAGCCCAUUCCUCAGA<br>GCUUUGCAGCGGAGCUUCCCGCAGUUUGAGGUAGAAGCCAAGCAGG<br>UCACUGAUAAUGACCAUGCUAAUGCCAGAGCGUUUUCGCAUCUGGC<br>UUCAAAACUGAUCGAAACGGAGGUGGACCCAUCCGACACGAUCCUU<br>GACAUUGGAAGUGCGCCCGCCCGCAGAAUGUAUUCUAAGCACAAGU<br>AUCAUUGUAUCUGUCCGAUGAGAUGUGCGGAAGAUCCGGACAGAUU<br>GUAUAAGUAUGCAACUAAGCUGAAGAAAAACUGUAAGGAAAUAACU<br>GAUAAGGAAUUGGACAAGAAAAUGAAGGAGCUGGCCGCCGUCAUGA<br>GCGACCCUGACCUGGAAACUGAGACUAUGUGCCUCCACGACGACGA<br>GUCGUGUCGCUACGAAGGGCAAGUCGCUGUUUACCAGGAUGUAUAC<br>GCCGUCGACGGCCCCACCAGCCUGUACCACCAGGCCAACAAGGGCG<br>UGAGGGUGGCCUACUGGAUCGGCUUCGACACCACACCCUUCAUGUU<br>CAAGAACCUGGCCGGCGCCUACCCCAGCUACAGCACCAACUGGGCC<br>GACGAGACCGUGCUGACCGCCAGGAACAUCGGCCUGUGCAGCAGCG |

TABLE 9-continued

ACGUGAUGGAGAGGAGCCGGAGAGGCAUGAGCAUCCUGAGGAAGAA
AUACCUGAAGCCCAGCAACAACGUGCUGUUCAGCGUGGGCAGCACC
AUCUACCACGAGAAGAGGGACCUGCUCAGGAGCUGGCACCUGCCCA
GCGUGUUCCACCUGAGGGGCAAGCAGAACUACACCUGCAGGUGCGA
GACCAUCGUGAGCUGCGACGGCUACGUGGUGAAGAGGAUCGCCAUC
AGCCCCGGCCUGUACGGCAAGCCCAGCGGCUACGCCGCUACAAUGC
ACAGGGAGGGCUUCCUGUGCUGCAAGGUGACCGACACCCUGAACGG
CGAGAGGGUGAGCUUCCCCGUGUGCACCUACGUGCCCGCCACCCUG
UGCGACCAGAUGACCGGCAUCCUGGCCACCGACGUGAGCGCCGACG
ACGCCCAGAAGCUGCUCGUGGGCCUGAACCAGAGGAUCGUGGUCAA
CGGCAGGACCCAGAGGAACACCAACACAAUGAAGAACUACCUGCUG
CCCGUGGUGGCCCAGGCUUUCGCCAGGUGGGCCAAGGAGUACAAGG
AGGACCAGGAAGACGAGAGGCCCCUGGGCCUGAGGGACAGGCAGCU
GGUGAUGGGCUGCUGCUGGGCCUUCAGGCGGCACAAGAUCACCAGC
AUCUACAAGAGGCCCGACACCCAGACCAUCAUCAAGGUGAACAGCG
ACUUCCACAGCUUCGUGCUGCCCAGGAUCGGCAGCAACACCCUGGA
GAUCGGCCUGAGGACCCGGAUCAGGAAGAUGCUGGAGGAACACAAG
GAGCCCAGCCCACUGAUCACCGCCGAGGACGUGCAGGAGGCCAAGU
GCGCUGCCGACGAGGCCAAGGAGGUGAGGGAGGCCGAGGAACUGAG
GGCCGCCCUGCCACCCCUGGCUGCCGACGUGGAGGAACCCACCCUG
GAAGCCGACGUGGACCUGAUGCUGCAGGAGGCCGGCGCCGGAAGCG
UGGAGACACCCAGGGGCCUGAUCAAGGUGACCAGCUACGACGGCGA
GGACAAGAUCGGCAGCUACGCCGUGCUGAGCCCACAGGCCGUGCUG
AAGUCCGAGAAGCUGAGCUGCAUCCACCCACUGGCCGAGCAGGUGA
UCGUGAUCACCCACAGCGGCAGGAAGGGCAGGUACGCCGUGGAGCC
CUACCACGGCAAGGUGGUCGUGCCCGAGGGCCACGCCAUCCCCGUG
CAGGACUUCCAGGCCCUGAGCGAGAGCGCCACCAUCGUGUACAACG
AGAGGGAGUUCGUGAACAGGUACCUGCACCAUAUCGCCACCCACGG
CGGAGCCCUGAACACCGACGAGGAAUACUACAAGACCGUGAAGCCC
AGCGAGCACGACGGCGAGUACCUGUACGACAUCGACAGGAAGCAGU
GCGUGAAGAAAGAGCUGGUGACCGGCCUGGGACUGACCGGCGAGCU
GGUGGACCCACCCUUCCACGAGUUCGCCUACGAGAGCCUGAGGACC
AGACCCGCCGCUCCCUACCAGGUGCCCACCAUCGGCGUGUACGGCG
UGCCCGGCAGCGGAAAGAGCGGCAUCAUCAAGAGCGCCGUGACCAA
GAAAGACCUGGUGGUCAGCGCCAAGAAAGAGAACUGCGCCGAGAUC
AUCAGGGACGUGAAGAAGAUGAAAGGCCUGGACGUGAACGCGCGCA
CCGUGGACAGCGUGCUGCUGAACGGCUGCAAGCACCCCGUGGAGAC
CCUGUACAUCGACGAGGCCUUCGCUUGCCACGCCGGCACCCUGAGG
GCCCUGAUCGCCAUCAUCAGGCCCAAGAAAGCCGUGCUGUGCGGCG
ACCCCAAGCAGUGCGGCUUCUUCAACAUGAUGUGCCUGAAGGUGCA
CUUCAACCACGAGAUCUGCACCCAGGUGUUCCACAAGAGCAUCAGC
AGGCGGUGCACCAAGAGCGUGACCAGCGUCGUGAGCACCCUGUUCU
ACGACAAGAAAAUGAGGACCACCAACCCCAAGGAGACCAAAAUCGU
GAUCGACACCACAGGCAGCACCAAGCCCAAGCAGGACGACCUGAUC
CUGACCUGCUUCAGGGGCUGGGUGAAGCAGCUGCAGAUCGACUACA
AGGGCAACGAGAUCAUGACCGCCGCUGCCAGCCAGGGCCUGACCAG
GAAGGGCGUGUACGCCGUGAGGUACAAGGUGAACGAGAACCCACUG
UACGCUCCCACCAGCGAGCACGUGAACGUGCUGCUGACCAGGACCG
AGGACAGGAUCGUGUGGAAGACCCUGGCCGGCGACCCCUGGAUCAA
GACCCUGACCGCCAAGUACCCCGGCAACUUCACCGCCACCAUCGAA
GAGUGGCAGGCCGAGCACGACGCCAUCAUGAGGCACAUCCUGGAGA
GGCCCGACCCCACCGACGUGUUCCAGAACAAGGCCAACGUGUGCUG
GGCCAAGGCCCUGGUGCCCGUGCUGAAGACCGCCGGCAUCGACAUG
ACCACAGAGCAGUGGAACACCGUGGACUACUUCGAGACCGACAAGG
CCCACAGCGCCGAGAUCGUGCUGAACCAGCUGUGCGUGAGGUUCUU
CGGCCUGGACCUGGACAGCGGCCUGUUCAGCGCCCCCACCGUGCCA
CUGAGCAUCAGGAACAACCACUGGGACAACAGCCCCAGCCCAAACA
UGUACGGCCUGAACAAGGAGGUGGUCAGGCAGCUGAGCAGGCGGUA
CCCACAGCUGCCCAGGGCCGUGGCCACCGGCAGGGUGUACGACAUG
AACACCGGCACCCUGAGGAACUACGACCCCAGGAUCAACCUGGUGC
CCGUGAACAGGCGGCUGCCCCACGCCCUGGUGCUGCACCACAACGA
GCACCCACAGAGCGACUUCAGCUCCUUCGUGAGCAAGCUGAAAGGC
AGGACCGUGCUGGUCGUGGGCGAGAAGCUGAGCGUGCCCGGCAAGA
UGGUGGACUGGCUGAGCGACAGGCCCGAGGCCACCUUCCGGGCCAG
GCUGGACCUCGGCAUCCCCGGCGACGUGCCCAAGUACGACAUCAUC
UUCGUGAACGUCAGGACCCCAUACAAGUACCACCAUUACCAGCAGU
GCGAGGACCACGCCAUCAAGCUGAGCAUGCUGACCAAGAAGGCCUG
CCUGCACCUGAACCCCGGAGGCACCUGCGUGAGCAUCGGCUACGGC
UACGCCGACAGGGCCAGCGAGAGCAUCAUUGGCGCCAUCGCCAGGC
UGUUCAAGUUCAGCAGGGUGUGCAAACCCAAGAGCAGCCUGGAGGA
AACCGAGGUGCUGUUCGUGUUCAUCGGCUACGACCGGAAGGCCAGG
ACCCACAACCCCUACAAGCUGAGCAGCACCCUGACAAACAUCUACA
CCGGCAGCAGGCUGCACGAGGCCGGCUGCGCCCCCAGCUACCACGU
GGUCAGGGGCGAUAUCGCCACCGCCACCGAGGGCGUGAUCAUCAAC
GCUGCCAACAGCAAGGGCCAGCCCGGAGGCGGAGUGUGCGGCGCCC
UGUACAAGAAGUUCCCCGAGAGCUUCGACCUGCAGCCCAUCGAGGU
GGGCAAGGCCAGGCUGGUGAAGGGCGCCGCUAAGCACAUCAUCCAC
GCCGUGGGCCCCAACUUCAACAAGGUGAGCGAGGUGGAAGGCGACA
AGCAGCUGGCCGAAGCCUACGAGAGCAUCGCCAAGAUCGUGAACGA
CAAUAACUACAAGAGCGUGGCCAUCCCACUGCUCAGCACCGGCAUC

TABLE 9-continued

UUCAGCGGCAACAAGGACAGGCUGACCCAGAGCCUGAACCACCUGC
UCACCGCCCUGGACACCACCGAUGCCGACGUGGCCAUCUACUGCAG
GGACAAGAAGUGGGAGAUGACCCUGAAGGAGGCCGUGGCCAGGCGG
GAGGCCGUGGAAGAGAUCUGCAUCAGCGACGACUCCAGCGUGACCG
AGCCCGACGCCGAGCUGGUGAGGGUGCACCCCAAGAGCUCCCUGGC
CGGCAGGAAGGGCUACAGCACCAGCGACGGCAAGACCUUCAGCUAC
CUGGAGGGCACCAAGUUCCACCAGGCCGCUAAGGACAUCGCCGAGA
UCAACGCUAUGUGGCCCGUGGCCACCGAGGCCAACGAGCAGGUGUG
CAUGUACAUCCUGGGCGAGAGCAUGUCCAGCAUCAGGAGCAAGUGC
CCCGUGGAGGAAAGCGAGGCCAGCACACCACCCAGCACCCUGCCCU
GCCUGUGCAUCCACGCUAUGACACCCGAGAGGGUGCAGCGGCUGAA
GGCCAGCAGGCCCGAGCAGAUCACCGUGUGCAGCUCCUUCCCACUG
CCCAAGUACAGGAUCACCGGCGUGCAGAAGAUCCAGUGCAGCCAGC
CCAUCCUGUUCAGCCCAAAGGUGCCCGCCUACAUCCACCCCAGGAA
GUACCUGGUGGAGACCCCACCCGUGGACGAGACACCCGAGCCAAGC
GCCGAGAACCAGAGCACCGAGGGCACACCCGAGCAGCCACCCCUGA
UCACCGAGGACGAGACAAGGACCCGGACCCCAGAGCCCAUCAUUAU
CGAGGAAGAGGAAGAGGACAGCAUCAGCCUGCUGAGCGACGGCCCC
ACCCACCAGGUGCUGCAGGUGGAGGCCGACAUCCACGGCCCACCCA
GCGUGUCCAGCUCCAGCUGGAGCAUCCCACACGCCAGCGACUUCGA
CGUGGACAGCCUGAGCAUCCUGGACACCCUGGAGGGCGCCAGCGUG
ACCUCCGGCGCCACCAGCGCCGAGACCAACAGCUACUUCGCCAAGA
GCAUGGAGUUCCUGGCCAGGCCCGUGCCAGCUCCCAGGACCGUGUU
CAGGAACCCACCCCACCCAGCUCCCAGGACCAGGACCCCAAGCCUG
GCUCCCAGCAGGGCCUGCAGCAGGACCAGCCUGGUGAGCACCCCAC
CCGGCGUGAACAGGGUGAUCACCAGGGAGGAACUGGAGGCCCUGAC
ACCCAGCAGGACCCCCAGCAGGUCCGUGAGCAGGACUAGUCUGGUG
UCCAACCCACCCGGCGUGAACAGGGUGAUCACCAGGGAGGAAUUCG
AGGCCUUCGUGGCCCAGCAACAGAGACGGUUCGACGCCGGCGCCUA
CAUCUUCAGCAGCGACACCGGCCAGGGACACCUGCAGCAAAAGAGC
GUGAGGCAGACCGUGCUGAGCGAGGUGGUGCUGGAGAGGACCGAGC
UGGAAAUCAGCUACGCCCCCAGGCUGGACCAGGAGAAGGAGGAACU
GCUCAGGAAGAAACUGCAGCUGAACCCCACCCCAGCCAACAGGAGC
AGGUACCAGAGCAGGAAGGUGGAGAACAUGAAGGCCAUCACCGCCA
GGCGGAUCCUGCAGGGCCUGGGACACUACCUGAAGGCCGAGGGCAA
GGUGGAGUGCUACAGGACCCUGCACCCCGUGCCACUGUACAGCUCC
AGCGUGAACAGGGCCUUCUCCAGCCCCAAGGUGGCCGUGGAGGCCU
GCAACGCUAUGCUGAAGGAGAACUUCCCCACCGUGGCCAGCUACUG
CAUCAUCCCCGAGUACGACGCCUACCUGGACAUGGUGGACGGCGCC
AGCUGCUGCCUGGACACCGCCAGCUUCUGCCCCGCCAAGCUGAGGA
GCUUCCCCAAGAAACACAGCUACCUGGAGCCCACCAUCAGGAGCGC
CGUGCCCAGCGCCAUCCAGAACACCCUGCAGAACGUGCUGGCCGCU
GCCACCAAGAGGAACUGCAACGUGACCCAGAUGAGGGAGCUGCCCG
UGCUGGACAGCGCUGCCUUCAACGUGGAGUGCUUCAAGAAAUACGC
CUGCAACAACGAGUACUGGGAGACCUUCAAGGAGAACCCCAUCAGG
CUGACCGAAGAGAACGUGGUGAACUACAUCACCAAGCUGAAGGGCC
CCAAGGCCGCUGCCCUGUUCGCUAAGACCCACAACCUGAACAUGCU
GCAGGACAUCCCAAUGGACAGGUUCGUGAUGGACCUGAAGAGGGAC
GUGAAGGUGACACCCGGCACCAAGCACACCGAGGAGAGGCCCAAGG
UGCAGGUGAUCCAGGCCGCUGACCCACUGGCCACCGCCUACCUGUG
CGGCAUCCACAGGGAGCUGGUGAGGCGGCUGAACGCCGUGCUGCUG
CCCAACAUCCACACCCUGUUCGACAUGAGCGCCGAGGACUUCGACG
CCAUCAUCGCCGAGCACUUCCAGCCCGGCGACUGCGUGCUGGAGAC
CGACAUCGCCAGCUUCGACAAGAGCGAGGAUGACGCUAUGGCCCUG
ACCGCUCUGAUGAUCCUGGAGGACCUGGGCGUGGACGCCGAGCUGC
UCACCCUGAUCGAGGCUGCCUUCGGCGAGAUCAGCUCCAUCCACCU
GCCCACCAAGACCAAGUUCAAGUUCGGCGCUAUGAUGAAAAGCGGA
AUGUUCCUGACCCUGUUCGUGAACACCGUGAUCAACAUUGUGAUCG
CCAGCAGGGUGCUGCGGGAGAGGCUGACCGGCAGCCCCUGCGCUGC
CUUCAUCGGCGACGACAACAUCGUGAAGGGCGUGAAAAGCGACAAG
CUGAUGGCCGACAGGUGCGCCACCUGGCUGAACAUGGAGGUGAAGA
UCAUCGACGCCGUGGUGGGCGAGAAGGCCCCCUACUUCUGCGGCGG
AUUCAUCCUGUGCGACAGCGUGACCGGCACCGCCUGCAGGGUGGCC
GACCCCCUGAAGAGGCUGUUCAAGCUGGGCAAGCCACUGGCCGCUG
ACGAUGAGCACGACGAUGACAGGCGGAGGGCCCUGCACGAGGAAAG
CACCAGGUGGAACAGGGUGGGCAUCCUGAGCGAGCUGUGCAAGGCC
GUGGAGAGCAGGUACGAGACCGUGGGCACCAGCAUCAUCGUGAUGG
CUAUGACCACACUGGCCAGCUCCGUCAAGAGCUUCUCCUACCUGAG
GGGGGCCCCUAUAACUCUCUACGGCUAACCUGAAUGGACUACGACA
UAGUCUAGUCCGCCAAGGCCGCCACCAUGAGAGUGACAGCCCCUAG
AACCUUACUGCUUCUGCUUUGGGGAGCUGUUGCUCUGACAGAGACA
UGGGCUGGAUCUCUGAGCGAGGUGACCGGCCAGGGCCUGUGCAUCG
GCGCCGUGCCCAAGACCCACCAGGUGCUGUGCAACACCACCCAGAA
GACCAGCGACGGCAGCUACUACCUGGCCGCUCCCACCGGCACCACC
UGGGCCUGCAGCACCGGCCUGACCCCUUGCAUCAGCACCACCAUCC
UGAACCUGACCACCGACUACUGCGUGCUGGUGGAGCUGUGGCCCAG
GGUGACCUACCACAGCCCCAGCUACGCCUACCACCAGUUCGAGAGG
AGGGCCAAGUACAAGAGGGAGCCCGUGAGCCUGACCCUGGCCCUGC
UGCUGGGCGGCCUGACAAUGGGCGGCAUCGCCGCCGGCGUGGGCAC
CGGCACCACCGCCCUGGUGGCCACCCAGCAGUUCCAGCAGCUGCAG

TABLE 9-continued

| | | | |
|---|---|---|---|
| | | | GCCGCCAUGCACGACGACCUGAAGGAGGUGGAGAAGUCCAUCACCA<br>ACCUGGAGAAGUCCCUGACCAGCCUGAGCGAGGUGGUGCUGCAGAA<br>CAGGAGGGGCCUGGACCUGCUGUUCCUGAAGGAGGGCGGCCUGUGC<br>GCCGCCCUGAAGGAGGAGUGCUGCCUGUACGCCGACCACACCGGCC<br>UGGUGAUCGUGGGCAUUGUCGCUGGCCUGGCCGUCCUCGCCGUGGU<br>GGUGAUUGGAGCUGUGGUCGCAGCUGUUAUGUGCAGAAGAAAGUCA<br>UCCGGCGGAAAGGGAGGCUCCUACUCUCAGGCUGCUUCUGCUACAG<br>UGCCUAGAGCUCUUAUGUGUUUAUCUCAGCUGUAAACUCGAGUAUG<br>UUACGUGCAAAGGUGAUUGUCACCCCCCGAAAGACCAUAUUGUGAC<br>ACACCCUCAGUAUCACGCCCAAACAUUUACAGCCGCGGUGUCAAAA<br>ACCGCGUGGACGUGGUUAACAUCCCUGCUGGGAGGAUCAGCCGUAA<br>UUAUUAUAAUUGGCUUGGUGCUGGCUACUAUUGUGGCCAUGUACGU<br>GCUGACCAACCAGAAACAUAAUUGAAUACAGCAGCAAUUGGCAAGC<br>UGCUUACAUAGAACUCGCGGCGAUUGGCAUGCCGCCUUAAAAUUUU<br>UAUUUUAUUUUUUCUUUUCUUUUCCGAAUCGGAUUUUGUUUUUAAU<br>AUUUCAAAAAAAAAAAAAAAAAAAAAAAAAAUCUAGAAAAAAAAAAAA<br>AAAAAAAAAAAAAAAAAAAAAAAAAAAAAAAAAAAAAAAAAAAAAA<br>AAAAAAAAAAAAAAAAAAAAAAAAAAAAAAAAAAAAAAAAAAA |
| 3061 (SEQ ID NO:106) | STARR$^{TM}$ AH1A5 | 3061 | AUGGGCGGCGCAUGAGAGAAGCCCAGACCAAUUACCUACCCAAA<br>AUGGAGAAAGUUCACGUUGACAUCGAGGAAGACAGCCCAUUCCU<br>CAGAGCUUUGCAGCGGAGCUUCCCGCAGUUUGAGGUAGAAGCCA<br>AGCAGGUCACUGAUAAUGACCAUGCUAAUGCCAGAGCGUUUUCG<br>CAUCUGGCUUCAAAACUGAUCGAAACGGAGGUGGACCCAUCCGA<br>CACGAUCCUUGACAUUGGAAGUGCGCCCGCCCGCAGAAUGUAUU<br>CUAAGCACAAGUAUCAUUGUAUCUGUCCGAUGAGAUGUGCGGAA<br>GAUCCGGACAGAUUGUAUAAGUAUGCAACUAAGCUGAAGAAAAA<br>CUGUAAGGAAAUAACUGAUAAGGAAUUGGACAAGAAAAUGAAGG<br>AGCUGGCCGCCGUCAUGAGCGACCCUGACCUGGAAACUGAGACU<br>AUGUGCCUCCACGACGACGAGUCGUGUCGCUACGAAGGGCAAGU<br>CGCUGUUUACCAGGAUGUAUACGCCGUCGACGGCCCCACCAGCC<br>UGUACCACCAGGCCAACAAGGGCGUGAGGGUGGCCUACUGGAUC<br>GGCUUCGACACCACACCCUUCAUGUUCAAGAACCUGGCCGGCGC<br>CUACCCCAGCUACAGCACCAACUGGGCCGACGAGACCGUGCUGA<br>CCGCCAGGAACAUCGGCCUGUGCAGCAGCGACGUGAUGGAGAGG<br>AGCCGGAGAGGCAUGAGCAUCCUGAGGAAGAAAUACCUGAAGCC<br>CAGCAACAACGUGCUGUUCAGCGUGGGCAGCACCAUCUACCACG<br>AGAAGAGGGACCUGCUCAGGAGCUGGCACCUGCCCAGCGUGUUC<br>CACCUGAGGGGCAAGCAGAACUACACCUGCAGGUGCGAGACCAU<br>CGUGAGCUGCGACGGCUACGUGGUGAAGAGGAUCGCCAUCAGCC<br>CCGGCCUGUACGGCAAGCCCAGCGGCUACGCCGCUACAAUGCAC<br>AGGGAGGGCUUCCUGUGCUGCAAGGUGACCGACACCCUGAACGG<br>CGAGAGGGUGAGCUUCCCCGUGUGCACCUACGUGCCCGCCACCC<br>UGUGCGACCAGAUGACCGGCAUCCUGGCCACCGACGUGAGCGCC<br>GACGACGCCCAGAAGCUGCUCGUGGGCCUGAACCAGAGGAUCGU<br>GGUCAACGGCAGGACCCAGAGGAACACCAACACAAUGAAGAACU<br>ACCUGCUGCCCGUGGUGGCCCAGGCUUUCGCCAGGUGGGCCAAG<br>GAGUACAAGGAGGACCAGGAAGACGAGAGGCCCCUGGGCCUGAG<br>GGACAGGCAGCUGGUGAUGGGCUGCUGCUGGGCCUUCAGGCGGC<br>ACAAGAUCACCAGCAUCUACAAGAGGCCCGACACCCAGACCAUC<br>AUCAAGGUGAACAGCGACUUCCACAGCUUCGUGCUGCCCAGGAU<br>CGGCAGCAACACCCUGGAGAUCGGCCUGAGGACCCGGAUCAGGA<br>AGAUGCUGGAGGAACACAAGGAGCCCAGCCCACUGAUCACCGCC<br>GAGGACGUGCAGGAGGCCAAGUGCGCUGCCGACGAGGCCAAGGA<br>GGUGAGGGAGGCCGAGGAACUGAGGGCCGCCCUGCCACCCCUGG<br>CUGCCGACGUGGAGGAACCCACCCUGGAAGCCGACGUGGACCUG<br>AUGCUGCAGGAGGCCGGCGCCGGAAGCGUGGAGACACCCAGGGG<br>CCUGAUCAAGGUGACCAGCUACGACGGCGAGGACAAGAUCGGCA<br>GCUACGCCGUGCUGAGCCCACAGGCCGUGCUGAAGUCCGAGAAG<br>CUGAGCUGCAUCCACCCACUGGCCGAGCAGGUGAUCGUGAUCAC<br>CCACAGCGGCAGGAAGGGCAGGUACGCCGUGGAGCCCUACCACG<br>GCAAGGUGGUCGUGCCCGAGGGCCACGCCAUCCCCGUGCAGGAC<br>UUCCAGGCCCUGAGCGAGAGCGCCACCAUCGUGUACAACGAGAG<br>GGAGUUCGUGAACAGGUACCUGCACCAUAUCGCCACCCACGGCG<br>GAGCCCUGAACACCGACGAGGAAUACUACAAGACCGUGAAGCCC<br>AGCGAGCACGACGGCGAGUACCUGUACGACAUCGACAGGAAGCA<br>GUGCGUGAAGAAAGAGCUGGUGACCGGCCUGGGACUGACCGGCG<br>AGCUGGUGGACCCACCCUUCCACGAGUUCGCCUACGAGAGCCUG<br>AGGACCAGACCCGCCGCUCCCUACCAGGUGCCCACCAUCGGCGU<br>GUACGGCGUGCCCGGCAGCGGAAAGAGCGGCAUCAUCAAGAGCG<br>CCGUGACCAAGAAAGACCUGGUGGUCAGCGCCAAGAAAGAGAAC<br>UGCGCCGAGAUCAUCAGGGACGUGAAGAAGAUGAAAGGCCUGGA<br>CGUGAACGCGCGCACCGUGGACAGCGUGCUGCUGAACGGCUGCA<br>AGCACCCCGUGGAGACCCUGUACAUCGACGAGGCCUUCGCUUGC<br>CACGCCGGCACCCUGAGGGCCCUGAUCGCCAUCAUCAGGCCCAA<br>GAAAGCCGUGCUGUGCGGCGACCCCAAGCAGUGCGGCUUCUUCA<br>ACAUGAUGUGCCUGAAGGUGCACUUCAACCACGAGAUCUGCACC<br>CAGGUGUUCCACAAGAGCAUCAGCAGGCGGUGCACCAAGAGCGU<br>GACCAGCGUCGUGAGCACCCUGUUCUACGACAAGAAAAUGAGGA<br>CCACCAACCCCAAGGAGACCAAAAUCGUGAUCGACACCACAGGC |

TABLE 9-continued

| |
|---|
| AGCACCAAGCCCAAGCAGGACGACCUGAUCCUGACCUGCUUCAG<br>GGGCUGGGUGAAGCAGCUGCAGAUCGACUACAAGGGCAACGAGA<br>UCAUGACCGCCGCUGCCAGCCAGGGCCUGACCAGGAAGGGCGUG<br>UACGCCGUGAGGUACAAGGUGAACGAGAACCCACUGUACGCUCC<br>CACCAGCGAGCACGUGAACGUGCUGCUGACCAGGACCGAGGACA<br>GGAUCGUGUGGAAGACCCUGGCCGGCGACCCCUGGAUCAAGACC<br>CUGACCGCCAAGUACCCCGGCAACUUCACCGCCACCAUCGAAGA<br>GUGGCAGGCCGAGCACGACGCCAUCAUGAGGCACAUCCUGGAGA<br>GGCCCGACCCCACCGACGUGUUCCAGAACAAGGCCAACGUGUGC<br>UGGGCCAAGGCCCUGGUGCCCGUGCUGAAGACCGCCGGCAUCGA<br>CAUGACCACAGAGCAGUGGAACACCGUGGACUACUUCGAGACCG<br>ACAAGGCCCACAGCGCCGAGAUCGUGCUGAACCAGCUGUGCGUG<br>AGGUUCUUCGGCCUGGACCUGGACAGCGGCCUGUUCAGCGCCCC<br>CACCGUGCCACUGAGCAUCAGGAACAACCACUGGGACAACAGCC<br>CCAGCCCAAACAUGUACGGCCUGAACAAGGAGGUGGUCAGGCAG<br>CUGAGCAGGCGGUACCCACAGCUGCCCAGGGCCGUGGCCACCGG<br>CAGGGUGUACGACAUGAACACCGGCACCCUGAGGAACUACGACC<br>CCAGGAUCAACCUGGUGCCCGUGAACAGGCGGCUGCCCCACGCC<br>CUGGUGCUGCACCACAACGAGCACCCACAGAGCGACUUCAGCUC<br>CUUCGUGAGCAAGCUGAAAGGCAGGACCGUGCUGGUCGUGGGCG<br>AGAAGCUGAGCGUGCCCGGCAAGAUGGUGGACUGGCUGAGCGAC<br>AGGCCCGAGGCCACCUUCCGGGCCAGGCUGGACCUCGGCAUCCC<br>CGGCGACGUGCCCAAGUACGACAUCAUCUUCGUGAACGUCAGGA<br>CCCCAUACAAGUACCACCAUUACCAGCAGUGCGAGGACCACGCC<br>AUCAAGCUGAGCAUGCUGACCAAGAAGGCCUGCCUGCACCUGAA<br>CCCCGGAGGCACCUGCGUGAGCAUCGGCUACGGCUACGCCGACA<br>GGGCCAGCGAGAGCAUCAUUGGCGCCAUCGCCAGGCUGUUCAAG<br>UUCAGCAGGGUGUGCAAACCCAAGAGCAGCCUGGAGGAAACCGA<br>GGUGCUGUUCGUGUUCAUCGGCUACGACCGGAAGGCCAGGACCC<br>ACAACCCCUACAAGCUGAGCAGCACCCUGACAAACAUCUACACC<br>GGCAGCAGGCUGCACGAGGCCGGCUGCGCCCCCAGCUACCACGU<br>GGUCAGGGGCGAUAUCGCCACCGCCACCGAGGGCGUGAUCAUCA<br>ACGCUGCCAACAGCAAGGGCCAGCCCGGAGGCGGAGUGUGCGGC<br>GCCCUGUACAAGAAGUUCCCCGAGAGCUUCGACCUGCAGCCCAU<br>CGAGGUGGGCAAGGCCAGGCUGGUGAAGGGCGCCGCUAAGCACA<br>UCAUCCACGCCGUGGGCCCCAACUUCAACAAGGUGAGCGAGGUG<br>GAAGGCGACAAGCAGCUGGCCGAAGCCUACGAGAGCAUCGCCAA<br>GAUCGUGAACGACAAUAACUACAAGAGCGUGGCCAUCCCACUGC<br>UCAGCACCGGCAUCUUCAGCGGCAACAAGGACAGGCUGACCCAG<br>AGCCUGAACCACCUGCUCACCGCCCUGGACACCACCGAUGCCGA<br>CGUGGCCAUCUACUGCAGGGACAAGAAGUGGGAGAUGACCCUGA<br>AGGAGGCCGUGGCCAGGCGGGAGGCCGUGGAAGAGAUCUGCAUC<br>AGCGACGACUCCAGCGUGACCGAGCCCGACGCCGAGCUGGUGAG<br>GGUGCACCCCAAGAGCUCCCUGGCCGGCAGGAAGGGCUACAGCA<br>CCAGCGACGGCAAGACCUUCAGCUACCUGGAGGGCACCAAGUUC<br>CACCAGGCCGCUAAGGACAUCGCCGAGAUCAACGCUAUGUGGCC<br>CGUGGCCACCGAGGCCAACGAGCAGGUGUGCAUGUACAUCCUGG<br>GCGAGAGCAUGUCCAGCAUCAGGAGCAAGUGCCCCGUGGAGGAA<br>AGCGAGGCCAGCACACCACCCAGCACCCUGCCCUGCCUGUGCAU<br>CCACGCUAUGACACCCGAGAGGGUGCAGCGGCUGAAGGCCAGCA<br>GGCCCGAGCAGAUCACCGUGUGCAGCUCCUUCCCACUGCCCAAG<br>UACAGGAUCACCGGCGUGCAGAAGAUCCAGUGCAGCCAGCCCAU<br>CCUGUUCAGCCCAAAGGUGCCCGCCUACAUCCACCCCAGGAAGU<br>ACCUGGUGGAGACCCCACCCGUGGACGAGACACCCGAGCCAAGC<br>GCCGAGAACCAGAGCACCGAGGGCACACCCGAGCAGCCACCCCU<br>GAUCACCGAGGACGAGACAAGGACCCGGACCCCAGAGCCCAUCA<br>UUAUCGAGGAAGAGGAAGAGGACAGCAUCAGCCUGCUGAGCGAC<br>GGCCCCACCCACCAGGUGCUGCAGGUGGAGGCCGACAUCCACGG<br>CCCACCCAGCGUGUCCAGCUCCAGCUGGAGCAUCCCACACGCCA<br>GCGACUUCGACGUGGACAGCCUGAGCAUCCUGGACACCCUGGAG<br>GGCGCCAGCGUGACCUCCGGCGCCACCAGCGCCGAGACCAACAG<br>CUACUUCGCCAAGAGCAUGGAGUUCCUGGCCAGGCCCGUGCCAG<br>CUCCCAGGACCGUGUUCAGGAACCCACCCCACCCAGCUCCCAGG<br>ACCAGGACCCCAAGCCUGGCUCCCAGCAGGGCCUGCAGCAGGAC<br>CAGCCUGGUGAGCACCCCACCCGGCGUGAACAGGGUGAUCACCA<br>GGGAGGAACUGGAGGCCCUGACACCCAGCAGGACCCCCAGCAGG<br>UCCGUGAGCAGGACUAGUCUGGUGUCCAACCCACCCGGCGUGAA<br>CAGGGUGAUCACCAGGGAGGAAUUCGAGGCCUUCGUGGCCCAGC<br>AACAGAGACGGUUCGACGCCGGCGCCUACAUCUUCAGCAGCGAC<br>ACCGGCCAGGGACACCUGCAGCAAAAGAGCGUGAGGCAGACCGU<br>GCUGAGCGAGGUGGUGCUGGAGAGGACCGAGCUGGAAAUCAGCU<br>ACGCCCCCAGGCUGGACCAGGAGAAGGAGGAACUGCUCAGGAAG<br>AAACUGCAGCUGAACCCCACCCCAGCCAACAGGAGCAGGUACCA<br>GAGCAGGAAGGUGGAGAACAUGAAGGCCAUCACCGCCAGGCGGA<br>UCCUGCAGGGCCUGGGACACUACCUGAAGGCCGAGGGCAAGGUG<br>GAGUGCUACAGGACCCUGCACCCCGUGCCACUGUACAGCUCCAG<br>CGUGAACAGGGCCUUCUCCAGCCCCAAGGUGGCCGUGGAGGCCU<br>GCAACGCUAUGCUGAAGGAGAACUUCCCCACCGUGGCCAGCUAC<br>UGCAUCAUCCCCGAGUACGACGCCUACCUGGACAUGGUGGACGG<br>CGCCAGCUGCUGCCUGGACACCGCCAGCUUCUGCCCCGCCAAGC |

TABLE 9-continued

| | | | |
|---|---|---|---|
| | | | UGAGGAGCUUCCCCAAGAAACACAGCUACCUGGAGCCCACCAUC<br>AGGAGCGCCGUGCCCAGCGCCAUCCAGAACACCCUGCAGAACGU<br>GCUGGCCGCUGCCACCAAGAGGAACUGCAACGUGACCCAGAUGA<br>GGGAGCUGCCCGUGCUGGACAGCGCUGCCUUCAACGUGGAGUGC<br>UUCAAGAAAUACGCCUGCAACAACGAGUACUGGGAGACCUUCAA<br>GGAGAACCCCAUCAGGCUGACCGAAGAGAACGUGGUGAACUACA<br>UCACCAAGCUGAAGGGCCCCAAGGCCGCUGCCCUGUUCGCUAAG<br>ACCCACAACCUGAACAUGCUGCAGGACAUCCCAAUGGACAGGUU<br>CGUGAUGGACCUGAAGAGGGACGUGAAGGUGACACCCGGCACCA<br>AGCACACCGAGGAGAGGCCCAAGGUGCAGGUGAUCCAGGCCGCU<br>GACCCACUGGCCACCGCCUACCUGUGCGGCAUCCACAGGGAGCU<br>GGUGAGGCGGCUGAACGCCGUGCUGCUGCCCAACAUCCACACCC<br>UGUUCGACAUGAGCGCCGAGGACUUCGACGCCAUCAUCGCCGAG<br>CACUUCCAGCCCGGCGACUGCGUGCUGGAGACCGACAUCGCCAG<br>CUUCGACAAGAGCGAGGAUGACGCUAUGGCCCUGACCGCUCUGA<br>UGAUCCUGGAGGACCUGGGCGUGGACGCCGAGCUGCUCACCCUG<br>AUCGAGGCUGCCUUCGGCGAGAUCAGCUCCAUCCACCUGCCCAC<br>CAAGACCAAGUUCAAGUUCGGCGCUAUGAUGAAAAGCGGAAUGU<br>UCCUGACCCUGUUCGUGAACACCGUGAUCAACAUUGUGAUCGCC<br>AGCAGGGUGCUGCGGGAGAGGCUGACCGGCAGCCCCUGCGCUGC<br>CUUCAUCGGCGACGACAACAUCGUGAAGGGCGUGAAAAGCGACA<br>AGCUGAUGGCCGACAGGUGCGCCACCUGGCUGAACAUGGAGGUG<br>AAGAUCAUCGACGCCGUGGUGGGCGAGAAGGCCCCCUACUUCUG<br>CGGCGGAUUCAUCCUGUGCGACAGCGUGACCGGCACCGCCUGCA<br>GGGUGGCCGACCCCCUGAAGAGGCUGUUCAAGCUGGGCAAGCCA<br>CUGGCCGCUGACGAUGAGCACGACGAUGACAGGCGGAGGGCCCU<br>GCACGAGGAAAGCACCAGGUGGAACAGGGUGGGCAUCCUGAGCG<br>AGCUGUGCAAGGCCGUGGAGAGCAGGUACGAGACCGUGGGCACC<br>AGCAUCAUCGUGAUGGCUAUGACCACACUGGCCAGCUCCGUCAA<br>GAGCUUCUCCUACCUGAGGGGGGCCCCUAUAACUCUCUACGGCU<br>AACCUGAAUGGACUACGACAUAGUCUAGUCCGCCAAGGCCGCCA<br>CCAUGAGAGUGACAGCCCCUAGAACCUUACUGCUUCUGCUUUGG<br>GGAGCUGUUGCUCUGACAGAGACAUGGGCUGGAUCUUACCACAG<br>CCCCAGCUACGCCUACCACCAGUUCGAGAGGGGGGGAGGAGGCU<br>CCGGGGGAGGAGGCUCCCUGAAGAUCAGCCAGGCCGUGCACGCC<br>GCCCACGCCGAGAUCAACGAGGCCGGCCGGGAGGUGAUCGUGGG<br>CAUUGUCGCUGGCCUGGCCGUCCUCGCCGUGGUGGUGAUUGGAG<br>CUGUGGUCGCAGCUGUUAUGUGCAGAAGAAAGUCAUCCGGCGGA<br>AAGGGAGGCUCCUACUCUCAGGCUGCUUCUGCUACAGUGCCUAG<br>AGCUCUUAUGUGUUUAUCUCAGCUGUAAACUCGAGUAUGUUACG<br>UGCAAAGGUGAUUGUCACCCCCCGAAAGACCAUAUUGUGACACA<br>CCCUCAGUAUCACGCCCAAACAUUUACAGCCGCGGUGUCAAAAA<br>CCGCGUGGACGUGGUUAACAUCCCUGCUGGGAGGAUCAGCCGUA<br>AUUAUUAUAAUUGGCUUGGUGCUGGCUACUAUUGUGGCCAUGUA<br>CGUGCUGACCAACCAGAAACAUAAUUGAAUACAGCAGCAAUUGG<br>CAAGCUGCUUACAUAGAACUCGCGGCGAUUGGCAUGCCGCCUUA<br>AAAUUUUUAUUUUAUUUUUUCUUUUCUUUUCCGAAUCGGAUUUU<br>GUUUUUAAUAUUUCAAAAAAAAAAAAAAAAAAAAAAAAAAUCUAG<br>AAAAAAAAAAAAAAAAAAAAAAAAAAAAAAAAAAAAAAAAAAAA<br>AAAAAAAAAAAAAAAAAAAAAAAAAAAAAAAAAAAAAAAAAAAA<br>AAAAAAAAAAAA |
| 3067 (SEQ ID NO:107) | STARR™ gp70-FLAG | 3067 | AUGGGCGGCGCAUGAGAGAAGCCCAGACCAAUUACCUACCCAAAAU<br>GGAGAAAGUUCACGUUGACAUCGAGGAAGACAGCCCAUUCCUCAGA<br>GCUUUGCAGCGGAGCUUCCCGCAGUUUGAGGUAGAAGCCAAGCAGG<br>UCACUGAUAAUGACCAUGCUAAUGCCAGAGCGUUUUCGCAUCUGGC<br>UUCAAAACUGAUCGAAACGGAGGUGGACCCAUCCGACACGAUCCUU<br>GACAUUGGAAGUGCGCCCGCCCGCAGAAUGUAUUCUAAGCACAAGU<br>AUCAUUGUAUCUGUCCGAUGAGAUGUGCGGAAGAUCCGGACAGAUU<br>GUAUAAGUAUGCAACUAAGCUGAAGAAAAACUGUAAGGAAAUAACU<br>GAUAAGGAAUUGGACAAGAAAAUGAAGGAGCUGGCCGCCGUCAUGA<br>GCGACCCUGACCUGGAAACUGAGACUAUGUGCCUCCACGACGACGA<br>GUCGUGUCGCUACGAAGGGCAAGUCGCUGUUUACCAGGAUGUAUAC<br>GCCGUCGACGGCCCCACCAGCCUGUACCACCAGGCCAACAAGGGCG<br>UGAGGGUGGCCUACUGGAUCGGCUUCGACACCACACCCUUCAUGUU<br>CAAGAACCUGGCCGGCGCCUACCCCAGCUACAGCACCAACUGGGCC<br>GACGAGACCGUGCUGACCGCCAGGAACAUCGGCCUGUGCAGCAGCG<br>ACGUGAUGGAGAGGAGCCGGAGAGGCAUGAGCAUCCUGAGGAAGAA<br>AUACCUGAAGCCCAGCAACAACGUGCUGUUCAGCGUGGGCAGCACC<br>AUCUACCACGAGAAGAGGGACCUGCUCAGGAGCUGGCACCUGCCCA<br>GCGUGUUCCACCUGAGGGGCAAGCAGAACUACACCUGCAGGUGCGA<br>GACCAUCGUGAGCUGCGACGGCUACGUGGUGAAGAGGAUCGCCAUC<br>AGCCCCGGCCUGUACGGCAAGCCCAGCGGCUACGCCGCUACAAUGC<br>ACAGGGAGGGCUUCCUGUGCUGCAAGGUGACCGACACCCUGAACGG<br>CGAGAGGGUGAGCUUCCCCGUGUGCACCUACGUGCCCGCCACCCUG<br>UGCGACCAGAUGACCGGCAUCCUGGCCACCGACGUGAGCGCCGACG<br>ACGCCCAGAAGCUGCUCGUGGGCCUGAACCAGAGGAUCGUGGUCAA<br>CGGCAGGACCCAGAGGAACACCAACACAAUGAAGAACUACCUGCUG<br>CCCGUGGUGGCCCAGGCUUUCGCCAGGUGGGCCAAGGAGUACAAGG<br>AGGACCAGGAAGACGAGAGGCCCCUGGGCCUGAGGGACAGGCAGCU |

TABLE 9-continued

GGUGAUGGGCUGCUGCUGGGCCUUCAGGCGGCACAAGAUCACCAGC
AUCUACAAGAGGCCCGACACCCAGACCAUCAUCAAGGUGAACAGCG
ACUUCCACAGCUUCGUGCUGCCCAGGAUCGGCAGCAACACCCUGGA
GAUCGGCCUGAGGACCCGGAUCAGGAAGAUGCUGGAGGAACACAAG
GAGCCCAGCCCACUGAUCACCGCCGAGGACGUGCAGGAGGCCAAGU
GCGCUGCCGACGAGGCCAAGGAGGUGAGGGAGGCCGAGGAACUGAG
GGCCGCCCUGCCACCCCUGGCUGCCGACGUGGAGGAACCCACCCUG
GAAGCCGACGUGGACCUGAUGCUGCAGGAGGCCGGCGCCGGAAGCG
UGGAGACACCCAGGGGCCUGAUCAAGGUGACCAGCUACGACGGCGA
GGACAAGAUCGGCAGCUACGCCGUGCUGAGCCCACAGGCCGUGCUG
AAGUCCGAGAAGCUGAGCUGCAUCCACCCACUGGCCGAGCAGGUGA
UCGUGAUCACCCACAGCGGCAGGAAGGGCAGGUACGCCGUGGAGCC
CUACCACGGCAAGGUGGUCGUGCCCGAGGGCCACGCCAUCCCCGUG
CAGGACUUCCAGGCCCUGAGCGAGAGCGCCACCAUCGUGUACAACG
AGAGGGAGUUCGUGAACAGGUACCUGCACCAUAUCGCCACCCACGG
CGGAGCCCUGAACACCGACGAGGAAUACUACAAGACCGUGAAGCCC
AGCGAGCACGACGGCGAGUACCUGUACGACAUCGACAGGAAGCAGU
GCGUGAAGAAAGAGCUGGUGACCGGCCUGGGACUGACCGGCGAGCU
GGUGGACCCACCCUUCCACGAGUUCGCCUACGAGAGCCUGAGGACC
AGACCCGCCGCUCCCUACCAGGUGCCCACCAUCGGCGUGUACGGCG
UGCCCGGCAGCGGAAAGAGCGGCAUCAUCAAGAGCGCCGUGACCAA
GAAAGACCUGGUGGUCAGCGCCAAGAAAGAGAACUGCGCCGAGAUC
AUCAGGGACGUGAAGAAGAUGAAAGGCCUGGACGUGAACGCGCGCA
CCGUGGACAGCGUGCUGCUGAACGGCUGCAAGCACCCCGUGGAGAC
CCUGUACAUCGACGAGGCCUUCGCUUGCCACGCCGGCACCCUGAGG
GCCCUGAUCGCCAUCAUCAGGCCCAAGAAAGCCGUGCUGUGCGGCG
ACCCCAAGCAGUGCGGCUUCUUCAACAUGAUGUGCCUGAAGGUGCA
CUUCAACCACGAGAUCUGCACCCAGGUGUUCCACAAGAGCAUCAGC
AGGCGGUGCACCAAGAGCGUGACCAGCGUCGUGAGCACCCUGUUCU
ACGACAAGAAAAUGAGGACCACCAACCCCAAGGAGACCAAAAUCGU
GAUCGACACCACAGGCAGCACCAAGCCCAAGCAGGACGACCUGAUC
CUGACCUGCUUCAGGGGCUGGGUGAAGCAGCUGCAGAUCGACUACA
AGGGCAACGAGAUCAUGACCGCCGCUGCCAGCCAGGGCCUGACCAG
GAAGGGCGUGUACGCCGUGAGGUACAAGGUGAACGAGAACCCACUG
UACGCUCCCACCAGCGAGCACGUGAACGUGCUGCUGACCAGGACCG
AGGACAGGAUCGUGUGGAAGACCCUGGCCGGCGACCCCUGGAUCAA
GACCCUGACCGCCAAGUACCCCGGCAACUUCACCGCCACCAUCGAA
GAGUGGCAGGCCGAGCACGACGCCAUCAUGAGGCACAUCCUGGAGA
GGCCCGACCCCACCGACGUGUUCCAGAACAAGGCCAACGUGUGCUG
GGCCAAGGCCCUGGUGCCCGUGCUGAAGACCGCCGGCAUCGACAUG
ACCACAGAGCAGUGGAACACCGUGGACUACUUCGAGACCGACAAGG
CCCACAGCGCCGAGAUCGUGCUGAACCAGCUGUGCGUGAGGUUCUU
CGGCCUGGACCUGGACAGCGGCCUGUUCAGCGCCCCCACCGUGCCA
CUGAGCAUCAGGAACAACCACUGGGACAACAGCCCCAGCCCAAACA
UGUACGGCCUGAACAAGGAGGUGGUCAGGCAGCUGAGCAGGCGGUA
CCCACAGCUGCCCAGGGCCGUGGCCACCGGCAGGGUGUACGACAUG
AACACCGGCACCCUGAGGAACUACGACCCCAGGAUCAACCUGGUGC
CCGUGAACAGGCGGCUGCCCCACGCCCUGGUGCUGCACCACAACGA
GCACCCACAGAGCGACUUCAGCUCCUUCGUGAGCAAGCUGAAAGGC
AGGACCGUGCUGGUCGUGGGCGAGAAGCUGAGCGUGCCCGGCAAGA
UGGUGGACUGGCUGAGCGACAGGCCCGAGGCCACCUUCCGGGCCAG
GCUGGACCUCGGCAUCCCCGGCGACGUGCCCAAGUACGACAUCAUC
UUCGUGAACGUCAGGACCCCAUACAAGUACCACCAUUACCAGCAGU
GCGAGGACCACGCCAUCAAGCUGAGCAUGCUGACCAAGAAGGCCUG
CCUGCACCUGAACCCCGGAGGCACCUGCGUGAGCAUCGGCUACGGC
UACGCCGACAGGGCCAGCGAGAGCAUCAUUGGCGCCAUCGCCAGGC
UGUUCAAGUUCAGCAGGGUGUGCAAACCCAAGAGCAGCCUGGAGGA
AACCGAGGUGCUGUUCGUGUUCAUCGGCUACGACCGGAAGGCCAGG
ACCCACAACCCCUACAAGCUGAGCAGCACCCUGACAAACAUCUACA
CCGGCAGCAGGCUGCACGAGGCCGGCUGCGCCCCCAGCUACCACGU
GGUCAGGGGCGAUAUCGCCACCGCCACCGAGGGCGUGAUCAUCAAC
GCUGCCAACAGCAAGGGCCAGCCCGGAGGCGGAGUGUGCGGCGCCC
UGUACAAGAAGUUCCCCGAGAGCUUCGACCUGCAGCCCAUCGAGGU
GGGCAAGGCCAGGCUGGUGAAGGGCGCCGCUAAGCACAUCAUCCAC
GCCGUGGGCCCCAACUUCAACAAGGUGAGCGAGGUGGAAGGCGACA
AGCAGCUGGCCGAAGCCUACGAGAGCAUCGCCAAGAUCGUGAACGA
CAAUAACUACAAGAGCGUGGCCAUCCCACUGCUCAGCACCGGCAUC
UUCAGCGGCAACAAGGACAGGCUGACCCAGAGCCUGAACCACCUGC
UCACCGCCCUGGACACCACCGAUGCCGACGUGGCCAUCUACUGCAG
GGACAAGAAGUGGGAGAUGACCCUGAAGGAGGCCGUGGCCAGGCGG
GAGGCCGUGGAAGAGAUCUGCAUCAGCGACGACUCCAGCGUGACCG
AGCCCGACGCCGAGCUGGUGAGGGUGCACCCCAAGAGCUCCCUGGC
CGGCAGGAAGGGCUACAGCACCAGCGACGGCAAGACCUUCAGCUAC
CUGGAGGGCACCAAGUUCCACCAGGCCGCUAAGGACAUCGCCGAGA
UCAACGCUAUGUGGCCCGUGGCCACCGAGGCCAACGAGCAGGUGUG
CAUGUACAUCCUGGGCGAGAGCAUGUCCAGCAUCAGGAGCAAGUGC
CCCGUGGAGGAAAGCGAGGCCAGCACACCACCCAGCACCCUGCCCU
GCCUGUGCAUCCACGCUAUGACACCCGAGAGGGUGCAGCGGCUGAA
GGCCAGCAGGCCCGAGCAGAUCACCGUGUGCAGCUCCUUCCCACUG
CCCAAGUACAGGAUCACCGGCGUGCAGAAGAUCCAGUGCAGCCAGC

TABLE 9-continued

| |
|---|
| CCAUCCUGUUCAGCCCAAAGGUGCCCGCCUACAUCCACCCCAGGAA |
| GUACCUGGUGGAGACCCCACCCGUGGACGAGACACCCGAGCCAAGC |
| GCCGAGAACCAGAGCACCGAGGGCACACCCGAGCAGCCACCCCUGA |
| UCACCGAGGACGAGACAAGGACCCGGACCCCAGAGCCCAUCAUUAU |
| CGAGGAAGAGGAAGAGGACAGCAUCAGCCUGCUGAGCGACGGCCCC |
| ACCCACCAGGUGCUGCAGGUGGAGGCCGACAUCCACGGCCCACCCA |
| GCGUGUCCAGCUCCAGCUGGAGCAUCCCACACGCCAGCGACUUCGA |
| CGUGGACAGCCUGAGCAUCCUGGACACCCUGGAGGGCGCCAGCGUG |
| ACCUCCGGCGCCACCAGCGCCGAGACCAACAGCUACUUCGCCAAGA |
| GCAUGGAGUUCCUGGCCAGGCCCGUGCCAGCUCCCAGGACCGUGUU |
| CAGGAACCCACCCCACCCAGCUCCCAGGACCAGGACCCCAAGCCUG |
| GCUCCCAGCAGGGCCUGCAGCAGGACCAGCCUGGUGAGCACCCCAC |
| CCGGCGUGAACAGGGUGAUCACCAGGGAGGAACUGGAGGCCCUGAC |
| ACCCAGCAGGACCCCCAGCAGGUCCGUGAGCAGGACUAGUCUGGUG |
| UCCAACCCACCCGGCGUGAACAGGGUGAUCACCAGGGAGGAAUUCG |
| AGGCCUUCGUGGCCCAGCAACAGAGACGGUUCGACGCCGGCGCCUA |
| CAUCUUCAGCAGCGACACCGGCCAGGGACACCUGCAGCAAAAGAGC |
| GUGAGGCAGACCGUGCUGAGCGAGGUGGUGCUGGAGAGGACCGAGC |
| UGGAAAUCAGCUACGCCCCCAGGCUGGACCAGGAGAAGGAGGAACU |
| GCUCAGGAAGAAACUGCAGCUGAACCCCACCCCAGCCAACAGGAGC |
| AGGUACCAGAGCAGGAAGGUGGAGAACAUGAAGGCCAUCACCGCCA |
| GGCGGAUCCUGCAGGGCCUGGGACACUACCUGAAGGCCGAGGGCAA |
| GGUGGAGUGCUACAGGACCCUGCACCCCGUGCCACUGUACAGCUCC |
| AGCGUGAACAGGGCCUUCUCCAGCCCCAAGGUGGCCGUGGAGGCCU |
| GCAACGCUAUGCUGAAGGAGAACUUCCCCACCGUGGCCAGCUACUG |
| CAUCAUCCCCGAGUACGACGCCUACCUGGACAUGGUGGACGGCGCC |
| AGCUGCUGCCUGGACACCGCCAGCUUCUGCCCCGCCAAGCUGAGGA |
| GCUUCCCCAAGAAACACAGCUACCUGGAGCCCACCAUCAGGAGCGC |
| CGUGCCCAGCGCCAUCCAGAACACCCUGCAGAACGUGCUGGCCGCU |
| GCCACCAAGAGGAACUGCAACGUGACCCAGAUGAGGGAGCUGCCCG |
| UGCUGGACAGCGCUGCCUUCAACGUGGAGUGCUUCAAGAAAUACGC |
| CUGCAACAACGAGUACUGGGAGACCUUCAAGGAGAACCCCAUCAGG |
| CUGACCGAAGAGAACGUGGUGAACUACAUCACCAAGCUGAAGGGCC |
| CCAAGGCCGCUGCCCUGUUCGCUAAGACCCACAACCUGAACAUGCU |
| GCAGGACAUCCCAAUGGACAGGUUCGUGAUGGACCUGAAGAGGGAC |
| GUGAAGGUGACACCCGGCACCAAGCACACCGAGGAGAGGCCCAAGG |
| UGCAGGUGAUCCAGGCCGCUGACCCACUGGCCACCGCCUACCUGUG |
| CGGCAUCCACAGGGAGCUGGUGAGGCGGCUGAACGCCGUGCUGCUG |
| CCCAACAUCCACACCCUGUUCGACAUGAGCGCCGAGGACUUCGACG |
| CCAUCAUCGCCGAGCACUUCCAGCCCGGCGACUGCGUGCUGGAGAC |
| CGACAUCGCCAGCUUCGACAAGAGCGAGGAUGACGCUAUGGCCCUG |
| ACCGCUCUGAUGAUCCUGGAGGACCUGGGCGUGGACGCCGAGCUGC |
| UCACCCUGAUCGAGGCUGCCUUCGGCGAGAUCAGCUCCAUCCACCU |
| GCCCACCAAGACCAAGUUCAAGUUCGGCGCUAUGAUGAAAAGCGGA |
| AUGUUCCUGACCCUGUUCGUGAACACCGUGAUCAACAUUGUGAUCG |
| CCAGCAGGGUGCUGCGGGAGAGGCUGACCGGCAGCCCCUGCGCUGC |
| CUUCAUCGGCGACGACAACAUCGUGAAGGGCGUGAAAAGCGACAAG |
| CUGAUGGCCGACAGGUGCGCCACCUGGCUGAACAUGGAGGUGAAGA |
| UCAUCGACGCCGUGGUGGGCGAGAAGGCCCCCUACUUCUGCGGCGG |
| AUUCAUCCUGUGCGACAGCGUGACCGGCACCGCCUGCAGGGUGGCC |
| GACCCCCUGAAGAGGCUGUUCAAGCUGGGCAAGCCACUGGCCGCUG |
| ACGAUGAGCACGACGAUGACAGGCGGAGGGCCCUGCACGAGGAAAG |
| CACCAGGUGGAACAGGGUGGGCAUCCUGAGCGAGCUGUGCAAGGCC |
| GUGGAGAGCAGGUACGAGACCGUGGGCACCAGCAUCAUCGUGAUGG |
| CUAUGACCACACUGGCCAGCUCCGUCAAGAGCUUCUCCUACCUGAG |
| GGGGGCCCCUAUAACUCUCUACGGCUAACCUGAAUGGACUACGACA |
| UAGUCUAGUCCGCCAAGGCCGCCACCAUGAGAGUGACAGCCCCUAG |
| AACCUUACUGCUUCUGCUUUGGGGAGCUGUUGCUCUGACAGAGACA |
| UGGGCUGGAUCUCUGAGCGAGGUGACCGGCCAGGGCCUGUGCAUCG |
| GCGCCGUGCCCAAGACCCACCAGGUGCUGUGCAACACCACCCAGAA |
| GACCAGCGACGGCAGCUACUACCUGGCCGCUCCCACCGGCACCACC |
| UGGGCCUGCAGCACCGGCCUGACCCCUUGCAUCAGCACCACCAUCC |
| UGAACCUGACCACCGACUACUGCGUGCUGGUGGAGCUGUGGCCCAG |
| GGUGACCUACCACAGCCCCAGCUACGCCUACCACCAGUUCGAGAGG |
| AGGGCCAAGUACAAGAGGGAGCCCGUGAGCCUGACCCUGGCCCUGC |
| UGCUGGGCGGCCUGACAAUGGGCGGCAUCGCCGCCGGCGUGGGCAC |
| CGGCACCACCGCCCUGGUGGCCACCCAGCAGUUCCAGCAGCUGCAG |
| GCCGCCAUGCACGACGACCUGAAGGAGGUGGAGAAGUCCAUCACCA |
| ACCUGGAGAAGUCCCUGACCAGCCUGAGCGAGGUGGUGCUGCAGAA |
| CAGGAGGGGCCUGGACCUGCUGUUCCUGAAGGAGGGCGGCCUGUGC |
| GCCGCCCUGAAGGAGGAGUGCUGCCUGUACGCCGACCACACCGGCC |
| UGGUGAUCGUGGGCAUUGUCGCUGGCCUGGCCGUCCUCGCCGUGGU |
| GGUGAUUGGAGCUGUGGUCGCAGCUGUUAUGUGCAGAAGAAAGUCA |
| UCCGGCGGAAAGGGAGGCUCCUACUCUCAGGCUGCUUCUGCUACAG |
| UGCCUAGAGCUCUUAUGUGUUUAUCUCAGCUGGGCGGCGGAGGCAG |
| CGACUACAAGGACGACGAUGACAAGUAAACUCGAGUAUGUUACGUG |
| CAAAGGUGAUUGUCACCCCCCGAAAGACCAUAUUGUGACACACCCU |
| CAGUAUCACGCCCAAACAUUUACAGCCGCGGUGUCAAAAACCGCGU |
| GGACGUGGUUAACAUCCCUGCUGGGAGGAUCAGCCGUAAUUAUUAU |
| AAUUGGCUUGGUGCUGGCUACUAUUGUGGCCAUGUACGUGCUGACC |

TABLE 9-continued

| | | | |
|---|---|---|---|
| | | | AACCAGAAACAUAAUUGAAUACAGCAGCAAUUGGCAAGCUGCUUAC<br>AUAGAACUCGCGGCGAUUGGCAUGCCGCCUUAAAAUUUUUAUUUUA<br>UUUUUUCUUUUCUUUUCCGAAUCGGAUUUUGUUUUUAAUAUUUCAA<br>AAAAAAAAAAAAAAAAAAAAAAAUCUAGAAAAAAAAAAAAAAAAAA<br>AAAAAAAAAAAAAAAAAAAAAAAAAAAAAAAAAAAAAAAAAAAAAA<br>AAAAAAAAAAAAAAAAAAAAAAAAAAAAAAAAAAAA |
| 3068 (SEQ ID NO:108) | STARR$^{TM}$ AH1A 5-FLAG | 3068 | AUGGGCGGCGCAUGAGAGAAGCCCAGACCAAUUACCUACCCAAAAU<br>GGAGAAAGUUCACGUUGACAUCGAGGAAGACAGCCCAUUCCUCAGA<br>GCUUUGCAGCGGAGCUUCCCGCAGUUUGAGGUAGAAGCCAAGCAGG<br>UCACUGAUAAUGACCAUGCUAAUGCCAGAGCGUUUUCGCAUCUGGC<br>UUCAAAACUGAUCGAAACGGAGGUGGACCCAUCCGACACGAUCCUU<br>GACAUUGGAAGUGCGCCCGCCCGCAGAAUGUAUUCUAAGCACAAGU<br>AUCAUUGUAUCUGUCCGAUGAGAUGUGCGGAAGAUCCGGACAGAUU<br>GUAUAAGUAUGCAACUAAGCUGAAGAAAAACUGUAAGGAAAUAACU<br>GAUAAGGAAUUGGACAAGAAAAUGAAGGAGCUGGCCGCCGUCAUGA<br>GCGACCCUGACCUGGAAACUGAGACUAUGUGCCUCCACGACGACGA<br>GUCGUGUCGCUACGAAGGGCAAGUCGCUGUUUACCAGGAUGUAUAC<br>GCCGUCGACGGCCCCACCAGCCUGUACCACCAGGCCAACAAGGGCG<br>UGAGGGUGGCCUACUGGAUCGGCUUCGACACCACACCCUUCAUGUU<br>CAAGAACCUGGCCGGCGCCUACCCCAGCUACAGCACCAACUGGGCC<br>GACGAGACCGUGCUGACCGCCAGGAACAUCGGCCUGUGCAGCAGCG<br>ACGUGAUGGAGAGGAGCCGGAGAGGCAUGAGCAUCCUGAGGAAGAA<br>AUACCUGAAGCCCAGCAACAACGUGCUGUUCAGCGUGGGCAGCACC<br>AUCUACCACGAGAAGAGGGACCUGCUCAGGAGCUGGCACCUGCCCA<br>GCGUGUUCCACCUGAGGGGCAAGCAGAACUACACCUGCAGGUGCGA<br>GACCAUCGUGAGCUGCGACGGCUACGUGGUGAAGAGGAUCGCCAUC<br>AGCCCCGGCCUGUACGGCAAGCCCAGCGGCUACGCCGCUACAAUGC<br>ACAGGGAGGGCUUCCUGUGCUGCAAGGUGACCGACACCCUGAACGG<br>CGAGAGGGUGAGCUUCCCCGUGUGCACCUACGUGCCCGCCACCCUG<br>UGCGACCAGAUGACCGGCAUCCUGGCCACCGACGUGAGCGCCGACG<br>ACGCCCAGAAGCUGCUCGUGGGCCUGAACCAGAGGAUCGUGGUCAA<br>CGGCAGGACCCAGAGGAACACCAACACAAUGAAGAACUACCUGCUG<br>CCCGUGGUGGCCCAGGCUUUCGCCAGGUGGGCCAAGGAGUACAAGG<br>AGGACCAGGAAGACGAGAGGCCCCUGGGCCUGAGGGACAGGCAGCU<br>GGUGAUGGGCUGCUGCUGGGCCUUCAGGCGGCACAAGAUCACCAGC<br>AUCUACAAGAGGCCCGACACCCAGACCAUCAUCAAGGUGAACAGCG<br>ACUUCCACAGCUUCGUGCUGCCCAGGAUCGGCAGCAACACCCUGGA<br>GAUCGGCCUGAGGACCCGGAUCAGGAAGAUGCUGGAGGAACACAAG<br>GAGCCCAGCCCACUGAUCACCGCCGAGGACGUGCAGGAGGCCAAGU<br>GCGCUGCCGACGAGGCCAAGGAGGUGAGGGAGGCCGAGGAACUGAG<br>GGCCGCCCUGCCACCCCUGGCUGCCGACGUGGAGGAACCCACCCUG<br>GAAGCCGACGUGGACCUGAUGCUGCAGGAGGCCGGCGCCGGAAGCG<br>UGGAGACACCCAGGGGCCUGAUCAAGGUGACCAGCUACGACGGCGA<br>GGACAAGAUCGGCAGCUACGCCGUGCUGAGCCCACAGGCCGUGCUG<br>AAGUCCGAGAAGCUGAGCUGCAUCCACCCACUGGCCGAGCAGGUGA<br>UCGUGAUCACCCACAGCGGCAGGAAGGGCAGGUACGCCGUGGAGCC<br>CUACCACGGCAAGGUGGUCGUGCCCGAGGGCCACGCCAUCCCCGUG<br>CAGGACUUCCAGGCCCUGAGCGAGAGCGCCACCAUCGUGUACAACG<br>AGAGGGAGUUCGUGAACAGGUACCUGCACCAUAUCGCCACCCACGG<br>CGGAGCCCUGAACACCGACGAGGAAUACUACAAGACCGUGAAGCCC<br>AGCGAGCACGACGGCGAGUACCUGUACGACAUCGACAGGAAGCAGU<br>GCGUGAAGAAAGAGCUGGUGACCGGCCUGGGACUGACCGGCGAGCU<br>GGUGGACCCACCCUUCCACGAGUUCGCCUACGAGAGCCUGAGGACC<br>AGACCCGCCGCUCCCUACCAGGUGCCCACCAUCGGCGUGUACGGCG<br>UGCCCGGCAGCGGAAAGAGCGGCAUCAUCAAGAGCGCCGUGACCAA<br>GAAAGACCUGGUGGUCAGCGCCAAGAAAGAGAACUGCGCCGAGAUC<br>AUCAGGGACGUGAAGAAGAUGAAAGGCCUGGACGUGAACGCGCGCA<br>CCGUGGACAGCGUGCUGCUGAACGGCUGCAAGCACCCCGUGGAGAC<br>CCUGUACAUCGACGAGGCCUUCGCUUGCCACGCCGGCACCCUGAGG<br>GCCCUGAUCGCCAUCAUCAGGCCCAAGAAAGCCGUGCUGUGCGGCG<br>ACCCCAAGCAGUGCGGCUUCUUCAACAUGAUGUGCCUGAAGGUGCA<br>CUUCAACCACGAGAUCUGCACCCAGGUGUUCCACAAGAGCAUCAGC<br>AGGCGGUGCACCAAGAGCGUGACCAGCGUCGUGAGCACCCUGUUCU<br>ACGACAAGAAAAUGAGGACCACCAACCCCAAGGAGACCAAAAUCGU<br>GAUCGACACCACAGGCAGCACCAAGCCCAAGCAGGACGACCUGAUC<br>CUGACCUGCUUCAGGGGCUGGGUGAAGCAGCUGCAGAUCGACUACA<br>AGGGCAACGAGAUCAUGACCGCCGCUGCCAGCCAGGGCCUGACCAG<br>GAAGGGCGUGUACGCCGUGAGGUACAAGGUGAACGAGAACCCACUG<br>UACGCUCCCACCAGCGAGCACGUGAACGUGCUGCUGACCAGGACCG<br>AGGACAGGAUCGUGUGGAAGACCCUGGCCGGCGACCCCUGGAUCAA<br>GACCCUGACCGCCAAGUACCCCGGCAACUUCACCGCCACCAUCGAA<br>GAGUGGCAGGCCGAGCACGACGCCAUCAUGAGGCACAUCCUGGAGA<br>GGCCCGACCCCACCGACGUGUUCCAGAACAAGGCCAACGUGUGCUG<br>GGCCAAGGCCCUGGUGCCCGUGCUGAAGACCGCCGGCAUCGACAUG<br>ACCACAGAGCAGUGGAACACCGUGGACUACUUCGAGACCGACAAGG<br>CCCACAGCGCCGAGAUCGUGCUGAACCAGCUGUGCGUGAGGUUCUU<br>CGGCCUGGACCUGGACAGCGGCCUGUUCAGCGCCCCCACCGUGCCA<br>CUGAGCAUCAGGAACAACCACUGGGACAACAGCCCCAGCCCAAACA<br>UGUACGGCCUGAACAAGGAGGUGGUCAGGCAGCUGAGCAGGCGGUA |

TABLE 9-continued

CCCACAGCUGCCCAGGGCCGUGGCCACCGGCAGGGUGUACGACAUG
AACACCGGCACCCUGAGGAACUACGACCCCAGGAUCAACCUGGUGC
CCGUGAACAGGCGGCUGCCCCACGCCCUGGUGCUGCACCACAACGA
GCACCCACAGAGCGACUUCAGCUCCUUCGUGAGCAAGCUGAAAGGC
AGGACCGUGCUGGUCGUGGGCGAGAAGCUGAGCGUGCCCGGCAAGA
UGGUGGACUGGCUGAGCGACAGGCCCGAGGCCACCUUCCGGGCCAG
GCUGGACCUCGGCAUCCCCGGCGACGUGCCCAAGUACGACAUCAUC
UUCGUGAACGUCAGGACCCCAUACAAGUACCACCAUUACCAGCAGU
GCGAGGACCACGCCAUCAAGCUGAGCAUGCUGACCAAGAAGGCCUG
CCUGCACCUGAACCCCGGAGGCACCUGCGUGAGCAUCGGCUACGGC
UACGCCGACAGGGCCAGCGAGAGCAUCAUUGGCGCCAUCGCCAGGC
UGUUCAAGUUCAGCAGGGUGUGCAAACCCAAGAGCAGCCUGGAGGA
AACCGAGGUGCUGUUCGUGUUCAUCGGCUACGACCGGAAGGCCAGG
ACCCACAACCCCUACAAGCUGAGCAGCACCCUGACAAACAUCUACA
CCGGCAGCAGGCUGCACGAGGCCGGCUGCGCCCCCAGCUACCACGU
GGUCAGGGGCGAUAUCGCCACCGCCACCGAGGGCGUGAUCAUCAAC
GCUGCCAACAGCAAGGGCCAGCCCGGAGGCGGAGUGUGCGGCGCCC
UGUACAAGAAGUUCCCCGAGAGCUUCGACCUGCAGCCCAUCGAGGU
GGGCAAGGCCAGGCUGGUGAAGGGCGCCGCUAAGCACAUCAUCCAC
GCCGUGGGCCCCAACUUCAACAAGGUGAGCGAGGUGGAAGGCGACA
AGCAGCUGGCCGAAGCCUACGAGAGCAUCGCCAAGAUCGUGAACGA
CAAUAACUACAAGAGCGUGGCCAUCCCACUGCUCAGCACCGGCAUC
UUCAGCGGCAACAAGGACAGGCUGACCCAGAGCCUGAACCACCUGC
UCACCGCCCUGGACACCACCGAUGCCGACGUGGCCAUCUACUGCAG
GGACAAGAAGUGGGAGAUGACCCUGAAGGAGGCCGUGGCCAGGCGG
GAGGCCGUGGAAGAGAUCUGCAUCAGCGACGACUCCAGCGUGACCG
AGCCCGACGCCGAGCUGGUGAGGGUGCACCCCAAGAGCUCCCUGGC
CGGCAGGAAGGGCUACAGCACCAGCGACGGCAAGACCUUCAGCUAC
CUGGAGGGCACCAAGUUCCACCAGGCCGCUAAGGACAUCGCCGAGA
UCAACGCUAUGUGGCCCGUGGCCACCGAGGCCAACGAGCAGGUGUG
CAUGUACAUCCUGGGCGAGAGCAUGUCCAGCAUCAGGAGCAAGUGC
CCCGUGGAGGAAAGCGAGGCCAGCACACCACCCAGCACCCUGCCCU
GCCUGUGCAUCCACGCUAUGACACCCGAGAGGGUGCAGCGGCUGAA
GGCCAGCAGGCCCGAGCAGAUCACCGUGUGCAGCUCCUUCCCACUG
CCCAAGUACAGGAUCACCGGCGUGCAGAAGAUCCAGUGCAGCCAGC
CCAUCCUGUUCAGCCCAAAGGUGCCCGCCUACAUCCACCCCAGGAA
GUACCUGGUGGAGACCCCACCCGUGGACGAGACACCCGAGCCAAGC
GCCGAGAACCAGAGCACCGAGGGCACACCCGAGCAGCCACCCCUGA
UCACCGAGGACGAGACAAGGACCCGGACCCCAGAGCCCAUCAUUAU
CGAGGAAGAGGAAGAGGACAGCAUCAGCCUGCUGAGCGACGGCCCC
ACCCACCAGGUGCUGCAGGUGGAGGCCGACAUCCACGGCCCACCCA
GCGUGUCCAGCUCCAGCUGGAGCAUCCCACACGCCAGCGACUUCGA
CGUGGACAGCCUGAGCAUCCUGGACACCCUGGAGGGCGCCAGCGUG
ACCUCCGGCGCCACCAGCGCCGAGACCAACAGCUACUUCGCCAAGA
GCAUGGAGUUCCUGGCCAGGCCCGUGCCAGCUCCCAGGACCGUGUU
CAGGAACCCACCCCACCCAGCUCCCAGGACCAGGACCCCAAGCCUG
GCUCCCAGCAGGGCCUGCAGCAGGACCAGCCUGGUGAGCACCCCAC
CCGGCGUGAACAGGGUGAUCACCAGGGAGGAACUGGAGGCCCUGAC
ACCCAGCAGGACCCCCAGCAGGUCCGUGAGCAGGACUAGUCUGGUG
UCCAACCCACCCGGCGUGAACAGGGUGAUCACCAGGGAGGAAUUCG
AGGCCUUCGUGGCCCAGCAACAGAGACGGUUCGACGCCGGCGCCUA
CAUCUUCAGCAGCGACACCGGCCAGGGACACCUGCAGCAAAAGAGC
GUGAGGCAGACCGUGCUGAGCGAGGUGGUGCUGGAGAGGACCGAGC
UGGAAAUCAGCUACGCCCCCAGGCUGGACCAGGAGAAGGAGGAACU
GCUCAGGAAGAAACUGCAGCUGAACCCCACCCCAGCCAACAGGAGC
AGGUACCAGAGCAGGAAGGUGGAGAACAUGAAGGCCAUCACCGCCA
GGCGGAUCCUGCAGGGCCUGGGACACUACCUGAAGGCCGAGGGCAA
GGUGGAGUGCUACAGGACCCUGCACCCCGUGCCACUGUACAGCUCC
AGCGUGAACAGGGCCUUCUCCAGCCCCAAGGUGGCCGUGGAGGCCU
GCAACGCUAUGCUGAAGGAGAACUUCCCCACCGUGGCCAGCUACUG
CAUCAUCCCCGAGUACGACGCCUACCUGGACAUGGUGGACGGCGCC
AGCUGCUGCCUGGACACCGCCAGCUUCUGCCCCGCCAAGCUGAGGA
GCUUCCCCAAGAAACACAGCUACCUGGAGCCCACCAUCAGGAGCGC
CGUGCCCAGCGCCAUCCAGAACACCCUGCAGAACGUGCUGGCCGCU
GCCACCAAGAGGAACUGCAACGUGACCCAGAUGAGGGAGCUGCCCG
UGCUGGACAGCGCUGCCUUCAACGUGGAGUGCUUCAAGAAAUACGC
CUGCAACAACGAGUACUGGGAGACCUUCAAGGAGAACCCCAUCAGG
CUGACCGAAGAGAACGUGGUGAACUACAUCACCAAGCUGAAGGGCC
CCAAGGCCGCUGCCCUGUUCGCUAAGACCCACAACCUGAACAUGCU
GCAGGACAUCCCAAUGGACAGGUUCGUGAUGGACCUGAAGAGGGAC
GUGAAGGUGACACCCGGCACCAAGCACACCGAGGAGAGGCCCAAGG
UGCAGGUGAUCCAGGCCGCUGACCCACUGGCCACCGCCUACCUGUG
CGGCAUCCACAGGGAGCUGGUGAGGCGGCUGAACGCCGUGCUGCUG
CCCAACAUCCACACCCUGUUCGACAUGAGCGCCGAGGACUUCGACG
CCAUCAUCGCCGAGCACUUCCAGCCCGGCGACUGCGUGCUGGAGAC
CGACAUCGCCAGCUUCGACAAGAGCGAGGAUGACGCUAUGGCCCUG
ACCGCUCUGAUGAUCCUGGAGGACCUGGGCGUGGACGCCGAGCUGC
UCACCCUGAUCGAGGCUGCCUUCGGCGAGAUCAGCUCCAUCCACCU
GCCCACCAAGACCAAGUUCAAGUUCGGCGCUAUGAUGAAAAGCGGA
AUGUUCCUGACCCUGUUCGUGAACACCGUGAUCAACAUUGUGAUCG

TABLE 9-continued

| | | |
|---|---|---|
| | | CCAGCAGGGUGCUGCGGGAGAGGCUGACCGGCAGCCCCUGCGCUGC<br>CUUCAUCGGCGACGACAACAUCGUGAAGGGCGUGAAAAGCGACAAG<br>CUGAUGGCCGACAGGUGCGCCACCUGGCUGAACAUGGAGGUGAAGA<br>UCAUCGACGCCGUGGUGGGCGAGAAGGCCCCCUACUUCUGCGGCGG<br>AUUCAUCCUGUGCGACAGCGUGACCGGCACCGCCUGCAGGGUGGCC<br>GACCCCCUGAAGAGGCUGUUCAAGCUGGGCAAGCCACUGGCCGCUG<br>ACGAUGAGCACGACGAUGACAGGCGGAGGGCCCUGCACGAGGAAAG<br>CACCAGGUGGAACAGGGUGGGCAUCCUGAGCGAGCUGUGCAAGGCC<br>GUGGAGAGCAGGUACGAGACCGUGGGCACCAGCAUCAUCGUGAUGG<br>CUAUGACCACACUGGCCAGCUCCGUCAAGAGCUUCUCCUACCUGAG<br>GGGGGCCCCUAUAACUCUCUACGGCUAACCUGAAUGGACUACGACA<br>UAGUCUAGUCCGCCAAGGCCGCCACCAUGAGAGUGACAGCCCCUAG<br>AACCUUACUGCUUCUGCUUUGGGGAGCUGUUGCUCUGACAGAGACA<br>UGGGCUGGAUCUUACCACAGCCCCAGCUACGCCUACCACCAGUUCG<br>AGAGGGGGGGAGGAGGCUCCGGGGGAGGAGGCUCCCUGAAGAUCAG<br>CCAGGCCGUGCACGCCGCCCACGCCGAGAUCAACGAGGCCGGCCGG<br>GAGGUGAUCGUGGGCAUUGUCGCUGGCCUGGCCGUCCUCGCCGUGG<br>UGGUGAUUGGAGCUGUGGUCGCAGCUGUUAUGUGCAGAAGAAAGUC<br>AUCCGGCGGAAAGGGAGGCUCCUACUCUCAGGCUGCUUCUGCUACA<br>GUGCCUAGAGCUCUUAUGUGUUUAUCUCAGCUGGGCGGCGGAGGCA<br>GCGACUACAAGGACGACGAUGACAAGUAAACUCGAGUAUGUUACGU<br>GCAAAGGUGAUUGUCACCCCCCGAAAGACCAUAUUGUGACACACCC<br>UCAGUAUCACGCCCAAACAUUUACAGCCGCGGUGUCAAAAACCGCG<br>UGGACGUGGUUAACAUCCCUGCUGGGAGGAUCAGCCGUAAUUAUUA<br>UAAUUGGCUUGGUGCUGGCUACUAUUGUGGCCAUGUACGUGCUGAC<br>CAACCAGAAACAUAAUUGAAUACAGCAGCAAUUGGCAAGCUGCUUA<br>CAUAGAACUCGCGGCGAUUGGCAUGCCGCCUUAAAAUUUUUAUUUU<br>AUUUUUUCUUUUCUUUUCCGAAUCGGAUUUUGUUUUUAAUAUUUCA<br>AAAAAAAAAAAAAAAAAAAAAAAAUCUAGAAAAAAAAAAAAAAAAA<br>AAAAAAAAAAAAAAAAAAAAAAAAAAAAAAAAAAAAAAAAAAAAAA<br>AAAAAAAAAAAAAAAAAAAAAAAAAAAAAAAAAAAAAA |
| non structural protein of SINV | | |
| mARM # | | |
| 2842 and 2862 (SEQ ID NO:109) | SINV nsP1-4 AA | MEKPVVNVDVDPQSPFVVQLQKSFPQFEVVAQQVTPNDHANARAFS<br>HLASKLIELEVPTTATILDIGSAPARRMFSEHQYHCVCPMRSPEDP<br>DRMMKYASKLAEKACKITNKNLHEKIKDLRTVLDTPDAETPSLCFH<br>NDVTCNMRAEYSVMQDVYINAPGTIYHQAMKGVRTLYWIGFDTTQF<br>MFSAMAGSYPAYNTNWADEKVLEARNIGLCSTKLSEGRTGKLSIMR<br>KKELKPGSRVYFSVGSTLYPEHRASLQSWHLPSVFHLNGKQSYTCR<br>CDTVVSCEGYVVKKITISPGITGETVGYAVTHNSEGFLLCKVTDTV<br>KGERVSFPVCTYIPATICDQMTGIMATDISPDDAQKLLVGLNQRIV<br>INGRTNRNTNTMQNYLLPIIAQGFSKWAKERKDDLDNEKMLGTRER<br>KLTYGCLWAFRTKKVHSFYRPPGTQTCVKVPASFSAFPMSSVWTTS<br>LPMSLRQKLKLALQPKKEEKLLQVSEELVMEAKAAFEDAQEEARAE<br>KLREALPPLVADKGIEAAAEVVCEVEGLQADIGAALVETPRGHVRI<br>IPQANDRMIGQYIVVSPNSVLKNAKLAPAHPLADQVKIITHSGRSG<br>RYAVEPYDAKVLMPAGGAVPWPEFLALSESATLVYNEREFVNRKLY<br>HIAMHGPAKNTEEEQYKVTKAELAETEYVFDVDKKRCVKKEEASGL<br>VLSGELTNPPYHELALEGLKTRPAVPYKVETIGVIGTPGSGKSAII<br>KSTVTARDLVTSGKKENCREIEADVLRLRGMQITSKTVDSVMLNGC<br>HKAVEVLYVDEAFACHAGALLALIAIVRPRKKVVLCGDPMQCGFFN<br>MMQLKVHFNHPEKDICTKTFYKYISRRCTQPVTAIVSTLHYDGKMK<br>TTNPCKKNIEIDITGATKPKPGDIILTCFRGWVKQLQIDYPGHEVM<br>TAAASQGLTRKGVYAVRQKVNENPLYAITSEHVNVLLTRTEDRLVW<br>KTLQGDPWIKQLTNIPKGNFQATIEDWEAEHKGIIAAINSPTPRAN<br>PFSCKTNVCWAKALEPILATAGIVLTGCQWSELFPQFADDKPHSAI<br>YALDVICIKFFGMDLTSGLFSKQSIPLTYHPADSARPVAHWDNSPG<br>TRKYGYDHAIAAELSRRFPVFQLAGKGTQLDLQTGRTRVISAQHNL<br>VPVNRNLPHALVPEYKEKQPGPVEKFLNQFKHHSVLVVSEEKIEAP<br>RKRIEWIAPIGIAGADKNYNLAFGFPPQARYDLVFINIGTKYRNHH<br>FQQCEDHAATLKTLSRSALNCLNPGGTLVVKSYGYADRNSEDVVTA<br>LARKFVRVSAARPDCVSSNTEMYLIFRQLDNSRTRQFTPHHLNCVI<br>SSVYEGTRDGVGAAPSYRTKRENIADCQEEAVVNAANPLGRPGEGV<br>CRAIYKRWPTSFTDSATETGTARMTVCLGKKVIHAVGPDFRKHPEA<br>EALKLLQNAYHAVADLVNEHNIKSVAIPLLSTGIYAAGKDRLEVSL<br>NCLTTALDRTDADVTIYCLDKKWKERIDAALQLKESVTELKDEDME<br>IDDELVWIHPDSCLKGRKGFSTTKGKLYSYFEGTKFHQAAKDMAEI<br>KVLFPNDQESNEQLCAYILGETMEAIREKCPVDHNPSSSPPKTLPC<br>LCMYAMTPERVHRLRSNNVKEVTVCSSTPLPKHKIKNVQKVQCTKV<br>VLFNPHTPAFVPARKYIEVPEQPTAPPAQAEEAPEVVATPSPSTAD<br>NTSLDVTDISLDMDDSSEGSLFSSFSGSDNSITSMDSWSSGPSSLE<br>IVDRRQVVVADVHAVQEPAPIPPPRLKKMARLAAARKEPTPPASNS<br>SESLHLSFGGVSMSLGSIFDGETARQAAVQPLATGPTDVPMSFGSF<br>SDGEIDELSRRVTESEPVLFGSFEPGEVNSIISSRSAVSFPLRKQR<br>RRRRSRRTEY*LTGVGGYIFSTDTGPGHLQKKSVLQNQLTEPTLER<br>NVLERIHAPVLDTSKEEQLKLRYQMMPTEANKSRYQSRKVENQKAI |

TABLE 9-continued

| |
|---|
| TTERLLSGLRLYNSATDQPECYKITYPKPLYSSSVPANYSDPQFAV |
| AVCNNYLHENYPTVASYQITDEYDAYLDMVDGTVACLDTATFCPAK |
| LRSYPKKHEYRAPNIRSAVPSAMQNTLQNVLIAATKRNCNVTQMRE |
| LPTLDSATFNVECFRKYACNDEYWEEFARKPIRITTEFVTAYVARL |
| KGPKAAALFAKTYNLVPLQEVPMDRFVMDMKRDVKVTPGTKHTEER |
| PKVQVIQAAEPLATAYICGIHRELVRRLTAVLLPNIHTLFDMSAED |
| FDAIIAEHFKQGDPVLETDIASFDKSQDDAMALTGLMILEDLGVDQ |
| PLLDLIECAFGEISSTHLPTGTRFKFGAMMKSGMFLTLFVNTVLNV |
| VIASRVLEERLKTSRCAAFIGDDNIIHGVVSDKEMAERCATWLNME |
| VKIIDAVIGERPPYFCGGFILQDSVTSTACRVADPLKRLFKLGKPL |
| PADDEQDEDRRRALLDETKAWFRVGITGTLAVAVTTRYEVDNITPV |
| LLALRTFAQSKRAFQAIRGEIKHLYGGPK |

Example 2

This example describes analysis of the immunogenicity of influenza hemagglutinin (HA) expressed from self-replicating RNA or mRNA.

Self-replicating RNA and mRNA vaccine constructs were designed to encode the full-length hemagglutinin (HA) protein from influenza virus A/California/07/2009 (H1N1) (SEQ ID NO:113 and 114). The mRNA vaccine construct encoding HA included a tobacco etch virus (TEV) 5' UTR and a *Xenopus* beta-globin (Xbg) 3' UTR. Both self-replicating RNA (SEQ ID NO:56; entire RNA mARM3039) and mRNA vaccine constructs (SEQ ID NO:116; entire RNA sequence mARM3038) were encapsulated in the same lipid nanoparticle (LNP) composition that included four lipid excipients (an ionizable cationic lipid, 1,2-distearoyl-sn-glycero-3-phosphocholine (DSPC), cholesterol, and PEG2000-DMG) dispersed in HEPES buffer (pH 8.0) containing sodium chloride and the cryoprotectants sucrose and glycerol. The N:P ratio of complexing lipid and RNA was approximately 9:1. The ionizable cationic lipid had the following structure:

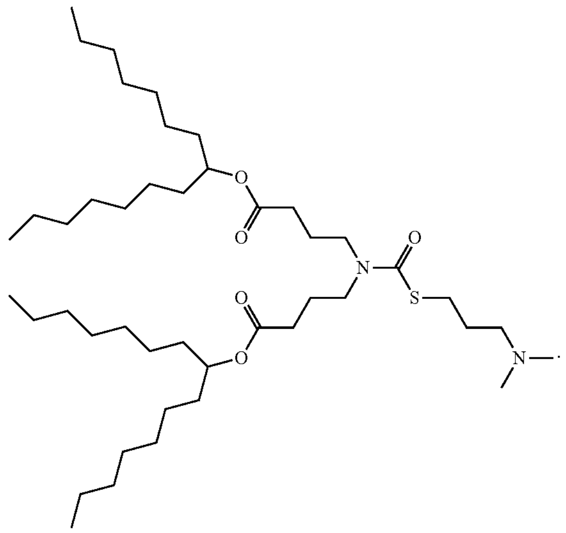 [SMILES: CCCCCCCC(CCCCCCC)OC(=O)CCCN(CCCC(=O)OC(CCCCCCC)CCCCCCC)C(=O)SCCCN(C)C]

Five female, 8-10 week old Balb/c mice were injected intramuscularly with 2 mg of mRNA or self-replicating RNA encoding HA. Mice were bled on days 14, 28, 42, and 56, followed by hemagglutination inhibition (HAI) assay using serially diluted sera. The reciprocal of the highest dilution of serum that caused inhibition of hemagglutination was considered the HAI titer, with a titer of 1/40 being protective against influenza virus infection and four-fold higher titers than baseline indicating seroconversion.

Results in FIG. 7 show that greater HAI titers were obtained with self-replicating RNA encoding HA as compared to mRNA encoding HA. HAI titers for the self-replicating RNA construct encoding HA were greater than HAI titers for the mRNA encoding HA at all time points beginning at day 28. In addition, protective HAI titers were seen for the self-replicating RNA construct encoding HA beginning at day 28 that were maintained for at least 56 days. By contrast, mRNA encoding HA showed protective HAI titers only at day 56 that were lower than HAI titers seen for the self-replicating RNA HA construct. At all other time points, HAI titers for the mRNA construct encoding HA were below the protective titer threshold, with an HAI titer that was comparable to injection with PBS control at day 28.

These results show that the self-replicating RNA construct encoding HA elicited protective HA antibody titers, with greater HAI titers as compared to the mRNA construct encoding HA.

Example 3

This example describes dsRNA production and luciferase expression for self-replicating RNA.

Several self-replicating RNA systems from different alphaviruses were tested for expression in vitro using either green fluorescent protein (GFP) or firefly luciferase (Luc) as reporter genes. Initial transfection of cells with increasing amounts of self-replicating RNA resulted in expression of reporter genes at a lower dose compared to mRNA. However, as the amount of input self-replicating RNA increased, detectable expression of the reporter gene decreased.

Self-replicating RNA produces double stranded RNA (dsRNA) as an intermediate in the amplification process. Overproduction of dsRNA can suppress translation. To evaluate the effect of dsRNA production on transgene expression, dsRNA and the expression of reporter gene luciferase were measured simultaneously. HEK293 cells were transfected with 2 μg of replicon A (SEQ ID NO:115; entire RNA sequence mARM2826) or replicon B (SEQ ID NO:100, entire RNA sequence mARM2809) self-replicating RNA, or mRNA expressing Luc (SEQ ID NO:102, entire mRNA sequence mARM1782) using a commercial RNA transfection reagent. Untransfected cells (UTC) served as a control. dsRNA production (FIG. 8A) was quantified using immunohistochemical staining for dsRNA, followed by fluorescence quantification using a fluorescence scanner 24 hours after transfection. Luciferase expression (FIG. 8B) was assayed by measuring bioluminescence in parallel.

Replicon A produced a 3-fold higher level of dsRNA than replicon B 24 hrs after transfection (FIG. 8A). However, replicon B produced a 2.4-fold higher expression level of luciferase compared to replicon A. Furthermore, the level of luciferase expression from replicon A was equivalent to that observed for mRNA. Thus, even though replicon A had the ability to amplify the amount of replicon RNA and transcribed mRNA encoding luciferase, translation of the amplified mRNA was inhibited, consistent with overproduction of dsRNA inhibiting translation. Furthermore, higher levels of luciferase gene expression were seen for replicon RNA as compared to mRNA at 24, 48, and 72 hours after transfection of HEK293 cells (FIG. 9A). Self-replicating RNA with an expression cassette that included a luciferase reporter gene followed by an IRES and E3L also showed robust luciferase expression (FIGS. 9B, 9C; SEQ ID NOs: 118 and 119). Luciferase expression was also seen for a self-replicating RNA that expressed E3L from a first subgenomic promoter and a luciferase reporter gene from a second subgenomic promoter located 3' of the E3L open reading frame (not shown). Thus, not only did replicon RNA produce higher levels of luciferase gene expression compared to mRNA, but replicon RNA also showed increased duration of expression over a 72-hr period.

Example Sequences

Additional illustrative sequences are provided below, features of which are described in Table 7:

TABLE 7

| SEQ ID NO | Description |
|---|---|
| SEQ ID NO: 72 | nsP1-4 ORF, codon-optimized |
| SEQ ID NO: 73 | 5' UTR |
| SEQ ID NO: 74 | 5' UTR |
| SEQ ID NO: 75 | 5' UTR |
| SEQ ID NO: 76 | 3' UTR |
| SEQ ID NO: 77 | Intergenic region between nsP1-4 ORF and antigenic protein ORF |
| SEQ ID NO: 78 | Replicon sequence comprising SEQ ID NO: 72, SEQ ID NO: 73, SEQ ID NO: 76, and SEQ ID NO: 77 |
| SEQ ID NO: 79 | nsP1-4 protein sequence |
| SEQ ID NO: 80 | nsP1-4 protein sequence |
| SEQ ID NO: 81 | nsP1-4 protein sequence |
| SEQ ID NO: 82 | 5' UTR (TEV) |
| SEQ ID NO: 83 | 3' UTR (Xbg) |

SEQ ID NO: 72

ATGGAGAAAGTTCACGTTGACATCGAGGAAGACAGCCCATTCCTCAGAGCTTTG

CAGCGGAGCTTCCCGCAGTTTGAGGTAGAAGCCAAGCAGGTCACTGATAATGAC

CATGCTAATGCCAGAGCGTTTTCGCATCTGGCTTCAAAACTGATCGAAACGGAGG

TGGACCCATCCGACACGATCCTTGACATTGGAAGTGCGCCCGCCCGCAGAATGT

ATTCTAAGCACAAGTATCATTGTATCTGTCCGATGAGATGTGCGGAAGATCCGGA

CAGATTGTATAAGTATGCAACTAAGCTGAAGAAAAACTGTAAGGAAATAACTGA

TAAGGAATTGGACAAGAAAATGAAGGAGCTGGCCGCCGTCATGAGCGACCCTGA

CCTGGAAACTGAGACTATGTGCCTCCACGACGACGAGTCGTGTCGCTACGAAGG

GCAAGTCGCTGTTTACCAGGATGTATACGCCGTCGACGGCCCCACCAGCCTGTAC

CACCAGGCCAACAAGGGCGTGAGGGTGGCCTACTGGATCGGCTTCGACACCACA

CCCTTCATGTTCAAGAACCTGGCCGGCGCCTACCCCAGCTACAGCACCAACTGGG

CCGACGAGACCGTGCTGACCGCCAGGAACATCGGCCTGTGCAGCAGCGACGTGA

TGGAGAGGAGCCGGAGAGGCATGAGCATCCTGAGGAAGAAATACCTGAAGCCC

AGCAACAACGTGCTGTTCAGCGTGGGCAGCACCATCTACCACGAGAAGAGGGAC

CTGCTCAGGAGCTGGCACCTGCCCAGCGTGTTCCACCTGAGGGGCAAGCAGAAC

TACACCTGCAGGTGCGAGACCATCGTGAGCTGCGACGGCTACGTGGTGAAGAGG

ATCGCCATCAGCCCCGGCCTGTACGGCAAGCCCAGCGGCTACGCCGCTACAATG

TABLE 7-continued

CACAGGGAGGGCTTCCTGTGCTGCAAGGTGACCGACACCCTGAACGGCGAGAGG

GTGAGCTTCCCCGTGTGCACCTACGTGCCCGCCACCCTGTGCGACCAGATGACCG

GCATCCTGGCCACCGACGTGAGCGCCGACGACGCCCAGAAGCTGCTCGTGGGCC

TGAACCAGAGGATCGTGGTCAACGGCAGGACCCAGAGGAACACCAACACAATG

AAGAACTACCTGCTGCCCGTGGTGGCCCAGGCTTTCGCCAGGTGGGCCAAGGAG

TACAAGGAGGACCAGGAAGACGAGAGGCCCCTGGGCCTGAGGGACAGGCAGCT

GGTGATGGGCTGCTGCTGGGCCTTCAGGCGGCACAAGATCACCAGCATCTACAA

GAGGCCCGACACCCAGACCATCATCAAGGTGAACAGCGACTTCCACAGCTTCGT

GCTGCCCAGGATCGGCAGCAACACCCTGGAGATCGGCCTGAGGACCCGGATCAG

GAAGATGCTGGAGGAACACAAGGAGCCCAGCCCACTGATCACCGCCGAGGACGT

GCAGGAGGCCAAGTGCGCTGCCGACGAGGCCAAGGAGGTGAGGGAGGCCGAGG

AACTGAGGGCCGCCCTGCCACCCCTGGCTGCCGACGTGGAGGAACCCACCCTGG

AAGCCGACGTGGACCTGATGCTGCAGGAGGCCGGCGCCGGAAGCGTGGAGACA

CCCAGGGGCCTGATCAAGGTGACCAGCTACGACGGCGAGGACAAGATCGGCAGC

TACGCCGTGCTGAGCCCACAGGCCGTGCTGAAGTCCGAGAAGCTGAGCTGCATC

CACCCACTGGCCGAGCAGGTGATCGTGATCACCCACAGCGGCAGGAAGGGCAGG

TACGCCGTGGAGCCCTACCACGGCAAGGTGGTCGTGCCCGAGGGCCACGCCATC

CCCGTGCAGGACTTCCAGGCCCTGAGCGAGAGCGCCACCATCGTGTACAACGAG

AGGGAGTTCGTGAACAGGTACCTGCACCATATCGCCACCCACGGCGGAGCCCTG

AACACCGACGAGGAATACTACAAGACCGTGAAGCCCAGCGAGCACGACGGCGA

GTACCTGTACGACATCGACAGGAAGCAGTGCGTGAAGAAAGAGCTGGTGACCGG

CCTGGGACTGACCGGCGAGCTGGTGGACCCACCCTTCCACGAGTTCGCCTACGA

GAGCCTGAGGACCAGACCCGCCGCTCCCTACCAGGTGCCCACCATCGGCGTGTA

CGGCGTGCCCGGCAGCGGAAAGAGCGGCATCATCAAGAGCGCCGTGACCAAGA

AAGACCTGGTGGTCAGCGCCAAGAAAGAGAACTGCGCCGAGATCATCAGGGAC

GTGAAGAAGATGAAAGGCCTGGACGTGAACGCGCGCACCGTGGACAGCGTGCTG

CTGAACGGCTGCAAGCACCCCGTGGAGACCCTGTACATCGACGAGGCCTTCGCTT

GCCACGCCGGCACCCTGAGGGCCCTGATCGCCATCATCAGGCCCAAGAAAGCCG

TGCTGTGCGGCGACCCCAAGCAGTGCGGCTTCTTCAACATGATGTGCCTGAAGGT

GCACTTCAACCACGAGATCTGCACCCAGGTGTTCCACAAGAGCATCAGCAGGCG

GTGCACCAAGAGCGTGACCAGCGTCGTGAGCACCCTGTTCTACGACAAGAAAAT

GAGGACCACCAACCCCAAGGAGACCAAAATCGTGATCGACACCACAGGCAGCA

CCAAGCCCAAGCAGGACGACCTGATCCTGACCTGCTTCAGGGGCTGGGTGAAGC

AGCTGCAGATCGACTACAAGGGCAACGAGATCATGACCGCCGCTGCCAGCCAGG

GCCTGACCAGGAAGGGCGTGTACGCCGTGAGGTACAAGGTGAACGAGAACCCAC

TGTACGCTCCCACCAGCGAGCACGTGAACGTGCTGCTGACCAGGACCGAGGACA

GGATCGTGTGGAAGACCCTGGCCGGCGACCCCTGGATCAAGACCCTGACCGCCA

AGTACCCCGGCAACTTCACCGCCACCATCGAAGAGTGGCAGGCCGAGCACGACG

CCATCATGAGGCACATCCTGGAGAGGCCCGACCCCACCGACGTGTTCCAGAACA

AGGCCAACGTGTGCTGGGCCAAGGCCCTGGTGCCCGTGCTGAAGACCGCCGGCA

TABLE 7-continued

TCGACATGACCACAGAGCAGTGGAACACCGTGGACTACTTCGAGACCGACAAGG

CCCACAGCGCCGAGATCGTGCTGAACCAGCTGTGCGTGAGGTTCTTCGGCCTGGA

CCTGGACAGCGGCCTGTTCAGCGCCCCCACCGTGCCACTGAGCATCAGGAACAA

CCACTGGGACAACAGCCCCAGCCCAAACATGTACGGCCTGAACAAGGAGGTGGT

CAGGCAGCTGAGCAGGCGGTACCCACAGCTGCCCAGGGCCGTGGCCACCGGCAG

GGTGTACGACATGAACACCGGCACCCTGAGGAACTACGACCCCAGGATCAACCT

GGTGCCCGTGAACAGGCGGCTGCCCCACGCCCTGGTGCTGCACCACAACGAGCA

CCCACAGAGCGACTTCAGCTCCTTCGTGAGCAAGCTGAAAGGCAGGACCGTGCT

GGTCGTGGGCGAGAAGCTGAGCGTGCCCGGCAAGATGGTGGACTGGCTGAGCGA

CAGGCCCGAGGCCACCTTCCGGGCCAGGCTGGACCTCGGCATCCCCGGCGACGT

GCCCAAGTACGACATCATCTTCGTGAACGTCAGGACCCCATACAAGTACCACCAT

TACCAGCAGTGCGAGGACCACGCCATCAAGCTGAGCATGCTGACCAAGAAGGCC

TGCCTGCACCTGAACCCCGGAGGCACCTGCGTGAGCATCGGCTACGGCTACGCC

GACAGGGCCAGCGAGAGCATCATTGGCGCCATCGCCAGGCTGTTCAAGTTCAGC

AGGGTGTGCAAACCCAAGAGCAGCCTGGAGGAAACCGAGGTGCTGTTCGTGTTC

ATCGGCTACGACCGGAAGGCCAGGACCCACAACCCCTACAAGCTGAGCAGCACC

CTGACAAACATCTACACCGGCAGCAGGCTGCACGAGGCCGGCTGCGCCCCCAGC

TACCACGTGGTCAGGGGCGATATCGCCACCGCCACCGAGGGCGTGATCATCAAC

GCTGCCAACAGCAAGGGCCAGCCCGGAGGCGGAGTGTGCGGCGCCCTGTACAAG

AAGTTCCCCGAGAGCTTCGACCTGCAGCCCATCGAGGTGGGCAAGGCCAGGCTG

GTGAAGGGCGCCGCTAAGCACATCATCCACGCCGTGGGCCCCAACTTCAACAAG

GTGAGCGAGGTGGAAGGCGACAAGCAGCTGGCCGAAGCCTACGAGAGCATCGC

CAAGATCGTGAACGACAATAACTACAAGAGCGTGGCCATCCCACTGCTCAGCAC

CGGCATCTTCAGCGGCAACAAGGACAGGCTGACCCAGAGCCTGAACCACCTGCT

CACCGCCCTGGACACCACCGATGCCGACGTGGCCATCTACTGCAGGGACAAGAA

GTGGGAGATGACCCTGAAGGAGGCCGTGGCCAGGCGGGAGGCCGTGGAAGAGA

TCTGCATCAGCGACGACTCCAGCGTGACCGAGCCCGACGCCGAGCTGGTGAGGG

TGCACCCCAAGAGCTCCCTGGCCGGCAGGAAGGGCTACAGCACCAGCGACGGCA

AGACCTTCAGCTACCTGGAGGGCACCAAGTTCCACCAGGCCGCTAAGGACATCG

CCGAGATCAACGCTATGTGGCCCGTGGCCACCGAGGCCAACGAGCAGGTGTGCA

TGTACATCCTGGGCGAGAGCATGTCCAGCATCAGGAGCAAGTGCCCCGTGGAGG

AAAGCGAGGCCAGCACACCACCCAGCACCCTGCCCTGCCTGTGCATCCACGCTA

TGACACCCGAGAGGGTGCAGCGGCTGAAGGCCAGCAGGCCCGAGCAGATCACC

GTGTGCAGCTCCTTCCCACTGCCCAAGTACAGGATCACCGGCGTGCAGAAGATCC

AGTGCAGCCAGCCCATCCTGTTCAGCCCAAAGGTGCCCGCCTACATCCACCCCAG

GAAGTACCTGGTGGAGACCCCACCCGTGGACGAGACACCCGAGCCAAGCGCCGA

GAACCAGAGCACCGAGGGCACACCCGAGCAGCCACCCCTGATCACCGAGGACG

AGACAAGGACCCGGACCCCAGAGCCCATCATTATCGAGGAAGAGGAAGAGGAC

AGCATCAGCCTGCTGAGCGACGGCCCCACCCACCAGGTGCTGCAGGTGGAGGCC

GACATCCACGGCCCACCCAGCGTGTCCAGCTCCAGCTGGAGCATCCCACACGCC

TABLE 7-continued

AGCGACTTCGACGTGGACAGCCTGAGCATCCTGGACACCCTGGAGGGCGCCAGC

GTGACCTCCGGCGCCACCAGCGCCGAGACCAACAGCTACTTCGCCAAGAGCATG

GAGTTCCTGGCCAGGCCCGTGCCAGCTCCCAGGACCGTGTTCAGGAACCCACCCC

ACCCAGCTCCCAGGACCAGGACCCCAAGCCTGGCTCCCAGCAGGGCCTGCAGCA

GGACCAGCCTGGTGAGCACCCCACCCGGCGTGAACAGGGTGATCACCAGGGAGG

AACTGGAGGCCCTGACACCCAGCAGGACCCCCAGCAGGTCCGTGAGCAGGACTA

GTCTGGTGTCCAACCCACCCGGCGTGAACAGGGTGATCACCAGGGAGGAATTCG

AGGCCTTCGTGGCCCAGCAACAGAGACGGTTCGACGCCGGCGCCTACATCTTCA

GCAGCGACACCGGCCAGGGACACCTGCAGCAAAAGAGCGTGAGGCAGACCGTG

CTGAGCGAGGTGGTGCTGGAGAGGACCGAGCTGGAAATCAGCTACGCCCCCAGG

CTGGACCAGGAGAAGGAGGAACTGCTCAGGAAGAAACTGCAGCTGAACCCCAC

CCCAGCCAACAGGAGCAGGTACCAGAGCAGGAAGGTGGAGAACATGAAGGCCA

TCACCGCCAGGCGGATCCTGCAGGGCCTGGGACACTACCTGAAGGCCGAGGGCA

AGGTGGAGTGCTACAGGACCCTGCACCCCGTGCCACTGTACAGCTCCAGCGTGA

ACAGGGCCTTCTCCAGCCCCAAGGTGGCCGTGGAGGCCTGCAACGCTATGCTGA

AGGAGAACTTCCCCACCGTGGCCAGCTACTGCATCATCCCCGAGTACGACGCCTA

CCTGGACATGGTGGACGGCGCCAGCTGCTGCCTGGACACCGCCAGCTTCTGCCCC

GCCAAGCTGAGGAGCTTCCCCAAGAAACACAGCTACCTGGAGCCCACCATCAGG

AGCGCCGTGCCCAGCGCCATCCAGAACACCCTGCAGAACGTGCTGGCCGCTGCC

ACCAAGAGGAACTGCAACGTGACCCAGATGAGGGAGCTGCCCGTGCTGGACAGC

GCTGCCTTCAACGTGGAGTGCTTCAAGAAATACGCCTGCAACAACGAGTACTGG

GAGACCTTCAAGGAGAACCCCATCAGGCTGACCGAAGAGAACGTGGTGAACTAC

ATCACCAAGCTGAAGGGCCCCAAGGCCGCTGCCCTGTTCGCTAAGACCCACAAC

CTGAACATGCTGCAGGACATCCCAATGGACAGGTTCGTGATGGACCTGAAGAGG

GACGTGAAGGTGACACCCGGCACCAAGCACACCGAGGAGAGGCCCAAGGTGCA

GGTGATCCAGGCCGCTGACCCACTGGCCACCGCCTACCTGTGCGGCATCCACAG

GGAGCTGGTGAGGCGGCTGAACGCCGTGCTGCTGCCCAACATCCACACCCTGTTC

GACATGAGCGCCGAGGACTTCGACGCCATCATCGCCGAGCACTTCCAGCCCGGC

GACTGCGTGCTGGAGACCGACATCGCCAGCTTCGACAAGAGCGAGGATGACGCT

ATGGCCCTGACCGCTCTGATGATCCTGGAGGACCTGGGCGTGGACGCCGAGCTG

CTCACCCTGATCGAGGCTGCCTTCGGCGAGATCAGCTCCATCCACCTGCCCACCA

AGACCAAGTTCAAGTTCGGCGCTATGATGAAAAGCGGAATGTTCCTGACCCTGTT

CGTGAACACCGTGATCAACATTGTGATCGCCAGCAGGGTGCTGCGGGAGAGGCT

GACCGGCAGCCCCTGCGCTGCCTTCATCGGCGACGACAACATCGTGAAGGGCGT

GAAAAGCGACAAGCTGATGGCCGACAGGTGCGCCACCTGGCTGAACATGGAGGT

GAAGATCATCGACGCCGTGGTGGGCGAGAAGGCCCCCTACTTCTGCGGCGGATT

CATCCTGTGCGACAGCGTGACCGGCACCGCCTGCAGGGTGGCCGACCCCCTGAA

GAGGCTGTTCAAGCTGGGCAAGCCACTGGCCGCTGACGATGAGCACGACGATGA

CAGGCGGAGGGCCCTGCACGAGGAAAGCACCAGGTGGAACAGGGTGGGCATCC

TGAGCGAGCTGTGCAAGGCCGTGGAGAGCAGGTACGAGACCGTGGGCACCAGC

TABLE 7-continued

ATCATCGTGATGGCTATGACCACACTGGCCAGCTCCGTCAAGAGCTTCTCCTACC

TGAGGGGGGCCCCTATAACTCTCTACGGCTAA

SEQ ID NO: 73
ATGGGCGGCGCATGAGAGAAGCCCAGACCAATTACCTACCCAAA

SEQ ID NO: 74
GATGGGCGGCGCATGAGAGAAGCCCAGACCAATTACCTACCCAAA

SEQ ID NO: 75
GATAGGCGGCGCATGAGAGAAGCCCAGACCAATTACCTACCCAAA

SEQ ID NO: 76
ACTCGAGTATGTTACGTGCAAAGGTGATTGTCACCCCCCGAAAGACCATATTGTG

ACACACCCTCAGTATCACGCCCAAACATTTACAGCCGCGGTGTCAAAAACCGCG

TGGACGTGGTTAACATCCCTGCTGGGAGGATCAGCCGTAATTATTATAATTGGCT

TGGTGCTGGCTACTATTGTGGCCATGTACGTGCTGACCAACCAGAAACATAATTG

AATACAGCAGCAATTGGCAAGCTGCTTACATAGAACTCGCGGCGATTGGCATGC

CGCCTTAAAATTTTTATTTTATTTTTTCTTTTCTTTTCCGAATCGGATTTTGTTTTTA

ATATTTCAAAAAAAAAAAAAAAAAAAAAAAAAATCTAGAAAAAAAAAAAAAAAA

AAAAAAAAAAAAAAAAAAAAAAAAAAAAAAAAAAAAAAAAAAAAAAAAAAAAA

AAAAAAAAAAAAAAAAAAAAAAAAAAAAAAAAA

SEQ ID NO: 77
CCTGAATGGACTACGACATAGTCTAGTCCGCCAAGGCCGCCACC

SEQ ID NO: 78
ATGGGCGGCGCATGAGAGAAGCCCAGACCAATTACCTACCCAAAATGGAGAAA

GTTCACGTTGACATCGAGGAAGACAGCCCATTCCTCAGAGCTTTGCAGCGGAGCT

TCCCGCAGTTTGAGGTAGAAGCCAAGCAGGTCACTGATAATGACCATGCTAATG

CCAGAGCGTTTTCGCATCTGGCTTCAAAACTGATCGAAACGGAGGTGGACCCATC

CGACACGATCCTTGACATTGGAAGTGCGCCCGCCCGCAGAATGTATTCTAAGCAC

AAGTATCATTGTATCTGTCCGATGAGATGTGCGGAAGATCCGGACAGATTGTATA

AGTATGCAACTAAGCTGAAGAAAAACTGTAAGGAAATAACTGATAAGGAATTGG

ACAAGAAAATGAAGGAGCTGGCCGCCGTCATGAGCGACCCTGACCTGGAAACTG

AGACTATGTGCCTCCACGACGACGAGTCGTGTCGCTACGAAGGGCAAGTCGCTG

TTTACCAGGATGTATACGCCGTCGACGGCCCCACCAGCCTGTACCACCAGGCCAA

CAAGGGCGTGAGGGTGGCCTACTGGATCGGCTTCGACACCACACCCTTCATGTTC

AAGAACCTGGCCGGCGCCTACCCCAGCTACAGCACCAACTGGGCCGACGAGACC

GTGCTGACCGCCAGGAACATCGGCCTGTGCAGCAGCGACGTGATGGAGAGGAGC

CGGAGAGGCATGAGCATCCTGAGGAAGAAATACCTGAAGCCCAGCAACAACGT

GCTGTTCAGCGTGGGCAGCACCATCTACCACGAGAAGAGGGACCTGCTCAGGAG

CTGGCACCTGCCCAGCGTGTTCCACCTGAGGGGCAAGCAGAACTACACCTGCAG

GTGCGAGACCATCGTGAGCTGCGACGGCTACGTGGTGAAGAGGATCGCCATCAG

CCCCGGCCTGTACGGCAAGCCCAGCGGCTACGCCGCTACAATGCACAGGGAGGG

CTTCCTGTGCTGCAAGGTGACCGACACCCTGAACGGCGAGAGGGTGAGCTTCCC

CGTGTGCACCTACGTGCCCGCCACCCTGTGCGACCAGATGACCGGCATCCTGGCC

ACCGACGTGAGCGCCGACGACGCCCAGAAGCTGCTCGTGGGCCTGAACCAGAGG

ATCGTGGTCAACGGCAGGACCCAGAGGAACACCAACACAATGAAGAACTACCTG

TABLE 7-continued

CTGCCCGTGGTGGCCCAGGCTTTCGCCAGGTGGGCCAAGGAGTACAAGGAGGAC

CAGGAAGACGAGAGGCCCCTGGGCCTGAGGGACAGGCAGCTGGTGATGGGCTG

CTGCTGGGCCTTCAGGCGGCACAAGATCACCAGCATCTACAAGAGGCCCGACAC

CCAGACCATCATCAAGGTGAACAGCGACTTCCACAGCTTCGTGCTGCCCAGGATC

GGCAGCAACACCCTGGAGATCGGCCTGAGGACCCGGATCAGGAAGATGCTGGAG

GAACACAAGGAGCCCAGCCCACTGATCACCGCCGAGGACGTGCAGGAGGCCAA

GTGCGCTGCCGACGAGGCCAAGGAGGTGAGGGAGGCCGAGGAACTGAGGGCCG

CCCTGCCACCCCTGGCTGCCGACGTGGAGGAACCCACCCTGGAAGCCGACGTGG

ACCTGATGCTGCAGGAGGCCGGCGCCGGAAGCGTGGAGACACCCAGGGGCCTGA

TCAAGGTGACCAGCTACGACGGCGAGGACAAGATCGGCAGCTACGCCGTGCTGA

GCCCACAGGCCGTGCTGAAGTCCGAGAAGCTGAGCTGCATCCACCCACTGGCCG

AGCAGGTGATCGTGATCACCCACAGCGGCAGGAAGGGCAGGTACGCCGTGGAGC

CCTACCACGGCAAGGTGGTCGTGCCCGAGGGCCACGCCATCCCCGTGCAGGACT

TCCAGGCCCTGAGCGAGAGCGCCACCATCGTGTACAACGAGAGGGAGTTCGTGA

ACAGGTACCTGCACCATATCGCCACCCACGGCGGAGCCCTGAACACCGACGAGG

AATACTACAAGACCGTGAAGCCCAGCGAGCACGACGGCGAGTACCTGTACGACA

TCGACAGGAAGCAGTGCGTGAAGAAAGAGCTGGTGACCGGCCTGGGACTGACCG

GCGAGCTGGTGGACCCACCCTTCCACGAGTTCGCCTACGAGAGCCTGAGGACCA

GACCCGCCGCTCCCTACCAGGTGCCCACCATCGGCGTGTACGGCGTGCCCGGCA

GCGGAAAGAGCGGCATCATCAAGAGCGCCGTGACCAAGAAAGACCTGGTGGTC

AGCGCCAAGAAAGAGAACTGCGCCGAGATCATCAGGGACGTGAAGAAGATGAA

AGGCCTGGACGTGAACGCGCGCACCGTGGACAGCGTGCTGCTGAACGGCTGCAA

GCACCCCGTGGAGACCCTGTACATCGACGAGGCCTTCGCTTGCCACGCCGGCACC

CTGAGGGCCCTGATCGCCATCATCAGGCCCAAGAAAGCCGTGCTGTGCGGCGAC

CCCAAGCAGTGCGGCTTCTTCAACATGATGTGCCTGAAGGTGCACTTCAACCACG

AGATCTGCACCCAGGTGTTCCACAAGAGCATCAGCAGGCGGTGCACCAAGAGCG

TGACCAGCGTCGTGAGCACCCTGTTCTACGACAAGAAAATGAGGACCACCAACC

CCAAGGAGACCAAAATCGTGATCGACACCACAGGCAGCACCAAGCCCAAGCAG

GACGACCTGATCCTGACCTGCTTCAGGGGCTGGGTGAAGCAGCTGCAGATCGAC

TACAAGGGCAACGAGATCATGACCGCCGCTGCCAGCCAGGGCCTGACCAGGAAG

GGCGTGTACGCCGTGAGGTACAAGGTGAACGAGAACCCACTGTACGCTCCCACC

AGCGAGCACGTGAACGTGCTGCTGACCAGGACCGAGGACAGGATCGTGTGGAAG

ACCCTGGCCGGCGACCCCTGGATCAAGACCCTGACCGCCAAGTACCCCGGCAAC

TTCACCGCCACCATCGAAGAGTGGCAGGCCGAGCACGACGCCATCATGAGGCAC

ATCCTGGAGAGGCCCGACCCCACCGACGTGTTCCAGAACAAGGCCAACGTGTGC

TGGGCCAAGGCCCTGGTGCCCGTGCTGAAGACCGCCGGCATCGACATGACCACA

GAGCAGTGGAACACCGTGGACTACTTCGAGACCGACAAGGCCCACAGCGCCGAG

ATCGTGCTGAACCAGCTGTGCGTGAGGTTCTTCGGCCTGGACCTGGACAGCGGCC

TGTTCAGCGCCCCCACCGTGCCACTGAGCATCAGGAACAACCACTGGGACAACA

GCCCCAGCCCAAACATGTACGGCCTGAACAAGGAGGTGGTCAGGCAGCTGAGCA

TABLE 7-continued

GGCGGTACCCACAGCTGCCCAGGGCCGTGGCCACCGGCAGGGTGTACGACATGA

ACACCGGCACCCTGAGGAACTACGACCCCAGGATCAACCTGGTGCCCGTGAACA

GGCGGCTGCCCCACGCCCTGGTGCTGCACCACAACGAGCACCCACAGAGCGACT

TCAGCTCCTTCGTGAGCAAGCTGAAAGGCAGGACCGTGCTGGTCGTGGGCGAGA

AGCTGAGCGTGCCCGGCAAGATGGTGGACTGGCTGAGCGACAGGCCCGAGGCCA

CCTTCCGGGCCAGGCTGGACCTCGGCATCCCCGGCGACGTGCCCAAGTACGACA

TCATCTTCGTGAACGTCAGGACCCCATACAAGTACCACCATTACCAGCAGTGCGA

GGACCACGCCATCAAGCTGAGCATGCTGACCAAGAAGGCCTGCCTGCACCTGAA

CCCCGGAGGCACCTGCGTGAGCATCGGCTACGGCTACGCCGACAGGGCCAGCGA

GAGCATCATTGGCGCCATCGCCAGGCTGTTCAAGTTCAGCAGGGTGTGCAAACC

CAAGAGCAGCCTGGAGGAAACCGAGGTGCTGTTCGTGTTCATCGGCTACGACCG

GAAGGCCAGGACCCACAACCCCTACAAGCTGAGCAGCACCCTGACAAACATCTA

CACCGGCAGCAGGCTGCACGAGGCCGGCTGCGCCCCCAGCTACCACGTGGTCAG

GGGCGATATCGCCACCGCCACCGAGGGCGTGATCATCAACGCTGCCAACAGCAA

GGGCCAGCCCGGAGGCGGAGTGTGCGGCGCCCTGTACAAGAAGTTCCCCGAGAG

CTTCGACCTGCAGCCCATCGAGGTGGGCAAGGCCAGGCTGGTGAAGGGCGCCGC

TAAGCACATCATCCACGCCGTGGGCCCCAACTTCAACAAGGTGAGCGAGGTGGA

AGGCGACAAGCAGCTGGCCGAAGCCTACGAGAGCATCGCCAAGATCGTGAACG

ACAATAACTACAAGAGCGTGGCCATCCCACTGCTCAGCACCGGCATCTTCAGCG

GCAACAAGGACAGGCTGACCCAGAGCCTGAACCACCTGCTCACCGCCCTGGACA

CCACCGATGCCGACGTGGCCATCTACTGCAGGGACAAGAAGTGGGAGATGACCC

TGAAGGAGGCCGTGGCCAGGCGGGAGGCCGTGGAAGAGATCTGCATCAGCGAC

GACTCCAGCGTGACCGAGCCCGACGCCGAGCTGGTGAGGGTGCACCCCAAGAGC

TCCCTGGCCGGCAGGAAGGGCTACAGCACCAGCGACGGCAAGACCTTCAGCTAC

CTGGAGGGCACCAAGTTCCACCAGGCCGCTAAGGACATCGCCGAGATCAACGCT

ATGTGGCCCGTGGCCACCGAGGCCAACGAGCAGGTGTGCATGTACATCCTGGGC

GAGAGCATGTCCAGCATCAGGAGCAAGTGCCCCGTGGAGGAAAGCGAGGCCAG

CACACCACCCAGCACCCTGCCCTGCCTGTGCATCCACGCTATGACACCCGAGAGG

GTGCAGCGGCTGAAGGCCAGCAGGCCCGAGCAGATCACCGTGTGCAGCTCCTTC

CCACTGCCCAAGTACAGGATCACCGGCGTGCAGAAGATCCAGTGCAGCCAGCCC

ATCCTGTTCAGCCCAAAGGTGCCCGCCTACATCCACCCCAGGAAGTACCTGGTGG

AGACCCCACCCGTGGACGAGACACCCGAGCCAAGCGCCGAGAACCAGAGCACC

GAGGGCACACCCGAGCAGCCACCCCTGATCACCGAGGACGAGACAAGGACCCG

GACCCCAGAGCCCATCATTATCGAGGAAGAGGAAGAGGACAGCATCAGCCTGCT

GAGCGACGGCCCCACCCACCAGGTGCTGCAGGTGGAGGCCGACATCCACGGCCC

ACCCAGCGTGTCCAGCTCCAGCTGGAGCATCCCACACGCCAGCGACTTCGACGT

GGACAGCCTGAGCATCCTGGACACCCTGGAGGGCGCCAGCGTGACCTCCGGCGC

CACCAGCGCCGAGACCAACAGCTACTTCGCCAAGAGCATGGAGTTCCTGGCCAG

GCCCGTGCCAGCTCCCAGGACCGTGTTCAGGAACCCACCCCACCCAGCTCCCAG

GACCAGGACCCCAAGCCTGGCTCCCAGCAGGGCCTGCAGCAGGACCAGCCTGGT

TABLE 7-continued

GAGCACCCCACCCGGCGTGAACAGGGTGATCACCAGGGAGGAACTGGAGGCCCT

GACACCCAGCAGGACCCCCAGCAGGTCCGTGAGCAGGACTAGTCTGGTGTCCAA

CCCACCCGGCGTGAACAGGGTGATCACCAGGGAGGAATTCGAGGCCTTCGTGGC

CCAGCAACAGAGACGGTTCGACGCCGGCGCCTACATCTTCAGCAGCGACACCGG

CCAGGGACACCTGCAGCAAAAGAGCGTGAGGCAGACCGTGCTGAGCGAGGTGG

TGCTGGAGAGGACCGAGCTGGAAATCAGCTACGCCCCCAGGCTGGACCAGGAGA

AGGAGGAACTGCTCAGGAAGAAACTGCAGCTGAACCCCACCCCAGCCAACAGG

AGCAGGTACCAGAGCAGGAAGGTGGAGAACATGAAGGCCATCACCGCCAGGCG

GATCCTGCAGGGCCTGGGACACTACCTGAAGGCCGAGGGCAAGGTGGAGTGCTA

CAGGACCCTGCACCCCGTGCCACTGTACAGCTCCAGCGTGAACAGGGCCTTCTCC

AGCCCCAAGGTGGCCGTGGAGGCCTGCAACGCTATGCTGAAGGAGAACTTCCCC

ACCGTGGCCAGCTACTGCATCATCCCCGAGTACGACGCCTACCTGGACATGGTGG

ACGGCGCCAGCTGCTGCCTGGACACCGCCAGCTTCTGCCCCGCCAAGCTGAGGA

GCTTCCCCAAGAAACACAGCTACCTGGAGCCCACCATCAGGAGCGCCGTGCCCA

GCGCCATCCAGAACACCCTGCAGAACGTGCTGGCCGCTGCCACCAAGAGGAACT

GCAACGTGACCCAGATGAGGGAGCTGCCCGTGCTGGACAGCGCTGCCTTCAACG

TGGAGTGCTTCAAGAAATACGCCTGCAACAACGAGTACTGGGAGACCTTCAAGG

AGAACCCCATCAGGCTGACCGAAGAGAACGTGGTGAACTACATCACCAAGCTGA

AGGGCCCCAAGGCCGCTGCCCTGTTCGCTAAGACCCACAACCTGAACATGCTGC

AGGACATCCCAATGGACAGGTTCGTGATGGACCTGAAGAGGGACGTGAAGGTGA

CACCCGGCACCAAGCACACCGAGGAGAGGCCCAAGGTGCAGGTGATCCAGGCC

GCTGACCCACTGGCCACCGCCTACCTGTGCGGCATCCACAGGGAGCTGGTGAGG

CGGCTGAACGCCGTGCTGCTGCCCAACATCCACACCCTGTTCGACATGAGCGCCG

AGGACTTCGACGCCATCATCGCCGAGCACTTCCAGCCCGGCGACTGCGTGCTGG

AGACCGACATCGCCAGCTTCGACAAGAGCGAGGATGACGCTATGGCCCTGACCG

CTCTGATGATCCTGGAGGACCTGGGCGTGGACGCCGAGCTGCTCACCCTGATCGA

GGCTGCCTTCGGCGAGATCAGCTCCATCCACCTGCCCACCAAGACCAAGTTCAAG

TTCGGCGCTATGATGAAAAGCGGAATGTTCCTGACCCTGTTCGTGAACACCGTGA

TCAACATTGTGATCGCCAGCAGGGTGCTGCGGGAGAGGCTGACCGGCAGCCCCT

GCGCTGCCTTCATCGGCGACGACAACATCGTGAAGGGCGTGAAAAGCGACAAGC

TGATGGCCGACAGGTGCGCCACCTGGCTGAACATGGAGGTGAAGATCATCGACG

CCGTGGTGGGCGAGAAGGCCCCCTACTTCTGCGGCGGATTCATCCTGTGCGACAG

CGTGACCGGCACCGCCTGCAGGGTGGCCGACCCCCTGAAGAGGCTGTTCAAGCT

GGGCAAGCCACTGGCCGCTGACGATGAGCACGACGATGACAGGCGGAGGGCCCT

GCACGAGGAAAGCACCAGGTGGAACAGGGTGGGCATCCTGAGCGAGCTGTGCA

AGGCCGTGGAGAGCAGGTACGAGACCGTGGGCACCAGCATCATCGTGATGGCTA

TGACCACACTGGCCAGCTCCGTCAAGAGCTTCTCCTACCTGAGGGGGGCCCCTAT

AACTCTCTACGGCTAACCTGAATGGACTACGACATAGTCTAGTCCGCCAAGGCCG

CCACCACTCGAGTATGTTACGTGCAAAGGTGATTGTCACCCCCCGAAAGACCATA

TTGTGACACACCCTCAGTATCACGCCCAAACATTTACAGCCGCGGTGTCAAAAAC

TABLE 7-continued

CGCGTGGACGTGGTTAACATCCCTGCTGGGAGGATCAGCCGTAATTATTATAATT
GGCTTGGTGCTGGCTACTATTGTGGCCATGTACGTGCTGACCAACCAGAAACATA
ATTGAATACAGCAGCAATTGGCAAGCTGCTTACATAGAACTCGCGGCGATTGGC
ATGCCGCCTTAAAATTTTTATTTTATTTTTTCTTTTCTTTTCCGAATCGGATTTTGT
TTTTAATATTTCAAAAAAAAAAAAAAAAAAAAAAAAAATCTAGAAAAAAAAAAAA
AAAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAA

SEQ ID NO: 79

MEKVHVDIEEDSPFLRALQRSFPQFEVEAKQVTDNDHANARAFSHLASKLIETEVDP
SDTILDIGSAPARRMYSKHKYHCICPMRCAEDPDRLYKYATKLKKNCKEITDKELDK
KMKELAAVMSDPDLETETMCLHDDESCRYEGQVAVYQDVYAVDGPTSLYHQANK
GVRVAYWIGFDTTPFMFKNLAGAYPSYSTNWADETVLTARNIGLCSSDVMERSRRG
MSILRKKYLKPSNNVLFSVGSTIYHEKRDLLRSWHLPSVFHLRGKQNYTCRCETIVSC
DGYVVKRIAISPGLYGKPSGYAATMHREGFLCCKVTDTLNGERVSFPVCTYVPATLC
DQMTGILATDVSADDAQKLLVGLNQRIVVNGRTQRNTNTMKNYLLPVVAQAFARW
AKEYKEDQEDERPLGLRDRQLVMGCCWAFRRHKITSIYKRPDTQTIIKVNSDFHSFV
LPRIGSNTLEIGLRTRIRKMLEEHKEPSPLITAEDVQEAKCAADEAKEVREAEELRAA
LPPLAADVEEPTLEADVDLMLQEAGAGSVETPRGLIKVTSYDGEDKIGSYAVLSPQA
VLKSEKLSCIHPLAEQVIVITHSGRKGRYAVEPYHGKVVVPEGHAIPVQDFQALSESA
TIVYNEREFVNRYLHHIATHGGALNTDEEYYKTVKPSEHDGEYLYDIDRKQCVKKEL
VTGLGLTGELVDPPFHEFAYESLRTRPAAPYQVPTIGVYGVPGSGKSGIIKSAVTKKD
LVVSAKKENCAEIIRDVKKMKGLDVNARTVDSVLLNGCKHPVETLYIDEAFACHAG
TLRALIAIIRPKKAVLCGDPKQCGFFNMMCLKVHFNHEICTQVFHKSISRRCTKSVTS
VVSTLFYDKKMRTTNPKETKIVIDTTGSTKPKQDDLILTCFRGWVKQLQIDYKGNEI
MTAAASQGLTRKGVYAVRYKVNENPLYAPTSEHVNVLLTRTEDRIVWKTLAGDPW
IKTLTAKYPGNFTATIEEWQAEHDAIMRHILERPDPTDVFQNKANVCWAKALVPVL
KTAGIDMTTEQWNTVDYFETDKAHSAEIVLNQLCVRFFGLDLDSGLFSAPTVPLSIR
NNHWDNSPSPNMYGLNKEVVRQLSRRYPQLPRAVATGRVYDMNTGTLRNYDPRIN
LVPVNRRLPHALVLHHNEHPQSDFSSFVSKLKGRTVLVVGEKLSVPGKMVDWLSDR
PEATFRARLDLGIPGDVPKYDIIFVNVRTPYKYHHYQQCEDHAIKLSMLTKKACLHL
NPGGTCVSIGYGYADRASESIIGAIARLFKFSRVCKPKSSLEETEVLFVFIGYDRKART
HNPYKLSSTLTNIYTGSRLHEAGCAPSYHVVRGDIATATEGVIINAANSKGQPGGGV
CGALYKKFPESFDLQPIEVGKARLVKGAAKHIIHAVGPNFNKVSEVEGDKQLAEAYE
SIAKIVNDNNYKSVAIPLLSTGIFSGNKDRLTQSLNHLLTALDTTDADVAIYCRDKKW
EMTLKEAVARREAVEEICISDDSSVTEPDAELVRVHPKSSLAGRKGYSTSDGKTFSYL
EGTKFHQAAKDIAEINAMWPVATEANEQVCMYILGESMSSIRSKCPVEESEASTPPST
LPCLCIHAMTPERVQRLKASRPEQITVCSSFPLPKYRITGVQKIQCSQPILFSPKVPAYI
HPRKYLVETPPVDETPEPSAENQSTEGTPEQPPLITEDETRTRTPEPIIIEEEEEDSISLLS
DGPTHQVLQVEADIHGPPSVSSSSWSIPHASDFDVDSLSILDTLEGASVTSGATSAETN
SYFAKSMEFLARPVPAPRTVFRNPPHPAPRTRTPSLAPSRACSRTSLVSTPPGVNRVIT
REELEALTPSRTPSRSVSRTSLVSNPPGVNRVITREEFEAFVAQQQRRFDAGAYIFSSD

TABLE 7-continued

TGQGHLQQKSVRQTVLSEVVLERTELEISYAPRLDQEKEELLRKKLQLNPTPANRSR

YQSRKVENMKAITARRILQGLGHYLKAEGKVECYRTLHPVPLYSSSVNRAFSSPKVA

VEACNAMLKENFPTVASYCIIPEYDAYLDMVDGASCCLDTASFCPAKLRSFPKKHSY

LEPTIRSAVPSAIQNTLQNVLAAATKRNCNVTQMRELPVLDSAAFNVECFKKYACNN

EYWETFKENPIRLTEENVVNYITKLKGPKAAALFAKTHNLNMLQDIPMDRFVMDLK

RDVKVTPGTKHTEERPKVQVIQAADPLATAYLCGIHRELVRRLNAVLLPNIHTLFDM

SAEDFDAIIAEHFQPGDCVLETDIASFDKSEDDAMALTALMILEDLGVDAELLTLIEA

AFGEISSIHLPTKTKFKFGAMMKSGMFLTLFVNTVINIVIASRVLRERLTGSPCAAFIG

DDNIVKGVKSDKLMADRCATWLNMEVKIIDAVVGEKAPYFCGGFILCDSVTGTACR

VADPLKRLFKLGKPLAADDEHDDDRRRALHEESTRWNRVGILSELCKAVESRYETV

GTSIIVMAMTTLASSVKSFSYLRGAPITLYG

MPEKVHVDIEEDSPFLRALQRSFPQFEVEAKQVTDNDHANARAFSHLASKLIETEVD    SEQ ID NO: 80

PSDTILDIGSAPARRMYSKHKYHCICPMRCAEDPDRLYKYATKLKKNCKEITDKELD

KKMKELAAVMSDPDLETETMCLHDDESCRYEGQVAVYQDVYAVDGPTSLYHQAN

KGVRVAYWIGFDTTPFMFKNLAGAYPSYSTNWADETVLTARNIGLCSSDVMERSRR

GMSILRKKYLKPSNNVLFSVGSTIYHEKRDLLRSWHLPSVFHLRGKQNYTCRCETIVS

CDGYVVKRIAISPGLYGKPSGYAATMHREGFLCCKVTDTLNGERVSFPVCTYVPATL

CDQMTGILATDVSADDAQKLLVGLNQRIVVNGRTQRNTNTMKNYLLPVVAQAFAR

WAKEYKEDQEDERPLGLRDRQLVMGCCWAFRRHKITSIYKRPDTQTIIKVNSDFHSF

VLPRIGSNTLEIGLRTRIRKMLEEHKEPSPLITAEDVQEAKCAADEAKEVREAEELRA

ALPPLAADVEEPTLEADVDLMLQEAGAGSVETPRGLIKVTSYDGEDKIGSYAVLSPQ

AVLKSEKLSCIHPLAEQVIVITHSGRKGRYAVEPYHGKVVVPEGHAIPVQDFQALSES

ATIVYNEREFVNRYLHHIATHGGALNTDEEYYKTVKPSEHDGEYLYDIDRKQCVKK

ELVTGLGLTGELVDPPFHEFAYESLRTRPAAPYQVPTIGVYGVPGSGKSGIIKSAVTK

KDLVVSAKKENCAEIIRDVKKMKGLDVNARTVDSVLLNGCKHPVETLYIDEAFACH

AGTLRALIAIIRPKKAVLCGDPKQCGFFNMMCLKVHFNHEICTQVFHKSISRRCTKSV

TSVVSTLFYDKKMRTTNPKETKIVIDTTGSTKPKQDDLILTCFRGWVKQLQIDYKGN

EIMTAAASQGLTRKGVYAVRYKVNENPLYAPTSEHVNVLLTRTEDRIVWKTLAGDP

WIKTLTAKYPGNFTATIEEWQAEHDAIMRHILERPDPTDVFQNKANVCWAKALVPV

LKTAGIDMTTEQWNTVDYFETDKAHSAEIVLNQLCVRFFGLDLDSGLFSAPTVPLSIR

NNHWDNSPSPNMYGLNKEVVRQLSRRYPQLPRAVATGRVYDMNTGTLRNYDPRIN

LVPVNRRLPHALVLHHNEHPQSDFSSFVSKLKGRTVLVVGEKLSVPGKMVDWLSDR

PEATFRARLDLGIPGDVPKYDIIFVNVRTPYKYHHYQQCEDHAIKLSMLTKKACLHL

NPGGTCVSIGYGYADRASESIIGAIARLFKFSRVCKPKSSLEETEVLFVFIGYDRKART

HNPYKLSSTLTNIYTGSRLHEAGCAPSYHVVRGDIATATEGVIINAANSKGQPGGGV

CGALYKKFPESFDLQPIEVGKARLVKGAAKHIIHAVGPNFNKVSEVEGDKQLAEAYE

SIAKIVNDNNYKSVAIPLLSTGIFSGNKDRLTQSLNHLLTALDTTDADVAIYCRDKKW

EMTLKEAVARREAVEEICISDDSSVTEPDAELVRVHPKSSLAGRKGYSTSDGKTFSYL

EGTKFHQAAKDIAEINAMWPVATEANEQVCMYILGESMSSIRSKCPVEESEASTPPST

TABLE 7-continued

LPCLCIHAMTPERVQRLKASRPEQITVCSSFPLPKYRITGVQKIQCSQPILFSPKVPAYI

HPRKYLVETPPVDETPEPSAENQSTEGTPEQPPLITEDETRTRTPEPIIIEEEEEDSISLLS

DGPTHQVLQVEADIHGPPSVSSSSWSIPHASDFDVDSLSILDTLEGASVTSGATSAETN

SYFAKSMEFLARPVPAPRTVFRNPPHPAPRTRTPSLAPSRACSRTSLVSTPPGVNRVIT

REELEALTPSRTPSRSVSRTSLVSNPPGVNRVITREEFEAFVAQQQRRFDAGAYIFSSD

TGQGHLQQKSVRQTVLSEVVLERTELEISYAPRLDQEKEELLRKKLQLNPTPANRSR

YQSRKVENMKAITARRILQGLGHYLKAEGKVECYRTLHPVPLYSSSVNRAFSSPKVA

VEACNAMLKENFPTVASYCIIPEYDAYLDMVDGASCCLDTASFCPAKLRSFPKKHSY

LEPTIRSAVPSAIQNTLQNVLAAATKRNCNVTQMRELPVLDSAAFNVECFKKYACNN

EYWETFKENPIRLTEENVVNYITKLKGPKAAALFAKTHNLNMLQDIPMDRFVMDLK

RDVKVTPGTKHTEERPKVQVIQAADPLATAYLCGIHRELVRRLNAVLLPNIHTLFDM

SAEDFDAIIAEHFQPGDCVLETDIASFDKSEDDAMALTALMILEDLGVDAELLTLIEA

AFGEISSIHLPTKTKFKFGAMMKSGMFLTLFVNTVINIVIASRVLRERLTGSPCAAFIG

DDNIVKGVKSDKLMADRCATWLNMEVKIIDAVVGEKAPYFCGGFILCDSVTGTACR

VADPLKRLFKLGKPLAADDEHDDDRRRALHEESTRWNRVGILSELCKAVESRYETV

GTSIIVMAMTTLASSVKSFSYLRGAPITLYG

SEQ ID NO: 81

MEKVHVDIEEDSPFLRALQRSFPQFEVEAKQVTDNDHANARAFSHLASKLIETEVDP

SDTILDIGSAPARRMYSKHKYHCICPMRCAEDPDRLYKYATKLKKNCKEITDKELDK

KMKELAAVMSDPDLETETMCLHDDESCRYEGQVAVYQDVYAVDGPTSLYHQANK

GVRVAYWIGFDTTPFMFKNLAGAYPSYSTNWADETVLTARNIGLCSSDVMERSRRG

MSILRKKYLKPSNNVLFSVGSTIYHEKRDLLRSWHLPSVFHLRGKQNYTCRCETIVSC

DGYVVKRIAISPGLYGKPSGYAATMHREGFLCCKVTDTLNGERVSFPVCTYVPATLC

DQMTGILATDVSADDAQKLLVGLNQRIVVNGRTQRNTNTMKNYLLPVVAQAFARW

AKEYKEDQEDERPLGLRDRQLVMGCCWAFRRHKITSIYKRPDTQTIIKVNSDFHSFV

LPRIGSNTLEIGLRTRIRKMLEEHKEPSPLITAEDIQEAKCAADEAKEVREAEELRAAL

PPLAADFEEPTLEADVDLMLQEAGAGSVETPRGLIKVTSYAGEDKIGSYAVLSPQAV

LKSEKLSCIHPLAEQVIVITHSGRKGRYAVEPYHGKVVVPEGHAIPVQDFQALSESAT

IVYNEREFVNRYLHHIATHGGALNTDEEYYKTVKPSEHDGEYLYDIDRKQCVKKEL

VTGLGLTGELVDPPFHEFAYESLRTRPAAPYQVPTIGVYGVPGSGKSGIIKSAVTKKD

LVVSAKKENCAEIIRDVKKMKGLDVNARTVDSVLLNGCKHPVETLYIDEAFACHAG

TLRALIAIIRPKKAVLCGDPKQCGFFNMMCLKVHFNHEICTQVFHKSISRRCTKSVTS

VVSTLFYDKRMRTTNPKETKIVIDTTGSTKPKQDDLILTCFRGWVKQLQIDYKGNEI

MTAAASQGLTRKGVYAVRYKVNENPLYAPTSEHVNVLLTRTEDRIVWKTLAGDPW

IKILTAKYPGNFTATIEEWQAEHDAIMRHILERPDPTDVFQNKANVCWAKALVPVLK

TAGIDMTTEQWNTVDYFETDKAHSAEIVLNQLCVRFFGLDLDSGLFSAPTVPLSIRN

NHWDNSPSPNMYGLNKEVVRQLSRRYPQLPRAVATGRVYDMNTGTLRNYDPRINL

VPVNRRLPHALVLHHNEHPQSDFSSFVSKLKGRTVLVVGEKLSVPGKKVDWLSDQP

EATFRARLDLGIPGDVPKYDIVFINVRTPYKYHHYQQCEDHAIKLSMLTKKACLHLN

PGGTCVSIGYGYADRASESIIGAIARQFKFSRVCKPKSSHEETEVLFVFIGYDRKARTH

NPYKLSSTLTNIYTGSRLHEAGCAPSYHVVRGDIATATEGVIINAANSKGQPGGGVC

TABLE 7-continued

```
GALYKKFPESFDLQPIEVGKARLVKGAAKHIIHAVGPNFNKVSEVEGDKQLAEAYES

IAKIVNDNNYKSVAIPLLSTGIFSGNKDRLTQSLNHLLTALDTTDADVAIYCRDKKWE

MTLKEAVARREAVEEICISDDSSVTEPDAELVRVHPKSSLAGRKGYSTSDGKTFSYLE

GTKFHQAAKDIAEINAMWPVATEANEQVCMYILGESMSSIRSKCPVEESEASTPPSTL

PCLCIHAMTPERVQRLKASRPEQITVCSSFPLPKYRITGVQKIQCSQPILFSPKVPAYIH

PRKYLVETPPVEETPESPAENQSTEGTPEQPALVNVDATRTRMPEPIIIEEEEEDSISLL

SDGPTHQVLQVEADIHGSPSVSSSSWSIPHASDFDVDSLSILDTLDGASVTSGAVSAET

NSYFARSMEFRARPVPAPRTVFRNPPHPAPRTRTPPLAHSRASSRTSLVSTPPGVNRVI

TREELEALTPSRAPSRSASRTSLVSNPPGVNRVITREEFEAFVAQQQ*RFDAGAYIFSS

DTGQGHLQQKSVRQTVLSEVVLERTELEISYAPRLDQEKEELLRKKLQLNPTPANRS

RYQSRRVENMKAITARRILQGLGHYLKAEGKVECYRTLHPVPLYSSSVNRAFSSPKV

AVEACNAMLKENFPTVASYCIIPEYDAYLDMVDGASCCLDTASFCPAKLRSFPKKHS

YLEPTIRSAVPSAIQNTLQNVLAAATKRNCNVTQMRELPVLDSAAFNVECFKKYACN

NEYWETFKENPIRLTEENVVNYITKLKGPKAAALFAKTHNLNMLQDIPMDRFVMDL

KRDVKVTPGTKHTEERPKVQVIQAADPLATADLCGIHRELVRRLNAVLLPNIHTLFD

MSAEDFDAIIAEHFQPGDCVLETDIASFDKSEDDAMALTALMILEDLGVDAELLTLIE

AAFGEISSIHLPTKTKFKFGAMMKSGMFLTLFVNTVINIVIASRVLRERLTGSPCAAFI

GDDNIVKGVKSDKLMADRCATWLNMEVKIIDAVVGEKAPYFCGGFILCDSVTGTAC

RVADPLKRLFKLGKPLAVDDEHDDDRRRALHEESTRWNRVGILPELCKAVESRYET

VGTSIIVMAMTTLASSVKSFSYLRGAPITLYG*
```

SEQ ID NO: 82
```
AGGAAACTTAAGTCAACACAACATATACAAAACAAACGAATCTCAAGCAATCAA

GCATTCTACTTCTATTGCAGCAATTTAAATCATTTCTTTTAAAGCAAAAGCAATTT

TCTGAAAATTTTCACCATTTACGAACGATAGCCACC
```

SEQ ID NO: 83
```
ACTCGAGCTAGTGACTGACTAGGATCTGGTTACCACTAAACCAGCCTCAAGAAC

ACCCGAATGGAGTCTCTAAGCTACATAATACCAACTTACACTTACAAAATGTTGT

CCCCCAAAATGTAGCCATTCGTATCTGCTCCTAATAAAAAGAAAGTTTCTTCACA

TTCTAGAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAA

AA
```

SEQ ID NO: 1
```
GAGGAAACTT AAGAUGGG
```

SEQ ID NO: 2
```
GGAUGGG
```

SEQ ID NO: 3
```
GGAUAGG
```

SEQ ID NO: 4
```
GGAGAGG
```

SEQ ID NO: 58
```
GGGAUGGG
```

SEQ ID NO: 59
```
GAGAGG
```

TABLE 7-continued

SEQ ID NO: 60
GAGGG

SEQ ID NO: 61
GAGAUGGG

SEQ ID NO: 62
GAGUGG

SEQ ID NO: 63
GAGGGG

SEQ ID NO: 64
GAGUAGG

SEQ ID NO: 65
GAGUGGG

SEQ ID NO: 66
GAUGGG (RNA sequence for a construct with two subgenomic promoters, Luc, and E3L)
SEQ ID NO: 117
atgggcggcgcatgagagaagcccagaccaattacctacccaaaatggagaaagttcacgttgacatcgaggaagacagcccatt cctcagagctttgcagcggagcttcccgcagtttgaggtagaagccaagcaggtcactgataatgaccatgctaatgccagagcgtt ttcgcatctggcttcaaaactgatcgaaacggaggtggacccatccgacacgatccttgacattggaagtgcgcccgcccgcagaat gtattctaagcacaagtatcattgtatctgtccgatgagatgtgcggaagatccggacagattgtataagtatgcaactaagctgaa gaaaaactgtaaggaaataactgataaggaattggacaagaaaatgaaggagctggccgccgtcatgagcgaccctgacctgga aactgagactatgtgcctccacgacgacgagtcgtgtcgctacgaagggcaagtcgctgtttaccaggatgtatacgcCGTCGAC

GGCCCCACCAGCCTGTACCACCAGGCCAACAAGGGCGTGAGGGTGGCCTACTGGATCGGCTTCGAC

ACCACACCCTTCATGTTCAAGAACCTGGCCGGCGCCTACCCCAGCTACAGCACCAACTGGGCCGACG

AGACCGTGCTGACCGCCAGGAACATCGGCCTGTGCAGCAGCGACGTGATGGAGAGGAGCCGGAGA

GGCATGAGCATCCTGAGGAAGAAATACCTGAAGCCCAGCAACAACGTGCTGTTCAGCGTGGGCAGC

ACCATCTACCACGAGAAGAGGGACCTGCTCAGGAGCTGGCACCTGCCCAGCGTGTTCCACCTGAGG

GGCAAGCAGAACTACACCTGCAGGTGCGAGACCATCGTGAGCTGCGACGGCTACGTGGTGAAGAG

GATCGCCATCAGCCCCGGCCTGTACGGCAAGCCCAGCGGCTACGCCGCTACAATGCACAGGGAGGG

CTTCCTGTGCTGCAAGGTGACCGACACCCTGAACGGCGAGAGGGTGAGCTTCCCCGTGTGCACCTA

CGTGCCCGCCACCCTGTGCGACCAGATGACCGGCATCCTGGCCACCGACGTGAGCGCCGACGACGC

CCAGAAGCTGCTCGTGGGCCTGAACCAGAGGATCGTGGTCAACGGCAGGACCCAGAGGAACACCA

ACACAATGAAGAACTACCTGCTGCCCGTGGTGGCCCAGGCTTTCGCCAGGTGGGCCAAGGAGTACA

AGGAGGACCAGGAAGACGAGAGGCCCCTGGGCCTGAGGGACAGGCAGCTGGTGATGGGCTGCTG

CTGGGCCTTCAGGCGGCACAAGATCACCAGCATCTACAAGAGGCCCGACACCCAGACCATCATCAA

GGTGAACAGCGACTTCCACAGCTTCGTGCTGCCCAGGATCGGCAGCAACACCCTGGAGATCGGCCT

GAGGACCCGGATCAGGAAGATGCTGGAGGAACACAAGGAGCCCAGCCCACTGATCACCGCCGAGG

ACGTGCAGGAGGCCAAGTGCGCTGCCGACGAGGCCAAGGAGGTGAGGGAGGCCGAGGAACTGAG

GGCCGCCCTGCCACCCCTGGCTGCCGACGTGGAGGAACCCACCCTGGAAGCCGACGTGGACCTGAT

GCTGCAGGAGGCCGGCGCCGGAAGCGTGGAGACACCCAGGGGCCTGATCAAGGTGACCAGCTACG

ACGGCGAGGACAAGATCGGCAGCTACGCCGTGCTGAGCCCACAGGCCGTGCTGAAGTCCGAGAAG

CTGAGCTGCATCCACCCACTGGCCGAGCAGGTGATCGTGATCACCCACAGCGGCAGGAAGGGCAG

GTACGCCGTGGAGCCCTACCACGGCAAGGTGGTCGTGCCCGAGGGCCACGCCATCCCCGTGCAGGA

CTTCCAGGCCCTGAGCGAGAGCGCCACCATCGTGTACAACGAGAGGGAGTTCGTGAACAGGTACCT

TABLE 7-continued

GCACCATATCGCCACCCACGGCGGAGCCCTGAACACCGACGAGGAATACTACAAGACCGTGAAGCC

CAGCGAGCACGACGGCGAGTACCTGTACGACATCGACAGGAAGCAGTGCGTGAAGAAAGAGCTGG

TGACCGGCCTGGGACTGACCGGCGAGCTGGTGGACCCACCCTTCCACGAGTTCGCCTACGAGAGCC

TGAGGACCAGACCCGCCGCTCCCTACCAGGTGCCCACCATCGGCGTGTACGGCGTGCCCGGCAGCG

GAAAGAGCGGCATCATCAAGAGCGCCGTGACCAAGAAAGACCTGGTGGTCAGCGCCAAGAAAGAG

AACTGCGCCGAGATCATCAGGGACGTGAAGAAGATGAAAGGCCTGGACGTGAACGCGCGCACCGT

GGACAGCGTGCTGCTGAACGGCTGCAAGCACCCCGTGGAGACCCTGTACATCGACGAGGCCTTCGC

TTGCCACGCCGGCACCCTGAGGGCCCTGATCGCCATCATCAGGCCCAAGAAAGCCGTGCTGTGCGG

CGACCCCAAGCAGTGCGGCTTCTTCAACATGATGTGCCTGAAGGTGCACTTCAACCACGAGATCTGC

ACCCAGGTGTTCCACAAGAGCATCAGCAGGCGGTGCACCAAGAGCGTGACCAGCGTCGTGAGCACC

CTGTTCTACGACAAGAAAATGAGGACCACCAACCCCAAGGAGACCAAAATCGTGATCGACACCACA

GGCAGCACCAAGCCCAAGCAGGACGACCTGATCCTGACCTGCTTCAGGGGCTGGGTGAAGCAGCTG

CAGATCGACTACAAGGGCAACGAGATCATGACCGCCGCTGCCAGCCAGGGCCTGACCAGGAAGGG

CGTGTACGCCGTGAGGTACAAGGTGAACGAGAACCCACTGTACGCTCCCACCAGCGAGCACGTGAA

CGTGCTGCTGACCAGGACCGAGGACAGGATCGTGTGGAAGACCCTGGCCGGCGACCCCTGGATCA

AGACCCTGACCGCCAAGTACCCCGGCAACTTCACCGCCACCATCGAAGAGTGGCAGGCCGAGCACG

ACGCCATCATGAGGCACATCCTGGAGAGGCCCGACCCCACCGACGTGTTCCAGAACAAGGCCAACG

TGTGCTGGGCCAAGGCCCTGGTGCCCGTGCTGAAGACCGCCGGCATCGACATGACCACAGAGCAGT

GGAACACCGTGGACTACTTCGAGACCGACAAGGCCCACAGCGCCGAGATCGTGCTGAACCAGCTGT

GCGTGAGGTTCTTCGGCCTGGACCTGGACAGCGGCCTGTTCAGCGCCCCCACCGTGCCACTGAGCAT

CAGGAACAACCACTGGGACAACAGCCCCAGCCCAAACATGTACGGCCTGAACAAGGAGGTGGTCA

GGCAGCTGAGCAGGCGGTACCCACAGCTGCCCAGGGCCGTGGCCACCGGCAGGGTGTACGACATG

AACACCGGCACCCTGAGGAACTACGACCCCAGGATCAACCTGGTGCCCGTGAACAGGCGGCTGCCC

CACGCCCTGGTGCTGCACCACAACGAGCACCCACAGAGCGACTTCAGCTCCTTCGTGAGCAAGCTGA

AAGGCAGGACCGTGCTGGTCGTGGGCGAGAAGCTGAGCGTGCCCGGCAAGATGGTGGACTGGCTG

AGCGACAGGCCCGAGGCCACCTTCCGGGCCAGGCTGGACCTCGGCATCCCCGGCGACGTGCCCAAG

TACGACATCATCTTCGTGAACGTCAGGACCCCATACAAGTACCACCATTACCAGCAGTGCGAGGACC

ACGCCATCAAGCTGAGCATGCTGACCAAGAAGGCCTGCCTGCACCTGAACCCCGGAGGCACCTGCG

TGAGCATCGGCTACGGCTACGCCGACAGGGCCAGCGAGAGCATCATTGGCGCCATCGCCAGGCTGT

TCAAGTTCAGCAGGGTGTGCAAACCCAAGAGCAGCCTGGAGGAAACCGAGGTGCTGTTCGTGTTCA

TCGGCTACGACCGGAAGGCCAGGACCCACAACCCCTACAAGCTGAGCAGCACCCTGACAAACATCT

ACACCGGCAGCAGGCTGCACGAGGCCGGCTGCGCCCCCAGCTACCACGTGGTCAGGGGCGATATC

GCCACCGCCACCGAGGGCGTGATCATCAACGCTGCCAACAGCAAGGGCCAGCCCGGAGGCGGAGT

GTGCGGCGCCCTGTACAAGAAGTTCCCCGAGAGCTTCGACCTGCAGCCCATCGAGGTGGGCAAGGC

CAGGCTGGTGAAGGGCGCCGCTAAGCACATCATCCACGCCGTGGGCCCCAACTTCAACAAGGTGAG

CGAGGTGGAAGGCGACAAGCAGCTGGCCGAAGCCTACGAGAGCATCGCCAAGATCGTGAACGACA

ATAACTACAAGAGCGTGGCCATCCCACTGCTCAGCACCGGCATCTTCAGCGGCAACAAGGACAGGC

TGACCCAGAGCCTGAACCACCTGCTCACCGCCCTGGACACCACCGATGCCGACGTGGCCATCTACTG

CAGGGACAAGAAGTGGGAGATGACCCTGAAGGAGGCCGTGGCCAGGCGGGAGGCCGTGGAAGAG

ATCTGCATCAGCGACGACTCCAGCGTGACCGAGCCCGACGCCGAGCTGGTGAGGGTGCACCCCAAG

TABLE 7-continued

AGCTCCCTGGCCGGCAGGAAGGGCTACAGCACCAGCGACGGCAAGACCTTCAGCTACCTGGAGGG

CACCAAGTTCCACCAGGCCGCTAAGGACATCGCCGAGATCAACGCTATGTGGCCCGTGGCCACCGA

GGCCAACGAGCAGGTGTGCATGTACATCCTGGGCGAGAGCATGTCCAGCATCAGGAGCAAGTGCCC

CGTGGAGGAAAGCGAGGCCAGCACACCACCCAGCACCCTGCCCTGCCTGTGCATCCACGCTATGAC

ACCCGAGAGGGTGCAGCGGCTGAAGGCCAGCAGGCCCGAGCAGATCACCGTGTGCAGCTCCTTCCC

ACTGCCCAAGTACAGGATCACCGGCGTGCAGAAGATCCAGTGCAGCCAGCCCATCCTGTTCAGCCCA

AAGGTGCCCGCCTACATCCACCCCAGGAAGTACCTGGTGGAGACCCCACCCGTGGACGAGACACCC

GAGCCAAGCGCCGAGAACCAGAGCACCGAGGGCACACCCGAGCAGCCACCCCTGATCACCGAGGA

CGAGACAAGGACCCGGACCCCAGAGCCCATCATTATCGAGGAAGAGGAAGAGGACAGCATCAGCC

TGCTGAGCGACGGCCCCACCCACCAGGTGCTGCAGGTGGAGGCCGACATCCACGGCCCACCCAGCG

TGTCCAGCTCCAGCTGGAGCATCCCACACGCCAGCGACTTCGACGTGGACAGCCTGAGCATCCTGG

ACACCCTGGAGGGCGCCAGCGTGACCTCCGGCGCCACCAGCGCCGAGACCAACAGCTACTTCGCCA

AGAGCATGGAGTTCCTGGCCAGGCCCGTGCCAGCTCCCAGGACCGTGTTCAGGAACCCACCCCACC

CAGCTCCCAGGACCAGGACCCCAAGCCTGGCTCCCAGCAGGGCCTGCAGCAGGACCAGCCTGGTGA

GCACCCCACCCGGCGTGAACAGGGTGATCACCAGGGAGGAACTGGAGGCCCTGACACCCAGCAGG

ACCCCCAGCAGGTCCGTGAGCAGGACTAGTCTGGTGTCCAACCCACCCGGCGTGAACAGGGTGATC

ACCAGGGAGGAATTCGAGGCCTTCGTGGCCCAGCAACAGAGACGGTTCGACGCCGGCGCCTACATC

TTCAGCAGCGACACCGGCCAGGGACACCTGCAGCAAAAGAGCGTGAGGCAGACCGTGCTGAGCGA

GGTGGTGCTGGAGAGGACCGAGCTGGAAATCAGCTACGCCCCCAGGCTGGACCAGGAGAAGGAG

GAACTGCTCAGGAAGAAACTGCAGCTGAACCCCACCCCAGCCAACAGGAGCAGGTACCAGAGCAG

GAAGGTGGAGAACATGAAGGCCATCACCGCCAGGCGGATCCTGCAGGGCCTGGGACACTACCTGA

AGGCCGAGGGCAAGGTGGAGTGCTACAGGACCCTGCACCCCGTGCCACTGTACAGCTCCAGCGTGA

ACAGGGCCTTCTCCAGCCCCAAGGTGGCCGTGGAGGCCTGCAACGCTATGCTGAAGGAGAACTTCC

CCACCGTGGCCAGCTACTGCATCATCCCCGAGTACGACGCCTACCTGGACATGGTGGACGGCGCCA

GCTGCTGCCTGGACACCGCCAGCTTCTGCCCCGCCAAGCTGAGGAGCTTCCCCAAGAAACACAGCTA

CCTGGAGCCCACCATCAGGAGCGCCGTGCCCAGCGCCATCCAGAACACCCTGCAGAACGTGCTGGC

CGCTGCCACCAAGAGGAACTGCAACGTGACCCAGATGAGGGAGCTGCCCGTGCTGGACAGCGCTG

CCTTCAACGTGGAGTGCTTCAAGAAATACGCCTGCAACAACGAGTACTGGGAGACCTTCAAGGAGA

ACCCCATCAGGCTGACCGAAGAGAACGTGGTGAACTACATCACCAAGCTGAAGGGCCCCAAGGCCG

CTGCCCTGTTCGCTAAGACCCACAACCTGAACATGCTGCAGGACATCCCAATGGACAGGTTCGTGAT

GGACCTGAAGAGGGACGTGAAGGTGACACCCGGCACCAAGCACACCGAGGAGAGGCCCAAGGTG

CAGGTGATCCAGGCCGCTGACCCACTGGCCACCGCCTACCTGTGCGGCATCCACAGGGAGCTGGTG

AGGCGGCTGAACGCCGTGCTGCTGCCCAACATCCACACCCTGTTCGACATGAGCGCCGAGGACTTC

GACGCCATCATCGCCGAGCACTTCCAGCCCGGCGACTGCGTGCTGGAGACCGACATCGCCAGCTTC

GACAAGAGCGAGGATGACGCTATGGCCCTGACCGCTCTGATGATCCTGGAGGACCTGGGCGTGGA

CGCCGAGCTGCTCACCCTGATCGAGGCTGCCTTCGGCGAGATCAGCTCCATCCACCTGCCCACCAAG

ACCAAGTTCAAGTTCGGCGCTATGATGAAAAGCGGAATGTTCCTGACCCTGTTCGTGAACACCGTGA

TCAACATTGTGATCGCCAGCAGGGTGCTGCGGGAGAGGCTGACCGGCAGCCCCTGCGCTGCCTTCA

TCGGCGACGACAACATCGTGAAGGGCGTGAAAAGCGACAAGCTGATGGCCGACAGGTGCGCCACC

TGGCTGAACATGGAGGTGAAGATCATCGACGCCGTGGTGGGCGAGAAGGCCCCCTACTTCTGCGGC

TABLE 7-continued

| |
|---|
| GGATTCATCCTGTGCGACAGCGTGACCGGCACCGCCTGCAGGGTGGCCGACCCCCTGAAGAGGCTG |
| TTCAAGCTGGGCAAGCCACTGGCCGCTGACGATGAGCACGACGATGACAGGCGGAGGGCCCTGCA |
| CGAGGAAAGCACCAGGTGGAACAGGGTGGGCATCCTGAGCGAGCTGTGCAAGGCCGTGGAGAGC |
| AGGTACGAGACCGTGGGCACCAGCATCATCGTGATGGCTATGACCACACTGGCCAGCTCCGTCAAG |
| AGCTTCTCCTACCTGAGGGGGGCCCCTATAACTCTCTACGGCTAACCTGAATGGACTACGACATAGT |
| CTAgccaccATGagcaagatctacatcgacgagcggagcaacgccgagatcgtgtgcgaggccatcaagaccatcggcatcga |
| gggcgccaccgccgcccagctgaccaggcagctgaacatggagaagcgggaggtgaacaaggccctgtacgacctgcagaggag |
| cgctatggtgtactccagcgacgacatccctccccggtggttcatgaccaccgaggccgacaagcccgacgccgacgctatggccg |
| acgtgatcatcgacgacgtgagcagggagaagtccatgagggaggaccacaagagcttcgacgacgtgatccccgccaagaaga |
| tcatcgactggaagggcgccaaccccgtgaccgtgatcaacgagtactgccagatcaccaggagggactggagcttccggatcga |
| gagcgtgggccccagcaacagccccaccttctacgcctgcgtggacatcgacggcagggtgttcgacaaggccgacggcaagagc |
| aagcgggacgccaagaacaacgccgccaagctggccgtggacaagctgctgggctacgtgatcatccggttcTAAactcgagcta |
| gtgactgactaggatctggttaccactaaaccagcctcaagaacacccgaatggagtctctaagctacataataccaacttacactt |
| acaaaatgttgtcccccaaaatgtagccattcgtatctgctcctaataaaaagaaagtttcttcacattctagAGCTCCGTCAAG |
| AGCTTCTCCTACCTGAGGGGGGCCCCTATAACTCTCTACGGCTAACCTGAATGGACTACGACATAGT |
| CTAGCCACCATGGAAGATGCCAAAAACATTAAGAAGGGCCCAGCGCCATTCTACCCACTCGAAGAC |
| GGGACCGCCGGCGAGCAGCTGCACAAAGCCATGAAGCGCTACGCCCTGGTGCCCGGCACCATCGCC |
| TTTACCGACGCACATATCGAGGTGGACATTACCTACGCCGAGTACTTCGAGATGAGCGTTCGGCTGG |
| CAGAAGCTATGAAGCGCTATGGGCTGAATACAAACCATCGGATCGTGGTGTGCAGCGAGAATAGCT |
| TGCAGTTCTTCATGCCCGTGTTGGGTGCCCTGTTCATCGGTGTGGCTGTGGCCCCAGCTAACGACAT |
| CTACAACGAGCGCGAGCTGCTGAACAGCATGGGCATCAGCCAGCCCACCGTCGTATTCGTGAGCAA |
| GAAAGGGCTGCAAAAGATCCTCAACGTGCAAAAGAAGCTACCGATCATACAAAAGATCATCATCAT |
| GGATAGCAAGACCGACTACCAGGGCTTCCAAAGCATGTACACCTTCGTGACTTCCCATTTGCCACCC |
| GGCTTCAACGAGTACGACTTCGTGCCCGAGAGCTTCGACCGGGACAAAACCATCGCCCTGATCATGA |
| ACAGTAGTGGCAGTACCGGATTGCCCAAGGGCGTAGCCCTACCGCACCGCACCGCTTGTGTCCGATT |
| CAGTCATGCCCGCGACCCCATCTTCGGCAACCAGATCATCCCCGACACCGCTATCCTCAGCGTGGTG |
| CCATTTCACCACGGCTTCGGCATGTTCACCACGCTGGGCTACTTGATCTGCGGCTTTCGGGTCGTGCT |
| CATGTACCGCTTCGAGGAGGAGCTATTCTTGCGCAGCTTGCAAGACTATAAGATTCAATCTGCCCTG |
| CTGGTGCCCACACTATTTAGCTTCTTCGCTAAGAGCACTCTCATCGACAAGTACGACCTAAGCAACTT |
| GCACGAGATCGCCAGCGGCGGGGCGCCGCTCAGCAAGGAGGTAGGTGAGGCCGTGGCCAAACGC |
| TTCCACCTACCAGGCATCCGACAGGGCTACGGCCTGACAGAAACAACCAGCGCCATTCTGATCACCC |
| CCGAAGGGGACGACAAGCCTGGCGCAGTAGGCAAGGTGGTGCCCTTCTTCGAGGCTAAGGTGGTG |
| GACTTGGACACCGGTAAGACACTGGGTGTGAACCAGCGCGGCGAGCTGTGCGTCCGTGGCCCCATG |
| ATCATGAGCGGCTACGTTAACAACCCCGAGGCTACAAACGCTCTCATCGACAAGGACGGCTGGCTG |
| CACAGCGGCGACATCGCCTACTGGGACGAGGACGAGCACTTCTTCATCGTGGACCGGCTGAAGTCC |
| CTGATCAAATACAAGGGCTACCAGGTAGCCCCAGCCGAACTGGAGAGCATCCTGCTGCAACACCCC |
| AACATCTTCGACGCCGGGGTCGCCGGCCTGCCCGACGACGATGCCGGCGAGCTGCCCGCCGCAGTC |
| GTCGTGCTGGAACACGGTAAAACCATGACCGAGAAGGAGATCGTGGACTATGTGGCCAGCCAGGTT |
| ACAACCGCCAAGAAGCTGCGCGGTGGTGTTGTGTTCGTGGACGAGGTGCCTAAAGGACTGACCGG |
| CAAGTTGGACGCCCGCAAGATCCGCGAGATTCTCATTAAGGCCAAGAAGGGCGGCAAGATCGCCGT |

TABLE 7-continued

GTAACTCGAGTATGTTACGTGCAAAGGTGATTGTCACCCCCCGAAAGACCATATTGTGACACACCCT

CAGTATCACGCCCAAACATTTACAGCCGCGGTGTCAAAAACCGCGTGGACGTGGTTAACATCCCTGC

TGGGAGGATCAGCCGTAATTATTATAATTGGCTTGGTGCTGGCTACTATTGTGGCCATGTACGTGCT

GACCAACCAGAAACATAATTGAATACAGCAGCAATTGGCAAGCTGCTTACATAGAACTCGCGGCGA

TTGGCATGCCGCCTTAAAATTTTTATTTTATTTTTTCTTTTCTTTTCCGAATCGGATTTTGTTTTTAATAT

TTCAAAAAAAAAAAAAAAAAAAAAAAAATctagAAAAAAAAAAAAAAAAAAAAAAAAAAAAAAAA

AAAAAAAAAAAAAAAAAAAAAAAAAAAAAAAAAAAAAAAAAAAAAAaaaaaaaaaaaaaaaaaaaa (RNA sequence for STARR Fluc IRES-E3L)

SEQ ID NO: 118

AUGGGCGGCGCAUGAGAGAAGCCCAGACCAAUUACCUACCCAAAAUGGAGAAA

GUUCACGUUGACAUCGAGGAAGACAGCCCAUUCCUCAGAGCUUUGCAGCGGAG

CUUCCCGCAGUUUGAGGUAGAAGCCAAGCAGGUCACUGAUAAUGACCAUGCUA

AUGCCAGAGCGUUUUCGCAUCUGGCUUCAAAACUGAUCGAAACGGAGGUGGA

CCCAUCCGACACGAUCCUUGACAUUGGAAGUGCGCCCGCCCGCAGAAUGUAUU

CUAAGCACAAGUAUCAUUGUAUCUGUCCGAUGAGAUGUGCGGAAGAUCCGGA

CAGAUUGUAUAAGUAUGCAACUAAGCUGAAGAAAAACUGUAAGGAAAUAACU

GAUAAGGAAUUGGACAAGAAAAUGAAGGAGCUGGCCGCCGUCAUGAGCGACC

CUGACCUGGAAACUGAGACUAUGUGCCUCCACGACGACGAGUCGUGUCGCUAC

GAAGGGCAAGUCGCUGUUUACCAGGAUGUAUACGCCGUCGACGGCCCCACCAG

CCUGUACCACCAGGCCAACAAGGGCGUGAGGGUGGCCUACUGGAUCGGCUUCG

ACACCACACCCUUCAUGUUCAAGAACCUGGCCGGCGCCUACCCCAGCUACAGC

ACCAACUGGGCCGACGAGACCGUGCUGACCGCCAGGAACAUCGGCCUGUGCAG

CAGCGACGUGAUGGAGAGGAGCCGGAGAGGCAUGAGCAUCCUGAGGAAGAAA

UACCUGAAGCCCAGCAACAACGUGCUGUUCAGCGUGGGCAGCACCAUCUACCA

CGAGAAGAGGGACCUGCUCAGGAGCUGGCACCUGCCCAGCGUGUUCCACCUGA

GGGGCAAGCAGAACUACACCUGCAGGUGCGAGACCAUCGUGAGCUGCGACGGC

UACGUGGUGAAGAGGAUCGCCAUCAGCCCCGGCCUGUACGGCAAGCCCAGCGG

CUACGCCGCUACAAUGCACAGGGAGGGCUUCCUGUGCUGCAAGGUGACCGACA

CCCUGAACGGCGAGAGGGUGAGCUUCCCCGUGUGCACCUACGUGCCCGCCACC

CUGUGCGACCAGAUGACCGGCAUCCUGGCCACCGACGUGAGCGCCGACGACGC

CCAGAAGCUGCUCGUGGGCCUGAACCAGAGGAUCGUGGUCAACGGCAGGACCC

AGAGGAACACCAACACAAUGAAGAACUACCUGCUGCCCGUGGUGGCCCAGGCU

UUCGCCAGGUGGGCCAAGGAGUACAAGGAGGACCAGGAAGACGAGAGGCCCCU

GGGCCUGAGGGACAGGCAGCUGGUGAUGGGCUGCUGCUGGGCCUUCAGGCGGC

ACAAGAUCACCAGCAUCUACAAGAGGCCCGACACCCAGACCAUCAUCAAGGUG

AACAGCGACUUCCACAGCUUCGUGCUGCCCAGGAUCGGCAGCAACACCCUGGA

GAUCGGCCUGAGGACCCGGAUCAGGAAGAUGCUGGAGGAACACAAGGAGCCCA

GCCCACUGAUCACCGCCGAGGACGUGCAGGAGGCCAAGUGCGCUGCCGACGAG

GCCAAGGAGGUGAGGGAGGCCGAGGAACUGAGGGCCGCCCUGCCACCCCUGGC

UGCCGACGUGGAGGAACCCACCCUGGAAGCCGACGUGGACCUGAUGCUGCAGG

AGGCCGGCGCCGGAAGCGUGGAGACACCCAGGGGCCUGAUCAAGGUGACCAGC

TABLE 7-continued

UACGACGGCGAGGACAAGAUCGGCAGCUACGCCGUGCUGAGCCCACAGGCCGU
GCUGAAGUCCGAGAAGCUGAGCUGCAUCCACCCACUGGCCGAGCAGGUGAUCG
UGAUCACCCACAGCGGCAGGAAGGGCAGGUACGCCGUGGAGCCCUACCACGGC
AAGGUGGUCGUGCCCGAGGGCCACGCCAUCCCCGUGCAGGACUUCCAGGCCCU
GAGCGAGAGCGCCACCAUCGUGUACAACGAGAGGGAGUUCGUGAACAGGUACC
UGCACCAUAUCGCCACCCACGGCGGAGCCCUGAACACCGACGAGGAAUACUAC
AAGACCGUGAAGCCCAGCGAGCACGACGGCGAGUACCUGUACGACAUCGACAG
GAAGCAGUGCGUGAAGAAAGAGCUGGUGACCGGCCUGGGACUGACCGGCGAG
CUGGUGGACCCACCCUUCCACGAGUUCGCCUACGAGAGCCUGAGGACCAGACC
CGCCGCUCCCUACCAGGUGCCCACCAUCGGCGUGUACGGCGUGCCCGGCAGCG
GAAAGAGCGGCAUCAUCAAGAGCGCCGUGACCAAGAAAGACCUGGUGGUCAGC
GCCAAGAAAGAGAACUGCGCCGAGAUCAUCAGGGACGUGAAGAAGAUGAAAG
GCCUGGACGUGAACGCGCGCACCGUGGACAGCGUGCUGCUGAACGGCUGCAAG
CACCCCGUGGAGACCCUGUACAUCGACGAGGCCUUCGCUUGCCACGCCGGCAC
CCUGAGGGCCCUGAUCGCCAUCAUCAGGCCCAAGAAAGCCGUGCUGUGCGGCG
ACCCCAAGCAGUGCGGCUUCUUCAACAUGAUGUGCCUGAAGGUGCACUUCAAC
CACGAGAUCUGCACCCAGGUGUUCCACAAGAGCAUCAGCAGGCGGUGCACCAA
GAGCGUGACCAGCGUCGUGAGCACCCUGUUCUACGACAAGAAAAUGAGGACCA
CCAACCCCAAGGAGACCAAAAUCGUGAUCGACACCACAGGCAGCACCAAGCCC
AAGCAGGACGACCUGAUCCUGACCUGCUUCAGGGGCUGGGUGAAGCAGCUGCA
GAUCGACUACAAGGGCAACGAGAUCAUGACCGCCGCUGCCAGCCAGGGCCUGA
CCAGGAAGGGCGUGUACGCCGUGAGGUACAAGGUGAACGAGAACCCACUGUAC
GCUCCCACCAGCGAGCACGUGAACGUGCUGCUGACCAGGACCGAGGACAGGAU
CGUGUGGAAGACCCUGGCCGGCGACCCCUGGAUCAAGACCCUGACCGCCAAGU
ACCCCGGCAACUUCACCGCCACCAUCGAAGAGUGGCAGGCCGAGCACGACGCC
AUCAUGAGGCACAUCCUGGAGAGGCCCGACCCCACCGACGUGUUCCAGAACAA
GGCCAACGUGUGCUGGGCCAAGGCCCUGGUGCCCGUGCUGAAGACCGCCGGCA
UCGACAUGACCACAGAGCAGUGGAACACCGUGGACUACUUCGAGACCGACAAG
GCCCACAGCGCCGAGAUCGUGCUGAACCAGCUGUGCGUGAGGUUCUUCGGCCU
GGACCUGGACAGCGGCCUGUUCAGCGCCCCCACCGUGCCACUGAGCAUCAGGA
ACAACCACUGGGACAACAGCCCCAGCCCAAACAUGUACGGCCUGAACAAGGAG
GUGGUCAGGCAGCUGAGCAGGCGGUACCCACAGCUGCCCAGGGCCGUGGCCAC
CGGCAGGGUGUACGACAUGAACACCGGCACCCUGAGGAACUACGACCCCAGGA
UCAACCUGGUGCCCGUGAACAGGCGGCUGCCCCACGCCCUGGUGCUGCACCAC
AACGAGCACCCACAGAGCGACUUCAGCUCCUUCGUGAGCAAGCUGAAAGGCAG
GACCGUGCUGGUCGUGGGCGAGAAGCUGAGCGUGCCCGGCAAGAUGGUGGAC
UGGCUGAGCGACAGGCCCGAGGCCACCUUCCGGGCCAGGCUGGACCUCGGCAU
CCCCGGCGACGUGCCCAAGUACGACAUCAUCUUCGUGAACGUCAGGACCCCAU
ACAAGUACCACCAUUACCAGCAGUGCGAGGACCACGCCAUCAAGCUGAGCAUG
CUGACCAAGAAGGCCUGCCUGCACCUGAACCCCGGAGGCACCUGCGUGAGCAU

TABLE 7-continued

CGGCUACGGCUACGCCGACAGGGCCAGCGAGAGCAUCAUUGGCGCCAUCGCCA

GGCUGUUCAAGUUCAGCAGGGUGUGCAAACCCAAGAGCAGCCUGGAGGAAACC

GAGGUGCUGUUCGUGUUCAUCGGCUACGACCGGAAGGCCAGGACCCACAACCC

CUACAAGCUGAGCAGCACCCUGACAAACAUCUACACCGGCAGCAGGCUGCACG

AGGCCGGCUGCGCCCCCAGCUACCACGUGGUCAGGGGCGAUAUCGCCACCGCC

ACCGAGGGCGUGAUCAUCAACGCUGCCAACAGCAAGGGCCAGCCCGGAGGCGG

AGUGUGCGGCGCCCUGUACAAGAAGUUCCCCGAGAGCUUCGACCUGCAGCCCA

UCGAGGUGGGCAAGGCCAGGCUGGUGAAGGGCGCCGCUAAGCACAUCAUCCAC

GCCGUGGGCCCCAACUUCAACAAGGUGAGCGAGGUGGAAGGCGACAAGCAGCU

GGCCGAAGCCUACGAGAGCAUCGCCAAGAUCGUGAACGACAAUAACUACAAGA

GCGUGGCCAUCCCACUGCUCAGCACCGGCAUCUUCAGCGGCAACAAGGACAGG

CUGACCCAGAGCCUGAACCACCUGCUCACCGCCCUGGACACCACCGAUGCCGA

CGUGGCCAUCUACUGCAGGGACAAGAAGUGGGAGAUGACCCUGAAGGAGGCC

GUGGCCAGGCGGGAGGCCGUGGAAGAGAUCUGCAUCAGCGACGACUCCAGCGU

GACCGAGCCCGACGCCGAGCUGGUGAGGGUGCACCCCAAGAGCUCCCUGGCCG

GCAGGAAGGGCUACAGCACCAGCGACGGCAAGACCUUCAGCUACCUGGAGGGC

ACCAAGUUCCACCAGGCCGCUAAGGACAUCGCCGAGAUCAACGCUAUGUGGCC

CGUGGCCACCGAGGCCAACGAGCAGGUGUGCAUGUACAUCCUGGGCGAGAGCA

UGUCCAGCAUCAGGAGCAAGUGCCCCGUGGAGGAAAGCGAGGCCAGCACACCA

CCCAGCACCCUGCCCUGCCUGUGCAUCCACGCUAUGACACCCGAGAGGGUGCA

GCGGCUGAAGGCCAGCAGGCCCGAGCAGAUCACCGUGUGCAGCUCCUUCCCAC

UGCCCAAGUACAGGAUCACCGGCGUGCAGAAGAUCCAGUGCAGCCAGCCCAUC

CUGUUCAGCCCAAAGGUGCCCGCCUACAUCCACCCCAGGAAGUACCUGGUGGA

GACCCCACCCGUGGACGAGACACCCGAGCCAAGCGCCGAGAACCAGAGCACCG

AGGGCACACCCGAGCAGCCACCCCUGAUCACCGAGGACGAGACAAGGACCCGG

ACCCCAGAGCCCAUCAUUAUCGAGGAAGAGGAAGAGGACAGCAUCAGCCUGCU

GAGCGACGGCCCCACCCACCAGGUGCUGCAGGUGGAGGCCGACAUCCACGGCC

CACCCAGCGUGUCCAGCUCCAGCUGGAGCAUCCCACACGCCAGCGACUUCGAC

GUGGACAGCCUGAGCAUCCUGGACACCCUGGAGGGCGCCAGCGUGACCUCCGG

CGCCACCAGCGCCGAGACCAACAGCUACUUCGCCAAGAGCAUGGAGUUCCUGG

CCAGGCCCGUGCCAGCUCCCAGGACCGUGUUCAGGAACCCACCCCACCCAGCUC

CCAGGACCAGGACCCCAAGCCUGGCUCCCAGCAGGGCCUGCAGCAGGACCAGC

CUGGUGAGCACCCCACCCGGCGUGAACAGGGUGAUCACCAGGGAGGAACUGGA

GGCCCUGACACCCAGCAGGACCCCCAGCAGGUCCGUGAGCAGGACUAGUCUGG

UGUCCAACCCACCCGGCGUGAACAGGGUGAUCACCAGGGAGGAAUUCGAGGCC

UUCGUGGCCCAGCAACAGAGACGGUUCGACGCCGGCGCCUACAUCUUCAGCAG

CGACACCGGCCAGGGACACCUGCAGCAAAAGAGCGUGAGGCAGACCGUGCUGA

GCGAGGUGGUGCUGGAGAGGACCGAGCUGGAAAUCAGCUACGCCCCCAGGCUG

GACCAGGAGAAGGAGGAACUGCUCAGGAAGAAACUGCAGCUGAACCCCACCCC

AGCCAACAGGAGCAGGUACCAGAGCAGGAAGGUGGAGAACAUGAAGGCCAUC

TABLE 7-continued

ACCGCCAGGCGGAUCCUGCAGGGCCUGGGACACUACCUGAAGGCCGAGGGCAA

GGUGGAGUGCUACAGGACCCUGCACCCCGUGCCACUGUACAGCUCCAGCGUGA

ACAGGGCCUUCUCCAGCCCCAAGGUGGCCGUGGAGGCCUGCAACGCUAUGCUG

AAGGAGAACUUCCCCACCGUGGCCAGCUACUGCAUCAUCCCCGAGUACGACGC

CUACCUGGACAUGGUGGACGGCGCCAGCUGCUGCCUGGACACCGCCAGCUUCU

GCCCCGCCAAGCUGAGGAGCUUCCCCAAGAAACACAGCUACCUGGAGCCCACC

AUCAGGAGCGCCGUGCCCAGCGCCAUCCAGAACACCCUGCAGAACGUGCUGGC

CGCUGCCACCAAGAGGAACUGCAACGUGACCCAGAUGAGGGAGCUGCCCGUGC

UGGACAGCGCUGCCUUCAACGUGGAGUGCUUCAAGAAAUACGCCUGCAACAAC

GAGUACUGGGAGACCUUCAAGGAGAACCCCAUCAGGCUGACCGAAGAGAACGU

GGUGAACUACAUCACCAAGCUGAAGGGCCCCAAGGCCGCUGCCCUGUUCGCUA

AGACCCACAACCUGAACAUGCUGCAGGACAUCCCAAUGGACAGGUUCGUGAUG

GACCUGAAGAGGGACGUGAAGGUGACACCCGGCACCAAGCACACCGAGGAGAG

GCCCAAGGUGCAGGUGAUCCAGGCCGCUGACCCACUGGCCACCGCCUACCUGU

GCGGCAUCCACAGGGAGCUGGUGAGGCGGCUGAACGCCGUGCUGCUGCCCAAC

AUCCACACCCUGUUCGACAUGAGCGCCGAGGACUUCGACGCCAUCAUCGCCGA

GCACUUCCAGCCCGGCGACUGCGUGCUGGAGACCGACAUCGCCAGCUUCGACA

AGAGCGAGGAUGACGCUAUGGCCCUGACCGCUCUGAUGAUCCUGGAGGACCUG

GGCGUGGACGCCGAGCUGCUCACCCUGAUCGAGGCUGCCUUCGGCGAGAUCAG

CUCCAUCCACCUGCCCACCAAGACCAAGUUCAAGUUCGGCGCUAUGAUGAAAA

GCGGAAUGUUCCUGACCCUGUUCGUGAACACCGUGAUCAACAUUGUGAUCGCC

AGCAGGGUGCUGCGGGAGAGGCUGACCGGCAGCCCCUGCGCUGCCUUCAUCGG

CGACGACAACAUCGUGAAGGGCGUGAAAAGCGACAAGCUGAUGGCCGACAGG

UGCGCCACCUGGCUGAACAUGGAGGUGAAGAUCAUCGACGCCGUGGUGGGCGA

GAAGGCCCCCUACUUCUGCGGCGGAUUCAUCCUGUGCGACAGCGUGACCGGCA

CCGCCUGCAGGGUGGCCGACCCCCUGAAGAGGCUGUUCAAGCUGGGCAAGCCA

CUGGCCGCUGACGAUGAGCACGACGAUGACAGGCGGAGGGCCCUGCACGAGGA

AAGCACCAGGUGGAACAGGGUGGGCAUCCUGAGCGAGCUGUGCAAGGCCGUG

GAGAGCAGGUACGAGACCGUGGGCACCAGCAUCAUCGUGAUGGCUAUGACCAC

ACUGGCCAGCUCCGUCAAGAGCUUCUCCUACCUGAGGGGGGCCCCUAUAACUC

UCUACGGCUAACCUGAAUGGACUACGACAUAGUCUAGUCCGCCAAGGCCGCCA

CCAUGGAAGAUGCCAAAAACAUUAAGAAGGGCCCAGCGCCAUUCUACCCACUC

GAAGACGGGACCGCCGGCGAGCAGCUGCACAAAGCCAUGAAGCGCUACGCCCU

GGUGCCCGGCACCAUCGCCUUUACCGACGCACAUAUCGAGGUGGACAUUACCU

ACGCCGAGUACUUCGAGAUGAGCGUUCGGCUGGCAGAAGCUAUGAAGCGCUA

UGGGCUGAAUACAAACCAUCGGAUCGUGGUGUGCAGCGAGAAUAGCUUGCAG

UUCUUCAUGCCCGUGUUGGGUGCCCUGUUCAUCGGUGUGGCUGUGGCCCCAGC

UAACGACAUCUACAACGAGCGCGAGCUGCUGAACAGCAUGGGCAUCAGCCAGC

CCACCGUCGUAUUCGUGAGCAAGAAAGGGCUGCAAAAGAUCCUCAACGUGCAA

AAGAAGCUACCGAUCAUACAAAAGAUCAUCAUCAUGGAUAGCAAGACCGACU

TABLE 7-continued

ACCAGGGCUUCCAAAGCAUGUACACCUUCGUGACUUCCCAUUUGCCACCCGGC

UUCAACGAGUACGACUUCGUGCCCGAGAGCUUCGACCGGGACAAAACCAUCGC

CCUGAUCAUGAACAGUAGUGGCAGUACCGGAUUGCCCAAGGGCGUAGCCCUAC

CGCACCGCACCGCUUGUGUCCGAUUCAGUCAUGCCCGCGACCCCAUCUUCGGC

AACCAGAUCAUCCCCGACACCGCUAUCCUCAGCGUGGUGCCAUUUCACCACGG

CUUCGGCAUGUUCACCACGCUGGGCUACUUGAUCUGCGGCUUUCGGGUCGUGC

UCAUGUACCGCUUCGAGGAGGAGCUAUUCUUGCGCAGCUUGCAAGACUAUAA

GAUUCAAUCUGCCCUGCUGGUGCCCACACUAUUUAGCUUCUUCGCUAAGAGCA

CUCUCAUCGACAAGUACGACCUAAGCAACUUGCACGAGAUCGCCAGCGGCGGG

GCGCCGCUCAGCAAGGAGGUAGGUGAGGCCGUGGCCAAACGCUUCCACCUACC

AGGCAUCCGACAGGGCUACGGCCUGACAGAAACAACCAGCGCCAUUCUGAUCA

CCCCCGAAGGGGACGACAAGCCUGGCGCAGUAGGCAAGGUGGUGCCCUUCUUC

GAGGCUAAGGUGGUGGACUUGGACACCGGUAAGACACUGGGUGUGAACCAGC

GCGGCGAGCUGUGCGUCCGUGGCCCCAUGAUCAUGAGCGGCUACGUUAACAAC

CCCGAGGCUACAAACGCUCUCAUCGACAAGGACGGCUGGCUGCACAGCGGCGA

CAUCGCCUACUGGGACGAGGACGAGCACUUCUUCAUCGUGGACCGGCUGAAGU

CCCUGAUCAAAUACAAGGGCUACCAGGUAGCCCCAGCCGAACUGGAGAGCAUC

CUGCUGCAACACCCCAACAUCUUCGACGCCGGGGUCGCCGGCCUGCCCGACGA

CGAUGCCGGCGAGCUGCCCGCCGCAGUCGUCGUGCUGGAACACGGUAAAACCA

UGACCGAGAAGGAGAUCGUGGACUAUGUGGCCAGCCAGGUUACAACCGCCAAG

AAGCUGCGCGGUGGUGUUGUGUUCGUGGACGAGGUGCCUAAAGGACUGACCG

GCAAGUUGGACGCCCGCAAGAUCCGCGAGAUUCUCAUUAAGGCCAAGAAGGGC

GGCAAGAUCGCCGUGUAACUCGAGCCGGAAACGCAAUAGCCGAAAAACAAAAA

ACAAAAAAAACAAAAAAAAAACCAAAAAAACAAAACACAUUAAAACAGCCUG

UGGGUUGAUCCCACCCACAGGCCCAUUGGGCGCUAGCACUCUGGUAUCACGGU

ACCUUUGUGCGCCUGUUUUAUACCCCCUCCCCCAACUGUAACUUAGAAGUAAC

ACACACCGAUCAACAGUCAGCGUGGCACACCAGCCACGUUUUGAUCAAGCACU

UCUGUUACCCCGGACUGAGUAUCAAUAGACUGCUCACGCGGUUGAAGGAGAA

AGCGUUCGUUAUCCGGCCAACUACUUCGAAAAACCUAGUAACACCGUGGAAGU

UGCAGAGUGUUUCGCUCAGCACUACCCCAGUGUAGAUCAGGUCGAUGAGUCAC

CGCAUUCCCCACGGGCGACCGUGGCGGUGGCUGCGUUGGCGGCCUGCCCAUGG

GGAAACCCAUGGGACGCUCUAAUACAGACAUGGUGCGAAGAGUCUAUUGAGC

UAGUUGGUAGUCCUCCGGCCCCUGAAUGCGGCUAAUCCUAACUGCGGAGCACA

CACCCUCAAGCCAGAGGGCAGUGUGUCGUAACGGGCAACUCUGCAGCGGAACC

GACUACUUUGGGUGUCCGUGUUUCAUUUUAUUCCUAUACUGGCUGCUUAUGG

UGACAAUUGAGAGAUCGUUACCAUAUAGCUAUUGGAUUGGCCAUCCGGUGAC

UAAUAGAGCUAUUAUAUAUCCCUUUGUUGGGUUUAUACCACUUAGCUUGAAA

GAGGUUAAAACAUUACAAUUCAUUGUUAAGUUGAAUACAGCAAAAUGAGCAA

GAUCUACAUCGACGAGCGGAGCAACGCCGAGAUCGUGUGCGAGGCCAUCAAGA

CCAUCGGCAUCGAGGGCGCCACCGCCGCCCAGCUGACCAGGCAGCUGAACAUG

TABLE 7-continued

GAGAAGCGGGAGGUGAACAAGGCCCUGUACGACCUGCAGAGGAGCGCUAUGG

UGUACUCCAGCGACGACAUCCCUCCCCGGUGGUUCAUGACCACCGAGGCCGAC

AAGCCCGACGCCGACGCUAUGGCCGACGUGAUCAUCGACGACGUGAGCAGGGA

GAAGUCCAUGAGGGAGGACCACAAGAGCUUCGACGACGUGAUCCCCGCCAAGA

AGAUCAUCGACUGGAAGGGCGCCAACCCCGUGACCGUGAUCAACGAGUACUGC

CAGAUCACCAGGAGGGACUGGAGCUUCCGGAUCGAGAGCGUGGGCCCCAGCAA

CAGCCCCACCUUCUACGCCUGCGUGGACAUCGACGGCAGGGUGUUCGACAAGG

CCGACGGCAAGAGCAAGCGGGACGCCAAGAACAACGCCGCCAAGCUGGCCGUG

GACAAGCUGCUGGGCUACGUGAUCAUCCGGUUCUAAACGUAUGUUACGUGCA

AAGGUGAUUGUCACCCCCCGAAAGACCAUAUUGUGACACACCCUCAGUAUCAC

GCCCAAACAUUUACAGCCGCGGUGUCAAAAACCGCGUGGACGUGGUUAACAUC

CCUGCUGGGAGGAUCAGCCGUAAUUAUUAUAAUUGGCUUGGUGCUGGCUACU

AUUGUGGCCAUGUACGUGCUGACCAACCAGAAACAUAAUUGAAUACAGCAGC

AAUUGGCAAGCUGCUUACAUAGAACUCGCGGCGAUUGGCAUGCCGCCUUAAAA

UUUUUAUUUUAUUUUUUCUUUUCUUUUCCGAAUCGGAUUUUGUUUUUAAUAU

UUCAAAAAAAAAAAAAAAAAAAAAAAAAUCUAGAAAAAAAAAAAAAAAAAAA

AAAAAAAAAAAAAAAAAAAAAAAAAAAAAAAAAAAAAAAAAAAAAAAAAAAA

AAAAAAAAAAAAAAAAAAAAAAAAAAAAA (RNA sequence for STARR Fluc IRES-E3L (short 3' UTR))

SEQ ID NO: 119

AUGGGCGGCGCAUGAGAGAAGCCCAGACCAAUUACCUACCCAAAAUGGAGAAA

GUUCACGUUGACAUCGAGGAAGACAGCCCAUUCCUCAGAGCUUUGCAGCGGAG

CUUCCCGCAGUUUGAGGUAGAAGCCAAGCAGGUCACUGAUAAUGACCAUGCUA

AUGCCAGAGCGUUUUCGCAUCUGGCUUCAAAACUGAUCGAAACGGAGGUGGA

CCCAUCCGACACGAUCCUUGACAUUGGAAGUGCGCCCGCCCGCAGAAUGUAUU

CUAAGCACAAGUAUCAUUGUAUCUGUCCGAUGAGAUGUGCGGAAGAUCCGGA

CAGAUUGUAUAAGUAUGCAACUAAGCUGAAGAAAAACUGUAAGGAAAUAACU

GAUAAGGAAUUGGACAAGAAAAUGAAGGAGCUGGCCGCCGUCAUGAGCGACC

CUGACCUGGAAACUGAGACUAUGUGCCUCCACGACGACGAGUCGUGUCGCUAC

GAAGGGCAAGUCGCUGUUUACCAGGAUGUAUACGCCGUCGACGGCCCCACCAG

CCUGUACCACCAGGCCAACAAGGGCGUGAGGGUGGCCUACUGGAUCGGCUUCG

ACACCACACCCUUCAUGUUCAAGAACCUGGCCGGCGCCUACCCCAGCUACAGC

ACCAACUGGGCCGACGAGACCGUGCUGACCGCCAGGAACAUCGGCCUGUGCAG

CAGCGACGUGAUGGAGAGGAGCCGGAGAGGCAUGAGCAUCCUGAGGAAGAAA

UACCUGAAGCCCAGCAACAACGUGCUGUUCAGCGUGGGCAGCACCAUCUACCA

CGAGAAGAGGGACCUGCUCAGGAGCUGGCACCUGCCCAGCGUGUUCCACCUGA

GGGGCAAGCAGAACUACACCUGCAGGUGCGAGACCAUCGUGAGCUGCGACGGC

UACGUGGUGAAGAGGAUCGCCAUCAGCCCCGGCCUGUACGGCAAGCCCAGCGG

CUACGCCGCUACAAUGCACAGGGAGGGCUUCCUGUGCUGCAAGGUGACCGACA

CCCUGAACGGCGAGAGGGUGAGCUUCCCCGUGUGCACCUACGUGCCCGCCACC

CUGUGCGACCAGAUGACCGGCAUCCUGGCCACCGACGUGAGCGCCGACGACGC

TABLE 7-continued

CCAGAAGCUGCUCGUGGGCCUGAACCAGAGGAUCGUGGUCAACGGCAGGACCC
AGAGGAACACCAACACAAUGAAGAACUACCUGCUGCCCGUGGUGGCCCAGGCU
UUCGCCAGGUGGGCCAAGGAGUACAAGGAGGACCAGGAAGACGAGAGGCCCCU
GGGCCUGAGGGACAGGCAGCUGGUGAUGGGCUGCUGCUGGGCCUUCAGGCGGC
ACAAGAUCACCAGCAUCUACAAGAGGCCCGACACCCAGACCAUCAUCAAGGUG
AACAGCGACUUCCACAGCUUCGUGCUGCCCAGGAUCGGCAGCAACACCCUGGA
GAUCGGCCUGAGGACCCGGAUCAGGAAGAUGCUGGAGGAACACAAGGAGCCCA
GCCCACUGAUCACCGCCGAGGACGUGCAGGAGGCCAAGUGCGCUGCCGACGAG
GCCAAGGAGGUGAGGGAGGCCGAGGAACUGAGGGCCGCCCUGCCACCCCUGGC
UGCCGACGUGGAGGAACCCACCCUGGAAGCCGACGUGGACCUGAUGCUGCAGG
AGGCCGGCGCCGGAAGCGUGGAGACACCCAGGGGCCUGAUCAAGGUGACCAGC
UACGACGGCGAGGACAAGAUCGGCAGCUACGCCGUGCUGAGCCCACAGGCCGU
GCUGAAGUCCGAGAAGCUGAGCUGCAUCCACCCACUGGCCGAGCAGGUGAUCG
UGAUCACCCACAGCGGCAGGAAGGGCAGGUACGCCGUGGAGCCCUACCACGGC
AAGGUGGUCGUGCCCGAGGGCCACGCCAUCCCCGUGCAGGACUUCCAGGCCCU
GAGCGAGAGCGCCACCAUCGUGUACAACGAGAGGGAGUUCGUGAACAGGUACC
UGCACCAUAUCGCCACCCACGGCGGAGCCCUGAACACCGACGAGGAAUACUAC
AAGACCGUGAAGCCCAGCGAGCACGACGGCGAGUACCUGUACGACAUCGACAG
GAAGCAGUGCGUGAAGAAAGAGCUGGUGACCGGCCUGGGACUGACCGGCGAG
CUGGUGGACCCACCCUUCCACGAGUUCGCCUACGAGAGCCUGAGGACCAGACC
CGCCGCUCCCUACCAGGUGCCCACCAUCGGCGUGUACGGCGUGCCCGGCAGCG
GAAAGAGCGGCAUCAUCAAGAGCGCCGUGACCAAGAAAGACCUGGUGGUCAGC
GCCAAGAAAGAGAACUGCGCCGAGAUCAUCAGGGACGUGAAGAAGAUGAAAG
GCCUGGACGUGAACGCGCGCACCGUGGACAGCGUGCUGCUGAACGGCUGCAAG
CACCCCGUGGAGACCCUGUACAUCGACGAGGCCUUCGCUUGCCACGCCGGCAC
CCUGAGGGCCCUGAUCGCCAUCAUCAGGCCCAAGAAAGCCGUGCUGUGCGGCG
ACCCCAAGCAGUGCGGCUUCUUCAACAUGAUGUGCCUGAAGGUGCACUUCAAC
CACGAGAUCUGCACCCAGGUGUUCCACAAGAGCAUCAGCAGGCGGUGCACCAA
GAGCGUGACCAGCGUCGUGAGCACCCUGUUCUACGACAAGAAAAUGAGGACCA
CCAACCCCAAGGAGACCAAAAUCGUGAUCGACACCACAGGCAGCACCAAGCCC
AAGCAGGACGACCUGAUCCUGACCUGCUUCAGGGGCUGGGUGAAGCAGCUGCA
GAUCGACUACAAGGGCAACGAGAUCAUGACCGCCGCUGCCAGCCAGGGCCUGA
CCAGGAAGGGCGUGUACGCCGUGAGGUACAAGGUGAACGAGAACCCACUGUAC
GCUCCCACCAGCGAGCACGUGAACGUGCUGCUGACCAGGACCGAGGACAGGAU
CGUGUGGAAGACCCUGGCCGGCGACCCCUGGAUCAAGACCCUGACCGCCAAGU
ACCCCGGCAACUUCACCGCCACCAUCGAAGAGUGGCAGGCCGAGCACGACGCC
AUCAUGAGGCACAUCCUGGAGAGGCCCGACCCCACCGACGUGUUCCAGAACAA
GGCCAACGUGUGCUGGGCCAAGGCCCUGGUGCCCGUGCUGAAGACCGCCGGCA
UCGACAUGACCACAGAGCAGUGGAACACCGUGGACUACUUCGAGACCGACAAG
GCCCACAGCGCCGAGAUCGUGCUGAACCAGCUGUGCGUGAGGUUCUUCGGCCU

TABLE 7-continued

GGACCUGGACAGCGGCCUGUUCAGCGCCCCCACCGUGCCACUGAGCAUCAGGA
ACAACCACUGGGACAACAGCCCCAGCCCAAACAUGUACGGCCUGAACAAGGAG
GUGGUCAGGCAGCUGAGCAGGCGGUACCCACAGCUGCCCAGGGCCGUGGCCAC
CGGCAGGGUGUACGACAUGAACACCGGCACCCUGAGGAACUACGACCCCAGGA
UCAACCUGGUGCCCGUGAACAGGCGGCUGCCCCACGCCCUGGUGCUGCACCAC
AACGAGCACCCACAGAGCGACUUCAGCUCCUUCGUGAGCAAGCUGAAAGGCAG
GACCGUGCUGGUCGUGGGCGAGAAGCUGAGCGUGCCCGGCAAGAUGGUGGAC
UGGCUGAGCGACAGGCCCGAGGCCACCUUCCGGGCCAGGCUGGACCUCGGCAU
CCCCGGCGACGUGCCCAAGUACGACAUCAUCUUCGUGAACGUCAGGACCCCAU
ACAAGUACCACCAUUACCAGCAGUGCGAGGACCACGCCAUCAAGCUGAGCAUG
CUGACCAAGAAGGCCUGCCUGCACCUGAACCCCGGAGGCACCUGCGUGAGCAU
CGGCUACGGCUACGCCGACAGGGCCAGCGAGAGCAUCAUUGGCGCCAUCGCCA
GGCUGUUCAAGUUCAGCAGGGUGUGCAAACCCAAGAGCAGCCUGGAGGAAACC
GAGGUGCUGUUCGUGUUCAUCGGCUACGACCGGAAGGCCAGGACCCACAACCC
CUACAAGCUGAGCAGCACCCUGACAAACAUCUACACCGGCAGCAGGCUGCACG
AGGCCGGCUGCGCCCCCAGCUACCACGUGGUCAGGGGCGAUAUCGCCACCGCC
ACCGAGGGCGUGAUCAUCAACGCUGCCAACAGCAAGGGCCAGCCCGGAGGCGG
AGUGUGCGGCGCCCUGUACAAGAAGUUCCCCGAGAGCUUCGACCUGCAGCCCA
UCGAGGUGGGCAAGGCCAGGCUGGUGAAGGGCGCCGCUAAGCACAUCAUCCAC
GCCGUGGGCCCCAACUUCAACAAGGUGAGCGAGGUGGAAGGCGACAAGCAGCU
GGCCGAAGCCUACGAGAGCAUCGCCAAGAUCGUGAACGACAAUAACUACAAGA
GCGUGGCCAUCCCACUGCUCAGCACCGGCAUCUUCAGCGGCAACAAGGACAGG
CUGACCCAGAGCCUGAACCACCUGCUCACCGCCCUGGACACCACCGAUGCCGA
CGUGGCCAUCUACUGCAGGGACAAGAAGUGGGAGAUGACCCUGAAGGAGGCC
GUGGCCAGGCGGGAGGCCGUGGAAGAGAUCUGCAUCAGCGACGACUCCAGCGU
GACCGAGCCCGACGCCGAGCUGGUGAGGGUGCACCCCAAGAGCUCCCUGGCCG
GCAGGAAGGGCUACAGCACCAGCGACGGCAAGACCUUCAGCUACCUGGAGGGC
ACCAAGUUCCACCAGGCCGCUAAGGACAUCGCCGAGAUCAACGCUAUGUGGCC
CGUGGCCACCGAGGCCAACGAGCAGGUGUGCAUGUACAUCCUGGGCGAGAGCA
UGUCCAGCAUCAGGAGCAAGUGCCCCGUGGAGGAAAGCGAGGCCAGCACACCA
CCCAGCACCCUGCCCUGCCUGUGCAUCCACGCUAUGACACCCGAGAGGGUGCA
GCGGCUGAAGGCCAGCAGGCCCGAGCAGAUCACCGUGUGCAGCUCCUUCCCAC
UGCCCAAGUACAGGAUCACCGGCGUGCAGAAGAUCCAGUGCAGCCAGCCCAUC
CUGUUCAGCCCAAAGGUGCCCGCCUACAUCCACCCCAGGAAGUACCUGGUGGA
GACCCCACCCGUGGACGAGACACCCGAGCCAAGCGCCGAGAACCAGAGCACCG
AGGGCACACCCGAGCAGCCACCCCUGAUCACCGAGGACGAGACAAGGACCCGG
ACCCCAGAGCCCAUCAUUAUCGAGGAAGAGGAAGAGGACAGCAUCAGCCUGCU
GAGCGACGGCCCCACCCACCAGGUGCUGCAGGUGGAGGCCGACAUCCACGGCC
CACCCAGCGUGUCCAGCUCCAGCUGGAGCAUCCCACACGCCAGCGACUUCGAC
GUGGACAGCCUGAGCAUCCUGGACACCCUGGAGGGCGCCAGCGUGACCUCCGG

TABLE 7-continued

| |
|---|
| CGCCACCAGCGCCGAGACCAACAGCUACUUCGCCAAGAGCAUGGAGUUCCUGG |
| CCAGGCCCGUGCCAGCUCCCAGGACCGUGUUCAGGAACCCACCCCACCCAGCUC |
| CCAGGACCAGGACCCCAAGCCUGGCUCCCAGCAGGGCCUGCAGCAGGACCAGC |
| CUGGUGAGCACCCCACCCGGCGUGAACAGGGUGAUCACCAGGGAGGAACUGGA |
| GGCCCUGACACCCAGCAGGACCCCCAGCAGGUCCGUGAGCAGGACUAGUCUGG |
| UGUCCAACCCACCCGGCGUGAACAGGGUGAUCACCAGGGAGGAAUUCGAGGCC |
| UUCGUGGCCCAGCAACAGAGACGGUUCGACGCCGGCGCCUACAUCUUCAGCAG |
| CGACACCGGCCAGGGACACCUGCAGCAAAAGAGCGUGAGGCAGACCGUGCUGA |
| GCGAGGUGGUGCUGGAGAGGACCGAGCUGGAAAUCAGCUACGCCCCCAGGCUG |
| GACCAGGAGAAGGAGGAACUGCUCAGGAAGAAACUGCAGCUGAACCCCACCCC |
| AGCCAACAGGAGCAGGUACCAGAGCAGGAAGGUGGAGAACAUGAAGGCCAUC |
| ACCGCCAGGCGGAUCCUGCAGGGCCUGGGACACUACCUGAAGGCCGAGGGCAA |
| GGUGGAGUGCUACAGGACCCUGCACCCCGUGCCACUGUACAGCUCCAGCGUGA |
| ACAGGGCCUUCUCCAGCCCCAAGGUGGCCGUGGAGGCCUGCAACGCUAUGCUG |
| AAGGAGAACUUCCCCACCGUGGCCAGCUACUGCAUCAUCCCCGAGUACGACGC |
| CUACCUGGACAUGGUGGACGGCGCCAGCUGCUGCCUGGACACCGCCAGCUUCU |
| GCCCCGCCAAGCUGAGGAGCUUCCCCAAGAAACACAGCUACCUGGAGCCCACC |
| AUCAGGAGCGCCGUGCCCAGCGCCAUCCAGAACACCCUGCAGAACGUGCUGGC |
| CGCUGCCACCAAGAGGAACUGCAACGUGACCCAGAUGAGGGAGCUGCCCGUGC |
| UGGACAGCGCUGCCUUCAACGUGGAGUGCUUCAAGAAAUACGCCUGCAACAAC |
| GAGUACUGGGAGACCUUCAAGGAGAACCCCAUCAGGCUGACCGAAGAGAACGU |
| GGUGAACUACAUCACCAAGCUGAAGGGCCCCAAGGCCGCUGCCCUGUUCGCUA |
| AGACCCACAACCUGAACAUGCUGCAGGACAUCCCAAUGGACAGGUUCGUGAUG |
| GACCUGAAGAGGGACGUGAAGGUGACACCCGGCACCAAGCACACCGAGGAGAG |
| GCCCAAGGUGCAGGUGAUCCAGGCCGCUGACCCACUGGCCACCGCCUACCUGU |
| GCGGCAUCCACAGGGAGCUGGUGAGGCGGCUGAACGCCGUGCUGCUGCCCAAC |
| AUCCACACCCUGUUCGACAUGAGCGCCGAGGACUUCGACGCCAUCAUCGCCGA |
| GCACUUCCAGCCCGGCGACUGCGUGCUGGAGACCGACAUCGCCAGCUUCGACA |
| AGAGCGAGGAUGACGCUAUGGCCCUGACCGCUCUGAUGAUCCUGGAGGACCUG |
| GGCGUGGACGCCGAGCUGCUCACCCUGAUCGAGGCUGCCUUCGGCGAGAUCAG |
| CUCCAUCCACCUGCCCACCAAGACCAAGUUCAAGUUCGGCGCUAUGAUGAAAA |
| GCGGAAUGUUCCUGACCCUGUUCGUGAACACCGUGAUCAACAUUGUGAUCGCC |
| AGCAGGGUGCUGCGGGAGAGGCUGACCGGCAGCCCCUGCGCUGCCUUCAUCGG |
| CGACGACAACAUCGUGAAGGGCGUGAAAAGCGACAAGCUGAUGGCCGACAGG |
| UGCGCCACCUGGCUGAACAUGGAGGUGAAGAUCAUCGACGCCGUGGUGGGCGA |
| GAAGGCCCCCUACUUCUGCGGCGGAUUCAUCCUGUGCGACAGCGUGACCGGCA |
| CCGCCUGCAGGGUGGCCGACCCCCUGAAGAGGCUGUUCAAGCUGGGCAAGCCA |
| CUGGCCGCUGACGAUGAGCACGACGAUGACAGGCGGAGGGCCCUGCACGAGGA |
| AAGCACCAGGUGGAACAGGGUGGGCAUCCUGAGCGAGCUGUGCAAGGCCGUG |
| GAGAGCAGGUACGAGACCGUGGGCACCAGCAUCAUCGUGAUGGCUAUGACCAC |

TABLE 7-continued

ACUGGCCAGCUCCGUCAAGAGCUUCUCCUACCUGAGGGGGGCCCCUAUAACUC

UCUACGGCUAACCUGAAUGGACUACGACAUAGUCUAGUCCGCCAAGGCCGCCA

CCAUGGAAGAUGCCAAAAACAUUAAGAAGGGCCCAGCGCCAUUCUACCCACUC

GAAGACGGGACCGCCGGCGAGCAGCUGCACAAAGCCAUGAAGCGCUACGCCCU

GGUGCCCGGCACCAUCGCCUUUACCGACGCACAUAUCGAGGUGGACAUUACCU

ACGCCGAGUACUUCGAGAUGAGCGUUCGGCUGGCAGAAGCUAUGAAGCGCUA

UGGGCUGAAUACAAACCAUCGGAUCGUGGUGUGCAGCGAGAAUAGCUUGCAG

UUCUUCAUGCCCGUGUUGGGUGCCCUGUUCAUCGGUGUGGCUGUGGCCCCAGC

UAACGACAUCUACAACGAGCGCGAGCUGCUGAACAGCAUGGGCAUCAGCCAGC

CCACCGUCGUAUUCGUGAGCAAGAAAGGGCUGCAAAAGAUCCUCAACGUGCAA

AAGAAGCUACCGAUCAUACAAAAGAUCAUCAUCAUGGAUAGCAAGACCGACU

ACCAGGGCUUCCAAAGCAUGUACACCUUCGUGACUUCCCAUUUGCCACCCGGC

UUCAACGAGUACGACUUCGUGCCCGAGAGCUUCGACCGGGACAAAACCAUCGC

CCUGAUCAUGAACAGUAGUGGCAGUACCGGAUUGCCCAAGGGCGUAGCCCUAC

CGCACCGCACCGCUUGUGUCCGAUUCAGUCAUGCCCGCGACCCCAUCUUCGGC

AACCAGAUCAUCCCCGACACCGCUAUCCUCAGCGUGGUGCCAUUUCACCACGG

CUUCGGCAUGUUCACCACGCUGGGCUACUUGAUCUGCGGCUUUCGGGUCGUGC

UCAUGUACCGCUUCGAGGAGGAGCUAUUCUUGCGCAGCUUGCAAGACUAUAA

GAUUCAAUCUGCCCUGCUGGUGCCCACACUAUUUAGCUUCUUCGCUAAGAGCA

CUCUCAUCGACAAGUACGACCUAAGCAACUUGCACGAGAUCGCCAGCGGCGGG

GCGCCGCUCAGCAAGGAGGUAGGUGAGGCCGUGGCCAAACGCUUCCACCUACC

AGGCAUCCGACAGGGCUACGGCCUGACAGAAACAACCAGCGCCAUUCUGAUCA

CCCCCGAAGGGGACGACAAGCCUGGCGCAGUAGGCAAGGUGGUGCCCUUCUUC

GAGGCUAAGGUGGUGGACUUGGACACCGGUAAGACACUGGGUGUGAACCAGC

GCGGCGAGCUGUGCGUCCGUGGCCCCAUGAUCAUGAGCGGCUACGUUAACAAC

CCCGAGGCUACAAACGCUCUCAUCGACAAGGACGGCUGGCUGCACAGCGGCGA

CAUCGCCUACUGGGACGAGGACGAGCACUUCUUCAUCGUGGACCGGCUGAAGU

CCCUGAUCAAAUACAAGGGCUACCAGGUAGCCCCAGCCGAACUGGAGAGCAUC

CUGCUGCAACACCCCAACAUCUUCGACGCCGGGGUCGCCGGCCUGCCCGACGA

CGAUGCCGGCGAGCUGCCCGCCGCAGUCGUCGUGCUGGAACACGGUAAAACCA

UGACCGAGAAGGAGAUCGUGGACUAUGUGGCCAGCCAGGUUACAACCGCCAAG

AAGCUGCGCGGUGGUGUUGUGUUCGUGGACGAGGUGCCUAAAGGACUGACCG

GCAAGUUGGACGCCCGCAAGAUCCGCGAGAUUCUCAUUAAGGCCAAGAAGGGC

GGCAAGAUCGCCGUGUAACUCGAGCCGGAAACGCAAUAGCCGAAAAACAAAAA

ACAAAAAAAACAAAAAAAAAACCAAAAAAACAAAACACAUUAAAACAGCCUG

UGGGUUGAUCCCACCCACAGGCCCAUUGGGCGCUAGCACUCUGGUAUCACGGU

ACCUUUGUGCGCCUGUUUUAUACCCCCUCCCCCAACUGUAACUUAGAAGUAAC

ACACACCGAUCAACAGUCAGCGUGGCACACCAGCCACGUUUUGAUCAAGCACU

UCUGUUACCCCGGACUGAGUAUCAAUAGACUGCUCACGCGGUUGAAGGAGAA

AGCGUUCGUUAUCCGGCCAACUACUUCGAAAAACCUAGUAACACCGUGGAAGU

TABLE 7-continued

| |
|---|
| UGCAGAGUGUUUCGCUCAGCACUACCCCAGUGUAGAUCAGGUCGAUGAGUCAC |
| CGCAUUCCCCACGGGCGACCGUGGCGGUGGCUGCGUUGGCGGCCUGCCCAUGG |
| GGAAACCCAUGGGACGCUCUAAUACAGACAUGGUGCGAAGAGUCUAUUGAGC |
| UAGUUGGUAGUCCUCCGGCCCCUGAAUGCGGCUAAUCCUAACUGCGGAGCACA |
| CACCCUCAAGCCAGAGGGCAGUGUGUCGUAACGGGCAACUCUGCAGCGGAACC |
| GACUACUUUGGGUGUCCGUGUUUCAUUUUAUUCCUAUACUGGCUGCUUAUGG |
| UGACAAUUGAGAGAUCGUUACCAUAUAGCUAUUGGAUUGGCCAUCCGGUGAC |
| UAAUAGAGCUAUUAUAUAUCCCUUUGUUGGGUUUAUACCACUUAGCUUGAAA |
| GAGGUUAAAACAUUACAAUUCAUUGUUAAGUUGAAUACAGCAAAAUGAGCAA |
| GAUCUACAUCGACGAGCGGAGCAACGCCGAGAUCGUGUGCGAGGCCAUCAAGA |
| CCAUCGGCAUCGAGGGCGCCACCGCCGCCCAGCUGACCAGGCAGCUGAACAUG |
| GAGAAGCGGGAGGUGAACAAGGCCCUGUACGACCUGCAGAGGAGCGCUAUGG |
| UGUACUCCAGCGACGACAUCCCUCCCCGGUGGUUCAUGACCACCGAGGCCGAC |
| AAGCCCGACGCCGACGCUAUGGCCGACGUGAUCAUCGACGACGUGAGCAGGGA |
| GAAGUCCAUGAGGGAGGACCACAAGAGCUUCGACGACGUGAUCCCCGCCAAGA |
| AGAUCAUCGACUGGAAGGGCGCCAACCCCGUGACCGUGAUCAACGAGUACUGC |
| CAGAUCACCAGGAGGGACUGGAGCUUCCGGAUCGAGAGCGUGGGCCCCAGCAA |
| CAGCCCCACCUUCUACGCCUGCGUGGACAUCGACGGCAGGGUGUUCGACAAGG |
| CCGACGGCAAGAGCAAGCGGGACGCCAAGAACAACGCCGCCAAGCUGGCCGUG |
| GACAAGCUGCUGGGCUACGUGAUCAUCCGGUUCUAAACAAUUGGCAAGCUGCU |
| UACAUAGAACUCGCGGCGAUUGGCAUGCCGCCUUAAAAUUUUUAUUUUAUUU |
| UUUCUUUUCUUUUCCGAAUCGGAUUUUGUUUUUAAUAUUUCAAAAAAAAAAA |
| AAAAAAAAAAAAAUCUAGAAAAAAAAAAAAAAAAAAAAAAAAAAAAAAAAAA |
| AAAAAAAAAAAAAAAAAAAAAAAAAAAAAAAAAAAAAAAAAAAAAAAAAAAA |
| AAAAAAAAAAAAAAA |

What is claimed is:

1. A nucleic acid molecule comprising:

(i) a first polynucleotide encoding one or more viral replication proteins, wherein the first polynucleotide is codon-optimized as compared to a wild-type polynucleotide encoding the one or more viral replication proteins and wherein the first polynucleotide comprises a sequence having at least 80% identity to a sequence of SEQ ID NO:72; and (ii) a second polynucleotide comprising a first transgene encoding a first antigenic protein or a fragment thereof.

2. The nucleic acid molecule of claim 1, further comprising a 5' untranslated region (UTR), wherein the 5' UTR comprises an alphavirus 5' UTR sequence.

3. The nucleic acid molecule of claim 2, wherein the 5' UTR comprises a sequence of SEQ ID NO:73, SEQ ID NO:74, or SEQ ID NO:75.

4. The nucleic acid molecule of claim 1, further comprising a 3' untranslated region (UTR), wherein the 3' UTR comprises an alphavirus 3' UTR sequence.

5. The nucleic acid molecule of claim 4, wherein the 3' UTR comprises a poly-A sequence.

6. The nucleic acid molecule of claim 4, wherein the 3' UTR comprises a sequence of SEQ ID NO:76.

7. The nucleic acid molecule of claim 1, wherein the first antigenic protein is a viral protein, a bacterial protein, a fungal protein, a protozoan protein, a parasite protein, or a tumor protein.

8. The nucleic acid molecule of claim 7, wherein the viral protein is an orthomyxovirus protein, a paramyxovirus protein, a picornavirus protein, a flavivirus protein, a filovirus protein, a rhabdovirus protein, a togavirus protein, an arterivirus protein, a bunyavirus protein, an arenavirus protein, a reovirus protein, a bornavirus protein, a retrovirus protein, an adenovirus protein, a herpesvirus protein, a polyomavirus protein, a papillomavirus protein, a poxvirus protein, or a hepadnavirus protein.

9. The nucleic acid molecule of claim 7, wherein the first antigenic protein is an influenza virus protein, a respiratory syncytial virus (RSV) protein, a human immunodeficiency virus (HIV) protein, a hepatitis C virus (HCV) protein, a cytomegalovirus (CMV) protein, a Lassa Fever Virus (LFV) protein, an Ebola Virus (EBOV) protein, a *Mycobacterium* protein, a *Bacillus* protein, a *Yersinia* protein, a *Streptococcus* protein, a *Pseudomonas* protein, a *Shigella* protein, a *Campylobacter* protein, a *Salmonella* protein, a *Plasmodium* protein, or a *Toxoplasma* protein.

10. The nucleic acid molecule of claim 7, wherein the tumor protein is a kidney cancer, renal cancer, urinary bladder cancer, prostate cancer, uterine cancer, breast cancer, cervical cancer, ovarian cancer, lung cancer, liver cancer, stomach cancer, colon cancer, rectal cancer, oral cavity cancer, pharynx cancer, pancreatic cancer, thyroid cancer, melanoma, skin cancer, head and neck cancer, brain cancer, hematopoietic cancer, leukemia, lymphoma, bone cancer, or sarcoma protein.

11. The nucleic acid molecule of claim 1, wherein the second polynucleotide comprises at least two transgenes.

12. The nucleic acid molecule of claim 11, wherein a second transgene encodes a second antigenic protein or a fragment thereof, an immunomodulatory protein, or a reporter protein.

13. The nucleic acid molecule of claim 11, wherein the second polynucleotide further comprises a sequence encoding a 2A peptide, an internal ribosomal entry site (IRES), a subgenomic promoter, or a combination thereof, located between transgenes.

14. The nucleic acid molecule of claim 11, wherein the first and second transgenes encode viral proteins, bacterial proteins, fungal proteins, protozoan proteins, parasite proteins, tumor proteins, immunomodulatory proteins, reporter proteins, or any combination thereof.

15. The nucleic acid molecule of claim 1, wherein the first polynucleotide is located 5' of the second polynucleotide.

16. The nucleic acid molecule of claim 15, further comprising an intergenic region located between the first polynucleotide and the second polynucleotide.

17. The nucleic acid molecule of claim 16, wherein the intergenic region comprises a sequence having at least 85% identity to a sequence of SEQ ID NO:77.

18. The nucleic acid molecule of claim 1, wherein the nucleic acid molecule is (a) a DNA molecule; or (b) an RNA molecule, wherein T is substituted with U.

19. The nucleic acid molecule of claim 18, wherein the DNA molecule further comprises a promoter located 5' of the 5' UTR, wherein the promoter is a T7 promoter, a T3 promoter, or an SP6 promoter.

20. The nucleic acid molecule of claim 18, wherein the RNA molecule is a self-replicating RNA molecule.

21. The nucleic acid molecule of claim 18, wherein the RNA molecule further comprises a 5' cap having a Cap 1 structure, a Cap 1 ($^{m6}$A) structure, a Cap 2 structure, or a Cap 0 structure.

22. A nucleic acid molecule comprising (a) a sequence of SEQ ID NO:78; or (b) a sequence of SEQ ID NO:72, SEQ ID NO:73, SEQ ID NO:76, and SEQ ID NO:77, wherein T is substituted with U.

23. A pharmaceutical composition comprising the nucleic acid molecule of claim 1 and a lipid formulation.

24. The pharmaceutical composition of claim 23, wherein the lipid formulation comprises an ionizable cationic lipid.

25. The pharmaceutical composition of claim 24, wherein the ionizable cationic lipid has a structure of Formula I:

(I)

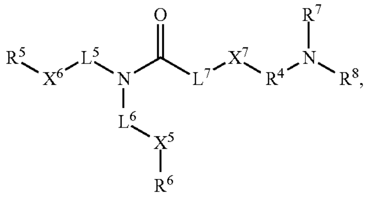

or a pharmaceutically acceptable salt thereof, wherein $R^5$ and $R^6$ are each independently selected from the group consisting of a linear or branched $C_1$-$C_{31}$ alkyl, $C_2$-$C_{31}$ alkenyl or $C_2$-$C_{31}$ alkynyl and cholesteryl; $L^5$ and $L^6$ are each independently selected from the group consisting of a linear $C_1$-$C_{20}$ alkyl and $C_2$-$C_{20}$ alkenyl; $X^5$ is —C(O)O—, whereby —C(O)O—$R^6$ is formed or —OC(O)— whereby —OC(O)—$R^6$ is formed; $X^6$ is —C(O)O— whereby —C(O)O—$R^5$ is formed or —OC(O)— whereby —OC(O)—$R^5$ is formed; $X^7$ is S or O; $L^7$ is absent or lower alkyl; $R^4$ is a linear or branched $C_1$-$C_6$ alkyl; and $R^7$ and $R^8$ are each independently selected from the group consisting of a hydrogen and a linear or branched $C_1$-$C_6$ alkyl.

26. A method of inducing an immune response to an antigenic protein in a subject comprising:

administering to the subject an effective amount of a nucleic acid molecule of claim 1, thereby inducing an immune response to the first antigenic protein.

27. A method of inducing an immune response to an antigenic protein in a subject comprising:

administering to the subject an effective amount of a pharmaceutical composition of claim 23, thereby inducing an immune response to the first antigenic protein.

* * * * *

SEQUENCE LISTING

<160> NUMBER OF SEQ ID NOS: 119

<210> SEQ ID NO 1
<211> LENGTH: 18
<212> TYPE: DNA
<213> ORGANISM: Artificial sequence
<220> FEATURE:
<223> OTHER INFORMATION: Synthetic polynucleotide

<400> SEQUENCE: 1
gaggaaactt aagauggg 18

<210> SEQ ID NO 2
<211> LENGTH: 7
<212> TYPE: RNA
<213> ORGANISM: Artificial sequence
<220> FEATURE:
<223> OTHER INFORMATION: Synthetic polynucleotide

<400> SEQUENCE: 2 ggauggg 7

<210> SEQ ID NO 3
<211> LENGTH: 7
<212> TYPE: RNA
<213> ORGANISM: Artificial sequence
<220> FEATURE:
<223> OTHER INFORMATION: Synthetic polynucleotide

<400> SEQUENCE: 3 ggauagg 7

<210> SEQ ID NO 4
<211> LENGTH: 7
<212> TYPE: RNA
<213> ORGANISM: Artificial sequence
<220> FEATURE:
<223> OTHER INFORMATION: Synthetic polynucleotide

<400> SEQUENCE: 4 ggagagg 7

<210> SEQ ID NO 5
<211> LENGTH: 129
<212> TYPE: RNA
<213> ORGANISM: Artificial sequence
<220> FEATURE:
<223> OTHER INFORMATION: Synthetic polynucleotide

<400> SEQUENCE: 5
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauag 129

<210> SEQ ID NO 6
<211> LENGTH: 28
<212> TYPE: RNA
<213> ORGANISM: Artificial sequence
<220> FEATURE:
<223> OTHER INFORMATION: Synthetic polynucleotide

<400> SEQUENCE: 6
auuauuacau caaaacaaaa agccgcca 28

<210> SEQ ID NO 7
<211> LENGTH: 245
<212> TYPE: RNA
<213> ORGANISM: Artificial sequence
<220> FEATURE:
<223> OTHER INFORMATION: Synthetic polynucleotide

<400> SEQUENCE: 7
cuuaaggggg cgcugccuac ggagguggca gccaucuccu ucucggcauc aagcuuacca 60
uggugcccca ggcccugcuc uugguccgc ugcugguguu cccccucugc uucggcaagu 120 ucccca ucua caccaucccc gacaagcugg ggccguggag ccccaucgac auccaccacc 180
uguccugccc caacaaccuc guggucgagg acgagggcug caccaaccug agcggguucu 240
ccuac 245

<210> SEQ ID NO 8
<211> LENGTH: 177
<212> TYPE: RNA
<213> ORGANISM: Artificial sequence
<220> FEATURE:
<223> OTHER INFORMATION: Synthetic polynucleotide

<400> SEQUENCE: 8
ugagugucgu acagccucca ggcccccccc ucccgggaga gccauagugg ucugcggaac 60
cggugaguac accggaauug ccgggaagac ugggucuuu cuuggauaaa cccacucuau 120
gcccggccau uugggcgugc ccccgcaaga cugcuagccg aguaguguug gguugcg 177

<210> SEQ ID NO 9
<211> LENGTH: 89
<212> TYPE: RNA
<213> ORGANISM: Artificial sequence
<220> FEATURE:
<223> OTHER INFORMATION: Synthetic polynucleotide

<400> SEQUENCE: 9
aauuauuggu uaaagaagua uauuagugcu aauuucccuc cguuuguccu agcuuuucuc 60
uucugucaac cccacacgcc uuuggcaca 89

<210> SEQ ID NO 10
<211> LENGTH: 569
<212> TYPE: RNA
<213> ORGANISM: Artificial sequence
<220> FEATURE:
<223> OTHER INFORMATION: Synthetic polynucleotide

<400> SEQUENCE: 10
cuccccuccc cccccuaac guuacuggcc gaagccgcuu ggaauaaggc cggugugcgu 60
uugucuauau guuauuuucc accauauugc cgucuuuugg caaugugagg gcccggaaac 120
cuggcccugu cuucuugacg agcauuccua ggggucuuuc cccucucgcc aaaggaaugc 180
aaggucuguu gaaugucgug aaggaagcag uuccucugga agcuucuuga agacaaacaa 240
cgucuguagc gacccuuugc aggcagcgga acccccacc uggcgacagg ugccucugcg 300
gccaaaagcc acguguauaa gauacaccug caaaggcggc acaaccccag ugccacguug 360
ugaguuggau aguuguggaa agagucaaau ggcucuccuc aagcguauuc aacaaggggc 420
ugaaggaugc ccagaaggua ccccauugua ugggaucuga ucuggggccu cggugcacau 480
gcuuuacgug uguuuagucg agguuaaaaa acgucuaggc cccccgaacc acggggacgu 540
gguuuuccuu ugaaaaacac gaugauaau 569

<210> SEQ ID NO 11
<211> LENGTH: 44
<212> TYPE: RNA
<213> ORGANISM: Artificial sequence
<220> FEATURE:
<223> OTHER INFORMATION: Synthetic polynucleotide

<400> SEQUENCE: 11
gucagcuuuc aaacucuuug uuucuuguuu guugauugag aaua 44

<210> SEQ ID NO 12
<211> LENGTH: 54
<212> TYPE: RNA
<213> ORGANISM: Artificial sequence
<220> FEATURE:
<223> OTHER INFORMATION: Synthetic polynucleotide

<400> SEQUENCE: 12
cucucgccug agaaaaaaaa uccacgaacc aauuucucag caaccagcag cacg 54

<210> SEQ ID NO 13
<211> LENGTH: 52
<212> TYPE: RNA
<213> ORGANISM: Artificial sequence
<220> FEATURE:
<223> OTHER INFORMATION: Synthetic polynucleotide

<400> SEQUENCE: 13
accugugagg guucgaagga aguagcagug uuuuuuguuc cuagaggaag ag 52

<210> SEQ ID NO 14
<211> LENGTH: 71
<212> TYPE: RNA
<213> ORGANISM: Artificial sequence
<220> FEATURE:
<223> OTHER INFORMATION: Synthetic polynucleotide

<400> SEQUENCE: 14
acacagaaac auucgcaaaa acaaaauccc aguaucaaaa uucuucucuu uuuuucauau 60
uucgcaaaga c 71

<210> SEQ ID NO 15
<211> LENGTH: 52
<212> TYPE: RNA
<213> ORGANISM: Artificial sequence
<220> FEATURE:
<223> OTHER INFORMATION: Synthetic polynucleotide

<400> SEQUENCE: 15
cagaaaaauu ugcuacauug uuucacaaac uucaaauauu auucauuuau uu 52

<210> SEQ ID NO 16
<211> LENGTH: 158
<212> TYPE: RNA
<213> ORGANISM: Artificial sequence
<220> FEATURE:
<223> OTHER INFORMATION: Synthetic polynucleotide

<400> SEQUENCE: 16
cuagugacug acuaggaucu gguuaccacu aaaccagccu caagaacacc cgaauggagu 60
cucuaagcua cauaauacca acuuacacuu acaaaauguu gucccccaaa auguagccau 120
ucguaucugc uccuaauaaa aagaaaguuu cuucacau 158

<210> SEQ ID NO 17
<211> LENGTH: 166
<212> TYPE: RNA
<213> ORGANISM: Artificial sequence
<220> FEATURE:
<223> OTHER INFORMATION: Synthetic polynucleotide

<400> SEQUENCE: 17
ugcaaggcug gccggaagcc cuugccugaa agcaagauuu cagccuggaa gagggcaaag 60
uggacgggag uggacaggag uggaugcgau aagauguggu uugaagcuga ugggugccag 120
cccugcauug cugagucaau caauaaagag cuuucuuuug acccau 166

<210> SEQ ID NO 18
<211> LENGTH: 143
<212> TYPE: RNA
<213> ORGANISM: Artificial sequence
<220> FEATURE:
<223> OTHER INFORMATION: Synthetic polynucleotide

<400> SEQUENCE: 18
acgccgaagc cugcagccau gcgaccccac gccaccccgu gccuccugcc uccgcgcagc 60
cugcagcggg agacccuguc cccgccccag ccguccuccu ggggguggacc cuaguuuaau 120 aaagauucac caaguuucac gca 143

<210> SEQ ID NO 19
<211> LENGTH: 220
<212> TYPE: RNA
<213> ORGANISM: Artificial sequence
<220> FEATURE:
<223> OTHER INFORMATION: Synthetic polynucleotide

<400> SEQUENCE: 19
uagagcggca aacccuagcu acacuccaua gcuaguuucu uuuuuuuuug uuuuuuuuuu 60
uuuuuuuuuu uuuuuuuuuu uuuuuuuuuc cuuucuuuuc cuucuuuuuu uccucuuuuc 120 uuggguggcuc caucuuagcc cuagucacgg cuagcuguga aagguccgug agccgcauga 180
cugcagagag ugccguaacu ggucucucug cagaucaugu 220

<210> SEQ ID NO 20
<211> LENGTH: 170
<212> TYPE: RNA
<213> ORGANISM: Artificial sequence
<220> FEATURE:
<223> OTHER INFORMATION: Synthetic polynucleotide

<400> SEQUENCE: 20
acacaucaca accacaaccu ucucaggcua cccugagaaa aaaagacaug aagacucagg 60
acucaucuuu ucuguuggug uaaaaucaac acccuaagga acacaaauuu cuuuaaacau 120
uugacuucuu gucucugugc ugcaauuaau aaaaaaugga aagaaucuac 170

<210> SEQ ID NO 21
<211> LENGTH: 110
<212> TYPE: RNA
<213> ORGANISM: Artificial sequence
<220> FEATURE:
<223> OTHER INFORMATION: Synthetic polynucleotide

<400> SEQUENCE: 21
gcuggagccu cgguagccgu ucccuccugcc cgcugggccu cccaacgggc ccuccucccc 60
uccuugcacc ggcccuuccu ggucuuugaa uaaagucuga gugggcagca 110

<210> SEQ ID NO 22
<211> LENGTH: 123
<212> TYPE: RNA
<213> ORGANISM: Artificial sequence
<220> FEATURE:
<223> OTHER INFORMATION: Synthetic polynucleotide

<400> SEQUENCE: 22
uagugcaguc acuggcacaa cgcguugccc gguaagccaa ucggguauac acggucguca 60
uacugcagac aggguucuuc uacuuugcaa gauagucuag aguaguaaaa uaaauaguau 120
aag 123

<210> SEQ ID NO 23
<211> LENGTH: 6
<212> TYPE: RNA
<213> ORGANISM: Artificial sequence
<220> FEATURE:
<223> OTHER INFORMATION: Synthetic polynucleotide

<400> SEQUENCE: 23 gccacc 6

<210> SEQ ID NO 24
<211> LENGTH: 4
<212> TYPE: RNA
<213> ORGANISM: Artificial sequence
<220> FEATURE:
<223> OTHER INFORMATION: Synthetic polynucleotide

<400> SEQUENCE: 24 gcca 4

<210> SEQ ID NO 25
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 25
cacaaagagu aaagaagaac a 21

<210> SEQ ID NO 26
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 26
aacacuaaaa guagaagaaa a 21

<210> SEQ ID NO 27
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 27
cucagaaaga uaagaucagc c 21

<210> SEQ ID NO 28
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 28
aaccaaucga aagaaaccaa a 21

<210> SEQ ID NO 29
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 29
cucuaaucac caggaguaaa a 21

<210> SEQ ID NO 30
<211> LENGTH: 21

<212> TYPE: RNA
<213> ORGANISM: Artificial sequence
<220> FEATURE:
<223> OTHER INFORMATION: Synthetic polynucleotide

<400> SEQUENCE: 30
gagagagauc uuaacaaaaa a 21

<210> SEQ ID NO 31
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 31
uguguaacaa caacaacaac a 21

<210> SEQ ID NO 32
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 32
ccgcaguagg aagagaaagc c 21

<210> SEQ ID NO 33
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 33
aaaaaaaaaa gaaaucauaa a 21

<210> SEQ ID NO 34
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 34
gagagaagaa agaagaagac g 21

<210> SEQ ID NO 35
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 35
caauuaaaaa uacuuaccaa a 21

<210> SEQ ID NO 36
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 36
gcaaacagag uaagcgaaac g 21

<210> SEQ ID NO 37
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 37
gcgaagaaga cgaacgcaaa g 21

<210> SEQ ID NO 38
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 38
uuaggacugu auugacuggc c 21

<210> SEQ ID NO 39
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 39
aucaucggaa uucggaaaaa g 21

<210> SEQ ID NO 40
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 40
aaaacaaaag uuaaagcaga c 21

<210> SEQ ID NO 41
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 41
uuuaucucaa auaagaaggc a 21

<210> SEQ ID NO 42
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 42
gguggggagg ugagauuucu u 21

<210> SEQ ID NO 43
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 43
ugauuaggaa acuacaaagc c 21

<210> SEQ ID NO 44
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 44
cauuuuucaa uuucauaaaa c 21

<210> SEQ ID NO 45
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 45
uuacuuuuaa gcccaacaaa a 21

<210> SEQ ID NO 46
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 46
ggcgugugug uguguuguug a 21

<210> SEQ ID NO 47
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 47
guggugaagg ggaagguuua g 21

<210> SEQ ID NO 48
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 48
uuguuuuuuu uugguuuggu u 21

<210> SEQ ID NO 49
<211> LENGTH: 44
<212> TYPE: DNA
<213> ORGANISM: Artificial sequence
<220> FEATURE:
<223> OTHER INFORMATION: Synthetic polynucleotide

<400> SEQUENCE: 49
atgggcggcg catgagagaa gcccagacca attacctacc caaa 44

<210> SEQ ID NO 50
<211> LENGTH: 7482
<212> TYPE: DNA
<213> ORGANISM: Artificial sequence
<220> FEATURE:
<223> OTHER INFORMATION: Synthetic polynucleotide

<400> SEQUENCE: 50
atggagaaag ttcacgttga catcgaggaa gacagcccat tcctcagagc tttgcagcgg 60
agcttcccgc agtttgaggt agaagccaag caggtcactg ataatgacca tgctaatgcc 120
agagcgtttt cgcatctggc ttcaaaactg atcgaaacgg aggtggaccc atccgacacg 180
atccttgaca ttggaagtgc gcccgcccgc agaatgtatt ctaagcacaa gtatcattgt 240
atctgtccga tgagatgtgc ggaagatccg gacagattgt ataagtatgc aactaagctg 300
aagaaaaact gtaaggaaat aactgataag gaattggaca agaaaatgaa ggagctggcc 360
gccgtcatga gcgaccctga cctggaaact gagactatgt gcctccacga cgacgagtcg 420
tgtcgctacg aagggcaagt cgctgtttac caggatgtat acgccgtcga cggcccccacc 480 agcctgtacc accaggccaa caagggcgtg agggtggcct actggatcgg cttcgacacc 540
acacccttca tgttcaagaa cctggccggc gcctacccca gctacagcac caactgggcc 600
gacgagaccg tgctgaccgc caggaacatc ggcctgtgca gcagcgacgt gatggagagg 660
agccggagag gcatgagcat cctgaggaag aaatacctga agcccagcaa caacgtgctg 720
ttcagcgtgg gcagcaccat ctaccacgag aagagggacc tgctcaggag ctggcacctg 780
cccagcgtgt tccacctgag gggcaagcag aactacacct gcaggtgcga gaccatcgtg 840
agctgcgacg gctacgtggt gaagaggatc gccatcagcc ccggcctgta cggcaagccc 900
agcggctacg ccgctacaat gcacagggag ggcttcctgt gctgcaaggt gaccgacacc 960
ctgaacggcg agagggtgag cttccccgtg tgcacctacg tgcccgccac cctgtgcgac 1020
cagatgaccg gcatcctggc caccgacgtg agcgccgacg acgcccagaa gctgctcgtg 1080
ggcctgaacc agaggatcgt ggtcaacggc aggacccaga ggaacaccaa cacaatgaag 1140
aactacctgc tgcccgtggt ggcccaggct ttcgccaggt gggccaagga gtacaaggag 1200
gaccaggaag acgagaggcc cctgggcctg agggacaggc agctggtgat gggctgctgc 1260
tgggccttca ggcggcacaa gatcaccagc atctacaaga ggcccgacac ccagaccatc 1320
atcaaggtga acagcgactt ccacagcttc gtgctgccca ggatcggcag caacaccctg 1380
gagatcggcc tgaggacccg gatcaggaag atgctggagg aacacaagga gcccagccca 1440
ctgatcaccg ccgaggacgt gcaggaggcc aagtgcgctg ccgacgaggc caaggaggtg 1500
agggaggccg aggaactgag ggccgccctg ccacccctgg ctgccgacgt ggaggaaccc 1560
accctggaag ccgacgtgga cctgatgctg caggaggccg gcgccggaag cgtggagaca 1620
cccaggggcc tgatcaaggt gaccagctac gacggcgagg acaagatcgg cagctacgcc 1680
gtgctgagcc cacaggccgt gctgaagtcc gagaagctga gctgcatcca cccactggcc 1740
gagcaggtga tcgtgatcac ccacagcggc aggaagggca ggtacgccgt ggagccctac 1800
cacggcaagg tggtcgtgcc cgagggccac gccatccccg tgcaggactt ccaggccctg 1860
agcgagagcg ccaccatcgt gtacaacgag agggagttcg tgaacaggta cctgcaccat 1920
atcgccaccc acggcggagc cctgaacacc gacgaggaat actacaagac cgtgaagccc 1980
agcgagcacg acggcgagta cctgtacgac atcgacagga agcagtgcgt gaagaaagag 2040
ctggtgaccg gcctgggact gaccggcgag ctggtggacc cacccttcca cgagttcgcc 2100

-continued

```
tacgagagcc tgaggaccag acccgccgct ccctaccagg tgcccaccat cggcgtgtac   2160
ggcgtgcccg gcagcggaaa gagcggcatc atcaagagcg ccgtgaccaa gaaagacctg   2220
gtggtcagcg ccaagaaaga gaactgcgcc gagatcatca gggacgtgaa gaagatgaaa   2280
ggcctggacg tgaacgcgcg caccgtggac agcgtgctgc tgaacggctg caagcacccc   2340
gtggagaccc tgtacatcga cgaggccttc gcttgccacg ccggcaccct gagggccctg   2400
atcgccatca tcaggcccaa gaaagccgtg ctgtgcggcg accccaagca gtgcggcttc   2460
ttcaacatga tgtgcctgaa ggtgcacttc aaccacgaga tctgcaccca ggtgttccac   2520
aagagcatca gcaggcggtg caccaagagc gtgaccagcg tcgtgagcac cctgttctac   2580
gacaagaaaa tgaggaccac caaccccaag gagaccaaaa tcgtgatcga caccacaggc   2640
agcaccaagc ccaagcagga cgacctgatc ctgacctgct tcaggggctg ggtgaagcag   2700
ctgcagatcg actacaaggg caacgagatc atgaccgccg ctgccagcca gggcctgacc   2760
aggaagggcg tgtacgccgt gaggtacaag gtgaacgaga acccactgta cgctcccacc   2820
agcgagcacg tgaacgtgct gctgaccagg accgaggaca ggatcgtgtg gaagaccctg   2880
gccggcgacc cctggatcaa gaccctgacc gccaagtacc ccggcaactt caccgccacc   2940
atcgaagagt ggcaggccga gcacgacgcc atcatgaggc acatcctgga gaggcccgac   3000
cccaccgacg tgttccagaa caaggccaac gtgtgctggg ccaaggccct ggtgcccgtg   3060
ctgaagaccg ccggcatcga catgaccaca gagcagtgga acaccgtgga ctacttcgag   3120
accgacaagg cccacagcgc cgagatcgtg ctgaaccagc tgtgcgtgag gttcttcggc   3180
ctggacctgg acagcggcct gttcagcgcc cccaccgtgc cactgagcat caggaacaac   3240
cactgggaca acagccccag cccaaacatg tacggcctga acaaggaggt ggtcaggcag   3300
ctgagcaggc ggtacccaca gctgcccagg gccgtggcca ccggcagggt gtacgacatg   3360
aacaccggca ccctgaggaa ctacgacccc aggatcaacc tggtgcccgt gaacaggcgg   3420
ctgccccacg ccctggtgct gcaccacaac gagcacccac agagcgactt cagctccttc   3480
gtgagcaagc tgaaaggcag gaccgtgctg gtcgtgggcg agaagctgag cgtgcccggc   3540
aagatggtgg actggctgag cgacaggccc gaggccacct tccgggccag gctggacctc   3600
ggcatccccg gcgacgtgcc caagtacgac atcatcttcg tgaacgtcag gaccccatac   3660
aagtaccacc attaccagca gtgcgaggac cacgccatca agctgagcat gctgaccaag   3720
aaggcctgcc tgcacctgaa ccccggaggc acctgcgtga gcatcggcta cggctacgcc   3780
gacagggcca gcgagagcat cattggcgcc atcgccaggc tgttcaagtt cagcagggtg   3840
tgcaaaccca agagcagcct ggaggaaacc gaggtgctgt tcgtgttcat cggctacgac   3900
cggaaggcca ggacccacaa cccctacaag ctgagcagca ccctgacaaa catctacacc   3960
ggcagcaggc tgcacgaggc cggctgcgcc cccagctacc acgtggtcag gggcgatatc   4020
gccaccgcca ccgagggcgt gatcatcaac gctgccaaca gcaagggcca gcccggaggc   4080
ggagtgtgcg gcgccctgta caagaagttc cccgagagct tcgacctgca gcccatcgag   4140
gtgggcaagg ccaggctggt gaagggcgcc gctaagcaca tcatccacgc cgtgggcccc   4200
aacttcaaca aggtgagcga ggtggaaggc gacaagcagc tggccgaagc ctacgagagc   4260
atcgccaaga tcgtgaacga caataactac aagagcgtgg ccatccccact gctcagcacc   4320
ggcatcttca gcggcaacaa ggacaggctg acccagagcc tgaaccacct gctcaccgcc   4380
ctggacacca ccgatgccga cgtggccatc tactgcaggg acaagaagtg ggagatgacc   4440
```

-continued

```
ctgaaggagg ccgtggccag gcgggaggcc gtggaagaga tctgcatcag cgacgactcc   4500
agcgtgaccg agcccgacgc cgagctggtg agggtgcacc ccaagagctc cctggccggc   4560
aggaagggct acagcaccag cgacggcaag accttcagct acctggaggg caccaagttc   4620
caccaggccg ctaaggacat cgccgagatc aacgctatgt ggcccgtggc caccgaggcc   4680
aacgagcagg tgtgcatgta catcctgggc gagagcatgt ccagcatcag gagcaagtgc   4740
cccgtggagg aaagcgaggc cagcacacca cccagcaccc tgccctgcct gtgcatccac   4800
gctatgacac ccgagagggt gcagcggctg aaggccagca ggcccgagca gatcaccgtg   4860
tgcagctcct tcccactgcc caagtacagg atcaccggcg tgcagaagat ccagtgcagc   4920
cagcccatcc tgttcagccc aaaggtgccc gcctacatcc accccaggaa gtacctggtg   4980
gagaccccac ccgtggacga gacacccgag ccaagcgccg agaaccagag caccgagggc   5040
acacccgagc agccacccct gatcaccgag gacgagacaa ggacccggac cccagagccc   5100
atcattatcg aggaagagga agaggacagc atcagcctgc tgagcgacgg ccccacccac   5160
caggtgctgc aggtggaggc cgacatccac ggcccaccca gcgtgtccag ctccagctgg   5220
agcatcccac acgccagcga cttcgacgtg gacagcctga gcatcctgga caccctggag   5280
ggcgccagcg tgacctccgg cgccaccagc gccgagacca acagctactt cgccaagagc   5340
atggagttcc tggccaggcc cgtgccagct cccaggaccg tgttcaggaa cccaccccac   5400
ccagctccca ggaccaggac cccaagcctg gctcccagca gggcctgcag caggaccagc   5460
ctggtgagca ccccacccgg cgtgaacagg gtgatcacca gggaggaact ggaggccctg   5520
acacccagca ggacccccag caggtccgtg agcaggacta gtctggtgtc caacccaccc   5580
ggcgtgaaca gggtgatcac cagggaggaa ttcgaggcct tcgtggccca gcaacagaga   5640
cggttcgacg ccggcgccta catcttcagc agcgacaccg gccagggaca cctgcagcaa   5700
aagagcgtga ggcagaccgt gctgagcgag gtggtgctgg agaggaccga gctggaaatc   5760
agctacgccc ccaggctgga ccaggagaag gaggaactgc tcaggaagaa actgcagctg   5820
aaccccaccc cagccaacag gagcaggtac cagagcagga aggtggagaa catgaaggcc   5880
atcaccgcca ggcggatcct gcagggcctg ggacactacc tgaaggccga gggcaaggtg   5940
gagtgctaca ggaccctgca ccccgtgcca ctgtacagct ccagcgtgaa cagggccttc   6000
tccagcccca aggtggccgt ggaggcctgc aacgctatgc tgaaggagaa cttccccacc   6060
gtggccagct actgcatcat ccccgagtac gacgcctacc tggacatggt ggacggcgcc   6120
agctgctgcc tggacaccgc cagcttctgc cccgccaagc tgaggagctt ccccaagaaa   6180
cacagctacc tggagcccac catcaggagc gccgtgccca gcgccatcca gaacaccctg   6240
cagaacgtgc tggccgctgc caccaagagg aactgcaacg tgacccagat gagggagctg   6300
cccgtgctgg acagcgctgc cttcaacgtg gagtgcttca agaaatacgc ctgcaacaac   6360
gagtactggg agaccttcaa ggagaacccc atcaggctga ccgaagagaa cgtggtgaac   6420
tacatcacca agctgaaggg ccccaaggcc gctgccctgt tcgctaagac ccacaacctg   6480
aacatgctgc aggacatccc aatggacagg ttcgtgatgg acctgaagag ggacgtgaag   6540
gtgacacccg gcaccaagca caccgaggag aggcccaagg tgcaggtgat ccaggccgct   6600
gacccactgg ccaccgccta cctgtgcggc atccacaggg agctggtgag gcggctgaac   6660
gccgtgctgc tgcccaacat ccacaccctg ttcgacatga gcgccgagga cttcgacgcc   6720
atcatcgccg agcacttcca gcccggcgac tgcgtgctgg agaccgacat cgccagcttc   6780
gacaagagcg aggatgacgc tatggccctg accgctctga tgatcctgga ggacctgggc   6840
```

gtggacgccg agctgctcac cctgatcgag gctgccttcg gcgagatcag ctccatccac 6900
ctgcccacca agaccaagtt caagttcggc gctatgatga aaagcggaat gttcctgacc 6960
ctgttcgtga acaccgtgat caacattgtg atcgccagca gggtgctgcg ggagaggctg 7020
accggcagcc cctgcgctgc cttcatcggc gacgacaaca tcgtgaaggg cgtgaaaagc 7080
gacaagctga tggccgacag gtgcgccacc tggctgaaca tggaggtgaa gatcatcgac 7140
gccgtggtgg gcgagaaggc cccctacttc tgcggcggat tcatcctgtg cgacagcgtg 7200
accggcaccg cctgcagggt ggccgacccc ctgaagaggc tgttcaagct gggcaagcca 7260
ctggccgctg acgatgagca cgacgatgac aggcggaggg ccctgcacga ggaaagcacc 7320
aggtggaaca gggtgggcat cctgagcgag ctgtgcaagg ccgtggagag caggtacgag 7380
accgtgggca ccagcatcat cgtgatggct atgaccacac tggccagctc cgtcaagagc 7440
ttctcctacc tgaggggggc ccctataact ctctacggct aa 7482

<210> SEQ ID NO 51
<211> LENGTH: 2493
<212> TYPE: PRT
<213> ORGANISM: Artificial sequence
<220> FEATURE:
<223> OTHER INFORMATION: Synthetic polypeptide

<400> SEQUENCE: 51

Met Glu Lys Val His Val Asp Ile Glu Glu Asp Ser Pro Phe Leu Arg
1 5 10 15

Ala Leu Gln Arg Ser Phe Pro Gln Phe Glu Val Glu Ala Lys Gln Val
20 25 30

Thr Asp Asn Asp His Ala Asn Ala Arg Ala Phe Ser His Leu Ala Ser
35 40 45

Lys Leu Ile Glu Thr Glu Val Asp Pro Ser Asp Thr Ile Leu Asp Ile
50 55 60

Gly Ser Ala Pro Ala Arg Arg Met Tyr Ser Lys His Lys Tyr His Cys
65 70 75 80

Ile Cys Pro Met Arg Cys Ala Glu Asp Pro Asp Arg Leu Tyr Lys Tyr
85 90 95

Ala Thr Lys Leu Lys Lys Asn Cys Lys Glu Ile Thr Asp Lys Glu Leu
100 105 110

Asp Lys Lys Met Lys Glu Leu Ala Ala Val Met Ser Asp Pro Asp Leu
115 120 125

Glu Thr Glu Thr Met Cys Leu His Asp Asp Glu Ser Cys Arg Tyr Glu
130 135 140

Gly Gln Val Ala Val Tyr Gln Asp Val Tyr Ala Val Asp Gly Pro Thr
145 150 155 160

Ser Leu Tyr His Gln Ala Asn Lys Gly Val Arg Val Ala Tyr Trp Ile
165 170 175

Gly Phe Asp Thr Thr Pro Phe Met Phe Lys Asn Leu Ala Gly Ala Tyr
180 185 190

Pro Ser Tyr Ser Thr Asn Trp Ala Asp Glu Thr Val Leu Thr Ala Arg
195 200 205

Asn Ile Gly Leu Cys Ser Ser Asp Val Met Glu Arg Ser Arg Arg Gly
210 215 220

Met Ser Ile Leu Arg Lys Lys Tyr Leu Lys Pro Ser Asn Asn Val Leu
225 230 235 240

Phe Ser Val Gly Ser Thr Ile Tyr His Glu Lys Arg Asp Leu Leu Arg

-continued

```
                245                 250                 255

Ser Trp His Leu Pro Ser Val Phe His Leu Arg Gly Lys Gln Asn Tyr
            260                 265                 270

Thr Cys Arg Cys Glu Thr Ile Val Ser Cys Asp Gly Tyr Val Val Lys
        275                 280                 285

Arg Ile Ala Ile Ser Pro Gly Leu Tyr Gly Lys Pro Ser Gly Tyr Ala
    290                 295                 300

Ala Thr Met His Arg Glu Gly Phe Leu Cys Cys Lys Val Thr Asp Thr
305                 310                 315                 320

Leu Asn Gly Glu Arg Val Ser Phe Pro Val Cys Thr Tyr Val Pro Ala
                325                 330                 335

Thr Leu Cys Asp Gln Met Thr Gly Ile Leu Ala Thr Asp Val Ser Ala
            340                 345                 350

Asp Asp Ala Gln Lys Leu Leu Val Gly Leu Asn Gln Arg Ile Val Val
        355                 360                 365

Asn Gly Arg Thr Gln Arg Asn Thr Asn Thr Met Lys Asn Tyr Leu Leu
    370                 375                 380

Pro Val Val Ala Gln Ala Phe Ala Arg Trp Ala Lys Glu Tyr Lys Glu
385                 390                 395                 400

Asp Gln Glu Asp Glu Arg Pro Leu Gly Leu Arg Asp Arg Gln Leu Val
                405                 410                 415

Met Gly Cys Cys Trp Ala Phe Arg Arg His Lys Ile Thr Ser Ile Tyr
            420                 425                 430

Lys Arg Pro Asp Thr Gln Thr Ile Ile Lys Val Asn Ser Asp Phe His
        435                 440                 445

Ser Phe Val Leu Pro Arg Ile Gly Ser Asn Thr Leu Glu Ile Gly Leu
    450                 455                 460

Arg Thr Arg Ile Arg Lys Met Leu Glu Glu His Lys Glu Pro Ser Pro
465                 470                 475                 480

Leu Ile Thr Ala Glu Asp Val Gln Glu Ala Lys Cys Ala Ala Asp Glu
                485                 490                 495

Ala Lys Glu Val Arg Glu Ala Glu Glu Leu Arg Ala Ala Leu Pro Pro
            500                 505                 510

Leu Ala Ala Asp Val Glu Glu Pro Thr Leu Glu Ala Asp Val Asp Leu
        515                 520                 525

Met Leu Gln Glu Ala Gly Ala Gly Ser Val Glu Thr Pro Arg Gly Leu
    530                 535                 540

Ile Lys Val Thr Ser Tyr Asp Gly Glu Asp Lys Ile Gly Ser Tyr Ala
545                 550                 555                 560

Val Leu Ser Pro Gln Ala Val Leu Lys Ser Glu Lys Leu Ser Cys Ile
                565                 570                 575

His Pro Leu Ala Glu Gln Val Ile Val Ile Thr His Ser Gly Arg Lys
            580                 585                 590

Gly Arg Tyr Ala Val Glu Pro Tyr His Gly Lys Val Val Val Pro Glu
        595                 600                 605

Gly His Ala Ile Pro Val Gln Asp Phe Gln Ala Leu Ser Glu Ser Ala
    610                 615                 620

Thr Ile Val Tyr Asn Glu Arg Glu Phe Val Asn Arg Tyr Leu His His
625                 630                 635                 640

Ile Ala Thr His Gly Gly Ala Leu Asn Thr Asp Glu Glu Tyr Tyr Lys
                645                 650                 655

Thr Val Lys Pro Ser Glu His Asp Gly Glu Tyr Leu Tyr Asp Ile Asp
            660                 665                 670
```

-continued

```
Arg Lys Gln Cys Val Lys Lys Glu Leu Val Thr Gly Leu Gly Leu Thr
        675                 680                 685

Gly Glu Leu Val Asp Pro Pro Phe His Glu Phe Ala Tyr Glu Ser Leu
    690                 695                 700

Arg Thr Arg Pro Ala Ala Pro Tyr Gln Val Pro Thr Ile Gly Val Tyr
705                 710                 715                 720

Gly Val Pro Gly Ser Gly Lys Ser Gly Ile Ile Lys Ser Ala Val Thr
                725                 730                 735

Lys Lys Asp Leu Val Val Ser Ala Lys Lys Glu Asn Cys Ala Glu Ile
            740                 745                 750

Ile Arg Asp Val Lys Lys Met Lys Gly Leu Asp Val Asn Ala Arg Thr
        755                 760                 765

Val Asp Ser Val Leu Leu Asn Gly Cys Lys His Pro Val Glu Thr Leu
    770                 775                 780

Tyr Ile Asp Glu Ala Phe Ala Cys His Ala Gly Thr Leu Arg Ala Leu
785                 790                 795                 800

Ile Ala Ile Ile Arg Pro Lys Lys Ala Val Leu Cys Gly Asp Pro Lys
                805                 810                 815

Gln Cys Gly Phe Phe Asn Met Met Cys Leu Lys Val His Phe Asn His
            820                 825                 830

Glu Ile Cys Thr Gln Val Phe His Lys Ser Ile Ser Arg Arg Cys Thr
        835                 840                 845

Lys Ser Val Thr Ser Val Val Ser Thr Leu Phe Tyr Asp Lys Lys Met
    850                 855                 860

Arg Thr Thr Asn Pro Lys Glu Thr Lys Ile Val Ile Asp Thr Thr Gly
865                 870                 875                 880

Ser Thr Lys Pro Lys Gln Asp Asp Leu Ile Leu Thr Cys Phe Arg Gly
                885                 890                 895

Trp Val Lys Gln Leu Gln Ile Asp Tyr Lys Gly Asn Glu Ile Met Thr
            900                 905                 910

Ala Ala Ala Ser Gln Gly Leu Thr Arg Lys Gly Val Tyr Ala Val Arg
        915                 920                 925

Tyr Lys Val Asn Glu Asn Pro Leu Tyr Ala Pro Thr Ser Glu His Val
    930                 935                 940

Asn Val Leu Leu Thr Arg Thr Glu Asp Arg Ile Val Trp Lys Thr Leu
945                 950                 955                 960

Ala Gly Asp Pro Trp Ile Lys Thr Leu Thr Ala Lys Tyr Pro Gly Asn
                965                 970                 975

Phe Thr Ala Thr Ile Glu Glu Trp Gln Ala Glu His Asp Ala Ile Met
            980                 985                 990

Arg His Ile Leu Glu Arg Pro Asp  Pro Thr Asp Val Phe  Gln Asn Lys
        995                 1000                1005

Ala Asn  Val Cys Trp Ala Lys  Ala Leu Val Pro Val  Leu Lys Thr
    1010                1015                1020

Ala Gly  Ile Asp Met Thr Thr  Glu Gln Trp Asn Thr  Val Asp Tyr
    1025                1030                1035

Phe Glu  Thr Asp Lys Ala His  Ser Ala Glu Ile Val  Leu Asn Gln
    1040                1045                1050

Leu Cys  Val Arg Phe Phe Gly  Leu Asp Leu Asp Ser  Gly Leu Phe
    1055                1060                1065

Ser Ala  Pro Thr Val Pro Leu  Ser Ile Arg Asn Asn  His Trp Asp
    1070                1075                1080
```

Asn Ser Pro Ser Pro Asn Met Tyr Gly Leu Asn Lys Glu Val Val
    1085 1090 1095

Arg Gln Leu Ser Arg Arg Tyr Pro Gln Leu Pro Arg Ala Val Ala
    1100 1105 1110

Thr Gly Arg Val Tyr Asp Met Asn Thr Gly Thr Leu Arg Asn Tyr
    1115 1120 1125

Asp Pro Arg Ile Asn Leu Val Pro Val Asn Arg Arg Leu Pro His
    1130 1135 1140

Ala Leu Val Leu His His Asn Glu His Pro Gln Ser Asp Phe Ser
    1145 1150 1155

Ser Phe Val Ser Lys Leu Lys Gly Arg Thr Val Leu Val Val Gly
    1160 1165 1170

Glu Lys Leu Ser Val Pro Gly Lys Met Val Asp Trp Leu Ser Asp
    1175 1180 1185

Arg Pro Glu Ala Thr Phe Arg Ala Arg Leu Asp Leu Gly Ile Pro
    1190 1195 1200

Gly Asp Val Pro Lys Tyr Asp Ile Ile Phe Val Asn Val Arg Thr
    1205 1210 1215

Pro Tyr Lys Tyr His His Tyr Gln Gln Cys Glu Asp His Ala Ile
    1220 1225 1230

Lys Leu Ser Met Leu Thr Lys Lys Ala Cys Leu His Leu Asn Pro
    1235 1240 1245

Gly Gly Thr Cys Val Ser Ile Gly Tyr Gly Tyr Ala Asp Arg Ala
    1250 1255 1260

Ser Glu Ser Ile Ile Gly Ala Ile Ala Arg Leu Phe Lys Phe Ser
    1265 1270 1275

Arg Val Cys Lys Pro Lys Ser Ser Leu Glu Glu Thr Glu Val Leu
    1280 1285 1290

Phe Val Phe Ile Gly Tyr Asp Arg Lys Ala Arg Thr His Asn Pro
    1295 1300 1305

Tyr Lys Leu Ser Ser Thr Leu Thr Asn Ile Tyr Thr Gly Ser Arg
    1310 1315 1320

Leu His Glu Ala Gly Cys Ala Pro Ser Tyr His Val Val Arg Gly
    1325 1330 1335

Asp Ile Ala Thr Ala Thr Glu Gly Val Ile Ile Asn Ala Ala Asn
    1340 1345 1350

Ser Lys Gly Gln Pro Gly Gly Gly Val Cys Gly Ala Leu Tyr Lys
    1355 1360 1365

Lys Phe Pro Glu Ser Phe Asp Leu Gln Pro Ile Glu Val Gly Lys
    1370 1375 1380

Ala Arg Leu Val Lys Gly Ala Ala Lys His Ile Ile His Ala Val
    1385 1390 1395

Gly Pro Asn Phe Asn Lys Val Ser Glu Val Glu Gly Asp Lys Gln
    1400 1405 1410

Leu Ala Glu Ala Tyr Glu Ser Ile Ala Lys Ile Val Asn Asp Asn
    1415 1420 1425

Asn Tyr Lys Ser Val Ala Ile Pro Leu Leu Ser Thr Gly Ile Phe
    1430 1435 1440

Ser Gly Asn Lys Asp Arg Leu Thr Gln Ser Leu Asn His Leu Leu
    1445 1450 1455

Thr Ala Leu Asp Thr Thr Asp Ala Asp Val Ala Ile Tyr Cys Arg
    1460 1465 1470

Asp Lys Lys Trp Glu Met Thr Leu Lys Glu Ala Val Ala Arg Arg

```
    1475                1480                1485

Glu Ala  Val Glu Glu Ile Cys  Ile Ser Asp Asp Ser  Ser Val Thr
    1490                1495                1500

Glu Pro  Asp Ala Glu Leu Val  Arg Val His Pro Lys  Ser Ser Leu
    1505                1510                1515

Ala Gly  Arg Lys Gly Tyr Ser  Thr Ser Asp Gly Lys  Thr Phe Ser
    1520                1525                1530

Tyr Leu  Glu Gly Thr Lys Phe  His Gln Ala Ala Lys  Asp Ile Ala
    1535                1540                1545

Glu Ile  Asn Ala Met Trp Pro  Val Ala Thr Glu Ala  Asn Glu Gln
    1550                1555                1560

Val Cys  Met Tyr Ile Leu Gly  Glu Ser Met Ser Ser  Ile Arg Ser
    1565                1570                1575

Lys Cys  Pro Val Glu Glu Ser  Glu Ala Ser Thr Pro  Pro Ser Thr
    1580                1585                1590

Leu Pro  Cys Leu Cys Ile His  Ala Met Thr Pro Glu  Arg Val Gln
    1595                1600                1605

Arg Leu  Lys Ala Ser Arg Pro  Glu Gln Ile Thr Val  Cys Ser Ser
    1610                1615                1620

Phe Pro  Leu Pro Lys Tyr Arg  Ile Thr Gly Val Gln  Lys Ile Gln
    1625                1630                1635

Cys Ser  Gln Pro Ile Leu Phe  Ser Pro Lys Val Pro  Ala Tyr Ile
    1640                1645                1650

His Pro  Arg Lys Tyr Leu Val  Glu Thr Pro Pro Val  Asp Glu Thr
    1655                1660                1665

Pro Glu  Pro Ser Ala Glu Asn  Gln Ser Thr Glu Gly  Thr Pro Glu
    1670                1675                1680

Gln Pro  Pro Leu Ile Thr Glu  Asp Glu Thr Arg Thr  Arg Thr Pro
    1685                1690                1695

Glu Pro  Ile Ile Ile Glu Glu  Glu Glu Glu Asp Ser  Ile Ser Leu
    1700                1705                1710

Leu Ser  Asp Gly Pro Thr His  Gln Val Leu Gln Val  Glu Ala Asp
    1715                1720                1725

Ile His  Gly Pro Pro Ser Val  Ser Ser Ser Ser Trp  Ser Ile Pro
    1730                1735                1740

His Ala  Ser Asp Phe Asp Val  Asp Ser Leu Ser Ile  Leu Asp Thr
    1745                1750                1755

Leu Glu  Gly Ala Ser Val Thr  Ser Gly Ala Thr Ser  Ala Glu Thr
    1760                1765                1770

Asn Ser  Tyr Phe Ala Lys Ser  Met Glu Phe Leu Ala  Arg Pro Val
    1775                1780                1785

Pro Ala  Pro Arg Thr Val Phe  Arg Asn Pro Pro His  Pro Ala Pro
    1790                1795                1800

Arg Thr  Arg Thr Pro Ser Leu  Ala Pro Ser Arg Ala  Cys Ser Arg
    1805                1810                1815

Thr Ser  Leu Val Ser Thr Pro  Pro Gly Val Asn Arg  Val Ile Thr
    1820                1825                1830

Arg Glu  Glu Leu Glu Ala Leu  Thr Pro Ser Arg Thr  Pro Ser Arg
    1835                1840                1845

Ser Val  Ser Arg Thr Ser Leu  Val Ser Asn Pro Pro  Gly Val Asn
    1850                1855                1860

Arg Val  Ile Thr Arg Glu Glu  Phe Glu Ala Phe Val  Ala Gln Gln
    1865                1870                1875
```

```
Gln Arg  Arg Phe Asp Ala Gly  Ala Tyr Ile Phe Ser  Ser Asp Thr
    1880                 1885                 1890

Gly Gln  Gly His Leu Gln Gln  Lys Ser Val Arg Gln  Thr Val Leu
    1895                 1900                 1905

Ser Glu  Val Val Leu Glu Arg  Thr Glu Leu Glu Ile  Ser Tyr Ala
    1910                 1915                 1920

Pro Arg  Leu Asp Gln Glu Lys  Glu Glu Leu Leu Arg  Lys Lys Leu
    1925                 1930                 1935

Gln Leu  Asn Pro Thr Pro Ala  Asn Arg Ser Arg Tyr  Gln Ser Arg
    1940                 1945                 1950

Lys Val  Glu Asn Met Lys Ala  Ile Thr Ala Arg Arg  Ile Leu Gln
    1955                 1960                 1965

Gly Leu  Gly His Tyr Leu Lys  Ala Glu Gly Lys Val  Glu Cys Tyr
    1970                 1975                 1980

Arg Thr  Leu His Pro Val Pro  Leu Tyr Ser Ser Ser  Val Asn Arg
    1985                 1990                 1995

Ala Phe  Ser Ser Pro Lys Val  Ala Val Glu Ala Cys  Asn Ala Met
    2000                 2005                 2010

Leu Lys  Glu Asn Phe Pro Thr  Val Ala Ser Tyr Cys  Ile Ile Pro
    2015                 2020                 2025

Glu Tyr  Asp Ala Tyr Leu Asp  Met Val Asp Gly Ala  Ser Cys Cys
    2030                 2035                 2040

Leu Asp  Thr Ala Ser Phe Cys  Pro Ala Lys Leu Arg  Ser Phe Pro
    2045                 2050                 2055

Lys Lys  His Ser Tyr Leu Glu  Pro Thr Ile Arg Ser  Ala Val Pro
    2060                 2065                 2070

Ser Ala  Ile Gln Asn Thr Leu  Gln Asn Val Leu Ala  Ala Ala Thr
    2075                 2080                 2085

Lys Arg  Asn Cys Asn Val Thr  Gln Met Arg Glu Leu  Pro Val Leu
    2090                 2095                 2100

Asp Ser  Ala Ala Phe Asn Val  Glu Cys Phe Lys Lys  Tyr Ala Cys
    2105                 2110                 2115

Asn Asn  Glu Tyr Trp Glu Thr  Phe Lys Glu Asn Pro  Ile Arg Leu
    2120                 2125                 2130

Thr Glu  Glu Asn Val Val Asn  Tyr Ile Thr Lys Leu  Lys Gly Pro
    2135                 2140                 2145

Lys Ala  Ala Ala Leu Phe Ala  Lys Thr His Asn Leu  Asn Met Leu
    2150                 2155                 2160

Gln Asp  Ile Pro Met Asp Arg  Phe Val Met Asp Leu  Lys Arg Asp
    2165                 2170                 2175

Val Lys  Val Thr Pro Gly Thr  Lys His Thr Glu Glu  Arg Pro Lys
    2180                 2185                 2190

Val Gln  Val Ile Gln Ala Ala  Asp Pro Leu Ala Thr  Ala Tyr Leu
    2195                 2200                 2205

Cys Gly  Ile His Arg Glu Leu  Val Arg Arg Leu Asn  Ala Val Leu
    2210                 2215                 2220

Leu Pro  Asn Ile His Thr Leu  Phe Asp Met Ser Ala  Glu Asp Phe
    2225                 2230                 2235

Asp Ala  Ile Ile Ala Glu His  Phe Gln Pro Gly Asp  Cys Val Leu
    2240                 2245                 2250

Glu Thr  Asp Ile Ala Ser Phe  Asp Lys Ser Glu Asp  Asp Ala Met
    2255                 2260                 2265
```

-continued

```
Ala Leu  Thr Ala Leu Met Ile  Leu Glu Asp Leu Gly  Val Asp Ala
    2270                 2275                 2280

Glu Leu  Leu Thr Leu Ile Glu  Ala Ala Phe Gly Glu  Ile Ser Ser
    2285                 2290                 2295

Ile His  Leu Pro Thr Lys Thr  Lys Phe Lys Phe Gly  Ala Met Met
    2300                 2305                 2310

Lys Ser  Gly Met Phe Leu Thr  Leu Phe Val Asn Thr  Val Ile Asn
    2315                 2320                 2325

Ile Val  Ile Ala Ser Arg Val  Leu Arg Glu Arg Leu  Thr Gly Ser
    2330                 2335                 2340

Pro Cys  Ala Ala Phe Ile Gly  Asp Asp Asn Ile Val  Lys Gly Val
    2345                 2350                 2355

Lys Ser  Asp Lys Leu Met Ala  Asp Arg Cys Ala Thr  Trp Leu Asn
    2360                 2365                 2370

Met Glu  Val Lys Ile Ile Asp  Ala Val Val Gly Glu  Lys Ala Pro
    2375                 2380                 2385

Tyr Phe  Cys Gly Gly Phe Ile  Leu Cys Asp Ser Val  Thr Gly Thr
    2390                 2395                 2400

Ala Cys  Arg Val Ala Asp Pro  Leu Lys Arg Leu Phe  Lys Leu Gly
    2405                 2410                 2415

Lys Pro  Leu Ala Ala Asp Asp  Glu His Asp Asp Asp  Arg Arg Arg
    2420                 2425                 2430

Ala Leu  His Glu Glu Ser Thr  Arg Trp Asn Arg Val  Gly Ile Leu
    2435                 2440                 2445

Ser Glu  Leu Cys Lys Ala Val  Glu Ser Arg Tyr Glu  Thr Val Gly
    2450                 2455                 2460

Thr Ser  Ile Ile Val Met Ala  Met Thr Thr Leu Ala  Ser Ser Val
    2465                 2470                 2475

Lys Ser  Phe Ser Tyr Leu Arg  Gly Ala Pro Ile Thr  Leu Tyr Gly
    2480                 2485                 2490
```

<210> SEQ ID NO 52
<211> LENGTH: 44
<212> TYPE: DNA
<213> ORGANISM: Artificial sequence
<220> FEATURE:
<223> OTHER INFORMATION: Synthetic polynucleotide

<400> SEQUENCE: 52

```
cctgaatgga ctacgacata gtctagtccg ccaaggccgc cacc                  44
```

<210> SEQ ID NO 53
<211> LENGTH: 468
<212> TYPE: DNA
<213> ORGANISM: Artificial sequence
<220> FEATURE:
<223> OTHER INFORMATION: Synthetic polynucleotide

<400> SEQUENCE: 53

```
actcgagtat gttacgtgca aaggtgattg tcaccccccg aaagaccata ttgtgacaca     60

ccctcagtat cacgcccaaa catttacagc cgcggtgtca aaaaccgcgt ggacgtggtt    120

aacatccctg ctgggaggat cagccgtaat tattataatt ggcttggtgc tggctactat    180

tgtggccatg tacgtgctga ccaaccagaa acataattga atacagcagc aattggcaag    240

ctgcttacat agaactcgcg gcgattggca tgccgcctta aaatttttat tttatttttt    300

cttttctttt ccgaatcgga ttttgttttt aatatttcaa aaaaaaaaaa aaaaaaaaaa    360
```

aaatctagaa aaaaaaaaaa aaaaaaaaaa aaaaaaaaaa aaaaaaaaaa aaaaaaaaaa 420
aaaaaaaaaa aaaaaaaaaa aaaaaaaaaa aaaaaaaaaa aaaaaaaa 468

<210> SEQ ID NO 54
<211> LENGTH: 7485
<212> TYPE: DNA
<213> ORGANISM: Artificial sequence
<220> FEATURE:
<223> OTHER INFORMATION: Synthetic polynucleotide

<400> SEQUENCE: 54
atgcccgaga aggtgcacgt ggacatcgag gaggacagcc ccttcctgag ggccctgcag 60
aggagcttcc cacagttcga agtggaggcc aagcaggtga ccgacaacga ccacgccaac 120
gccagggcct tcagccacct ggccagcaag ctgatcgaga ccgaggtgga ccccagcgac 180
accatcctgg acatcggcag cgccccagcc aggagaatgt acagcaagca caagtaccac 240
tgcatctgcc ccatgaggtg cgccgaggac cccgacaggc tgtacaagta cgccaccaaa 300
ctgaagaaga actgcaagga gatcaccgac aaggagctgg acaagaaaat gaaggagctg 360
gccgccgtga tgagcgaccc cgacctggag accgagacaa tgtgcctgca cgacgacgag 420
agctgcaggt acgagggcca ggtggccgtc taccaggacg tgtacgccgt cgacggcccc 480
accagcctgt accaccaggc caacaagggc gtgagggtgg cctactggat cggcttcgac 540
accacaccct tcatgttcaa gaacctggcc ggcgcctacc ccagctacag caccaactgg 600
gccgacgaga ccgtgctgac cgccaggaac atcggcctgt gcagcagcga cgtgatggag 660
aggagccgga gaggcatgag catcctgagg aagaaatacc tgaagcccag caacaacgtg 720
ctgttcagcg tgggcagcac catctaccac gagaagaggg acctgctcag gagctggcac 780
ctgcccagcg tgttccacct gaggggcaag cagaactaca cctgcaggtg cgagaccatc 840
gtgagctgcg acggctacgt ggtgaagagg atcgccatca gccccggcct gtacggcaag 900
cccagcggct acgccgctac aatgcacagg gagggcttcc tgtgctgcaa ggtgaccgac 960
accctgaacg gcgagagggt gagcttcccc gtgtgcacct acgtgcccgc caccctgtgc 1020
gaccagatga ccggcatcct ggccaccgac gtgagcgccg acgacgccca gaagctgctc 1080
gtgggcctga accagaggat cgtggtcaac ggcaggaccc agaggaacac caacacaatg 1140
aagaactacc tgctgcccgt ggtggcccag gctttcgcca ggtgggccaa ggagtacaag 1200
gaggaccagg aagacgagag gcccctgggc ctgagggaca ggcagctggt gatgggctgc 1260
tgctgggcct tcaggcggca caagatcacc agcatctaca agaggcccga cacccagacc 1320
atcatcaagg tgaacagcga cttccacagc ttcgtgctgc ccaggatcgg cagcaacacc 1380
ctggagatcg gcctgaggac ccggatcagg aagatgctgg aggaacacaa ggagcccagc 1440
ccactgatca ccgccgagga cgtgcaggag gccaagtgcg ctgccgacga ggccaaggag 1500
gtgagggagg ccgaggaact gagggccgcc ctgccacccc tggctgccga cgtggaggaa 1560
cccaccctgg aagccgacgt ggacctgatg ctgcaggagg ccggcgccgg aagcgtggag 1620
acacccaggg gcctgatcaa ggtgaccagc tacgacggcg aggacaagat cggcagctac 1680
gccgtgctga gcccacaggc cgtgctgaag tccgagaagc tgagctgcat ccacccactg 1740
gccgagcagg tgatcgtgat cacccacagc ggcaggaagg gcaggtacgc cgtggagccc 1800
taccacggca aggtggtcgt gcccgagggc cacgccatcc ccgtgcagga cttccaggcc 1860
ctgagcgaga gcgccaccat cgtgtacaac gagagggagt tcgtgaacag gtacctgcac 1920
catatcgcca cccacggcgg agccctgaac accgacgagg aatactacaa gaccgtgaag 1980

```
cccagcgagc acgacggcga gtacctgtac gacatcgaca ggaagcagtg cgtgaagaaa   2040
gagctggtga ccggcctggg actgaccggc gagctggtgg acccaccctt ccacgagttc   2100
gcctacgaga gcctgaggac cagacccgcc gctccctacc aggtgcccac catcggcgtg   2160
tacggcgtgc ccggcagcgg aaagagcggc atcatcaaga gcgccgtgac caagaaagac   2220
ctggtggtca gcgccaagaa agagaactgc gccgagatca tcagggacgt gaagaagatg   2280
aaaggcctgg acgtgaacgc gcgcaccgtg gacagcgtgc tgctgaacgg ctgcaagcac   2340
cccgtggaga ccctgtacat cgacgaggcc ttcgcttgcc acgccggcac cctgagggcc   2400
ctgatcgcca tcatcaggcc caagaaagcc gtgctgtgcg gcgaccccaa gcagtgcggc   2460
ttcttcaaca tgatgtgcct gaaggtgcac ttcaaccacg agatctgcac ccaggtgttc   2520
cacaagagca tcagcaggcg gtgcaccaag agcgtgacca gcgtcgtgag caccctgttc   2580
tacgacaaga aaatgaggac caccaacccc aaggagacca aaatcgtgat cgacaccaca   2640
ggcagcacca agcccaagca ggacgacctg atcctgacct gcttcagggg ctgggtgaag   2700
cagctgcaga tcgactacaa gggcaacgag atcatgaccg ccgctgccag ccagggcctg   2760
accaggaagg gcgtgtacgc cgtgaggtac aaggtgaacg agaacccact gtacgctccc   2820
accagcgagc acgtgaacgt gctgctgacc aggaccgagg acaggatcgt gtggaagacc   2880
ctggccggcg accccctggat caagaccctg accgccaagt accccggcaa cttcaccgcc   2940
accatcgaag agtggcaggc cgagcacgac gccatcatga ggcacatcct ggagaggccc   3000
gaccccaccg acgtgttcca gaacaaggcc aacgtgtgct gggccaaggc cctggtgccc   3060
gtgctgaaga ccgccggcat cgacatgacc acagagcagt ggaacaccgt ggactacttc   3120
gagaccgaca aggcccacag cgccgagatc gtgctgaacc agctgtgcgt gaggttcttc   3180
ggcctggacc tggacagcgg cctgttcagc gcccccaccg tgccactgag catcaggaac   3240
aaccactggg acaacagccc cagcccaaac atgtacggcc tgaacaagga ggtggtcagg   3300
cagctgagca ggcggtaccc acagctgccc agggccgtgg ccaccggcag ggtgtacgac   3360
atgaacaccg gcaccctgag gaactacgac cccaggatca acctggtgcc cgtgaacagg   3420
cggctgcccc acgccctggt gctgcaccac aacgagcacc cacagagcga cttcagctcc   3480
ttcgtgagca agctgaaagg caggaccgtg ctggtcgtgg gcgagaagct gagcgtgccc   3540
ggcaagatgg tggactggct gagcgacagg cccgaggcca ccttccgggc caggctggac   3600
ctcggcatcc ccggcgacgt gcccaagtac gacatcatct tcgtgaacgt caggacccca   3660
tacaagtacc accattacca gcagtgcgag gaccacgcca tcaagctgag catgctgacc   3720
aagaaggcct gcctgcacct gaaccccgga ggcacctgcg tgagcatcgg ctacggctac   3780
gccgacaggg ccagcgagag catcattggc gccatcgcca ggctgttcaa gttcagcagg   3840
gtgtgcaaac ccaagagcag cctggaggaa accgaggtgc tgttcgtgtt catcggctac   3900
gaccggaagg ccaggaccca caacccctac aagctgagca gcaccctgac aaacatctac   3960
accggcagca ggctgcacga ggccggctgc gcccccagct accacgtggt caggggcgat   4020
atcgccaccg ccaccgaggg cgtgatcatc aacgctgcca acagcaaggg ccagcccgga   4080
ggcggagtgt gcggcgccct gtacaagaag ttccccgaga gcttcgacct gcagcccatc   4140
gaggtgggca aggccaggct ggtgaagggc gccgctaagc acatcatcca cgccgtgggc   4200
cccaacttca acaaggtgag cgaggtggaa ggcgacaagc agctggccga agcctacgag   4260
agcatcgcca agatcgtgaa cgacaataac tacaagagcg tggccatccc actgctcagc   4320
```

accggcatct tcagcggcaa caaggacagg ctgacccaga gcctgaacca cctgctcacc 4380
gccctggaca ccaccgatgc cgacgtggcc atctactgca gggacaagaa gtgggagatg 4440
accctgaagg aggccgtggc caggcgggag gccgtggaag agatctgcat cagcgacgac 4500
tccagcgtga ccgagcccga cgccgagctg gtgagggtgc accccaagag ctccctggcc 4560
ggcaggaagg gctacagcac cagcgacggc aagaccttca gctacctgga gggcaccaag 4620
ttccaccagg ccgctaagga catcgccgag atcaacgcta tgtggcccgt ggccaccgag 4680
gccaacgagc aggtgtgcat gtacatcctg ggcgagagca tgtccagcat caggagcaag 4740
tgccccgtgg aggaaagcga ggccagcaca ccacccagca ccctgccctg cctgtgcatc 4800
cacgctatga cacccgagag ggtgcagcgg ctgaaggcca gcaggcccga gcagatcacc 4860
gtgtgcagct ccttcccact gcccaagtac aggatcaccg gcgtgcagaa gatccagtgc 4920
agccagccca tcctgttcag cccaaaggtg cccgcctaca tccaccccag gaagtacctg 4980
gtggagaccc cacccgtgga cgagacaccc gagccaagcg ccgagaacca gagcaccgag 5040
ggcacacccg agcagccacc cctgatcacc gaggacgaga caaggacccg gaccccagag 5100
cccatcatta tcgaggaaga ggaagaggac agcatcagcc tgctgagcga cggccccacc 5160
caccaggtgc tgcaggtgga ggccgacatc cacggcccac ccagcgtgtc cagctccagc 5220
tggagcatcc cacacgccag cgacttcgac gtggacagcc tgagcatcct ggacaccctg 5280
gagggcgcca gcgtgacctc cggcgccacc agcgccgaga ccaacagcta cttcgccaag 5340
agcatggagt tcctggccag gcccgtgcca gctcccagga ccgtgttcag gaacccaccc 5400
cacccagctc ccaggaccag gaccccaagc ctggctccca gcagggcctg cagcaggacc 5460
agcctggtga gcaccccacc cggcgtgaac agggtgatca ccagggagga actggaggcc 5520
ctgacaccca gcaggacccc cagcaggtcc gtgagcagga ctagtctggt gtccaaccca 5580
cccggcgtga acagggtgat caccagggag gaattcgagg ccttcgtggc ccagcaacag 5640
agacggttcg acgccggcgc ctacatcttc agcagcgaca ccggccaggg acacctgcag 5700
caaaagagcg tgaggcagac cgtgctgagc gaggtggtgc tggagaggac cgagctggaa 5760
atcagctacg cccccaggct ggaccaggag aaggaggaac tgctcaggaa gaaactgcag 5820
ctgaacccca ccccagccaa caggagcagg taccagagca ggaaggtgga gaacatgaag 5880
gccatcaccg ccaggcggat cctgcagggc ctgggacact acctgaaggc cgagggcaag 5940
gtggagtgct acaggaccct gcaccccgtg ccactgtaca gctccagcgt gaacagggcc 6000
ttctccagcc ccaaggtggc cgtggaggcc tgcaacgcta tgctgaagga gaacttcccc 6060
accgtggcca gctactgcat catccccgag tacgacgcct acctggacat ggtggacggc 6120
gccagctgct gcctggacac cgccagcttc tgccccgcca agctgaggag cttccccaag 6180
aaacacagct acctggagcc caccatcagg agcgccgtgc ccagcgccat ccagaacacc 6240
ctgcagaacg tgctggccgc tgccaccaag aggaactgca acgtgaccca gatgagggag 6300
ctgcccgtgc tggacagcgc tgccttcaac gtggagtgct tcaagaaata cgcctgcaac 6360
aacgagtact gggagacctt caaggagaac cccatcaggc tgaccgaaga gaacgtggtg 6420
aactacatca ccaagctgaa gggccccaag gccgctgccc tgttcgctaa gacccacaac 6480
ctgaacatgc tgcaggacat cccaatggac aggttcgtga tggacctgaa gagggacgtg 6540
aaggtgacac ccggcaccaa gcacaccgag gagaggccca aggtgcaggt gatccaggcc 6600
gctgacccac tggccaccgc ctacctgtgc ggcatccaca gggagctggt gaggcggctg 6660
aacgccgtgc tgctgcccaa catccacacc ctgttcgaca tgagcgccga ggacttcgac 6720

```
gccatcatcg ccgagcactt ccagcccggc gactgcgtgc tggagaccga catcgccagc   6780

ttcgacaaga gcgaggatga cgctatggcc ctgaccgctc tgatgatcct ggaggacctg   6840

ggcgtggacg ccgagctgct caccctgatc gaggctgcct tcggcgagat cagctccatc   6900

cacctgccca ccaagaccaa gttcaagttc ggcgctatga tgaaaagcgg aatgttcctg   6960

accctgttcg tgaacaccgt gatcaacatt gtgatcgcca gcagggtgct gcgggagagg   7020

ctgaccggca gcccctgcgc tgccttcatc ggcgacgaca acatcgtgaa gggcgtgaaa   7080

agcgacaagc tgatggccga caggtgcgcc acctggctga acatggaggt gaagatcatc   7140

gacgccgtgg tgggcgagaa ggcccctac ttctgcggcg gattcatcct gtgcgacagc    7200

gtgaccggca ccgcctgcag ggtggccgac cccctgaaga ggctgttcaa gctgggcaag   7260

ccactggccg ctgacgatga gcacgacgat gacaggcgga gggccctgca cgaggaaagc   7320

accaggtgga acagggtggg catcctgagc gagctgtgca aggccgtgga gagcaggtac   7380

gagaccgtgg gcaccagcat catcgtgatg gctatgacca cactggccag ctccgtcaag   7440

agcttctcct acctgagggg ggcccctata actctctacg gctaa                   7485


<210> SEQ ID NO 55
<211> LENGTH: 2494
<212> TYPE: PRT
<213> ORGANISM: Artificial sequence
<220> FEATURE:
<223> OTHER INFORMATION: Synthetic polypeptide

<400> SEQUENCE: 55

Met Pro Glu Lys Val His Val Asp Ile Glu Glu Asp Ser Pro Phe Leu
1               5                   10                  15

Arg Ala Leu Gln Arg Ser Phe Pro Gln Phe Glu Val Glu Ala Lys Gln
            20                  25                  30

Val Thr Asp Asn Asp His Ala Asn Ala Arg Ala Phe Ser His Leu Ala
        35                  40                  45

Ser Lys Leu Ile Glu Thr Glu Val Asp Pro Ser Asp Thr Ile Leu Asp
    50                  55                  60

Ile Gly Ser Ala Pro Ala Arg Arg Met Tyr Ser Lys His Lys Tyr His
65                  70                  75                  80

Cys Ile Cys Pro Met Arg Cys Ala Glu Asp Pro Asp Arg Leu Tyr Lys
                85                  90                  95

Tyr Ala Thr Lys Leu Lys Lys Asn Cys Lys Glu Ile Thr Asp Lys Glu
            100                 105                 110

Leu Asp Lys Lys Met Lys Glu Leu Ala Ala Val Met Ser Asp Pro Asp
        115                 120                 125

Leu Glu Thr Glu Thr Met Cys Leu His Asp Asp Glu Ser Cys Arg Tyr
    130                 135                 140

Glu Gly Gln Val Ala Val Tyr Gln Asp Val Tyr Ala Val Asp Gly Pro
145                 150                 155                 160

Thr Ser Leu Tyr His Gln Ala Asn Lys Gly Val Arg Val Ala Tyr Trp
                165                 170                 175

Ile Gly Phe Asp Thr Thr Pro Phe Met Phe Lys Asn Leu Ala Gly Ala
            180                 185                 190

Tyr Pro Ser Tyr Ser Thr Asn Trp Ala Asp Glu Thr Val Leu Thr Ala
        195                 200                 205

Arg Asn Ile Gly Leu Cys Ser Ser Asp Val Met Glu Arg Ser Arg Arg
    210                 215                 220
```

```
Gly Met Ser Ile Leu Arg Lys Lys Tyr Leu Lys Pro Ser Asn Asn Val
225                 230                 235                 240

Leu Phe Ser Val Gly Ser Thr Ile Tyr His Glu Lys Arg Asp Leu Leu
                245                 250                 255

Arg Ser Trp His Leu Pro Ser Val Phe His Leu Arg Gly Lys Gln Asn
            260                 265                 270

Tyr Thr Cys Arg Cys Glu Thr Ile Val Ser Cys Asp Gly Tyr Val Val
        275                 280                 285

Lys Arg Ile Ala Ile Ser Pro Gly Leu Tyr Gly Lys Pro Ser Gly Tyr
    290                 295                 300

Ala Ala Thr Met His Arg Glu Gly Phe Leu Cys Cys Lys Val Thr Asp
305                 310                 315                 320

Thr Leu Asn Gly Glu Arg Val Ser Phe Pro Val Cys Thr Tyr Val Pro
                325                 330                 335

Ala Thr Leu Cys Asp Gln Met Thr Gly Ile Leu Ala Thr Asp Val Ser
            340                 345                 350

Ala Asp Asp Ala Gln Lys Leu Leu Val Gly Leu Asn Gln Arg Ile Val
        355                 360                 365

Val Asn Gly Arg Thr Gln Arg Asn Thr Asn Thr Met Lys Asn Tyr Leu
    370                 375                 380

Leu Pro Val Val Ala Gln Ala Phe Ala Arg Trp Ala Lys Glu Tyr Lys
385                 390                 395                 400

Glu Asp Gln Glu Asp Glu Arg Pro Leu Gly Leu Arg Asp Arg Gln Leu
                405                 410                 415

Val Met Gly Cys Cys Trp Ala Phe Arg Arg His Lys Ile Thr Ser Ile
            420                 425                 430

Tyr Lys Arg Pro Asp Thr Gln Thr Ile Ile Lys Val Asn Ser Asp Phe
        435                 440                 445

His Ser Phe Val Leu Pro Arg Ile Gly Ser Asn Thr Leu Glu Ile Gly
    450                 455                 460

Leu Arg Thr Arg Ile Arg Lys Met Leu Glu Glu His Lys Glu Pro Ser
465                 470                 475                 480

Pro Leu Ile Thr Ala Glu Asp Val Gln Glu Ala Lys Cys Ala Ala Asp
                485                 490                 495

Glu Ala Lys Glu Val Arg Glu Ala Glu Glu Leu Arg Ala Ala Leu Pro
            500                 505                 510

Pro Leu Ala Ala Asp Val Glu Glu Pro Thr Leu Glu Ala Asp Val Asp
        515                 520                 525

Leu Met Leu Gln Glu Ala Gly Ala Gly Ser Val Glu Thr Pro Arg Gly
    530                 535                 540

Leu Ile Lys Val Thr Ser Tyr Asp Gly Glu Asp Lys Ile Gly Ser Tyr
545                 550                 555                 560

Ala Val Leu Ser Pro Gln Ala Val Leu Lys Ser Glu Lys Leu Ser Cys
                565                 570                 575

Ile His Pro Leu Ala Glu Gln Val Ile Val Ile Thr His Ser Gly Arg
            580                 585                 590

Lys Gly Arg Tyr Ala Val Glu Pro Tyr His Gly Lys Val Val Val Pro
        595                 600                 605

Glu Gly His Ala Ile Pro Val Gln Asp Phe Gln Ala Leu Ser Glu Ser
    610                 615                 620

Ala Thr Ile Val Tyr Asn Glu Arg Glu Phe Val Asn Arg Tyr Leu His
625                 630                 635                 640

His Ile Ala Thr His Gly Gly Ala Leu Asn Thr Asp Glu Glu Tyr Tyr
```

```
                645                 650                 655

Lys Thr Val Lys Pro Ser Glu His Asp Gly Glu Tyr Leu Tyr Asp Ile
            660                 665                 670

Asp Arg Lys Gln Cys Val Lys Lys Glu Leu Val Thr Gly Leu Gly Leu
        675                 680                 685

Thr Gly Glu Leu Val Asp Pro Pro Phe His Glu Phe Ala Tyr Glu Ser
    690                 695                 700

Leu Arg Thr Arg Pro Ala Ala Pro Tyr Gln Val Pro Thr Ile Gly Val
705                 710                 715                 720

Tyr Gly Val Pro Gly Ser Gly Lys Ser Gly Ile Ile Lys Ser Ala Val
                725                 730                 735

Thr Lys Lys Asp Leu Val Val Ser Ala Lys Lys Glu Asn Cys Ala Glu
            740                 745                 750

Ile Ile Arg Asp Val Lys Lys Met Lys Gly Leu Asp Val Asn Ala Arg
        755                 760                 765

Thr Val Asp Ser Val Leu Leu Asn Gly Cys Lys His Pro Val Glu Thr
    770                 775                 780

Leu Tyr Ile Asp Glu Ala Phe Ala Cys His Ala Gly Thr Leu Arg Ala
785                 790                 795                 800

Leu Ile Ala Ile Ile Arg Pro Lys Lys Ala Val Leu Cys Gly Asp Pro
                805                 810                 815

Lys Gln Cys Gly Phe Phe Asn Met Met Cys Leu Lys Val His Phe Asn
            820                 825                 830

His Glu Ile Cys Thr Gln Val Phe His Lys Ser Ile Ser Arg Arg Cys
        835                 840                 845

Thr Lys Ser Val Thr Ser Val Val Ser Thr Leu Phe Tyr Asp Lys Lys
    850                 855                 860

Met Arg Thr Thr Asn Pro Lys Glu Thr Lys Ile Val Ile Asp Thr Thr
865                 870                 875                 880

Gly Ser Thr Lys Pro Lys Gln Asp Asp Leu Ile Leu Thr Cys Phe Arg
                885                 890                 895

Gly Trp Val Lys Gln Leu Gln Ile Asp Tyr Lys Gly Asn Glu Ile Met
            900                 905                 910

Thr Ala Ala Ala Ser Gln Gly Leu Thr Arg Lys Gly Val Tyr Ala Val
        915                 920                 925

Arg Tyr Lys Val Asn Glu Asn Pro Leu Tyr Ala Pro Thr Ser Glu His
    930                 935                 940

Val Asn Val Leu Leu Thr Arg Thr Glu Asp Arg Ile Val Trp Lys Thr
945                 950                 955                 960

Leu Ala Gly Asp Pro Trp Ile Lys Thr Leu Thr Ala Lys Tyr Pro Gly
                965                 970                 975

Asn Phe Thr Ala Thr Ile Glu Glu Trp Gln Ala Glu His Asp Ala Ile
            980                 985                 990

Met Arg His Ile Leu Glu Arg Pro  Asp Pro Thr Asp Val  Phe Gln Asn
        995                 1000                1005

Lys Ala  Asn Val Cys Trp Ala  Lys Ala Leu Val Pro  Val Leu Lys
    1010                1015                1020

Thr Ala  Gly Ile Asp Met Thr  Thr Glu Gln Trp Asn  Thr Val Asp
    1025                1030                1035

Tyr Phe  Glu Thr Asp Lys Ala  His Ser Ala Glu Ile  Val Leu Asn
    1040                1045                1050

Gln Leu  Cys Val Arg Phe Phe  Gly Leu Asp Leu Asp  Ser Gly Leu
    1055                1060                1065
```

```
Phe Ser  Ala Pro Thr Val Pro  Leu Ser Ile Arg Asn  Asn His Trp
    1070                 1075                 1080

Asp Asn  Ser Pro Ser Pro Asn  Met Tyr Gly Leu Asn  Lys Glu Val
    1085                 1090                 1095

Val Arg  Gln Leu Ser Arg Arg  Tyr Pro Gln Leu Pro  Arg Ala Val
    1100                 1105                 1110

Ala Thr  Gly Arg Val Tyr Asp  Met Asn Thr Gly Thr  Leu Arg Asn
    1115                 1120                 1125

Tyr Asp  Pro Arg Ile Asn Leu  Val Pro Val Asn Arg  Arg Leu Pro
    1130                 1135                 1140

His Ala  Leu Val Leu His His  Asn Glu His Pro Gln  Ser Asp Phe
    1145                 1150                 1155

Ser Ser  Phe Val Ser Lys Leu  Lys Gly Arg Thr Val  Leu Val Val
    1160                 1165                 1170

Gly Glu  Lys Leu Ser Val Pro  Gly Lys Met Val Asp  Trp Leu Ser
    1175                 1180                 1185

Asp Arg  Pro Glu Ala Thr Phe  Arg Ala Arg Leu Asp  Leu Gly Ile
    1190                 1195                 1200

Pro Gly  Asp Val Pro Lys Tyr  Asp Ile Ile Phe Val  Asn Val Arg
    1205                 1210                 1215

Thr Pro  Tyr Lys Tyr His His  Tyr Gln Gln Cys Glu  Asp His Ala
    1220                 1225                 1230

Ile Lys  Leu Ser Met Leu Thr  Lys Lys Ala Cys Leu  His Leu Asn
    1235                 1240                 1245

Pro Gly  Gly Thr Cys Val Ser  Ile Gly Tyr Gly Tyr  Ala Asp Arg
    1250                 1255                 1260

Ala Ser  Glu Ser Ile Ile Gly  Ala Ile Ala Arg Leu  Phe Lys Phe
    1265                 1270                 1275

Ser Arg  Val Cys Lys Pro Lys  Ser Ser Leu Glu Glu  Thr Glu Val
    1280                 1285                 1290

Leu Phe  Val Phe Ile Gly Tyr  Asp Arg Lys Ala Arg  Thr His Asn
    1295                 1300                 1305

Pro Tyr  Lys Leu Ser Ser Thr  Leu Thr Asn Ile Tyr  Thr Gly Ser
    1310                 1315                 1320

Arg Leu  His Glu Ala Gly Cys  Ala Pro Ser Tyr His  Val Val Arg
    1325                 1330                 1335

Gly Asp  Ile Ala Thr Ala Thr  Glu Gly Val Ile Ile  Asn Ala Ala
    1340                 1345                 1350

Asn Ser  Lys Gly Gln Pro Gly  Gly Gly Val Cys Gly  Ala Leu Tyr
    1355                 1360                 1365

Lys Lys  Phe Pro Glu Ser Phe  Asp Leu Gln Pro Ile  Glu Val Gly
    1370                 1375                 1380

Lys Ala  Arg Leu Val Lys Gly  Ala Ala Lys His Ile  Ile His Ala
    1385                 1390                 1395

Val Gly  Pro Asn Phe Asn Lys  Val Ser Glu Val Glu  Gly Asp Lys
    1400                 1405                 1410

Gln Leu  Ala Glu Ala Tyr Glu  Ser Ile Ala Lys Ile  Val Asn Asp
    1415                 1420                 1425

Asn Asn  Tyr Lys Ser Val Ala  Ile Pro Leu Leu Ser  Thr Gly Ile
    1430                 1435                 1440

Phe Ser  Gly Asn Lys Asp Arg  Leu Thr Gln Ser Leu  Asn His Leu
    1445                 1450                 1455
```

```
Leu Thr  Ala Leu Asp Thr Thr  Asp Ala Asp Val Ala  Ile Tyr Cys
    1460                 1465                 1470

Arg Asp  Lys Lys Trp Glu Met  Thr Leu Lys Glu Ala  Val Ala Arg
    1475                 1480                 1485

Arg Glu  Ala Val Glu Glu Ile  Cys Ile Ser Asp Asp  Ser Ser Val
    1490                 1495                 1500

Thr Glu  Pro Asp Ala Glu Leu  Val Arg Val His Pro  Lys Ser Ser
    1505                 1510                 1515

Leu Ala  Gly Arg Lys Gly Tyr  Ser Thr Ser Asp Gly  Lys Thr Phe
    1520                 1525                 1530

Ser Tyr  Leu Glu Gly Thr Lys  Phe His Gln Ala Ala  Lys Asp Ile
    1535                 1540                 1545

Ala Glu  Ile Asn Ala Met Trp  Pro Val Ala Thr Glu  Ala Asn Glu
    1550                 1555                 1560

Gln Val  Cys Met Tyr Ile Leu  Gly Glu Ser Met Ser  Ser Ile Arg
    1565                 1570                 1575

Ser Lys  Cys Pro Val Glu Glu  Ser Glu Ala Ser Thr  Pro Pro Ser
    1580                 1585                 1590

Thr Leu  Pro Cys Leu Cys Ile  His Ala Met Thr Pro  Glu Arg Val
    1595                 1600                 1605

Gln Arg  Leu Lys Ala Ser Arg  Pro Glu Gln Ile Thr  Val Cys Ser
    1610                 1615                 1620

Ser Phe  Pro Leu Pro Lys Tyr  Arg Ile Thr Gly Val  Gln Lys Ile
    1625                 1630                 1635

Gln Cys  Ser Gln Pro Ile Leu  Phe Ser Pro Lys Val  Pro Ala Tyr
    1640                 1645                 1650

Ile His  Pro Arg Lys Tyr Leu  Val Glu Thr Pro Pro  Val Asp Glu
    1655                 1660                 1665

Thr Pro  Glu Pro Ser Ala Glu  Asn Gln Ser Thr Glu  Gly Thr Pro
    1670                 1675                 1680

Glu Gln  Pro Pro Leu Ile Thr  Glu Asp Glu Thr Arg  Thr Arg Thr
    1685                 1690                 1695

Pro Glu  Pro Ile Ile Ile Glu  Glu Glu Glu Glu Asp  Ser Ile Ser
    1700                 1705                 1710

Leu Leu  Ser Asp Gly Pro Thr  His Gln Val Leu Gln  Val Glu Ala
    1715                 1720                 1725

Asp Ile  His Gly Pro Pro Ser  Val Ser Ser Ser Ser  Trp Ser Ile
    1730                 1735                 1740

Pro His  Ala Ser Asp Phe Asp  Val Asp Ser Leu Ser  Ile Leu Asp
    1745                 1750                 1755

Thr Leu  Glu Gly Ala Ser Val  Thr Ser Gly Ala Thr  Ser Ala Glu
    1760                 1765                 1770

Thr Asn  Ser Tyr Phe Ala Lys  Ser Met Glu Phe Leu  Ala Arg Pro
    1775                 1780                 1785

Val Pro  Ala Pro Arg Thr Val  Phe Arg Asn Pro Pro  His Pro Ala
    1790                 1795                 1800

Pro Arg  Thr Arg Thr Pro Ser  Leu Ala Pro Ser Arg  Ala Cys Ser
    1805                 1810                 1815

Arg Thr  Ser Leu Val Ser Thr  Pro Pro Gly Val Asn  Arg Val Ile
    1820                 1825                 1830

Thr Arg  Glu Glu Leu Glu Ala  Leu Thr Pro Ser Arg  Thr Pro Ser
    1835                 1840                 1845

Arg Ser  Val Ser Arg Thr Ser  Leu Val Ser Asn Pro  Pro Gly Val
```

```
    1850                1855                1860

Asn Arg  Val Ile Thr Arg Glu  Glu Phe Glu Ala Phe  Val Ala Gln
    1865                1870                1875

Gln Gln  Arg Arg Phe Asp Ala  Gly Ala Tyr Ile Phe  Ser Ser Asp
    1880                1885                1890

Thr Gly  Gln Gly His Leu Gln  Gln Lys Ser Val Arg  Gln Thr Val
    1895                1900                1905

Leu Ser  Glu Val Val Leu Glu  Arg Thr Glu Leu Glu  Ile Ser Tyr
    1910                1915                1920

Ala Pro  Arg Leu Asp Gln Glu  Lys Glu Glu Leu Leu  Arg Lys Lys
    1925                1930                1935

Leu Gln  Leu Asn Pro Thr Pro  Ala Asn Arg Ser Arg  Tyr Gln Ser
    1940                1945                1950

Arg Lys  Val Glu Asn Met Lys  Ala Ile Thr Ala Arg  Arg Ile Leu
    1955                1960                1965

Gln Gly  Leu Gly His Tyr Leu  Lys Ala Glu Gly Lys  Val Glu Cys
    1970                1975                1980

Tyr Arg  Thr Leu His Pro Val  Pro Leu Tyr Ser Ser  Ser Val Asn
    1985                1990                1995

Arg Ala  Phe Ser Ser Pro Lys  Val Ala Val Glu Ala  Cys Asn Ala
    2000                2005                2010

Met Leu  Lys Glu Asn Phe Pro  Thr Val Ala Ser Tyr  Cys Ile Ile
    2015                2020                2025

Pro Glu  Tyr Asp Ala Tyr Leu  Asp Met Val Asp Gly  Ala Ser Cys
    2030                2035                2040

Cys Leu  Asp Thr Ala Ser Phe  Cys Pro Ala Lys Leu  Arg Ser Phe
    2045                2050                2055

Pro Lys  Lys His Ser Tyr Leu  Glu Pro Thr Ile Arg  Ser Ala Val
    2060                2065                2070

Pro Ser  Ala Ile Gln Asn Thr  Leu Gln Asn Val Leu  Ala Ala Ala
    2075                2080                2085

Thr Lys  Arg Asn Cys Asn Val  Thr Gln Met Arg Glu  Leu Pro Val
    2090                2095                2100

Leu Asp  Ser Ala Ala Phe Asn  Val Glu Cys Phe Lys  Lys Tyr Ala
    2105                2110                2115

Cys Asn  Asn Glu Tyr Trp Glu  Thr Phe Lys Glu Asn  Pro Ile Arg
    2120                2125                2130

Leu Thr  Glu Glu Asn Val Val  Asn Tyr Ile Thr Lys  Leu Lys Gly
    2135                2140                2145

Pro Lys  Ala Ala Ala Leu Phe  Ala Lys Thr His Asn  Leu Asn Met
    2150                2155                2160

Leu Gln  Asp Ile Pro Met Asp  Arg Phe Val Met Asp  Leu Lys Arg
    2165                2170                2175

Asp Val  Lys Val Thr Pro Gly  Thr Lys His Thr Glu  Glu Arg Pro
    2180                2185                2190

Lys Val  Gln Val Ile Gln Ala  Ala Asp Pro Leu Ala  Thr Ala Tyr
    2195                2200                2205

Leu Cys  Gly Ile His Arg Glu  Leu Val Arg Arg Leu  Asn Ala Val
    2210                2215                2220

Leu Leu  Pro Asn Ile His Thr  Leu Phe Asp Met Ser  Ala Glu Asp
    2225                2230                2235

Phe Asp  Ala Ile Ile Ala Glu  His Phe Gln Pro Gly  Asp Cys Val
    2240                2245                2250
```

Leu Glu Thr Asp Ile Ala Ser Phe Asp Lys Ser Glu Asp Asp Ala
2255 2260 2265

Met Ala Leu Thr Ala Leu Met Ile Leu Glu Asp Leu Gly Val Asp
2270 2275 2280

Ala Glu Leu Leu Thr Leu Ile Glu Ala Ala Phe Gly Glu Ile Ser
2285 2290 2295

Ser Ile His Leu Pro Thr Lys Thr Lys Phe Lys Phe Gly Ala Met
2300 2305 2310

Met Lys Ser Gly Met Phe Leu Thr Leu Phe Val Asn Thr Val Ile
2315 2320 2325

Asn Ile Val Ile Ala Ser Arg Val Leu Arg Glu Arg Leu Thr Gly
2330 2335 2340

Ser Pro Cys Ala Ala Phe Ile Gly Asp Asp Asn Ile Val Lys Gly
2345 2350 2355

Val Lys Ser Asp Lys Leu Met Ala Asp Arg Cys Ala Thr Trp Leu
2360 2365 2370

Asn Met Glu Val Lys Ile Ile Asp Ala Val Val Gly Glu Lys Ala
2375 2380 2385

Pro Tyr Phe Cys Gly Gly Phe Ile Leu Cys Asp Ser Val Thr Gly
2390 2395 2400

Thr Ala Cys Arg Val Ala Asp Pro Leu Lys Arg Leu Phe Lys Leu
2405 2410 2415

Gly Lys Pro Leu Ala Ala Asp Asp Glu His Asp Asp Asp Arg Arg
2420 2425 2430

Arg Ala Leu His Glu Glu Ser Thr Arg Trp Asn Arg Val Gly Ile
2435 2440 2445

Leu Ser Glu Leu Cys Lys Ala Val Glu Ser Arg Tyr Glu Thr Val
2450 2455 2460

Gly Thr Ser Ile Ile Val Met Ala Met Thr Thr Leu Ala Ser Ser
2465 2470 2475

Val Lys Ser Phe Ser Tyr Leu Arg Gly Ala Pro Ile Thr Leu Tyr
2480 2485 2490

Gly

<210> SEQ ID NO 56
<211> LENGTH: 9739
<212> TYPE: RNA
<213> ORGANISM: Artificial sequence
<220> FEATURE:
<223> OTHER INFORMATION: Synthetic polynucleotide

<400> SEQUENCE: 56
augggcggcg caugagagaa gcccagacca auuaccuacc caaaauggag aaaguucacg 60
uugacaucga ggaagacagc ccauuccuca gagcuuugca gcggagcuuc ccgcaguuug 120
agguagaagc caagcagguc acugauaaug accaugcuaa ugccagagcg uuuucgcauc 180
uggcuucaaa acugaucgaa acggaggugg acccauccga cacgauccuu gacauuggaa 240
gugcgcccgc ccgcagaaug uauucuaagc acaaguauca uuguaucugu ccgaugagau 300
gugcggaaga uccggacaga uuguauaagu augcaacuaa gcugaagaaa aacuguaagg 360
aaauaacuga uaaggaauug gacaagaaaa ugaaggagcu ggccgccguc augagcgacc 420
cugaccugga aacugagacu augugccucc acgacgacga gucgugucgc uacgaagggc 480
aagucgcugu uuaccaggau guauacgccg ucgacggccc caccagccug uaccaccagg 540

```
ccaacaaggg cgugagggug gccuacugga ucggcuucga caccacaccc uucauguuca    600
agaaccuggc cggcgccuac cccagcuaca gcaccaacug ggccgacgag accgugcuga    660
ccgccaggaa caucggccug ugcagcagcg acgugaugga gaggagccgg agaggcauga    720
gcauccugag gaagaaauac cugaagccca gcaacaacgu gcuguucagc gugggcagca    780
ccaucuacca cgagaagagg gaccugcuca ggagcuggca ccugcccagc guguuccacc    840
ugaggggcaa gcagaacuac accugcaggu gcgagaccau cgugagcugc gacggcuacg    900
uggugaagag gaucgccauc agccccggcc uguacggcaa gcccagcggc uacgccgcua    960
caaugcacag ggagggcuuc cugugcugca aggugaccga cacccugaac ggcgagaggg   1020
ugagcuuccc cgugugcacc uacgugcccg ccacccugug cgaccagaug accggcaucc   1080
uggccaccga cgugagcgcc gacgacgccc agaagcugcu cgugggccug aaccagagga   1140
ucguggucaa cggcaggacc cagaggaaca ccaacacaau gaagaacuac cugcugcccg   1200
ugguggccca ggcuuucgcc aggugggcca aggaguacaa ggaggaccag gaagacgaga   1260
ggccccuggg ccugagggac aggcagcugg ugaugggcug cugcugggcc uucaggcggc   1320
acaagaucac cagcaucuac aagaggcccg acacccagac caucaucaag gugaacagcg   1380
acuuccacag cuucgugcug cccaggaucg gcagcaacac ccuggagauc ggccugagga   1440
cccggaucag gaagaugcug gaggaacaca aggagcccag cccacugauc accgccgagg   1500
acgugcagga ggccaagugc gcugccgacg aggccaagga ggugagggag gccgaggaac   1560
ugagggccgc ccugccaccc cuggcugccg acguggagga acccacccug gaagccgacg   1620
uggaccugau gcugcaggag gccggcgccg gaagcgugga gacacccagg ggccugauca   1680
aggugaccag cuacgacggc gaggacaaga ucggcagcua cgccgugcug agcccacagg   1740
ccgugcugaa guccgagaag cugagcugca uccacccacu ggccgagcag gugaucguga   1800
ucacccacag cggcaggaag ggcagguacg ccguggagcc cuaccacggc aagguggucg   1860
ugcccgaggg ccacgccauc cccgugcagg acuuccaggc ccugagcgag agcgccacca   1920
ucguguacaa cgagagggag uucgugaaca gguaccugca ccauaucgcc acccacggcg   1980
gagcccugaa caccgacgag gaauacuaca agaccgugaa gcccagcgag cacgacggcg   2040
aguaccugua cgacaucgac aggaagcagu gcgugaagaa agagcuggug accggccugg   2100
gacugaccgg cgagcuggug gacccacccu uccacgaguu cgccuacgag agccugagga   2160
ccagacccgc cgcucccuac caggugccca ccaucggcgu guacggcgug cccggcagcg   2220
gaaagagcgg caucaucaag agcgccguga ccaagaaaga ccugguggua agcgccaaga   2280
aagagaacug cgccgagauc aucagggacg ugaagaagau gaaaggccug gacgugaacg   2340
cgcgcaccgu ggacagcgug cugcugaacg gcugcaagca ccccguggag acccuguaca   2400
ucgacgaggc cuucgcuugc cacgccggca cccugagggc ccugaucgcc aucaucaggc   2460
ccaagaaagc cgugcugugc ggcgacccca agcagugcgg cuucuucaac augaugugcc   2520
ugaaggugca cuucaaccac gagaucugca cccagguguu ccacaagagc aucagcaggc   2580
ggugcaccaa gagcgugacc agcgucguga gcacccuguu cuacgacaag aaaaugagga   2640
ccaccaaccc caaggagacc aaaaucguga ucgacaccac aggcagcacc aagcccaagc   2700
aggacgaccu gauccugacc ugcuucaggg gcugggugaa gcagcugcag aucgacuaca   2760
agggcaacga gaucaugacc gccgcugcca gccagggccu gaccaggaag ggcguguacg   2820
ccgugaggua caaggugaac gagaacccac uguacgcucc caccagcgag cacgugaacg   2880
ugcugcugac caggaccgag gacaggaucg uguggaagac ccuggccggc gaccccugga   2940
```

ucaagacccu gaccgccaag uaccccggca acuucaccgc caccaucgaa gaguggcagg 3000
ccgagcacga cgccaucaug aggcacaucc uggagaggcc cgaccccacc gacguguucc 3060
agaacaaggc caacgugugc ugggccaagg cccuggugcc cgugcugaag accgccggca 3120
ucgacaugac cacagagcag uggaacaccg uggacuacuu cgagaccgac aaggcccaca 3180
gcgccgagau cgugcugaac cagcugugcg ugagguucuu cggccuggac cuggacagcg 3240
gccuguucag cgcccccacc gugccacuga gcaucaggaa caaccacugg gacaacagcc 3300
ccagcccaaa cauguacggc cugaacaagg agguggucag gcagcugagc aggcgguacc 3360
cacagcugcc cagggccgug gccaccggca ggguguacga caugaacacc ggcacccuga 3420
ggaacuacga ccccaggauc aaccuggugc ccgugaacag gcggcugccc cacgcccugg 3480
ugcugcacca caacgagcac cccacagagcg acuucagcuc cuucgugagc aagcugaaag 3540
gcaggaccgu gcuggucgug ggcgagaagc ugagcgugcc cggcaagaug guggacuggc 3600
ugagcgacag gcccgaggcc accuuccggg ccaggcugga ccucggcauc cccggcgacg 3660
ugcccaagua cgacaucauc uucgugaacg ucaggacccc auacaaguac caccauuacc 3720
agcagugcga ggaccacgcc aucaagcuga gcaugcugac caagaaggcc ugccugcacc 3780
ugaaccccgg aggcaccugc gugagcaucg gcuacggcua cgccgacagg gccagcgaga 3840
gcaucauugg cgccaucgcc aggcuguuca aguucagcag ggugugcaaa cccaagagca 3900
gccuggagga aaccgaggug cuguucgugu ucaucggcua cgaccggaag gccaggaccc 3960
acaaccccua caagcugagc agcacccuga caaacaucua caccggcagc aggcugcacg 4020
aggccggcug cgcccccagc uaccacgugg ucaggggcga uaucgccacc gccaccgagg 4080
gcgugaucau caacgcugcc aacagcaagg gccagcccgg aggcggagug ugcggcgccc 4140
uguacaagaa guuccccgag agcuucgacc ugcagcccau cgaggugggc aaggccaggc 4200
uggugaaggg cgccgcuaag cacaucaucc acgccguggg ccccaacuuc aacaagguga 4260
gcgaggugga aggcgacaag cagcuggccg aagccuacga gagcaucgcc aagaucguga 4320
acgacaauaa cuacaagagc guggccaucc cacugcucag caccggcauc uucagcggca 4380
acaaggacag gcugacccag agccugaacc accugcucac cgcccuggac accaccgaug 4440
ccgacguggc caucuacugc agggacaaga agugggagau gacccugaag gaggccgugg 4500
ccaggcggga ggccguggaa gagaucugca ucagcgacga cuccagcgug accgagcccg 4560
acgccgagcu ggugagggug caccccaaga gcucccuggc cggcaggaag ggcuacagca 4620
ccagcgacgg caagaccuuc agcuaccugg agggcaccaa guuccaccag gccgcuaagg 4680
acaucgccga gaucaacgcu auguggcccg uggccaccga ggccaacgag caggugugca 4740
uguacauccu gggcgagagc auguccagca ucaggagcaa gugccccgug gaggaaagcg 4800
aggccagcac accacccagc acccugcccu gccugugcau ccacgcuaug acacccgaga 4860
gggugcagcg gcugaaggcc agcaggcccg agcagaucac cgugugcagc uccuucccac 4920
ugcccaagua caggaucacc ggcgugcaga agauccagug cagccagccc auccuguuca 4980
gcccaaaggu gcccgccuac auccacccca ggaaguaccu gguggagacc ccacccgugg 5040
acgagacacc cgagccaagc gccgagaacc agagcaccga gggcacaccc gagcagccac 5100
cccugaucac cgaggacgag acaaggaccc ggaccccaga gcccaucauu aucgaggaag 5160
aggaagagga cagcaucagc cugcugagcg acggccccac ccaccaggug cugcaggugg 5220
aggccgacau ccacggccca cccagcgugu ccagcuccag cuggagcauc ccacacgcca 5280

-continued

```
gcgacuucga cguggacagc cugagcaucc uggacacccu ggagggcgcc agcgugaccu   5340
ccggcgccac cagcgccgag accaacagcu acuucgccaa gagcauggag uuccuggcca   5400
ggcccgugcc agcucccagg accguguuca ggaacccacc ccacccagcu cccaggacca   5460
ggaccccaag ccuggcuccc agcagggccu gcagcaggac cagccuggug agcaccccac   5520
ccggcgugaa cagggugauc accagggagg aacuggaggc ccugacaccc agcaggaccc   5580
ccagcagguc cgugagcagg acuagucugg uguccaaccc acccggcgug aacaggguga   5640
ucaccaggga ggaauucgag gccuucgugg cccagcaaca gagacgguuc gacgccggcg   5700
ccuacaucuu cagcagcgac accggccagg gacaccugca gcaaaagagc gugaggcaga   5760
ccgugcugag cgagguggug cuggagagga ccgagcugga aaucagcuac gcccccaggc   5820
uggaccagga gaaggaggaa cugcucagga agaaacugca gcugaacccc accccagcca   5880
acaggagcag guaccagagc aggaaggugg agaacaugaa ggccaucacc gccaggcgga   5940
uccugcaggg ccugggacac uaccugaagg ccgagggcaa gguggagugc uacaggaccc   6000
ugcaccccgu gccacuguac agcuccagcg ugaacagggc cuucuccagc cccaaggugg   6060
ccguggaggc cugcaacgcu augcugaagg agaacuuccc caccguggcc agcuacugca   6120
ucauccccga guacgacgcc uaccuggaca ugguggacgg cgccagcugc ugccuggaca   6180
ccgccagcuu cugccccgcc aagcugagga gcuuccccaa gaaacacagc uaccuggagc   6240
ccaccaucag gagcgccgug cccagcgcca uccagaacac ccugcagaac gugcuggccg   6300
cugccaccaa gaggaacugc aacgugaccc agaugaggga gcugcccgug cuggacagcg   6360
cugccuucaa cguggagugc uucaagaaau acgccugcaa caacgaguac ugggagaccu   6420
ucaaggagaa ccccaucagg cugaccgaag agaacguggu gaacuacauc accaagcuga   6480
agggccccaa ggccgcugcc cuguucgcua agacccacaa ccugaacaug cugcaggaca   6540
ucccaaugga cagguucgug auggaccuga agagggacgu gaaggugaca cccggcacca   6600
agcacaccga ggagaggccc aaggugcagg ugauccaggc cgcugaccca cuggccaccg   6660
ccuaccugug cggcauccac agggagcugg ugaggcggcu gaacgccgug cugcugccca   6720
acauccacac ccuguucgac augagcgccg aggacuucga cgccaucauc gccgagcacu   6780
uccagcccgg cgacugcgug cuggagaccg acaucgccag cuucgacaag agcgaggaug   6840
acgcuauggc ccugaccgcu cugaugaucc uggaggaccu gggcguggac gccgagcugc   6900
ucacccugau cgaggcugcc uucggcgaga ucagcuccau ccaccugccc accaagacca   6960
aguucaaguu cggcgcuaug augaaaagcg gaauguuccu gacccuguuc gugaacaccg   7020
ugaucaacau ugugaucgcc agcagggugc ugcgggagag gcugaccggc agccccugcg   7080
cugccuucau cggcgacgac aacaucguga agggcgugaa aagcgacaag cugauggccg   7140
acaggugcgc caccuggcug aacauggagg ugaagaucau cgacgccgug gugggcgaga   7200
aggcccccua cuucugcggc ggauucaucc ugugcgacag cgugaccggc accgccugca   7260
ggguggccga cccccugaag aggcuguuca agcugggcaa gccacuggcc gcugacgaug   7320
agcacgacga ugacaggcgg agggcccugc acgaggaaag caccaggugg aacagggugg   7380
gcauccugag cgagcugugc aaggccgugg agagcaggua cgagaccgug ggcaccagca   7440
ucaucgugau ggcuaugacc acacuggcca gcuccgucaa gagcuucucc uaccugaggg   7500
gggccccuau aacucucuac ggcuaaccug aauggacuac gacauagucu aguccgccaa   7560
ggccgccacc augaaggcua uccuggugga gcugcucuac accuuugcca cagccaaugc   7620
ugacacccug uguauuggcu accaugccaa caacagcaca gacacagugg acacaguguu   7680
```

```
ggagaagaau gugacaguga cccacucugu gaaccuguug gaggacaaac acaauggcaa   7740
acuguguaaa cugaggggag uggcuccacu gcaccugggc aaguguaaca uugcuggcug   7800
gauucugggc aacccugagu gugagucccu gagcacagcc uccuccuggu ccuacauugu   7860
ggagacacca uccucugaca auggcacuug uuacccugga gacuucauug acuaugagga   7920
acugagggaa caacuuuccu cuguguccuc cuuugagagg uuugagauuu uuccaaagac   7980
cuccuccugg ccaaaccaug acagcaacaa gggagugaca gcagccuguc cacaugcugg   8040
agccaagucc uucuacaaga accugauuug gcuggugaag aagggcaacu ccuacccaaa   8100
acugagcaag uccuacauca augacaaggg caaggaggug cuggugcugu ggggcaucca   8160
ccacccaagc accucugcug accaacaguc ccucuaccag aaugcugacg ccuauguguu   8220
ugugggcucc agcagauaca gcaagaaguu caagccugag auugccauca gaccaaaggu   8280
gagggaucag gagggcagga ugaacuacua cuggacccug guggaaccug gagacaagau   8340
uaccuuugag gcuacaggca accuggugu gccaagauau gccuuugcua uggagaggaa   8400
ugcuggcucu ggcaucauca ucucugacac accuguccau gacuguaaca ccacuuguca   8460
gacaccaaag ggagccauca acaccucccu gccauuccag aacauccacc caaucaccau   8520
uggcaagugu ccaaaauaug ucaagagcac caaacugaga cuggcuacag gacugaggaa   8580
caucccaagc auccagagca ggggacuguu uggagccauu gcuggcuuca uugagggagg   8640
cuggacaggg augguggaug gcugguaugg cuaccaccac cagaaugaac agggcucugg   8700
cuaugcugcu gaccugaaaa gcacccagaa ugccauugau gagauuacca acaaggugaa   8760
cucugugauu gagaagauga acacccaguu cacagcagug ggcaaggagu ucaaccacuu   8820
ggagaagagg auugagaacc ugaacaagaa gguggaugau ggcuuccugg acaucuggac   8880
cuacaaugcu gaacugcugg ugcuguugga gaaugagagg acccuggacu accaugacag   8940
caaugugaag aaccucuaug agaaggugag gagccaacuu aaaaacaaug ccaaggagau   9000
uggcaauggc uguuuugagu ucuaccacaa gugugacaac acuuguaugg agucugugaa   9060
gaauggcacc uaugacuacc caaaauacuc ugaggaggcu aaacugaaca gggaggagau   9120
ugauggagug aaauuggaga gcaccaggau uuaccagauc cuggccaucu acagcaccgu   9180
ggccagcagc cuggugcugg uggugagccu gggcgccauc agcuucugga ugugcagcaa   9240
cggcagcuug cagugcagga ucugcaucua aacucgagua uguuacgugc aaaggugauu   9300
gucacccccc gaaagaccau auugugacac acccucagua ucacgcccaa acauuuacag   9360
ccgcggugc aaaaaccgcg uggacguggu uaacaucccu gcugggagga ucagccguaa   9420
uuauuauaau uggcuuggug cuggcuacua uuguggccau guacgugcug accaaccaga   9480
aacauaauug aauacagcag caauuggcaa gcugcuuaca uagaacucgc ggcgauuggc   9540
augccgccuu aaaauuuuua uuuuauuuuu ucuuuucuuu uccgaaucgg auuuuguuuu   9600
uaauauuuca aaaaaaaaaa aaaaaaaaaa aaaaucuaga aaaaaaaaaa aaaaaaaaaa   9660
aaaaaaaaaa aaaaaaaaaa aaaaaaaaaa aaaaaaaaaa aaaaaaaaaa aaaaaaaaaa   9720
aaaaaaaaaa aaaaaaaaa                                                9739
```

<210> SEQ ID NO 57
<211> LENGTH: 448
<212> TYPE: RNA
<213> ORGANISM: Artificial sequence
<220> FEATURE:
<223> OTHER INFORMATION: Synthetic polynucleotide

<400> SEQUENCE: 57
gauaggcggc gcaugagaga agcccagacc aauuaccuac ccaaauagga gaaaguucac 60
guugacaucg aggaagacag cccauuccuc agagcuuugc agcggagcuu cccgcaguuu 120
gagguagaag ccaagcaggu cacugauaau gaccaugcua augccagagc guuuucgcau 180
cuggcuucaa aacugaucga aacggaggug gacccauccg acacgauccu ugacauugga 240
auagucagca uaguacauuu caucugacua auacuacaac accaccacca ugaauagagg 300
auucuuuaac augcucggcc gccgccccuu cccggccccc acugccaugu ggaggccgcg 360
gagaaggagg caggcggccc cgggaagcgg agcuacuaac uucagccugc ugaagcaggc 420
uggagacgug gaggagaacc cuggaccu 448

<210> SEQ ID NO 58
<211> LENGTH: 8
<212> TYPE: RNA
<213> ORGANISM: Artificial sequence
<220> FEATURE:
<223> OTHER INFORMATION: Synthetic polynucleotide

<400> SEQUENCE: 58 gggauggg 8

<210> SEQ ID NO 59
<211> LENGTH: 6
<212> TYPE: RNA
<213> ORGANISM: Artificial sequence
<220> FEATURE:
<223> OTHER INFORMATION: Synthetic polynucleotide

<400> SEQUENCE: 59 gagagg 6

<210> SEQ ID NO 60
<211> LENGTH: 5
<212> TYPE: RNA
<213> ORGANISM: Artificial sequence
<220> FEATURE:
<223> OTHER INFORMATION: Synthetic polynucleotide

<400> SEQUENCE: 60 gaggg 5

<210> SEQ ID NO 61
<211> LENGTH: 8
<212> TYPE: RNA
<213> ORGANISM: Artificial sequence
<220> FEATURE:
<223> OTHER INFORMATION: Synthetic polynucleotide

<400> SEQUENCE: 61 gagauggg 8

<210> SEQ ID NO 62
<211> LENGTH: 6
<212> TYPE: RNA
<213> ORGANISM: Artificial sequence
<220> FEATURE:
<223> OTHER INFORMATION: Synthetic polynucleotide

<400> SEQUENCE: 62 gagugg 6

<210> SEQ ID NO 63
<211> LENGTH: 6
<212> TYPE: RNA
<213> ORGANISM: Artificial sequence
<220> FEATURE:
<223> OTHER INFORMATION: Synthetic polynucleotide

<400> SEQUENCE: 63 gagggg 6

<210> SEQ ID NO 64
<211> LENGTH: 7
<212> TYPE: RNA
<213> ORGANISM: Artificial sequence
<220> FEATURE:
<223> OTHER INFORMATION: Synthetic polynucleotide

<400> SEQUENCE: 64 gaguagg 7

<210> SEQ ID NO 65
<211> LENGTH: 7
<212> TYPE: RNA
<213> ORGANISM: Artificial sequence
<220> FEATURE:
<223> OTHER INFORMATION: Synthetic polynucleotide

<400> SEQUENCE: 65 gaguggg 7

<210> SEQ ID NO 66
<211> LENGTH: 6
<212> TYPE: RNA
<213> ORGANISM: Artificial sequence
<220> FEATURE:
<223> OTHER INFORMATION: Synthetic polynucleotide

<400> SEQUENCE: 66 gauggg 6

<210> SEQ ID NO 67
<211> LENGTH: 30
<212> TYPE: DNA
<213> ORGANISM: Artificial sequence
<220> FEATURE:
<223> OTHER INFORMATION: Synthetic polynucleotide

<400> SEQUENCE: 67
atggactacg acatagtcta gtccgccaag 30

<210> SEQ ID NO 68
<211> LENGTH: 16
<212> TYPE: DNA
<213> ORGANISM: Artificial sequence
<220> FEATURE:
<223> OTHER INFORMATION: Synthetic polynucleotide

<400> SEQUENCE: 68
atggactacg acatag 16

<210> SEQ ID NO 69
<211> LENGTH: 15
<212> TYPE: DNA
<213> ORGANISM: Artificial sequence
<220> FEATURE:
<223> OTHER INFORMATION: Synthetic polynucleotide

<400> SEQUENCE: 69
atggactacg acata 15

<210> SEQ ID NO 70
<211> LENGTH: 5
<212> TYPE: DNA
<213> ORGANISM: Artificial sequence
<220> FEATURE:
<223> OTHER INFORMATION: Synthetic polynucleotide

<400> SEQUENCE: 70 atgga 5

<210> SEQ ID NO 71
<211> LENGTH: 3
<212> TYPE: DNA
<213> ORGANISM: Artificial sequence
<220> FEATURE:
<223> OTHER INFORMATION: Synthetic polynucleotide

<400> SEQUENCE: 71 atg 3

<210> SEQ ID NO 72
<211> LENGTH: 7482
<212> TYPE: DNA
<213> ORGANISM: Artificial sequence
<220> FEATURE:
<223> OTHER INFORMATION: Synthetic polynucleotide

<400> SEQUENCE: 72
atggagaaag ttcacgttga catcgaggaa gacagcccat tcctcagagc tttgcagcgg 60
agcttcccgc agtttgaggt agaagccaag caggtcactg ataatgacca tgctaatgcc 120
agagcgtttt cgcatctggc ttcaaaactg atcgaaacgg aggtggaccc atccgacacg 180
atccttgaca ttggaagtgc gcccgcccgc agaatgtatt ctaagcacaa gtatcattgt 240
atctgtccga tgagatgtgc ggaagatccg gacagattgt ataagtatgc aactaagctg 300
aagaaaaact gtaaggaaat aactgataag gaattggaca agaaaatgaa ggagctggcc 360
gccgtcatga gcgaccctga cctggaaact gagactatgt gcctccacga cgacgagtcg 420
tgtcgctacg aagggcaagt cgctgtttac caggatgtat acgccgtcga cggcccccacc 480 agcctgtacc accaggccaa caagggcgtg agggtggcct actggatcgg cttcgacacc 540
acacccttca tgttcaagaa cctggccggc gcctacccca gctacagcac caactgggcc 600
gacgagaccg tgctgaccgc caggaacatc ggcctgtgca gcagcgacgt gatggagagg 660
agccggagag gcatgagcat cctgaggaag aaatacctga agcccagcaa caacgtgctg 720
ttcagcgtgg gcagcaccat ctaccacgag aagagggacc tgctcaggag ctggcacctg 780
cccagcgtgt tccacctgag ggcaagcag aactacacct gcaggtgcga gaccatcgtg 840
agctgcgacg gctacgtggt gaagaggatc gccatcagcc ccggcctgta cggcaagccc 900
agcggctacg ccgctacaat gcacagggag ggcttcctgt gctgcaaggt gaccgacacc 960
ctgaacggcg agagggtgag cttccccgtg tgcacctacg tgcccgccac cctgtgcgac 1020
cagatgaccg gcatcctggc caccgacgtg agcgccgacg acgcccagaa gctgctcgtg 1080
ggcctgaacc agaggatcgt ggtcaacggc aggacccaga ggaacaccaa cacaatgaag 1140
aactacctgc tgcccgtggt ggcccaggct ttcgccaggt gggccaagga gtacaaggag 1200
gaccaggaag acgagaggcc cctgggcctg agggacaggc agctggtgat gggctgctgc 1260
tgggccttca ggcggcacaa gatcaccagc atctacaaga ggcccgacac ccagaccatc 1320
atcaaggtga acagcgactt ccacagcttc gtgctgccca ggatcggcag caacaccctg 1380
gagatcggcc tgaggacccg gatcaggaag atgctggagg aacacaagga gcccagccca 1440
ctgatcaccg ccgaggacgt gcaggaggcc aagtgcgctg ccgacgaggc caaggaggtg 1500
agggaggccg aggaactgag ggccgccctg ccacccctgg ctgccgacgt ggaggaaccc 1560
accctggaag ccgacgtgga cctgatgctg caggaggccg gcgccggaag cgtggagaca 1620
cccagggggcc tgatcaaggt gaccagctac gacggcgagg acaagatcgg cagctacgcc 1680
gtgctgagcc cacaggccgt gctgaagtcc gagaagctga gctgcatcca cccactggcc 1740
gagcaggtga tcgtgatcac ccacagcggc aggaagggca ggtacgccgt ggagccctac 1800
cacggcaagg tggtcgtgcc cgagggccac gccatccccg tgcaggactt ccaggccctg 1860
agcgagagcg ccaccatcgt gtacaacgag agggagttcg tgaacaggta cctgcaccat 1920
atcgccaccc acggcggagc cctgaacacc gacgaggaat actacaagac cgtgaagccc 1980
agcgagcacg acggcgagta cctgtacgac atcgacagga agcagtgcgt gaagaaagag 2040
ctggtgaccg gcctgggact gaccggcgag ctggtggacc cacccttcca cgagttcgcc 2100
tacgagagcc tgaggaccag acccgccgct ccctaccagg tgcccaccat cggcgtgtac 2160
ggcgtgcccg gcagcggaaa gagcggcatc atcaagagcg ccgtgaccaa gaaagacctg 2220
gtggtcagcg ccaagaaaga gaactgcgcc gagatcatca gggacgtgaa gaagatgaaa 2280
ggcctggacg tgaacgcgcg caccgtggac agcgtgctgc tgaacggctg caagcacccc 2340
gtggagaccc tgtacatcga cgaggccttc gcttgccacg ccggcaccct gagggccctg 2400
atcgccatca tcaggcccaa gaaagccgtg ctgtgcggcg accccaagca gtgcggcttc 2460
ttcaacatga tgtgcctgaa ggtgcacttc aaccacgaga tctgcaccca ggtgttccac 2520
aagagcatca gcaggcggtg caccaagagc gtgaccagcg tcgtgagcac cctgttctac 2580
gacaagaaaa tgaggaccac caaccccaag gagaccaaaa tcgtgatcga caccacaggc 2640
agcaccaagc ccaagcagga cgacctgatc ctgacctgct tcaggggctg ggtgaagcag 2700
ctgcagatcg actacaaggg caacgagatc atgaccgccg ctgccagcca gggcctgacc 2760
aggaagggcg tgtacgccgt gaggtacaag gtgaacgaga acccactgta cgctcccacc 2820
agcgagcacg tgaacgtgct gctgaccagg accgaggaca ggatcgtgtg gaagaccctg 2880
gccggcgacc cctggatcaa gaccctgacc gccaagtacc ccggcaactt caccgccacc 2940
atcgaagagt ggcaggccga gcacgacgcc atcatgaggc acatcctgga gaggcccgac 3000
cccaccgacg tgttccagaa caaggccaac gtgtgctggg ccaaggccct ggtgcccgtg 3060
ctgaagaccg ccggcatcga catgaccaca gagcagtgga acaccgtgga ctacttcgag 3120
accgacaagg cccacagcgc cgagatcgtg ctgaaccagc tgtgcgtgag gttcttcggc 3180
ctggacctgg acagcggcct gttcagcgcc cccaccgtgc cactgagcat caggaacaac 3240
cactgggaca acagccccag cccaaacatg tacggcctga acaaggaggt ggtcaggcag 3300
ctgagcaggc ggtacccaca gctgcccagg gccgtggcca ccggcagggt gtacgacatg 3360
aacaccggca ccctgaggaa ctacgacccc aggatcaacc tggtgcccgt gaacaggcgg 3420
ctgccccacg ccctggtgct gcaccacaac gagcacccac agagcgactt cagctccttc 3480
gtgagcaagc tgaaaggcag gaccgtgctg gtcgtgggcg agaagctgag cgtgcccggc 3540
aagatggtgg actggctgag cgacaggccc gaggccacct tccgggccag gctggacctc 3600

-continued

```
ggcatccccg gcgacgtgcc caagtacgac atcatcttcg tgaacgtcag gaccccatac   3660
aagtaccacc attaccagca gtgcgaggac cacgccatca agctgagcat gctgaccaag   3720
aaggcctgcc tgcacctgaa ccccggaggc acctgcgtga gcatcggcta cggctacgcc   3780
gacagggcca gcgagagcat cattggcgcc atcgccaggc tgttcaagtt cagcagggtg   3840
tgcaaaccca agagcagcct ggaggaaacc gaggtgctgt tcgtgttcat cggctacgac   3900
cggaaggcca ggacccacaa cccctacaag ctgagcagca ccctgacaaa catctacacc   3960
ggcagcaggc tgcacgaggc cggctgcgcc cccagctacc acgtggtcag gggcgatatc   4020
gccaccgcca ccgagggcgt gatcatcaac gctgccaaca gcaagggcca gcccggaggc   4080
ggagtgtgcg gcgccctgta caagaagttc cccgagagct tcgacctgca gcccatcgag   4140
gtgggcaagg ccaggctggt gaagggcgcc gctaagcaca tcatccacgc cgtgggcccc   4200
aacttcaaca aggtgagcga ggtggaaggc gacaagcagc tggccgaagc ctacgagagc   4260
atcgccaaga tcgtgaacga caataactac aagagcgtgg ccatcccact gctcagcacc   4320
ggcatcttca gcggcaacaa ggacaggctg acccagagcc tgaaccacct gctcaccgcc   4380
ctggacacca ccgatgccga cgtggccatc tactgcaggg acaagaagtg ggagatgacc   4440
ctgaaggagg ccgtggccag gcgggaggcc gtggaagaga tctgcatcag cgacgactcc   4500
agcgtgaccg agcccgacgc cgagctggtg agggtgcacc ccaagagctc cctggccggc   4560
aggaagggct acagcaccag cgacggcaag accttcagct acctggaggg caccaagttc   4620
caccaggccg ctaaggacat cgccgagatc aacgctatgt ggcccgtggc caccgaggcc   4680
aacgagcagg tgtgcatgta catcctgggc gagagcatgt ccagcatcag gagcaagtgc   4740
cccgtggagg aaagcgaggc cagcacacca cccagcaccc tgccctgcct gtgcatccac   4800
gctatgacac ccgagagggt gcagcggctg aaggccagca ggcccgagca gatcaccgtg   4860
tgcagctcct tcccactgcc caagtacagg atcaccggcg tgcagaagat ccagtgcagc   4920
cagcccatcc tgttcagccc aaaggtgccc gcctacatcc accccaggaa gtacctggtg   4980
gagaccccac ccgtggacga gacacccgag ccaagcgccg agaaccagag caccgagggc   5040
acacccgagc agccacccct gatcaccgag gacgagacaa ggacccggac cccagagccc   5100
atcattatcg aggaagagga agaggacagc atcagcctgc tgagcgacgg ccccacccac   5160
caggtgctgc aggtggaggc cgacatccac ggcccaccca gcgtgtccag ctccagctgg   5220
agcatcccac acgccagcga cttcgacgtg gacagcctga gcatcctgga caccctggag   5280
ggcgccagcg tgacctccgg cgccaccagc gccgagacca acagctactt cgccaagagc   5340
atggagttcc tggccaggcc cgtgccagct cccaggaccg tgttcaggaa cccaccccac   5400
ccagctccca ggaccaggac cccaagcctg gctcccagca gggcctgcag caggaccagc   5460
ctggtgagca ccccacccgg cgtgaacagg gtgatcacca gggaggaact ggaggccctg   5520
acacccagca ggacccccag caggtccgtg agcaggacta gtctggtgtc caacccaccc   5580
ggcgtgaaca gggtgatcac cagggaggaa ttcgaggcct tcgtggccca gcaacagaga   5640
cggttcgacg ccggcgccta catcttcagc agcgacaccg gccagggaca cctgcagcaa   5700
aagagcgtga ggcagaccgt gctgagcgag gtggtgctgg agaggaccga gctggaaatc   5760
agctacgccc ccaggctgga ccaggagaag gaggaactgc tcaggaagaa actgcagctg   5820
aaccccaccc cagccaacag gagcaggtac cagagcagga aggtggagaa catgaaggcc   5880
atcaccgcca ggcggatcct gcagggcctg ggacactacc tgaaggccga gggcaaggtg   5940
gagtgctaca ggaccctgca ccccgtgcca ctgtacagct ccagcgtgaa cagggccttc   6000
```

tccagcccca aggtggccgt ggaggcctgc aacgctatgc tgaaggagaa cttccccacc 6060
gtggccagct actgcatcat ccccgagtac gacgcctacc tggacatggt ggacggcgcc 6120
agctgctgcc tggacaccgc cagcttctgc cccgccaagc tgaggagctt ccccaagaaa 6180
cacagctacc tggagcccac catcaggagc gccgtgccca gcgccatcca gaacaccctg 6240
cagaacgtgc tggccgctgc caccaagagg aactgcaacg tgacccagat gagggagctg 6300
cccgtgctgg acagcgctgc cttcaacgtg gagtgcttca agaaatacgc ctgcaacaac 6360
gagtactggg agaccttcaa ggagaacccc atcaggctga ccgaagagaa cgtggtgaac 6420
tacatcacca agctgaaggg ccccaaggcc gctgccctgt tcgctaagac ccacaacctg 6480
aacatgctgc aggacatccc aatggacagg ttcgtgatgg acctgaagag ggacgtgaag 6540
gtgacacccg gcaccaagca caccgaggag aggcccaagg tgcaggtgat ccaggccgct 6600
gacccactgg ccaccgccta cctgtgcggc atccacaggg agctggtgag gcggctgaac 6660
gccgtgctgc tgcccaacat ccacaccctg ttcgacatga gcgccgagga cttcgacgcc 6720
atcatcgccg agcacttcca gcccggcgac tgcgtgctgg agaccgacat cgccagcttc 6780
gacaagagcg aggatgacgc tatggccctg accgctctga tgatcctgga ggacctgggc 6840
gtggacgccg agctgctcac cctgatcgag gctgccttcg gcgagatcag ctccatccac 6900
ctgcccacca agaccaagtt caagttcggc gctatgatga aaagcggaat gttcctgacc 6960
ctgttcgtga acaccgtgat caacattgtg atcgccagca gggtgctgcg ggagaggctg 7020
accggcagcc cctgcgctgc cttcatcggc gacgacaaca tcgtgaaggg cgtgaaaagc 7080
gacaagctga tggccgacag gtgcgccacc tggctgaaca tggaggtgaa gatcatcgac 7140
gccgtggtgg gcgagaaggc cccctacttc tgcggcggat tcatcctgtg cgacagcgtg 7200
accggcaccg cctgcagggt ggccgacccc ctgaagaggc tgttcaagct gggcaagcca 7260
ctggccgctg acgatgagca cgacgatgac aggcggaggg ccctgcacga ggaaagcacc 7320
aggtggaaca gggtgggcat cctgagcgag ctgtgcaagg ccgtggagag caggtacgag 7380
accgtgggca ccagcatcat cgtgatggct atgaccacac tggccagctc cgtcaagagc 7440
ttctcctacc tgaggggggc ccctataact ctctacggct aa 7482

<210> SEQ ID NO 73
<211> LENGTH: 44
<212> TYPE: DNA
<213> ORGANISM: Artificial sequence
<220> FEATURE:
<223> OTHER INFORMATION: Synthetic polynucleotide

<400> SEQUENCE: 73
atgggcggcg catgagagaa gcccagacca attacctacc caaa 44

<210> SEQ ID NO 74
<211> LENGTH: 45
<212> TYPE: DNA
<213> ORGANISM: Artificial sequence
<220> FEATURE:
<223> OTHER INFORMATION: Synthetic polynucleotide

<400> SEQUENCE: 74
gatgggcggc gcatgagaga agcccagacc aattacctac ccaaa 45

<210> SEQ ID NO 75
<211> LENGTH: 45
<212> TYPE: DNA

<213> ORGANISM: Artificial sequence
<220> FEATURE:
<223> OTHER INFORMATION: Synthetic polynucleotide

<400> SEQUENCE: 75
gataggcggc gcatgagaga agcccagacc aattacctac ccaaa 45

<210> SEQ ID NO 76
<211> LENGTH: 468
<212> TYPE: DNA
<213> ORGANISM: Artificial sequence
<220> FEATURE:
<223> OTHER INFORMATION: Synthetic polynucleotide

<400> SEQUENCE: 76
actcgagtat gttacgtgca aaggtgattg tcacccccg aaagaccata ttgtgacaca 60
ccctcagtat cacgcccaaa catttacagc cgcggtgtca aaaaccgcgt ggacgtggtt 120
aacatccctg ctgggaggat cagccgtaat tattataatt ggcttggtgc tggctactat 180
tgtggccatg tacgtgctga ccaaccagaa acataattga atacagcagc aattggcaag 240
ctgcttacat agaactcgcg gcgattggca tgccgcctta aaattttat tttatttttt 300 cttttctttt ccgaatcgga ttttgttttt aatatttcaa aaaaaaaaaa aaaaaaaaaa 360
aaatctagaa aaaaaaaaaa aaaaaaaaaa aaaaaaaaaa aaaaaaaaaa aaaaaaaaaa 420
aaaaaaaaaa aaaaaaaaaa aaaaaaaaaa aaaaaaaaaa aaaaaaaa 468

<210> SEQ ID NO 77
<211> LENGTH: 44
<212> TYPE: DNA
<213> ORGANISM: Artificial sequence
<220> FEATURE:
<223> OTHER INFORMATION: Synthetic polynucleotide

<400> SEQUENCE: 77
cctgaatgga ctacgacata gtctagtccg ccaaggccgc cacc 44

<210> SEQ ID NO 78
<211> LENGTH: 8038
<212> TYPE: DNA
<213> ORGANISM: Artificial sequence
<220> FEATURE:
<223> OTHER INFORMATION: Synthetic polynucleotide

<400> SEQUENCE: 78
atgggcggcg catgagagaa gcccagacca attacctacc caaaatggag aaagttcacg 60
ttgacatcga ggaagacagc ccattcctca gagctttgca gcggagcttc ccgcagtttg 120
aggtagaagc caagcaggtc actgataatg accatgctaa tgccagagcg ttttcgcatc 180
tggcttcaaa actgatcgaa acggaggtgg acccatccga cacgatcctt gacattggaa 240
gtgcgcccgc ccgcagaatg tattctaagc acaagtatca ttgtatctgt ccgatgagat 300
gtgcggaaga tccggacaga ttgtataagt atgcaactaa gctgaagaaa aactgtaagg 360
aaataactga taaggaattg gacaagaaaa tgaaggagct ggccgccgtc atgagcgacc 420
ctgacctgga aactgagact atgtgcctcc acgacgacga gtcgtgtcgc tacgaagggc 480
aagtcgctgt ttaccaggat gtatacgccg tcgacggccc caccagcctg taccaccagg 540
ccaacaaggg cgtgagggtg gcctactgga tcggcttcga caccacaccc ttcatgttca 600
agaacctggc cggcgcctac cccagctaca gcaccaactg ggccgacgag accgtgctga 660
ccgccaggaa catcggcctg tgcagcagcg acgtgatgga gaggagccgg agaggcatga 720

-continued gcatcctgag gaagaaatac ctgaagccca gcaacaacgt gctgttcagc gtgggcagca 780
ccatctacca cgagaagagg gacctgctca ggagctggca cctgcccagc gtgttccacc 840
tgaggggcaa gcagaactac acctgcaggt gcgagaccat cgtgagctgc gacggctacg 900
tggtgaagag gatcgccatc agccccggcc tgtacggcaa gcccagcggc tacgccgcta 960
caatgcacag ggagggcttc ctgtgctgca aggtgaccga caccctgaac ggcgagaggg 1020
tgagcttccc cgtgtgcacc tacgtgcccg ccaccctgtg cgaccagatg accggcatcc 1080
tggccaccga cgtgagcgcc gacgacgccc agaagctgct cgtgggcctg aaccagagga 1140
tcgtggtcaa cggcaggacc cagaggaaca ccaacacaat gaagaactac ctgctgcccg 1200
tggtggccca ggctttcgcc aggtgggcca aggagtacaa ggaggaccag gaagacgaga 1260
ggcccctggg cctgagggac aggcagctgg tgatgggctg ctgctgggcc ttcaggcggc 1320
acaagatcac cagcatctac aagaggcccg acacccagac catcatcaag gtgaacagcg 1380
acttccacag cttcgtgctg cccaggatcg gcagcaacac cctggagatc ggcctgagga 1440
cccggatcag gaagatgctg gaggaacaca aggagcccag cccactgatc accgccgagg 1500
acgtgcagga ggccaagtgc gctgccgacg aggccaagga ggtgagggag gccgaggaac 1560
tgagggccgc cctgccaccc ctggctgccg acgtggagga acccaccctg gaagccgacg 1620
tggacctgat gctgcaggag gccggcgccg gaagcgtgga gacacccagg ggcctgatca 1680
aggtgaccag ctacgacggc gaggacaaga tcggcagcta cgccgtgctg agcccacagg 1740
ccgtgctgaa gtccgagaag ctgagctgca tccacccact ggccgagcag gtgatcgtga 1800
tcacccacag cggcaggaag ggcaggtacg ccgtggagcc ctaccacggc aaggtggtcg 1860
tgcccgaggg ccacgccatc cccgtgcagg acttccaggc cctgagcgag agcgccacca 1920
tcgtgtacaa cgagagggag ttcgtgaaca ggtacctgca ccatatcgcc acccacggcg 1980
gagccctgaa caccgacgag gaatactaca agaccgtgaa gcccagcgag cacgacggcg 2040
agtacctgta cgacatcgac aggaagcagt gcgtgaagaa agagctggtg accggcctgg 2100
gactgaccgg cgagctggtg gacccaccct tccacgagtt cgcctacgag agcctgagga 2160
ccagacccgc cgctccctac caggtgccca ccatcggcgt gtacggcgtg cccggcagcg 2220
gaaagagcgg catcatcaag agcgccgtga ccaagaaaga cctggtggtc agcgccaaga 2280
aagagaactg cgccgagatc atcagggacg tgaagaagat gaaaggcctg gacgtgaacg 2340
cgcgcaccgt ggacagcgtg ctgctgaacg gctgcaagca ccccgtggag accctgtaca 2400
tcgacgaggc cttcgcttgc cacgccggca ccctgagggc cctgatcgcc atcatcaggc 2460
ccaagaaagc cgtgctgtgc ggcgacccca agcagtgcgg cttcttcaac atgatgtgcc 2520
tgaaggtgca cttcaaccac gagatctgca cccaggtgtt ccacaagagc atcagcaggc 2580
ggtgcaccaa gagcgtgacc agcgtcgtga gcaccctgtt ctacgacaag aaaatgagga 2640
ccaccaaccc caaggagacc aaaatcgtga tcgacaccac aggcagcacc aagcccaagc 2700
aggacgacct gatcctgacc tgcttcaggg gctgggtgaa gcagctgcag atcgactaca 2760
agggcaacga gatcatgacc gccgctgcca gccagggcct gaccaggaag ggcgtgtacg 2820
ccgtgaggta caaggtgaac gagaacccac tgtacgctcc caccagcgag cacgtgaacg 2880
tgctgctgac caggaccgag gacaggatcg tgtggaagac cctggccggc gacccctgga 2940
tcaagaccct gaccgccaag taccccggca acttcaccgc caccatcgaa gagtggcagg 3000
ccgagcacga cgccatcatg aggcacatcc tggagaggcc cgaccccacc gacgtgttcc 3060

-continued

```
agaacaaggc caacgtgtgc tgggccaagg ccctggtgcc cgtgctgaag accgccggca   3120
tcgacatgac cacagagcag tggaacaccg tggactactt cgagaccgac aaggcccaca   3180
gcgccgagat cgtgctgaac cagctgtgcg tgaggttctt cggcctggac ctggacagcg   3240
gcctgttcag cgcccccacc gtgccactga gcatcaggaa caaccactgg gacaacagcc   3300
ccagcccaaa catgtacggc ctgaacaagg aggtggtcag gcagctgagc aggcggtacc   3360
cacagctgcc cagggccgtg gccaccggca gggtgtacga catgaacacc ggcaccctga   3420
ggaactacga ccccaggatc aacctggtgc ccgtgaacag gcggctgccc cacgccctgg   3480
tgctgcacca caacgagcac ccacagagcg acttcagctc cttcgtgagc aagctgaaag   3540
gcaggaccgt gctggtcgtg ggcgagaagc tgagcgtgcc cggcaagatg gtggactggc   3600
tgagcgacag gcccgaggcc accttccggg ccaggctgga cctcggcatc cccggcgacg   3660
tgcccaagta cgacatcatc ttcgtgaacg tcaggacccc atacaagtac caccattacc   3720
agcagtgcga ggaccacgcc atcaagctga gcatgctgac caagaaggcc tgcctgcacc   3780
tgaaccccgg aggcacctgc gtgagcatcg gctacggcta cgccgacagg gccagcgaga   3840
gcatcattgg cgccatcgcc aggctgttca agttcagcag ggtgtgcaaa cccaagagca   3900
gcctggagga aaccgaggtg ctgttcgtgt tcatcggcta cgaccggaag gccaggaccc   3960
acaaccccta caagctgagc agcaccctga caaacatcta caccggcagc aggctgcacg   4020
aggccggctg cgcccccagc taccacgtgg tcaggggcga tatcgccacc gccaccgagg   4080
gcgtgatcat caacgctgcc aacagcaagg gccagcccgg aggcggagtg tgcggcgccc   4140
tgtacaagaa gttccccgag agcttcgacc tgcagcccat cgaggtgggc aaggccaggc   4200
tggtgaaggg cgccgctaag cacatcatcc acgccgtggg ccccaacttc aacaaggtga   4260
gcgaggtgga aggcgacaag cagctggccg aagcctacga gagcatcgcc aagatcgtga   4320
acgacaataa ctacaagagc gtggccatcc cactgctcag caccggcatc ttcagcggca   4380
acaaggacag gctgacccag agcctgaacc acctgctcac cgccctggac accaccgatg   4440
ccgacgtggc catctactgc agggacaaga agtgggagat gaccctgaag gaggccgtgg   4500
ccaggcggga ggccgtggaa gagatctgca tcagcgacga ctccagcgtg accgagcccg   4560
acgccgagct ggtgagggtg caccccaaga gctccctggc cggcaggaag ggctacagca   4620
ccagcgacgg caagaccttc agctacctgg agggcaccaa gttccaccag gccgctaagg   4680
acatcgccga gatcaacgct atgtggcccg tggccaccga ggccaacgag caggtgtgca   4740
tgtacatcct gggcgagagc atgtccagca tcaggagcaa gtgccccgtg gaggaaagcg   4800
aggccagcac accacccagc accctgccct gcctgtgcat ccacgctatg acacccgaga   4860
gggtgcagcg gctgaaggcc agcaggcccg agcagatcac cgtgtgcagc tccttcccac   4920
tgcccaagta caggatcacc ggcgtgcaga agatccagtg cagccagccc atcctgttca   4980
gcccaaaggt gcccgcctac atccacccca ggaagtacct ggtggagacc ccacccgtgg   5040
acgagacacc cgagccaagc gccgagaacc agagcaccga gggcacaccc gagcagccac   5100
ccctgatcac cgaggacgag acaaggaccc ggaccccaga gcccatcatt atcgaggaag   5160
aggaagagga cagcatcagc ctgctgagcg acggccccac ccaccaggtg ctgcaggtgg   5220
aggccgacat ccacggccca cccagcgtgt ccagctccag ctggagcatc ccacacgcca   5280
gcgacttcga cgtggacagc ctgagcatcc tggacaccct ggagggcgcc agcgtgacct   5340
ccggcgccac cagcgccgag accaacagct acttcgccaa gagcatggag ttcctggcca   5400
ggcccgtgcc agctcccagg accgtgttca ggaacccacc ccacccagct cccaggacca   5460
```

```
ggaccccaag cctggctccc agcagggcct gcagcaggac cagcctggtg agcaccccac   5520
ccggcgtgaa cagggtgatc accagggagg aactggaggc cctgacaccc agcaggaccc   5580
ccagcaggtc cgtgagcagg actagtctgg tgtccaaccc acccggcgtg aacagggtga   5640
tcaccaggga ggaattcgag gccttcgtgg cccagcaaca gagacggttc gacgccggcg   5700
cctacatctt cagcagcgac accggccagg gacacctgca gcaaaagagc gtgaggcaga   5760
ccgtgctgag cgaggtggtg ctggagagga ccgagctgga aatcagctac gcccccaggc   5820
tggaccagga gaaggaggaa ctgctcagga agaaactgca gctgaacccc accccagcca   5880
acaggagcag gtaccagagc aggaaggtgg agaacatgaa ggccatcacc gccaggcgga   5940
tcctgcaggg cctgggacac tacctgaagg ccgagggcaa ggtggagtgc tacaggaccc   6000
tgcaccccgt gccactgtac agctccagcg tgaacagggc cttctccagc cccaaggtgg   6060
ccgtggaggc ctgcaacgct atgctgaagg agaacttccc caccgtggcc agctactgca   6120
tcatccccga gtacgacgcc tacctggaca tggtggacgg cgccagctgc tgcctggaca   6180
ccgccagctt ctgccccgcc aagctgagga gcttccccaa gaaacacagc tacctggagc   6240
ccaccatcag gagcgccgtg cccagcgcca tccagaacac cctgcagaac gtgctggccg   6300
ctgccaccaa gaggaactgc aacgtgaccc agatgaggga gctgcccgtg ctggacagcg   6360
ctgccttcaa cgtggagtgc ttcaagaaat acgcctgcaa caacgagtac tgggagacct   6420
tcaaggagaa ccccatcagg ctgaccgaag agaacgtggt gaactacatc accaagctga   6480
agggccccaa ggccgctgcc ctgttcgcta agacccacaa cctgaacatg ctgcaggaca   6540
tcccaatgga caggttcgtg atggacctga agagggacgt gaaggtgaca cccggcacca   6600
agcacaccga ggagaggccc aaggtgcagg tgatccaggc cgctgaccca ctggccaccg   6660
cctacctgtg cggcatccac agggagctgg tgaggcggct gaacgccgtg ctgctgccca   6720
acatccacac cctgttcgac atgagcgccg aggacttcga cgccatcatc gccgagcact   6780
tccagcccgg cgactgcgtg ctggagaccg acatcgccag cttcgacaag agcgaggatg   6840
acgctatggc cctgaccgct ctgatgatcc tggaggacct gggcgtggac gccgagctgc   6900
tcaccctgat cgaggctgcc ttcggcgaga tcagctccat ccacctgccc accaagacca   6960
agttcaagtt cggcgctatg atgaaaagcg gaatgttcct gaccctgttc gtgaacaccg   7020
tgatcaacat tgtgatcgcc agcagggtgc tgcgggagag gctgaccggc agcccctgcg   7080
ctgccttcat cggcgacgac aacatcgtga agggcgtgaa aagcgacaag ctgatggccg   7140
acaggtgcgc cacctggctg aacatggagg tgaagatcat cgacgccgtg gtgggcgaga   7200
aggcccccta cttctgcggc ggattcatcc tgtgcgacag cgtgaccggc accgcctgca   7260
gggtggccga ccccctgaag aggctgttca agctgggcaa gccactggcc gctgacgatg   7320
agcacgacga tgacaggcgg agggccctgc acgaggaaag caccaggtgg aacagggtgg   7380
gcatcctgag cgagctgtgc aaggccgtgg agagcaggta cgagaccgtg ggcaccagca   7440
tcatcgtgat ggctatgacc acactggcca gctccgtcaa gagcttctcc tacctgaggg   7500
gggcccctat aactctctac ggctaacctg aatggactac gacatagtct agtccgccaa   7560
ggccgccacc actcgagtat gttacgtgca aaggtgattg tcaccccccg aaagaccata   7620
ttgtgacaca ccctcagtat cacgcccaaa catttacagc cgcggtgtca aaaaccgcgt   7680
ggacgtggtt aacatccctg ctgggaggat cagccgtaat tattataatt ggcttggtgc   7740
tggctactat tgtggccatg tacgtgctga ccaaccagaa acataattga atacagcagc   7800
```

-continued aattggcaag ctgcttacat agaactcgcg gcgattggca tgccgcctta aaatttttat 7860
tttatttttt cttttctttt ccgaatcgga ttttgttttt aatatttcaa aaaaaaaaaa 7920
aaaaaaaaaa aaatctagaa aaaaaaaaaa aaaaaaaaaa aaaaaaaaaa aaaaaaaaaa 7980
aaaaaaaaaa aaaaaaaaaa aaaaaaaaaa aaaaaaaaaa aaaaaaaaaa aaaaaaaa 8038

<210> SEQ ID NO 79
<211> LENGTH: 2493
<212> TYPE: PRT
<213> ORGANISM: Artificial sequence
<220> FEATURE:
<223> OTHER INFORMATION: Synthetic polypeptide

<400> SEQUENCE: 79

Met Glu Lys Val His Val Asp Ile Glu Glu Asp Ser Pro Phe Leu Arg
1 5 10 15

Ala Leu Gln Arg Ser Phe Pro Gln Phe Glu Val Glu Ala Lys Gln Val
20 25 30

Thr Asp Asn Asp His Ala Asn Ala Arg Ala Phe Ser His Leu Ala Ser
35 40 45

Lys Leu Ile Glu Thr Glu Val Asp Pro Ser Asp Thr Ile Leu Asp Ile
50 55 60

Gly Ser Ala Pro Ala Arg Arg Met Tyr Ser Lys His Lys Tyr His Cys
65 70 75 80

Ile Cys Pro Met Arg Cys Ala Glu Asp Pro Asp Arg Leu Tyr Lys Tyr
85 90 95

Ala Thr Lys Leu Lys Lys Asn Cys Lys Glu Ile Thr Asp Lys Glu Leu
100 105 110

Asp Lys Lys Met Lys Glu Leu Ala Ala Val Met Ser Asp Pro Asp Leu
115 120 125

Glu Thr Glu Thr Met Cys Leu His Asp Asp Glu Ser Cys Arg Tyr Glu
130 135 140

Gly Gln Val Ala Val Tyr Gln Asp Val Tyr Ala Val Asp Gly Pro Thr
145 150 155 160

Ser Leu Tyr His Gln Ala Asn Lys Gly Val Arg Val Ala Tyr Trp Ile
165 170 175

Gly Phe Asp Thr Thr Pro Phe Met Phe Lys Asn Leu Ala Gly Ala Tyr
180 185 190

Pro Ser Tyr Ser Thr Asn Trp Ala Asp Glu Thr Val Leu Thr Ala Arg
195 200 205

Asn Ile Gly Leu Cys Ser Ser Asp Val Met Glu Arg Ser Arg Arg Gly
210 215 220

Met Ser Ile Leu Arg Lys Lys Tyr Leu Lys Pro Ser Asn Asn Val Leu
225 230 235 240

Phe Ser Val Gly Ser Thr Ile Tyr His Glu Lys Arg Asp Leu Leu Arg
245 250 255

Ser Trp His Leu Pro Ser Val Phe His Leu Arg Gly Lys Gln Asn Tyr
260 265 270

Thr Cys Arg Cys Glu Thr Ile Val Ser Cys Asp Gly Tyr Val Val Lys
275 280 285

Arg Ile Ala Ile Ser Pro Gly Leu Tyr Gly Lys Pro Ser Gly Tyr Ala
290 295 300

Ala Thr Met His Arg Glu Gly Phe Leu Cys Cys Lys Val Thr Asp Thr
305 310 315 320

Leu Asn Gly Glu Arg Val Ser Phe Pro Val Cys Thr Tyr Val Pro Ala

```
                325                 330                 335

Thr Leu Cys Asp Gln Met Thr Gly Ile Leu Ala Thr Asp Val Ser Ala
            340                 345                 350

Asp Asp Ala Gln Lys Leu Leu Val Gly Leu Asn Gln Arg Ile Val Val
        355                 360                 365

Asn Gly Arg Thr Gln Arg Asn Thr Asn Thr Met Lys Asn Tyr Leu Leu
    370                 375                 380

Pro Val Val Ala Gln Ala Phe Ala Arg Trp Ala Lys Glu Tyr Lys Glu
385                 390                 395                 400

Asp Gln Glu Asp Glu Arg Pro Leu Gly Leu Arg Asp Arg Gln Leu Val
                405                 410                 415

Met Gly Cys Cys Trp Ala Phe Arg Arg His Lys Ile Thr Ser Ile Tyr
            420                 425                 430

Lys Arg Pro Asp Thr Gln Thr Ile Ile Lys Val Asn Ser Asp Phe His
        435                 440                 445

Ser Phe Val Leu Pro Arg Ile Gly Ser Asn Thr Leu Glu Ile Gly Leu
    450                 455                 460

Arg Thr Arg Ile Arg Lys Met Leu Glu Glu His Lys Glu Pro Ser Pro
465                 470                 475                 480

Leu Ile Thr Ala Glu Asp Val Gln Glu Ala Lys Cys Ala Ala Asp Glu
                485                 490                 495

Ala Lys Glu Val Arg Glu Ala Glu Glu Leu Arg Ala Ala Leu Pro Pro
            500                 505                 510

Leu Ala Ala Asp Val Glu Glu Pro Thr Leu Glu Ala Asp Val Asp Leu
        515                 520                 525

Met Leu Gln Glu Ala Gly Ala Gly Ser Val Glu Thr Pro Arg Gly Leu
    530                 535                 540

Ile Lys Val Thr Ser Tyr Asp Gly Glu Asp Lys Ile Gly Ser Tyr Ala
545                 550                 555                 560

Val Leu Ser Pro Gln Ala Val Leu Lys Ser Glu Lys Leu Ser Cys Ile
                565                 570                 575

His Pro Leu Ala Glu Gln Val Ile Val Ile Thr His Ser Gly Arg Lys
            580                 585                 590

Gly Arg Tyr Ala Val Glu Pro Tyr His Gly Lys Val Val Val Pro Glu
        595                 600                 605

Gly His Ala Ile Pro Val Gln Asp Phe Gln Ala Leu Ser Glu Ser Ala
    610                 615                 620

Thr Ile Val Tyr Asn Glu Arg Glu Phe Val Asn Arg Tyr Leu His His
625                 630                 635                 640

Ile Ala Thr His Gly Gly Ala Leu Asn Thr Asp Glu Glu Tyr Tyr Lys
                645                 650                 655

Thr Val Lys Pro Ser Glu His Asp Gly Glu Tyr Leu Tyr Asp Ile Asp
            660                 665                 670

Arg Lys Gln Cys Val Lys Lys Glu Leu Val Thr Gly Leu Gly Leu Thr
        675                 680                 685

Gly Glu Leu Val Asp Pro Pro Phe His Glu Phe Ala Tyr Glu Ser Leu
    690                 695                 700

Arg Thr Arg Pro Ala Ala Pro Tyr Gln Val Pro Thr Ile Gly Val Tyr
705                 710                 715                 720

Gly Val Pro Gly Ser Gly Lys Ser Gly Ile Ile Lys Ser Ala Val Thr
                725                 730                 735

Lys Lys Asp Leu Val Val Ser Ala Lys Lys Glu Asn Cys Ala Glu Ile
            740                 745                 750
```

Ile Arg Asp Val Lys Lys Met Lys Gly Leu Asp Val Asn Ala Arg Thr
755 760 765

Val Asp Ser Val Leu Leu Asn Gly Cys Lys His Pro Val Glu Thr Leu
770 775 780

Tyr Ile Asp Glu Ala Phe Ala Cys His Ala Gly Thr Leu Arg Ala Leu
785 790 795 800

Ile Ala Ile Ile Arg Pro Lys Lys Ala Val Leu Cys Gly Asp Pro Lys
805 810 815

Gln Cys Gly Phe Phe Asn Met Met Cys Leu Lys Val His Phe Asn His
820 825 830

Glu Ile Cys Thr Gln Val Phe His Lys Ser Ile Ser Arg Arg Cys Thr
835 840 845

Lys Ser Val Thr Ser Val Val Ser Thr Leu Phe Tyr Asp Lys Lys Met
850 855 860

Arg Thr Thr Asn Pro Lys Glu Thr Lys Ile Val Ile Asp Thr Thr Gly
865 870 875 880

Ser Thr Lys Pro Lys Gln Asp Asp Leu Ile Leu Thr Cys Phe Arg Gly
885 890 895

Trp Val Lys Gln Leu Gln Ile Asp Tyr Lys Gly Asn Glu Ile Met Thr
900 905 910

Ala Ala Ala Ser Gln Gly Leu Thr Arg Lys Gly Val Tyr Ala Val Arg
915 920 925

Tyr Lys Val Asn Glu Asn Pro Leu Tyr Ala Pro Thr Ser Glu His Val
930 935 940

Asn Val Leu Leu Thr Arg Thr Glu Asp Arg Ile Val Trp Lys Thr Leu
945 950 955 960

Ala Gly Asp Pro Trp Ile Lys Thr Leu Thr Ala Lys Tyr Pro Gly Asn
965 970 975

Phe Thr Ala Thr Ile Glu Glu Trp Gln Ala Glu His Asp Ala Ile Met
980 985 990

Arg His Ile Leu Glu Arg Pro Asp Pro Thr Asp Val Phe Gln Asn Lys
995 1000 1005

Ala Asn Val Cys Trp Ala Lys Ala Leu Val Pro Val Leu Lys Thr
1010 1015 1020

Ala Gly Ile Asp Met Thr Thr Glu Gln Trp Asn Thr Val Asp Tyr
1025 1030 1035

Phe Glu Thr Asp Lys Ala His Ser Ala Glu Ile Val Leu Asn Gln
1040 1045 1050

Leu Cys Val Arg Phe Phe Gly Leu Asp Leu Asp Ser Gly Leu Phe
1055 1060 1065

Ser Ala Pro Thr Val Pro Leu Ser Ile Arg Asn Asn His Trp Asp
1070 1075 1080

Asn Ser Pro Ser Pro Asn Met Tyr Gly Leu Asn Lys Glu Val Val
1085 1090 1095

Arg Gln Leu Ser Arg Arg Tyr Pro Gln Leu Pro Arg Ala Val Ala
1100 1105 1110

Thr Gly Arg Val Tyr Asp Met Asn Thr Gly Thr Leu Arg Asn Tyr
1115 1120 1125

Asp Pro Arg Ile Asn Leu Val Pro Val Asn Arg Arg Leu Pro His
1130 1135 1140

Ala Leu Val Leu His His Asn Glu His Pro Gln Ser Asp Phe Ser
1145 1150 1155

```
Ser Phe  Val Ser Lys Leu Lys  Gly Arg Thr Val Leu  Val Val Gly
    1160                 1165                 1170

Glu Lys  Leu Ser Val Pro Gly  Lys Met Val Asp Trp  Leu Ser Asp
    1175                 1180                 1185

Arg Pro  Glu Ala Thr Phe Arg  Ala Arg Leu Asp Leu  Gly Ile Pro
    1190                 1195                 1200

Gly Asp  Val Pro Lys Tyr Asp  Ile Ile Phe Val Asn  Val Arg Thr
    1205                 1210                 1215

Pro Tyr  Lys Tyr His His Tyr  Gln Gln Cys Glu Asp  His Ala Ile
    1220                 1225                 1230

Lys Leu  Ser Met Leu Thr Lys  Lys Ala Cys Leu His  Leu Asn Pro
    1235                 1240                 1245

Gly Gly  Thr Cys Val Ser Ile  Gly Tyr Gly Tyr Ala  Asp Arg Ala
    1250                 1255                 1260

Ser Glu  Ser Ile Ile Gly Ala  Ile Ala Arg Leu Phe  Lys Phe Ser
    1265                 1270                 1275

Arg Val  Cys Lys Pro Lys Ser  Ser Leu Glu Glu Thr  Glu Val Leu
    1280                 1285                 1290

Phe Val  Phe Ile Gly Tyr Asp  Arg Lys Ala Arg Thr  His Asn Pro
    1295                 1300                 1305

Tyr Lys  Leu Ser Ser Thr Leu  Thr Asn Ile Tyr Thr  Gly Ser Arg
    1310                 1315                 1320

Leu His  Glu Ala Gly Cys Ala  Pro Ser Tyr His Val  Val Arg Gly
    1325                 1330                 1335

Asp Ile  Ala Thr Ala Thr Glu  Gly Val Ile Ile Asn  Ala Ala Asn
    1340                 1345                 1350

Ser Lys  Gly Gln Pro Gly Gly  Gly Val Cys Gly Ala  Leu Tyr Lys
    1355                 1360                 1365

Lys Phe  Pro Glu Ser Phe Asp  Leu Gln Pro Ile Glu  Val Gly Lys
    1370                 1375                 1380

Ala Arg  Leu Val Lys Gly Ala  Ala Lys His Ile Ile  His Ala Val
    1385                 1390                 1395

Gly Pro  Asn Phe Asn Lys Val  Ser Glu Val Glu Gly  Asp Lys Gln
    1400                 1405                 1410

Leu Ala  Glu Ala Tyr Glu Ser  Ile Ala Lys Ile Val  Asn Asp Asn
    1415                 1420                 1425

Asn Tyr  Lys Ser Val Ala Ile  Pro Leu Leu Ser Thr  Gly Ile Phe
    1430                 1435                 1440

Ser Gly  Asn Lys Asp Arg Leu  Thr Gln Ser Leu Asn  His Leu Leu
    1445                 1450                 1455

Thr Ala  Leu Asp Thr Thr Asp  Ala Asp Val Ala Ile  Tyr Cys Arg
    1460                 1465                 1470

Asp Lys  Lys Trp Glu Met Thr  Leu Lys Glu Ala Val  Ala Arg Arg
    1475                 1480                 1485

Glu Ala  Val Glu Glu Ile Cys  Ile Ser Asp Asp Ser  Ser Val Thr
    1490                 1495                 1500

Glu Pro  Asp Ala Glu Leu Val  Arg Val His Pro Lys  Ser Ser Leu
    1505                 1510                 1515

Ala Gly  Arg Lys Gly Tyr Ser  Thr Ser Asp Gly Lys  Thr Phe Ser
    1520                 1525                 1530

Tyr Leu  Glu Gly Thr Lys Phe  His Gln Ala Ala Lys  Asp Ile Ala
    1535                 1540                 1545

Glu Ile  Asn Ala Met Trp Pro  Val Ala Thr Glu Ala  Asn Glu Gln
```

```
    1550                1555                1560

Val Cys  Met Tyr Ile Leu Gly  Glu Ser Met Ser Ser  Ile Arg Ser
    1565                1570                1575

Lys Cys  Pro Val Glu Glu Ser  Glu Ala Ser Thr Pro  Pro Ser Thr
    1580                1585                1590

Leu Pro  Cys Leu Cys Ile His  Ala Met Thr Pro Glu  Arg Val Gln
    1595                1600                1605

Arg Leu  Lys Ala Ser Arg Pro  Glu Gln Ile Thr Val  Cys Ser Ser
    1610                1615                1620

Phe Pro  Leu Pro Lys Tyr Arg  Ile Thr Gly Val Gln  Lys Ile Gln
    1625                1630                1635

Cys Ser  Gln Pro Ile Leu Phe  Ser Pro Lys Val Pro  Ala Tyr Ile
    1640                1645                1650

His Pro  Arg Lys Tyr Leu Val  Glu Thr Pro Pro Val  Asp Glu Thr
    1655                1660                1665

Pro Glu  Pro Ser Ala Glu Asn  Gln Ser Thr Glu Gly  Thr Pro Glu
    1670                1675                1680

Gln Pro  Pro Leu Ile Thr Glu  Asp Glu Thr Arg Thr  Arg Thr Pro
    1685                1690                1695

Glu Pro  Ile Ile Ile Glu Glu  Glu Glu Glu Asp Ser  Ile Ser Leu
    1700                1705                1710

Leu Ser  Asp Gly Pro Thr His  Gln Val Leu Gln Val  Glu Ala Asp
    1715                1720                1725

Ile His  Gly Pro Pro Ser Val  Ser Ser Ser Ser Trp  Ser Ile Pro
    1730                1735                1740

His Ala  Ser Asp Phe Asp Val  Asp Ser Leu Ser Ile  Leu Asp Thr
    1745                1750                1755

Leu Glu  Gly Ala Ser Val Thr  Ser Gly Ala Thr Ser  Ala Glu Thr
    1760                1765                1770

Asn Ser  Tyr Phe Ala Lys Ser  Met Glu Phe Leu Ala  Arg Pro Val
    1775                1780                1785

Pro Ala  Pro Arg Thr Val Phe  Arg Asn Pro Pro His  Pro Ala Pro
    1790                1795                1800

Arg Thr  Arg Thr Pro Ser Leu  Ala Pro Ser Arg Ala  Cys Ser Arg
    1805                1810                1815

Thr Ser  Leu Val Ser Thr Pro  Pro Gly Val Asn Arg  Val Ile Thr
    1820                1825                1830

Arg Glu  Glu Leu Glu Ala Leu  Thr Pro Ser Arg Thr  Pro Ser Arg
    1835                1840                1845

Ser Val  Ser Arg Thr Ser Leu  Val Ser Asn Pro Pro  Gly Val Asn
    1850                1855                1860

Arg Val  Ile Thr Arg Glu Glu  Phe Glu Ala Phe Val  Ala Gln Gln
    1865                1870                1875

Gln Arg  Arg Phe Asp Ala Gly  Ala Tyr Ile Phe Ser  Ser Asp Thr
    1880                1885                1890

Gly Gln  Gly His Leu Gln Gln  Lys Ser Val Arg Gln  Thr Val Leu
    1895                1900                1905

Ser Glu  Val Val Leu Glu Arg  Thr Glu Leu Glu Ile  Ser Tyr Ala
    1910                1915                1920

Pro Arg  Leu Asp Gln Glu Lys  Glu Glu Leu Leu Arg  Lys Lys Leu
    1925                1930                1935

Gln Leu  Asn Pro Thr Pro Ala  Asn Arg Ser Arg Tyr  Gln Ser Arg
    1940                1945                1950
```

Lys Val Glu Asn Met Lys Ala Ile Thr Ala Arg Arg Ile Leu Gln
1955 1960 1965

Gly Leu Gly His Tyr Leu Lys Ala Glu Gly Lys Val Glu Cys Tyr
1970 1975 1980

Arg Thr Leu His Pro Val Pro Leu Tyr Ser Ser Ser Val Asn Arg
1985 1990 1995

Ala Phe Ser Ser Pro Lys Val Ala Val Glu Ala Cys Asn Ala Met
2000 2005 2010

Leu Lys Glu Asn Phe Pro Thr Val Ala Ser Tyr Cys Ile Ile Pro
2015 2020 2025

Glu Tyr Asp Ala Tyr Leu Asp Met Val Asp Gly Ala Ser Cys Cys
2030 2035 2040

Leu Asp Thr Ala Ser Phe Cys Pro Ala Lys Leu Arg Ser Phe Pro
2045 2050 2055

Lys Lys His Ser Tyr Leu Glu Pro Thr Ile Arg Ser Ala Val Pro
2060 2065 2070

Ser Ala Ile Gln Asn Thr Leu Gln Asn Val Leu Ala Ala Ala Thr
2075 2080 2085

Lys Arg Asn Cys Asn Val Thr Gln Met Arg Glu Leu Pro Val Leu
2090 2095 2100

Asp Ser Ala Ala Phe Asn Val Glu Cys Phe Lys Lys Tyr Ala Cys
2105 2110 2115

Asn Asn Glu Tyr Trp Glu Thr Phe Lys Glu Asn Pro Ile Arg Leu
2120 2125 2130

Thr Glu Glu Asn Val Val Asn Tyr Ile Thr Lys Leu Lys Gly Pro
2135 2140 2145

Lys Ala Ala Ala Leu Phe Ala Lys Thr His Asn Leu Asn Met Leu
2150 2155 2160

Gln Asp Ile Pro Met Asp Arg Phe Val Met Asp Leu Lys Arg Asp
2165 2170 2175

Val Lys Val Thr Pro Gly Thr Lys His Thr Glu Glu Arg Pro Lys
2180 2185 2190

Val Gln Val Ile Gln Ala Ala Asp Pro Leu Ala Thr Ala Tyr Leu
2195 2200 2205

Cys Gly Ile His Arg Glu Leu Val Arg Arg Leu Asn Ala Val Leu
2210 2215 2220

Leu Pro Asn Ile His Thr Leu Phe Asp Met Ser Ala Glu Asp Phe
2225 2230 2235

Asp Ala Ile Ile Ala Glu His Phe Gln Pro Gly Asp Cys Val Leu
2240 2245 2250

Glu Thr Asp Ile Ala Ser Phe Asp Lys Ser Glu Asp Asp Ala Met
2255 2260 2265

Ala Leu Thr Ala Leu Met Ile Leu Glu Asp Leu Gly Val Asp Ala
2270 2275 2280

Glu Leu Leu Thr Leu Ile Glu Ala Ala Phe Gly Glu Ile Ser Ser
2285 2290 2295

Ile His Leu Pro Thr Lys Thr Lys Phe Lys Phe Gly Ala Met Met
2300 2305 2310

Lys Ser Gly Met Phe Leu Thr Leu Phe Val Asn Thr Val Ile Asn
2315 2320 2325

Ile Val Ile Ala Ser Arg Val Leu Arg Glu Arg Leu Thr Gly Ser
2330 2335 2340

```
Pro Cys  Ala Ala Phe Ile Gly  Asp Asp Asn Ile Val  Lys Gly Val
    2345                 2350                 2355

Lys Ser  Asp Lys Leu Met Ala  Asp Arg Cys Ala Thr  Trp Leu Asn
    2360                 2365                 2370

Met Glu  Val Lys Ile Ile Asp  Ala Val Val Gly Glu  Lys Ala Pro
    2375                 2380                 2385

Tyr Phe  Cys Gly Gly Phe Ile  Leu Cys Asp Ser Val  Thr Gly Thr
    2390                 2395                 2400

Ala Cys  Arg Val Ala Asp Pro  Leu Lys Arg Leu Phe  Lys Leu Gly
    2405                 2410                 2415

Lys Pro  Leu Ala Ala Asp Asp  Glu His Asp Asp Asp  Arg Arg Arg
    2420                 2425                 2430

Ala Leu  His Glu Glu Ser Thr  Arg Trp Asn Arg Val  Gly Ile Leu
    2435                 2440                 2445

Ser Glu  Leu Cys Lys Ala Val  Glu Ser Arg Tyr Glu  Thr Val Gly
    2450                 2455                 2460

Thr Ser  Ile Ile Val Met Ala  Met Thr Thr Leu Ala  Ser Ser Val
    2465                 2470                 2475

Lys Ser  Phe Ser Tyr Leu Arg  Gly Ala Pro Ile Thr  Leu Tyr Gly
    2480                 2485                 2490


<210> SEQ ID NO 80
<211> LENGTH: 2494
<212> TYPE: PRT
<213> ORGANISM: Artificial sequence
<220> FEATURE:
<223> OTHER INFORMATION: Synthetic polypeptide

<400> SEQUENCE: 80

Met Pro Glu Lys Val His Val Asp Ile Glu Glu Asp Ser Pro Phe Leu
1               5                   10                  15

Arg Ala Leu Gln Arg Ser Phe Pro Gln Phe Glu Val Glu Ala Lys Gln
            20                  25                  30

Val Thr Asp Asn Asp His Ala Asn Ala Arg Ala Phe Ser His Leu Ala
        35                  40                  45

Ser Lys Leu Ile Glu Thr Glu Val Asp Pro Ser Asp Thr Ile Leu Asp
    50                  55                  60

Ile Gly Ser Ala Pro Ala Arg Arg Met Tyr Ser Lys His Lys Tyr His
65                  70                  75                  80

Cys Ile Cys Pro Met Arg Cys Ala Glu Asp Pro Asp Arg Leu Tyr Lys
                85                  90                  95

Tyr Ala Thr Lys Leu Lys Lys Asn Cys Lys Glu Ile Thr Asp Lys Glu
            100                 105                 110

Leu Asp Lys Lys Met Lys Glu Leu Ala Ala Val Met Ser Asp Pro Asp
        115                 120                 125

Leu Glu Thr Glu Thr Met Cys Leu His Asp Asp Glu Ser Cys Arg Tyr
    130                 135                 140

Glu Gly Gln Val Ala Val Tyr Gln Asp Val Tyr Ala Val Asp Gly Pro
145                 150                 155                 160

Thr Ser Leu Tyr His Gln Ala Asn Lys Gly Val Arg Val Ala Tyr Trp
                165                 170                 175

Ile Gly Phe Asp Thr Thr Pro Phe Met Phe Lys Asn Leu Ala Gly Ala
            180                 185                 190

Tyr Pro Ser Tyr Ser Thr Asn Trp Ala Asp Glu Thr Val Leu Thr Ala
        195                 200                 205
```

```
Arg Asn Ile Gly Leu Cys Ser Ser Asp Val Met Glu Arg Ser Arg Arg
    210                 215                 220

Gly Met Ser Ile Leu Arg Lys Lys Tyr Leu Lys Pro Ser Asn Asn Val
225                 230                 235                 240

Leu Phe Ser Val Gly Ser Thr Ile Tyr His Glu Lys Arg Asp Leu Leu
                245                 250                 255

Arg Ser Trp His Leu Pro Ser Val Phe His Leu Arg Gly Lys Gln Asn
            260                 265                 270

Tyr Thr Cys Arg Cys Glu Thr Ile Val Ser Cys Asp Gly Tyr Val Val
        275                 280                 285

Lys Arg Ile Ala Ile Ser Pro Gly Leu Tyr Gly Lys Pro Ser Gly Tyr
    290                 295                 300

Ala Ala Thr Met His Arg Glu Gly Phe Leu Cys Cys Lys Val Thr Asp
305                 310                 315                 320

Thr Leu Asn Gly Glu Arg Val Ser Phe Pro Val Cys Thr Tyr Val Pro
                325                 330                 335

Ala Thr Leu Cys Asp Gln Met Thr Gly Ile Leu Ala Thr Asp Val Ser
            340                 345                 350

Ala Asp Asp Ala Gln Lys Leu Leu Val Gly Leu Asn Gln Arg Ile Val
        355                 360                 365

Val Asn Gly Arg Thr Gln Arg Asn Thr Asn Thr Met Lys Asn Tyr Leu
    370                 375                 380

Leu Pro Val Val Ala Gln Ala Phe Ala Arg Trp Ala Lys Glu Tyr Lys
385                 390                 395                 400

Glu Asp Gln Glu Asp Glu Arg Pro Leu Gly Leu Arg Asp Arg Gln Leu
                405                 410                 415

Val Met Gly Cys Cys Trp Ala Phe Arg Arg His Lys Ile Thr Ser Ile
            420                 425                 430

Tyr Lys Arg Pro Asp Thr Gln Thr Ile Ile Lys Val Asn Ser Asp Phe
        435                 440                 445

His Ser Phe Val Leu Pro Arg Ile Gly Ser Asn Thr Leu Glu Ile Gly
    450                 455                 460

Leu Arg Thr Arg Ile Arg Lys Met Leu Glu Glu His Lys Glu Pro Ser
465                 470                 475                 480

Pro Leu Ile Thr Ala Glu Asp Val Gln Glu Ala Lys Cys Ala Ala Asp
                485                 490                 495

Glu Ala Lys Glu Val Arg Glu Ala Glu Glu Leu Arg Ala Ala Leu Pro
            500                 505                 510

Pro Leu Ala Ala Asp Val Glu Glu Pro Thr Leu Glu Ala Asp Val Asp
        515                 520                 525

Leu Met Leu Gln Glu Ala Gly Ala Gly Ser Val Glu Thr Pro Arg Gly
    530                 535                 540

Leu Ile Lys Val Thr Ser Tyr Asp Gly Glu Asp Lys Ile Gly Ser Tyr
545                 550                 555                 560

Ala Val Leu Ser Pro Gln Ala Val Leu Lys Ser Glu Lys Leu Ser Cys
                565                 570                 575

Ile His Pro Leu Ala Glu Gln Val Ile Val Ile Thr His Ser Gly Arg
            580                 585                 590

Lys Gly Arg Tyr Ala Val Glu Pro Tyr His Gly Lys Val Val Val Pro
        595                 600                 605

Glu Gly His Ala Ile Pro Val Gln Asp Phe Gln Ala Leu Ser Glu Ser
    610                 615                 620

Ala Thr Ile Val Tyr Asn Glu Arg Glu Phe Val Asn Arg Tyr Leu His
```

-continued

```
625                 630                 635                 640

His Ile Ala Thr His Gly Gly Ala Leu Asn Thr Asp Glu Glu Tyr Tyr
                645                 650                 655

Lys Thr Val Lys Pro Ser Glu His Asp Gly Glu Tyr Leu Tyr Asp Ile
            660                 665                 670

Asp Arg Lys Gln Cys Val Lys Lys Glu Leu Val Thr Gly Leu Gly Leu
        675                 680                 685

Thr Gly Glu Leu Val Asp Pro Pro Phe His Glu Phe Ala Tyr Glu Ser
    690                 695                 700

Leu Arg Thr Arg Pro Ala Ala Pro Tyr Gln Val Pro Thr Ile Gly Val
705                 710                 715                 720

Tyr Gly Val Pro Gly Ser Gly Lys Ser Gly Ile Ile Lys Ser Ala Val
                725                 730                 735

Thr Lys Lys Asp Leu Val Val Ser Ala Lys Lys Glu Asn Cys Ala Glu
            740                 745                 750

Ile Ile Arg Asp Val Lys Lys Met Lys Gly Leu Asp Val Asn Ala Arg
        755                 760                 765

Thr Val Asp Ser Val Leu Leu Asn Gly Cys Lys His Pro Val Glu Thr
    770                 775                 780

Leu Tyr Ile Asp Glu Ala Phe Ala Cys His Ala Gly Thr Leu Arg Ala
785                 790                 795                 800

Leu Ile Ala Ile Ile Arg Pro Lys Lys Ala Val Leu Cys Gly Asp Pro
                805                 810                 815

Lys Gln Cys Gly Phe Phe Asn Met Met Cys Leu Lys Val His Phe Asn
            820                 825                 830

His Glu Ile Cys Thr Gln Val Phe His Lys Ser Ile Ser Arg Arg Cys
        835                 840                 845

Thr Lys Ser Val Thr Ser Val Val Ser Thr Leu Phe Tyr Asp Lys Lys
    850                 855                 860

Met Arg Thr Thr Asn Pro Lys Glu Thr Lys Ile Val Ile Asp Thr Thr
865                 870                 875                 880

Gly Ser Thr Lys Pro Lys Gln Asp Asp Leu Ile Leu Thr Cys Phe Arg
                885                 890                 895

Gly Trp Val Lys Gln Leu Gln Ile Asp Tyr Lys Gly Asn Glu Ile Met
            900                 905                 910

Thr Ala Ala Ala Ser Gln Gly Leu Thr Arg Lys Gly Val Tyr Ala Val
        915                 920                 925

Arg Tyr Lys Val Asn Glu Asn Pro Leu Tyr Ala Pro Thr Ser Glu His
    930                 935                 940

Val Asn Val Leu Leu Thr Arg Thr Glu Asp Arg Ile Val Trp Lys Thr
945                 950                 955                 960

Leu Ala Gly Asp Pro Trp Ile Lys Thr Leu Thr Ala Lys Tyr Pro Gly
                965                 970                 975

Asn Phe Thr Ala Thr Ile Glu Glu Trp Gln Ala Glu His Asp Ala Ile
            980                 985                 990

Met Arg His Ile Leu Glu Arg Pro  Asp Pro Thr Asp Val  Phe Gln Asn
        995                 1000                1005

Lys Ala  Asn Val Cys Trp Ala  Lys Ala Leu Val Pro  Val Leu Lys
    1010                1015                1020

Thr Ala  Gly Ile Asp Met Thr  Thr Glu Gln Trp Asn  Thr Val Asp
    1025                1030                1035

Tyr Phe  Glu Thr Asp Lys Ala  His Ser Ala Glu Ile  Val Leu Asn
    1040                1045                1050
```

Gln Leu Cys Val Arg Phe Phe Gly Leu Asp Leu Asp Ser Gly Leu
1055 1060 1065

Phe Ser Ala Pro Thr Val Pro Leu Ser Ile Arg Asn Asn His Trp
1070 1075 1080

Asp Asn Ser Pro Ser Pro Asn Met Tyr Gly Leu Asn Lys Glu Val
1085 1090 1095

Val Arg Gln Leu Ser Arg Arg Tyr Pro Gln Leu Pro Arg Ala Val
1100 1105 1110

Ala Thr Gly Arg Val Tyr Asp Met Asn Thr Gly Thr Leu Arg Asn
1115 1120 1125

Tyr Asp Pro Arg Ile Asn Leu Val Pro Val Asn Arg Arg Leu Pro
1130 1135 1140

His Ala Leu Val Leu His His Asn Glu His Pro Gln Ser Asp Phe
1145 1150 1155

Ser Ser Phe Val Ser Lys Leu Lys Gly Arg Thr Val Leu Val Val
1160 1165 1170

Gly Glu Lys Leu Ser Val Pro Gly Lys Met Val Asp Trp Leu Ser
1175 1180 1185

Asp Arg Pro Glu Ala Thr Phe Arg Ala Arg Leu Asp Leu Gly Ile
1190 1195 1200

Pro Gly Asp Val Pro Lys Tyr Asp Ile Ile Phe Val Asn Val Arg
1205 1210 1215

Thr Pro Tyr Lys Tyr His His Tyr Gln Gln Cys Glu Asp His Ala
1220 1225 1230

Ile Lys Leu Ser Met Leu Thr Lys Lys Ala Cys Leu His Leu Asn
1235 1240 1245

Pro Gly Gly Thr Cys Val Ser Ile Gly Tyr Gly Tyr Ala Asp Arg
1250 1255 1260

Ala Ser Glu Ser Ile Ile Gly Ala Ile Ala Arg Leu Phe Lys Phe
1265 1270 1275

Ser Arg Val Cys Lys Pro Lys Ser Ser Leu Glu Glu Thr Glu Val
1280 1285 1290

Leu Phe Val Phe Ile Gly Tyr Asp Arg Lys Ala Arg Thr His Asn
1295 1300 1305

Pro Tyr Lys Leu Ser Ser Thr Leu Thr Asn Ile Tyr Thr Gly Ser
1310 1315 1320

Arg Leu His Glu Ala Gly Cys Ala Pro Ser Tyr His Val Val Arg
1325 1330 1335

Gly Asp Ile Ala Thr Ala Thr Glu Gly Val Ile Ile Asn Ala Ala
1340 1345 1350

Asn Ser Lys Gly Gln Pro Gly Gly Gly Val Cys Gly Ala Leu Tyr
1355 1360 1365

Lys Lys Phe Pro Glu Ser Phe Asp Leu Gln Pro Ile Glu Val Gly
1370 1375 1380

Lys Ala Arg Leu Val Lys Gly Ala Ala Lys His Ile Ile His Ala
1385 1390 1395

Val Gly Pro Asn Phe Asn Lys Val Ser Glu Val Glu Gly Asp Lys
1400 1405 1410

Gln Leu Ala Glu Ala Tyr Glu Ser Ile Ala Lys Ile Val Asn Asp
1415 1420 1425

Asn Asn Tyr Lys Ser Val Ala Ile Pro Leu Leu Ser Thr Gly Ile
1430 1435 1440

```
Phe Ser Gly Asn Lys Asp Arg Leu Thr Gln Ser Leu Asn His Leu
    1445                1450                1455

Leu Thr Ala Leu Asp Thr Thr Asp Ala Asp Val Ala Ile Tyr Cys
    1460                1465                1470

Arg Asp Lys Lys Trp Glu Met Thr Leu Lys Glu Ala Val Ala Arg
    1475                1480                1485

Arg Glu Ala Val Glu Glu Ile Cys Ile Ser Asp Asp Ser Ser Val
    1490                1495                1500

Thr Glu Pro Asp Ala Glu Leu Val Arg Val His Pro Lys Ser Ser
    1505                1510                1515

Leu Ala Gly Arg Lys Gly Tyr Ser Thr Ser Asp Gly Lys Thr Phe
    1520                1525                1530

Ser Tyr Leu Glu Gly Thr Lys Phe His Gln Ala Ala Lys Asp Ile
    1535                1540                1545

Ala Glu Ile Asn Ala Met Trp Pro Val Ala Thr Glu Ala Asn Glu
    1550                1555                1560

Gln Val Cys Met Tyr Ile Leu Gly Glu Ser Met Ser Ser Ile Arg
    1565                1570                1575

Ser Lys Cys Pro Val Glu Glu Ser Glu Ala Ser Thr Pro Pro Ser
    1580                1585                1590

Thr Leu Pro Cys Leu Cys Ile His Ala Met Thr Pro Glu Arg Val
    1595                1600                1605

Gln Arg Leu Lys Ala Ser Arg Pro Glu Gln Ile Thr Val Cys Ser
    1610                1615                1620

Ser Phe Pro Leu Pro Lys Tyr Arg Ile Thr Gly Val Gln Lys Ile
    1625                1630                1635

Gln Cys Ser Gln Pro Ile Leu Phe Ser Pro Lys Val Pro Ala Tyr
    1640                1645                1650

Ile His Pro Arg Lys Tyr Leu Val Glu Thr Pro Pro Val Asp Glu
    1655                1660                1665

Thr Pro Glu Pro Ser Ala Glu Asn Gln Ser Thr Glu Gly Thr Pro
    1670                1675                1680

Glu Gln Pro Pro Leu Ile Thr Glu Asp Glu Thr Arg Thr Arg Thr
    1685                1690                1695

Pro Glu Pro Ile Ile Ile Glu Glu Glu Glu Glu Asp Ser Ile Ser
    1700                1705                1710

Leu Leu Ser Asp Gly Pro Thr His Gln Val Leu Gln Val Glu Ala
    1715                1720                1725

Asp Ile His Gly Pro Pro Ser Val Ser Ser Ser Ser Trp Ser Ile
    1730                1735                1740

Pro His Ala Ser Asp Phe Asp Val Asp Ser Leu Ser Ile Leu Asp
    1745                1750                1755

Thr Leu Glu Gly Ala Ser Val Thr Ser Gly Ala Thr Ser Ala Glu
    1760                1765                1770

Thr Asn Ser Tyr Phe Ala Lys Ser Met Glu Phe Leu Ala Arg Pro
    1775                1780                1785

Val Pro Ala Pro Arg Thr Val Phe Arg Asn Pro Pro His Pro Ala
    1790                1795                1800

Pro Arg Thr Arg Thr Pro Ser Leu Ala Pro Ser Arg Ala Cys Ser
    1805                1810                1815

Arg Thr Ser Leu Val Ser Thr Pro Pro Gly Val Asn Arg Val Ile
    1820                1825                1830

Thr Arg Glu Glu Leu Glu Ala Leu Thr Pro Ser Arg Thr Pro Ser
```

```
    1835                1840                1845

Arg Ser  Val Ser Arg Thr Ser  Leu Val Ser Asn Pro  Pro Gly Val
    1850                1855                1860

Asn Arg  Val Ile Thr Arg Glu  Glu Phe Glu Ala Phe  Val Ala Gln
    1865                1870                1875

Gln Gln  Arg Arg Phe Asp Ala  Gly Ala Tyr Ile Phe  Ser Ser Asp
    1880                1885                1890

Thr Gly  Gln Gly His Leu Gln  Gln Lys Ser Val Arg  Gln Thr Val
    1895                1900                1905

Leu Ser  Glu Val Val Leu Glu  Arg Thr Glu Leu Glu  Ile Ser Tyr
    1910                1915                1920

Ala Pro  Arg Leu Asp Gln Glu  Lys Glu Glu Leu Leu  Arg Lys Lys
    1925                1930                1935

Leu Gln  Leu Asn Pro Thr Pro  Ala Asn Arg Ser Arg  Tyr Gln Ser
    1940                1945                1950

Arg Lys  Val Glu Asn Met Lys  Ala Ile Thr Ala Arg  Arg Ile Leu
    1955                1960                1965

Gln Gly  Leu Gly His Tyr Leu  Lys Ala Glu Gly Lys  Val Glu Cys
    1970                1975                1980

Tyr Arg  Thr Leu His Pro Val  Pro Leu Tyr Ser Ser  Ser Val Asn
    1985                1990                1995

Arg Ala  Phe Ser Ser Pro Lys  Val Ala Val Glu Ala  Cys Asn Ala
    2000                2005                2010

Met Leu  Lys Glu Asn Phe Pro  Thr Val Ala Ser Tyr  Cys Ile Ile
    2015                2020                2025

Pro Glu  Tyr Asp Ala Tyr Leu  Asp Met Val Asp Gly  Ala Ser Cys
    2030                2035                2040

Cys Leu  Asp Thr Ala Ser Phe  Cys Pro Ala Lys Leu  Arg Ser Phe
    2045                2050                2055

Pro Lys  Lys His Ser Tyr Leu  Glu Pro Thr Ile Arg  Ser Ala Val
    2060                2065                2070

Pro Ser  Ala Ile Gln Asn Thr  Leu Gln Asn Val Leu  Ala Ala Ala
    2075                2080                2085

Thr Lys  Arg Asn Cys Asn Val  Thr Gln Met Arg Glu  Leu Pro Val
    2090                2095                2100

Leu Asp  Ser Ala Ala Phe Asn  Val Glu Cys Phe Lys  Lys Tyr Ala
    2105                2110                2115

Cys Asn  Asn Glu Tyr Trp Glu  Thr Phe Lys Glu Asn  Pro Ile Arg
    2120                2125                2130

Leu Thr  Glu Glu Asn Val Val  Asn Tyr Ile Thr Lys  Leu Lys Gly
    2135                2140                2145

Pro Lys  Ala Ala Ala Leu Phe  Ala Lys Thr His Asn  Leu Asn Met
    2150                2155                2160

Leu Gln  Asp Ile Pro Met Asp  Arg Phe Val Met Asp  Leu Lys Arg
    2165                2170                2175

Asp Val  Lys Val Thr Pro Gly  Thr Lys His Thr Glu  Glu Arg Pro
    2180                2185                2190

Lys Val  Gln Val Ile Gln Ala  Ala Asp Pro Leu Ala  Thr Ala Tyr
    2195                2200                2205

Leu Cys  Gly Ile His Arg Glu  Leu Val Arg Arg Leu  Asn Ala Val
    2210                2215                2220

Leu Leu  Pro Asn Ile His Thr  Leu Phe Asp Met Ser  Ala Glu Asp
    2225                2230                2235
```

Phe Asp Ala Ile Ile Ala Glu His Phe Gln Pro Gly Asp Cys Val
2240 2245 2250

Leu Glu Thr Asp Ile Ala Ser Phe Asp Lys Ser Glu Asp Asp Ala
2255 2260 2265

Met Ala Leu Thr Ala Leu Met Ile Leu Glu Asp Leu Gly Val Asp
2270 2275 2280

Ala Glu Leu Leu Thr Leu Ile Glu Ala Ala Phe Gly Glu Ile Ser
2285 2290 2295

Ser Ile His Leu Pro Thr Lys Thr Lys Phe Lys Phe Gly Ala Met
2300 2305 2310

Met Lys Ser Gly Met Phe Leu Thr Leu Phe Val Asn Thr Val Ile
2315 2320 2325

Asn Ile Val Ile Ala Ser Arg Val Leu Arg Glu Arg Leu Thr Gly
2330 2335 2340

Ser Pro Cys Ala Ala Phe Ile Gly Asp Asp Asn Ile Val Lys Gly
2345 2350 2355

Val Lys Ser Asp Lys Leu Met Ala Asp Arg Cys Ala Thr Trp Leu
2360 2365 2370

Asn Met Glu Val Lys Ile Ile Asp Ala Val Val Gly Glu Lys Ala
2375 2380 2385

Pro Tyr Phe Cys Gly Gly Phe Ile Leu Cys Asp Ser Val Thr Gly
2390 2395 2400

Thr Ala Cys Arg Val Ala Asp Pro Leu Lys Arg Leu Phe Lys Leu
2405 2410 2415

Gly Lys Pro Leu Ala Ala Asp Asp Glu His Asp Asp Asp Arg Arg
2420 2425 2430

Arg Ala Leu His Glu Glu Ser Thr Arg Trp Asn Arg Val Gly Ile
2435 2440 2445

Leu Ser Glu Leu Cys Lys Ala Val Glu Ser Arg Tyr Glu Thr Val
2450 2455 2460

Gly Thr Ser Ile Ile Val Met Ala Met Thr Thr Leu Ala Ser Ser
2465 2470 2475

Val Lys Ser Phe Ser Tyr Leu Arg Gly Ala Pro Ile Thr Leu Tyr
2480 2485 2490

Gly

<210> SEQ ID NO 81
<211> LENGTH: 2492
<212> TYPE: PRT
<213> ORGANISM: Artificial sequence
<220> FEATURE:
<223> OTHER INFORMATION: Synthetic polypeptide

<400> SEQUENCE: 81

Met Glu Lys Val His Val Asp Ile Glu Glu Asp Ser Pro Phe Leu Arg
1 5 10 15

Ala Leu Gln Arg Ser Phe Pro Gln Phe Glu Val Glu Ala Lys Gln Val
20 25 30

Thr Asp Asn Asp His Ala Asn Ala Arg Ala Phe Ser His Leu Ala Ser
35 40 45

Lys Leu Ile Glu Thr Glu Val Asp Pro Ser Asp Thr Ile Leu Asp Ile
50 55 60

Gly Ser Ala Pro Ala Arg Arg Met Tyr Ser Lys His Lys Tyr His Cys
65 70 75 80

-continued

```
Ile Cys Pro Met Arg Cys Ala Glu Asp Pro Asp Arg Leu Tyr Lys Tyr
                85                  90                  95

Ala Thr Lys Leu Lys Lys Asn Cys Lys Glu Ile Thr Asp Lys Glu Leu
            100                 105                 110

Asp Lys Lys Met Lys Glu Leu Ala Ala Val Met Ser Asp Pro Asp Leu
        115                 120                 125

Glu Thr Glu Thr Met Cys Leu His Asp Asp Glu Ser Cys Arg Tyr Glu
    130                 135                 140

Gly Gln Val Ala Val Tyr Gln Asp Val Tyr Ala Val Asp Gly Pro Thr
145                 150                 155                 160

Ser Leu Tyr His Gln Ala Asn Lys Gly Val Arg Val Ala Tyr Trp Ile
                165                 170                 175

Gly Phe Asp Thr Thr Pro Phe Met Phe Lys Asn Leu Ala Gly Ala Tyr
            180                 185                 190

Pro Ser Tyr Ser Thr Asn Trp Ala Asp Glu Thr Val Leu Thr Ala Arg
        195                 200                 205

Asn Ile Gly Leu Cys Ser Ser Asp Val Met Glu Arg Ser Arg Arg Gly
    210                 215                 220

Met Ser Ile Leu Arg Lys Lys Tyr Leu Lys Pro Ser Asn Asn Val Leu
225                 230                 235                 240

Phe Ser Val Gly Ser Thr Ile Tyr His Glu Lys Arg Asp Leu Leu Arg
                245                 250                 255

Ser Trp His Leu Pro Ser Val Phe His Leu Arg Gly Lys Gln Asn Tyr
            260                 265                 270

Thr Cys Arg Cys Glu Thr Ile Val Ser Cys Asp Gly Tyr Val Val Lys
        275                 280                 285

Arg Ile Ala Ile Ser Pro Gly Leu Tyr Gly Lys Pro Ser Gly Tyr Ala
    290                 295                 300

Ala Thr Met His Arg Glu Gly Phe Leu Cys Cys Lys Val Thr Asp Thr
305                 310                 315                 320

Leu Asn Gly Glu Arg Val Ser Phe Pro Val Cys Thr Tyr Val Pro Ala
                325                 330                 335

Thr Leu Cys Asp Gln Met Thr Gly Ile Leu Ala Thr Asp Val Ser Ala
            340                 345                 350

Asp Asp Ala Gln Lys Leu Leu Val Gly Leu Asn Gln Arg Ile Val Val
        355                 360                 365

Asn Gly Arg Thr Gln Arg Asn Thr Asn Thr Met Lys Asn Tyr Leu Leu
    370                 375                 380

Pro Val Val Ala Gln Ala Phe Ala Arg Trp Ala Lys Glu Tyr Lys Glu
385                 390                 395                 400

Asp Gln Glu Asp Glu Arg Pro Leu Gly Leu Arg Asp Arg Gln Leu Val
                405                 410                 415

Met Gly Cys Cys Trp Ala Phe Arg Arg His Lys Ile Thr Ser Ile Tyr
            420                 425                 430

Lys Arg Pro Asp Thr Gln Thr Ile Ile Lys Val Asn Ser Asp Phe His
        435                 440                 445

Ser Phe Val Leu Pro Arg Ile Gly Ser Asn Thr Leu Glu Ile Gly Leu
    450                 455                 460

Arg Thr Arg Ile Arg Lys Met Leu Glu Glu His Lys Glu Pro Ser Pro
465                 470                 475                 480

Leu Ile Thr Ala Glu Asp Ile Gln Glu Ala Lys Cys Ala Ala Asp Glu
                485                 490                 495

Ala Lys Glu Val Arg Glu Ala Glu Glu Leu Arg Ala Ala Leu Pro Pro
```

```
            500                 505                 510

Leu Ala Ala Asp Phe Glu Glu Pro Thr Leu Glu Ala Asp Val Asp Leu
        515                 520                 525

Met Leu Gln Glu Ala Gly Ala Gly Ser Val Glu Thr Pro Arg Gly Leu
    530                 535                 540

Ile Lys Val Thr Ser Tyr Ala Gly Glu Asp Lys Ile Gly Ser Tyr Ala
545                 550                 555                 560

Val Leu Ser Pro Gln Ala Val Leu Lys Ser Glu Lys Leu Ser Cys Ile
                565                 570                 575

His Pro Leu Ala Glu Gln Val Ile Val Ile Thr His Ser Gly Arg Lys
            580                 585                 590

Gly Arg Tyr Ala Val Glu Pro Tyr His Gly Lys Val Val Val Pro Glu
        595                 600                 605

Gly His Ala Ile Pro Val Gln Asp Phe Gln Ala Leu Ser Glu Ser Ala
    610                 615                 620

Thr Ile Val Tyr Asn Glu Arg Glu Phe Val Asn Arg Tyr Leu His His
625                 630                 635                 640

Ile Ala Thr His Gly Gly Ala Leu Asn Thr Asp Glu Glu Tyr Tyr Lys
                645                 650                 655

Thr Val Lys Pro Ser Glu His Asp Gly Glu Tyr Leu Tyr Asp Ile Asp
            660                 665                 670

Arg Lys Gln Cys Val Lys Lys Glu Leu Val Thr Gly Leu Gly Leu Thr
        675                 680                 685

Gly Glu Leu Val Asp Pro Pro Phe His Glu Phe Ala Tyr Glu Ser Leu
    690                 695                 700

Arg Thr Arg Pro Ala Ala Pro Tyr Gln Val Pro Thr Ile Gly Val Tyr
705                 710                 715                 720

Gly Val Pro Gly Ser Gly Lys Ser Gly Ile Ile Lys Ser Ala Val Thr
                725                 730                 735

Lys Lys Asp Leu Val Val Ser Ala Lys Lys Glu Asn Cys Ala Glu Ile
            740                 745                 750

Ile Arg Asp Val Lys Lys Met Lys Gly Leu Asp Val Asn Ala Arg Thr
        755                 760                 765

Val Asp Ser Val Leu Leu Asn Gly Cys Lys His Pro Val Glu Thr Leu
    770                 775                 780

Tyr Ile Asp Glu Ala Phe Ala Cys His Ala Gly Thr Leu Arg Ala Leu
785                 790                 795                 800

Ile Ala Ile Ile Arg Pro Lys Lys Ala Val Leu Cys Gly Asp Pro Lys
                805                 810                 815

Gln Cys Gly Phe Phe Asn Met Met Cys Leu Lys Val His Phe Asn His
            820                 825                 830

Glu Ile Cys Thr Gln Val Phe His Lys Ser Ile Ser Arg Arg Cys Thr
        835                 840                 845

Lys Ser Val Thr Ser Val Val Ser Thr Leu Phe Tyr Asp Lys Arg Met
    850                 855                 860

Arg Thr Thr Asn Pro Lys Glu Thr Lys Ile Val Ile Asp Thr Thr Gly
865                 870                 875                 880

Ser Thr Lys Pro Lys Gln Asp Asp Leu Ile Leu Thr Cys Phe Arg Gly
                885                 890                 895

Trp Val Lys Gln Leu Gln Ile Asp Tyr Lys Gly Asn Glu Ile Met Thr
            900                 905                 910

Ala Ala Ala Ser Gln Gly Leu Thr Arg Lys Gly Val Tyr Ala Val Arg
        915                 920                 925
```

-continued

```
Tyr Lys Val Asn Glu Asn Pro Leu Tyr Ala Pro Thr Ser Glu His Val
    930                 935                 940

Asn Val Leu Leu Thr Arg Thr Glu Asp Arg Ile Val Trp Lys Thr Leu
945                 950                 955                 960

Ala Gly Asp Pro Trp Ile Lys Ile Leu Thr Ala Lys Tyr Pro Gly Asn
                965                 970                 975

Phe Thr Ala Thr Ile Glu Glu Trp Gln Ala Glu His Asp Ala Ile Met
            980                 985                 990

Arg His Ile Leu Glu Arg Pro Asp  Pro Thr Asp Val Phe  Gln Asn Lys
        995                 1000                1005

Ala Asn  Val Cys Trp Ala Lys  Ala Leu Val Pro Val  Leu Lys Thr
    1010                 1015                 1020

Ala Gly  Ile Asp Met Thr Thr  Glu Gln Trp Asn Thr  Val Asp Tyr
    1025                 1030                 1035

Phe Glu  Thr Asp Lys Ala His  Ser Ala Glu Ile Val  Leu Asn Gln
    1040                 1045                 1050

Leu Cys  Val Arg Phe Phe Gly  Leu Asp Leu Asp Ser  Gly Leu Phe
    1055                 1060                 1065

Ser Ala  Pro Thr Val Pro Leu  Ser Ile Arg Asn Asn  His Trp Asp
    1070                 1075                 1080

Asn Ser  Pro Ser Pro Asn Met  Tyr Gly Leu Asn Lys  Glu Val Val
    1085                 1090                 1095

Arg Gln  Leu Ser Arg Arg Tyr  Pro Gln Leu Pro Arg  Ala Val Ala
    1100                 1105                 1110

Thr Gly  Arg Val Tyr Asp Met  Asn Thr Gly Thr Leu  Arg Asn Tyr
    1115                 1120                 1125

Asp Pro  Arg Ile Asn Leu Val  Pro Val Asn Arg Arg  Leu Pro His
    1130                 1135                 1140

Ala Leu  Val Leu His His Asn  Glu His Pro Gln Ser  Asp Phe Ser
    1145                 1150                 1155

Ser Phe  Val Ser Lys Leu Lys  Gly Arg Thr Val Leu  Val Val Gly
    1160                 1165                 1170

Glu Lys  Leu Ser Val Pro Gly  Lys Lys Val Asp Trp  Leu Ser Asp
    1175                 1180                 1185

Gln Pro  Glu Ala Thr Phe Arg  Ala Arg Leu Asp Leu  Gly Ile Pro
    1190                 1195                 1200

Gly Asp  Val Pro Lys Tyr Asp  Ile Val Phe Ile Asn  Val Arg Thr
    1205                 1210                 1215

Pro Tyr  Lys Tyr His His Tyr  Gln Gln Cys Glu Asp  His Ala Ile
    1220                 1225                 1230

Lys Leu  Ser Met Leu Thr Lys  Lys Ala Cys Leu His  Leu Asn Pro
    1235                 1240                 1245

Gly Gly  Thr Cys Val Ser Ile  Gly Tyr Gly Tyr Ala  Asp Arg Ala
    1250                 1255                 1260

Ser Glu  Ser Ile Ile Gly Ala  Ile Ala Arg Gln Phe  Lys Phe Ser
    1265                 1270                 1275

Arg Val  Cys Lys Pro Lys Ser  Ser His Glu Glu Thr  Glu Val Leu
    1280                 1285                 1290

Phe Val  Phe Ile Gly Tyr Asp  Arg Lys Ala Arg Thr  His Asn Pro
    1295                 1300                 1305

Tyr Lys  Leu Ser Ser Thr Leu  Thr Asn Ile Tyr Thr  Gly Ser Arg
    1310                 1315                 1320
```

-continued

```
Leu His  Glu Ala Gly Cys Ala  Pro Ser Tyr His Val  Val Arg Gly
    1325                 1330                 1335

Asp Ile  Ala Thr Ala Thr Glu  Gly Val Ile Ile Asn  Ala Ala Asn
    1340                 1345                 1350

Ser Lys  Gly Gln Pro Gly Gly  Gly Val Cys Gly Ala  Leu Tyr Lys
    1355                 1360                 1365

Lys Phe  Pro Glu Ser Phe Asp  Leu Gln Pro Ile Glu  Val Gly Lys
    1370                 1375                 1380

Ala Arg  Leu Val Lys Gly Ala  Ala Lys His Ile Ile  His Ala Val
    1385                 1390                 1395

Gly Pro  Asn Phe Asn Lys Val  Ser Glu Val Glu Gly  Asp Lys Gln
    1400                 1405                 1410

Leu Ala  Glu Ala Tyr Glu Ser  Ile Ala Lys Ile Val  Asn Asp Asn
    1415                 1420                 1425

Asn Tyr  Lys Ser Val Ala Ile  Pro Leu Leu Ser Thr  Gly Ile Phe
    1430                 1435                 1440

Ser Gly  Asn Lys Asp Arg Leu  Thr Gln Ser Leu Asn  His Leu Leu
    1445                 1450                 1455

Thr Ala  Leu Asp Thr Thr Asp  Ala Asp Val Ala Ile  Tyr Cys Arg
    1460                 1465                 1470

Asp Lys  Lys Trp Glu Met Thr  Leu Lys Glu Ala Val  Ala Arg Arg
    1475                 1480                 1485

Glu Ala  Val Glu Glu Ile Cys  Ile Ser Asp Asp Ser  Ser Val Thr
    1490                 1495                 1500

Glu Pro  Asp Ala Glu Leu Val  Arg Val His Pro Lys  Ser Ser Leu
    1505                 1510                 1515

Ala Gly  Arg Lys Gly Tyr Ser  Thr Ser Asp Gly Lys  Thr Phe Ser
    1520                 1525                 1530

Tyr Leu  Glu Gly Thr Lys Phe  His Gln Ala Ala Lys  Asp Ile Ala
    1535                 1540                 1545

Glu Ile  Asn Ala Met Trp Pro  Val Ala Thr Glu Ala  Asn Glu Gln
    1550                 1555                 1560

Val Cys  Met Tyr Ile Leu Gly  Glu Ser Met Ser Ser  Ile Arg Ser
    1565                 1570                 1575

Lys Cys  Pro Val Glu Glu Ser  Glu Ala Ser Thr Pro  Pro Ser Thr
    1580                 1585                 1590

Leu Pro  Cys Leu Cys Ile His  Ala Met Thr Pro Glu  Arg Val Gln
    1595                 1600                 1605

Arg Leu  Lys Ala Ser Arg Pro  Glu Gln Ile Thr Val  Cys Ser Ser
    1610                 1615                 1620

Phe Pro  Leu Pro Lys Tyr Arg  Ile Thr Gly Val Gln  Lys Ile Gln
    1625                 1630                 1635

Cys Ser  Gln Pro Ile Leu Phe  Ser Pro Lys Val Pro  Ala Tyr Ile
    1640                 1645                 1650

His Pro  Arg Lys Tyr Leu Val  Glu Thr Pro Pro Val  Glu Glu Thr
    1655                 1660                 1665

Pro Glu  Ser Pro Ala Glu Asn  Gln Ser Thr Glu Gly  Thr Pro Glu
    1670                 1675                 1680

Gln Pro  Ala Leu Val Asn Val  Asp Ala Thr Arg Thr  Arg Met Pro
    1685                 1690                 1695

Glu Pro  Ile Ile Ile Glu Glu  Glu Glu Glu Asp Ser  Ile Ser Leu
    1700                 1705                 1710

Leu Ser  Asp Gly Pro Thr His  Gln Val Leu Gln Val  Glu Ala Asp
```

```
    1715                1720                1725

Ile His Gly Ser Pro Ser Val Ser Ser Ser Ser Trp Ser Ile Pro
    1730                1735                1740

His Ala Ser Asp Phe Asp Val Asp Ser Leu Ser Ile Leu Asp Thr
    1745                1750                1755

Leu Asp Gly Ala Ser Val Thr Ser Gly Ala Val Ser Ala Glu Thr
    1760                1765                1770

Asn Ser Tyr Phe Ala Arg Ser Met Glu Phe Arg Ala Arg Pro Val
    1775                1780                1785

Pro Ala Pro Arg Thr Val Phe Arg Asn Pro Pro His Pro Ala Pro
    1790                1795                1800

Arg Thr Arg Thr Pro Pro Leu Ala His Ser Arg Ala Ser Ser Arg
    1805                1810                1815

Thr Ser Leu Val Ser Thr Pro Pro Gly Val Asn Arg Val Ile Thr
    1820                1825                1830

Arg Glu Glu Leu Glu Ala Leu Thr Pro Ser Arg Ala Pro Ser Arg
    1835                1840                1845

Ser Ala Ser Arg Thr Ser Leu Val Ser Asn Pro Pro Gly Val Asn
    1850                1855                1860

Arg Val Ile Thr Arg Glu Glu Phe Glu Ala Phe Val Ala Gln Gln
    1865                1870                1875

Gln Arg Phe Asp Ala Gly Ala Tyr Ile Phe Ser Ser Asp Thr Gly
    1880                1885                1890

Gln Gly His Leu Gln Gln Lys Ser Val Arg Gln Thr Val Leu Ser
    1895                1900                1905

Glu Val Val Leu Glu Arg Thr Glu Leu Glu Ile Ser Tyr Ala Pro
    1910                1915                1920

Arg Leu Asp Gln Glu Lys Glu Glu Leu Leu Arg Lys Lys Leu Gln
    1925                1930                1935

Leu Asn Pro Thr Pro Ala Asn Arg Ser Arg Tyr Gln Ser Arg Arg
    1940                1945                1950

Val Glu Asn Met Lys Ala Ile Thr Ala Arg Arg Ile Leu Gln Gly
    1955                1960                1965

Leu Gly His Tyr Leu Lys Ala Glu Gly Lys Val Glu Cys Tyr Arg
    1970                1975                1980

Thr Leu His Pro Val Pro Leu Tyr Ser Ser Ser Val Asn Arg Ala
    1985                1990                1995

Phe Ser Ser Pro Lys Val Ala Val Glu Ala Cys Asn Ala Met Leu
    2000                2005                2010

Lys Glu Asn Phe Pro Thr Val Ala Ser Tyr Cys Ile Ile Pro Glu
    2015                2020                2025

Tyr Asp Ala Tyr Leu Asp Met Val Asp Gly Ala Ser Cys Cys Leu
    2030                2035                2040

Asp Thr Ala Ser Phe Cys Pro Ala Lys Leu Arg Ser Phe Pro Lys
    2045                2050                2055

Lys His Ser Tyr Leu Glu Pro Thr Ile Arg Ser Ala Val Pro Ser
    2060                2065                2070

Ala Ile Gln Asn Thr Leu Gln Asn Val Leu Ala Ala Ala Thr Lys
    2075                2080                2085

Arg Asn Cys Asn Val Thr Gln Met Arg Glu Leu Pro Val Leu Asp
    2090                2095                2100

Ser Ala Ala Phe Asn Val Glu Cys Phe Lys Lys Tyr Ala Cys Asn
    2105                2110                2115
```

Asn Glu Tyr Trp Glu Thr Phe Lys Glu Asn Pro Ile Arg Leu Thr
2120 2125 2130

Glu Glu Asn Val Val Asn Tyr Ile Thr Lys Leu Lys Gly Pro Lys
2135 2140 2145

Ala Ala Ala Leu Phe Ala Lys Thr His Asn Leu Asn Met Leu Gln
2150 2155 2160

Asp Ile Pro Met Asp Arg Phe Val Met Asp Leu Lys Arg Asp Val
2165 2170 2175

Lys Val Thr Pro Gly Thr Lys His Thr Glu Glu Arg Pro Lys Val
2180 2185 2190

Gln Val Ile Gln Ala Ala Asp Pro Leu Ala Thr Ala Asp Leu Cys
2195 2200 2205

Gly Ile His Arg Glu Leu Val Arg Arg Leu Asn Ala Val Leu Leu
2210 2215 2220

Pro Asn Ile His Thr Leu Phe Asp Met Ser Ala Glu Asp Phe Asp
2225 2230 2235

Ala Ile Ile Ala Glu His Phe Gln Pro Gly Asp Cys Val Leu Glu
2240 2245 2250

Thr Asp Ile Ala Ser Phe Asp Lys Ser Glu Asp Asp Ala Met Ala
2255 2260 2265

Leu Thr Ala Leu Met Ile Leu Glu Asp Leu Gly Val Asp Ala Glu
2270 2275 2280

Leu Leu Thr Leu Ile Glu Ala Ala Phe Gly Glu Ile Ser Ser Ile
2285 2290 2295

His Leu Pro Thr Lys Thr Lys Phe Lys Phe Gly Ala Met Met Lys
2300 2305 2310

Ser Gly Met Phe Leu Thr Leu Phe Val Asn Thr Val Ile Asn Ile
2315 2320 2325

Val Ile Ala Ser Arg Val Leu Arg Glu Arg Leu Thr Gly Ser Pro
2330 2335 2340

Cys Ala Ala Phe Ile Gly Asp Asp Asn Ile Val Lys Gly Val Lys
2345 2350 2355

Ser Asp Lys Leu Met Ala Asp Arg Cys Ala Thr Trp Leu Asn Met
2360 2365 2370

Glu Val Lys Ile Ile Asp Ala Val Val Gly Glu Lys Ala Pro Tyr
2375 2380 2385

Phe Cys Gly Gly Phe Ile Leu Cys Asp Ser Val Thr Gly Thr Ala
2390 2395 2400

Cys Arg Val Ala Asp Pro Leu Lys Arg Leu Phe Lys Leu Gly Lys
2405 2410 2415

Pro Leu Ala Val Asp Asp Glu His Asp Asp Asp Arg Arg Arg Ala
2420 2425 2430

Leu His Glu Glu Ser Thr Arg Trp Asn Arg Val Gly Ile Leu Pro
2435 2440 2445

Glu Leu Cys Lys Ala Val Glu Ser Arg Tyr Glu Thr Val Gly Thr
2450 2455 2460

Ser Ile Ile Val Met Ala Met Thr Thr Leu Ala Ser Ser Val Lys
2465 2470 2475

Ser Phe Ser Tyr Leu Arg Gly Ala Pro Ile Thr Leu Tyr Gly
2480 2485 2490

<210> SEQ ID NO 82
<211> LENGTH: 146

<212> TYPE: DNA
<213> ORGANISM: Artificial sequence
<220> FEATURE:
<223> OTHER INFORMATION: Synthetic polynucleotide

<400> SEQUENCE: 82
aggaaactta agtcaacaca acatatacaa aacaaacgaa tctcaagcaa tcaagcattc 60
tacttctatt gcagcaattt aaatcatttc ttttaaagca aaagcaattt tctgaaaatt 120
ttcaccattt acgaacgata gccacc 146

<210> SEQ ID NO 83
<211> LENGTH: 270
<212> TYPE: DNA
<213> ORGANISM: Artificial sequence
<220> FEATURE:
<223> OTHER INFORMATION: Synthetic polynucleotide

<400> SEQUENCE: 83
actcgagcta gtgactgact aggatctggt taccactaaa ccagcctcaa gaacacccga 60
atggagtctc taagctacat aataccaact tacacttaca aaatgttgtc ccccaaaatg 120
tagccattcg tatctgctcc taataaaaag aaagtttctt cacattctag aaaaaaaaaa 180
aaaaaaaaaa aaaaaaaaaa aaaaaaaaaa aaaaaaaaaa aaaaaaaaaa aaaaaaaaaa 240
aaaaaaaaaa aaaaaaaaaa aaaaaaaaaa 270

<210> SEQ ID NO 84
<211> LENGTH: 1653
<212> TYPE: RNA
<213> ORGANISM: Artificial sequence
<220> FEATURE:
<223> OTHER INFORMATION: Synthetic polynucleotide

<400> SEQUENCE: 84
auggaagaug ccaaaaacau uaagaagggc ccagcgccau ucuacccacu cgaagacggg 60
accgccggcg agcagcugca caaagccaug aagcgcuacg cccuggugcc cggcaccauc 120
gccuuuaccg acgcacauau cgagguggac auuaccuacg ccgaguacuu cgagaugagc 180
guucggcugg cagaagcuau gaagcgcuau gggcugaaua caaaccaucg gaucguggug 240
ugcagcgaga auagcuugca guucuucaug cccguguugg gugcccuguu caucggugug 300
gcuguggccc cagcuaacga caucuacaac gagcgcgagc ugcugaacag caugggcauc 360
agccagccca ccgucguauu cgugagcaag aaagggcugc aaaagauccu caacgugcaa 420
aagaagcuac cgaucauaca aaagaucauc aucauggaua gcaagaccga cuaccagggc 480
uuccaaagca uguacaccuu cgugacuucc cauuugccac ccggcuucaa cgaguacgac 540
uucgugcccg agagcuucga ccgggacaaa accaucgccc ugaucaugaa caguaguggc 600
aguaccggau ugcccaaggg cguagcccua ccgcaccgca ccgcuugugu ccgauucagu 660
caugcccgcg accccaucuu cggcaaccag aucauccccg acaccgcuau ccucagcgug 720
gugccauuuc accacggcuu cggcauguuc accacgcugg gcuacuugau cugcggcuuu 780
cgggucgugc ucauguaccg cuucgaggag gagcuauucu ugcgcagcuu gcaagacuau 840
aagauucaau cugcccugcu ggugcccaca cuauuuagcu ucuucgcuaa gagcacucuc 900
aucgacaagu acgaccuaag caacuugcac gagaucgcca gcggcggggc gccgcucagc 960
aaggagguag gugaggccgu ggccaaacgc uuccaccuac caggcauccg acagggcuac 1020
ggccugacag aaacaaccag cgccauucug aucacccccg aaggggacga caagccuggc 1080
gcaguaggca agguggugcc cuucuucgag gcuaaggugg uggacuugga caccgguaag 1140
acacugggug ugaaccagcg cggcgagcug ugcguccgug gccccaugau caugagcggc 1200
uacguuaaca accccgaggc uacaaacgcu cucaucgaca aggacggcug gcugcacagc 1260
ggcgacaucg ccuacuggga cgaggacgag cacuucuuca ucguggaccg gcugaagucc 1320
cugaucaaau acaagggcua ccagguagcc ccagccgaac uggagagcau ccugcugcaa 1380
caccccaaca ucuucgacgc cggggucgcc ggccugcccg acgacgaugc cggcgagcug 1440
cccgccgcag ucgucgugcu ggaacacggu aaaaccauga ccgagaagga gaucguggac 1500
uauguggcca gccagguuac aaccgccaag aagcugcgcg gugguguugu guucguggac 1560
gaggugccua aaggacugac cggcaaguug gacgcccgca agauccgcga gauucucauu 1620
aaggccaaga agggcggcaa gaucgccgug uaa 1653

<210> SEQ ID NO 85
<211> LENGTH: 1653
<212> TYPE: RNA
<213> ORGANISM: Artificial sequence
<220> FEATURE:
<223> OTHER INFORMATION: Synthetic polynucleotide

<400> SEQUENCE: 85
auggaagaug ccaaaaacau uaagaagggc ccagcgccau ucuacccacu cgaagacggg 60
accgccggcg agcagcugca caaagccaug aagcgcuacg cccuggugcc cggcaccauc 120
gccuuuaccg acgcacauau cgagguggac auuaccuacg ccgaguacuu cgagaugagc 180
guucggcugg cagaagcuau gaagcgcuau gggcugaaua caaaccaucg gaucguggug 240
ugcagcgaga auagcuugca guucuucaug cccguguugg gugcccuguu caucggugug 300
gcuguggccc cagcuaacga caucuacaac gagcgcgagc ugcugaacag caugggcauc 360
agccagccca ccgucguauu cgugagcaag aaagggcugc aaaagauccu caacgugcaa 420
aagaagcuac cgaucauaca aaagaucauc aucauggaua gcaagaccga cuaccagggc 480
uuccaaagca uguacaccuu cgugacuucc cauuugccac ccggcuucaa cgaguacgac 540
uucgugcccg agagcuucga ccgggacaaa accaucgccc ugaucaugaa caguaguggc 600
aguaccggau ugcccaaggg cguagcccua ccgcaccgca ccgcuugugu ccgauucagu 660
caugcccgcg accccaucuu cggcaaccag aucauccccg acaccgcuau ccucagcgug 720
gugccauuuc accacggcuu cggcauguuc accacgcugg gcuacuugau cugcggcuuu 780
cgggucgugc ucauguaccg cuucgaggag gagcuauucu ugcgcagcuu gcaagacuau 840
aagauucaau cugcccugcu ggugcccaca cuauuuagcu ucuucgcuaa gagcacucuc 900
aucgacaagu acgaccuaag caacuugcac gagaucgcca gcggcggggc gccgcucagc 960
aaggagguag gugaggccgu ggccaaacgc uuccaccuac caggcauccg acagggcuac 1020
ggccugacag aaacaaccag cgccauucug aucacccccg aaggggacga caagccuggc 1080
gcaguaggca agguggugcc cuucuucgag gcuaaggugg uggacuugga caccgguaag 1140
acacugggug ugaaccagcg cggcgagcug ugcguccgug gccccaugau caugagcggc 1200
uacguuaaca accccgaggc uacaaacgcu cucaucgaca aggacggcug gcugcacagc 1260
ggcgacaucg ccuacuggga cgaggacgag cacuucuuca ucguggaccg gcugaagucc 1320
cugaucaaau acaagggcua ccagguagcc ccagccgaac uggagagcau ccugcugcaa 1380
caccccaaca ucuucgacgc cggggucgcc ggccugcccg acgacgaugc cggcgagcug 1440
cccgccgcag ucgucgugcu ggaacacggu aaaaccauga ccgagaagga gaucguggac 1500
uauguggcca gccagguuac aaccgccaag aagcugcgcg gugguguugu guucguggac 1560
gaggugccua aaggacugac cggcaaguug gacgcccgca agauccgcga gauucucauu 1620
aaggccaaga agggcggcaa gaucgccgug uaa 1653

<210> SEQ ID NO 86
<211> LENGTH: 1653
<212> TYPE: RNA
<213> ORGANISM: Artificial sequence
<220> FEATURE:
<223> OTHER INFORMATION: Synthetic polynucleotide

<400> SEQUENCE: 86
auggaagaug ccaaaaacau uaagaagggc ccagcgccau ucuacccacu cgaagacggg 60
accgccggcg agcagcugca caaagccaug aagcgcuacg cccuggugcc cggcaccauc 120
gccuuuaccg acgcacauau cgagguggac auuaccuacg ccgaguacuu cgagaugagc 180
guucggcugg cagaagcuau gaagcgcuau gggcugaaua caaaccaucg gaucguggug 240
ugcagcgaga auagcuugca guucuucaug cccguguugg gugcccuguu caucggugug 300
gcuguggccc cagcuaacga caucuacaac gagcgcgagc ugcugaacag caugggcauc 360
agccagccca ccgucguauu cgugagcaag aaagggcugc aaaagauccu caacgugcaa 420
aagaagcuac cgaucauaca aaagaucauc aucauggaua gcaagaccga cuaccagggc 480
uuccaaagca uguacaccuu cgugacuucc cauuugccac ccggcuucaa cgaguacgac 540
uucgugcccg agagcuucga ccgggacaaa accaucgccc ugaucaugaa caguaguggc 600
aguaccggau ugcccaaggg cguagcccua ccgcaccgca ccgcuugugu ccgauucagu 660
caugcccgcg accccaucuu cggcaaccag aucauccccg acaccgcuau ccucagcgug 720
gugccauuuc accacggcuu cggcauguuc accacgcugg gcuacuugau cugcggcuuu 780
cgggucgugc ucauguaccg cuucgaggag gagcuauucu ugcgcagcuu gcaagacuau 840
aagauucaau cugcccugcu ggugcccaca cuauuuagcu ucuucgcuaa gagcacucuc 900
aucgacaagu acgaccuaag caacuugcac gagaucgcca gcggcggggc gccgcucagc 960
aaggagguag gugaggccgu ggccaaacgc uuccaccuac caggcauccg acagggcuac 1020
ggccugacag aaacaaccag cgccauucug aucacccccg aaggggacga caagccuggc 1080
gcaguaggca agguggugcc cuucuucgag gcuaaggugg uggacuugga caccgguaag 1140
acacugggug ugaaccagcg cggcgagcug ugcguccgug gccccaugau caugagcggc 1200
uacguuaaca accccgaggc uacaaacgcu cucaucgaca aggacggcug gcugcacagc 1260
ggcgacaucg ccuacuggga cgaggacgag cacuucuuca ucguggaccg gcugaagucc 1320
cugaucaaau acaagggcua ccagguagcc ccagccgaac uggagagcau ccugcugcaa 1380
caccccaaca ucuucgacgc cggggucgcc ggccugcccg acgacgaugc cggcgagcug 1440
cccgccgcag ucgucgugcu ggaacacggu aaaaccauga ccgagaagga gaucguggac 1500
uauguggcca gccagguuac aaccgccaag aagcugcgcg gugguguugu guucguggac 1560
gaggugccua aaggacugac cggcaaguug gacgcccgca agauccgcga gauucucauu 1620
aaggccaaga agggcggcaa gaucgccgug uaa 1653

<210> SEQ ID NO 87
<211> LENGTH: 57
<212> TYPE: RNA
<213> ORGANISM: Artificial sequence
<220> FEATURE:

<223> OTHER INFORMATION: Synthetic polynucleotide

<400> SEQUENCE: 87
augaaguugg ugguuguggg ggccgggggu guuggcaaaa gcgcccuuac aauuuga 57

<210> SEQ ID NO 88
<211> LENGTH: 66
<212> TYPE: RNA
<213> ORGANISM: Artificial sequence
<220> FEATURE:
<223> OTHER INFORMATION: Synthetic polynucleotide

<400> SEQUENCE: 88
auggauccua gacgcuacgc cccaaugauc cgaccagcaa aacucgaugu acuuccgagg 60
aacuga 66

<210> SEQ ID NO 89
<211> LENGTH: 837
<212> TYPE: RNA
<213> ORGANISM: Artificial sequence
<220> FEATURE:
<223> OTHER INFORMATION: Synthetic polynucleotide

<400> SEQUENCE: 89
augagaguga cagccccuag aaccuuacug cuucugcuuu ggggagcugu ugcucugaca 60
gagacauggg cuggaucucu gagcgaggug accggccagg gccugugcau cggcgccgug 120
cccaagaccc accaggugcu gugcaacacc acccagaaga ccagcgacgg cagcuacuac 180
cuggccgcuc ccaccggcac caccugggcc ugcagcaccg gccugacccc uugcaucagc 240
accaccaucc ugaaccugac caccgacuac ugcgugcugg uggagcugug gcccagggug 300
accuaccaca gccccagcua cgccuaccac caguucgaga ggagggccaa guacaagagg 360
gagcccguga gccugacccu ggcccugcug cugggcggcc ugacaauggg cggcaucgcc 420
gccggcgugg gcaccggcac caccgcccug guggccaccc agcaguucca gcagcugcag 480
gccgccaugc acgacgaccu gaaggaggug gagaagucca ucaccaaccu ggagaagucc 540
cugaccagcc ugagcgaggu ggugcugcag aacaggaggg gccuggaccu gcuguuccug 600
aaggagggcg gccugugcgc cgcccugaag gaggagugcu gccuguacgc cgaccacacc 660
ggccugguga ucgugggcau ugucgcuggc cuggccgucc ucgccguggu ggugauugga 720 gcugugg ucg cagcuguuau gugcagaaga aagucauccg gcggaaaggg aggcuccuac 780
ucucaggcug cuucugcuac agugccuaga gcucuuaugu guuuaucuca gcuguaa 837

<210> SEQ ID NO 90
<211> LENGTH: 378
<212> TYPE: RNA
<213> ORGANISM: Artificial sequence
<220> FEATURE:
<223> OTHER INFORMATION: Synthetic polynucleotide

<400> SEQUENCE: 90
augagaguga cagccccuag aaccuuacug cuucugcuuu ggggagcugu ugcucugaca 60
gagacauggg cuggaucuua ccacagcccc agcuacgccu accaccaguu cgagaggggg 120
ggaggaggcu ccgggggagg aggcucccug aagaucagcc aggccgugca cgccgcccac 180
gccgagauca acgaggccgg ccgggaggug aucgugggca uugucgcugg ccuggccguc 240
cucgccgugg uggugauugg agcugugguc gcagcuguua ugugcagaag aaagucaucc 300
ggcggaaagg gaggcuccua cucucaggcu gcuucugcua cagugccuag agcucuuaug 360
uguuuaucuc agcuguaa 378

<210> SEQ ID NO 91
<211> LENGTH: 876
<212> TYPE: RNA
<213> ORGANISM: Artificial sequence
<220> FEATURE:
<223> OTHER INFORMATION: Synthetic polynucleotide

<400> SEQUENCE: 91
augagaguga cagccccuag aaccuuacug cuucugcuuu ggggagcugu ugcucugaca 60
gagacauggg cuggaucucu gagcgaggug accggccagg gccugugcau cggcgccgug 120
cccaagaccc accaggugcu gugcaacacc acccagaaga ccagcgacgg cagcuacuac 180
cuggccgcuc ccaccggcac caccugggcc ugcagcaccg gccugacccc uugcaucagc 240
accaccaucc ugaaccugac caccgacuac ugcgugcugg uggagcugug gcccagggug 300
accuaccaca gccccagcua cgccuaccac caguucgaga ggagggccaa guacaagagg 360
gagcccguga gccugacccu ggcccugcug cugggcggcc ugacaauggg cggcaucgcc 420
gccggcgugg gcaccggcac caccgcccug guggccaccc agcaguucca gcagcugcag 480
gccgccaugc acgacgaccu gaaggaggug gagaagucca ucaccaaccu ggagaagucc 540
cugaccagcc ugagcgaggu ggugcugcag aacaggaggg gccuggaccu gcuguuccug 600
aaggagggcg gccugugcgc cgcccugaag gaggagugcu gccuguacgc cgaccacacc 660
ggccugguga ucgugggcau ugucgcuggc cuggccgucc ucgccguggu ggugauugga 720 gcugugggucg cagcuguuau gugcagaaga aagucauccg gcggaaaggg aggcuccuac 780
ucucaggcug cuucugcuac agugccuaga gcucuuaugu guuuaucuca gcugggcggc 840
ggaggcagcg acuacaagga cgacgaugac aaguaa 876

<210> SEQ ID NO 92
<211> LENGTH: 417
<212> TYPE: RNA
<213> ORGANISM: Artificial sequence
<220> FEATURE:
<223> OTHER INFORMATION: Synthetic polynucleotide

<400> SEQUENCE: 92
augagaguga cagccccuag aaccuuacug cuucugcuuu ggggagcugu ugcucugaca 60
gagacauggg cuggaucuua ccacagcccc agcuacgccu accaccaguu cgagaggggg 120
ggaggaggcu ccgggggagg aggcucccug aagaucagcc aggccgugca cgccgcccac 180
gccgagauca acgaggccgg ccgggaggug aucgugggca uugucgcugg ccuggccguc 240
cucgccgugg uggugauugg agcuguggguc gcagcuguua ugugcagaag aaagucaucc 300
ggcggaaagg gaggcuccua cucucaggcu gcuucugcua cagugccuag agcucuuaug 360
uguuuaucuc agcugggcgg cggaggcagc gacuacaagg acgacgauga caaguaa 417

<210> SEQ ID NO 93
<211> LENGTH: 550
<212> TYPE: PRT
<213> ORGANISM: Artificial sequence
<220> FEATURE:
<223> OTHER INFORMATION: Synthetic polypeptide

<400> SEQUENCE: 93

Met Glu Asp Ala Lys Asn Ile Lys Lys Gly Pro Ala Pro Phe Tyr Pro
1 5 10 15

```
Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asp Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Gly Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
    210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
    290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Glu Gly Asp Asp Lys Pro Gly Ala Val Gly Lys Val Val Pro Phe
        355                 360                 365

Phe Glu Ala Lys Val Val Asp Leu Asp Thr Gly Lys Thr Leu Gly Val
    370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp Glu His Phe
            420                 425                 430
```

```
Phe Ile Val Asp Arg Leu Lys Ser Leu Ile Lys Tyr Lys Gly Tyr Gln
        435                 440                 445

Val Ala Pro Ala Glu Leu Glu Ser Ile Leu Leu Gln His Pro Asn Ile
    450                 455                 460

Phe Asp Ala Gly Val Ala Gly Leu Pro Asp Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
        515                 520                 525

Lys Leu Asp Ala Arg Lys Ile Arg Glu Ile Leu Ile Lys Ala Lys Lys
    530                 535                 540

Gly Gly Lys Ile Ala Val
545                 550


<210> SEQ ID NO 94
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 94

Met Lys Leu Val Val Val Gly Ala Gly Gly Val Gly Lys Ser Ala Leu
1               5                   10                  15

Thr Ile


<210> SEQ ID NO 95
<211> LENGTH: 21
<212> TYPE: PRT
<213> ORGANISM: Artificial sequence
<220> FEATURE:
<223> OTHER INFORMATION: Synthetic polypeptide

<400> SEQUENCE: 95

Met Asp Pro Arg Arg Tyr Ala Pro Met Ile Arg Pro Ala Lys Leu Asp
1               5                   10                  15

Val Leu Pro Arg Asn
            20


<210> SEQ ID NO 96
<211> LENGTH: 278
<212> TYPE: PRT
<213> ORGANISM: Artificial sequence
<220> FEATURE:
<223> OTHER INFORMATION: Synthetic polypeptide

<400> SEQUENCE: 96

Met Arg Val Thr Ala Pro Arg Thr Leu Leu Leu Leu Leu Trp Gly Ala
1               5                   10                  15

Val Ala Leu Thr Glu Thr Trp Ala Gly Ser Leu Ser Glu Val Thr Gly
            20                  25                  30

Gln Gly Leu Cys Ile Gly Ala Val Pro Lys Thr His Gln Val Leu Cys
        35                  40                  45

Asn Thr Thr Gln Lys Thr Ser Asp Gly Ser Tyr Tyr Leu Ala Ala Pro
    50                  55                  60

Thr Gly Thr Thr Trp Ala Cys Ser Thr Gly Leu Thr Pro Cys Ile Ser
65                  70                  75                  80
```

```
Thr Thr Ile Leu Asn Leu Thr Thr Asp Tyr Cys Val Leu Val Glu Leu
                85                  90                  95

Trp Pro Arg Val Thr Tyr His Ser Pro Ser Tyr Ala Tyr His Gln Phe
            100                 105                 110

Glu Arg Arg Ala Lys Tyr Lys Arg Glu Pro Val Ser Leu Thr Leu Ala
        115                 120                 125

Leu Leu Leu Gly Gly Leu Thr Met Gly Gly Ile Ala Ala Gly Val Gly
    130                 135                 140

Thr Gly Thr Thr Ala Leu Val Ala Thr Gln Gln Phe Gln Gln Leu Gln
145                 150                 155                 160

Ala Ala Met His Asp Asp Leu Lys Glu Val Glu Lys Ser Ile Thr Asn
                165                 170                 175

Leu Glu Lys Ser Leu Thr Ser Leu Ser Glu Val Val Leu Gln Asn Arg
            180                 185                 190

Arg Gly Leu Asp Leu Leu Phe Leu Lys Glu Gly Gly Leu Cys Ala Ala
        195                 200                 205

Leu Lys Glu Glu Cys Cys Leu Tyr Ala Asp His Thr Gly Leu Val Ile
    210                 215                 220

Val Gly Ile Val Ala Gly Leu Ala Val Leu Ala Val Val Val Ile Gly
225                 230                 235                 240

Ala Val Val Ala Ala Val Met Cys Arg Arg Lys Ser Ser Gly Gly Lys
                245                 250                 255

Gly Gly Ser Tyr Ser Gln Ala Ala Ser Ala Thr Val Pro Arg Ala Leu
            260                 265                 270

Met Cys Leu Ser Gln Leu
        275
```

<210> SEQ ID NO 97
<211> LENGTH: 125
<212> TYPE: PRT
<213> ORGANISM: Artificial sequence
<220> FEATURE:
<223> OTHER INFORMATION: Synthetic polypeptide

<400> SEQUENCE: 97

```
Met Arg Val Thr Ala Pro Arg Thr Leu Leu Leu Leu Leu Trp Gly Ala
1               5                   10                  15

Val Ala Leu Thr Glu Thr Trp Ala Gly Ser Tyr His Ser Pro Ser Tyr
            20                  25                  30

Ala Tyr His Gln Phe Glu Arg Gly Gly Gly Gly Ser Gly Gly Gly Gly
        35                  40                  45

Ser Leu Lys Ile Ser Gln Ala Val His Ala Ala His Ala Glu Ile Asn
    50                  55                  60

Glu Ala Gly Arg Glu Val Ile Val Gly Ile Val Ala Gly Leu Ala Val
65                  70                  75                  80

Leu Ala Val Val Val Ile Gly Ala Val Val Ala Ala Val Met Cys Arg
                85                  90                  95

Arg Lys Ser Ser Gly Gly Lys Gly Gly Ser Tyr Ser Gln Ala Ala Ser
            100                 105                 110

Ala Thr Val Pro Arg Ala Leu Met Cys Leu Ser Gln Leu
        115                 120                 125
```

<210> SEQ ID NO 98
<211> LENGTH: 291
<212> TYPE: PRT
<213> ORGANISM: Artificial sequence
<220> FEATURE:
<223> OTHER INFORMATION: Synthetic polypeptide

<400> SEQUENCE: 98

```
Met Arg Val Thr Ala Pro Arg Thr Leu Leu Leu Leu Leu Trp Gly Ala
1               5                   10                  15

Val Ala Leu Thr Glu Thr Trp Ala Gly Ser Leu Ser Glu Val Thr Gly
            20                  25                  30

Gln Gly Leu Cys Ile Gly Ala Val Pro Lys Thr His Gln Val Leu Cys
        35                  40                  45

Asn Thr Thr Gln Lys Thr Ser Asp Gly Ser Tyr Tyr Leu Ala Ala Pro
    50                  55                  60

Thr Gly Thr Thr Trp Ala Cys Ser Thr Gly Leu Thr Pro Cys Ile Ser
65                  70                  75                  80

Thr Thr Ile Leu Asn Leu Thr Thr Asp Tyr Cys Val Leu Val Glu Leu
                85                  90                  95

Trp Pro Arg Val Thr Tyr His Ser Pro Ser Tyr Ala Tyr His Gln Phe
            100                 105                 110

Glu Arg Arg Ala Lys Tyr Lys Arg Glu Pro Val Ser Leu Thr Leu Ala
        115                 120                 125

Leu Leu Leu Gly Gly Leu Thr Met Gly Gly Ile Ala Ala Gly Val Gly
    130                 135                 140

Thr Gly Thr Thr Ala Leu Val Ala Thr Gln Gln Phe Gln Gln Leu Gln
145                 150                 155                 160

Ala Ala Met His Asp Asp Leu Lys Glu Val Glu Lys Ser Ile Thr Asn
                165                 170                 175

Leu Glu Lys Ser Leu Thr Ser Leu Ser Glu Val Val Leu Gln Asn Arg
            180                 185                 190

Arg Gly Leu Asp Leu Leu Phe Leu Lys Glu Gly Gly Leu Cys Ala Ala
        195                 200                 205

Leu Lys Glu Glu Cys Cys Leu Tyr Ala Asp His Thr Gly Leu Val Ile
    210                 215                 220

Val Gly Ile Val Ala Gly Leu Ala Val Leu Ala Val Val Val Ile Gly
225                 230                 235                 240

Ala Val Val Ala Ala Val Met Cys Arg Arg Lys Ser Ser Gly Gly Lys
                245                 250                 255

Gly Gly Ser Tyr Ser Gln Ala Ala Ser Ala Thr Val Pro Arg Ala Leu
            260                 265                 270

Met Cys Leu Ser Gln Leu Gly Gly Gly Gly Ser Asp Tyr Lys Asp Asp
        275                 280                 285

Asp Asp Lys
    290
```

<210> SEQ ID NO 99
<211> LENGTH: 138
<212> TYPE: PRT
<213> ORGANISM: Artificial sequence
<220> FEATURE:
<223> OTHER INFORMATION: Synthetic polypeptide

<400> SEQUENCE: 99

```
Met Arg Val Thr Ala Pro Arg Thr Leu Leu Leu Leu Leu Trp Gly Ala
1               5                   10                  15

Val Ala Leu Thr Glu Thr Trp Ala Gly Ser Tyr His Ser Pro Ser Tyr
            20                  25                  30

Ala Tyr His Gln Phe Glu Arg Gly Gly Gly Gly Ser Gly Gly Gly Gly
```

```
        35                  40                  45

Ser Leu Lys Ile Ser Gln Ala Val His Ala Ala His Ala Glu Ile Asn
    50                  55                  60

Glu Ala Gly Arg Glu Val Ile Val Gly Ile Val Ala Gly Leu Ala Val
65                  70                  75                  80

Leu Ala Val Val Val Ile Gly Ala Val Val Ala Ala Val Met Cys Arg
                85                  90                  95

Arg Lys Ser Ser Gly Gly Lys Gly Gly Ser Tyr Ser Gln Ala Ala Ser
            100                 105                 110

Ala Thr Val Pro Arg Ala Leu Met Cys Leu Ser Gln Leu Gly Gly Gly
        115                 120                 125

Gly Ser Asp Tyr Lys Asp Asp Asp Asp Lys
    130                 135
```

<210> SEQ ID NO 100
<211> LENGTH: 9690
<212> TYPE: RNA
<213> ORGANISM: Artificial sequence
<220> FEATURE:
<223> OTHER INFORMATION: Synthetic polynucleotide

<400> SEQUENCE: 100

```
augggcggcg caugagagaa gcccagacca auuaccuacc caaaauggag aaaguucacg     60
uugacaucga ggaagacagc ccauuccuca gagcuuugca gcggagcuuc ccgcaguuug    120
agguagaagc caagcagguc acugauaaug accaugcuaa ugccagagcg uuuucgcauc    180
uggcuucaaa acugaucgaa acggaggugg acccauccga cacgauccuu gacauuggaa    240
gugcgcccgc ccgcagaaug uauucuaagc acaaguauca uuguaucugu ccgaugagau    300
gugcggaaga uccggacaga uuguauaagu augcaacuaa gcugaagaaa aacuguaagg    360
aaauaacuga uaaggaauug gacaagaaaa ugaaggagcu ggccgccguc augagcgacc    420
cugaccugga aacugagacu augugccucc acgacgacga gucgugucgc uacgaagggc    480
aagucgcugu uuaccaggau guauacgccg ucgacggccc caccagccug uaccaccagg    540
ccaacaaggg cgugagggug gccuacugga ucggcuucga caccacaccc uucauguuca    600
agaaccuggc cggcgccuac cccagcuaca gcaccaacug ggccgacgag accgugcuga    660
ccgccaggaa caucggccug ugcagcagcg acgugaugga gaggagccgg agaggcauga    720
gcauccugag gaagaaauac cugaagccca gcaacaacgu gcuguucagc gugggcagca    780
ccaucuacca cgagaagagg gaccugcuca ggagcuggca ccugcccagc guguuccacc    840
ugaggggcaa gcagaacuac accugcaggu gcgagaccau cgugagcugc gacggcuacg    900
uggugaagag gaucgccauc agccccggcc uguacggcaa gcccagcggc uacgccgcua    960
caaugcacag ggagggcuuc cugugcugca aggugaccga cacccugaac ggcgagaggg   1020
ugagcuuccc cgugugcacc uacgugcccg ccacccugug cgaccagaug accggcaucc   1080
uggccaccga cgugagcgcc gacgacgccc agaagcugcu cgugggccug aaccagagga   1140
ucgugcucaa cggcaggacc cagaggaaca ccaacacaau gaagaacuac cugcugcccg   1200
ugguggccca ggcuuucgcc aggugggcca aggaguacaa ggaggaccag gaagacgaga   1260
ggccccuggg ccugagggac aggcagcugg ugaugggcug cugcugggcc uucaggcggc   1320
acaagaucac cagcaucuac aagaggcccg acacccagac caucaucaag gugaacagcg   1380
acuuccacag cuucgugcug cccaggaucg gcagcaacac ccuggagauc ggccugagga   1440
cccggaucag gaagaugcug gaggaacaca aggagcccag cccacugauc accgccgagg   1500
```

```
acgugcagga ggccaagugc gcugccgacg aggccaagga ggugagggag gccgaggaac   1560
ugagggccgc ccugccaccc cuggcugccg acguggagga acccacccug gaagccgacg   1620
uggaccugau gcugcaggag gccggcgccg gaagcgugga gacacccagg ggccugauca   1680
aggugaccag cuacgacggc gaggacaaga ucggcagcua cgccgugcug agcccacagg   1740
ccgugcugaa guccgagaag cugagcugca uccacccacu ggccgagcag gugaucguga   1800
ucacccacag cggcaggaag ggcagguacg ccguggagcc cuaccacggc aagguggucg   1860
ugcccgaggg ccacgccauc cccgugcagg acuuccaggc ccugagcgag agcgccacca   1920
ucguguacaa cgagagggag uucgugaaca gguaccugca ccauaucgcc acccacggcg   1980
gagcccugaa caccgacgag gaauacuaca agaccgugaa gcccagcgag cacgacggcg   2040
aguaccugua cgacaucgac aggaagcagu gcgugaagaa agagcuggug accggccugg   2100
gacugaccgg cgagcuggug gacccacccu uccacgaguu cgccuacgag agccugagga   2160
ccagacccgc cgcucccuac caggugccca ccaucggcgu guacggcgug cccggcagcg   2220
gaaagagcgg caucaucaag agcgccguga ccaagaaaga ccugguggu agcgccaaga   2280
aagagaacug cgccgagauc aucagggacg ugaagaagau gaaaggccug gacgugaacg   2340
cgcgcaccgu ggacagcgug cugcugaacg gcugcaagca ccccguggag acccuguaca   2400
ucgacgaggc cuucgcuugc cacgccggca cccugagggc ccugaucgcc aucaucaggc   2460
ccaagaaagc cgugcugugc ggcgacccca agcagugcgg cuucuucaac augaugugcc   2520
ugaaggugca cuucaaccac gagaucugca cccagguguu ccacaagagc aucagcaggc   2580
ggugcaccaa gagcgugacc agcgucguga gcacccuguu cuacgacaag aaaaugagga   2640
ccaccaaccc caaggagacc aaaaucguga ucgacaccac aggcagcacc aagcccaagc   2700
aggacgaccu gauccugacc ugcuucaggg gcugggugaa gcagcugcag aucgacuaca   2760
agggcaacga gaucaugacc gccgcugcca gccagggccu gaccaggaag ggcguguacg   2820
ccgugaggua caaggugaac gagaacccac uguacgcucc caccagcgag cacgugaacg   2880
ugcugcugac caggaccgag gacaggaucg uguggaagac ccuggccggc gaccccugga   2940
ucaagacccu gaccgccaag uaccccggca acuucaccgc caccaucgaa gaguggcagg   3000
ccgagcacga cgccaucaug aggcacaucc uggagaggcc cgaccccacc gacguguucc   3060
agaacaaggc caacgugugc ugggccaagg cccuggugcc cgugcugaag accgccggca   3120
ucgacaugac cacagagcag uggaacaccg uggacuacuu cgagaccgac aaggcccaca   3180
gcgccgagau cgugcugaac cagcugugcg ugagguucuu cggccuggac cuggacagcg   3240
gccuguucag cgcccccacc gugccacuga gcaucaggaa caaccacugg gacaacagcc   3300
ccagcccaaa cauguacggc cugaacaagg aggugucag gcagcugagc aggcgguacc   3360
cacagcugcc cagggccgug gccaccggca gggugacga caugaacacc ggcacccuga   3420
ggaacuacga ccccaggauc aaccuggugc ccgugaacag gcggcugccc cacgcccugg   3480
ugcugcacca caacgagcac cccacagagcg acuucagcuc cuucgugagc aagcugaaag   3540
gcaggaccgu gcuggucgug ggcgagaagc ugagcgugcc cggcaagaug guggacuggc   3600
ugagcgacag gcccgaggcc accuuccggg ccaggcugga ccucggcauc cccggcgacg   3660
ugcccaagua cgacaucauc uucgugaacg ucaggacccc auacaaguac caccauuacc   3720
agcagugcga ggaccacgcc aucaagcuga gcaugcugac caagaaggcc ugccugcacc   3780
ugaaccccgg aggcaccugc gugagcaucg gcuacggcua cgccgacagg gccagcgaga   3840
```

-continued gcaucauugg cgccaucgcc aggcuguuca aguucagcag ggugugcaaa cccaagagca 3900
gccuggagga aaccgaggug cuguucgugu ucaucggcua cgaccggaag gccaggaccc 3960
acaaccccua caagcugagc agcacccuga caaacaucua caccggcagc aggcugcacg 4020
aggccggcug cgcccccagc uaccacgugg ucaggggcga uaucgccacc gccaccgagg 4080
gcgugaucau caacgcugcc aacagcaagg gccagcccgg aggcggagug ugcggcgccc 4140
uguacaagaa guuccccgag agcuucgacc ugcagcccau cgaggugggc aaggccaggc 4200
uggugaaggg cgccgcuaag cacaucaucc acgccguggg ccccaacuuc aacaagguga 4260
gcgaggugga aggcgacaag cagcuggccg aagccuacga gagcaucgcc aagaucguga 4320
acgacaauaa cuacaagagc guggccaucc cacugcucag caccggcauc uucagcggca 4380
acaaggacag gcugacccag agccugaacc accugcucac cgcccuggac accaccgaug 4440
ccgacguggc caucuacugc agggacaaga agugggagau gacccugaag gaggccgugg 4500
ccaggcggga ggccguggaa gagaucugca ucagcgacga cuccagcgug accgagcccg 4560
acgccgagcu ggugagggug caccccaaga gcucccuggc cggcaggaag ggcuacagca 4620
ccagcgacgg caagaccuuc agcuaccugg agggcaccaa guuccaccag gccgcuaagg 4680
acaucgccga gaucaacgcu auguggcccg uggccaccga ggccaacgag caggugugca 4740
uguacauccu gggcgagagc auguccagca ucaggagcaa gugccccgug gaggaaagcg 4800
aggccagcac accacccagc acccugcccu gccugugcau ccacgcuaug acacccgaga 4860
gggugcagcg gcugaaggcc agcaggcccg agcagaucac cgugugcagc uccuucccac 4920
ugcccaagua caggaucacc ggcgugcaga agauccagug cagccagccc auccuguuca 4980
gcccaaaggu gcccgccuac auccacccca ggaaguaccu gguggagacc ccacccgugg 5040
acgagacacc cgagccaagc gccgagaacc agagcaccga gggcacaccc gagcagccac 5100
cccugaucac cgaggacgag acaaggaccc ggaccccaga gcccaucauu aucgaggaag 5160
aggaagagga cagcaucagc cugcugagcg acggccccac ccaccaggug cugcaggugg 5220
aggccgacau ccacggccca cccagcgugu ccagcuccag cuggagcauc ccacacgcca 5280
gcgacuucga cguggacagc cugagcaucc uggacacccu ggagggcgcc agcgugaccu 5340
ccggcgccac cagcgccgag accaacagcu acuucgccaa gagcauggag uuccuggcca 5400
ggcccgugcc agcucccagg accguguuca ggaacccacc ccacccagcu cccaggacca 5460
ggaccccaag ccuggcuccc agcagggccu gcagcaggac cagccuggug agcacccccac 5520 ccggcgugaa cagggugauc accagggagg aacuggaggc ccugacaccc agcaggaccc 5580
ccagcagguc cgugagcagg acuagucugg uguccaaccc acccggcgug aacaggguga 5640
ucaccaggga ggaauucgag gccuucgugg cccagcaaca gagacgguuc gacgccggcg 5700
ccuacaucuu cagcagcgac accggccagg gacaccugca gcaaaagagc gugaggcaga 5760
ccgugcugag cgagguggug cuggagagga ccgagcugga aaucagcuac gcccccaggc 5820
uggaccagga gaaggaggaa cugcucagga agaaacugca gcugaacccc accccagcca 5880
acaggagcag guaccagagc aggaaggugg agaacaugaa ggccaucacc gccaggcgga 5940
uccugcaggg ccugggacac uaccugaagg ccgagggcaa gguggagugc uacaggaccc 6000
ugcaccccgu gccacuguac agcuccagcg ugaacagggc cuucuccagc cccaaggugg 6060
ccguggaggc cugcaacgcu augcugaagg agaacuuccc caccguggcc agcuacugca 6120
ucauccccga guacgacgcc uaccuggaca ugguggacgg cgccagcugc ugccuggaca 6180
ccgccagcuu cugccccgcc aagcugagga gcuuccccaa gaaacacagc uaccuggagc 6240

```
ccaccaucag gagcgccgug cccagcgcca uccagaacac ccugcagaac gugcuggccg   6300
cugccaccaa gaggaacugc aacgugaccc agaugaggga gcugcccgug cuggacagcg   6360
cugccuucaa cguggagugc uucaagaaau acgccugcaa caacgaguac ugggagaccu   6420
ucaaggagaa ccccaucagg cugaccgaag agaacguggu gaacuacauc accaagcuga   6480
agggccccaa ggccgcugcc cuguucgcua agacccacaa ccugaacaug cugcaggaca   6540
ucccaaugga cagguucgug auggaccuga agagggacgu gaaggugaca cccggcacca   6600
agcacaccga ggagaggccc aaggugcagg ugauccaggc cgcugaccca cuggccaccg   6660
ccuaccugug cggcauccac agggagcugg ugaggcggcu gaacgccgug cugcugccca   6720
acauccacac ccuguucgac augagcgccg aggacuucga cgccaucauc gccgagcacu   6780
uccagcccgg cgacugcgug cuggagaccg acaucgccag cuucgacaag agcgaggaug   6840
acgcuauggc ccugaccgcu cugaugaucc uggaggaccu gggcguggac gccgagcugc   6900
ucacccugau cgaggcugcc uucggcgaga ucagcuccau ccaccugccc accaagacca   6960
aguucaaguu cggcgcuaug augaaaagcg gaauguuccu gacccuguuc gugaacaccg   7020
ugaucaacau ugugaucgcc agcagggugc ugcgggagag gcugaccggc agccccugcg   7080
cugccuucau cggcgacgac aacaucguga agggcgugaa aagcgacaag cugauggccg   7140
acaggugcgc caccuggcug aacauggagg ugaagaucau cgacgccgug gugggcgaga   7200
aggcccccua cuucugcggc ggauucaucc ugugcgacag cgugaccggc accgccugca   7260
gggugccga  cccccugaag aggcuguuca agcugggcaa gccacuggcc gcugacgaug   7320
agcacgacga ugacaggcgg agggcccugc acgaggaaag caccaggugg aacagggugg   7380
gcauccugag cgagcugugc aaggccgugg agagcaggua cgagaccgug ggcaccagca   7440
ucaucgugau ggcuaugacc acacuggcca gcuccgucaa gagcuucucc uaccugaggg   7500
gggccccuau aacucucuac ggcuaaccug aauggacuac gacauagucu aguccgccaa   7560
ggccgccacc auggaagaug ccaaaaacau uaagaagggc ccagcgccau ucuacccacu   7620
cgaagacggg accgccggcg agcagcugca caaagccaug aagcgcuacg cccuggugcc   7680
cggcaccauc gccuuuaccg acgcacauau cgagguggac auuaccuacg ccgaguacuu   7740
cgagaugagc guucggcugg cagaagcuau gaagcgcuau gggcugaaua caaaccaucg   7800
gaucguggug ugcagcgaga auagcuugca guucuucaug cccguguugg gugcccuguu   7860
caucggugug gcuguggccc cagcuaacga caucuacaac gagcgcgagc ugcugaacag   7920
caugggcauc agccagccca ccgucguauu cgugagcaag aaagggcugc aaaagauccu   7980
caacgugcaa aagaagcuac cgaucauaca aaagaucauc aucauggaua gcaagaccga   8040
cuaccagggc uuccaaagca uguacaccuu cgugacuucc cauuugccac ccggcuucaa   8100
cgaguacgac uucgugcccg agagcuucga ccgggacaaa accaucgccc ugaucaugaa   8160
caguaguggc aguaccggau ugcccaaggg cguagcccua ccgcaccgca ccgcuugugu   8220
ccgauucagu caugcccgcg accccaucuu cggcaaccag aucaucccg  acaccgcuau   8280
ccucagcgug gugccauuuc accacggcuu cggcauguuc accacgcugg gcuacuugau   8340
cugcggcuuu cgggucgugc ucauguaccg cuucgaggag gagcuauucu ugcgcagcuu   8400
gcaagacuau aagauucaau cugcccugcu ggugcccaca cuauuuagcu ucuucgcuaa   8460
gagcacucuc aucgacaagu acgaccuaag caacuugcac gagaucgcca gcggcggggc   8520
gccgcucagc aaggagguag gugaggccgu ggccaaacgc uuccaccuac caggcauccg   8580
```

```
acagggcuac ggccugacag aaacaaccag cgccauucug aucacccccg aaggggacga   8640

caagccuggc gcaguaggca agguggugcc cuucuucgag gcuaaggugg uggacuugga   8700

caccgguaag acacugggug ugaaccagcg cggcgagcug ugcguccgug gccccaugau   8760

caugagcggc uacguuaaca accccgaggc uacaaacgcu cucaucgaca aggacggcug   8820

gcugcacagc ggcgacaucg ccuacuggga cgaggacgag cacuucuuca ucguggaccg   8880

gcugaagucc cugaucaaau acaagggcua ccagguagcc ccagccgaac uggagagcau   8940

ccugcugcaa caccccaaca ucuucgacgc cggggucgcc ggccugcccg acgacgaugc   9000

cggcgagcug cccgccgcag ucgucgugcu ggaacacggu aaaaccauga ccgagaagga   9060

gaucguggac uauguggcca gccagguuac aaccgccaag aagcugcgcg guggguguugu   9120

guucguggac gaggugccua aaggacugac cggcaaguug gacgcccgca agauccgcga   9180

gauucucauu aaggccaaga agggcggcaa gaucgccgug uaacucgagu auguuacgug   9240

caaaggugau ugucaccccc cgaaagacca uauugugaca cacccucagu aucacgccca   9300

aacauuuaca gccgcggugu caaaaaccgc guggacgugg uuaacauccc ugcugggagg   9360

aucagccgua auuauuauaa uuggcuuggu gcuggcuacu auuguggcca uguacgugcu   9420

gaccaaccag aaacauaauu gaauacagca gcaauuggca agcugcuuac auagaacucg   9480

cggcgauugg caugccgccu uaaaauuuuu auuuuauuuu uucuuuucuu uuccgaaucg   9540

gauuuuguuu uuaauauuuc aaaaaaaaaa aaaaaaaaaa aaaaaucuag aaaaaaaaaa   9600

aaaaaaaaaa aaaaaaaaaa aaaaaaaaaa aaaaaaaaaa aaaaaaaaaa aaaaaaaaaa   9660

aaaaaaaaaa aaaaaaaaaa aaaaaaaaaa                                    9690


<210> SEQ ID NO 101
<211> LENGTH: 9773
<212> TYPE: RNA
<213> ORGANISM: Artificial sequence
<220> FEATURE:
<223> OTHER INFORMATION: Synthetic polynucleotide

<400> SEQUENCE: 101

auugacggcg uaguacacac uauugaauca aacagccgac caauugcacu accaucacaa     60

uggagaagcc aguaguaaac guagacguag acccccagag uccguuuguc gugcaacugc    120

aaaaaagcuu cccgcaauuu gagguaguag cacagcaggu cacuccaaau gaccaugcua    180

augccagagc auuuucgcau cuggccagua aacuaaucga gcuggagguu ccuaccacag    240

cgacgaucuu ggacauaggc agcgcaccgg cucguagaau guuuuccgag caccaguauc    300

auugugucug ccccaugcgu aguccagaag acccggaccg caugaugaaa uaugccagua    360

aacuggcgga aaaagcgugc aagauuacaa acaagaacuu gcaugagaag auuaaggauc    420

uccggaccgu acuugauacg ccggaugcug aaacaccauc gcucugcuuu cacaacgaug    480

uuaccugcaa caugcgugcc gaauauuccg ucaugcagga cguguauauc aacgcucccg    540

gaacuaucua ucaucaggcu augaaaggcg ugcggacccu guacuggauu ggcuucgaca    600

ccacccaguu cauguucucg gcuauggcag guucguaccc ugcguacaac accaacuggg    660

ccgacgagaa aguccuugaa gcgcguaaca ucggacuuug cagcacaaag cugagugaag    720

guaggacagg aaaauugucg auaaugagga agaaggaguu gaagcccggg ucgcggguuu    780

auuucuccgu aggaucgaca cuuuauccag aacacagagc cagcuugcag agcuggcauc    840

uuccaucggu guuccacuug aauggaaagc agucguacac uugccgcugu gauacagugg    900

ugaguugcga aggcuacgua gugaagaaaa ucaccaucag ucccgggauc acgggagaaa    960
```

```
ccgugggaua cgcgguuaca cacaauagcg agggcuucuu gcuaugcaaa guuacugaca   1020
caguaaaagg agaacgggua ucguucccug ugugcacgua caucccggcc accauaugcg   1080
aucagaugac ugguauaaug gccacggaua uaucaccuga cgaugcacaa aaacuucugg   1140
uugggcucaa ccagcgaauu gucauuaacg guaggacuaa caggaacacc aacaccaugc   1200
aaaauuaccu ucugccgauc auagcacaag gguucagcaa augggcuaag gagcgcaagg   1260
augaucuuga uaacgagaaa augcugggua cuagagaacg caagcuuacg uauggcugcu   1320
ugugggcguu ucgcacuaag aaaguacauu cguuuuaucg cccaccugga acgcagaccu   1380
gcguaaaagu cccagccucu uuuagcgcuu uucccauguc guccguaugg acgaccucuu   1440
ugcccauguc gcugaggcag aaauugaaac uggcauugca accaaagaag gaggaaaaac   1500
ugcugcaggu cucggaggaa uuagucaugg aggccaaggc ugcuuuugag gaugcucagg   1560
aggaagccag agcggagaag cuccgagaag cacuuccacc auuaguggca gacaaaggca   1620
ucgaggcagc cgcagaaguu gucugcgaag uggaggggcu ccaggcggac aucggagcag   1680
cauuaguuga aaccccgcgc ggucacguaa ggauaauacc ucaagcaaau gaccguauga   1740
ucggacagua uaucguuguc ucgccaaacu cugugcugaa gaaugccaaa cucgcaccag   1800
cgcacccgcu agcagaucag guuaagauca uaacacacuc cggaagauca ggaagguacg   1860
cggucgaacc auacgacgcu aaaguacuga ugccagcagg aggugccgua ccauggccag   1920
aauuccuagc acugagugag agcgccacgu uaguguacaa cgaaagagag uuugugaacc   1980
gcaaacuaua ccacauugcc augcauggcc ccgccaagaa uacagaagag gagcaguaca   2040
agguuacaaa ggcagagcuu gcagaaacag aguacguguu ugacguggac aagaagcguu   2100
gcguuaagaa ggaagaagcc ucaggucugg uccucucggg agaacugacc aacccucccu   2160
aucaugagcu agcucuggag ggacugaaga cccgaccugc ggucccguac aaggucgaaa   2220
caauaggagu gauaggcaca ccggggucgg gcaagucagc uauuaucaag ucaacuguca   2280
cggcacgaga ucuuguuacc agcggaaaga aagaaaauug ucgcgaaauu gaggccgacg   2340
ugcuaagacu gaggggguaug cagauuacgu cgaagacagu agauucgguu augcucaacg   2400
gaugccacaa agccguagaa gugcuguacg uugacgaagc guucgcgugc cacgcaggag   2460
cacuacuugc cuugauugcu aucgucaggc cccgcaagaa gguaguacua ugcggagacc   2520
ccaugcaaug cggauucuuc aacaugaugc aacuaaaggu acauuucaau cacccugaaa   2580
aagacauaug caccaagaca uucuacaagu auaucucccg gcguugcaca cagccaguua   2640
cagcuauugu aucgacacug cauuacgaug gaaagaugaa aaccacgaac ccgugcaaga   2700
agaacauuga aaucgauauu acaggggcca caaagccgaa gccaggggau aucauccuga   2760
cauguuuccg cgggugggu aagcaauugc aaaucgacua ucccggacau gaaguaauga   2820
cagccgcggc cucacaaggg cuaaccagaa aaggagugua ugccguccgg caaaaaguca   2880
augaaaaccc acuguacgcg aucacaucag agcaugugaa cguguugcuc acccgcacug   2940
aggacaggcu aguguggaaa accuugcagg gcgacccaug gauuaagcag cucacuaaca   3000
uaccuaaagg aaacuuucag gcuacuauag aggacuggga agcugaacac aagggaauaa   3060
uugcugcaau aaacagcccc acucccgug ccaauccguu cagcugcaag accaacguuu   3120
gcugggcgaa agcauuggaa ccgauacuag ccacggccgg uaucguacuu accgguugcc   3180
aguggagcga acuguuccca caguuugcgg augacaaacc acauucggcc auuuacgccu   3240
uagacguaau uugcauuaag uuuuucggca uggacuugac aagcggacug uuuucuaaac   3300
```

agagcauccc acuaacguac caucccgccg auucagcgag gccgguagcu cauugggaca 3360
acagcccagg aacccgcaag uaugggguacg aucacgccau ugccgccgaa cucucccgua 3420
gauuuccggu guuccagcua gcugggaagg gcacacaacu ugauuugcag acggggagaa 3480
ccagaguuau cucugcacag cauaaccugg ucccggugaa ccgcaaucuu ccucacgccu 3540
uaguccccga guacaaggag aagcaacccg gcccggucga aaaauucuug aaccaguuca 3600
aacaccacuc aguacuugug guaucagagg aaaaaauuga agcuccccgu aagagaaucg 3660
aauggaucgc cccgauuggc auagccggug cagauaagaa cuacaaccug gcuuucgggu 3720
uuccgccgca ggcacgguac gaccuggugu ucaucaacau uggaacuaaa uacagaaacc 3780
accacuuuca gcagugcgaa gaccaugcgg cgaccuuaaa aacccuuucg cguucggccc 3840
ugaauugccu uaacccagga ggcacccucg uggugaaguc cuauggcuac gccgaccgca 3900
acagugagga cguagucacc gcucuugcca gaaaguuugu cagggugucu gcagcgagac 3960
cagauugugu cucaagcaau acagaaaugu accugauuuu ccgacaacua gacaacagcc 4020
guacacggca auucaccccg caccaucuga auugcgugau uucguccgug uaugagggua 4080
caagagaugg aguuggagcc gcgccgucau accgcaccaa aagggagaau auugcugacu 4140
gucaagagga agcaguuguc aacgcagcca auccgcuggg uagaccaggc gaaggagucu 4200
gccgugccau cuauaaacgu uggccgacca guuuuaccga uucagccacg gagacaggca 4260
ccgcaagaau gacugugugc cuaggaaaga aagugaucca cgcggucggc ccugauuucc 4320
ggaagcaccc agaagcagaa gccuugaaau ugcuacaaaa cgccuaccau gcaguggcag 4380
acuuaguaaa ugaacauaac aucaagucug ucgccauucc acugcuaucu acaggcauuu 4440
acgcagccgg aaaagaccgc cuugaaguau cacuuaacug cuugacaacc gcgcuagaca 4500
gaacugacgc ggacguaacc aucuauugcc uggauaagaa guggaaggaa agaaucgacg 4560
cggcacucca acuuaaggag ucuguaacag agcugaagga ugaagauaug gagaucgacg 4620
augaguuagu auggauccau ccagacaguu gcuugaaggg aagaaaggga uucaguacua 4680
caaaaggaaa auuguauucg uacuucgaag gcaccaaauu ccaucaagca gcaaaagaca 4740
uggcggagau aaagguccug uucccuaaug accaggaaag uaaugaacaa cugugugccu 4800
acauauuggg ugagaccaug gaagcaaucc gcgaaaagug cccggucgac cauaacccgu 4860
cgucuagccc gcccaaaacg uugccgugcc uuugcaugua ugccaugacg ccagaaaggg 4920
uccacagacu uagaagcaau aacgucaaag aaguuacagu augcuccucc accccccuuc 4980
cuaagcacaa aauuaagaau guucagaagg uucagugcac gaaaguaguc cuguuuaauc 5040
cgcacacucc cgcauucguu cccgcccgua aguacauaga agugccagaa cagccuaccg 5100
cuccuccugc acaggccgag gaggcccccg aaguuguagc gacaccguca ccaucuacag 5160
cugauaacac cucgcuugau gucacagaca ucucacugga uauggaugac aguagcgaag 5220
gcucacuuuu uucgagcuuu agcggaucgg acaacucuau uacuaguaug gacaguuggu 5280
cgucaggacc uaguucacua gagauaguag accgaaggca gguggugug gcugacguuc 5340
augccgucca agagccugcc ccuauuccac cgccaaggcu aaagaagaug gcccgccugg 5400
cagcggcaag aaaagagccc acuccaccgg caagcaauag cucugagucc cuccaccucu 5460
cuuuuggugg gguauccaug ucccucggau caauuuucga cggagagacg gcccgccagg 5520
cagcgguaca accccuggca acaggcccca cggaugugcc uaugucuuuc ggaucguuuu 5580
ccgacggaga gauugaugag cugagccgca gaguaacuga guccgaaccc guccuguuug 5640
gaucauuuga accgggcgaa gugaacucaa uuauaucguc ccgaucagcc guaucuuuuc 5700
cucuacgcaa gcagagacgu agacgcagga gcaggaggac ugaauacuga cuaaccgggg 5760
uaggugggua cauauuuucg acggacacag gcccugggca cuugcaaaag aaguccguuc 5820
ugcagaacca gcuuacagaa ccgaccuugg agcgcaaugu ccuggaaaga auucaugccc 5880
cggugcucga cacgucgaaa gaggaacaac ucaaacucag guaccagaug augcccaccg 5940
aagccaacaa aaguagguac cagucucgua aaguagaaaa ucagaaagcc auaaccacug 6000
agcgacuacu gucaggacua cgacuguaua acucugccac agaucagcca gaaugcuaua 6060
agaucaccua uccgaaacca uuguacucca guagcguacc ggcgaacuac uccgauccac 6120
aguucgcugu agcugucugu aacaacuauc ugcaugagaa cuauccgaca guagcaucuu 6180
aucagauuac ugacgaguac gaugcuuacu uggauauggu agacgggaca gucgccugcc 6240
uggacacugc aaccuucugc cccgcuaagc uuagaaguua cccgaaaaaa caugaguaua 6300
gagccccgaa uauccgcagu gcgguuccau cagcgaugca gaacacgcua caaaaugugc 6360
ucauugccgc aacuaaaaga aauugcaacg ucacgcagau gcgugaacug ccaacacugg 6420
acucagcgac auucaauguc gaaugcuuuc gaaaauaugc auguaaugac gaguauuggg 6480
aggaguucgc ucggaagcca auuaggauua ccacugaguu ugucaccgca uauguagcua 6540
gacugaaagg cccuaaggcc gccgcacuau uugcaaagac guauaauuug gucccauugc 6600
aagaagugcc uauggauaga uucgucaugg acaugaaaag agacgugaaa guuacaccag 6660
gcacgaaaca cacagaagaa agaccgaaag uacaagugau acaagccgca gaaccccugg 6720
cgacugcuua cuuaugcggg auucaccggg aauuagugcg uaggcuuacg gccgucuugc 6780
uuccaaacau ucacacgcuu uuugacaugu cggcggagga uuuugaugca aucauagcag 6840
aacacuucaa gcaaggcgac ccgguacugg agacggauau cgcaucauuc gacaaaagcc 6900
aagacgacgc uauggcguua accggucuga ugaucuugga ggaccugggu guggaucaac 6960
cacuacucga cuugaucgag ugcgccuuug gagaaauauc auccacccau cuaccuacgg 7020
guacucguuu uaaauucggg gcgaugauga aauccggaau guuccucaca cuuuuuguca 7080
acacaguuuu gaaugucguu aucgccagca gaguacuaga ggagcggcuu aaaacgucca 7140
gaugugcagc guucauuggc gacgacaaca ucauacaugg aguaguaucu gacaaagaaa 7200
uggcugagag gugcgccacc uggcucaaca uggagguuaa gaucaucgac gcagucaucg 7260
gugagagacc accuuacuuc ugcggcggau uuaucuugca agauucgguu acuuccacag 7320
cgugccgcgu ggcggauccc cugaaaaggc uguuuaaguu ggguaaaccg cucccagccg 7380
acgacgagca agacgaagac agaagacgcg cucugcuaga ugaaacaaag gcgugguuua 7440
gaguagguau aacaggcacu uuagcagugg ccgugacgac ccgguaugag guagacaaua 7500
uuacaccugu ccuacuggca uugagaacuu uugcccagag caaaagagca uuccaagcca 7560
ucagagggga aauaaagcau cucuacggug guccuaaaua gucagcauag uacauuucau 7620
cugacuaaua cuacaacacc accaccaugg aagaugccaa aaacauuaag aagggcccag 7680
cgccauucua cccacucgaa gacgggaccg ccggcgagca gcugcacaaa gccaugaagc 7740
gcuacgcccu ggugcccggc accaucgccu uuaccgacgc acauaucgag guggacauua 7800
ccuacgccga guacuucgag augagcguuc ggcuggcaga agcuaugaag cgcuaugggc 7860
ugaauacaaa ccaucggauc guggugugca gcgagaauag cuugcaguuc uucaugcccg 7920
uguugggugc ccuguucauc ggugnggcug uggccccagc uaacgacauc uacaacgagc 7980
gcgagcugcu gaacagcaug ggcaucagcc agcccaccgu cguauucgug agcaagaaag 8040
ggcugcaaaa gauccucaac gugcaaaaga agcuaccgau cauacaaaag aucaucauca 8100
uggauagcaa gaccgacuac cagggcuucc aaagcaugua caccuucgug acuucccauu 8160
ugccacccgg cuucaacgag uacgacuucg ugcccgagag cuucgaccgg gacaaaacca 8220
ucgcccugau caugaacagu aguggcagua ccggauugcc caagggcgua gcccuaccgc 8280
accgcaccgc uuguguccga uucagucaug cccgcgaccc caucuucggc aaccagauca 8340
uccccgacac cgcuauccuc agcguggugc cauuucacca cggcuucggc auguucacca 8400
cgcugggcua cuugaucugc ggcuuucggg ucgugcucau guaccgcuuc gaggaggagc 8460
uauucuugcg cagcuugcaa gacuauaaga uucaaucugc ccugcuggug cccacacuau 8520
uuagcuucuu cgcuaagagc acucucaucg acaaguacga ccuaagcaac uugcacgaga 8580
ucgccagcgg cggggcgccg cucagcaagg agguagguga ggccguggcc aaacgcuucc 8640
accuaccagg cauccgacag ggcuacggcc ugacagaaac aaccagcgcc auucugauca 8700
cccccgaagg ggacgacaag ccuggcgcag uaggcaaggu ggugcccuuc uucgaggcua 8760
agguggugga cuuggacacc gguaagacac ugggugugaa ccagcgcggc gagcugugcg 8820
uccguggccc caugaucaug agcggcuacg uuaacaaccc cgaggcuaca aacgcucuca 8880
ucgacaagga cggcuggcug cacagcggcg acaucgccua cugggacgag gacgagcacu 8940
ucuucaucgu ggaccggcug aagucccuga ucaaauacaa gggcuaccag guagccccag 9000
ccgaacugga gagcauccug cugcaacacc ccaacaucuu cgacgccggg gucgccggcc 9060
ugcccgacga cgaugccggc gagcugcccg ccgcagucgu cgugcuggaa cacgguaaaa 9120
ccaugaccga gaaggagauc guggacuaug uggccagcca gguuacaacc gccaagaagc 9180
ugcgcggugg uguuguguuc guggacgagg ugccuaaagg acugaccggc aaguuggacg 9240
cccgcaagau ccgcgagauu cucauuaagg ccaagaaggg cggcaagauc gccguguaaa 9300
cgcgugcuag accauggauc cuagacgcua cgccccaaug auccgaccag caaaacucga 9360
uguacuuccg aggaacugau gugcauaaug caucaggcug guacauuaga uccccgcuua 9420
ccgcgggcaa uauagcaaca cuaaaaacuc gauguacuuc cgaggaagcg cagugcauaa 9480
ugcugcgcag uguugccaca uaaccacuau auuaaccauu uaucuagcgg acgccaaaaa 9540
cucaauguau uucugaggaa gcguggugca uaaugccacg cagcgucugc auaacuuuua 9600
uuauuucuuu uauuaaucaa caaaauuuug uuuuuaacau uucaaaaaaa aaaaaaaaaa 9660
aaaaaaaauc uagaaaaaaa aaaaaaaaaa aaaaaaaaaa aaaaaaaaaa aaaaaaaaaa 9720
aaaaaaaaaa aaaaaaaaaa aaaaaaaaaa aaaaaaaaaa aaaaaaaaaa aaa 9773

<210> SEQ ID NO 102
<211> LENGTH: 2086
<212> TYPE: RNA
<213> ORGANISM: Artificial sequence
<220> FEATURE:
<223> OTHER INFORMATION: Synthetic polynucleotide

<400> SEQUENCE: 102
aggaaacuua agucaacaca acauauacaa aacaaacgaa ucucaagcaa ucaagcauuc 60
uacuucuauu gcagcaauuu aaaucauuuc uuuuaaagca aaagcaauuu ucugaaaauu 120
uucaccauuu acgaacgaua gccauggaag augccaaaaa cauuaagaag ggcccagcgc 180
cauucuaccc acucgaagac gggaccgccg gcgagcagcu gcacaaagcc augaagcgcu 240
acgcccuggu gcccggcacc aucgccuuua ccgacgcaca uaucgaggug gacauuaccu 300
acgccgagua cuucgagaug agcguucggc uggcagaagc uaugaagcgc uaugggcuga 360

-continued auacaaacca ucggaucgug gugugcagcg agaauagcuu gcaguucuuc augcccgugu 420
ugggugcccu guucaucggu guggcugugg ccccagcuaa cgacaucuac aacgagcgcg 480
agcugcugaa cagcaugggc aucagccagc ccaccgucgu auucgugagc aagaaagggc 540
ugcaaaagau ccucaacgug caaaagaagc uaccgaucau acaaaagauc aucaucaugg 600
auagcaagac cgacuaccag ggcuuccaaa gcauguacac cuucgugacu ucccauuugc 660
cacccggcuu caacgaguac gacuucgugc ccgagagcuu cgaccgggac aaaaccaucg 720
cccugaucau gaacaguagu ggcaguaccg gauugcccaa gggcguagcc cuaccgcacc 780
gcaccgcuug uguccgauuc agucaugccc gcgaccccau cuucggcaac cagaucaucc 840
ccgacaccgc uauccucagc gugguggcau uucaccacgg cuucggcaug uucaccacgc 900
ugggcuacuu gaucugcggc uuucgggucg ugcucaugua ccgcuucgag gaggagcuau 960
ucuugcgcag cuugcaagac uauaagauuc aaucugcccu gcugguggccc acacuauuua 1020 gcuucuucgc uaagagcacu cucaucgaca aguacgaccu aagcaacuug cacgagaucg 1080
ccagcggcgg ggcgccgcuc agcaaggagg uaggugaggc cguggccaaa cgcuuccacc 1140
uaccaggcau ccgacagggc uacggccuga cagaaacaac cagcgccauu cugaucaccc 1200
ccgaagggga cgacaagccu ggcgcaguag gcaagguggu gcccuucuuc gaggcuaagg 1260
ugguggacuu ggacaccggu aagacacugg gugugaacca gcgcggcgag cugugcgucc 1320
guggccccau gaucaugagc ggcuacguua acaaccccga ggcuacaaac gcucucaucg 1380
acaaggacgg cuggcugcac agcggcgaca ucgccuacug ggacgaggac gagcacuucu 1440
ucaucgugga ccggcugaag ucccugauca aauacaaggg cuaccaggua gccccagccg 1500
aacuggagag cauccugcug caacacccca acaucuucga cgccggggguc gccggccugc 1560 ccgacgacga ugccggcgag cugcccgccg cagucgucgu gcuggaacac gguaaaacca 1620
ugaccgagaa ggagaucgug gacuaugugg ccagccaggu uacaaccgcc aagaagcugc 1680
gcgguggugu uguguucgug gacgaggugc cuaaaggacu gaccggcaag uuggacgccc 1740
gcaagauccg cgagauucuc auuaaggcca agaagggcgg caagaucgcc guguaacucg 1800
agcuagugac ugacuaggau cugguuacca cuaaaccagc cucaagaaca cccgaaugga 1860
gucucuaagc uacauaauac caacuuacac uuacaaaaug uuguccccca aaauguagcc 1920
auucguaucu gcuccuaaua aaaagaaagu uucuucacau ucuagaaaaa aaaaaaaaaa 1980
aaaaaaaaaa aaaaaaaaaa aaaaaaaaaa aaaaaaaaaa aaaaaaaaaa aaaaaaaaaa 2040
aaaaaaaaaa aaaaaaaaaa aaaaaaaaaa aaaaaaaaaa aaaaaa 2086

<210> SEQ ID NO 103
<211> LENGTH: 8095
<212> TYPE: RNA
<213> ORGANISM: Artificial sequence
<220> FEATURE:
<223> OTHER INFORMATION: Synthetic polynucleotide

<400> SEQUENCE: 103
augggcggcg caugagagaa gcccagacca auuaccuacc caaaauggag aaaguucacg 60
uugacaucga ggaagacagc ccauuccuca gagcuuugca gcggagcuuc ccgcaguuug 120
agguagaagc caagcagguc acugauaaug accaugcuaa ugccagagcg uuuucgcauc 180
uggcuucaaa acugaucgaa acggaggugg acccauccga cacgauccuu gacauuggaa 240
gugcgcccgc ccgcagaaug uauucuaagc acaaguauca uuguaucugu ccgaugagau 300

-continued

```
gugcggaaga uccggacaga uuguauaagu augcaacuaa gcugaagaaa aacuguaagg    360
aaauaacuga uaaggaauug gacaagaaaa ugaaggagcu ggccgccguc augagcgacc    420
cugaccugga aacugagacu augugccucc acgacgacga gucgugucgc uacgaagggc    480
aagucgcugu uuaccaggau guauacgccg ucgacggccc caccagccug uaccaccagg    540
ccaacaaggg cgugagggug gccuacugga ucggcuucga caccacaccc uucauguuca    600
agaaccuggc cggcgccuac cccagcuaca gcaccaacug ggccgacgag accgugcuga    660
ccgccaggaa caucggccug ugcagcagcg acgugaugga gaggagccgg agaggcauga    720
gcauccugag gaagaaauac cugaagccca gcaacaacgu gcuguucagc gugggcagca    780
ccaucuacca cgagaagagg gaccugcuca ggagcuggca ccugcccagc guguuccacc    840
ugaggggcaa gcagaacuac accugcaggu gcgagaccau cgugagcugc gacggcuacg    900
uggugaagag gaucgccauc agccccggcc uguacggcaa gcccagcggc uacgccgcua    960
caaugcacag ggagggcuuc cugugcugca aggugaccga cacccugaac ggcgagaggg   1020
ugagcuuccc cgugugcacc uacgugcccg ccacccugug cgaccagaug accggcaucc   1080
uggccaccga cgugagcgcc gacgacgccc agaagcugcu cgugggccug aaccagagga   1140
ucguggucaa cggcaggacc cagaggaaca ccaacacaau gaagaacuac cugcugcccg   1200
ugguggccca ggcuuucgcc aggugggcca aggaguacaa ggaggaccag gaagacgaga   1260
ggccccuggg ccugagggac aggcagcugg ugaugggcug cugcugggcc uucaggcggc   1320
acaagaucac cagcaucuac aagaggcccg acacccagac caucaucaag gugaacagcg   1380
acuuccacag cuucgugcug cccaggaucg gcagcaacac ccuggagauc ggccugagga   1440
cccggaucag gaagaugcug gaggaacaca aggagcccag cccacugauc accgccgagg   1500
acgugcagga ggccaagugc gcugccgacg aggccaagga ggugagggag gccgaggaac   1560
ugagggccgc ccugccaccc cuggcugccg acguggagga acccacccug gaagccgacg   1620
uggaccugau gcugcaggag gccggcgccg gaagcgugga gacacccagg ggccugauca   1680
aggugaccag cuacgacggc gaggacaaga ucggcagcua cgccgugcug agcccacagg   1740
ccgugcugaa guccgagaag cugagcugca uccacccacu ggccgagcag gugaucguga   1800
ucacccacag cggcaggaag ggcagguacg ccguggagcc cuaccacggc aagguggucg   1860
ugcccgaggg ccacgccauc cccgugcagg acuuccaggc ccugagcgag agcgccacca   1920
ucguguacaa cgagagggag uucgugaaca gguaccugca ccauaucgcc acccacggcg   1980
gagcccugaa caccgacgag gaauacuaca agaccgugaa gcccagcgag cacgacggcg   2040
aguaccugua cgacaucgac aggaagcagu gcgugaagaa agagcuggug accggccugg   2100
gacugaccgg cgagcuggug gacccacccu uccacgaguu cgccuacgag agccugagga   2160
ccagacccgc cgcucccuac caggugccca ccaucggcgu guacggcgug cccggcagcg   2220
gaaagagcgg caucaucaag agcgccguga ccaagaaaga ccugguggu  agcgccaaga   2280
aagagaacug cgccgagauc aucagggacg ugaagaagau gaaaggccug gacgugaacg   2340
cgcgcaccgu ggacagcgug cugcugaacg gcugcaagca ccccguggag acccuguaca   2400
ucgacgaggc cuucgcuugc cacgccggca cccugagggc ccugaucgcc aucaucaggc   2460
ccaagaaagc cgugcugugc ggcgacccca agcagugcgg cuucuucaac augaugugcc   2520
ugaaggugca cuucaaccac gagaucugca cccagguguu ccacaagagc aucagcaggc   2580
ggugcaccaa gagcgugacc agcgucguga gcacccuguu cuacgacaag aaaaugagga   2640
ccaccaaccc caaggagacc aaaaucguga ucgacaccac aggcagcacc aagcccaagc   2700
```

```
aggacgaccu gauccugacc ugcuucaggg gcugggugaa gcagcugcag aucgacuaca   2760
agggcaacga gaucaugacc gccgcugcca gccagggccu gaccaggaag ggcguguacg   2820
ccgugaggua caaggugaac gagaacccac uguacgcucc caccagcgag cacgugaacg   2880
ugcugcugac caggaccgag gacaggaucg uguggaagac ccuggccggc gaccccugga   2940
ucaagacccu gaccgccaag uaccccggca acuucaccgc caccaucgaa gaguggcagg   3000
ccgagcacga cgccaucaug aggcacaucc uggagaggcc cgaccccacc gacguguucc   3060
agaacaaggc caacgugugc ugggccaagg cccuggugcc cgugcugaag accgccggca   3120
ucgacaugac cacagagcag uggaacaccg uggacuacuu cgagaccgac aaggcccaca   3180
gcgccgagau cgugcugaac cagcugugcg ugagguucuu cggccuggac cuggacagcg   3240
gccuguucag cgcccccacc gugccacuga gcaucaggaa caaccacugg gacaacagcc   3300
ccagcccaaa cauguacggc cugaacaagg agguggucag gcagcugagc aggcgguacc   3360
cacagcugcc cagggccgug gccaccggca ggguguacga caugaacacc ggcacccuga   3420
ggaacuacga ccccaggauc aaccuggugc ccgugaacag gcggcugccc cacgcccugg   3480
ugcugcacca caacgagcac ccacagagcg acuucagcuc cuucgugagc aagcugaaag   3540
gcaggaccgu gcuggucgug ggcgagaagc ugagcgugcc cggcaagaug guggacuggc   3600
ugagcgacag gcccgaggcc accuuccggg ccaggcugga ccucggcauc ccggcgacg    3660
ugcccaagua cgacaucauc uucgugaacg ucaggacccc auacaaguac caccauuacc   3720
agcagugcga ggaccacgcc aucaagcuga gcaugcugac caagaaggcc ugccugcacc   3780
ugaaccccgg aggcaccugc gugagcaucg gcuacggcua cgccgacagg gccagcgaga   3840
gcaucauugg cgccaucgcc aggcuguuca aguucagcag ggugugcaaa cccaagagca   3900
gccuggagga aaccgaggug cuguucgugu ucaucggcua cgaccggaag gccaggaccc   3960
acaaccccua caagcugagc agcacccuga caaacaucua caccggcagc aggcugcacg   4020
aggccggcug cgcccccagc uaccacgugg ucaggggcga uaucgccacc gccaccgagg   4080
gcgugaucau caacgcugcc aacagcaagg gccagcccgg aggcggagug ugcggcgccc   4140
uguacaagaa guuccccgag agcuucgacc ugcagcccau cgaggugggc aaggccaggc   4200
uggugaaggg cgccgcuaag cacaucaucc acgccguggg ccccaacuuc aacaagguga   4260
gcgaggugga aggcgacaag cagcuggccg aagccuacga gagcaucgcc aagaucguga   4320
acgacaauaa cuacaagagc guggccaucc cacugcucag caccggcauc uucagcggca   4380
acaaggacag gcugacccag agccugaacc accugcucac cgcccuggac accaccgaug   4440
ccgacguggc caucuacugc agggacaaga agugggagau gacccugaag gaggccgugg   4500
ccaggcggga ggccguggaa gagaucugca ucagcgacga cuccagcgug accgagcccg   4560
acgccgagcu ggugagggug caccccaaga gcucccuggc cggcaggaag ggcuacagca   4620
ccagcgacgg caagaccuuc agcuaccugg agggcaccaa guuccaccag gccgcuaagg   4680
acaucgccga gaucaacgcu auguggcccg uggccaccga ggccaacgag caggugugca   4740
uguacauccu gggcgagagc auguccagca ucaggagcaa gugccccgug gaggaaagcg   4800
aggccagcac accacccagc acccugcccu gccugugcau ccacgcuaug acacccgaga   4860
gggugcagcg gcugaaggcc agcaggcccg agcagaucac cgugugcagc uccuucccac   4920
ugcccaagua caggaucacc ggcgugcaga agauccagug cagccagccc auccuguuca   4980
gcccaaaggu gcccgccuac auccacccca ggaaguaccu gguggagacc ccacccgugg   5040
```

-continued acgagacacc cgagccaagc gccgagaacc agagcaccga gggcacaccc gagcagccac 5100
cccugaucac cgaggacgag acaaggaccc ggaccccaga gcccaucauu aucgaggaag 5160
aggaagagga cagcaucagc cugcugagcg acggccccac ccaccaggug cugcaggugg 5220
aggccgacau ccacggccca cccagcgugu ccagcuccag cuggagcauc ccacacgcca 5280
gcgacuucga cguggacagc cugagcaucc uggacacccu ggagggcgcc agcgugaccu 5340
ccggcgccac cagcgccgag accaacagcu acuucgccaa gagcauggag uuccuggcca 5400
ggcccgugcc agcucccagg accguguuca ggaacccacc ccacccagcu cccaggacca 5460
ggaccccaag ccuggcuccc agcagggccu gcagcaggac cagccuggug agcaccccac 5520
ccggcgugaa cagggugauc accagggagg aacuggaggc ccugacaccc agcaggaccc 5580
ccagcagguc cgugagcagg acuagucugg uguccaaccc acccggcgug aacaggguga 5640
ucaccaggga ggaauucgag gccuucgugg cccagcaaca gagacgguuc gacgccggcg 5700
ccuacaucuu cagcagcgac accggccagg gacaccugca gcaaaagagc gugaggcaga 5760
ccgugcugag cgagguggug cuggagagga ccgagcugga aaucagcuac gcccccaggc 5820
uggaccagga gaaggaggaa cugcucagga agaaacugca gcugaacccc accccagcca 5880
acaggagcag guaccagagc aggaaggugg agaacaugaa ggccaucacc gccaggcgga 5940
uccugcaggg ccugggacac uaccugaagg ccgagggcaa gguggagugc uacaggaccc 6000
ugcaccccgu gccacuguac agcuccagcg ugaacagggc cuucuccagc cccaaggugg 6060
ccguggaggc cugcaacgcu augcugaagg agaacuuccc caccguggcc agcuacugca 6120
ucauccccga guacgacgcc uaccuggaca ugguggacgg cgccagcugc ugccuggaca 6180
ccgccagcuu cugccccgcc aagcugagga gcuuccccaa gaaacacagc uaccuggagc 6240
ccaccaucag gagcgccgug cccagcgcca uccagaacac ccugcagaac gugcuggccg 6300
cugccaccaa gaggaacugc aacgugaccc agaugaggga gcugcccgug cuggacagcg 6360
cugccuucaa cguggagugc uucaagaaau acgccugcaa caacgaguac ugggagaccu 6420
ucaaggagaa ccccaucagg cugaccgaag agaacguggu gaacuacauc accaagcuga 6480
agggccccaa ggccgcugcc cuguucgcua agacccacaa ccugaacaug cugcaggaca 6540
ucccaaugga cagguucgug auggaccuga agagggacgu gaaggugaca cccggcacca 6600
agcacaccga ggagaggccc aaggugcagg ugauccaggc cgcugaccca cuggccaccg 6660
ccuaccugug cggcauccac agggagcugg ugaggcggcu gaacgccgug cugcugccca 6720
acauccacac ccuguucgac augagcgccg aggacuucga cgccaucauc gccgagcacu 6780
uccagcccgg cgacugcgug cuggagaccg acaucgccag cuucgacaag agcgaggaug 6840
acgcuauggc ccugaccgcu cugaugaucc uggaggaccu gggcguggac gccgagcugc 6900
ucacccugau cgaggcugcc uucggcgaga ucagcuccau ccaccugccc accaagacca 6960
aguucaaguu cggcgcuaug augaaaagcg gaauguuccu gacccuguuc gugaacaccg 7020
ugaucaacau ugugaucgcc agcagggugc ugcgggagag gcugaccggc agccccugcg 7080
cugccuucau cggcgacgac aacaucguga agggcgugaa aagcgacaag cugauggccg 7140
acaggugcgc caccuggcug aacauggagg ugaagaucau cgacgccgug gugggcgaga 7200
aggcccccua cuucugcggc ggauucaucc ugugcgacag cgugaccggc accgccugca 7260 gggugggccga cccccugaag aggcuguuca agcugggcaa gccacuggcc gcugacgaug 7320
agcacgacga ugacaggcgg agggcccugc acgaggaaag caccaggugg aacagggugg 7380
gcauccugag cgagcugugc aaggccgugg agagcaggua cgagaccgug ggcaccagca 7440
ucaucgugau ggcuaugacc acacuggcca gcuccgucaa gagcuucucc uaccugaggg 7500
gggccccuau aacucucuac ggcuaaccug aauggacuac gacauagucu aguccgccaa 7560
ggccgccacc caugaaguug gugguugugg gggccggggg uguuggcaaa agcgcccuua 7620
caauuugacu cgaguauguu acgugcaaag gugauuguca ccccccgaaa gaccauauug 7680
ugacacaccc ucaguaucac gcccaaacau uuacagccgc ggugucaaaa accgcgugga 7740
cgugguuaac aucccugcug ggaggaucag ccguaauuau uauaauuggc uuggugcugg 7800
cuacuauugu ggccauguac gugcugacca accagaaaca uaauugaaua cagcagcaau 7860
uggcaagcug cuuacauaga acucgcggcg auuggcaugc cgccuuaaaa uuuuuauuuu 7920
auuuuuucuu uucuuuuccg aaucggauuu uguuuuuaau auuucaaaaa aaaaaaaaaa 7980
aaaaaaaaaa ucuagaaaaa aaaaaaaaaa aaaaaaaaaa aaaaaaaaaa aaaaaaaaaa 8040
aaaaaaaaaa aaaaaaaaaa aaaaaaaaaa aaaaaaaaaa aaaaaaaaaa aaaaa 8095

<210> SEQ ID NO 104
<211> LENGTH: 8120
<212> TYPE: RNA
<213> ORGANISM: Artificial sequence
<220> FEATURE:
<223> OTHER INFORMATION: Synthetic polynucleotide

<400> SEQUENCE: 104
auugacggcg uaguacacac uauugaauca aacagccgac caauugcacu accaucacaa 60
uggagaagcc aguaguaaac guagacguag accccccagag uccguuuguc gugcaacugc 120
aaaaaagcuu cccgcaauuu gagguaguag cacagcaggu cacuccaaau gaccaugcua 180
augccagagc auuuucgcau cuggccagua aacuaaucga gcuggagguu ccuaccacag 240
cgacgaucuu ggacauaggc agcgcaccgg cucguagaau guuuuccgag caccaguauc 300
auugugucug ccccaugcgu aguccagaag acccggaccg caugaugaaa uaugccagua 360
aacuggcgga aaaagcgugc aagauuacaa acaagaacuu gcaugagaag auuaaggauc 420
uccggaccgu acuugauacg ccggaugcug aaacaccauc gcucugcuuu cacaacgaug 480
uuaccugcaa caugcgugcc gaauauuccg ucaugcagga cguguauauc aacgcucccg 540
gaacuaucua ucaucaggcu augaaaggcg ugcggacccu guacuggauu ggcuucgaca 600
ccacccaguu cauguucucg gcuauggcag guucguaccc ugcguacaac accaacuggg 660
ccgacgagaa aguccuugaa gcgcguaaca ucggacuuug cagcacaaag cugagugaag 720
guaggacagg aaaauugucg auaaugagga agaaggaguu gaagcccggg ucgcggguuu 780
auuucuccgu aggaucgaca cuuuauccag aacacagagc cagcuugcag agcuggcauc 840
uuccaucggu guuccacuug aauggaaagc agucguacac uugccgcugu gauacagugg 900
ugaguugcga aggcuacgua gugaagaaaa ucaccaucag ucccgggauc acgggagaaa 960
ccgugggaua cgcgguuaca cacaauagcg agggcuucuu gcuaugcaaa guuacugaca 1020
caguaaaagg agaacgggua ucguucccug ugugcacgua caucccggcc accauaugcg 1080
aucagaugac ugguauaaug gccacggaua uaucaccuga cgaugcacaa aaacuucugg 1140
uugggcucaa ccagcgaauu gucauuaacg guaggacuaa caggaacacc aacaccaugc 1200
aaaauuaccu ucugccgauc auagcacaag gguucagcaa augggcuaag gagcgcaagg 1260
augaucuuga uaacgagaaa augcugggua cuagagaacg caagcuuacg uauggcugcu 1320 uguggggcguu ucgcacuaag aaaguacauu cguuuuaucg cccaccugga acgcagaccu 1380

-continued

```
gcguaaaagu cccagccucu uuuagcgcuu uucccauguc guccguaugg acgaccucuu   1440
ugcccauguc gcugaggcag aaauugaaac uggcauugca accaaagaag gaggaaaaac   1500
ugcugcaggu cucggaggaa uuagucaugg aggccaaggc ugcuuuugag gaugcucagg   1560
aggaagccag agcggagaag cuccgagaag cacuuccacc auuaguggca gacaaaggca   1620
ucgaggcagc cgcagaaguu gucugcgaag uggaggggcu ccaggcggac aucggagcag   1680
cauuaguuga aaccccgcgc ggucacguaa ggauaaauacc ucaagcaaau gaccguauga   1740
ucggacagua uaucguuguc ucgccaaacu cugugcugaa gaaugccaaa cucgcaccag   1800
cgcacccgcu agcagaucag guuaagauca uaacacacuc cggaagauca ggaagguacg   1860
cggucgaacc auacgacgcu aaaguacuga ugccagcagg aggugccgua ccauggccag   1920
aauuccuagc acugagugag agcgccacgu uaguguacaa cgaaagagag uuugugaacc   1980
gcaaacuaua ccacauugcc augcauggcc ccgccaagaa uacagaagag gagcaguaca   2040
agguuacaaa ggcagagcuu gcagaaacag aguacguguu ugacguggac aagaagcguu   2100
gcguuaagaa ggaagaagcc ucaggucugg uccucucggg agaacugacc aacccucccu   2160
aucaugagcu agcucuggag ggacugaaga cccgaccugc ggucccguac aaggucgaaa   2220
caauaggagu gauaggcaca ccggggucgg gcaagucagc uauuaucaag ucaacuguca   2280
cggcacgaga ucuuguuacc agcggaaaga aagaaaauug ucgcgaaauu gaggccgacg   2340
ugcuaagacu gaggggguaug cagauuacgu cgaagacagu agauucgguu augcucaacg   2400
gaugccacaa agccguagaa gugcuguacg uugacgaagc guucgcgugc cacgcaggag   2460
cacuacuugc cuugauugcu aucgucaggc cccgcaagaa gguaguacua ugcggagacc   2520
ccaugcaaug cggauucuuc aacaugaugc aacuaaaggu acauuucaau cacccugaaa   2580
aagacauaug caccaagaca uucuacaagu auaucucccg gcguugcaca cagccaguua   2640
cagcuauugu aucgacacug cauuacgaug gaaagaugaa aaccacgaac ccgugcaaga   2700
agaacauuga aaucgauauu acaggggcca caaagccgaa gccaggggau aucauccuga   2760
cauguuuccg cgggugggu u aagcaauugc aaaucgacua ucccggacau gaaguaauga   2820
cagccgcggc cucacaaggg cuaaccagaa aaggagugua ugccguccgg caaaaaguca   2880
augaaaaccc acuguacgcg aucacaucag agcaugugaa cguguugcuc acccgcacug   2940
aggacaggcu aguguggaaa accuugcagg gcgacccaug gauuaagcag cucacuaaca   3000
uaccuaaagg aaacuuucag gcuacuauag aggacuggga agcugaacac aagggaauaa   3060
uugcugcaau aaacagcccc acuccccgug ccaauccguu cagcugcaag accaacguuu   3120
gcugggcgaa agcauuggaa ccgauacuag ccacggccgg uaucguacuu accgguugcc   3180
aguggagcga acuguuccca caguuugcgg augacaaacc acauucggcc auuuacgccu   3240
uagacguaau uugcauuaag uuuuucggca uggacuugac aagcggacug uuuucuaaac   3300
agagcauccc acuaacguac caucccgccg auucagcgag gccgguagcu cauugggaca   3360
acagcccagg aacccgcaag uaugggguacg aucacgccau ugccgccgaa cucucccgua   3420
gauuuccggu guuccagcua gcugggaagg gcacacaacu ugauuugcag acggggagaa   3480
ccagaguuau cucugcacag cauaaccugg ucccggugaa ccgcaaucuu ccucacgccu   3540
uaguccccga guacaaggag aagcaacccg gcccggucga aaaauucuug aaccaguuca   3600
aacaccacuc aguacuugug guaucagagg aaaaaauuga agcuccccgu aagagaaucg   3660
aauggaucgc cccgauuggc auagccggug cagauaagaa cuacaaccug gcuuucgggu   3720
uuccgccgca ggcacgguac gaccuggugu ucaucaacau uggaacuaaa uacagaaacc   3780
```

accacuuuca gcagugcgaa gaccaugcgg cgaccuuaaa aacccuuucg cguucggccc 3840
ugaauugccu uaacccagga ggcacccucg uggugaaguc cuauggcuac gccgaccgca 3900
acagugagga cguagucacc gcucuugcca gaaaguuugu cagggugucu gcagcgagac 3960
cagauugugu cucaagcaau acagaaaugu accugauuuu ccgacaacua gacaacagcc 4020
guacacggca auucaccccg caccaucuga auugcgugau uucguccgug uaugagggua 4080
caagagaugg aguuggagcc gcgccgucau accgcaccaa aagggagaau auugcugacu 4140
gucaagagga agcaguuguc aacgcagcca auccgcuggg uagaccaggc gaaggagucu 4200
gccgugccau cuauaaacgu uggccgacca guuuuaccga uucagccacg gagacaggca 4260
ccgcaagaau gacugugugc cuaggaaaga aagugaucca cgcggucggc ccugauuucc 4320
ggaagcaccc agaagcagaa gccuugaaau ugcuacaaaa cgccuaccau gcaguggcag 4380
acuuaguaaa ugaacauaac aucaagucug ucgccauucc acugcuaucu acaggcauuu 4440
acgcagccgg aaaagaccgc cuugaaguau cacuuaacug cuugacaacc gcgcuagaca 4500
gaacugacgc ggacguaacc aucuauugcc uggauaagaa guggaaggaa agaaucgacg 4560
cggcacucca acuuaaggag ucuguaacag agcugaagga ugaagauaug gagaucgacg 4620
augaguuagu auggauccau ccagacaguu gcuugaaggg aagaaaggga uucaguacua 4680
caaaaggaaa auuguauucg uacuucgaag gcaccaaauu ccaucaagca gcaaaagaca 4740
uggcggagau aaagguccug uucccuaaug accaggaaag uaaugaacaa cugugugccu 4800
acauauuggg ugagaccaug gaagcaaucc gcgaaaagug cccggucgac cauaacccgu 4860
cgucuagccc gcccaaaacg uugccgugcc uuugcaugua ugccaugacg ccagaaaggg 4920
uccacagacu uagaagcaau aacgucaaag aaguuacagu augcuccucc acccccuuc 4980 cuaagcacaa aauuaagaau guucagaagg uucagugcac gaaaguaguc cuguuuaauc 5040
cgcacacucc cgcauucguu cccgcccgua aguacauaga agugccagaa cagccuaccg 5100
cuccuccugc acaggccgag gaggcccccg aaguuguagc gacaccguca ccaucuacag 5160
cugauaacac cucgcuugau gucacagaca ucucacugga uauggaugac aguagcgaag 5220
gcucacuuuu uucgagcuuu agcggaucgg acaacucuau uacuaguaug gacaguuggu 5280
cgucaggacc uaguucacua gagauaguag accgaaggca ggugguggug gcugacguuc 5340
augccgucca agagccugcc ccuauuccac cgccaaggcu aaagaagaug gcccgccugg 5400
cagcggcaag aaaagagccc acuccaccgg caagcaauag cucugagucc cuccaccucu 5460
cuuuuggugg gguauccaug ucccucggau caauuuucga cggagagacg gcccgccagg 5520
cagcgguaca accccuggca acaggcccca cggaugugcc uaugucuuuc ggaucguuuu 5580
ccgacggaga gauugaugag cugagccgca gaguaacuga guccgaaccc guccuguuug 5640
gaucauuuga accgggcgaa gugaacucaa uuauaucguc ccgaucagcc guaucuuuuc 5700
cucuacgcaa gcagagacgu agacgcagga gcaggaggac ugaauacuga cuaaccgggg 5760
uaggugggua cauauuuucg acggacacag gcccugggca cuugcaaaag aaguccguuc 5820
ugcagaacca gcuuacagaa ccgaccuugg agcgcaaugu ccuggaaaga auucaugccc 5880
cggugcucga cacgucgaaa gaggaacaac ucaaacucag guaccagaug augcccaccg 5940
aagccaacaa aaguagguac cagucucgua aaguagaaaa ucagaaagcc auaaccacug 6000
agcgacuacu gucaggacua cgacuguaua acucugccac agaucagcca gaaugcuaua 6060
agaucaccua uccgaaacca uuguacucca guagcguacc ggcgaacuac uccgauccac 6120
aguucgcugu agcugucugu aacaacuauc ugcaugagaa cuauccgaca guagcaucuu 6180
aucagauuac ugacgaguac gaugcuuacu uggauauggu agacgggaca gucgccugcc 6240
uggacacugc aaccuucugc cccgcuaagc uuagaaguua cccgaaaaaa caugaguaua 6300
gagccccgaa uauccgcagu gcgguuccau cagcgaugca gaacacgcua caaaaugugc 6360
ucauugccgc aacuaaaaga aauugcaacg ucacgcagau gcgugaacug ccaacacugg 6420
acucagcgac auucaauguc gaaugcuuuc gaaaauaugc auguaaugac gaguauuggg 6480
aggaguucgc ucggaagcca auuaggauua ccacugaguu ugucaccgca uauguagcua 6540
gacugaaagg cccuaaggcc gccgcacuau uugcaaagac guauaauuug gucccauugc 6600
aagaagugcc uauggauaga uucgucaugg acaugaaaag agacgugaaa guuacaccag 6660
gcacgaaaca cacagaagaa agaccgaaag uacaagugau acaagccgca gaaccccugg 6720
cgacugcuua cuuaugcggg auucaccggg aauuagugcg uaggcuuacg gccgucuugc 6780
uuccaaacau ucacacgcuu uuugacaugu cggcggagga uuuugaugca aucauagcag 6840
aacacuucaa gcaaggcgac ccgguacugg agacggauau cgcaucauuc gacaaaagcc 6900
aagacgacgc uauggcguua accggucuga ugaucuugga ggaccugggu guggaucaac 6960
cacuacucga cuugaucgag ugcgccuuug gagaaauauc auccacccau cuaccuacgg 7020
guacucguuu uaaauucggg gcgaugauga aauccggaau guuccucaca cuuuuuguca 7080
acacaguuuu gaaugucguu aucgccagca gaguacuaga ggagcggcuu aaaacgucca 7140
gaugugcagc guucauuggc gacgacaaca ucauacaugg aguaguaucu gacaaagaaa 7200
uggcugagag gugcgccacc uggcucaaca uggagguuaa gaucaucgac gcagucaucg 7260
gugagagacc accuuacuuc ugcggcggau uuaucuugca agauucgguu acuuccacag 7320
cgugccgcgu ggcggauccc cugaaaaggc uguuuaaguu ggguaaaccg cucccagccg 7380
acgacgagca agacgaagac agaagacgcg cucugcuaga ugaaacaaag gcgugguuua 7440
gaguagguau aacaggcacu uuagcagugg ccgugacgac ccgguaugag guagacaaua 7500
uuacaccugu ccuacuggca uugagaacuu uugcccagag caaaagagca uuccaagcca 7560
ucagagggga aauaaagcau cucuacggug guccuaaaua gucagcauag uacauuucau 7620
cugacuaaua cuacaacacc accaccacgc gugcuagacc auggauccua gacgcuacgc 7680
cccaaugauc cgaccagcaa aacucgaugu acuuccgagg aacugaugug cauaaugcau 7740
caggcuggua cauuagaucc ccgcuuaccg cgggcaauau agcaacacua aaaacucgau 7800
guacuuccga ggaagcgcag ugcauaaugc ugcgcagugu ugccacauaa ccacuauauu 7860
aaccauuuau cuagcggacg ccaaaaacuc aauguauuuc ugaggaagcg uggugcauaa 7920
ugccacgcag cgucugcaua acuuuuauua uuucuuuuau uaaucaacaa aauuuuguuu 7980
uuaacauuuc aaaaaaaaaa aaaaaaaaaa aaaaaucuag aaaaaaaaaa aaaaaaaaaa 8040
aaaaaaaaaa aaaaaaaaaa aaaaaaaaaa aaaaaaaaaa aaaaaaaaaa aaaaaaaaaa 8100
aaaaaaaaaa aaaaaaaaaa 8120

<210> SEQ ID NO 105
<211> LENGTH: 8875
<212> TYPE: RNA
<213> ORGANISM: Artificial sequence
<220> FEATURE:
<223> OTHER INFORMATION: Synthetic polynucleotide

<400> SEQUENCE: 105
augggcggcg caugagagaa gcccagacca auuaccuacc caaaauggag aaaguucacg 60
uugacaucga ggaagacagc ccauuccuca gagcuuugca gcggagcuuc ccgcaguuug 120
agguagaagc caagcagguc acugauaaug accaugcuaa ugccagagcg uuuucgcauc 180
uggcuucaaa acugaucgaa acggaggugg acccauccga cacgauccuu gacauuggaa 240
gugcgcccgc ccgcagaaug uauucuaagc acaaguauca uuguaucugu ccgaugagau 300
gugcggaaga uccggacaga uuguauaagu augcaacuaa gcugaagaaa aacuguaagg 360
aaauaacuga uaaggaauug gacaagaaaa ugaaggagcu ggccgccguc augagcgacc 420
cugaccugga aacugagacu augugccucc acgacgacga gucgugucgc uacgaagggc 480
aagucgcugu uuaccaggau guauacgccg ucgacggccc caccagccug uaccaccagg 540
ccaacaaggg cgugagggug gccuacugga ucggcuucga caccacaccc uucauguuca 600
agaaccuggc cggcgccuac ccccagcuaca gcaccaacug ggccgacgag accgugcuga 660
ccgccaggaa caucggccug ugcagcagcg acgugaugga gaggagccgg agaggcauga 720
gcauccugag gaagaaauac cugaagccca gcaacaacgu gcuguucagc gugggcagca 780
ccaucuacca cgagaagagg gaccugcuca ggagcuggca ccugcccagc guguuccacc 840
ugaggggcaa gcagaacuac accugcaggu gcgagaccau cgugagcugc gacggcuacg 900
uggugaagag gaucgccauc agccccggcc uguacggcaa gcccagcggc uacgccgcua 960
caaugcacag ggagggcuuc cugugcugca aggugaccga cacccugaac ggcgagaggg 1020
ugagcuuccc cgugugcacc uacgugcccg ccacccugug cgaccagaug accggcaucc 1080
uggccaccga cgugagcgcc gacgacgccc agaagcugcu cgugggccug aaccagagga 1140
ucgugguca a cggcaggacc cagaggaaca ccaacacaau gaagaacuac cugcugcccg 1200
ugguggccca ggcuuucgcc aggugggcca aggaguacaa ggaggaccag gaagacgaga 1260
ggccccuggg ccugagggac aggcagcugg ugaugggcug cugcugggcc uucaggcggc 1320
acaagaucac cagcaucuac aagaggcccg acacccagac caucaucaag gugaacagcg 1380
acuuccacag cuucgugcug cccaggaucg gcagcaacac ccuggagauc ggccugagga 1440
cccggaucag gaagaugcug gaggaacaca aggagcccag cccacugauc accgccgagg 1500
acgugcagga ggccaagugc gcugccgacg aggccaagga ggugagggag gccgaggaac 1560
ugagggccgc ccugccaccc cuggcugccg acguggagga acccacccug gaagccgacg 1620
uggaccugau gcugcaggag gccggcgccg gaagcgugga gacacccagg ggccugauca 1680
aggugaccag cuacgacggc gaggacaaga ucggcagcua cgccgugcug agcccacagg 1740
ccgugcugaa guccgagaag cugagcugca uccacccacu ggccgagcag gugaucguga 1800
ucacccacag cggcaggaag ggcagguacg ccguggagcc cuaccacggc aagguggucg 1860
ugcccgaggg ccacgccauc cccgugcagg acuuccaggc ccugagcgag agcgccacca 1920
ucguguacaa cgagagggag uucgugaaca gguaccugca ccauaucgcc acccacggcg 1980
gagcccugaa caccgacgag gaauacuaca agaccgugaa gcccagcgag cacgacggcg 2040
aguaccugua cgacaucgac aggaagcagu gcgugaagaa agagcuggug accggccugg 2100
gacugaccgg cgagcuggug gacccacccu uccacgaguu cgccuacgag agccugagga 2160
ccagacccgc cgcucccuac caggugccca ccaucggcgu guacggcgug cccggcagcg 2220
gaaagagcgg caucaucaag agcgccguga ccaagaaaga ccugguggucc agcgccaaga 2280
aagagaacug cgccgagauc aucagggacg ugaagaagau gaaaggccug gacgugaacg 2340
cgcgcaccgu ggacagcgug cugcugaacg gcugcaagca ccccguggag acccuguaca 2400
ucgacgaggc cuucgcuugc cacgccggca cccugagggc ccugaucgcc aucaucaggc 2460
ccaagaaagc cgugcugugc ggcgacccca agcagugcgg cuucuucaac augaugugcc 2520
ugaaggugca cuucaaccac gagaucugca cccaggugu ccacaagagc aucagcaggc 2580
ggugcaccaa gagcgugacc agcgucguga gcacccuguu cuacgacaag aaaaugagga 2640
ccaccaaccc caaggagacc aaaaucguga ucgacaccac aggcagcacc aagcccaagc 2700
aggacgaccu gauccugacc ugcuucaggg gcugggugaa gcagcugcag aucgacuaca 2760
agggcaacga gaucaugacc gccgcugcca gccagggccu gaccaggaag ggcguguacg 2820
ccgugaggua caaggugaac gagaacccac uguacgcucc caccagcgag cacgugaacg 2880
ugcugcugac caggaccgag gacaggaucg uguggaagac ccuggccggc gaccccugga 2940
ucaagacccu gaccgccaag uaccccggca acuucaccgc caccaucgaa gaguggcagg 3000
ccgagcacga cgccaucaug aggcacaucc uggagaggcc cgaccccacc gacguguucc 3060
agaacaaggc caacgugugc ugggccaagg cccuggugcc cgugcugaag accgccggca 3120
ucgacaugac cacagagcag uggaacaccg uggacuacuu cgagaccgac aaggcccaca 3180
gcgccgagau cgugcugaac cagcugugcg ugagguucuu cggccuggac cuggacagcg 3240
gccuguucag cgcccccacc gugccacuga gcaucaggaa caaccacugg gacaacagcc 3300
ccagcccaaa cauguacggc cugaacaagg agguggucag gcagcugagc aggcgguacc 3360
cacagcugcc cagggccgug gccaccggca ggguguacga caugaacacc ggcacccuga 3420
ggaacuacga ccccaggauc aaccuggugc ccgugaacag gcggcugccc cacgcccugg 3480
ugcugcacca caacgagcac ccacagagcg acuucagcuc cuucgugagc aagcugaaag 3540
gcaggaccgu gcuggucgug ggcgagaagc ugagcgugcc cggcaagaug guggacuggc 3600
ugagcgacag gcccgaggcc accuuccggg ccaggcugga ccucggcauc cccggcgacg 3660
ugcccaagua cgacaucauc uucgugaacg ucaggacccc auacaaguac caccauuacc 3720
agcagugcga ggaccacgcc aucaagcuga gcaugcugac caagaaggcc ugccugcacc 3780
ugaaccccgg aggcaccugc gugagcaucg gcuacggcua cgccgacagg gccagcgaga 3840
gcaucauugg cgccaucgcc aggcuguuca aguucagcag ggugugcaaa cccaagagca 3900
gccuggagga aaccgaggug cuguucgugu ucaucggcua cgaccggaag gccaggaccc 3960
acaaccccua caagcugagc agcacccuga caaacaucua caccggcagc aggcugcacg 4020
aggccggcug cgcccccagc uaccacgugg ucaggggcga uaucgccacc gccaccgagg 4080
gcgugaucau caacgcugcc aacagcaagg gccagcccgg aggcggagug ugcggcgccc 4140
uguacaagaa guuccccgag agcuucgacc ugcagcccau cgaggugggc aaggccaggc 4200
uggugaaggg cgccgcuaag cacaucaucc acgccguggg ccccaacuuc aacaaggüga 4260
gcgaggugga aggcgacaag cagcuggccg aagccuacga gagcaucgcc aagaucguga 4320
acgacaauaa cuacaagagc guggccaucc cacugcucag caccggcauc uucagcggca 4380
acaaggacag gcugacccag agccugaacc accugcucac cgcccuggac accaccgaug 4440
ccgacguggc caucuacugc agggacaaga agugggagau gacccugaag gaggccgugg 4500
ccaggcggga ggccguggaa gagaucugca ucagcgacga cuccagcgug accgagcccg 4560
acgccgagcu ggugagggug caccccaaga gcucccuggc cggcaggaag ggcuacagca 4620
ccagcgacgg caagaccuuc agcuaccugg agggcaccaa guuccaccag gccgcuaagg 4680
acaucgccga gaucaacgcu auguggcccg uggccaccga ggccaacgag caggugugca 4740
uguacauccu gggcgagagc auguccagca ucaggagcaa gugccccgug gaggaaagcg 4800

-continued aggccagcac accacccagc acccugcccu gccugugcau ccacgcuaug acacccgaga 4860
gggugcagcg gcugaaggcc agcaggcccg agcagaucac cgugugcagc uccuucccac 4920
ugcccaagua caggaucacc ggcgugcaga agauccagug cagccagccc auccuguuca 4980
gcccaaaggu gcccgccuac auccacccca ggaaguaccu gguggagacc ccacccgugg 5040
acgagacacc cgagccaagc gccgagaacc agagcaccga gggcacaccc gagcagccac 5100
cccugaucac cgaggacgag acaaggaccc ggaccccaga gcccaucauu aucgaggaag 5160
aggaagagga cagcaucagc cugcugagcg acggccccac ccaccaggug cugcaggugg 5220
aggccgacau ccacggccca cccagcgugu ccagcuccag cuggagcauc ccacacgcca 5280
gcgacuucga cguggacagc cugagcaucc uggacacccu ggagggcgcc agcgugaccu 5340
ccggcgccac cagcgccgag accaacagcu acuucgccaa gagcauggag uuccuggcca 5400
ggcccgugcc agcucccagg accguguuca ggaacccacc ccacccagcu cccaggacca 5460
ggaccccaag ccuggcuccc agcagggccu gcagcaggac cagccuggug agcaccccac 5520
ccggcgugaa cagggugauc accagggagg aacuggaggc ccugacaccc agcaggaccc 5580
ccagcagguc cgugagcagg acuagucugg uguccaaccc acccggcgug aacaggguga 5640
ucaccaggga ggaauucgag gccuucgugg cccagcaaca gagacgguuc gacgccggcg 5700
ccuacaucuu cagcagcgac accggccagg gacaccugca gcaaaagagc gugaggcaga 5760
ccgugcugag cgagguggug cuggagagga ccgagcugga aaucagcuac gcccccaggc 5820
uggaccagga gaaggaggaa cugcucagga agaaacugca gcugaacccc accccagcca 5880
acaggagcag guaccagagc aggaaggugg agaacaugaa ggccaucacc gccaggcgga 5940
uccugcaggg ccugggacac uaccugaagg ccgagggcaa gguggagugc uacaggaccc 6000
ugcaccccgu gccacuguac agcuccagcg ugaacagggc cuucuccagc cccaaggugg 6060
ccguggaggc cugcaacgcu augcugaagg agaacuuccc caccguggcc agcuacugca 6120
ucauccccga guacgacgcc uaccuggaca ugguggacgg cgccagcugc ugccuggaca 6180
ccgccagcuu cugccccgcc aagcugagga gcuuccccaa gaaacacagc uaccuggagc 6240
ccaccaucag gagcgccgug cccagcgcca uccagaacac ccugcagaac gugcuggccg 6300
cugccaccaa gaggaacugc aacgugaccc agaugaggga gcugcccgug cuggacagcg 6360
cugccuucaa cguggagugc uucaagaaau acgccugcaa caacgaguac ugggagaccu 6420
ucaaggagaa ccccaucagg cugaccgaag agaacguggu gaacuacauc accaagcuga 6480
agggccccaa ggccgcugcc cuguucgcua agacccacaa ccugaacaug cugcaggaca 6540
ucccaaugga cagguucgug auggaccuga agagggacgu gaaggugaca cccggcacca 6600
agcacaccga ggagaggccc aaggugcagg ugauccaggc cgcugaccca cuggccaccg 6660
ccuaccugug cggcauccac agggagcugg ugaggcggcu gaacgccgug cugcugccca 6720
acauccacac ccuguucgac augagcgccg aggacuucga cgccaucauc gccgagcacu 6780
uccagcccgg cgacugcgug cuggagaccg acaucgccag cuucgacaag agcgaggaug 6840
acgcuauggc ccugaccgcu cugaugaucc uggaggaccu gggcguggac gccgagcugc 6900
ucacccugau cgaggcugcc uucggcgaga ucagcuccau ccaccugccc accaagacca 6960
aguucaaguu cggcgcuaug augaaaagcg gaauguuccu gacccuguuc gugaacaccg 7020
ugaucaacau ugugaucgcc agcagggugc ugcgggagag gcugaccggc agccccugcg 7080
cugccuucau cggcgacgac aacaucguga agggcgugaa aagcgacaag cugauggccg 7140

-continued

```
acaggugcgc caccuggcug aacauggagg ugaagaucau cgacgccgug gugggcgaga   7200

aggcccccua cuucugcggc ggauucaucc ugugcgacag cgugaccggc accgccugca   7260

gggugccga cccccugaag aggcuguuca agcugggcaa gccacuggcc gcugacgaug   7320

agcacgacga ugacaggcgg agggcccugc acgaggaaag caccaggugg aacagggugg   7380

gcauccugag cgagcugugc aaggccgugg agagcaggua cgagaccgug ggcaccagca   7440

ucaucgugau ggcuaugacc acacuggcca gcuccgucaa gagcuucucc uaccugaggg   7500

gggcccuau aacucucuac ggcuaaccug aauggacuac gacauagucu aguccgccaa   7560

ggccgccacc augagaguga cagccccuag aaccuuacug cuucugcuuu ggggagcugu   7620

ugcucugaca gagacauggg cuggaucucu gagcgaggug accggccagg gccugugcau   7680

cggcgccgug cccaagaccc accaggugcu gugcaacacc acccagaaga ccagcgacgg   7740

cagcuacuac cuggccgcuc ccaccggcac caccugggcc ugcagcaccg gccugacccc   7800

uugcaucagc accaccaucc ugaaccugac caccgacuac ugcgugcugg uggagcugug   7860

gcccagggug accuaccaca gccccagcua cgccuaccac caguucgaga ggagggccaa   7920

guacaagagg gagcccguga gccugacccu ggcccugcug cugggcggcc ugacaauggg   7980

cggcaucgcc gccggcgugg gcaccggcac caccgcccug guggccaccc agcaguucca   8040

gcagcugcag gccgccaugc acgacgaccu gaaggaggug gagaagucca ucaccaaccu   8100

ggagaagucc cugaccagcc ugagcgaggu ggugcugcag aacaggaggg gccuggaccu   8160

gcuguuccug aaggagggcg gccugugcgc cgcccugaag gaggagugcu gccuguacgc   8220

cgaccacacc ggccuggug ucgugggcau ugucgcuggc cuggccgucc ucgccguggu   8280

ggugauugga gcuguggucg cagcuguuau gugcagaaga aagucauccg gcggaaaggg   8340

aggcuccuac ucucaggcug cuucugcuac agugccuaga gcucuuaugu guuuaucuca   8400

gcuguaaacu cgaguauguu acgugcaaag gugauuguca ccccccgaaa gaccauauug   8460

ugacacaccc ucaguaucac gcccaaacau uuacagccgc ggugucaaaa accgcgugga   8520

cgugguuaac aucccugcug ggaggaucag ccguaauuau uauaauuggc uuggugcugg   8580

cuacuauugu ggccauguac gugcugacca accagaaaca uaauugaaua cagcagcaau   8640

uggcaagcug cuuacauaga acucgcggcg auuggcaugc cgccuuaaaa uuuuuauuuu   8700

auuuuuucuu uucuuuuccg aaucggauuu uguuuuuaau auuucaaaaa aaaaaaaaaa   8760

aaaaaaaaaa ucuagaaaaa aaaaaaaaaa aaaaaaaaaa aaaaaaaaaa aaaaaaaaaa   8820

aaaaaaaaaa aaaaaaaaaa aaaaaaaaaa aaaaaaaaaa aaaaaaaaaa aaaaa        8875
```

<210> SEQ ID NO 106
<211> LENGTH: 8416
<212> TYPE: RNA
<213> ORGANISM: Artificial sequence
<220> FEATURE:
<223> OTHER INFORMATION: Synthetic polynucleotide

<400> SEQUENCE: 106

```
augggcggcg caugagagaa gcccagacca auuaccuacc caaaauggag aaaguucacg     60

uugacaucga ggaagacagc ccauuccuca gagcuuugca gcggagcuuc ccgcaguuug    120

agguagaagc caagcagguc acugauaaug accaugcuaa ugccagagcg uuuucgcauc    180

uggcuucaaa acugaucgaa acggaggugg acccauccga cacgauccuu gacauuggaa    240

gugcgcccgc ccgcagaaug uauucuaagc acaaguauca uuguaucugu ccgaugagau    300

gugcggaaga uccggacaga uuguauaagu augcaacuaa gcugaagaaa aacuguaagg    360
```

```
aaauaacuga uaaggaauug gacaagaaaa ugaaggagcu ggccgccguc augagcgacc    420
cugaccugga aacugagacu augugccucc acgacgacga gucgugucgc uacgaagggc    480
aagucgcugu uuaccaggau guauacgccg ucgacggccc caccagccug uaccaccagg    540
ccaacaaggg cgugagggug gccuacugga ucggcuucga caccacaccc uucauguuca    600
agaaccuggc cggcgccuac cccagcuaca gcaccaacug ggccgacgag accgugcuga    660
ccgccaggaa caucggccug ugcagcagcg acgugaugga gaggagccgg agaggcauga    720
gcauccugag gaagaaauac cugaagccca gcaacaacgu gcuguucagc gugggcagca    780
ccaucuacca cgagaagagg gaccugcuca ggagcuggca ccugcccagc guguuccacc    840
ugaggggcaa gcagaacuac accugcaggu gcgagaccau cgugagcugc gacggcuacg    900
uggugaagag gaucgccauc agccccggcc uguacggcaa gcccagcggc uacgccgcua    960
caaugcacag ggagggcuuc cugugcugca aggugaccga cacccugaac ggcgagaggg   1020
ugagcuuccc cgugugcacc uacgugcccg ccacccugug cgaccagaug accggcaucc   1080
uggccaccga cgugagcgcc gacgacgccc agaagcugcu cgugggccug aaccagagga   1140
ucguggucaa cggcaggacc cagaggaaca ccaacacaau gaagaacuac cugcugcccg   1200
ugguggccca ggcuuucgcc aggugggcca aggaguacaa ggaggaccag gaagacgaga   1260
ggccccuggg ccugagggac aggcagcugg ugaugggcug cugcugggcc uucaggcggc   1320
acaagaucac cagcaucuac aagaggcccg acacccagac caucaucaag gugaacagcg   1380
acuuccacag cuucgugcug cccaggaucg gcagcaacac ccuggagauc ggccugagga   1440
cccggaucag gaagaugcug gaggaacaca aggagcccag cccacugauc accgccgagg   1500
acgugcagga ggccaagugc gcugccgacg aggccaagga ggugagggag gccgaggaac   1560
ugagggccgc ccugccaccc cuggcugccg acguggagga acccacccug gaagccgacg   1620
uggaccugau gcugcaggag gccggcgccg gaagcgugga gacacccagg ggccugauca   1680
aggugaccag cuacgacggc gaggacaaga ucggcagcua cgccgugcug agcccacagg   1740
ccgugcugaa guccgagaag cugagcugca uccacccacu ggccgagcag gugaucguga   1800
ucacccacag cggcaggaag ggcagguacg ccguggagcc cuaccacggc aagguggucg   1860
ugcccgaggg ccacgccauc cccgugcagg acuuccaggc ccugagcgag agcgccacca   1920
ucguguacaa cgagagggag uucgugaaca gguaccugca ccauaucgcc acccacggcg   1980
gagcccugaa caccgacgag gaauacuaca agaccgugaa gcccagcgag cacgacggcg   2040
aguaccugua cgacaucgac aggaagcagu gcgugaagaa agagcuggug accggccugg   2100
gacugaccgg cgagcuggug gacccacccu uccacgaguu cgccuacgag agccugagga   2160
ccagacccgc cgcucccuac caggugccca ccaucggcgu guacggcgug cccggcagcg   2220
gaaagagcgg caucaucaag agcgccguga ccaagaaaga ccugguguc agcgccaaga    2280
aagagaacug cgccgagauc aucagggacg ugaagaagau gaaaggccug gacgugaacg   2340
cgcgcaccgu ggacagcgug cugcugaacg gcugcaagca ccccguggag acccuguaca   2400
ucgacgaggc cuucgcuugc cacgccggca cccugagggc ccugaucgcc aucaucaggc   2460
ccaagaaagc cgugcugugc ggcgacccca agcagugcgg cuucuucaac augaugugcc   2520
ugaaggugca cuucaaccac gagaucugca cccagguguu ccacaagagc aucagcaggc   2580
ggugcaccaa gagcgugacc agcgucguga gcacccuguu cuacgacaag aaaaugagga   2640
ccaccaaccc caaggagacc aaaaucguga ucgacaccac aggcagcacc aagcccaagc   2700
```

```
aggacgaccu gauccugacc ugcuucaggg gcugggugaa gcagcugcag aucgacuaca   2760
agggcaacga gaucaugacc gccgcugcca gccagggccu gaccaggaag ggcguguacg   2820
ccgugaggua caaggugaac gagaacccac uguacgcucc caccagcgag cacgugaacg   2880
ugcugcugac caggaccgag gacaggaucg uguggaagac ccuggccggc gaccccugga   2940
ucaagacccu gaccgccaag uaccccggca acuucaccgc caccaucgaa gaguggcagg   3000
ccgagcacga cgccaucaug aggcacaucc uggagaggcc cgaccccacc gacguguucc   3060
agaacaaggc caacgugugc ugggccaagg cccuggugcc cgugcugaag accgccggca   3120
ucgacaugac cacagagcag uggaacaccg uggacuacuu cgagaccgac aaggcccaca   3180
gcgccgagau cgugcugaac cagcugugcg ugagguucuu cggccuggac cuggacagcg   3240
gccuguucag cgcccccacc gugccacuga gcaucaggaa caaccacugg gacaacagcc   3300
ccagcccaaa cauguacggc cugaacaagg agguggucag gcagcugagc aggcgguacc   3360
cacagcugcc cagggccgug gccaccggca ggguguacga caugaacacc ggcacccuga   3420
ggaacuacga ccccaggauc aaccuggugc ccgugaacag gcggcugccc cacgcccugg   3480
ugcugcacca caacgagcac cccacagagcg acuucagcuc cuucgugagc aagcugaaag   3540
gcaggaccgu gcuggucgug ggcgagaagc ugagcgugcc cggcaagaug guggacuggc   3600
ugagcgacag gcccgaggcc accuuccggg ccaggcugga ccucggcauc cccggcgacg   3660
ugcccaagua cgacaucauc uucgugaacg ucaggacccc auacaaguac caccauuacc   3720
agcagugcga ggaccacgcc aucaagcuga gcaugcugac caagaaggcc ugccugcacc   3780
ugaaccccgg aggcaccugc gugagcaucg gcuacggcua cgccgacagg gccagcgaga   3840
gcaucauugg cgccaucgcc aggcuguuca aguucagcag ggugugcaaa cccaagagca   3900
gccuggagga aaccgaggug cuguucgugu ucaucggcua cgaccggaag gccaggaccc   3960
acaaccccua caagcugagc agcacccuga caaacaucua caccggcagc aggcugcacg   4020
aggccggcug cgcccccagc uaccacgugg ucaggggcga uaucgccacc gccaccgagg   4080
gcgugaucau caacgcugcc aacagcaagg gccagcccgg aggcggagug ugcggcgccc   4140
uguacaagaa guuccccgag agcuucgacc ugcagcccau cgaggugggc aaggccaggc   4200
uggugaaggg cgccgcuaag cacaucaucc acgccguggg ccccaacuuc aacaaggua    4260
gcgaggugga aggcgacaag cagcuggccg aagccuacga gagcaucgcc aagaucguga   4320
acgacaauaa cuacaagagc guggccaucc cacugcucag caccggcauc uucagcggca   4380
acaaggacag gcugacccag agccugaacc accugcucac cgcccuggac accaccgaug   4440
ccgacguggc caucuacugc agggacaaga agugggagau gacccugaag gaggccgugg   4500
ccaggcggga ggccguggaa gagaucugca ucagcgacga cuccagcgug accgagcccg   4560
acgccgagcu ggugagggug caccccaaga gcucccuggc cggcaggaag ggcuacagca   4620
ccagcgacgg caagaccuuc agcuaccugg agggcaccaa guuccaccag gccgcuaagg   4680
acaucgccga gaucaacgcu auguggcccg uggccaccga ggccaacgag cagguguca    4740
uguacauccu gggcgagagc auguccagca ucaggagcaa gugccccgug gaggaaagcg   4800
aggccagcac accacccagc acccugcccu gccugugcau ccacgcuaug acacccgaga   4860
gggugcagcg gcugaaggcc agcaggcccg agcagaucac cgugugcagc uccuucccac   4920
ugcccaagua caggaucacc ggcgugcaga agauccagug cagccagccc auccuguuca   4980
gcccaaaggu gcccgccuac auccacccca ggaaguaccu gguggagacc ccacccgugg   5040
acgagacacc cgagccaagc gccgagaacc agagcaccga gggcacaccc gagcagccac   5100
```

cccugaucac cgaggacgag acaaggaccc ggaccccaga gcccaucauu aucgaggaag 5160
aggaagagga cagcaucagc cugcugagcg acggccccac ccaccaggug cugcaggugg 5220
aggccgacau ccacggccca cccagcgugu ccagcuccag cuggagcauc ccacacgcca 5280
gcgacuucga cguggacagc cugagcaucc uggacacccu ggagggcgcc agcgugaccu 5340
ccggcgccac cagcgccgag accaacagcu acuucgccaa gagcauggag uuccuggcca 5400
ggcccgugcc agcucccagg accguguuca ggaacccacc ccacccagcu cccaggacca 5460
ggaccccaag ccuggcuccc agcagggccu gcagcaggac cagccuggug agcaccccac 5520
ccggcgugaa cagggugauc accagggagg aacuggaggc ccugacaccc agcaggaccc 5580
ccagcagguc cgugagcagg acuagucugg uguccaaccc acccggcgug aacaggguga 5640
ucaccaggga ggaauucgag gccuucgugg cccagcaaca gagacgguuc gacgccggcg 5700
ccuacaucuu cagcagcgac accggccagg gacaccugca gcaaaagagc gugaggcaga 5760
ccgugcugag cgagguggug cuggagagga ccgagcugga aaucagcuac gcccccaggc 5820
uggaccagga gaaggaggaa cugcucagga agaaacugca gcugaacccc accccagcca 5880
acaggagcag guaccagagc aggaaggugg agaacaugaa ggccaucacc gccaggcgga 5940
uccugcaggg ccugggacac uaccugaagg ccgagggcaa gguggagugc uacaggaccc 6000
ugcaccccgu gccacuguac agcuccagcg ugaacagggc cuucuccagc cccaaggugg 6060
ccguggaggc cugcaacgcu augcugaagg agaacuuccc caccguggcc agcuacugca 6120
ucauccccga guacgacgcc uaccuggaca ugguggacgg cgccagcugc ugccuggaca 6180
ccgccagcuu cugccccgcc aagcugagga gcuuccccaa gaaacacagc uaccuggagc 6240
ccaccaucag gagcgccgug cccagcgcca uccagaacac ccugcagaac gugcuggccg 6300
cugccaccaa gaggaacugc aacgugaccc agaugaggga gcugcccgug cuggacagcg 6360
cugccuucaa cguggagugc uucaagaaau acgccugcaa caacgaguac ugggagaccu 6420
ucaaggagaa ccccaucagg cugaccgaag agaacguggu gaacuacauc accaagcuga 6480
agggccccaa ggccgcugcc cuguucgcua agacccacaa ccugaacaug cugcaggaca 6540
ucccaaugga cagguucgug auggaccuga agagggacgu gaaggugaca cccggcacca 6600
agcacaccga ggagaggccc aaggugcagg ugauccaggc cgcugaccca cuggccaccg 6660
ccuaccugug cggcauccac agggagcugg ugaggcggcu gaacgccgug cugcugccca 6720
acauccacac ccuguucgac augagcgccg aggacuucga cgccaucauc gccgagcacu 6780
uccagcccgg cgacugcgug cuggagaccg acaucgccag cuucgacaag agcgaggaug 6840
acgcuauggc ccugaccgcu cugaugaucc uggaggaccu gggcguggac gccgagcugc 6900
ucacccugau cgaggcugcc uucggcgaga ucagcuccau ccaccugccc accaagacca 6960
aguucaaguu cggcgcuaug augaaaagcg gaauguuccu gacccuguuc gugaacaccg 7020
ugaucaacau ugugaucgcc agcagggugc ugcgggagag gcugaccggc agccccugcg 7080
cugccuucau cggcgacgac aacaucguga agggcgugaa aagcgacaag cugauggccg 7140
acaggugcgc caccuggcug aacauggagg ugaagaucau cgacgccgug gugggcgaga 7200
aggcccccua cuucugcggc ggauucaucc ugugcgacag cgugaccggc accgccugca 7260
gggugggcga cccccugaag aggcuguuca agcugggcaa gccacuggcc gcugacgaug 7320
agcacgacga ugacaggcgg agggcccugc acgaggaaag caccaggugg aacagggugg 7380
gcauccugag cgagcugugc aaggccgugg agagcaggua cgagaccgug ggcaccagca 7440
ucaucgugau ggcuaugacc acacuggcca gcuccgucaa gagcuucucc uaccugaggg 7500
gggccccuau aacucucuac ggcuaaccug aauggacuac gacauagucu aguccgccaa 7560
ggccgccacc augagaguga cagccccuag aaccuuacug cuucugcuuu ggggagcugu 7620
ugcucugaca gagacauggg cuggaucuua ccacagcccc agcuacgccu accaccaguu 7680
cgagaggggg ggaggaggcu ccgggggagg aggcucccug aagaucagcc aggccgugca 7740
cgccgcccac gccgagauca acgaggccgg ccgggaggug aucgugggca uugucgcugg 7800
ccuggccguc cucgccgugg uggugauugg agcugugguc gcagcuguua ugugcagaag 7860
aaagucaucc ggcggaaagg gaggcuccua cucucaggcu gcuucugcua cagugccuag 7920
agcucuuaug uguuuaucuc agcuguaaac ucgaguaugu uacgugcaaa ggugauuguc 7980 acccccccgaa agaccauauu gugacacacc cucaguauca cgcccaaaca uuuacagccg 8040
cggugucaaa aaccgcgugg acgugguuaa caucccugcu gggaggauca gccguaauua 8100
uuauaauugg cuuggugcug gcuacuauug uggccaugua cgugcugacc aaccagaaac 8160
auaauugaau acagcagcaa uuggcaagcu gcuuacauag aacucgcggc gauuggcaug 8220
ccgccuuaaa auuuuuauuu uauuuuuucu uuucuuuucc gaaucggauu uuguuuuuaa 8280
uauuucaaaa aaaaaaaaaa aaaaaaaaaa aucuagaaaa aaaaaaaaaa aaaaaaaaaa 8340
aaaaaaaaaa aaaaaaaaaa aaaaaaaaaa aaaaaaaaaa aaaaaaaaaa aaaaaaaaaa 8400
aaaaaaaaaa aaaaaa 8416

<210> SEQ ID NO 107
<211> LENGTH: 8914
<212> TYPE: RNA
<213> ORGANISM: Artificial sequence
<220> FEATURE:
<223> OTHER INFORMATION: Synthetic polynucleotide

<400> SEQUENCE: 107
augggcggcg caugagagaa gcccagacca auuaccuacc caaaauggag aaaguucacg 60
uugacaucga ggaagacagc ccauuccuca gagcuuugca gcggagcuuc ccgcaguuug 120
agguagaagc caagcagguc acugauaaug accaugcuaa ugccagagcg uuuucgcauc 180
uggcuucaaa acugaucgaa acggaggugg acccauccga cacgauccuu gacauuggaa 240
gugcgcccgc ccgcagaaug uauucuaagc acaaguauca uuguaucugu ccgaugagau 300
gugcggaaga uccggacaga uuguauaagu augcaacuaa gcugaagaaa aacuguaagg 360
aaauaacuga uaaggaauug gacaagaaaa ugaaggagcu ggccgccguc augagcgacc 420
cugaccugga aacugagacu augugccucc acgacgacga gucgugucgc uacgaagggc 480
aagucgcugu uuaccaggau guauacgccg ucgacggccc caccagccug uaccaccagg 540
ccaacaaggg cgugagggug gccuacugga ucggcuucga caccacaccc uucauguuca 600
agaaccuggc cggcgccuac cccagcuaca gcaccaacug ggccgacgag accgugcuga 660
ccgccaggaa caucggccug ugcagcagcg acgugaugga gaggagccgg agaggcauga 720
gcauccugag gaagaaauac cugaagccca gcaacaacgu gcuguucagc gugggcagca 780
ccaucuacca cgagaagagg gaccugcuca ggagcuggca ccugcccagc guguuccacc 840
ugaggggcaa gcagaacuac accugcaggu gcgagaccau cgugagcugc gacggcuacg 900
uggugaagag gaucgccauc agccccggcc uguacggcaa gcccagcggc uacgccgcua 960
caaugcacag ggagggcuuc cugugcugca aggugaccga cacccugaac ggcgagaggg 1020
ugagcuuccc cgugugcacc uacgugcccg ccacccugug cgaccagaug accggcaucc 1080
uggccaccga cgugagcgcc gacgacgccc agaagcugcu cgugggccug aaccagagga 1140
ucguggucaa cggcaggacc cagaggaaca ccaacacaau gaagaacuac cugcugcccg 1200
ugguggccca ggcuuucgcc aggugggcca aggaguacaa ggaggaccag gaagacgaga 1260
ggccccuggg ccugagggac aggcagcugg ugaugggcug cugcugggcc uucaggcggc 1320
acaagaucac cagcaucuac aagaggcccg acacccagac caucaucaag gugaacagcg 1380
acuuccacag cuucgugcug cccaggaucg gcagcaacac ccuggagauc ggccugagga 1440
cccggaucag gaagaugcug gaggaacaca aggagcccag cccacugauc accgccgagg 1500
acgugcagga ggccaagugc gcugccgacg aggccaagga ggugagggag gccgaggaac 1560
ugagggccgc ccugccaccc cuggcugccg acguggagga acccacccug gaagccgacg 1620
uggaccugau gcugcaggag gccggcgccg gaagcgugga gacacccagg ggccugauca 1680
aggugaccag cuacgacggc gaggacaaga ucggcagcua cgccgugcug agcccacagg 1740
ccgugcugaa guccgagaag cugagcugca uccacccacu ggccgagcag gugaucguga 1800
ucacccacag cggcaggaag ggcagguacg ccguggagcc cuaccacggc aagguggucg 1860
ugcccgaggg ccacgccauc cccgugcagg acuuccaggc ccugagcgag agcgccacca 1920
ucguguacaa cgagagggag uucgugaaca gguaccugca ccauaucgcc acccacggcg 1980
gagcccugaa caccgacgag gaauacuaca agaccgugaa gcccagcgag cacgacggcg 2040
aguaccugua cgacaucgac aggaagcagu gcgugaagaa agagcuggug accggccugg 2100
gacugaccgg cgagcuggug gacccacccu uccacgaguu cgccuacgag agccugagga 2160
ccagacccgc cgcucccuac caggugccca ccaucggcgu guacggcgug cccggcagcg 2220
gaaagagcgg caucaucaag agcgccguga ccaagaaaga ccugguggcuc agcgccaaga 2280
aagagaacug cgccgagauc aucagggacg ugaagaagau gaaaggccug gacgugaacg 2340
cgcgcaccgu ggacagcgug cugcugaacg gcugcaagca ccccguggag acccuguaca 2400
ucgacgaggc cuucgcuugc cacgccggca cccugagggc ccugaucgcc aucaucaggc 2460
ccaagaaagc cgugcugugc ggcgacccca agcagugcgg cuucuucaac augaugugcc 2520
ugaaggugca cuucaaccac gagaucugca cccagguguu ccacaagagc aucagcaggc 2580
ggugcaccaa gagcgugacc agcgucguga gcacccuguu cuacgacaag aaaaugagga 2640
ccaccaaccc caaggagacc aaaaucguga ucgacaccac aggcagcacc aagcccaagc 2700
aggacgaccu gauccugacc ugcuucaggg gcugggugaa gcagcugcag aucgacuaca 2760
agggcaacga gaucaugacc gccgcugcca gccagggccu gaccaggaag ggcguguacg 2820
ccgugaggua caaggugaac gagaacccac uguacgcucc caccagcgag cacgugaacg 2880
ugcugcugac caggaccgag gacaggaucg uguggaagac ccuggccggc gaccccugga 2940
ucaagacccu gaccgccaag uaccccggca acuucaccgc caccaucgaa gaguggcagg 3000
ccgagcacga cgccaucaug aggcacaucc uggagaggcc cgaccccacc gacguguucc 3060
agaacaaggc caacgugugc ugggccaagg cccuggugcc cgugcugaag accgccggca 3120
ucgacaugac cacagagcag uggaacaccg uggacuacuu cgagaccgac aaggcccaca 3180
gcgccgagau cgugcugaac cagcugugcg ugagguucuu cggccuggac cuggacagcg 3240
gccuguucag cgcccccacc gugccacuga gcaucaggaa caaccacugg gacaacagcc 3300
ccagcccaaa cauguacggc cugaacaagg agguggucag gcagcugagc aggcgguacc 3360
cacagcugcc cagggccgug gccaccggca ggguguacga caugaacacc ggcacccuga 3420
ggaacuacga ccccaggauc aaccuggugc ccgugaacag gcggcugccc cacgcccugg 3480
ugcugcacca caacgagcac cccacagagcg acuucagcuc cuucgugagc aagcugaaag 3540
gcaggaccgu gcuggucgug ggcgagaagc ugagcgugcc cggcaagaug guggacuggc 3600
ugagcgacag gcccgaggcc accuuccggg ccaggcugga ccucggcauc cccggcgacg 3660
ugcccaagua cgacaucauc uucgugaacg ucaggacccc auacaaguac caccauuacc 3720
agcagugcga ggaccacgcc aucaagcuga gcaugcugac caagaaggcc ugccugcacc 3780
ugaaccccgg aggcaccugc gugagcaucg gcuacggcua cgccgacagg gccagcgaga 3840
gcaucauugg cgccaucgcc aggcuguuca aguucagcag ggugugcaaa cccaagagca 3900
gccuggagga aaccgaggug cuguucgugu ucaucggcua cgaccggaag gccaggaccc 3960
acaaccccua caagcugagc agcacccuga caaacaucua caccggcagc aggcugcacg 4020
aggccggcug cgcccccagc uaccacgugg ucaggggcga uaucgccacc gccaccgagg 4080
gcgugaucau caacgcugcc aacagcaagg gccagcccgg aggcggagug ugcggcgccc 4140
uguacaagaa guuccccgag agcuucgacc ugcagcccau cgaggugggc aaggccaggc 4200
uggugaaggg cgccgcuaag cacaucaucc acgccguggg ccccaacuuc aacaaggug a 4260 gcgaggugga aggcgacaag cagcuggccg aagccuacga gagcaucgcc aagaucguga 4320
acgacaauaa cuacaagagc guggccaucc cacugcucag caccggcauc uucagcggca 4380
acaaggacag gcugacccag agccugaacc accugcucac cgcccuggac accaccgaug 4440
ccgacguggc caucuacugc agggacaaga agugggagau gacccugaag gaggccgugg 4500
ccaggcggga ggccguggaa gagaucugca ucagcgacga cuccagcgug accgagcccg 4560
acgccgagcu ggugagggug caccccaaga gcucccuggc cggcaggaag ggcuacagca 4620
ccagcgacgg caagaccuuc agcuaccugg agggcaccaa guuccaccag gccgcuaagg 4680
acaucgccga gaucaacgcu auguggcccg uggccaccga ggccaacgag caggugugca 4740
uguacauccu gggcgagagc auguccagca ucaggagcaa gugccccgug gaggaaagcg 4800
aggccagcac accacccagc acccugcccu gccugugcau ccacgcuaug acacccgaga 4860
gggugcagcg gcugaaggcc agcaggcccg agcagaucac cgugugcagc uccuucccac 4920
ugcccaagua caggaucacc ggcgugcaga agauccagug cagccagccc auccuguuca 4980
gcccaaaggu gcccgccuac auccacccca ggaaguaccu gguggagacc ccacccgugg 5040
acgagacacc cgagccaagc gccgagaacc agagcaccga gggcacaccc gagcagccac 5100
cccugaucac cgaggacgag acaaggaccc ggaccccaga gcccaucauu aucgaggaag 5160
aggaagagga cagcaucagc cugcugagcg acggccccac ccaccaggug cugcaggugg 5220
aggccgacau ccacggccca cccagcgugu ccagcuccag cuggagcauc ccacacgcca 5280
gcgacuucga cguggacagc cugagcaucc uggacacccu ggagggcgcc agcgugaccu 5340
ccggcgccac cagcgccgag accaacagcu acuucgccaa gagcauggag uuccuggcca 5400
ggcccgugcc agcucccagg accguguuca ggaacccacc ccacccagcu cccaggacca 5460
ggaccccaag ccuggcuccc agcagggccu gcagcaggac cagccuggug agcaccccac 5520
ccggcgugaa cagggugauc accagggagg aacuggaggc ccugacaccc agcaggaccc 5580
ccagcagguc cgugagcagg acuagucugg uguccaaccc acccggcgug aacagggug a 5640 ucaccaggga ggaauucgag gccuucgugg cccagcaaca gagacgguuc gacgccggcg 5700
ccuacaucuu cagcagcgac accggccagg gacaccugca gcaaaagagc gugaggcaga 5760
ccgugcugag cgaggguggug cuggagagga ccgagcugga aaucagcuac gcccccaggc 5820

-continued

```
uggaccagga gaaggaggaa cugcucagga agaaacugca gcugaacccc accccagcca   5880
acaggagcag guaccagagc aggaaggugg agaacaugaa ggccaucacc gccaggcgga   5940
uccugcaggg ccugggacac uaccugaagg ccgagggcaa gguggagugc uacaggaccc   6000
ugcaccccgu gccacuguac agcuccagcg ugaacagggc cuucuccagc cccaaggugg   6060
ccguggaggc cugcaacgcu augcugaagg agaacuuccc caccguggcc agcuacugca   6120
ucauccccga guacgacgcc uaccuggaca ugguggacgg cgccagcugc ugccuggaca   6180
ccgccagcuu cugccccgcc aagcugagga gcuuccccaa gaaacacagc uaccuggagc   6240
ccaccaucag gagcgccgug cccagcgcca uccagaacac ccugcagaac gugcuggccg   6300
cugccaccaa gaggaacugc aacgugaccc agaugaggga gcugcccgug cuggacagcg   6360
cugccuucaa cguggagugc uucaagaaau acgccugcaa caacgaguac ugggagaccu   6420
ucaaggagaa ccccaucagg cugaccgaag agaacguggu gaacuacauc accaagcuga   6480
agggccccaa ggccgcugcc cuguucgcua agacccacaa ccugaacaug cugcaggaca   6540
ucccaaugga cagguucgug auggaccuga agagggacgu gaaggugaca cccggcacca   6600
agcacaccga ggagaggccc aaggugcagg ugauccaggc cgcugaccca cuggccaccg   6660
ccuaccugug cggcauccac agggagcugg ugaggcggcu gaacgccgug cugcugccca   6720
acauccacac ccuguucgac augagcgccg aggacuucga cgccaucauc gccgagcacu   6780
uccagcccgg cgacugcgug cuggagaccg acaucgccag cuucgacaag agcgaggaug   6840
acgcuauggc ccugaccgcu cugaugaucc uggaggaccu gggcguggac gccgagcugc   6900
ucacccugau cgaggcugcc uucggcgaga ucagcuccau ccaccugccc accaagacca   6960
aguucaaguu cggcgcuaug augaaaagcg gaauguuccu gacccuguuc gugaacaccg   7020
ugaucaacau ugugaucgcc agcagggugc ugcgggagag gcugaccggc agccccugcg   7080
cugccuucau cggcgacgac aacaucguga agggcgugaa aagcgacaag cugauggccg   7140
acaggugcgc caccuggcug aacauggagg ugaagaucau cgacgccgug gugggcgaga   7200
aggcccccua cuucugcggc ggauucaucc ugugcgacag cgugaccggc accgccugca   7260
ggguggccga cccccugaag aggcuguuca agcugggcaa gccacuggcc gcugacgaug   7320
agcacgacga ugacaggcgg agggcccugc acgaggaaag caccaggugg aacagggugg   7380
gcauccugag cgagcugugc aaggccgugg agagcaggua cgagaccgug ggcaccagca   7440
ucaucgugau ggcuaugacc acacuggcca gcuccgucaa gagcuucucc uaccugaggg   7500
gggccccuau aacucucuac ggcuaaccug aauggacuac gacauagucu aguccgccaa   7560
ggccgccacc augagaguga cagccccuag aaccuuacug cuucugcuuu ggggagcugu   7620
ugcucugaca gagacauggg cuggaucucu gagcgaggug accggccagg gccugugcau   7680
cggcgccgug cccaagaccc accaggugcu gugcaacacc acccagaaga ccagcgacgg   7740
cagcuacuac cuggccgcuc ccaccggcac caccugggcc ugcagcaccg gccugacccc   7800
uugcaucagc accaccaucc ugaaccugac caccgacuac ugcgugcugg uggagcugug   7860
gcccagggug accuaccaca gccccagcua cgccuaccac caguucgaga ggagggccaa   7920
guacaagagg gagcccguga gccugacccu ggcccugcug cugggcggcc ugacaauggg   7980
cggcaucgcc gccggcgugg gcaccggcac caccgcccug guggccaccc agcaguucca   8040
gcagcugcag gccgccaugc acgacgaccu gaaggaggug gagaagucca ucaccaaccu   8100
ggagaagucc cugaccagcc ugagcgaggu ggugcugcag aacaggaggg gccuggaccu   8160
```

gcuguuccug aaggagggcg gccugugcgc cgcccugaag gaggagugcu gccuguacgc 8220
cgaccacacc ggccugguga ucgugggcau ugucgcuggc cuggccgucc ucgccguggu 8280
ggugauugga gcuguggucg cagcuguuau gugcagaaga aagucauccg gcggaaaggg 8340
aggcuccuac ucucaggcug cuucugcuac agugccuaga gcucuuaugu guuuaucuca 8400
gcugggcggc ggaggcagcg acuacaagga cgacgaugac aaguaaacuc gaguauguua 8460
cgugcaaagg ugauugucac ccccgaaag accauauugu gacacacccu caguaucacg 8520
cccaaacauu uacagccgcg gugucaaaaa ccgcguggac gugguuaaca ucccugcugg 8580
gaggaucagc cguaauuauu auaauuggcu uggugcuggc uacuauugug gccauguacg 8640
ugcugaccaa ccagaaacau aauugaauac agcagcaauu ggcaagcugc uuacauagaa 8700
cucgcggcga uuggcaugcc gccuuaaaau uuuuauuuua uuuuuucuuu ucuuuuccga 8760
aucggauuuu guuuuuaaua uuucaaaaaa aaaaaaaaaa aaaaaaaaau cuagaaaaaa 8820
aaaaaaaaaa aaaaaaaaaa aaaaaaaaaa aaaaaaaaaa aaaaaaaaaa aaaaaaaaaa 8880
aaaaaaaaaa aaaaaaaaaa aaaaaaaaaa aaaa 8914

<210> SEQ ID NO 108
<211> LENGTH: 8455
<212> TYPE: RNA
<213> ORGANISM: Artificial sequence
<220> FEATURE:
<223> OTHER INFORMATION: Synthetic polynucleotide

<400> SEQUENCE: 108
augggcggcg caugagagaa gcccagacca auuaccuacc caaaauggag aaaguucacg 60
uugacaucga ggaagacagc ccauuccuca gagcuuugca gcggagcuuc ccgcaguuug 120
agguagaagc caagcagguc acugauaaug accaugcuaa ugccagagcg uuuucgcauc 180
uggcuucaaa acugaucgaa acggaggugg acccauccga cacgauccuu gacauuggaa 240
gugcgcccgc ccgcagaaug uauucuaagc acaaguauca uuguaucugu ccgaugagau 300
gugcggaaga uccggacaga uuguauaagu augcaacuaa gcugaagaaa aacuguaagg 360
aaauaacuga uaaggaauug gacaagaaaa ugaaggagcu ggccgccguc augagcgacc 420
cugaccugga aacugagacu augugccucc acgacgacga gucgugucgc uacgaagggc 480
aagucgcugu uuaccaggau guauacgccg ucgacggccc caccagccug uaccaccagg 540
ccaacaaggg cgugagggug gccuacugga ucggcuucga caccacaccc uucauguuca 600
agaaccuggc cggcgccuac cccagcuaca gcaccaacug ggccgacgag accgugcuga 660
ccgccaggaa caucggccug ugcagcagcg acgugaugga gaggagccgg agaggcauga 720
gcauccugag gaagaaauac cugaagccca gcaacaacgu gcuguucagc gugggcagca 780
ccaucuacca cgagaagagg gaccugcuca ggagcuggca ccugcccagc guguuccacc 840
ugaggggcaa gcagaacuac accugcaggu gcgagaccau cgugagcugc gacggcuacg 900
uggugaagag gaucgccauc agccccggcc uguacggcaa gcccagcggc uacgccgcua 960
caaugcacag ggagggcuuc cugugcugca aggugaccga cacccugaac ggcgagaggg 1020
ugagcuuccc cgugugcacc uacgugcccg ccacccugug cgaccagaug accggcaucc 1080
uggccaccga cgugagcgcc gacgacgccc agaagcugcu cgugggccug aaccagagga 1140 ucgugguaa cggcaggacc cagaggaaca ccaacacaau gaagaacuac cugcugcccg 1200
ugguggccca ggcuuucgcc aggugggcca aggaguacaa ggaggaccag gaagacgaga 1260
ggccccuggg ccugagggac aggcagcugg ugaugggcug cugcugggcc uucaggcggc 1320
acaagaucac cagcaucuac aagaggcccg acacccagac caucaucaag gugaacagcg 1380
acuuccacag cuucgugcug cccaggaucg gcagcaacac ccuggagauc ggccugagga 1440
cccggaucag gaagaugcug gaggaacaca aggagcccag cccacugauc accgccgagg 1500
acgugcagga ggccaagugc gcugccgacg aggccaagga ggugagggag gccgaggaac 1560
ugagggccgc ccugccaccc cuggcugccg acguggagga acccacccug gaagccgacg 1620
uggaccugau gcugcaggag gccggcgccg gaagcgugga gacacccagg ggccugauca 1680
aggugaccag cuacgacggc gaggacaaga ucggcagcua cgccgugcug agcccacagg 1740
ccgugcugaa guccgagaag cugagcugca uccacccacu ggccgagcag gugaucguga 1800
ucacccacag cggcaggaag ggcagguacg ccguggagcc cuaccacggc aagguggucg 1860
ugcccgaggg ccacgccauc cccgugcagg acuuccaggc ccugagcgag agcgccacca 1920
ucguguacaa cgagagggag uucgugaaca gguaccugca ccauaucgcc acccacggcg 1980
gagcccugaa caccgacgag gaauacuaca agaccgugaa gcccagcgag cacgacggcg 2040
aguaccugua cgacaucgac aggaagcagu gcgugaagaa agagcuggug accggccugg 2100
gacugaccgg cgagcuggug gacccacccu uccacgaguu cgccuacgag agccugagga 2160
ccagacccgc cgcucccuac caggugccca ccaucggcgu guacggcgug cccggcagcg 2220
gaaagagcgg caucaucaag agcgccguga ccaagaaaga ccugguggug agcgccaaga 2280
aagagaacug cgccgagauc aucagggacg ugaagaagau gaaaggccug gacgugaacg 2340
cgcgcaccgu ggacagcgug cugcugaacg gcugcaagca ccccguggag acccuguaca 2400
ucgacgaggc cuucgcuugc cacgccggca cccugagggc ccugaucgcc aucaucaggc 2460
ccaagaaagc cgugcugugc ggcgacccca agcagugcgg cuucuucaac augaugugcc 2520
ugaaggugca cuucaaccac gagaucugca cccaggucuu ccacaagagc aucagcaggc 2580
ggugcaccaa gagcgugacc agcgucguga gcacccuguu cuacgacaag aaaaugagga 2640
ccaccaaccc caaggagacc aaaaucguga ucgacaccac aggcagcacc aagcccaagc 2700
aggacgaccu gauccugacc ugcuucaggg gcugggugaa gcagcugcag aucgacuaca 2760
agggcaacga gaucaugacc gccgcugcca gccagggccu gaccaggaag ggcguguacg 2820
ccgugaggua caaggugaac gagaacccac uguacgcucc caccagcgag cacgugaacg 2880
ugcugcugac caggaccgag gacaggaucg uguggaagac ccuggccggc gaccccugga 2940
ucaagacccu gaccgccaag uaccccggca acuucaccgc caccaucgaa gaguggcagg 3000
ccgagcacga cgccaucaug aggcacaucc uggagaggcc cgaccccacc gacguguucc 3060
agaacaaggc caacgugugc ugggccaagg cccuggugcc cgugcugaag accgccggca 3120
ucgacaugac cacagagcag uggaacaccg uggacuacuu cgagaccgac aaggcccaca 3180
gcgccgagau cgugcugaac cagcugugcg ugagguucuu cggccuggac cuggacagcg 3240
gccuguucag cgcccccacc gugccacuga gcaucaggaa caaccacugg gacaacagcc 3300
ccagcccaaa cauguacggc cugaacaagg agguggucag gcagcugagc aggcgguacc 3360
cacagcugcc cagggccgug gccaccggca gggugguacga caugaacacc ggcacccuga 3420
ggaacuacga ccccaggauc aaccuggugc ccgugaacag gcggcugccc cacgcccugg 3480
ugcugcacca caacgagcac cccacagagcg acuucagcuc cuucgugagc aagcugaaag 3540
gcaggaccgu gcuggucgug ggcgagaagc ugagcgugcc cggcaagaug guggacuggc 3600
ugagcgacag gcccgaggcc accuuccggg ccaggcugga ccucggcauc cccggcgacg 3660

-continued

```
ugcccaagua cgacaucauc uucgugaacg ucaggacccc auacaaguac caccauuacc   3720
agcagugcga ggaccacgcc aucaagcuga gcaugcugac caagaaggcc ugccugcacc   3780
ugaaccccgg aggcaccugc gugagcaucg gcuacggcua cgccgacagg gccagcgaga   3840
gcaucauugg cgccaucgcc aggcuguuca aguucagcag ggugugcaaa cccaagagca   3900
gccuggagga aaccgaggug cuguucgugu ucaucggcua cgaccggaag gccaggaccc   3960
acaaccccua caagcugagc agcacccuga caaacaucua caccggcagc aggcugcacg   4020
aggccggcug cgcccccagc uaccacgugg ucaggggcga uaucgccacc gccaccgagg   4080
gcgugaucau caacgcugcc aacagcaagg gccagcccgg aggcggagug ugcggcgccc   4140
uguacaagaa guuccccgag agcuucgacc ugcagcccau cgaggugggc aaggccaggc   4200
uggugaaggg cgccgcuaag cacaucaucc acgccguggg ccccaacuuc aacaagguga   4260
gcgaggugga aggcgacaag cagcuggccg aagccuacga gagcaucgcc aagaucguga   4320
acgacaauaa cuacaagagc guggccaucc cacugcucag caccggcauc uucagcggca   4380
acaaggacag gcugacccag agccugaacc accugcucac cgcccuggac accaccgaug   4440
ccgacguggc caucuacugc agggacaaga agugggagau gacccugaag gaggccgugg   4500
ccaggcggga ggccguggaa gagaucugca ucagcgacga cuccagcgug accgagcccg   4560
acgccgagcu ggugagggug caccccaaga gcucccuggc cggcaggaag ggcuacagca   4620
ccagcgacgg caagaccuuc agcuaccugg agggcaccaa guuccaccag gccgcuaagg   4680
acaucgccga gaucaacgcu auguggcccg uggccaccga ggccaacgag caggugugca   4740
uguacauccu gggcgagagc auguccagca ucaggagcaa gugccccgug gaggaaagcg   4800
aggccagcac accacccagc acccugcccu gccugugcau ccacgcuaug acacccgaga   4860
gggugcagcg gcugaaggcc agcaggcccg agcagaucac cgugugcagc uccuucccac   4920
ugcccaagua caggaucacc ggcgugcaga agauccagug cagccagccc auccuguuca   4980
gcccaaaggu gcccgccuac auccacccca ggaaguaccu gguggagacc ccacccgugg   5040
acgagacacc cgagccaagc gccgagaacc agagcaccga gggcacaccc gagcagccac   5100
cccugaucac cgaggacgag acaaggaccc ggaccccaga gcccaucauu aucgaggaag   5160
aggaagagga cagcaucagc cugcugagcg acggccccac ccaccaggug cugcaggugg   5220
aggccgacau ccacggccca cccagcgugu ccagcuccag cuggagcauc ccacacgcca   5280
gcgacuucga cguggacagc cugagcaucc uggacacccu ggagggcgcc agcgugaccu   5340
ccggcgccac cagcgccgag accaacagcu acuucgccaa gagcauggag uuccuggcca   5400
ggcccgugcc agcucccagg accguguuca ggaacccacc ccacccagcu cccaggacca   5460
ggaccccaag ccuggcuccc agcagggccu gcagcaggac cagccuggug agcaccccac   5520
ccggcgugaa cagggugauc accagggagg aacuggaggc ccugacaccc agcaggaccc   5580
ccagcagguc cgugagcagg acuagucugg uguccaaccc acccggcgug aacaggguga   5640
ucaccaggga ggaauucgag gccuucgugg cccagcaaca gagacgguuc gacgccggcg   5700
ccuacaucuu cagcagcgac accggccagg gacaccugca gcaaaagagc gugaggcaga   5760
ccgugcugag cgaggguggug cuggagagga ccgagcugga aaucagcuac gcccccaggc   5820
uggaccagga gaaggaggaa cugcucagga agaaacugca gcugaacccc accccagcca   5880
acaggagcag guaccagagc aggaaggugg agaacaugaa ggccaucacc gccaggcgga   5940
uccugcaggg ccugggacac uaccugaagg ccgagggcaa gguggagugc uacaggaccc   6000
ugcaccccgu gccacuguac agcuccagcg ugaacagggc cuucuccagc cccaaggugg   6060
```

```
ccguggaggc cugcaacgcu augcugaagg agaacuuccc caccguggcc agcuacugca   6120
ucauccccga guacgacgcc uaccuggaca ugguggacgg cgccagcugc ugccuggaca   6180
ccgccagcuu cugccccgcc aagcugagga gcuuccccaa gaaacacagc uaccuggagc   6240
ccaccaucag gagcgccgug cccagcgcca uccagaacac ccugcagaac gugcuggccg   6300
cugccaccaa gaggaacugc aacgugaccc agaugaggga gcugcccgug cuggacagcg   6360
cugccuucaa cguggagugc uucaagaaau acgccugcaa caacgaguac ugggagaccu   6420
ucaaggagaa ccccaucagg cugaccgaag agaacguggu gaacuacauc accaagcuga   6480
agggccccaa ggccgcugcc cuguucgcua agacccacaa ccugaacaug cugcaggaca   6540
ucccaaugga cagguucgug auggaccuga agagggacgu gaaggugaca cccggcacca   6600
agcacaccga ggagaggccc aaggugcagg ugauccaggc cgcugaccca cuggccaccg   6660
ccuaccugug cggcauccac agggagcugg ugaggcggcu gaacgccgug cugcugccca   6720
acauccacac ccuguucgac augagcgccg aggacuucga cgccaucauc gccgagcacu   6780
uccagcccgg cgacugcgug cuggagaccg acaucgccag cuucgacaag agcgaggaug   6840
acgcuauggc ccugaccgcu cugaugaucc uggaggaccu gggcguggac gccgagcugc   6900
ucacccugau cgaggcugcc uucggcgaga ucagcuccau ccaccugccc accaagacca   6960
aguucaaguu cggcgcuaug augaaaagcg gaauguuccu gacccuguuc gugaacaccg   7020
ugaucaacau ugugaucgcc agcagggugc ugcgggagag gcugaccggc agccccugcg   7080
cugccuucau cggcgacgac aacaucguga agggcgugaa aagcgacaag cugauggccg   7140
acaggugcgc caccuggcug aacauggagg ugaagaucau cgacgccgug gugggcgaga   7200
aggcccccua cuucugcggc ggauucaucc ugugcgacag cgugaccggc accgccugca   7260
gggugcccga cccccugaag aggcuguuca agcugggcaa gccacuggcc gcugacgaug   7320
agcacgacga ugacaggcgg agggcccugc acgaggaaag caccaggugg aacagggugg   7380
gcauccugag cgagcugugc aaggccgugg agagcaggua cgagaccgug ggcaccagca   7440
ucaucgugau ggcuaugacc acacuggcca gcuccgucaa gagcuucucc uaccugaggg   7500
gggccccuau aacucucuac ggcuaaccug aauggacuac gacauagucu aguccgccaa   7560
ggccgccacc augagaguga cagccccuag aaccuuacug cuucugcuuu ggggagcugu   7620
ugcucugaca gagacauggg cuggaucuua ccacagcccc agcuacgccu accaccaguu   7680
cgagaggggg ggaggaggcu ccgggggagg aggcucccug aagaucagcc aggccgugca   7740
cgccgcccac gccgagauca acgaggccgg ccgggaggug aucgugggca uugucgcugg   7800
ccuggccguc cucgccgugg uggugauugg agcuguggug gcagcuguua ugugcagaag   7860
aaagucaucc ggcggaaagg gaggcuccua cucucaggcu gcuucugcua cagugccuag   7920
agcucuuaug uguuuaucuc agcugggcgg cggaggcagc gacuacaagg acgacgauga   7980
caaguaaacu cgaguauguu acgugcaaag gugauuguca ccccccgaaa gaccauauug   8040
ugacacaccc ucaguaucac gcccaaacau uuacagccgc ggugucaaaa accgcgugga   8100
cgugguuaac aucccugcug ggaggaucag ccguaauuau uauaauuggc uuggugcugg   8160
cuacuauugu ggccauguac gugcugacca accagaaaca uaauugaaua cagcagcaau   8220
uggcaagcug cuuacauaga acucgcggcg auuggcaugc cgccuuaaaa uuuuuauuuu   8280
auuuuuucuu uucuuuuccg aaucggauuu uguuuuuaau auuucaaaaa aaaaaaaaaa   8340
aaaaaaaaaa ucuagaaaaa aaaaaaaaaa aaaaaaaaaa aaaaaaaaaa aaaaaaaaaa   8400
```

aaaaaaaaaa aaaaaaaaaa aaaaaaaaaa aaaaaaaaaa aaaaaaaaaa aaaaa 8455

<210> SEQ ID NO 109
<211> LENGTH: 2512
<212> TYPE: PRT
<213> ORGANISM: Artificial sequence
<220> FEATURE:
<223> OTHER INFORMATION: Synthetic polypeptide

<400> SEQUENCE: 109

Met Glu Lys Pro Val Val Asn Val Asp Val Asp Pro Gln Ser Pro Phe
1               5                   10                  15

Val Val Gln Leu Gln Lys Ser Phe Pro Gln Phe Glu Val Val Ala Gln
            20                  25                  30

Gln Val Thr Pro Asn Asp His Ala Asn Ala Arg Ala Phe Ser His Leu
        35                  40                  45

Ala Ser Lys Leu Ile Glu Leu Glu Val Pro Thr Thr Ala Thr Ile Leu
    50                  55                  60

Asp Ile Gly Ser Ala Pro Ala Arg Arg Met Phe Ser Glu His Gln Tyr
65                  70                  75                  80

His Cys Val Cys Pro Met Arg Ser Pro Glu Asp Pro Asp Arg Met Met
                85                  90                  95

Lys Tyr Ala Ser Lys Leu Ala Glu Lys Ala Cys Lys Ile Thr Asn Lys
            100                 105                 110

Asn Leu His Glu Lys Ile Lys Asp Leu Arg Thr Val Leu Asp Thr Pro
        115                 120                 125

Asp Ala Glu Thr Pro Ser Leu Cys Phe His Asn Asp Val Thr Cys Asn
    130                 135                 140

Met Arg Ala Glu Tyr Ser Val Met Gln Asp Val Tyr Ile Asn Ala Pro
145                 150                 155                 160

Gly Thr Ile Tyr His Gln Ala Met Lys Gly Val Arg Thr Leu Tyr Trp
                165                 170                 175

Ile Gly Phe Asp Thr Thr Gln Phe Met Phe Ser Ala Met Ala Gly Ser
            180                 185                 190

Tyr Pro Ala Tyr Asn Thr Asn Trp Ala Asp Glu Lys Val Leu Glu Ala
        195                 200                 205

Arg Asn Ile Gly Leu Cys Ser Thr Lys Leu Ser Glu Gly Arg Thr Gly
    210                 215                 220

Lys Leu Ser Ile Met Arg Lys Lys Glu Leu Lys Pro Gly Ser Arg Val
225                 230                 235                 240

Tyr Phe Ser Val Gly Ser Thr Leu Tyr Pro Glu His Arg Ala Ser Leu
                245                 250                 255

Gln Ser Trp His Leu Pro Ser Val Phe His Leu Asn Gly Lys Gln Ser
            260                 265                 270

Tyr Thr Cys Arg Cys Asp Thr Val Val Ser Cys Glu Gly Tyr Val Val
        275                 280                 285

Lys Lys Ile Thr Ile Ser Pro Gly Ile Thr Gly Glu Thr Val Gly Tyr
    290                 295                 300

Ala Val Thr His Asn Ser Glu Gly Phe Leu Leu Cys Lys Val Thr Asp
305                 310                 315                 320

Thr Val Lys Gly Glu Arg Val Ser Phe Pro Val Cys Thr Tyr Ile Pro
                325                 330                 335

Ala Thr Ile Cys Asp Gln Met Thr Gly Ile Met Ala Thr Asp Ile Ser
            340                 345                 350

Pro Asp Asp Ala Gln Lys Leu Leu Val Gly Leu Asn Gln Arg Ile Val

```
        355                 360                 365

Ile Asn Gly Arg Thr Asn Arg Asn Thr Asn Thr Met Gln Asn Tyr Leu
    370                 375                 380

Leu Pro Ile Ile Ala Gln Gly Phe Ser Lys Trp Ala Lys Glu Arg Lys
385                 390                 395                 400

Asp Asp Leu Asp Asn Glu Lys Met Leu Gly Thr Arg Glu Arg Lys Leu
                405                 410                 415

Thr Tyr Gly Cys Leu Trp Ala Phe Arg Thr Lys Lys Val His Ser Phe
            420                 425                 430

Tyr Arg Pro Pro Gly Thr Gln Thr Cys Val Lys Val Pro Ala Ser Phe
        435                 440                 445

Ser Ala Phe Pro Met Ser Ser Val Trp Thr Thr Ser Leu Pro Met Ser
    450                 455                 460

Leu Arg Gln Lys Leu Lys Leu Ala Leu Gln Pro Lys Lys Glu Glu Lys
465                 470                 475                 480

Leu Leu Gln Val Ser Glu Glu Leu Val Met Glu Ala Lys Ala Ala Phe
                485                 490                 495

Glu Asp Ala Gln Glu Glu Ala Arg Ala Glu Lys Leu Arg Glu Ala Leu
            500                 505                 510

Pro Pro Leu Val Ala Asp Lys Gly Ile Glu Ala Ala Ala Glu Val Val
        515                 520                 525

Cys Glu Val Glu Gly Leu Gln Ala Asp Ile Gly Ala Ala Leu Val Glu
    530                 535                 540

Thr Pro Arg Gly His Val Arg Ile Ile Pro Gln Ala Asn Asp Arg Met
545                 550                 555                 560

Ile Gly Gln Tyr Ile Val Val Ser Pro Asn Ser Val Leu Lys Asn Ala
                565                 570                 575

Lys Leu Ala Pro Ala His Pro Leu Ala Asp Gln Val Lys Ile Ile Thr
            580                 585                 590

His Ser Gly Arg Ser Gly Arg Tyr Ala Val Glu Pro Tyr Asp Ala Lys
        595                 600                 605

Val Leu Met Pro Ala Gly Gly Ala Val Pro Trp Pro Glu Phe Leu Ala
    610                 615                 620

Leu Ser Glu Ser Ala Thr Leu Val Tyr Asn Glu Arg Glu Phe Val Asn
625                 630                 635                 640

Arg Lys Leu Tyr His Ile Ala Met His Gly Pro Ala Lys Asn Thr Glu
                645                 650                 655

Glu Glu Gln Tyr Lys Val Thr Lys Ala Glu Leu Ala Glu Thr Glu Tyr
            660                 665                 670

Val Phe Asp Val Asp Lys Lys Arg Cys Val Lys Lys Glu Glu Ala Ser
        675                 680                 685

Gly Leu Val Leu Ser Gly Glu Leu Thr Asn Pro Pro Tyr His Glu Leu
    690                 695                 700

Ala Leu Glu Gly Leu Lys Thr Arg Pro Ala Val Pro Tyr Lys Val Glu
705                 710                 715                 720

Thr Ile Gly Val Ile Gly Thr Pro Gly Ser Gly Lys Ser Ala Ile Ile
                725                 730                 735

Lys Ser Thr Val Thr Ala Arg Asp Leu Val Thr Ser Gly Lys Lys Glu
            740                 745                 750

Asn Cys Arg Glu Ile Glu Ala Asp Val Leu Arg Leu Arg Gly Met Gln
        755                 760                 765

Ile Thr Ser Lys Thr Val Asp Ser Val Met Leu Asn Gly Cys His Lys
    770                 775                 780
```

```
Ala Val Glu Val Leu Tyr Val Asp Glu Ala Phe Ala Cys His Ala Gly
785                 790                 795                 800

Ala Leu Leu Ala Leu Ile Ala Ile Val Arg Pro Arg Lys Lys Val Val
                805                 810                 815

Leu Cys Gly Asp Pro Met Gln Cys Gly Phe Phe Asn Met Met Gln Leu
            820                 825                 830

Lys Val His Phe Asn His Pro Glu Lys Asp Ile Cys Thr Lys Thr Phe
        835                 840                 845

Tyr Lys Tyr Ile Ser Arg Arg Cys Thr Gln Pro Val Thr Ala Ile Val
    850                 855                 860

Ser Thr Leu His Tyr Asp Gly Lys Met Lys Thr Thr Asn Pro Cys Lys
865                 870                 875                 880

Lys Asn Ile Glu Ile Asp Ile Thr Gly Ala Thr Lys Pro Lys Pro Gly
                885                 890                 895

Asp Ile Ile Leu Thr Cys Phe Arg Gly Trp Val Lys Gln Leu Gln Ile
            900                 905                 910

Asp Tyr Pro Gly His Glu Val Met Thr Ala Ala Ala Ser Gln Gly Leu
        915                 920                 925

Thr Arg Lys Gly Val Tyr Ala Val Arg Gln Lys Val Asn Glu Asn Pro
    930                 935                 940

Leu Tyr Ala Ile Thr Ser Glu His Val Asn Val Leu Leu Thr Arg Thr
945                 950                 955                 960

Glu Asp Arg Leu Val Trp Lys Thr Leu Gln Gly Asp Pro Trp Ile Lys
                965                 970                 975

Gln Leu Thr Asn Ile Pro Lys Gly Asn Phe Gln Ala Thr Ile Glu Asp
            980                 985                 990

Trp Glu Ala Glu His Lys Gly Ile  Ile Ala Ala Ile Asn  Ser Pro Thr
        995                 1000                1005

Pro Arg  Ala Asn Pro Phe Ser  Cys Lys Thr Asn Val  Cys Trp Ala
    1010                1015                1020

Lys Ala  Leu Glu Pro Ile Leu  Ala Thr Ala Gly Ile  Val Leu Thr
    1025                1030                1035

Gly Cys  Gln Trp Ser Glu Leu  Phe Pro Gln Phe Ala  Asp Asp Lys
    1040                1045                1050

Pro His  Ser Ala Ile Tyr Ala  Leu Asp Val Ile Cys  Ile Lys Phe
    1055                1060                1065

Phe Gly  Met Asp Leu Thr Ser  Gly Leu Phe Ser Lys  Gln Ser Ile
    1070                1075                1080

Pro Leu  Thr Tyr His Pro Ala  Asp Ser Ala Arg Pro  Val Ala His
    1085                1090                1095

Trp Asp  Asn Ser Pro Gly Thr  Arg Lys Tyr Gly Tyr  Asp His Ala
    1100                1105                1110

Ile Ala  Ala Glu Leu Ser Arg  Arg Phe Pro Val Phe  Gln Leu Ala
    1115                1120                1125

Gly Lys  Gly Thr Gln Leu Asp  Leu Gln Thr Gly Arg  Thr Arg Val
    1130                1135                1140

Ile Ser  Ala Gln His Asn Leu  Val Pro Val Asn Arg  Asn Leu Pro
    1145                1150                1155

His Ala  Leu Val Pro Glu Tyr  Lys Glu Lys Gln Pro  Gly Pro Val
    1160                1165                1170

Glu Lys  Phe Leu Asn Gln Phe  Lys His His Ser Val  Leu Val Val
    1175                1180                1185
```

```
Ser Glu  Glu Lys Ile Glu Ala  Pro Arg Lys Arg Ile  Glu Trp Ile
    1190                 1195                 1200

Ala Pro  Ile Gly Ile Ala Gly  Ala Asp Lys Asn Tyr  Asn Leu Ala
    1205                 1210                 1215

Phe Gly  Phe Pro Pro Gln Ala  Arg Tyr Asp Leu Val  Phe Ile Asn
    1220                 1225                 1230

Ile Gly  Thr Lys Tyr Arg Asn  His His Phe Gln Gln  Cys Glu Asp
    1235                 1240                 1245

His Ala  Ala Thr Leu Lys Thr  Leu Ser Arg Ser Ala  Leu Asn Cys
    1250                 1255                 1260

Leu Asn  Pro Gly Gly Thr Leu  Val Val Lys Ser Tyr  Gly Tyr Ala
    1265                 1270                 1275

Asp Arg  Asn Ser Glu Asp Val  Val Thr Ala Leu Ala  Arg Lys Phe
    1280                 1285                 1290

Val Arg  Val Ser Ala Ala Arg  Pro Asp Cys Val Ser  Ser Asn Thr
    1295                 1300                 1305

Glu Met  Tyr Leu Ile Phe Arg  Gln Leu Asp Asn Ser  Arg Thr Arg
    1310                 1315                 1320

Gln Phe  Thr Pro His His Leu  Asn Cys Val Ile Ser  Ser Val Tyr
    1325                 1330                 1335

Glu Gly  Thr Arg Asp Gly Val  Gly Ala Ala Pro Ser  Tyr Arg Thr
    1340                 1345                 1350

Lys Arg  Glu Asn Ile Ala Asp  Cys Gln Glu Glu Ala  Val Val Asn
    1355                 1360                 1365

Ala Ala  Asn Pro Leu Gly Arg  Pro Gly Glu Gly Val  Cys Arg Ala
    1370                 1375                 1380

Ile Tyr  Lys Arg Trp Pro Thr  Ser Phe Thr Asp Ser  Ala Thr Glu
    1385                 1390                 1395

Thr Gly  Thr Ala Arg Met Thr  Val Cys Leu Gly Lys  Lys Val Ile
    1400                 1405                 1410

His Ala  Val Gly Pro Asp Phe  Arg Lys His Pro Glu  Ala Glu Ala
    1415                 1420                 1425

Leu Lys  Leu Leu Gln Asn Ala  Tyr His Ala Val Ala  Asp Leu Val
    1430                 1435                 1440

Asn Glu  His Asn Ile Lys Ser  Val Ala Ile Pro Leu  Leu Ser Thr
    1445                 1450                 1455

Gly Ile  Tyr Ala Ala Gly Lys  Asp Arg Leu Glu Val  Ser Leu Asn
    1460                 1465                 1470

Cys Leu  Thr Thr Ala Leu Asp  Arg Thr Asp Ala Asp  Val Thr Ile
    1475                 1480                 1485

Tyr Cys  Leu Asp Lys Lys Trp  Lys Glu Arg Ile Asp  Ala Ala Leu
    1490                 1495                 1500

Gln Leu  Lys Glu Ser Val Thr  Glu Leu Lys Asp Glu  Asp Met Glu
    1505                 1510                 1515

Ile Asp  Asp Glu Leu Val Trp  Ile His Pro Asp Ser  Cys Leu Lys
    1520                 1525                 1530

Gly Arg  Lys Gly Phe Ser Thr  Thr Lys Gly Lys Leu  Tyr Ser Tyr
    1535                 1540                 1545

Phe Glu  Gly Thr Lys Phe His  Gln Ala Ala Lys Asp  Met Ala Glu
    1550                 1555                 1560

Ile Lys  Val Leu Phe Pro Asn  Asp Gln Glu Ser Asn  Glu Gln Leu
    1565                 1570                 1575

Cys Ala  Tyr Ile Leu Gly Glu  Thr Met Glu Ala Ile  Arg Glu Lys
```

```
    1580                1585                1590

Cys Pro  Val Asp His Asn Pro  Ser Ser Ser Pro Pro  Lys Thr Leu
    1595                1600                1605

Pro Cys  Leu Cys Met Tyr Ala  Met Thr Pro Glu Arg  Val His Arg
    1610                1615                1620

Leu Arg  Ser Asn Asn Val Lys  Glu Val Thr Val Cys  Ser Ser Thr
    1625                1630                1635

Pro Leu  Pro Lys His Lys Ile  Lys Asn Val Gln Lys  Val Gln Cys
    1640                1645                1650

Thr Lys  Val Val Leu Phe Asn  Pro His Thr Pro Ala  Phe Val Pro
    1655                1660                1665

Ala Arg  Lys Tyr Ile Glu Val  Pro Glu Gln Pro Thr  Ala Pro Pro
    1670                1675                1680

Ala Gln  Ala Glu Glu Ala Pro  Glu Val Val Ala Thr  Pro Ser Pro
    1685                1690                1695

Ser Thr  Ala Asp Asn Thr Ser  Leu Asp Val Thr Asp  Ile Ser Leu
    1700                1705                1710

Asp Met  Asp Asp Ser Ser Glu  Gly Ser Leu Phe Ser  Ser Phe Ser
    1715                1720                1725

Gly Ser  Asp Asn Ser Ile Thr  Ser Met Asp Ser Trp  Ser Ser Gly
    1730                1735                1740

Pro Ser  Ser Leu Glu Ile Val  Asp Arg Arg Gln Val  Val Val Ala
    1745                1750                1755

Asp Val  His Ala Val Gln Glu  Pro Ala Pro Ile Pro  Pro Pro Arg
    1760                1765                1770

Leu Lys  Lys Met Ala Arg Leu  Ala Ala Ala Arg Lys  Glu Pro Thr
    1775                1780                1785

Pro Pro  Ala Ser Asn Ser Ser  Glu Ser Leu His Leu  Ser Phe Gly
    1790                1795                1800

Gly Val  Ser Met Ser Leu Gly  Ser Ile Phe Asp Gly  Glu Thr Ala
    1805                1810                1815

Arg Gln  Ala Ala Val Gln Pro  Leu Ala Thr Gly Pro  Thr Asp Val
    1820                1825                1830

Pro Met  Ser Phe Gly Ser Phe  Ser Asp Gly Glu Ile  Asp Glu Leu
    1835                1840                1845

Ser Arg  Arg Val Thr Glu Ser  Glu Pro Val Leu Phe  Gly Ser Phe
    1850                1855                1860

Glu Pro  Gly Glu Val Asn Ser  Ile Ile Ser Ser Arg  Ser Ala Val
    1865                1870                1875

Ser Phe  Pro Leu Arg Lys Gln  Arg Arg Arg Arg Arg  Ser Arg Arg
    1880                1885                1890

Thr Glu  Tyr Leu Thr Gly Val  Gly Gly Tyr Ile Phe  Ser Thr Asp
    1895                1900                1905

Thr Gly  Pro Gly His Leu Gln  Lys Lys Ser Val Leu  Gln Asn Gln
    1910                1915                1920

Leu Thr  Glu Pro Thr Leu Glu  Arg Asn Val Leu Glu  Arg Ile His
    1925                1930                1935

Ala Pro  Val Leu Asp Thr Ser  Lys Glu Glu Gln Leu  Lys Leu Arg
    1940                1945                1950

Tyr Gln  Met Met Pro Thr Glu  Ala Asn Lys Ser Arg  Tyr Gln Ser
    1955                1960                1965

Arg Lys  Val Glu Asn Gln Lys  Ala Ile Thr Thr Glu  Arg Leu Leu
    1970                1975                1980
```

Ser Gly Leu Arg Leu Tyr Asn Ser Ala Thr Asp Gln Pro Glu Cys
1985 1990 1995

Tyr Lys Ile Thr Tyr Pro Lys Pro Leu Tyr Ser Ser Ser Val Pro
2000 2005 2010

Ala Asn Tyr Ser Asp Pro Gln Phe Ala Val Ala Val Cys Asn Asn
2015 2020 2025

Tyr Leu His Glu Asn Tyr Pro Thr Val Ala Ser Tyr Gln Ile Thr
2030 2035 2040

Asp Glu Tyr Asp Ala Tyr Leu Asp Met Val Asp Gly Thr Val Ala
2045 2050 2055

Cys Leu Asp Thr Ala Thr Phe Cys Pro Ala Lys Leu Arg Ser Tyr
2060 2065 2070

Pro Lys Lys His Glu Tyr Arg Ala Pro Asn Ile Arg Ser Ala Val
2075 2080 2085

Pro Ser Ala Met Gln Asn Thr Leu Gln Asn Val Leu Ile Ala Ala
2090 2095 2100

Thr Lys Arg Asn Cys Asn Val Thr Gln Met Arg Glu Leu Pro Thr
2105 2110 2115

Leu Asp Ser Ala Thr Phe Asn Val Glu Cys Phe Arg Lys Tyr Ala
2120 2125 2130

Cys Asn Asp Glu Tyr Trp Glu Glu Phe Ala Arg Lys Pro Ile Arg
2135 2140 2145

Ile Thr Thr Glu Phe Val Thr Ala Tyr Val Ala Arg Leu Lys Gly
2150 2155 2160

Pro Lys Ala Ala Ala Leu Phe Ala Lys Thr Tyr Asn Leu Val Pro
2165 2170 2175

Leu Gln Glu Val Pro Met Asp Arg Phe Val Met Asp Met Lys Arg
2180 2185 2190

Asp Val Lys Val Thr Pro Gly Thr Lys His Thr Glu Glu Arg Pro
2195 2200 2205

Lys Val Gln Val Ile Gln Ala Ala Glu Pro Leu Ala Thr Ala Tyr
2210 2215 2220

Leu Cys Gly Ile His Arg Glu Leu Val Arg Arg Leu Thr Ala Val
2225 2230 2235

Leu Leu Pro Asn Ile His Thr Leu Phe Asp Met Ser Ala Glu Asp
2240 2245 2250

Phe Asp Ala Ile Ile Ala Glu His Phe Lys Gln Gly Asp Pro Val
2255 2260 2265

Leu Glu Thr Asp Ile Ala Ser Phe Asp Lys Ser Gln Asp Asp Ala
2270 2275 2280

Met Ala Leu Thr Gly Leu Met Ile Leu Glu Asp Leu Gly Val Asp
2285 2290 2295

Gln Pro Leu Leu Asp Leu Ile Glu Cys Ala Phe Gly Glu Ile Ser
2300 2305 2310

Ser Thr His Leu Pro Thr Gly Thr Arg Phe Lys Phe Gly Ala Met
2315 2320 2325

Met Lys Ser Gly Met Phe Leu Thr Leu Phe Val Asn Thr Val Leu
2330 2335 2340

Asn Val Val Ile Ala Ser Arg Val Leu Glu Glu Arg Leu Lys Thr
2345 2350 2355

Ser Arg Cys Ala Ala Phe Ile Gly Asp Asp Asn Ile Ile His Gly
2360 2365 2370

Val Val Ser Asp Lys Glu Met Ala Glu Arg Cys Ala Thr Trp Leu
2375 2380 2385

Asn Met Glu Val Lys Ile Ile Asp Ala Val Ile Gly Glu Arg Pro
2390 2395 2400

Pro Tyr Phe Cys Gly Gly Phe Ile Leu Gln Asp Ser Val Thr Ser
2405 2410 2415

Thr Ala Cys Arg Val Ala Asp Pro Leu Lys Arg Leu Phe Lys Leu
2420 2425 2430

Gly Lys Pro Leu Pro Ala Asp Asp Glu Gln Asp Glu Asp Arg Arg
2435 2440 2445

Arg Ala Leu Leu Asp Glu Thr Lys Ala Trp Phe Arg Val Gly Ile
2450 2455 2460

Thr Gly Thr Leu Ala Val Ala Val Thr Thr Arg Tyr Glu Val Asp
2465 2470 2475

Asn Ile Thr Pro Val Leu Leu Ala Leu Arg Thr Phe Ala Gln Ser
2480 2485 2490

Lys Arg Ala Phe Gln Ala Ile Arg Gly Glu Ile Lys His Leu Tyr
2495 2500 2505

Gly Gly Pro Lys
2510

<210> SEQ ID NO 110
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 110

Ser Pro Ser Tyr Val Tyr His Gln Phe
1 5

<210> SEQ ID NO 111
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 111

Ser Pro Ser Tyr Ala Tyr His Gln Phe
1 5

<210> SEQ ID NO 112
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 112

Thr Pro His Pro Ala Arg Ile Gly Leu
1 5

<210> SEQ ID NO 113
<211> LENGTH: 1701
<212> TYPE: RNA
<213> ORGANISM: Artificial sequence
<220> FEATURE:
<223> OTHER INFORMATION: Synthetic polynucleotide

<400> SEQUENCE: 113

```
augaaggcua uccugguggu gcugcucuac accuuugcca cagccaaugc ugacacccug      60

uguauuggcu accaugccaa caacagcaca gacacagugg acacaguguu ggagaagaau     120

gugacaguga cccacucugu gaaccuguug gaggacaaac acaauggcaa acuguguaaa     180

cugaggggag uggcuccacu gcaccugggc aaguguaaca uugcuggcug gauucugggc     240

aacccugagu gugagucccu gagcacagcc uccuccuggu ccuacauugu ggagacacca     300

uccucugaca auggcacuug uuacccugga gacuucauug acuaugagga acugagggaa     360

caacuuuccu cuguguccuc cuuugagagg uuugagauuu uuccaaagac cuccuccugg     420

ccaaaccaug acagcaacaa gggagugaca gcagccuguc cacaugcugg agccaagucc     480

uucuacaaga accugauuug gcuggugaag aagggcaacu ccuacccaaa acugagcaag     540

uccuacauca augacaaggg caaggaggug cuggugcugu ggggcaucca ccacccaagc     600

accucugcug accaacaguc ccucuaccag aaugcugacg ccuauguguu ugugggcucc     660

agcagauaca gcaagaaguu caagccugag auugccauca gaccaaaggu gagggaucag     720

gagggcagga ugaacuacua cuggacccug guggaaccug gagacaagau uaccuuugag     780

gcuacaggca accugguggu gccaagauau gccuuugcua uggagaggaa ugcuggcucu     840

ggcaucauca ucucugacac accuguccau gacuguaaca ccacuuguca gacaccaaag     900

ggagccauca acaccucccu gccauuccag aacauccacc caaucaccau uggcaagugu     960

ccaaaauaug ucaagagcac caaacugaga cuggcuacag gacugaggaa caucccaagc    1020

auccagagca ggggacuguu uggagccauu gcuggcuuca uugagggagg cuggacaggg    1080

augguggaug gcugguaugg cuaccaccac cagaaugaac agggcucugg cuaugcugcu    1140

gaccugaaaa gcacccagaa ugccauugau gagauuacca acaaggugaa cucugugauu    1200

gagaagauga acacccaguu cacagcagug ggcaaggagu ucaaccacuu ggagaagagg    1260

auugagaacc ugaacaagaa gguggaugau ggcuuccugg acaucuggac cuacaaugcu    1320

gaacugcugg ugcuguugga gaaugagagg acccuggacu accaugacag caaugugaag    1380

aaccucuaug agaaggugag gagccaacuu aaaaacaaug ccaaggagau uggcaauggc    1440

uguuuugagu ucuaccacaa gugugacaac acuuguaugg agucugugaa gaauggcacc    1500

uaugacuacc caaaauacuc ugaggaggcu aaacugaaca gggaggagau ugauggagug    1560

aaauuggaga gcaccaggau uuaccagauc cuggccaucu acagcaccgu ggccagcagc    1620

cuggugcugg uggugagccu gggcgccauc agcuucugga ugugcagcaa cggcagcuug    1680

cagugcagga ucugcaucua a                                              1701
```

<210> SEQ ID NO 114
<211> LENGTH: 566
<212> TYPE: PRT
<213> ORGANISM: Artificial sequence
<220> FEATURE:
<223> OTHER INFORMATION: Synthetic polypeptide

<400> SEQUENCE: 114

```
Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60
```

```
Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
        195                 200                 205

Tyr Gln Asn Ala Asp Ala Tyr Val Phe Val Gly Ser Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480
```

```
Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565
```

<210> SEQ ID NO 115
<211> LENGTH: 9911
<212> TYPE: RNA
<213> ORGANISM: Artificial sequence
<220> FEATURE:
<223> OTHER INFORMATION: Synthetic polynucleotide

<400> SEQUENCE: 115

```
gauaggcggc gcaugagaga agcccagacc aauuaccuac ccaaauagga gaaaguucac      60

guugacaucg aggaagacag cccauuccuc agagcuuugc agcggagcuu cccgcaguuu     120

gagguagaag ccaagcaggu cacugauaau gaccaugcua augccagagc guuuucgcau     180

cuggcuucaa aacugaucga aacggaggug gacccauccg acacgauccu ugacauugga     240

auagucagca uaguacauuu caucugacua auacuacaac accaccacca ugaauagagg     300

auucuuuaac augcucggcc gccgccccuu cccggccccc acugccaugu ggaggccgcg     360

gagaaggagg caggcggccc cgggaagcgg agcuacuaac uucagccugc ugaagcaggc     420

uggagacgug gaggagaacc cuggaccuga gaaaguucac guugacaucg aggaagacag     480

cccauuccuc agagcuuugc agcggagcuu cccgcaguuu gagguagaag ccaagcaggu     540

cacugauaau gaccaugcua augccagagc guuuucgcau cuggcuucaa aacugaucga     600

aacggaggug gacccauccg acacgauccu ugacauugga agugcgcccg cccgcagaau     660

guauucuaag cacaaguauc auuguaucug uccgaugaga ugugcggaag auccggacag     720

auuguauaag uaugcaacua agcugaagaa aaacuguaag gaaauaacug auaaggaauu     780

ggacaagaaa augaaggagc ucgccgccgu caugagcgac ccugaccugg aaacugagac     840

uaugugccuc cacgacgacg agucgugucg cuacgaaggg caagucgcug uuuaccagga     900

uguauacgcg guugacggac cgacaagucu cuaucaccaa gccaauaagg gaguuagagu     960

cgccuacugg auaggcuuug acaccacccc uuuuauguuu aagaacuugg cuggagcaua    1020

uccaucauac ucuaccaacu gggccgacga aaccguguua acggcucgua acauaggccu    1080

augcagcucu gacguuaugg agcggucacg uagagggaug uccauucuua gaaagaagua    1140

uuugaaacca uccaacaaug uucuauucuc uguuggcucg accaucuacc acgagaagag    1200

ggacuuacug aggagcuggc accugccguc uguauuucac uuacguggca agcaaaauua    1260

cacaugucgg ugugagacua uaguuaguug cgacggguac gucguuaaaa gaauagcuau    1320

caguccaggc cuguauggga agccuucagg cuaugcugcu acgaugcacc gcgagggauu    1380

cuugugcugc aaagugacag acacauugaa cggggagagg gucucuuuuc ccgugugcac    1440

guaugugcca gcuacauugu gugaccaaau gacuggcaua cuggcaacag augucagugc    1500

ggacgacgcg caaaaacugc ugguugggcu caaccagcgu auagucguca acggucgcac    1560
```

```
ccagagaaac accaauacca ugaaaaauua ccuuuugccc guaguggccc aggcauuugc   1620

uaggugggca aaggaauaua aggaagauca agaagaugaa aggccacuag gacuacgaga   1680

uagacaguua gucaugggu guuguugggc uuuuagaagg cacaagauaa caucuauuua   1740

uaagcgcccg gauacccaaa ccaucaucaa agugaacagc gauuuccacu cauucgugcu   1800

gcccaggaua ggcaguaaca cauuggagau cgggcugaga acaagaauca ggaaaauguu   1860

agaggagcac aaggagccgu caccucucau uaccgccgag gacguacaag aagcuaagug   1920

cgcagccgau gaggcuaagg aggugcguga agccgaggag uugcgcgcag cucuaccacc   1980

uuuggcagcu gauguugagg agcccacucu ggaagccgau gucgacuuga uguuacaaga   2040

ggcuggggcc ggcucagugg agacaccucg uggcuugaua aagguuacca gcuacgaugg   2100

cgaggacaag aucggcucuu acgcugugcu uucuccgcag gcuguacuca agagugaaaa   2160

auuaucuugc auccacccuc ucgcugaaca agucauagug auaacacacu cuggccgaaa   2220

agggcguuau gccguggaac cauaccaugg uaaaguagug gugccagagg gacaugcaau   2280

acccguccag gacuuucaag cucugaguga aagugccacc auuguguaca acgaacguga   2340

guucguaaac agguaccugc accauauugc cacacaugga ggagcgcuga acacugauga   2400

agaauauuac aaaacuguca agcccagcga gcacgacggc gaauaccugu acgacaucga   2460

caggaaacag ugcgucaaga aagaacuagu cacugggcua gggcucacag gcgagcuggu   2520

ggauccuccc uuccaugaau ucgccuacga gagucugaga acacgaccag ccgcuccuua   2580

ccaaguacca accauagggg uguauggcgu gccaggauca ggcaagucug gcaucauuaa   2640

aagcgcaguc accaaaaaag aucuaguggu gagcgccaag aaagaaaacu gugcagaaau   2700

uauaagggac gucaagaaaa ugaaagggcu ggacgucaau gccagaacug uggacucagu   2760

gcucuugaau ggaugcaaac accccguaga gacccuguau auugacgaag cuuuugcuug   2820

ucaugcaggu acucucagag cgcucauagc cauuauaaga ccuaaaaagg cagugcucug   2880

cggggauccc aaacagugcg guuuuuuuaa caugaugugc cugaaagugc auuuuaacca   2940

cgagauuugc acacaagucu uccacaaaag caucucucgc cguugcacua aaucugugac   3000

uucggucguc ucaaccuugu uuuacgacaa aaaaaugaga acgacgaauc cgaaagagac   3060

uaagauugug auugacacua ccggcaguac caaaccuaag caggacgauc ucauucucac   3120

uuguuucaga gggugggga agcaguugca aauagauuac aaaggcaacg aaauaaugac   3180

ggcagcugcc ucucaagggc ugacccguaa agguguguau gccguucggu acaaggugaa   3240

ugaaaauccu cuguacgcac ccaccucuga acaugugaac guccuacuga cccgcacgga   3300

ggaccgcauc guguggaaaa cacuagccgg cgacccaugg auaaaaacac ugacugccaa   3360

guacccuggg aauuucacug ccacgauaga ggaguggcaa gcagagcaug augccaucau   3420

gaggcacauc uuggagagac cggacccuac cgacgucuuc cagaauaagg caaacgugug   3480

uugggccaag gcuuuagugc cggugcugaa gaccgcuggc auagacauga ccacugaaca   3540

auggaacacu guggauuauu uugaaacgga caaagcucac ucagcagaga uaguauugaa   3600

ccaacuaugc gugagguucu uuggacucga ucuggacucc ggucuauuuu cugcacccac   3660

uguuccguua uccauuagga auaaucacug ggauaacucc ccgucgccua acauguacgg   3720

gcugaauaaa gaaguggucc gucagcucuc ucgcagguac ccacaacugc cucgggcagu   3780

ugccacugga agagucuaug acaugaacac ugguacacug cgcaauuaug auccgcgcau   3840

aaaccuagua ccuguaaaca gaagacugcc ucaugcuuua guccuccacc auaaugaaca   3900
```

cccacagagu gacuuuucuu cauucgucag caaauugaag ggcagaacug uccugguggu 3960
cggggaaaag uuguccgucc caggcaaaau gguugacugg uugucagacc ggccugaggc 4020
uaccuucaga gcucggcugg auuuaggcau cccaggugau gugcccaaau augacauaau 4080
auuuguuaau gugaggaccc cauauaaaua ccaucacuau cagcagugug aagaccaugc 4140
cauuaagcuu agcauguuga ccaagaaagc uugucugcau cugaaucccg gcggaaccug 4200
ugucagcaua gguuaugguu acgcugacag ggccagcgaa agcaucauug gugcuauagc 4260
gcggcaguuc aaguuuuccc ggguaugcaa accgaaaucc ucacuugaag agacggaagu 4320
ucuguuugua uucauugggu acgaucgcaa ggcccguacg cacaauccuu acaagcuuuc 4380
aucaaccuug accaacauuu auacagguuc cagacuccac gaagccggau gugcacccuc 4440
auaucaugug gugcgagggg auauugccac ggccaccgaa ggagugauua uaaaugcugc 4500
uaacagcaaa ggacaaccug gcggaggggu gugcggagcg cuguauaaga aauucccgga 4560
aagcuucgau uuacagccga ucgaaguagg aaaagcgcga cuggucaaag gugcagcuaa 4620
acauaucauu caugccguag gaccaaacuu caacaaaguu ucggagguug aaggugacaa 4680
acaguuggca gaggcuuaug aguccaucgc uaagauuguc aacgauaaca auuacaaguc 4740
aguagcgauu ccacuguugu ccaccggcau cuuuuccggg aacaaagauc gacuaaccca 4800
aucauugaac cauuugcuga cagcuuuaga caccacugau gcagauguag ccauauacug 4860
cagggacaag aaaugggaaa ugacucucaa ggaagcagug gcuaggagag aagcagugga 4920
ggagauaugc auauccgacg acucuucagu gacagaaccu gaugcagagc uggugagggu 4980
gcauccgaag aguucuuugg cuggaaggaa gggcuacagc acaagcgaug gcaaaacuuu 5040
cucauauuug gaagggacca aguuucacca ggcggccaag gauauagcag aaauuaaugc 5100
cauguggccc guugcaacgg aggccaauga gcagguaugc auguauaucc ucggagaaag 5160
caugagcagu auuaggucga aaugccccgu cgaagagucg gaagccucca caccaccuag 5220
cacgcugccu ugcuugugca uccaugccau gacuccagaa agaguacagc gccuaaaagc 5280
cucacgucca gaacaaauua cugugugcuc auccuuucca uugccgaagu auagaaucac 5340
uggugugcag aagauccaau gcucccagcc uauauuguuc ucaccgaaag ugccugcgua 5400
uauucaucca aggaaguauc ucguggaaac accaccggua gacgagacuc cggagccauc 5460
ggcagagaac caauccacag aggggacacc ugaacaacca ccacuuauaa ccgaggauga 5520
gaccaggacu agaacgccug agccgaucau caucgaagag gaagaagagg auagcauaag 5580
uuugcuguca gauggcccga cccaccaggu gcugcaaguc gaggcagaca uucacgggcc 5640
gcccucugua ucuagcucau ccugguccau uccucaugca uccgacuuug auguggacag 5700
uuuauccaua cuugacaccc uggagggagc uagcgugacc agcggggcaa cgucagccga 5760
gacuaacucu uacuucgcaa agaguaugga guuucuggcg cgaccggugc cugcgccucg 5820
aacaguauuc aggaacccuc cacaucccgc uccgcgcaca agaacaccgu cacuugcacc 5880
cagcagggcc ugcucgagaa ccagccuagu uuccaccccg ccaggcguga auagggugau 5940
cacuagagag gagcucgagg cgcuuacccc gucacgcacu ccuagcaggu cggucucgag 6000
aaccagccug gucuccaacc cgccaggcgu aaauagggug auuacaagag aggaguuuga 6060
ggcguucgua gcacaacaac aaugacgguu ugaugcgggu gcauacaucu uuuccuccga 6120
caccggucaa gggcauuuac aacaaaaauc aguaaggcaa acggugcuau ccgaaguggu 6180
guuggagagg accgaauugg agauuucgua ugccccgcgc cucgaccaag aaaaagaaga 6240
auuacuacgc aagaaauuac aguuaaaucc cacaccugcu aacagaagca gauaccaguc 6300
caggaaggug gagaacauga aagccauaac agcuagacgu auucugcaag gccuagggca 6360
uuauuugaag gcagaaggaa aaguggagug cuaccgaacc cugcauccug uuccuuugua 6420
uucaucuagu gugaaccgug ccuuuucaag ccccaagguc gcaguggaag ccuguaacgc 6480
cauguugaaa gagaacuuuc cgacuguggc uucuuacugu auuauuccag aguacgaugc 6540
cuauuuggac augguugacg gagcuucaug cugcuuagac acugccaguu uuugcccugc 6600
aaagcugcgc agcuuuccaa agaaacacuc cuauuuggaa cccacaauac gaucggcagu 6660
gccuucagcg auccagaaca cgcuccagaa cguccuggca gcugccacaa aaagaaauug 6720
caaugucacg caaaugagag aauugcccgu auuggauucg gcggccuuua auguggaaug 6780
cuucaagaaa uaugcgugua auaaugaaua uugggaaacg uuuaaagaaa accccaucag 6840
gcuuacugaa gaaaacgugg uaaauuacau uaccaaauua aaaggaccaa aagcugcugc 6900
ucuuuuugcg aagacacaua auuugaauau guugcaggac auaccaaugg acagguuugu 6960
aauggacuua aagagagacg ugaaagugac uccaggaaca aaacauacug aagaacggcc 7020
caagguacag gugauccagg cugccgaucc gcuagcaaca gcguaucugu gcggaaucca 7080
ccgagagcug guuaggagau uaaaugcggu ccugcuuccg aacauucaua cacuguuuga 7140
uaugucggcu gaagacuuug acgcuauuau agccgagcac uuccagccug ggauuguguu 7200
ucuggaaacu gacaucgcgu cguuugauaa aagugaggac gacgccaugg cucugaccgc 7260
guuaaugauu cuggaagacu uaggugugga cgcagagcug uugacgcuga uugaggcggc 7320
uuucggcgaa auuucaucaa uacauuugcu cacuaaaacu aaauuuaaau ucggagccau 7380
gaugaaaucu ggaauguucc ucacacuguu ugugaacaca gucauuaaca uuguaaucgc 7440
aagcagagug uugagagaac ggcuaaccgg aucaccaugu gcagcauuca uuggagauga 7500
caauaucgug aaaggaguca aaucggacaa auuaauggca gacaggugcg ccaccugguu 7560
gaauauggaa gucaagauua uagaugcugu ggugggcgag aaagcgccuu auuucugugg 7620
aggguuuauu uugugugacu ccgugaccgg cacagcgugc cguguggcag acccccuaaa 7680
aaggcuguuu aagcuuggca aaccucuggc agcagacgau gaacaugaug augacaggag 7740
aagggcauug caugaagagu caacacgcug gaaccgagug gguauucuuu cagagcugug 7800
caaggcagua gaaucaaggu augaaaccgu aggaacuucc aucauaguua uggccaugac 7860
uacucuagcu agcaguguua aaucauucag cuaccugaga ggggccccua uaacucucua 7920
cggcuaaccu gaauggacua cgacauaguc uaguccgcca agauaucgca ccauggaaga 7980
ugccaaaaac auuaagaagg gcccagcgcc auucuaccca cucgaagacg ggaccgccgg 8040
cgagcagcug cacaaagcca ugaagcgcua cgcccuggug cccggcacca ucgccuuuac 8100
cgacgcacau aucgaggugg acauuaccua cgccgaguac uucgagauga gcguucggcu 8160
ggcagaagcu augaagcgcu augggcugaa uacaaaccau cggaucgugg ugugcagcga 8220
gaauagcuug caguucuuca ugcccguguu gggugcccug uucaucggug uggcuguggc 8280
cccagcuaac gacaucuaca acgagcgcga gcugcugaac agcaugggca ucagccagcc 8340
caccgucgua uucgugagca agaaagggcu gcaaaagauc cucaacgugc aaaagaagcu 8400
accgaucaua caaaagauca ucaucaugga uagcaagacc gacuaccagg gcuuccaaag 8460
cauguacacc uucgugacuu cccauuugcc acccggcuuc aacgaguacg acuucgugcc 8520
cgagagcuuc gaccgggaca aaaccaucgc ccugaucaug aacaguagug gcaguaccgg 8580
auugcccaag ggcguagccc uaccgcaccg caccgcuugu guccgauuca gucaugcccg 8640
cgaccccauc uucggcaacc agaucauccc cgacaccgcu auccucagcg uggugccauu 8700
ucaccacggc uucggcaugu ucaccacgcu gggcuacuug aucugcggcu uucgggucgu 8760
gcucauguac cgcuucgagg aggagcuauu cuugcgcagc uugcaagacu auaagauuca 8820
aucugcccug cuggugccca cacuauuuag cuucuucgcu aagagcacuc ucaucgacaa 8880
guacgaccua agcaacuugc acgagaucgc cagcggcggg gcgccgcuca gcaaggaggu 8940
aggugaggcc guggccaaac gcuuccaccu accaggcauc cgacagggcu acggccugac 9000
agaaacaacc agcgccauuc ugaucacccc cgaaggggac gacaagccug gcgcaguagg 9060
caagguggug cccuucuucg aggcuaaggu gguggacuug gacaccggua agacacuggg 9120
ugugaaccag cgcggcgagc ugugcguccg uggccccaug aucaugagcg gcuacguuaa 9180
caaccccgag gcuacaaacg cucucaucga caaggacggc uggcugcaca gcggcgacau 9240
cgccuacugg gacgaggacg agcacuucuu caucguggac cggcugaagu cccugaucaa 9300
auacaagggc uaccagguag ccccagccga acuggagagc auccugcugc aacaccccaa 9360
caucuucgac gccgggggucg ccggccugcc cgacgacgau gccggcgagc ugcccgccgc 9420
agucgucgug cuggaacacg guaaaaccau gaccgagaag gagaucgugg acuauguggc 9480
cagccagguu acaaccgcca agaagcugcg cgguggugu guguucgugg acgaggugcc 9540
uaaaggacug accggcaagu uggacgcccg caagauccgc gagauucuca uuaaggccaa 9600
gaagggcggc aagaucgccg uguaaggcgc gccguuuaaa cggccggccu uaauuaagua 9660
acgauacagc agcaauuggc aagcugcuua cauagaacuc gcggcgauug gcaugccgcc 9720
uuaaaauuuu uauuuuauuu uuucuuuucu uuuccgaauc ggauuuuguu uuuaauauuu 9780
caaaaaaaaa aaaaaaaaaa aaaaaaucua gaaaaaaaaa aaaaaaaaaa aaaaaaaaaa 9840
aaaaaaaaaa aaaaaaaaaa aaaaaaaaaa aaaaaaaaaa aaaaaaaaaa aaaaaaaaaa 9900
aaaaaaaaaa a 9911

<210> SEQ ID NO 116
<211> LENGTH: 2117
<212> TYPE: RNA
<213> ORGANISM: Artificial sequence
<220> FEATURE:
<223> OTHER INFORMATION: Synthetic polynucleotide

<400> SEQUENCE: 116
aggaaacuua agucaacaca acauauacaa aacaaacgaa ucucaagcaa ucaagcauuc 60
uacuucuauu gcagcaauuu aaaucauuuc uuuuaaagca aaagcaauuu ucugaaaauu 120
uucaccauuu acgaacgaua gccaccauga aggcuauccu gguggugcug cucuacaccu 180
uugccacagc caaugcugac acccugugua uuggcuacca ugccaacaac agcacagaca 240
caguggacac aguguuggag aagaauguga cagugaccca cucugugaac cuguuggagg 300
acaaacacaa uggcaaacug uguaaacuga ggggaguggc uccacugcac cugggcaagu 360
guaacauugc uggcuggauu cugggcaacc cugaguguga gucccugagc acagccuccu 420
ccugguccua cauuguggag acaccauccu cugacaaugg cacuuguuac ccuggagacu 480
ucauugacua ugaggaacug agggaacaac uuuccucugu guccuccuuu gagagguuug 540
agauuuuucc aaagaccucc uccuggccaa accaugacag caacaaggga gugacagcag 600
ccuguccaca ugcuggagcc aaguccuucu acaagaaccu gauuuggcug gugaagaagg 660
gcaacuccua cccaaaacug agcaaguccu acaucaauga caagggcaag gaggugcugg 720 ugcuguggggg cauccaccac ccaagcaccu cugcugacca acagucccuc uaccagaaug 780

```
cugacgccua uguguuugug ggcuccagca gauacagcaa gaaguucaag ccugagauug    840
ccaucagacc aaaggugagg gaucaggagg gcaggaugaa cuacuacugg acccuggugg    900
aaccuggaga caagauuacc uuugaggcua caggcaaccu gguggugcca agauaugccu    960
uugcuaugga gaggaaugcu ggcucuggca ucaucaucuc ugacacaccu guccaugacu   1020
guaacaccac uugucagaca ccaaagggag ccaucaacac cucccugcca uuccagaaca   1080
uccacccaau caccauuggc aaguguccaa aauaugucaa gagcaccaaa cugagacugg   1140
cuacaggacu gaggaacauc ccaagcaucc agagcagggg acuguuugga gccauugcug   1200
gcuucauuga gggaggcugg acagggaugg uggauggcug guauggcuac caccaccaga   1260
augaacaggg cucuggcuau gcugcugacc ugaaaagcac ccagaaugcc auugaugaga   1320
uuaccaacaa ggugaacucu gugauugaga agaugaacac ccaguucaca gcagugggca   1380
aggaguucaa ccacuuggag aagaggauug agaaccugaa caagaaggug gaugauggcu   1440
uccuggacau cuggaccuac aaugcugaac ugcugguguu guuggagaau gagaggaccc   1500
uggacuacca ugacagcaau gugaagaacc ucuaugagaa ggugaggagc caacuuaaaa   1560
acaaugccaa ggagauuggc aauggcuguu uugaguucua ccacaagugu gacaacacuu   1620
guauggaguc ugugaagaau ggcaccuaug acuacccaaa auacucugag gaggcuaaac   1680
ugaacaggga ggagauugau ggagugaaau uggagagcac caggauuuac cagauccugg   1740
ccaucuacag caccguggcc agcagccugg ugcugguggu gagccugggc gccaucagcu   1800
ucuggaugug cagcaacggc agcuugcagu gcaggaucug caucuaaacu cgagcuagug   1860
acugacuagg aucugguuac cacuaaacca gccucaagaa cacccgaaug gagucucuaa   1920
gcuacauaau accaacuuac acuuacaaaa uguuguccccc caaaauguag ccauucguau   1980
cugcuccuaa uaaaaagaaa guuucuucac auucuagaaa aaaaaaaaaa aaaaaaaaaa   2040
aaaaaaaaaa aaaaaaaaaa aaaaaaaaaa aaaaaaaaaa aaaaaaaaaa aaaaaaaaaa   2100
aaaaaaaaaa aaaaaaa                                                 2117
```

```
<210> SEQ ID NO 117
<211> LENGTH: 10508
<212> TYPE: DNA
<213> ORGANISM: Artificial sequence
<220> FEATURE:
<223> OTHER INFORMATION: Synthetic polynucleotide

<400> SEQUENCE: 117
```

```
atgggcggcg catgagagaa gcccagacca attacctacc caaaatggag aaagttcacg     60
ttgacatcga ggaagacagc ccattcctca gagctttgca gcggagcttc ccgcagtttg    120
aggtagaagc caagcaggtc actgataatg accatgctaa tgccagagcg ttttcgcatc    180
tggcttcaaa actgatcgaa acggaggtgg acccatccga cacgatcctt gacattggaa    240
gtgcgcccgc ccgcagaatg tattctaagc acaagtatca ttgtatctgt ccgatgagat    300
gtgcggaaga tccggacaga ttgtataagt atgcaactaa gctgaagaaa aactgtaagg    360
aaataactga taaggaattg gacaagaaaa tgaaggagct ggccgccgtc atgagcgacc    420
ctgacctgga aactgagact atgtgcctcc acgacgacga gtcgtgtcgc tacgaagggc    480
aagtcgctgt ttaccaggat gtatacgccg tcgacggccc caccagcctg taccaccagg    540
ccaacaaggg cgtgagggtg gcctactgga tcggcttcga caccacaccc ttcatgttca    600
agaacctggc cggcgcctac cccagctaca gcaccaactg ggccgacgag accgtgctga    660
```

ccgccaggaa catcggcctg tgcagcagcg acgtgatgga gaggagccgg agaggcatga 720
gcatcctgag gaagaaatac ctgaagccca gcaacaacgt gctgttcagc gtgggcagca 780
ccatctacca cgagaagagg gacctgctca ggagctggca cctgcccagc gtgttccacc 840
tgaggggcaa gcagaactac acctgcaggt gcgagaccat cgtgagctgc gacggctacg 900
tggtgaagag gatcgccatc agccccggcc tgtacggcaa gcccagcggc tacgccgcta 960
caatgcacag ggagggcttc ctgtgctgca aggtgaccga caccctgaac ggcgagaggg 1020
tgagcttccc cgtgtgcacc tacgtgcccg ccaccctgtg cgaccagatg accggcatcc 1080
tggccaccga cgtgagcgcc gacgacgccc agaagctgct cgtgggcctg aaccagagga 1140
tcgtggtcaa cggcaggacc cagaggaaca ccaacacaat gaagaactac ctgctgcccg 1200
tggtggccca ggctttcgcc aggtgggcca aggagtacaa ggaggaccag gaagacgaga 1260
ggcccctggg cctgagggac aggcagctgg tgatgggctg ctgctgggcc ttcaggcggc 1320
acaagatcac cagcatctac aagaggcccg acacccagac catcatcaag gtgaacagcg 1380
acttccacag cttcgtgctg cccaggatcg gcagcaacac cctggagatc ggcctgagga 1440
cccggatcag gaagatgctg gaggaacaca aggagcccag cccactgatc accgccgagg 1500
acgtgcagga ggccaagtgc gctgccgacg aggccaagga ggtgagggag gccgaggaac 1560
tgagggccgc cctgccaccc ctggctgccg acgtggagga acccaccctg gaagccgacg 1620
tggacctgat gctgcaggag gccggcgccg gaagcgtgga gacacccagg ggcctgatca 1680
aggtgaccag ctacgacggc gaggacaaga tcggcagcta cgccgtgctg agcccacagg 1740
ccgtgctgaa gtccgagaag ctgagctgca tccacccact ggccgagcag gtgatcgtga 1800
tcacccacag cggcaggaag ggcaggtacg ccgtggagcc ctaccacggc aaggtggtcg 1860
tgcccgaggg ccacgccatc cccgtgcagg acttccaggc cctgagcgag agcgccacca 1920
tcgtgtacaa cgagagggag ttcgtgaaca ggtacctgca ccatatcgcc acccacggcg 1980
gagccctgaa caccgacgag gaatactaca agaccgtgaa gcccagcgag cacgacggcg 2040
agtacctgta cgacatcgac aggaagcagt gcgtgaagaa agagctggtg accggcctgg 2100
gactgaccgg cgagctggtg gacccaccct tccacgagtt cgcctacgag agcctgagga 2160
ccagacccgc cgctccctac caggtgccca ccatcggcgt gtacggcgtg cccggcagcg 2220
gaaagagcgg catcatcaag agcgccgtga ccaagaaaga cctggtggtc agcgccaaga 2280
aagagaactg cgccgagatc atcagggacg tgaagaagat gaaaggcctg gacgtgaacg 2340
cgcgcaccgt ggacagcgtg ctgctgaacg gctgcaagca ccccgtggag accctgtaca 2400
tcgacgaggc cttcgcttgc cacgccggca ccctgagggc cctgatcgcc atcatcaggc 2460
ccaagaaagc cgtgctgtgc ggcgacccca agcagtgcgg cttcttcaac atgatgtgcc 2520
tgaaggtgca cttcaaccac gagatctgca cccaggtgtt ccacaagagc atcagcaggc 2580
ggtgcaccaa gagcgtgacc agcgtcgtga gcaccctgtt ctacgacaag aaaatgagga 2640
ccaccaaccc caaggagacc aaaatcgtga tcgacaccac aggcagcacc aagcccaagc 2700
aggacgacct gatcctgacc tgcttcaggg gctgggtgaa gcagctgcag atcgactaca 2760
agggcaacga gatcatgacc gccgctgcca gccagggcct gaccaggaag ggcgtgtacg 2820
ccgtgaggta caaggtgaac gagaacccac tgtacgctcc caccagcgag cacgtgaacg 2880
tgctgctgac caggaccgag gacaggatcg tgtggaagac cctggccggc gacccctgga 2940
tcaagaccct gaccgccaag taccccggca acttcaccgc caccatcgaa gagtggcagg 3000
ccgagcacga cgccatcatg aggcacatcc tggagaggcc cgaccccacc gacgtgttcc 3060
agaacaaggc caacgtgtgc tgggccaagg ccctggtgcc cgtgctgaag accgccggca 3120
tcgacatgac cacagagcag tggaacaccg tggactactt cgagaccgac aaggcccaca 3180
gcgccgagat cgtgctgaac cagctgtgcg tgaggttctt cggcctggac ctggacagcg 3240
gcctgttcag cgcccccacc gtgccactga gcatcaggaa caaccactgg gacaacagcc 3300
ccagcccaaa catgtacggc ctgaacaagg aggtggtcag gcagctgagc aggcggtacc 3360
cacagctgcc cagggccgtg gccaccggca gggtgtacga catgaacacc ggcaccctga 3420
ggaactacga ccccaggatc aacctggtgc ccgtgaacag gcggctgccc cacgccctgg 3480
tgctgcacca caacgagcac ccacagagcg acttcagctc cttcgtgagc aagctgaaag 3540
gcaggaccgt gctggtcgtg ggcgagaagc tgagcgtgcc cggcaagatg gtggactggc 3600
tgagcgacag gcccgaggcc accttccggg ccaggctgga cctcggcatc cccggcgacg 3660
tgcccaagta cgacatcatc ttcgtgaacg tcaggacccc atacaagtac caccattacc 3720
agcagtgcga ggaccacgcc atcaagctga gcatgctgac caagaaggcc tgcctgcacc 3780
tgaaccccgg aggcacctgc gtgagcatcg gctacggcta cgccgacagg gccagcgaga 3840
gcatcattgg cgccatcgcc aggctgttca agttcagcag ggtgtgcaaa cccaagagca 3900
gcctggagga aaccgaggtg ctgttcgtgt tcatcggcta cgaccggaag gccaggaccc 3960
acaaccccta caagctgagc agcaccctga caaacatcta caccggcagc aggctgcacg 4020
aggccggctg cgcccccagc taccacgtgg tcaggggcga tatcgccacc gccaccgagg 4080
gcgtgatcat caacgctgcc aacagcaagg gccagcccgg aggcggagtg tgcggcgccc 4140
tgtacaagaa gttccccgag agcttcgacc tgcagcccat cgaggtgggc aaggccaggc 4200
tggtgaaggg cgccgctaag cacatcatcc acgccgtggg ccccaacttc aacaaggtga 4260
gcgaggtgga aggcgacaag cagctggccg aagcctacga gagcatcgcc aagatcgtga 4320
acgacaataa ctacaagagc gtggccatcc cactgctcag caccggcatc ttcagcggca 4380
acaaggacag gctgacccag agcctgaacc acctgctcac cgccctggac accaccgatg 4440
ccgacgtggc catctactgc agggacaaga agtgggagat gaccctgaag gaggccgtgg 4500
ccaggcggga ggccgtggaa gagatctgca tcagcgacga ctccagcgtg accgagcccg 4560
acgccgagct ggtgagggtg caccccaaga gctccctggc cggcaggaag ggctacagca 4620
ccagcgacgg caagaccttc agctacctgg agggcaccaa gttccaccag gccgctaagg 4680
acatcgccga gatcaacgct atgtggcccg tggccaccga ggccaacgag caggtgtgca 4740
tgtacatcct gggcgagagc atgtccagca tcaggagcaa gtgccccgtg gaggaaagcg 4800
aggccagcac accacccagc accctgccct gcctgtgcat ccacgctatg acacccgaga 4860
gggtgcagcg gctgaaggcc agcaggcccg agcagatcac cgtgtgcagc tccttcccac 4920
tgcccaagta caggatcacc ggcgtgcaga agatccagtg cagccagccc atcctgttca 4980
gcccaaaggt gcccgcctac atccacccca ggaagtacct ggtggagacc ccacccgtgg 5040
acgagacacc cgagccaagc gccgagaacc agagcaccga gggcacaccc gagcagccac 5100
ccctgatcac cgaggacgag acaaggaccc ggaccccaga gcccatcatt atcgaggaag 5160
aggaagagga cagcatcagc ctgctgagcg acggccccac ccaccaggtg ctgcaggtgg 5220
aggccgacat ccacggccca cccagcgtgt ccagctccag ctggagcatc ccacacgcca 5280
gcgacttcga cgtggacagc ctgagcatcc tggacaccct ggagggcgcc agcgtgacct 5340
ccggcgccac cagcgccgag accaacagct acttcgccaa gagcatggag ttcctggcca 5400

```
ggcccgtgcc agctcccagg accgtgttca ggaacccacc ccacccagct cccaggacca   5460
ggaccccaag cctggctccc agcagggcct gcagcaggac cagcctggtg agcaccccac   5520
ccggcgtgaa cagggtgatc accagggagg aactggaggc cctgacaccc agcaggaccc   5580
ccagcaggtc cgtgagcagg actagtctgg tgtccaaccc acccggcgtg aacagggtga   5640
tcaccaggga ggaattcgag gccttcgtgg cccagcaaca gagacggttc gacgccggcg   5700
cctacatctt cagcagcgac accggccagg gacacctgca gcaaaagagc gtgaggcaga   5760
ccgtgctgag cgaggtggtg ctggagagga ccgagctgga aatcagctac gcccccaggc   5820
tggaccagga gaaggaggaa ctgctcagga agaaactgca gctgaacccc accccagcca   5880
acaggagcag gtaccagagc aggaaggtgg agaacatgaa ggccatcacc gccaggcgga   5940
tcctgcaggg cctgggacac tacctgaagg ccgagggcaa ggtggagtgc tacaggaccc   6000
tgcaccccgt gccactgtac agctccagcg tgaacagggc cttctccagc cccaaggtgg   6060
ccgtggaggc ctgcaacgct atgctgaagg agaacttccc caccgtggcc agctactgca   6120
tcatccccga gtacgacgcc tacctggaca tggtggacgg cgccagctgc tgcctggaca   6180
ccgccagctt ctgccccgcc aagctgagga gcttccccaa gaaacacagc tacctggagc   6240
ccaccatcag gagcgccgtg cccagcgcca tccagaacac cctgcagaac gtgctggccg   6300
ctgccaccaa gaggaactgc aacgtgaccc agatgaggga gctgcccgtg ctggacagcg   6360
ctgccttcaa cgtggagtgc ttcaagaaat acgcctgcaa caacgagtac tgggagacct   6420
tcaaggagaa ccccatcagg ctgaccgaag agaacgtggt gaactacatc accaagctga   6480
agggccccaa ggccgctgcc ctgttcgcta agacccacaa cctgaacatg ctgcaggaca   6540
tcccaatgga caggttcgtg atggacctga agagggacgt gaaggtgaca cccggcacca   6600
agcacaccga ggagaggccc aaggtgcagg tgatccaggc cgctgaccca ctggccaccg   6660
cctacctgtg cggcatccac agggagctgg tgaggcggct gaacgccgtg ctgctgccca   6720
acatccacac cctgttcgac atgagcgccg aggacttcga cgccatcatc gccgagcact   6780
tccagcccgg cgactgcgtg ctggagaccg acatcgccag cttcgacaag agcgaggatg   6840
acgctatggc cctgaccgct ctgatgatcc tggaggacct gggcgtggac gccgagctgc   6900
tcaccctgat cgaggctgcc ttcggcgaga tcagctccat ccacctgccc accaagacca   6960
agttcaagtt cggcgctatg atgaaaagcg gaatgttcct gaccctgttc gtgaacaccg   7020
tgatcaacat tgtgatcgcc agcagggtgc tgcgggagag gctgaccggc agcccctgcg   7080
ctgccttcat cggcgacgac aacatcgtga agggcgtgaa aagcgacaag ctgatggccg   7140
acaggtgcgc cacctggctg aacatggagg tgaagatcat cgacgccgtg gtgggcgaga   7200
aggcccccta cttctgcggc ggattcatcc tgtgcgacag cgtgaccggc accgcctgca   7260
gggtggccga ccccctgaag aggctgttca agctgggcaa gccactggcc gctgacgatg   7320
agcacgacga tgacaggcgg agggccctgc acgaggaaag caccaggtgg aacagggtgg   7380
gcatcctgag cgagctgtgc aaggccgtgg agagcaggta cgagaccgtg ggcaccagca   7440
tcatcgtgat ggctatgacc acactggcca gctccgtcaa gagcttctcc tacctgaggg   7500
gggcccctat aactctctac ggctaacctg aatggactac gacatagtct agccaccatg   7560
agcaagatct acatcgacga gcggagcaac gccgagatcg tgtgcgaggc catcaagacc   7620
atcggcatcg agggcgccac cgccgcccag ctgaccaggc agctgaacat ggagaagcgg   7680
gaggtgaaca aggccctgta cgacctgcag aggagcgcta tggtgtactc cagcgacgac   7740
atccctcccc ggtggttcat gaccaccgag gccgacaagc ccgacgccga cgctatggcc   7800
```

gacgtgatca tcgacgacgt gagcagggag aagtccatga gggaggacca caagagcttc 7860
gacgacgtga tccccgccaa gaagatcatc gactggaagg gcgccaaccc cgtgaccgtg 7920
atcaacgagt actgccagat caccaggagg gactggagct tccggatcga gagcgtgggc 7980
cccagcaaca gccccacctt ctacgcctgc gtggacatcg acggcagggt gttcgacaag 8040
gccgacggca agagcaagcg ggacgccaag aacaacgccg ccaagctggc cgtggacaag 8100
ctgctgggct acgtgatcat ccggttctaa actcgagcta gtgactgact aggatctggt 8160
taccactaaa ccagcctcaa gaacacccga atggagtctc taagctacat aataccaact 8220
tacacttaca aaatgttgtc ccccaaaatg tagccattcg tatctgctcc taataaaaag 8280
aaagtttctt cacattctag agctccgtca agagcttctc ctacctgagg ggggccccta 8340
taactctcta cggctaacct gaatggacta cgacatagtc tagccaccat ggaagatgcc 8400
aaaaacatta agaagggccc agcgccattc tacccactcg aagacgggac cgccggcgag 8460
cagctgcaca aagccatgaa gcgctacgcc ctggtgcccg gcaccatcgc ctttaccgac 8520
gcacatatcg aggtggacat tacctacgcc gagtacttcg agatgagcgt tcggctggca 8580
gaagctatga agcgctatgg gctgaataca aaccatcgga tcgtggtgtg cagcgagaat 8640
agcttgcagt tcttcatgcc cgtgttgggt gccctgttca tcggtgtggc tgtggcccca 8700
gctaacgaca tctacaacga gcgcgagctg ctgaacagca tgggcatcag ccagcccacc 8760
gtcgtattcg tgagcaagaa agggctgcaa aagatcctca acgtgcaaaa gaagctaccg 8820
atcatacaaa agatcatcat catggatagc aagaccgact accagggctt ccaaagcatg 8880
tacaccttcg tgacttccca tttgccaccc ggcttcaacg agtacgactt cgtgcccgag 8940
agcttcgacc gggacaaaac catcgccctg atcatgaaca gtagtggcag taccggattg 9000
cccaagggcg tagccctacc gcaccgcacc gcttgtgtcc gattcagtca tgcccgcgac 9060
cccatcttcg gcaaccagat catccccgac accgctatcc tcagcgtggt gccatttcac 9120
cacggcttcg gcatgttcac cacgctgggc tacttgatct gcggctttcg ggtcgtgctc 9180
atgtaccgct tcgaggagga gctattcttg cgcagcttgc aagactataa gattcaatct 9240
gccctgctgg tgcccacact atttagcttc ttcgctaaga gcactctcat cgacaagtac 9300
gacctaagca acttgcacga gatcgccagc ggcggggcgc cgctcagcaa ggaggtaggt 9360
gaggccgtgg ccaaacgctt ccacctacca ggcatccgac agggctacgg cctgacagaa 9420
acaaccagcg ccattctgat cacccccgaa ggggacgaca agcctggcgc agtaggcaag 9480
gtggtgccct tcttcgaggc taaggtggtg gacttggaca ccggtaagac actgggtgtg 9540
aaccagcgcg gcgagctgtg cgtccgtggc cccatgatca tgagcggcta cgttaacaac 9600
cccgaggcta caaacgctct catcgacaag gacggctggc tgcacagcgg cgacatcgcc 9660
tactgggacg aggacgagca cttcttcatc gtggaccggc tgaagtccct gatcaaatac 9720
aagggctacc aggtagcccc agccgaactg gagagcatcc tgctgcaaca ccccaacatc 9780
ttcgacgccg gggtcgccgg cctgcccgac gacgatgccg gcgagctgcc cgccgcagtc 9840
gtcgtgctgg aacacggtaa aaccatgacc gagaaggaga tcgtggacta tgtggccagc 9900
caggttacaa ccgccaagaa gctgcgcggt ggtgttgtgt tcgtggacga ggtgcctaaa 9960
ggactgaccg gcaagttgga cgcccgcaag atccgcgaga ttctcattaa ggccaagaag 10020
ggcggcaaga tcgccgtgta actcgagtat gttacgtgca aaggtgattg tcaccccccg 10080
aaagaccata ttgtgacaca ccctcagtat cacgcccaaa catttacagc cgcggtgtca 10140

```
aaaaccgcgt ggacgtggtt aacatccctg ctgggaggat cagccgtaat tattataatt  10200

ggcttggtgc tggctactat tgtggccatg tacgtgctga ccaaccagaa acataattga  10260

atacagcagc aattggcaag ctgcttacat agaactcgcg gcgattggca tgccgcctta  10320

aaatttttat tttatttttt cttttctttt ccgaatcgga ttttgttttt aatatttcaa  10380

aaaaaaaaaa aaaaaaaaaa aaatctagaa aaaaaaaaaa aaaaaaaaaa aaaaaaaaaa  10440

aaaaaaaaaa aaaaaaaaaa aaaaaaaaaa aaaaaaaaaa aaaaaaaaaa aaaaaaaaaa  10500

aaaaaaaa                                                           10508
```

<210> SEQ ID NO 118
<211> LENGTH: 11075
<212> TYPE: RNA
<213> ORGANISM: Artificial sequence
<220> FEATURE:
<223> OTHER INFORMATION: Synthetic polynucleotide

<400> SEQUENCE: 118

```
augggcggcg caugagagaa gcccagacca auuaccuacc caaaauggag aaaguucacg     60

uugacaucga ggaagacagc ccauuccuca gagcuuugca gcggagcuuc ccgcaguuug    120

agguagaagc caagcagguc acugauaaug accaugcuaa ugccagagcg uuuucgcauc    180

uggcuucaaa acugaucgaa acggaggugg acccauccga cacgauccuu gacauuggaa    240

gugcgcccgc ccgcagaaug uauucuaagc acaaguauca uuguaucugu ccgaugagau    300

gugcggaaga uccggacaga uuguauaagu augcaacuaa gcugaagaaa aacuguaagg    360

aaauaacuga uaaggaauug gacaagaaaa ugaaggagcu ggccgccguc augagcgacc    420

cugaccugga aacugagacu augugccucc acgacgacga gucgugucgc uacgaagggc    480

aagucgcugu uuaccaggau guauacgccg ucgacggccc caccagccug uaccaccagg    540

ccaacaaggg cgugagggug gccuacugga ucggcuucga caccacaccc uucauguuca    600

agaaccuggc cggcgccuac cccagcuaca gcaccaacug ggccgacgag accgugcuga    660

ccgccaggaa caucggccug ugcagcagcg acgugaugga gaggagccgg agaggcauga    720

gcauccugag gaagaaauac cugaagccca gcaacaacgu gcuguucagc gugggcagca    780

ccaucuacca cgagaagagg gaccugcuca ggagcuggca ccugcccagc guguuccacc    840

ugaggggcaa gcagaacuac accugcaggu gcgagaccau cgugagcugc gacggcuacg    900

uggugaagag gaucgccauc agccccggcc uguacggcaa gcccagcggc uacgccgcua    960

caaugcacag ggagggcuuc cugugcugca aggugaccga cacccugaac ggcgagaggg   1020

ugagcuuccc cgugugcacc uacgugcccg ccacccugug cgaccagaug accggcaucc   1080

uggccaccga cgugagcgcc gacgacgccc agaagcugcu cgugggccug aaccagagga   1140

ucguggucaa cggcaggacc cagaggaaca ccaacacaau gaagaacuac cugcugcccg   1200

ugguggccca ggcuuucgcc aggugggcca aggaguacaa ggaggaccag gaagacgaga   1260

ggccccuggg ccugagggac aggcagcugg ugaugggcug cugcugggcc uucaggcggc   1320

acaagaucac cagcaucuac aagaggcccg acacccagac caucaucaag gugaacagcg   1380

acuuccacag cuucgugcug cccaggaucg gcagcaacac ccuggagauc ggccugagga   1440

cccggaucag gaagaugcug gaggaacaca aggagcccag cccacugauc accgccgagg   1500

acgugcagga ggccaagugc gcugccgacg aggccaagga ggugagggag gccgaggaac   1560

ugagggccgc ccugccaccc cuggcugccg acguggagga acccacccug gaagccgacg   1620

uggaccugau gcugcaggag gccggcgccg gaagcgugga gacacccagg ggccugauca   1680
```

```
aggugaccag cuacgacggc gaggacaaga ucggcagcua cgccgugcug agcccacagg   1740
ccgugcugaa guccgagaag cugagcugca uccacccacu ggccgagcag gugaucguga   1800
ucacccacag cggcaggaag ggcagguacg ccguggagcc cuaccacggc aagguggucg   1860
ugcccgaggg ccacgccauc cccgugcagg acuuccaggc ccugagcgag agcgccacca   1920
ucguguacaa cgagagggag uucgugaaca gguaccugca ccauaucgcc acccacggcg   1980
gagcccugaa caccgacgag gaauacuaca agaccgugaa gcccagcgag cacgacggcg   2040
aguaccugua cgacaucgac aggaagcagu gcgugaagaa agagcuggug accggccugg   2100
gacugaccgg cgagcuggug gacccacccu uccacgaguu cgccuacgag agccugagga   2160
ccagacccgc cgcucccuac caggugccca ccaucggcgu guacggcgug cccggcagcg   2220
gaaagagcgg caucaucaag agcgccguga ccaagaaaga ccugguGguc agcgccaaga   2280
aagagaacug cgccgagauc aucagggacg ugaagaagau gaaaggccug gacgugaacg   2340
cgcgcaccgu ggacagcgug cugcugaacg gcugcaagca ccccguggag acccuguaca   2400
ucgacgaggc cuucgcuugc cacgccggca cccugagggc ccugaucgcc aucaucaggc   2460
ccaagaaagc cgugcugugc ggcgacccca agcagugcgg cuucuucaac augaugugcc   2520
ugaaggugca cuucaaccac gagaucugca cccagguguu ccacaagagc aucagcaggc   2580
ggugcaccaa gagcgugacc agcgucguga gcacccuguu cuacgacaag aaaaugagga   2640
ccaccaaccc caaggagacc aaaaucguga ucgacaccac aggcagcacc aagcccaagc   2700
aggacgaccu gauccugacc ugcuucaggg gcugggugaa gcagcugcag aucgacuaca   2760
agggcaacga gaucaugacc gccgcugcca gccagggccu gaccaggaag ggcguguacg   2820
ccgugaggua caaggugaac gagaacccac uguacgcucc caccagcgag cacgugaacg   2880
ugcugcugac caggaccgag gacaggaucg uguggaagac ccuggccggc gaccccugga   2940
ucaagacccu gaccgccaag uaccccggca acuucaccgc caccaucgaa gaguggcagg   3000
ccgagcacga cgccaucaug aggcacaucc uggagaggcc cgaccccacc gacguguucc   3060
agaacaaggc caacgugugc ugggccaagg cccuggugcc cgugcugaag accgccggca   3120
ucgacaugac cacagagcag uggaacaccg uggacuacuu cgagaccgac aaggcccaca   3180
gcgccgagau cgugcugaac cagcugugcg ugagguucuu cggccuggac cuggacagcg   3240
gccuguucag cgcccccacc gugccacuga gcaucaggaa caaccacugg gacaacagcc   3300
ccagcccaaa cauguacggc cugaacaagg agguggucag gcagcugagc aggcgguacc   3360
cacagcugcc cagggccgug gccaccggca ggguguacga caugaacacc ggcacccuga   3420
ggaacuacga ccccaggauc aaccuggugc ccgugaacag gcggcugccc cacgcccugg   3480
ugcugcacca caacgagcac ccacagagcg acuucagcuc cuucgugagc aagcugaaag   3540
gcaggaccgu gcuggucgug ggcgagaagc ugagcgugcc cggcaagaug guggacuggc   3600
ugagcgacag gcccgaggcc accuuccggg ccaggcugga ccucggcauc cccggcgacg   3660
ugcccaagua cgacaucauc uucgugaacg ucaggacccc auacaaguac caccauuacc   3720
agcagugcga ggaccacgcc aucaagcuga gcaugcugac caagaaggcc ugccugcacc   3780
ugaaccccgg aggcaccugc gugagcaucg gcuacggcua cgccgacagg gccagcgaga   3840
gcaucauugg cgccaucgcc aggcuguuca aguucagcag ggugugcaaa cccaagagca   3900
gccuggagga aaccgaggug cuguucgugu ucaucggcua cgaccggaag gccaggaccc   3960
acaaccccua caagcugagc agcacccuga caaacaucua caccggcagc aggcugcacg   4020
```

aggccggcug cgcccccagc uaccacgugg ucaggggcga uaucgccacc gccaccgagg 4080
gcgugaucau caacgcugcc aacagcaagg gccagcccgg aggcggagug ugcggcgccc 4140
uguacaagaa guuccccgag agcuucgacc ugcagcccau cgaggugggc aaggccaggc 4200
uggugaaggg cgccgcuaag cacaucaucc acgccguggg ccccaacuuc aacaaggaga 4260
gcgaggugga aggcgacaag cagcuggccg aagccuacga gagcaucgcc aagaucguga 4320
acgacaauaa cuacaagagc guggccaucc cacugcucag caccggcauc uucagcggca 4380
acaaggacag gcugacccag agccugaacc accugcucac cgcccuggac accaccgaug 4440
ccgacguggc caucuacugc agggacaaga agugggagau gacccugaag gaggccgugg 4500
ccaggcggga ggccguggaa gagaucugca ucagcgacga cuccagcgug accgagcccg 4560
acgccgagcu ggugagggug caccccaaga gcucccuggc cggcaggaag ggcuacagca 4620
ccagcgacgg caagaccuuc agcuaccugg agggcaccaa guuccaccag gccgcuaagg 4680
acaucgccga gaucaacgcu auguggcccg uggccaccga ggccaacgag cagguguugca 4740
uguacauccu gggcgagagc auguccagca ucaggagcaa gugccccgug gaggaaagcg 4800
aggccagcac accacccagc acccugcccu gccugugcau ccacgcuaug acacccgaga 4860
gggugcagcg gcugaaggcc agcaggcccg agcagaucac cgugugcagc uccuucccac 4920
ugcccaagua caggaucacc ggcgugcaga agauccagug cagccagccc auccuguuca 4980
gcccaaaggu gcccgccuac auccacccca ggaaguaccu gguggagacc ccacccgugg 5040
acgagacacc cgagccaagc gccgagaacc agagcaccga gggcacaccc gagcagccac 5100
cccugaucac cgaggacgag acaaggaccc ggaccccaga gcccaucauu aucgaggaag 5160
aggaagagga cagcaucagc cugcugagcg acggccccac ccaccaggug cugcaggugg 5220
aggccgacau ccacggccca cccagcgugu ccagcuccag cuggagcauc ccacacgcca 5280
gcgacuucga cguggacagc cugagcaucc uggacacccu ggagggcgcc agcgugaccu 5340
ccggcgccac cagcgccgag accaacagcu acuucgccaa gagcauggag uuccuggcca 5400
ggcccgugcc agcucccagg accguguuca ggaacccacc ccacccagcu cccaggacca 5460
ggaccccaag ccuggcuccc agcagggccu gcagcaggac cagccuggug agcaccccac 5520
ccggcgugaa cagggugauc accagggagg aacuggaggc ccugacaccc agcaggaccc 5580
ccagcagguc cgugagcagg acuagucugg uguccaaccc acccggcgug aacaggguga 5640
ucaccaggga ggaauucgag gccuucgugg cccagcaaca gagacgguuc gacgccggcg 5700
ccuacaucuu cagcagcgac accggccagg gacaccugca gcaaaagagc gugaggcaga 5760
ccgugcugag cgaggguggug cuggagagga ccgagcugga aaucagcuac gcccccaggc 5820
uggaccagga gaaggaggaa cugcucagga agaaacugca gcugaacccc accccagcca 5880
acaggagcag guaccagagc aggaaggugg agaacaugaa ggccaucacc gccaggcgga 5940
uccugcaggg ccugggacac uaccugaagg ccgagggcaa gguggagugc uacaggaccc 6000
ugcaccccgu gccacuguac agcuccagcg ugaacagggc cuucuccagc cccaaggugg 6060
ccguggaggc cugcaacgcu augcugaagg agaacuuccc caccguggcc agcuacugca 6120
ucauccccga guacgacgcc uaccuggaca ugguggacgg cgccagcugc ugccuggaca 6180
ccgccagcuu cugccccgcc aagcugagga gcuuccccaa gaaacacagc uaccuggagc 6240
ccaccaucag gagcgccgug cccagcgcca uccagaacac ccugcagaac gugcuggccg 6300
cugccaccaa gaggaacugc aacgugaccc agaugaggga gcugcccgug cuggacagcg 6360
cugccuucaa cguggagugc uucaagaaau acgccugcaa caacgaguac ugggagaccu 6420

```
ucaaggagaa ccccaucagg cugaccgaag agaacguggu gaacuacauc accaagcuga   6480
agggccccaa ggccgcugcc cuguucgcua agacccacaa ccugaacaug cugcaggaca   6540
ucccaaugga cagguucgug auggaccuga agagggacgu gaaggugaca cccggcacca   6600
agcacaccga ggagaggccc aaggugcagg ugauccaggc cgcugaccca cuggccaccg   6660
ccuaccugug cggcauccac agggagcugg ugaggcggcu gaacgccgug cugcugccca   6720
acauccacac ccuguucgac augagcgccg aggacuucga cgccaucauc gccgagcacu   6780
uccagcccgg cgacugcgug cuggagaccg acaucgccag cuucgacaag agcgaggaug   6840
acgcuauggc ccugaccgcu cugaugaucc uggaggaccu gggcguggac gccgagcugc   6900
ucacccugau cgaggcugcc uucggcgaga ucagcuccau ccaccugccc accaagacca   6960
aguucaaguu cggcgcuaug augaaaagcg gaauguuccu gacccuguuc gugaacaccg   7020
ugaucaacau ugugaucgcc agcagggugc ugcgggagag gcugaccggc agccccugcg   7080
cugccuucau cggcgacgac aacaucguga agggcgugaa aagcgacaag cugauggccg   7140
acaggugcgc caccuggcug aacauggagg ugaagaucau cgacgccgug gugggcgaga   7200
aggcccccua cuucugcggc ggauucaucc ugugcgacag cgugaccggc accgccugca   7260
ggguggccga cccccugaag aggcuguuca agcugggcaa gccacuggcc gcugacgaug   7320
agcacgacga ugacaggcgg agggcccugc acgaggaaag caccaggugg aacagggugg   7380
gcauccugag cgagcugugc aaggccgugg agagcaggua cgagaccgug ggcaccagca   7440
ucaucgugau ggcuaugacc acacuggcca gcuccgucaa gagcuucucc uaccugaggg   7500
gggcccccau aacucucuac ggcuaaccug aauggacuac gacauagucu aguccgccaa   7560
ggccgccacc auggaagaug ccaaaaacau uaagaagggc ccagcgccau ucuacccacu   7620
cgaagacggg accgccggcg agcagcugca caaagccaug aagcgcuacg cccuggugcc   7680
cggcaccauc gccuuuaccg acgcacauau cgagguggac auuaccuacg ccgaguacuu   7740
cgagaugagc guucggcugg cagaagcuau gaagcgcuau gggcugaaua caaaccaucg   7800
gaucguggug ugcagcgaga auagcuugca guucuucaug cccguguugg gugcccuguu   7860
caucggugug gcuguggccc cagcuaacga caucuacaac gagcgcgagc ugcugaacag   7920
caugggcauc agccagccca ccgucguauu cgugagcaag aaagggcugc aaaagauccu   7980
caacgugcaa aagaagcuac cgaucauaca aaagaucauc aucauggaua gcaagaccga   8040
cuaccagggc uuccaaagca uguacaccuu cgugacuucc cauuugccac ccggcuucaa   8100
cgaguacgac uucgugcccg agagcuucga ccgggacaaa accaucgccc ugaucaugaa   8160
caguaguggc aguaccggau ugcccaaggg cguagcccua ccgcaccgca ccgcuugugu   8220
ccgauucagu caugcccgcg accccaucuu cggcaaccag aucauccccg acaccgcuau   8280
ccucagcgug gugccauuuc accacggcuu cggcauguuc accacgcugg gcuacuugau   8340
cugcggcuuu cgggucgugc ucauguaccg cuucgaggag gagcuauucu ugcgcagcuu   8400
gcaagacuau aagauucaau cugcccugcu ggugcccaca cuauuuagcu ucuucgcuaa   8460
gagcacucuc aucgacaagu acgaccuaag caacuugcac gagaucgcca gcggcggggc   8520
gccgcucagc aaggagguag gugaggccgu ggccaaacgc uuccaccuac caggcauccg   8580
acagggcuac ggccugacag aaacaaccag cgccauucug aucacccccg aaggggacga   8640
caagccuggc gcaguaggca agguggugcc cuucuucgag gcuaaggugg uggacuugga   8700
caccgguaag acacugggug ugaaccagcg cggcgagcug ugcguccgug gccccaugau   8760
```

caugagcggc uacguuaaca accccgaggc uacaaacgcu cucaucgaca aggacggcug 8820
gcugcacagc ggcgacaucg ccuacuggga cgaggacgag cacuucuuca ucguggaccg 8880
gcugaagucc cugaucaaau acaagggcua ccagguagcc ccagccgaac uggagagcau 8940
ccugcugcaa caccccaaca ucuucgacgc cggggucgcc ggccugcccg acgacgaugc 9000
cggcgagcug cccgccgcag ucgucgugcu ggaacacggu aaaaccauga ccgagaagga 9060
gaucguggac uauguggcca gccagguuac aaccgccaag aagcugcgcg gugguguugu 9120
guucguggac gaggugccua aaggacugac cggcaaguug gacgcccgca agauccgcga 9180
gauucucauu aaggccaaga agggcggcaa gaucgccgug uaacucgagc cggaaacgca 9240
auagccgaaa aacaaaaaac aaaaaaaaca aaaaaaaaac caaaaaaaca aaacacauua 9300
aaacagccug uggguugauc ccacccacag gcccauuggg cgcuagcacu cugguaucac 9360
gguaccuuug ugcgccuguu uuauaccccc ucccccaacu guaacuuaga aguaacacac 9420
accgaucaac agucagcgug gcacaccagc cacguuuuga ucaagcacuu cuguuacccc 9480
ggacugagua ucaauagacu gcucacgcgg uugaaggaga aagcguucgu uauccggcca 9540
acuacuucga aaaaccuagu aacaccgugg aaguugcaga guguuucgcu cagcacuacc 9600
ccaguguaga ucaggucgau gagucaccgc auuccccacg ggcgaccgug gcgguggcug 9660
cguuggcggc cugcccaugg ggaaacccau gggacgcucu aauacagaca uggugcgaag 9720
agucuauuga gcuaguuggu aguccuccgg ccccugaaug cggcuaaucc uaacugcgga 9780
gcacacaccc ucaagccaga gggcagugug ucguaacggg caacucugca gcggaaccga 9840
cuacuuuggg uguccguguu ucauuuuauu ccuauacugg cugcuuaugg ugacaauuga 9900
gagaucguua ccauauagcu auuggauugg ccauccggug acuaauagag cuauuauaua 9960
ucccuuuguu ggguuuauac cacuuagcuu gaaagagguu aaaacauuac aauucauugu 10020
uaaguugaau acagcaaaau gagcaagauc uacaucgacg agcggagcaa cgccgagauc 10080
gugugcgagg ccaucaagac caucggcauc gagggcgcca ccgccgccca gcugaccagg 10140
cagcugaaca uggagaagcg ggaggugaac aaggcccugu acgaccugca gaggagcgcu 10200
augguguacu ccagcgacga caucccuccc cgguugguuca ugaccaccga ggccgacaag 10260
cccgacgccg acgcuauggc cgacgugauc aucgacgacg ugagcaggga gaaguccaug 10320
agggaggacc acaagagcuu cgacgacgug aucccc gcca agaagaucau cgacuggaag 10380
ggcgccaacc ccgugaccgu gaucaacgag uacugccaga ucaccaggag ggacuggagc 10440
uuccggaucg agagcguggg ccccagcaac agccccaccu ucuacgccug cguggacauc 10500
gacggcaggg uguucgacaa ggccgacggc aagagcaagc gggacgccaa gaacaacgcc 10560
gccaagcugg ccguggacaa gcugcugggc uacgugauca uccgguucua aacguauguu 10620
acgugcaaag gugauuguca ccccccgaaa gaccauauug ugacacaccc ucaguaucac 10680
gcccaaacau uuacagccgc ggugucaaaa accgcgugga cgugguuaac aucccugcug 10740
ggaggaucag ccguaauuau uauaauuggc uuggugcugg cuacuauugu ggccauguac 10800
gugcugacca accagaaaca uaauugaaua cagcagcaau uggcaagcug cuuacauaga 10860
acucgcggcg auuggcaugc cgccuuaaaa uuuuuauuuu auuuuuucuu uucuuuuccg 10920
aaucggauuu uguuuuuaau auuucaaaaa aaaaaaaaaa aaaaaaaaaa ucuagaaaaa 10980
aaaaaaaaaa aaaaaaaaaa aaaaaaaaaa aaaaaaaaaa aaaaaaaaaa aaaaaaaaaa 11040
aaaaaaaaaa aaaaaaaaaa aaaaaaaaaa aaaaa 11075

<210> SEQ ID NO 119
<211> LENGTH: 10851
<212> TYPE: RNA
<213> ORGANISM: Artificial sequence
<220> FEATURE:
<223> OTHER INFORMATION: Synthetic polynucleotide

<400> SEQUENCE: 119

```
augggcggcg caugagagaa gcccagacca auuaccuacc caaaauggag aaaguucacg     60
uugacaucga ggaagacagc ccauuccuca gagcuuugca gcggagcuuc ccgcaguuug    120
agguagaagc caagcagguc acugauaaug accaugcuaa ugccagagcg uuuucgcauc    180
uggcuucaaa acugaucgaa acggaggugg acccauccga cacgauccuu gacauuggaa    240
gugcgcccgc ccgcagaaug uauucuaagc acaaguauca uuguaucugu ccgaugagau    300
gugcggaaga uccggacaga uuguauaagu augcaacuaa gcugaagaaa aacuguaagg    360
aaauaacuga uaaggaauug gacaagaaaa ugaaggagcu ggccgccguc augagcgacc    420
cugaccugga aacugagacu augugccucc acgacgacga gucgugucgc uacgaagggc    480
aagucgcugu uuaccaggau guauacgccg ucgacggccc caccagccug uaccaccagg    540
ccaacaaggg cgugagggug gccuacugga ucggcuucga caccacaccc uucauguuca    600
agaaccuggc cggcgccuac cccagcuaca gcaccaacug ggccgacgag accgugcuga    660
ccgccaggaa caucggccug ugcagcagcg acgugaugga gaggagccgg agaggcauga    720
gcauccugag gaagaaauac cugaagccca gcaacaacgu gcuguucagc gugggcagca    780
ccaucuacca cgagaagagg gaccugcuca ggagcuggca ccugcccagc guguuccacc    840
ugaggggcaa gcagaacuac accugcaggu gcgagaccau cgugagcugc gacggcuacg    900
uggugaagag gaucgccauc agccccggcc uguacggcaa gcccagcggc uacgccgcua    960
caaugcacag ggagggcuuc cugugcugca aggugaccga cacccugaac ggcgagaggg   1020
ugagcuuccc cgugugcacc uacgugcccg ccacccugug cgaccagaug accggcaucc   1080
uggccaccga cgugagcgcc gacgacgccc agaagcugcu cgugggccug aaccagagga   1140
ucgugguucaa cggcaggacc cagaggaaca ccaacacaau gaagaacuac cugcugcccg   1200
ugguggccca ggcuuucgcc aggugggcca aggaguacaa ggaggaccag gaagacgaga   1260
ggccccuggg ccugagggac aggcagcugg ugaugggcug cugcugggcc uucaggcggc   1320
acaagaucac cagcaucuac aagaggcccg acacccagac caucaucaag gugaacagcg   1380
acuuccacag cuucgugcug cccaggaucg gcagcaacac ccuggagauc ggccugagga   1440
cccggaucag gaagaugcug gaggaacaca aggagcccag cccacugauc accgccgagg   1500
acgugcagga ggccaagugc gcugccgacg aggccaagga ggugagggag gccgaggaac   1560
ugagggccgc ccugccaccc cuggcugccg acguggagga acccacccug gaagccgacg   1620
uggaccugau gcugcaggag gccggcgccg gaagcgugga gacacccagg ggccugauca   1680
aggugaccag cuacgacggc gaggacaaga ucggcagcua cgccgugcug agcccacagg   1740
ccgugcugaa guccgagaag cugagcugca uccacccacu ggccgagcag gugaucguga   1800
ucacccacag cggcaggaag ggcagguacg ccguggagcc cuaccacggc aagguggucg   1860
ugcccgaggg ccacgccauc cccgugcagg acuuccaggc ccugagcgag agcgccacca   1920
ucguguacaa cgagagggag uucgugaaca gguaccugca ccauaucgcc acccacggcg   1980
gagcccugaa caccgacgag gaauacuaca agaccgugaa gcccagcgag cacgacggcg   2040
aguaccugua cgacaucgac aggaagcagu gcgugaagaa agagcuggug accggccugg   2100
```

-continued

```
gacugaccgg cgagcuggug gacccacccu uccacgaguu cgccuacgag agccugagga   2160
ccagacccgc cgcucccuac caggugccca ccaucggcgu guacggcgug cccggcagcg   2220
gaaagagcgg caucaucaag agcgccguga ccaagaaaga ccugguggucc agcgccaaga   2280
aagagaacug cgccgagauc aucagggacg ugaagaagau gaaaggccug gacgugaacg   2340
cgcgcaccgu ggacagcgug cugcugaacg gcugcaagca ccccguggag acccuguaca   2400
ucgacgaggc cuucgcuugc cacgccggca cccugagggc ccugaucgcc aucaucaggc   2460
ccaagaaagc cgugcugugc ggcgacccca agcagugcgg cuucuucaac augaugugcc   2520
ugaaggugca cuucaaccac gagaucugca cccagguguu ccacaagagc aucagcaggc   2580
ggugcaccaa gagcgugacc agcgucguga gcacccuguu cuacgacaag aaaaugagga   2640
ccaccaaccc caaggagacc aaaaucguga ucgacaccac aggcagcacc aagcccaagc   2700
aggacgaccu gauccugacc ugcuucaggg gcugggugaa gcagcugcag aucgacuaca   2760
agggcaacga gaucaugacc gccgcugcca gccagggccu gaccaggaag ggcguguacg   2820
ccgugaggua caaggugaac gagaacccac uguacgcucc caccagcgag cacgugaacg   2880
ugcugcugac caggaccgag gacaggaucg uguggaagac ccuggccggc gaccccugga   2940
ucaagacccu gaccgccaag uaccccggca acuucaccgc caccaucgaa gaguggcagg   3000
ccgagcacga cgccaucaug aggcacaucc uggagaggcc cgaccccacc gacguguucc   3060
agaacaaggc caacgugugc ugggccaagg cccuggugcc cgugcugaag accgccggca   3120
ucgacaugac cacagagcag uggaacaccg uggacuacuu cgagaccgac aaggcccaca   3180
gcgccgagau cgugcugaac cagcugugcg ugagguucuu cggccuggac cuggacagcg   3240
gccuguucag cgcccccacc gugccacuga gcaucaggaa caaccacugg gacaacagcc   3300
ccagcccaaa cauguacggc cugaacaagg agguggucag gcagcugagc aggcgguacc   3360
cacagcugcc cagggccgug gccaccggca ggguguacga caugaacacc ggcacccuga   3420
ggaacuacga ccccaggauc aaccuggugc ccgugaacag gcggcugccc cacgcccugg   3480
ugcugcacca caacgagcac ccacagagcg acuucagcuc cuucgugagc aagcugaaag   3540
gcaggaccgu gcuggucgug ggcgagaagc ugagcgugcc cggcaagaug guggacuggc   3600
ugagcgacag gcccgaggcc accuuccggg ccaggcugga ccucggcauc cccggcgacg   3660
ugcccaagua cgacaucauc uucgugaacg ucaggacccc auacaaguac caccauuacc   3720
agcagugcga ggaccacgcc aucaagcuga gcaugcugac caagaaggcc ugccugcacc   3780
ugaaccccgg aggcaccugc gugagcaucg gcuacggcua cgccgacagg gccagcgaga   3840
gcaucauugg cgccaucgcc aggcuguuca aguucagcag ggugugcaaa cccaagagca   3900
gccuggagga aaccgaggug cuguucgugu ucaucggcua cgaccggaag gccaggaccc   3960
acaaccccua caagcugagc agcacccuga caaacaucua caccggcagc aggcugcacg   4020
aggccggcug cgcccccagc uaccacgugg ucaggggcga uaucgccacc gccaccgagg   4080
gcgugaucau caacgcugcc aacagcaagg gccagcccgg aggcggagug ugcggcgccc   4140
uguacaagaa guuccccgag agcuucgacc ugcagcccau cgaggugggc aaggccaggc   4200
uggugaaggg cgccgcuaag cacaucaucc acgccguggg ccccaacuuc aacaagguga   4260
gcgaggugga aggcgacaag cagcuggccg aagccuacga gagcaucgcc aagaucguga   4320
acgacaauaa cuacaagagc guggccaucc cacugcucag caccggcauc uucagcggca   4380
acaaggacag gcugacccag agccugaacc accugcucac cgcccuggac accaccgaug   4440
ccgacguggc caucuacugc agggacaaga agugggagau gacccugaag gaggccgugg   4500
```

```
ccaggcggga ggccguggaa gagaucugca ucagcgacga cuccagcgug accgagcccg   4560
acgccgagcu ggugagggug caccccaaga gcucccuggc cggcaggaag ggcuacagca   4620
ccagcgacgg caagaccuuc agcuaccugg agggcaccaa guuccaccag gccgcuaagg   4680
acaucgccga gaucaacgcu auguggcccg uggccaccga ggccaacgag caggugugca   4740
uguacauccu gggcgagagc auguccagca ucaggagcaa gugccccgug gaggaaagcg   4800
aggccagcac accacccagc acccugcccu gccugugcau ccacgcuaug acacccgaga   4860
gggugcagcg gcugaaggcc agcaggcccg agcagaucac cgugugcagc uccuucccac   4920
ugcccaagua caggaucacc ggcgugcaga agauccagug cagccagccc auccuguuca   4980
gcccaaaggu gcccgccuac auccacccca ggaaguaccu gguggagacc ccacccgugg   5040
acgagacacc cgagccaagc gccgagaacc agagcaccga gggcacaccc gagcagccac   5100
cccugaucac cgaggacgag acaaggaccc ggaccccaga gcccaucauu aucgaggaag   5160
aggaagagga cagcaucagc cugcugagcg acggccccac ccaccaggug cugcaggugg   5220
aggccgacau ccacggccca cccagcgugu ccagcuccag cuggagcauc ccacacgcca   5280
gcgacuucga cguggacagc cugagcaucc uggacacccu ggagggcgcc agcgugaccu   5340
ccggcgccac cagcgccgag accaacagcu acuucgccaa gagcauggag uuccuggcca   5400
ggcccgugcc agcucccagg accguguuca ggaacccacc ccacccagcu cccaggacca   5460
ggaccccaag ccuggcuccc agcagggccu gcagcaggac cagccuggug agcaccccac   5520
ccggcgugaa cagggugauc accagggagg aacuggaggc ccugacaccc agcaggaccc   5580
ccagcagguc cgugagcagg acuagucugg uguccaaccc acccggcgug aacaggguga   5640
ucaccaggga ggaauucgag gccuucgugg cccagcaaca gagacgguuc gacgccggcg   5700
ccuacaucuu cagcagcgac accggccagg gacaccugca gcaaaagagc gugaggcaga   5760
ccgugcugag cgagguggug cuggagagga ccgagcugga aaucagcuac gcccccaggc   5820
uggaccagga gaaggaggaa cugcucagga agaaacugca gcugaacccc accccagcca   5880
acaggagcag guaccagagc aggaaggugg agaacaugaa ggccaucacc gccaggcgga   5940
uccugcaggg ccugggacac uaccugaagg ccgagggcaa gguggagugc uacaggaccc   6000
ugcaccccgu gccacuguac agcuccagcg ugaacagggc cuucuccagc cccaaggugg   6060
ccguggaggc cugcaacgcu augcugaagg agaacuuccc caccguggcc agcuacugca   6120
ucauccccga guacgacgcc uaccuggaca ugguggacgg cgccagcugc ugccuggaca   6180
ccgccagcuu cugccccgcc aagcugagga gcuuccccaa gaaacacagc uaccuggagc   6240
ccaccaucag gagcgccgug cccagcgcca uccagaacac ccugcagaac gugcuggccg   6300
cugccaccaa gaggaacugc aacgugaccc agaugaggga gcugcccgug cuggacagcg   6360
cugccuucaa cguggagugc uucaagaaau acgccugcaa caacgaguac ugggagaccu   6420
ucaaggagaa ccccaucagg cugaccgaag agaacguggu gaacuacauc accaagcuga   6480
agggccccaa ggccgcugcc cuguucgcua agacccacaa ccugaacaug cugcaggaca   6540
ucccaaugga cagguucgug auggaccuga agagggacgu gaaggugaca cccggcacca   6600
agcacaccga ggagaggccc aaggugcagg ugauccaggc cgcugaccca cuggccaccg   6660
ccuaccugug cggcauccac agggagcugg ugaggcggcu gaacgccgug cugcugccca   6720
acauccacac ccuguucgac augagcgccg aggacuucga cgccaucauc gccgagcacu   6780
uccagcccgg cgacugcgug cuggagaccg acaucgccag cuucgacaag agcgaggaug   6840
```

acgcuauggc ccugaccgcu cugaugaucc uggaggaccu gggcguggac gccgagcugc 6900
ucacccugau cgaggcugcc uucggcgaga ucagcuccau ccaccugccc accaagacca 6960
aguucaaguu cggcgcuaug augaaaagcg gaauguuccu gacccuguuc gugaacaccg 7020
ugaucaacau ugugaucgcc agcagggugc ugcgggagag gcugaccggc agccccugcg 7080
cugccuucau cggcgacgac aacaucguga agggcgugaa aagcgacaag cugauggccg 7140
acaggugcgc caccuggcug aacauggagg ugaagaucau cgacgccgug gugggcgaga 7200
aggcccccua cuucugcggc ggauucaucc ugugcgacag cgugaccggc accgccugca 7260
ggguggccga cccccugaag aggcuguuca agcugggcaa gccacuggcc gcugacgaug 7320
agcacgacga ugacaggcgg agggcccugc acgaggaaag caccaggugg aacagggugg 7380
gcauccugag cgagcugugc aaggccgugg agagcaggua cgagaccgug ggcaccagca 7440
ucaucgugau ggcuaugacc acacuggcca gcuccgucaa gagcuucucc uaccugaggg 7500
gggccccuau aacucucuac ggcuaaccug aauggacuac gacauagucu aguccgccaa 7560
ggccgccacc auggaagaug ccaaaaacau uaagaagggc ccagcgccau ucuacccacu 7620
cgaagacggg accgccggcg agcagcugca caaagccaug aagcgcuacg cccuggugcc 7680
cggcaccauc gccuuuaccg acgcacauau cgagguggac auuaccuacg ccgaguacuu 7740
cgagaugagc guucggcugg cagaagcuau gaagcgcuau gggcugaaua caaaccaucg 7800
gaucguggug ugcagcgaga auagcuugca guucuucaug cccguguugg gugcccuguu 7860
caucggugug gcuguggccc cagcuaacga caucuacaac gagcgcgagc ugcugaacag 7920
caugggcauc agccagccca ccgucguauu cgugagcaag aaagggcugc aaaagauccu 7980
caacgugcaa aagaagcuac cgaucauaca aaagaucauc aucauggaua gcaagaccga 8040
cuaccagggc uuccaaagca uguacaccuu cgugacuucc cauuugccac ccggcuucaa 8100
cgaguacgac uucgugcccg agagcuucga ccgggacaaa accaucgccc ugaucaugaa 8160
caguaguggc aguaccggau ugcccaaggg cguagcccua ccgcaccgca ccgcuugugu 8220
ccgauucagu caugcccgcg accccaucuu cggcaaccag aucaucccccg acaccgcuau 8280
ccucagcgug gugccauuuc accacggcuu cggcauguuc accacgcugg gcuacuugau 8340
cugcggcuuu cgggucgugc ucauguaccg cuucgaggag gagcuauucu ugcgcagcuu 8400
gcaagacuau aagauucaau cugcccugcu ggugcccaca cuauuuagcu ucuucgcuaa 8460
gagcacucuc aucgacaagu acgaccuaag caacuugcac gagaucgcca gcggcggggc 8520
gccgcucagc aaggagguag gugaggccgu ggccaaacgc uuccaccuac caggcauccg 8580
acagggcuac ggccugacag aaacaaccag cgccauucug aucacccccg aaggggacga 8640
caagccuggc gcaguaggca agguggugcc cuucuucgag gcuaaggugg uggacuugga 8700
caccgguaag acacugggug ugaaccagcg cggcgagcug ugcguccgug gccccaugau 8760
caugagcggc uacguuaaca accccgaggc uacaaacgcu cucaucgaca aggacggcug 8820
gcugcacagc ggcgacaucg ccuacuggga cgaggacgag cacuucuuca ucguggaccg 8880
gcugaagucc cugaucaaau acaagggcua ccagguagcc ccagccgaac uggagagcau 8940
ccugcugcaa caccccaaca ucuucgacgc cggggucgcc ggccugcccg acgacgaugc 9000
cggcgagcug cccgccgcag ucgucgugcu ggaacacggu aaaaccauga ccgagaagga 9060
gaucguggac uauguggcca gccagguuac aaccgccaag aagcugcgcg gugguguugu 9120
guucguggac gaggugccua aaggacugac cggcaaguug gacgcccgca agauccgcga 9180
gauucucauu aaggccaaga agggcggcaa gaucgccgug uaacucgagc cggaaacgca 9240

-continued

```
auagccgaaa aacaaaaaac aaaaaaaaca aaaaaaaaac caaaaaaaca aaacacauua   9300

aaacagccug uggguugauc ccacccacag gcccauuggg cgcuagcacu cugguaucac   9360

gguaccuuug ugcgccuguu uuauaccccc ucccccaacu guaacuuaga aguaacacac   9420

accgaucaac agucagcgug gcacaccagc cacguuuuga ucaagcacuu cuguuacccc   9480

ggacugagua ucaauagacu gcucacgcgg uugaaggaga aagcguucgu uauccggcca   9540

acuacuucga aaaaccuagu aacaccgugg aaguugcaga guguuucgcu cagcacuacc   9600

ccaguguaga ucaggucgau gagucaccgc auuccccacg ggcgaccgug gcgguggcug   9660

cguuggcggc cugcccaugg ggaaacccau gggacgcucu aauacagaca uggugcgaag   9720

agucuauuga gcuaguuggu aguccuccgg ccccugaaug cggcuaaucc uaacugcgga   9780

gcacacaccc ucaagccaga gggcagugug ucguaacggg caacucugca gcggaaccga   9840

cuacuuuggg uguccguguu ucauuuuauu ccuauacugg cugcuuaugg ugacaauuga   9900

gagaucguua ccauauagcu auuggauugg ccauccggug acuaauagag cuauuauaua   9960

ucccuuuguu ggguuuauac cacuuagcuu gaaagagguu aaaacauuac aauucauugu  10020

uaaguugaau acagcaaaau gagcaagauc uacaucgacg agcggagcaa cgccgagauc  10080

gugugcgagg ccaucaagac caucggcauc gagggcgcca ccgccgccca gcugaccagg  10140

cagcugaaca uggagaagcg ggaggugaac aaggcccugu acgaccugca gaggagcgcu  10200

augguguacu ccagcgacga caucccuccc cggugguuca ugaccaccga ggccgacaag  10260

cccgacgccg acgcuauggc cgacgugauc aucgacgacg ugagcaggga gaaguccaug  10320

agggaggacc acaagagcuu cgacgacgug auccccgcca agaagaucau cgacuggaag  10380

ggcgccaacc ccgugaccgu gaucaacgag uacugccaga ucaccaggag ggacuggagc  10440

uuccggaucg agagcguggg ccccagcaac agccccaccu ucuacgccug cguggacauc  10500

gacggcaggg uguucgacaa ggccgacggc aagagcaagc gggacgccaa gaacaacgcc  10560

gccaagcugg ccguggacaa gcugcugggc uacgugauca uccgguucua aacaauuggc  10620

aagcugcuua cauagaacuc gcggcgauug gcaugccgcc uuaaaauuuu uauuuuauuu  10680

uuucuuuucu uuuccgaauc ggauuuuguu uuuaauauuu caaaaaaaaa aaaaaaaaaa  10740

aaaaaaucua gaaaaaaaaa aaaaaaaaaa aaaaaaaaaa aaaaaaaaaa aaaaaaaaaa  10800

aaaaaaaaaa aaaaaaaaaa aaaaaaaaaa aaaaaaaaaa aaaaaaaaaa a           10851
```